United States Patent
Yoo et al.

(10) Patent No.: US 11,807,630 B2
(45) Date of Patent: Nov. 7, 2023

(54) COMPOUND FOR ORGANIC ELECTRONIC ELEMENT, ORGANIC ELECTRONIC ELEMENT COMPRISING THE SAME, AND ELECTRONIC DEVICE THEREOF

(71) Applicant: DUK SAN NEOLUX CO., LTD., Cheonan-si (KR)

(72) Inventors: Jae Duk Yoo, Cheonan-si (KR); Jin Ho Yun, Yongin-si (KR); Jae Taek Kwon, Cheonan-si (KR); Moo Jin Park, Cheonan-si (KR); Sun Hee Lee, Hwaseong-si (KR); Byoung Yeop Kang, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 299 days.

(21) Appl. No.: 16/770,922

(22) PCT Filed: Nov. 22, 2018

(86) PCT No.: PCT/KR2018/014459
§ 371 (c)(1),
(2) Date: Jun. 8, 2020

(87) PCT Pub. No.: WO2019/112214
PCT Pub. Date: Jun. 13, 2019

(65) Prior Publication Data
US 2021/0163452 A1    Jun. 3, 2021

(30) Foreign Application Priority Data

Dec. 8, 2017    (KR) ........................ 10-2017-0168507

(51) Int. Cl.
*C07D 405/04*      (2006.01)
*H01L 51/00*        (2006.01)
*H10K 85/60*        (2023.01)
*H10K 50/15*        (2023.01)
*H10K 50/16*        (2023.01)
*H10K 50/17*        (2023.01)

(52) U.S. Cl.
CPC ......... *C07D 405/04* (2013.01); *H10K 85/624* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02)

(58) Field of Classification Search
None
See application file for complete search history.

(56) References Cited

U.S. PATENT DOCUMENTS

| 2006/0113905 | A1* | 6/2006 | Nakamura .......... H01L 27/3244 313/511 |
| 2016/0211456 | A1 | 7/2016 | Yen et al. |

FOREIGN PATENT DOCUMENTS

| CN | 108586368 A | 9/2018 |
| KR | 10-2011-0113469 A | 10/2011 |
| KR | 10-2012-0038032 A | 4/2012 |
| KR | 10-2017-0075645 | * 7/2017 |
| KR | 10-2017-0075645 A | 7/2017 |
| KR | 10-2017-0116944 A | 10/2017 |
| KR | 10-2018-0063709 A | 6/2018 |
| KR | 10-2019-0030391 A | 3/2019 |
| KR | 10-2019-0048091 A | 5/2019 |

OTHER PUBLICATIONS

Machine English translation of Heo et al. (KR 10-2017-0116944). Jun. 20, 2022.*
Machine English Translation of Park et al. (KR-10-2017-0075645). Oct. 17, 2022.*
Office action dated Apr. 20, 2022 from Korean Patent Office in a counterpart Korean Patent Application No. 10-2017-0168507 (all the cited references are listed in this IDS.) (English translation is also submitted herewith.).
Notice of Allowance dated Jul. 1, 2022 from Korean Patent Office in a counterpart Korean Patent Application No. 10-2017-0168507 (all the cited references are listed in this IDS.) (English translation is also submitted herewith.).

* cited by examiner

*Primary Examiner* — Jay Yang
(74) *Attorney, Agent, or Firm* — The PL Law Group, PLLC

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electric element can be lowered, and the luminous efficiency and life time of the organic electric element can be improved.

11 Claims, 1 Drawing Sheet

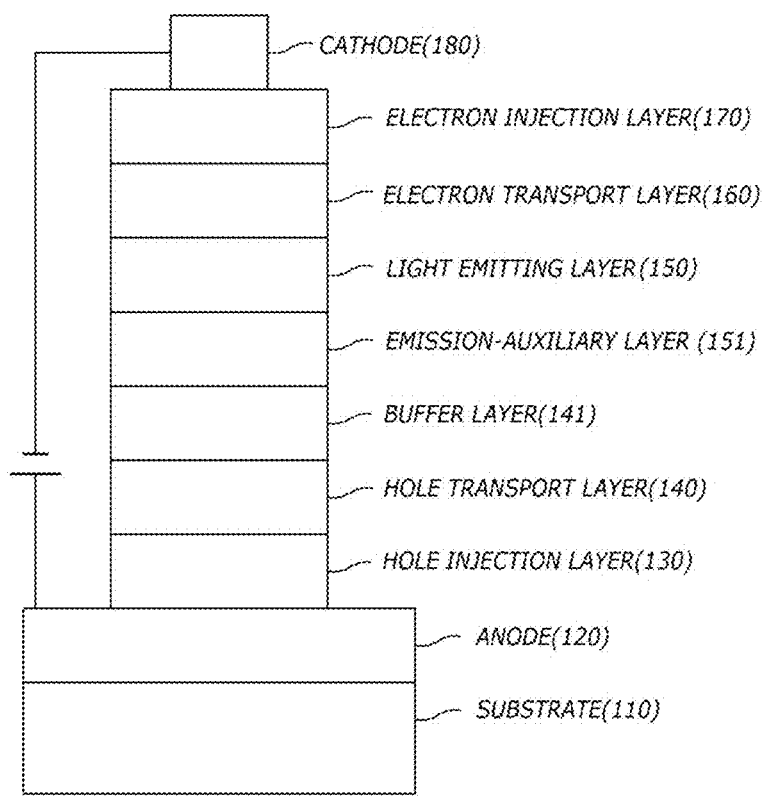

COMPOUND FOR ORGANIC ELECTRONIC ELEMENT, ORGANIC ELECTRONIC ELEMENT COMPRISING THE SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0168507, filed on Dec. 8, 2017 which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element comprising the same, and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, in particular, it is strongly required to develop host material of the light emitting layer.

Object, Technical Solution and Effects of the Invention

The present invention is to provide a compound lowering a driving voltage, improving luminous efficiency and lifetime of the element, an organic electric element comprising the same, and an electronic device thereof.

In an aspect of the present invention, the present invention provides the compound represented by the following formula.

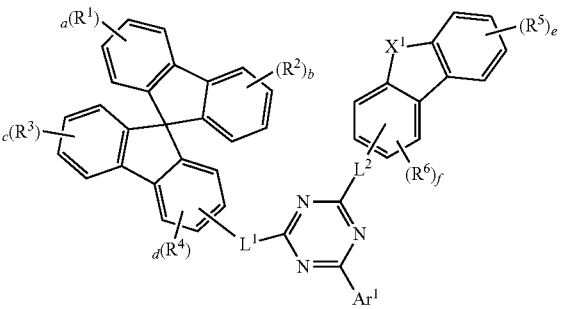

In another aspect of the present invention, the present invention provides an organic electric element using the compound represented by formula above and an electric device thereof.

By using the compound according to embodiment of the present invention, a driving voltage of element can be lowered and the luminous efficiency and lifetime of the element can be significantly improved.

BRIEF DESCRIPTION OF THE DRAWINGS

FIGURE illustrate an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

DETAILED DESCRIPTION

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl' when it is 'monovalent group', and as 'phenanthrylene' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl when it is 'monovalent group', and as 'pyrimidylen' when it is 'divalent group'.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon to which they are bonded.

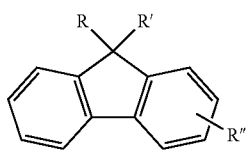

The term "Spiro compound" as used herein has, a Spiro union which means union having one atom as the only common member of two rings. The common atom is designated as 'spiro atom'. The compounds are defined as 'monospiro-', 'dispiro-' or 'trispiro' depending on the number of spiro atoms in one compound.

The term "heterocyclic group" as used herein means a ring comprising a heteroatom like N, O, S, P, Si or the like instead of carbon consisting of, it comprises a non-aromatic ring as well as an aromatic ring like "heteroaryl group" or "heteroarylene group" and the compound comprising heteroatom group like $SO_2$, $P=O$ or the like instead of carbon consisting of a ring such as the following compound.

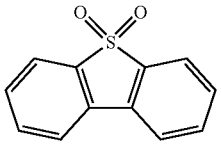 [SMILES: O=S1(=O)c2ccccc2-c2ccccc21]

Also, otherwise specified, the formulas used in the present invention are as defined in the index definition of the substituent of the following formula.

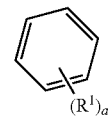

Here, the substituent $R^1$ is absent when a is an integer of zero, the sole $R^1$ is bonded to any one of the carbon atoms constituting the benzene ring when a is an integer of 1, when a is an integer of 2 or 3, the substituent $R^1$s may be bonded as follows and the substituents $R^1$s may be the same or different each other, and the substituent $R^1$s may be bonded to the carbon of the benzene ring in a similar manner when a is an integer of 4 to 6. Herein, the indication of the hydrogen bonded to the carbon which forms the benzene ring is omitted.

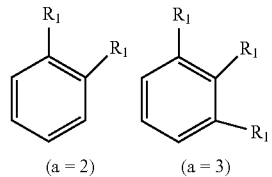

Hereinafter, a laminated structure of the electric element comprising the compound of the present invention will be described with reference to FIGURE.

The FIGURE illustrates a laminated structure of an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, a buffer layer 141, etc., and the electron transport layer 160 or the like may serve as a hole blocking layer.

In addition, although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, electron transport layer 160, an electron injection layer 170, a light emitting layer 150, a layer for improving luminous efficiency, an emission-auxiliary layer and so on. For example, the inventive compound may be used as material of a light emitting layer 150, preferably, as host material of a light emitting layer.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to the present invention may be one of an organic light emitting device (OLED), an organic solar cell, an organic photo conductor (OPC), an organic transistor, an element for monochromatic or white illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, and various kinds of computers, and the display device may comprise an electroluminescent display, a quantum dot display and so on.

Hereinafter, the compound according to an aspect of the present invention will be described.

The compound according to an aspect of the present invention is represented by Formula 1 below.

[Formula 1]

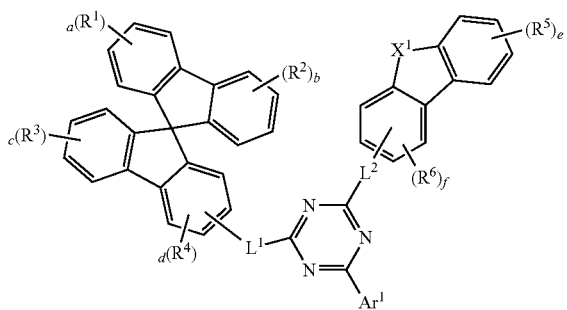

In the formula 1, each of symbols may be defined as follows.

$X^1$ is S, O or N(Ar'). Here, and Ar' is selected from the group consisting of a $C_6$-$C_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

Where Ar' is an aryl group, the aryl group may be preferably a $C_6$-$C_{30}$ aryl group, more preferably a $C_6$-$C_{12}$ aryl group, for example, phenyl, biphenyl, naphthyl and the like.

$R^1$ to $R^6$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), or adjacent groups together may be bonded to each other to form a ring. The ring formed by bonding between adjacent groups is a $C_6$-$C_{60}$ aromatic hydrocarbon, a $C_2$-$C_{60}$ heterocyclic ring, a $C_3$-$C_{60}$ aliphatic ring or a combination thereof.

Where $R^1$ to $R^6$ are an aryl group, the aryl group may be preferably a $C_6$-$C_{30}$ aryl group, more preferably a $C_6$-$C_{12}$ aryl group, for example, phenyl, biphenyl, naphthyl and the like. Where an aromatic hydrocarbon is formed by bonding between adjacent $R^1$ groups, adjacent $R^2$ groups, adjacent $R^3$ groups, adjacent $R^4$ groups, adjacent $R^5$ groups or adjacent $R^6$ groups, the aromatic hydrocarbon may be preferably a $C_6$-$C_{30}$ aromatic ring, more preferably a $C_6$-$C_{10}$ aromatic ring, for example, benzene, naphthalene and the like.

a, b, c and e are each an integer of 0 to 4, d and f are each an integer of 0 to 3, and where each of these is an integer of 2 or more, each of $R^1$s, each of $R^2$s, each of $R^3$s, each of $R^4$s, each of $R^5$s, each of $R^6$s is the same or different from each other.

$L^1$ is selected from the group consisting of a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof, and $L^2$ is selected from the group consisting of a single bond, a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof.

Where $L^1$ and $L^2$ are an arylene group, the arylene group may be preferably a $C_6$-$C_{30}$, more preferably a $C_6$-$C_{12}$ arylene group, for example, phenylene, naphthalene, biphenyl and the like.

$Ar^1$ is selected from the group consisting of a $C_6$-$C_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L'$-$N(R_a)(R_b)$.

Where $Ar^1$ is an aryl group, the aryl group may be preferably a $C_6$-$C_{30}$ aryl group, more preferably a $C_6$-$C_{12}$ aryl group, for example, phenyl, biphenyl, naphthyl and the like. Where $Ar^1$ is a heterocyclic group, the heterocyclic group may be preferably a $C_2$-$C_{30}$ heterocyclic group, more preferably a $C_2$-$C_{12}$ heterocyclic group, for example, dibenzofuran, dibenzothiophene and the like.

$L'$ is selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P.

$R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P.

The $R^1$ to $R^6$, $Ar^1$, $Ar'$, $L^1$, $L^2$, $L'$, $R_a$, $R_b$, a ring formed by bonding between adjacent $R^1$ groups, adjacent $R^2$ groups, adjacent $R^3$ groups, adjacent $R^4$ groups, adjacent $R^5$ groups and adjacent $R^6$ groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group and a $C_8$-$C_{20}$ arylalkenyl group.

Formula 1 may be represented by one of Formula 2 to Formula 5 below.

<Formula 2>

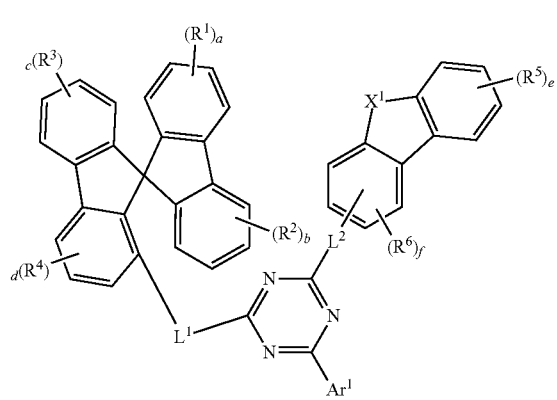

<Formula 3>

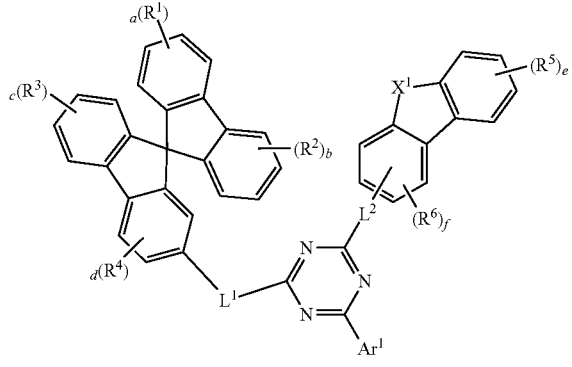

<Formula 4>

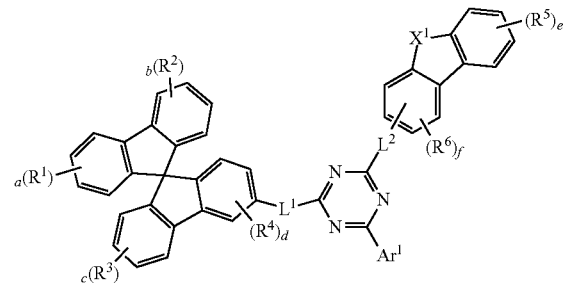

<Formula 5>

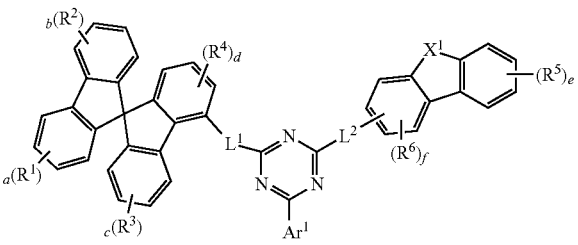

In Formulas 2 to 5, $X^1$, $R^1$ to $R^6$, a, b, c, e, d, f, $L^1$, $L^2$ and $Ar^1$ are the same as defined for Formula 1.

Also, Formula 1 may be represented by one of Formula 6 to Formula 9 below.

<Formula 6>

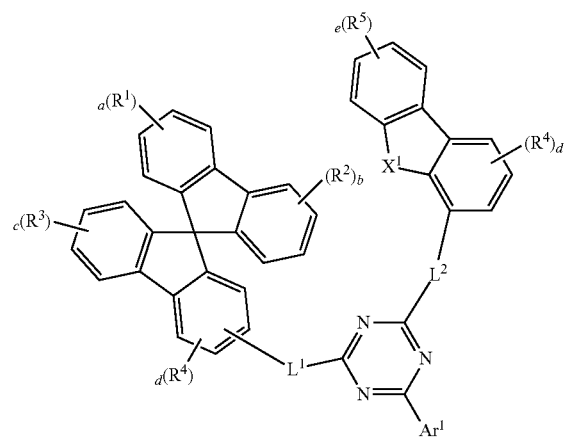

<Formula 7>
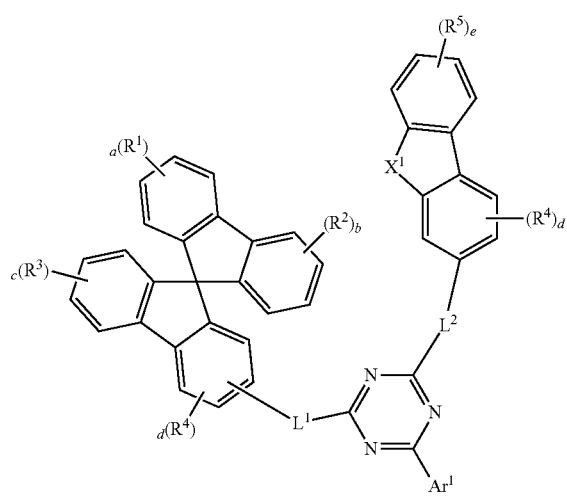
<Formula 8>
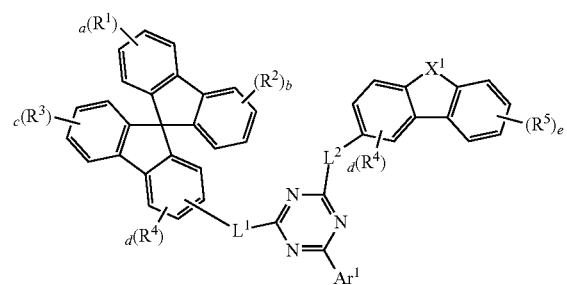
<Formula 9>
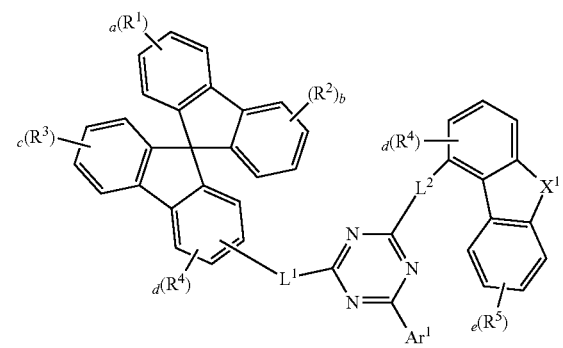
In Formulas 6 to 9, $X^1$, $R^1$ to $R^6$, a, b, c, e, d, f, $L^1$, $L^2$ and $Ar^1$ are the same as defined for Formula 1.
Specifically, the compound represented by formula 1 may be one of the following compounds.
c-1
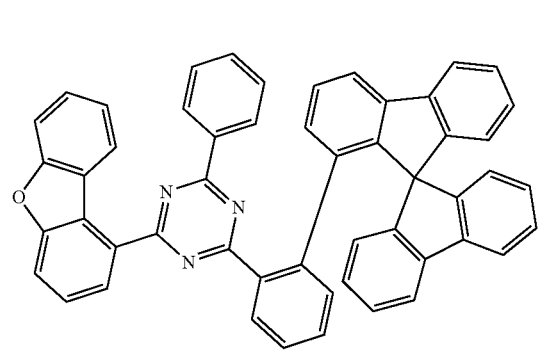
c-2
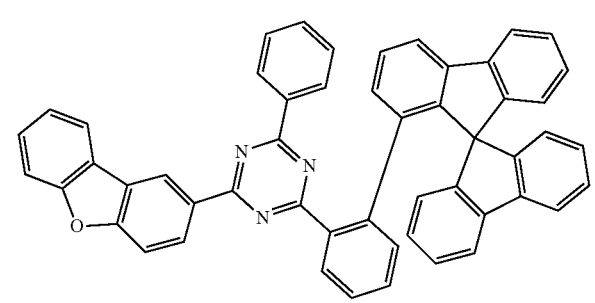
c-3
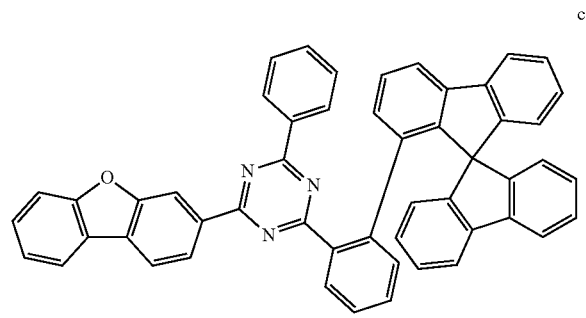
c-4
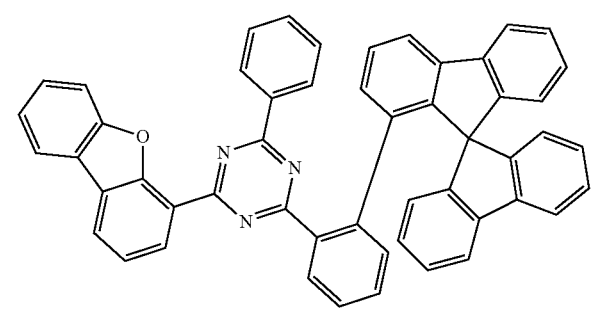

-continued
c-5
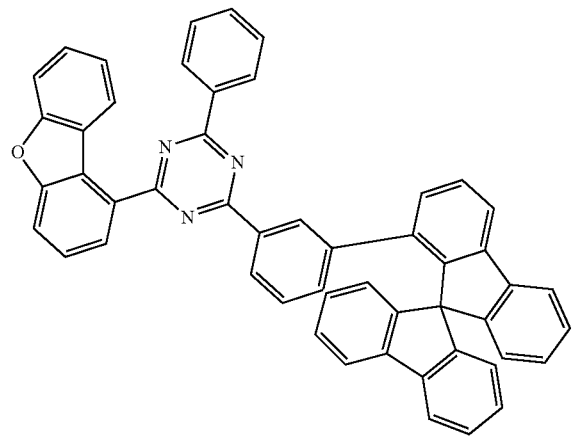
c-6
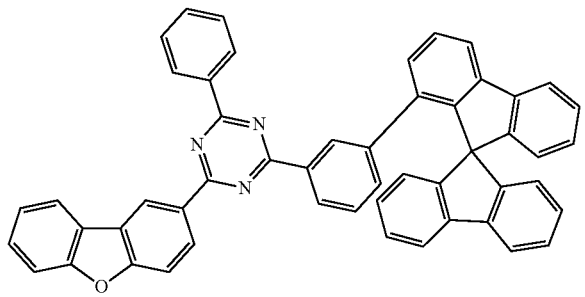
c-7
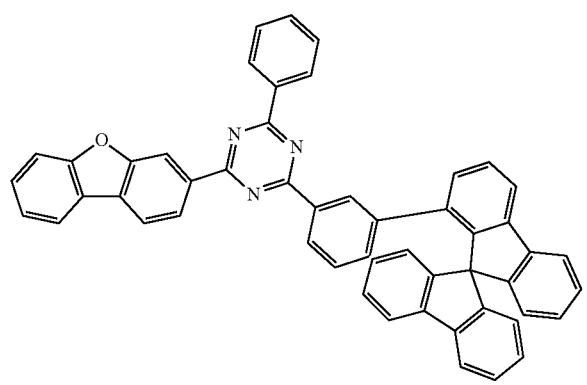
c-8
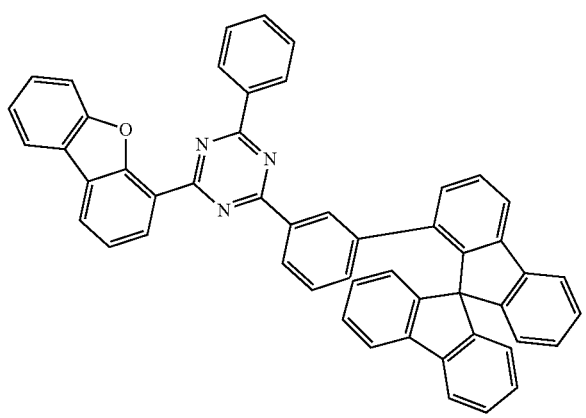
c-9
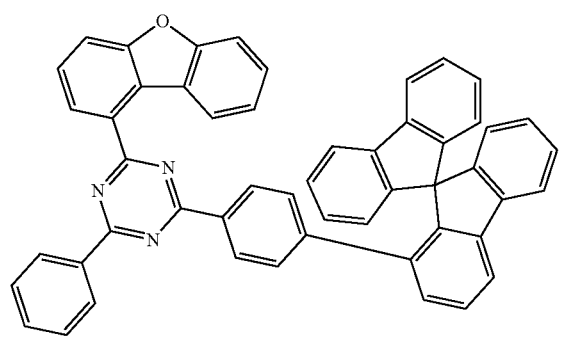
c-10
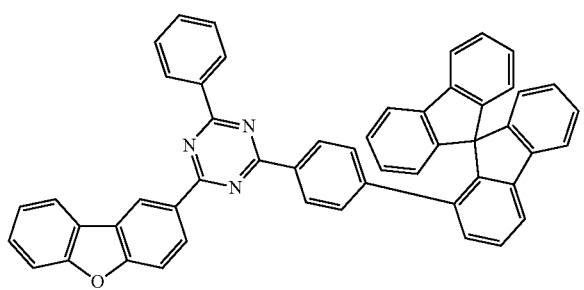
c-11
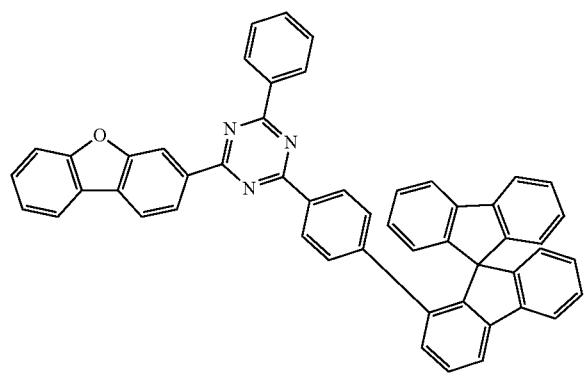
c-12
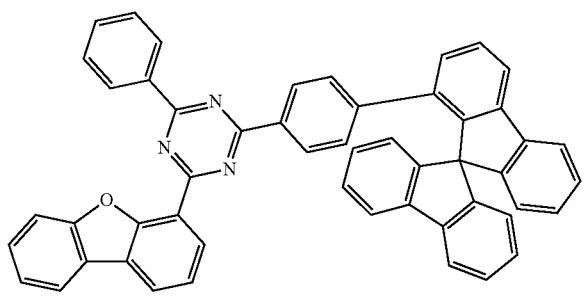

-continued
c-13
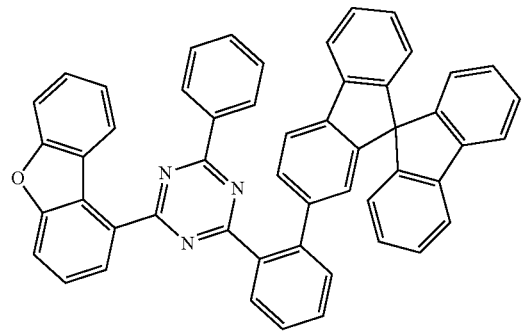
c-14
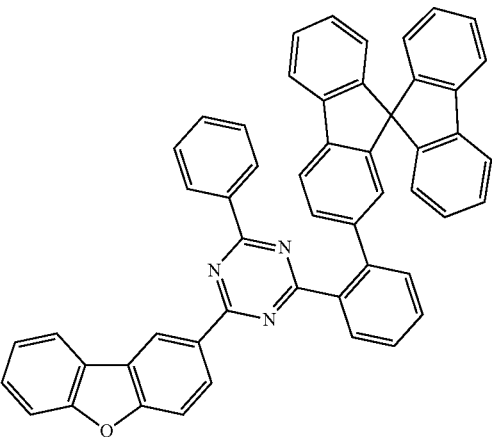
c-15
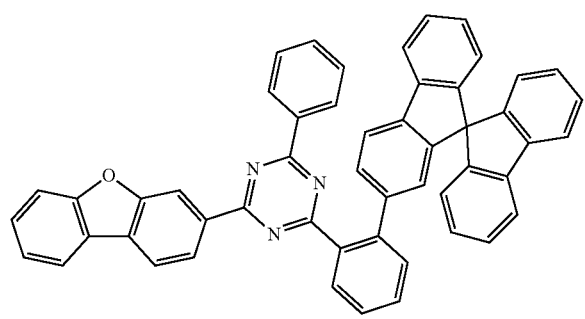
c-16
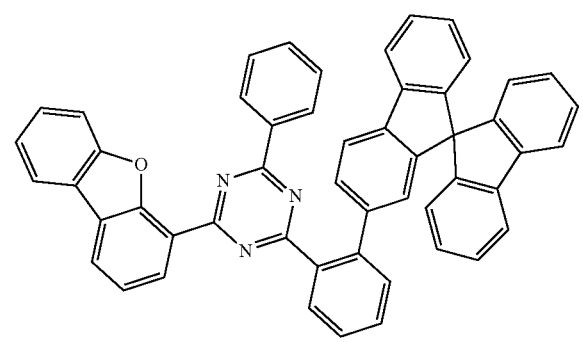
c-17
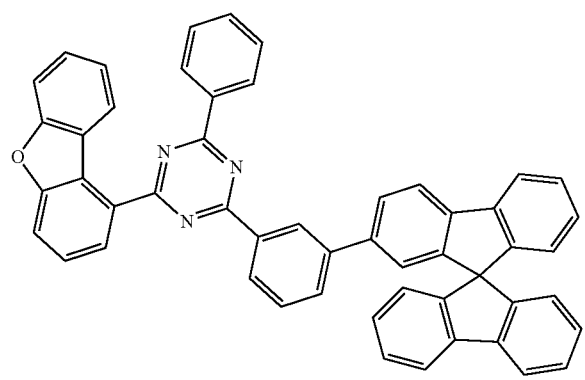
c-18
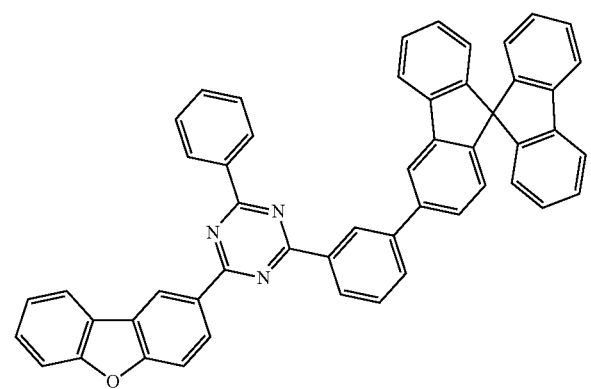
c-19
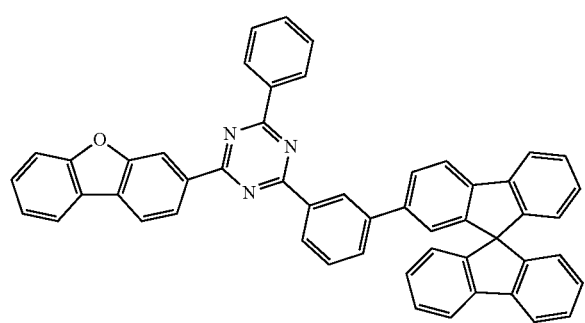
c-20
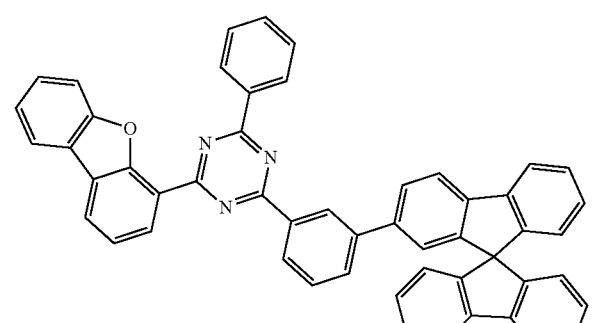

-continued
c-21
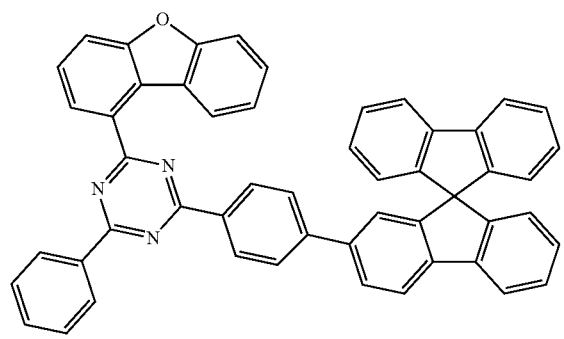
c-22
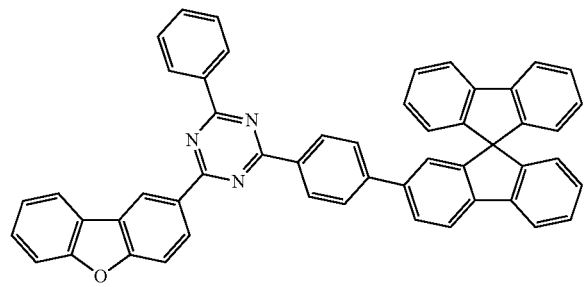
c-23
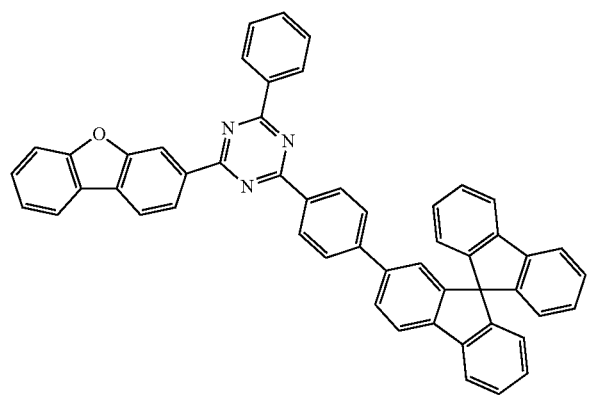
c-24
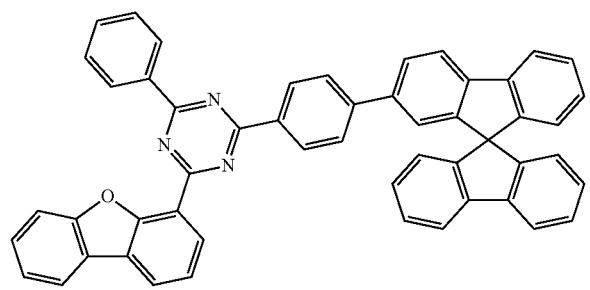
c-25
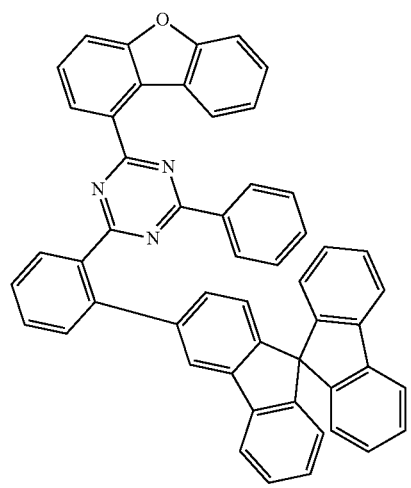
c-26
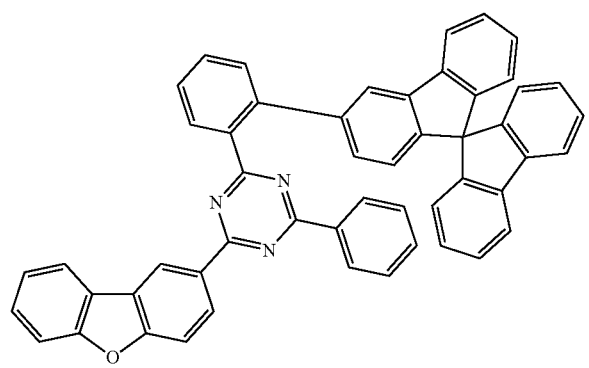

-continued
c-27
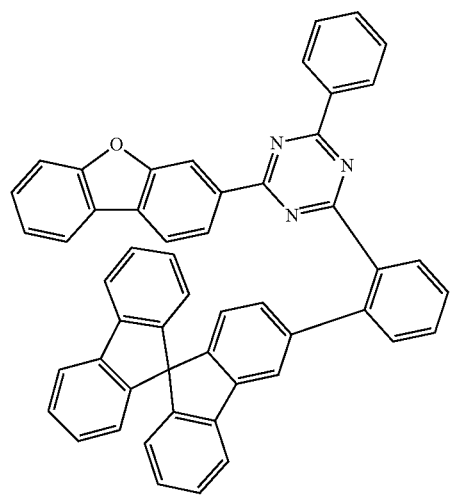
c-28
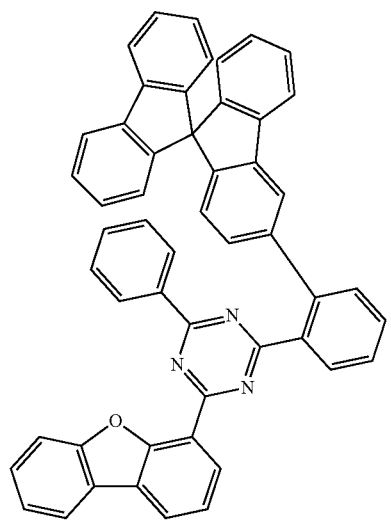
c-29
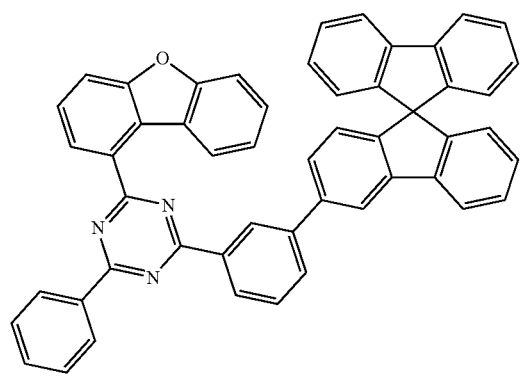
c-30
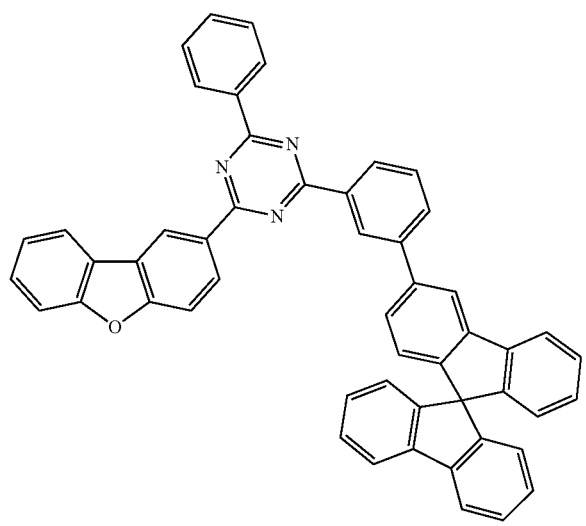
c-31
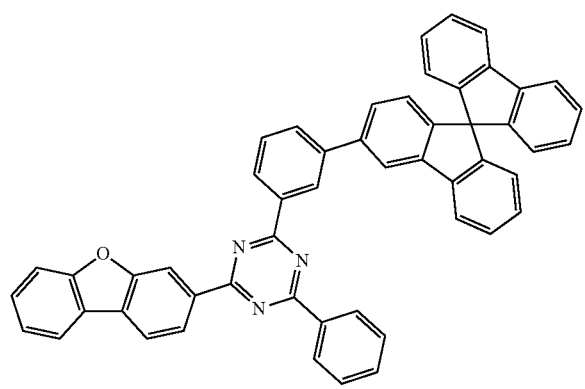
c-32
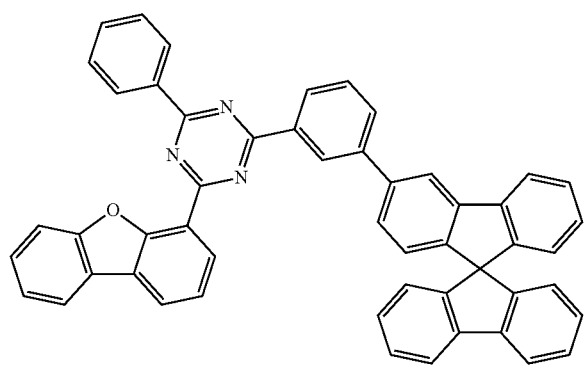

-continued
c-33
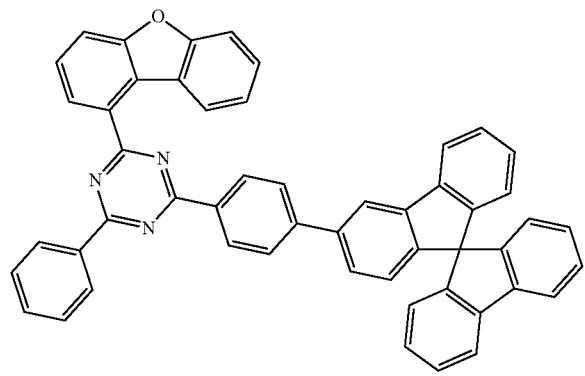
c-34
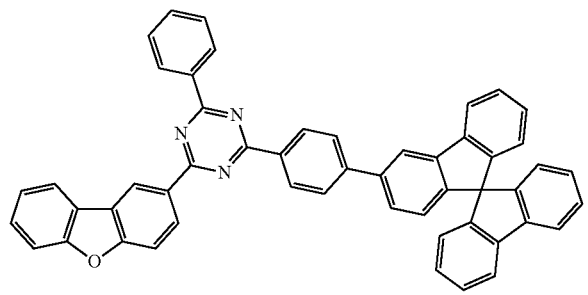
c-35
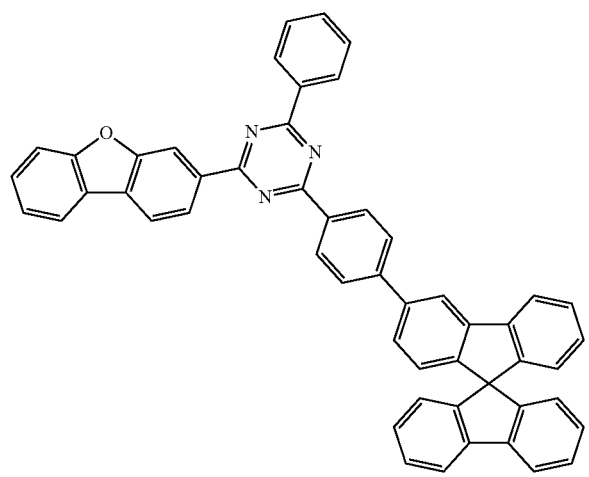
c-36
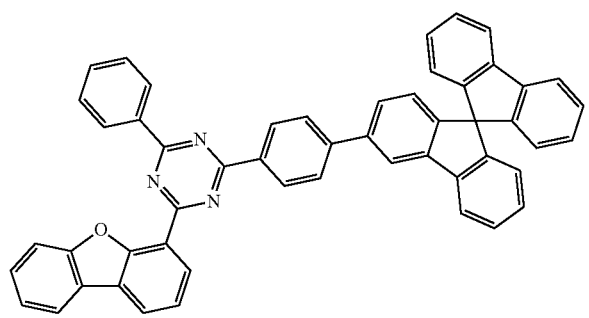
c-37
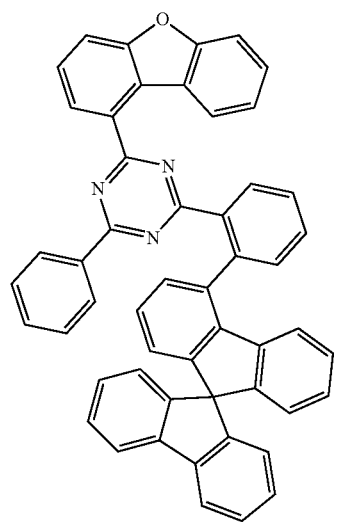
c-38
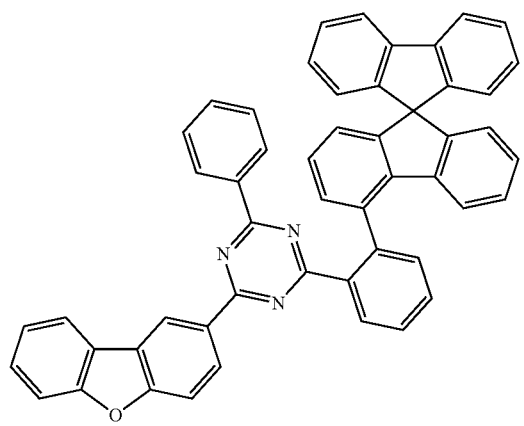

-continued
c-39
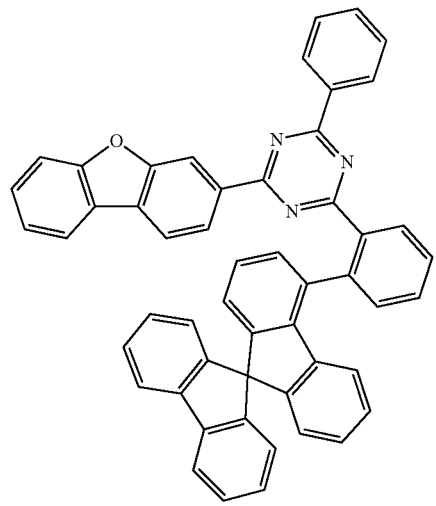
c-40
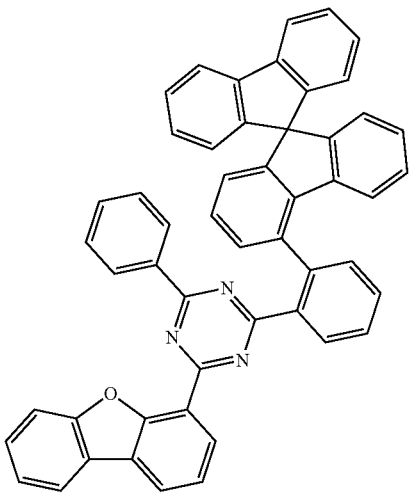
c-41
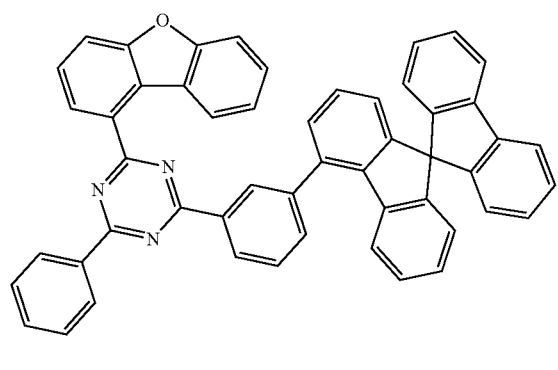
c-42
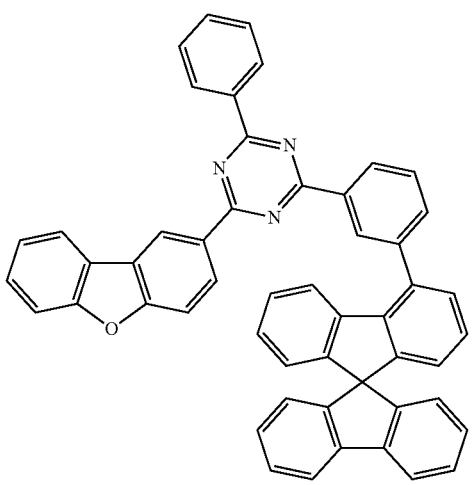
c-43
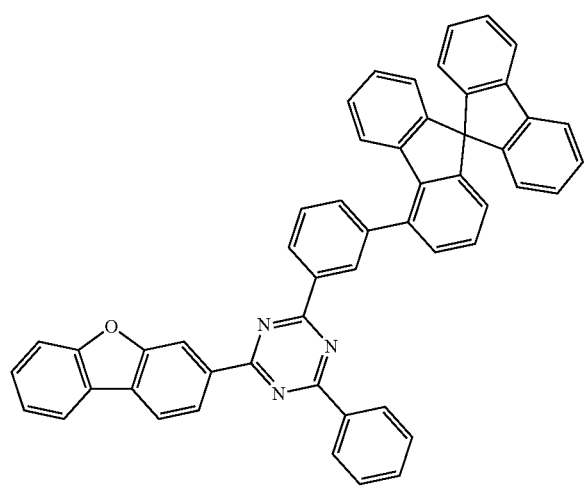
c-44
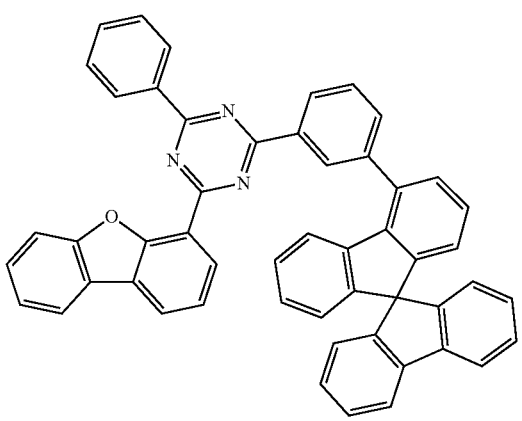

-continued
c-45
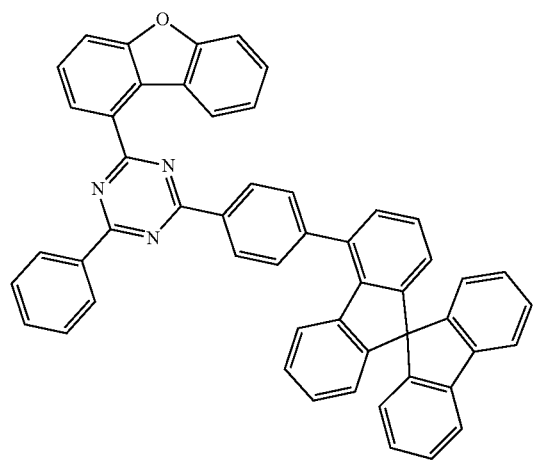
c-46
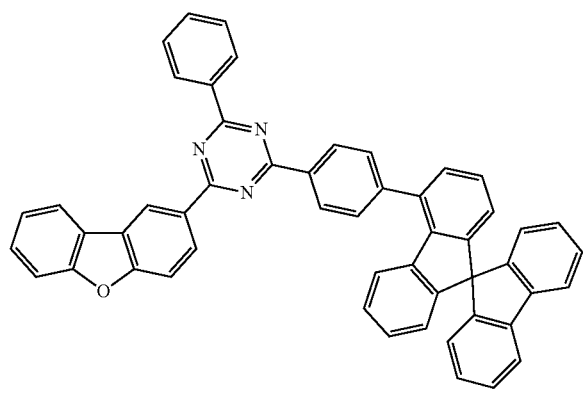
c-47
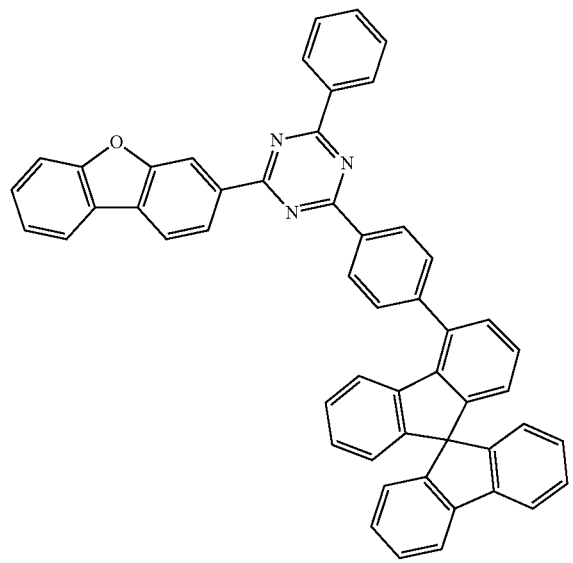
c-48
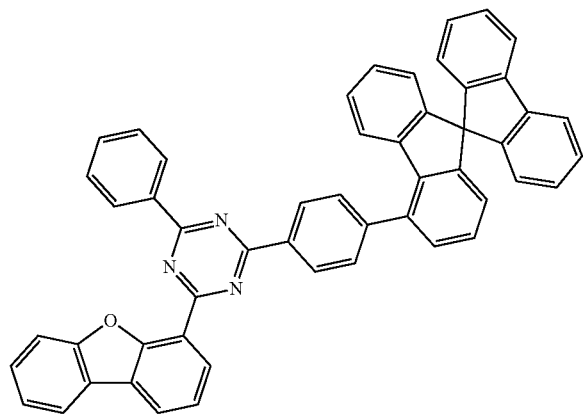
c-49
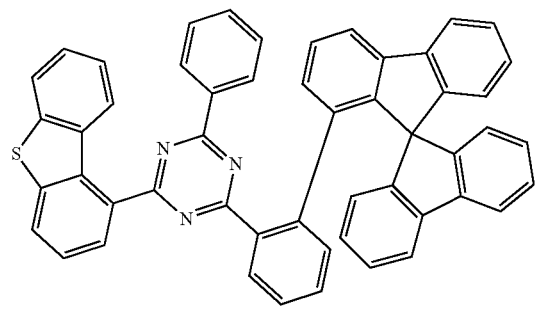
c-50
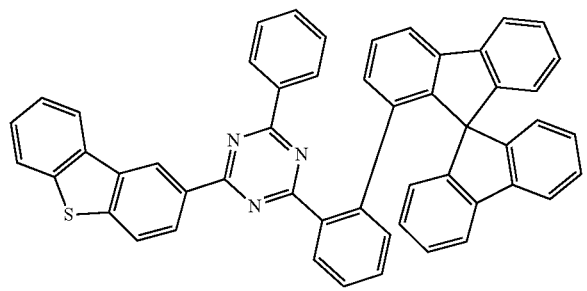

-continued
c-51
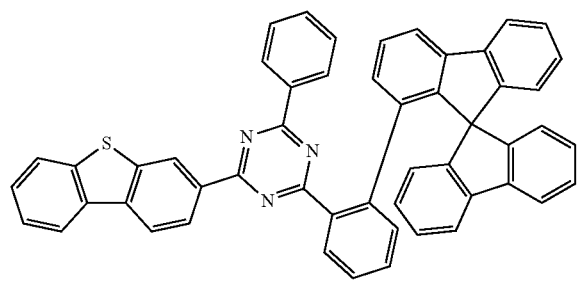
c-52
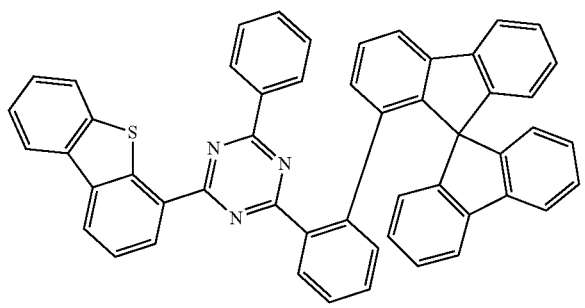
c-53
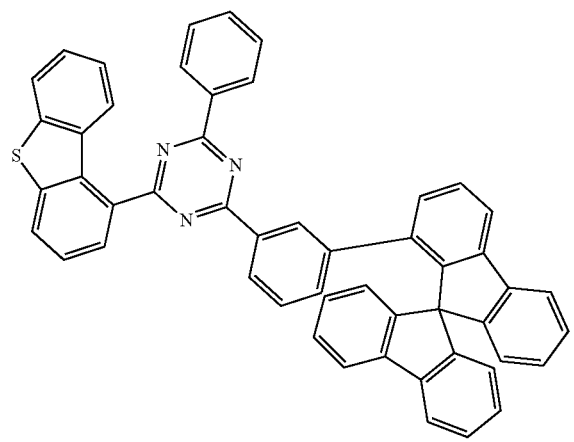
c-54
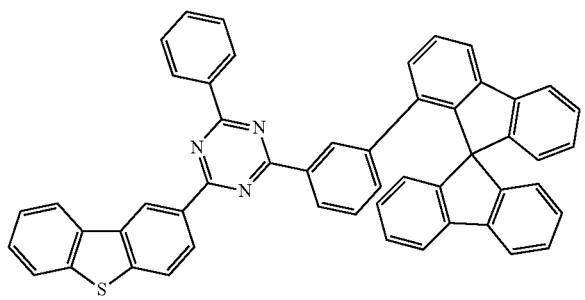
c55
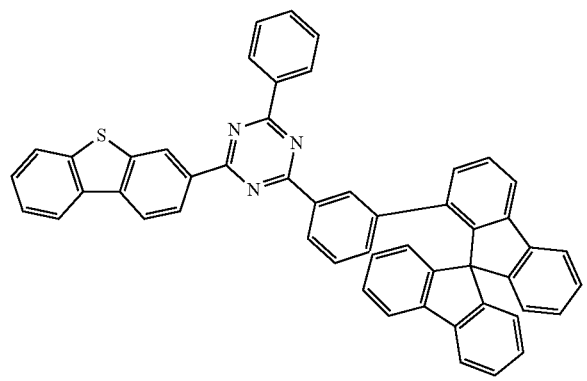
c-56
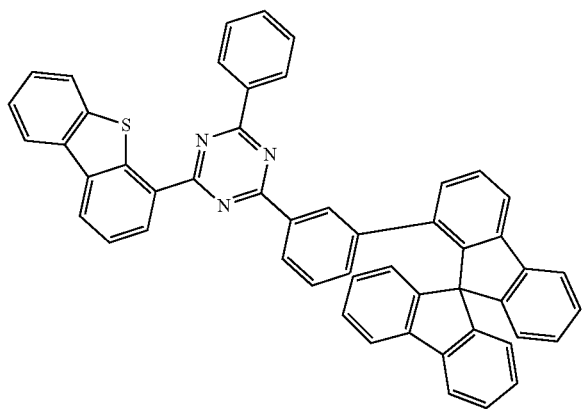
c-57
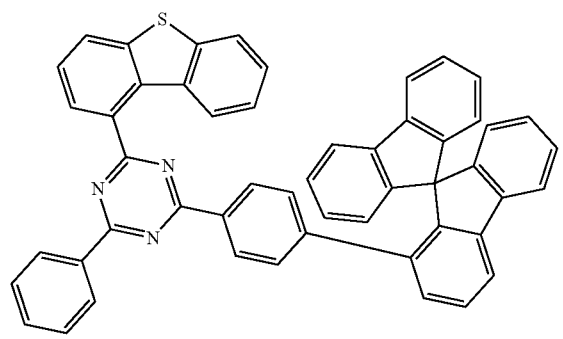
c-58
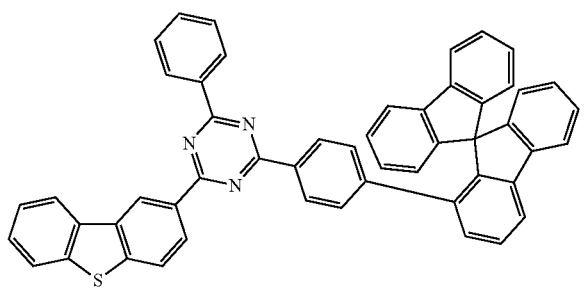

-continued
c-59
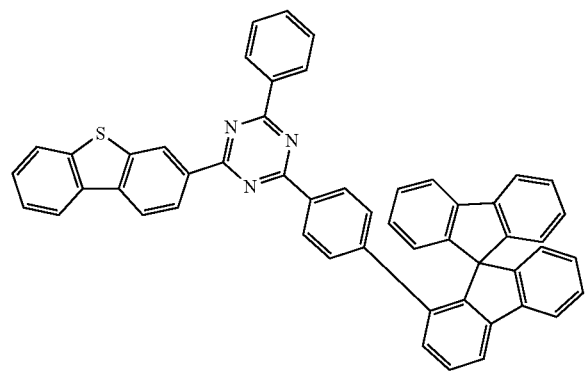
c-60
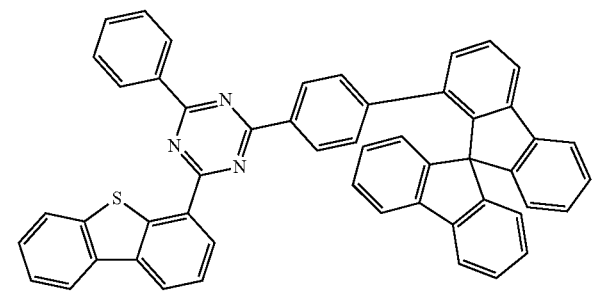
c-61
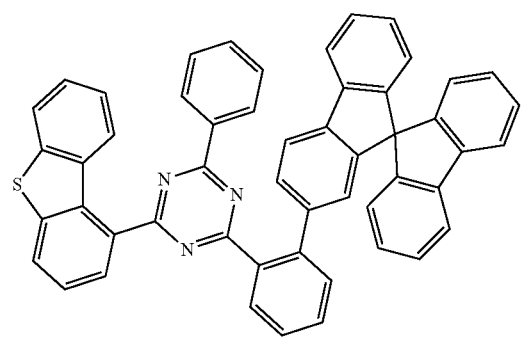
c-62
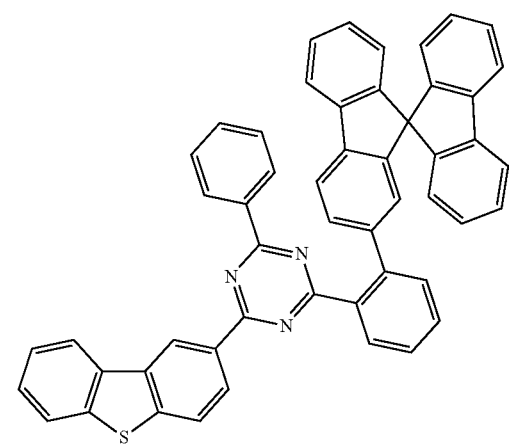
c-63
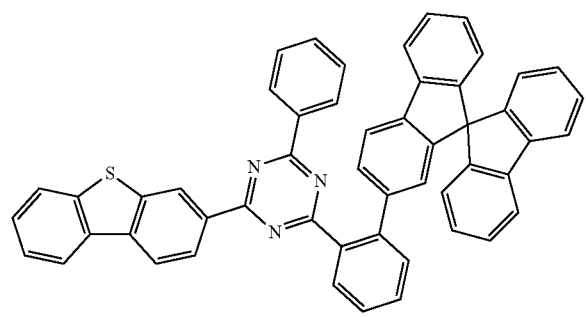
c-64
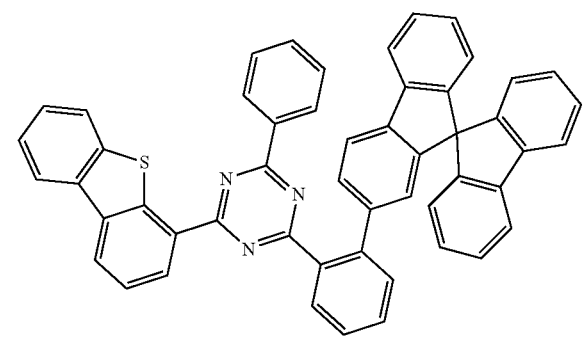
c65
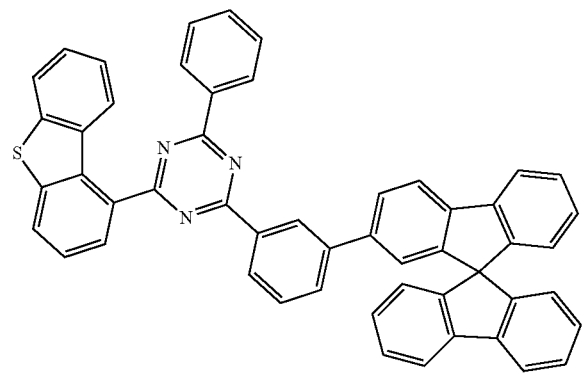
c-66
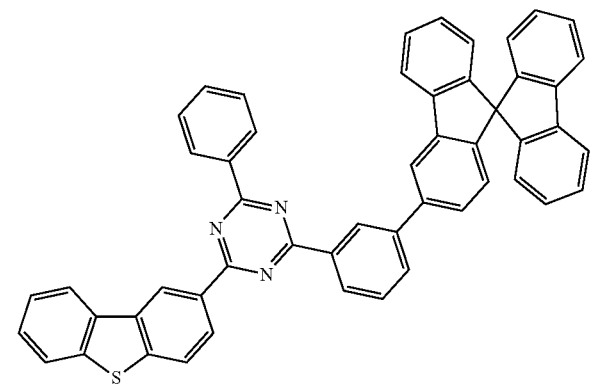

-continued
c-67
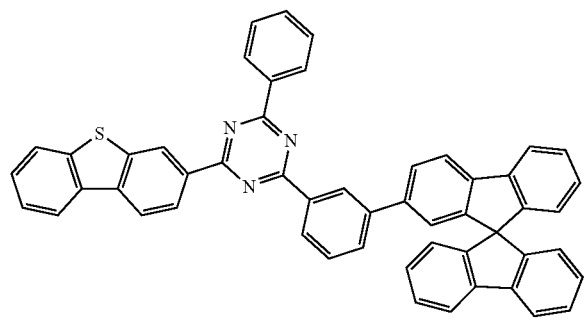
c-68
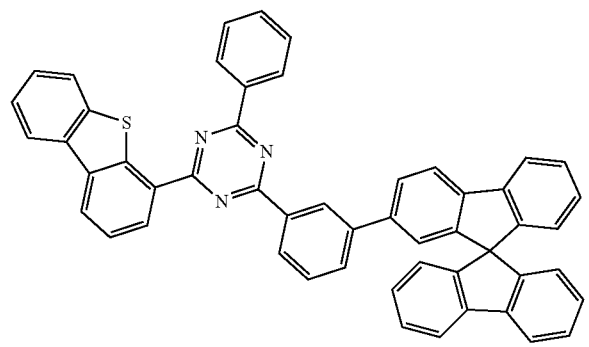
c-69
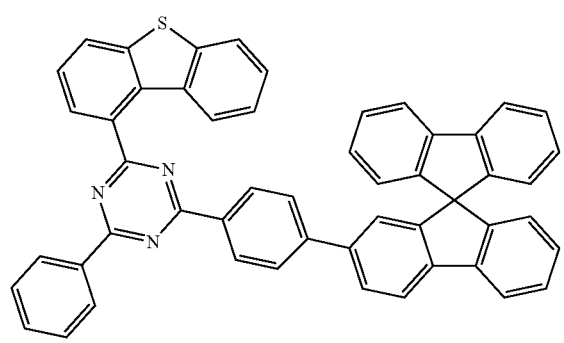
c-70
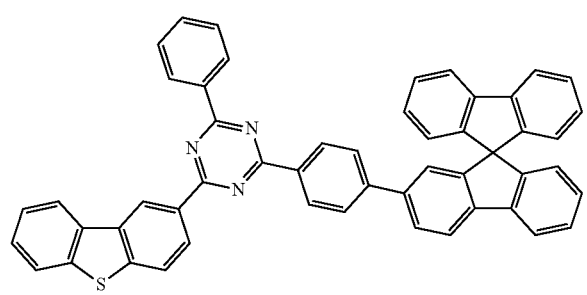
c-71
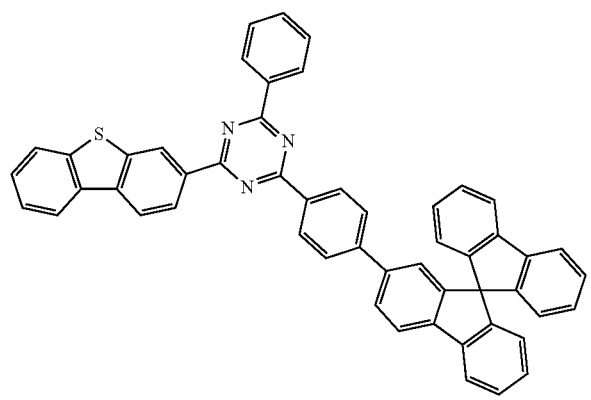
c-72
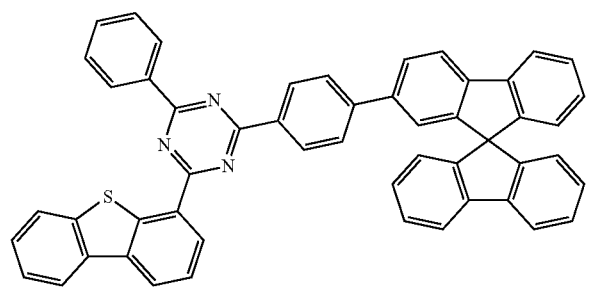
c-72
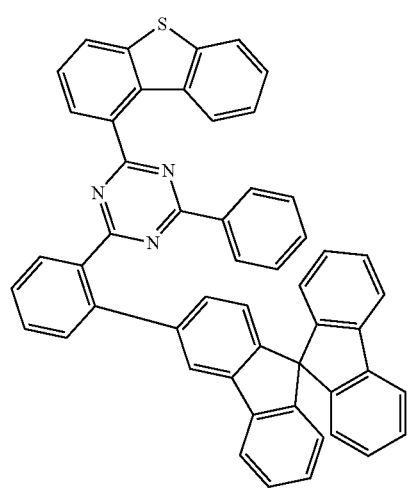
c-74
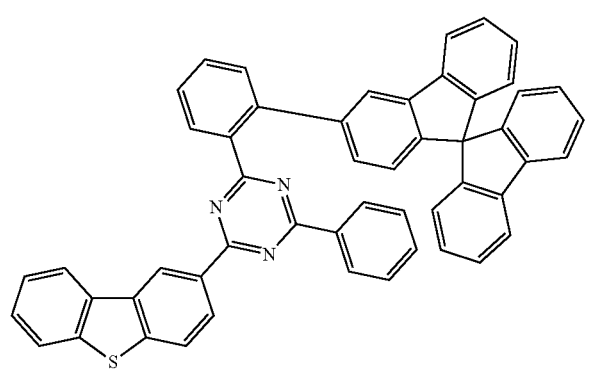

-continued
c-75
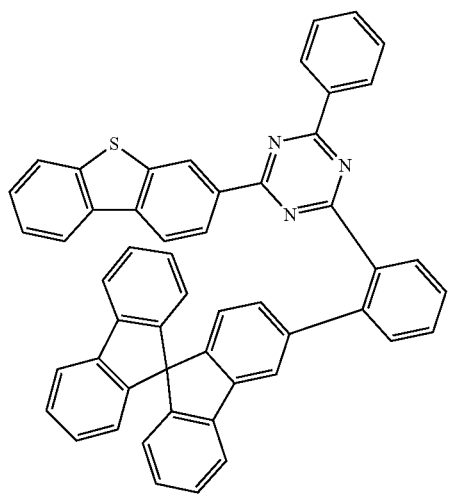
c-76
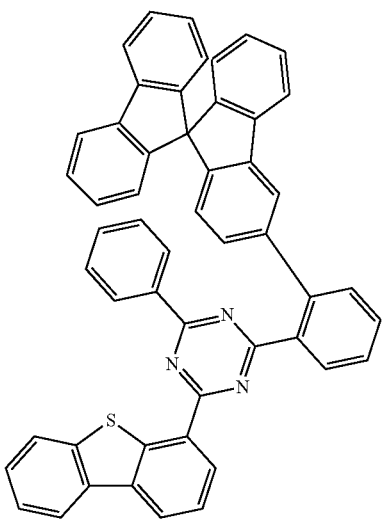
c-77
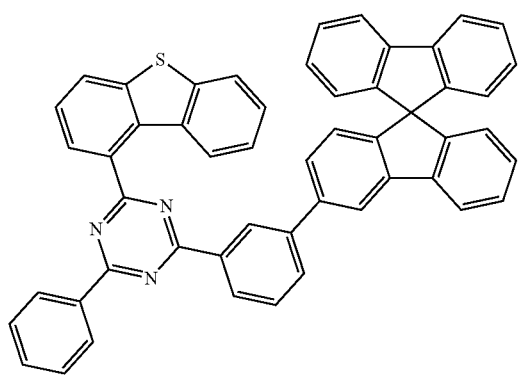
c-78
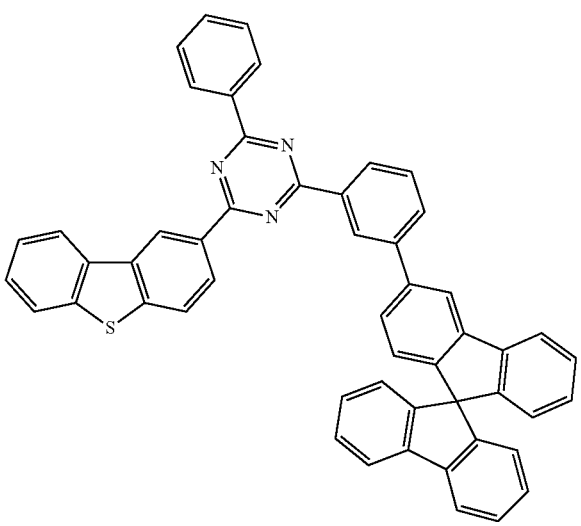
c-79
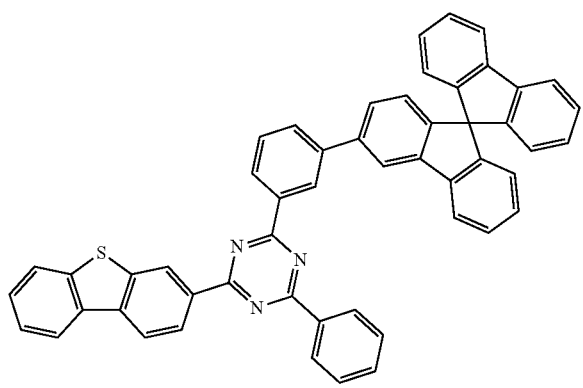
c80
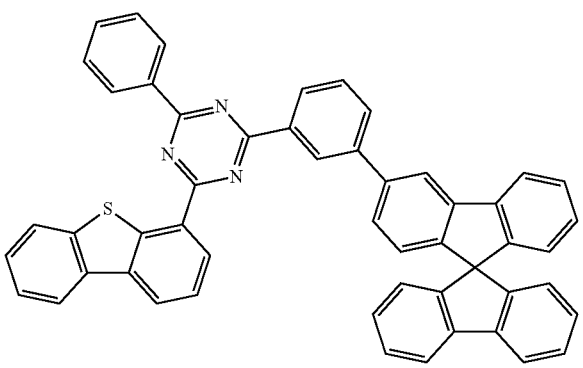

-continued
c-81
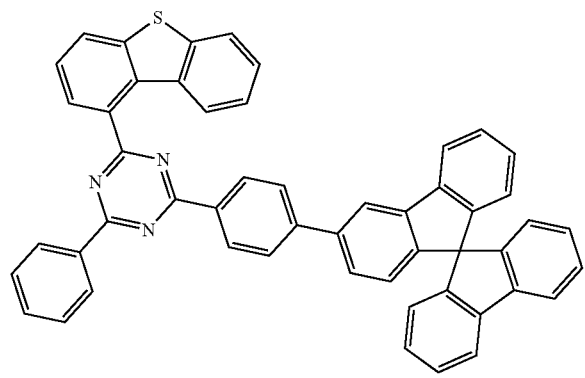
c-82
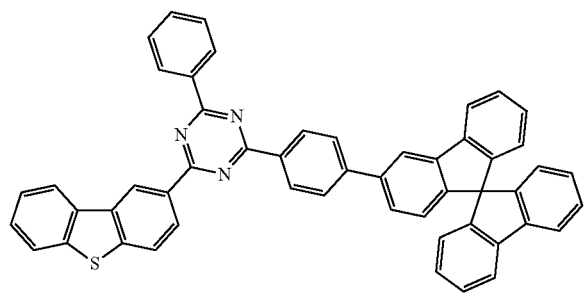
c-83
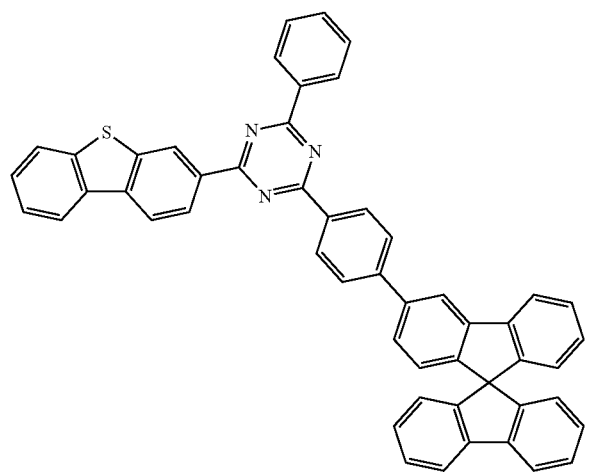
c-84
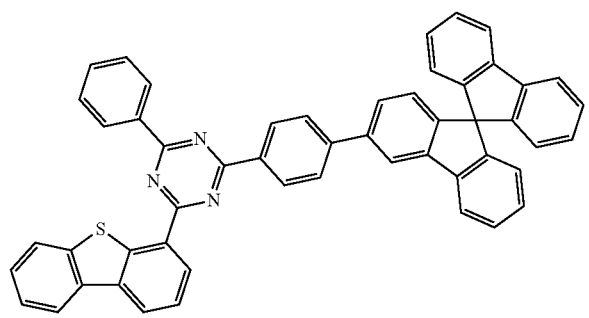
c-85
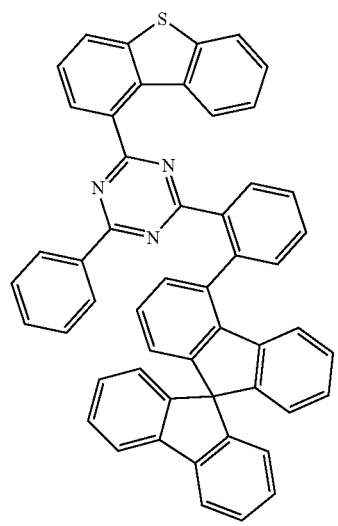
c-86
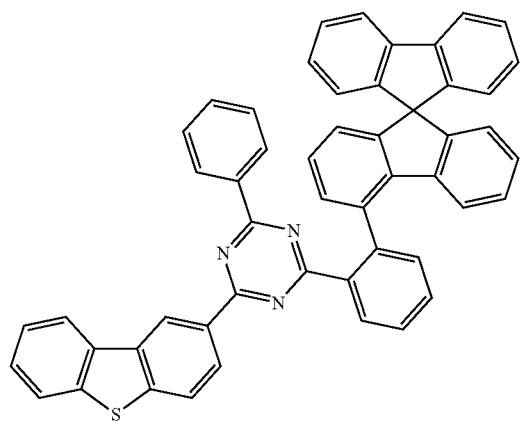

-continued
c-87
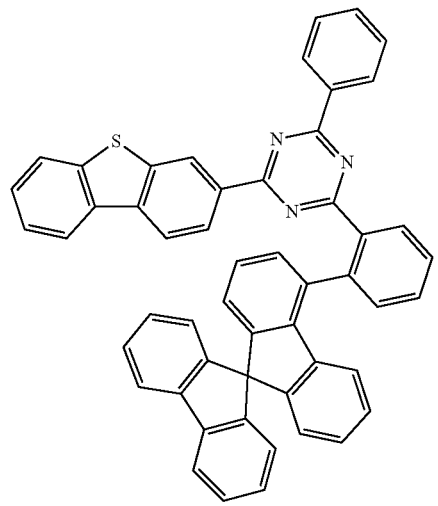
c-88
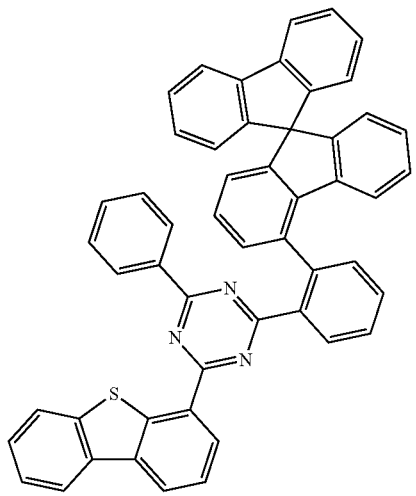
c-89
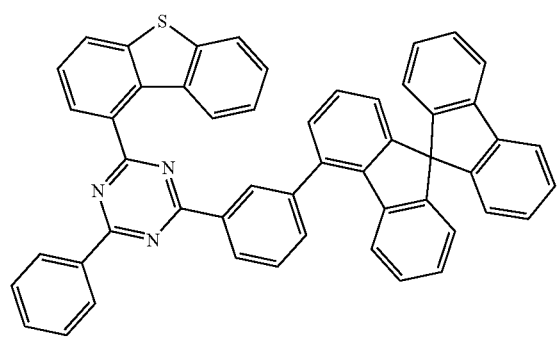
c-90
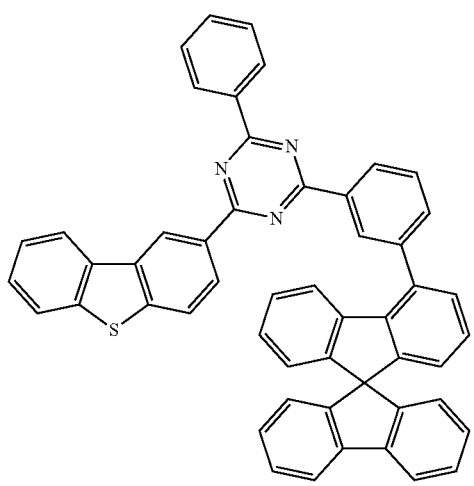
c-91
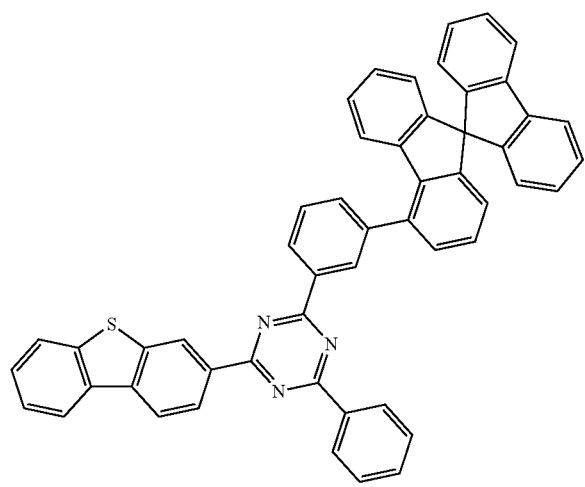
c-92
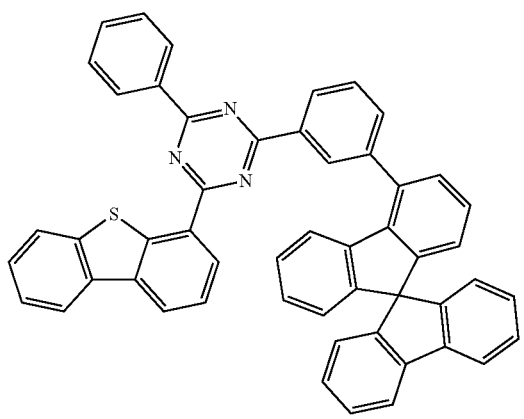

-continued
c-93
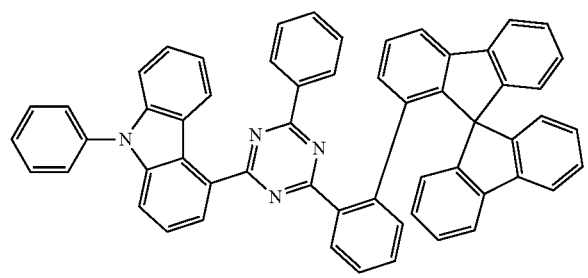
c-94
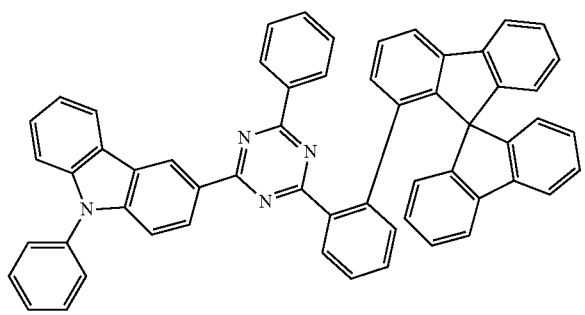
c-95
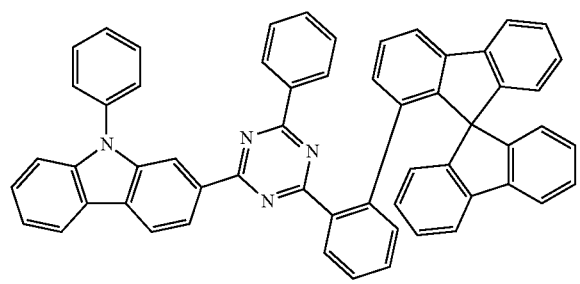
c-96
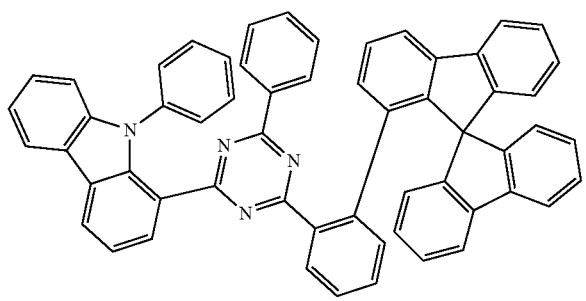
c-97
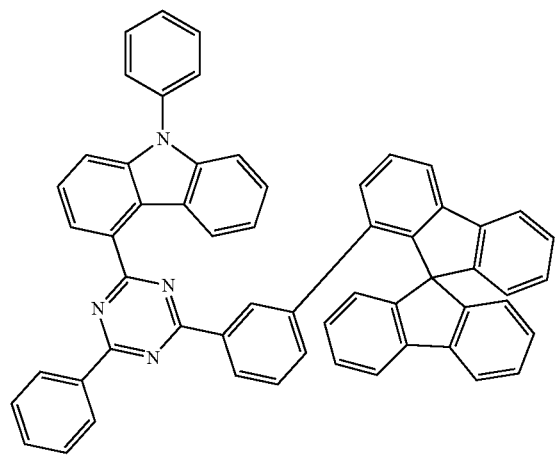
c-98
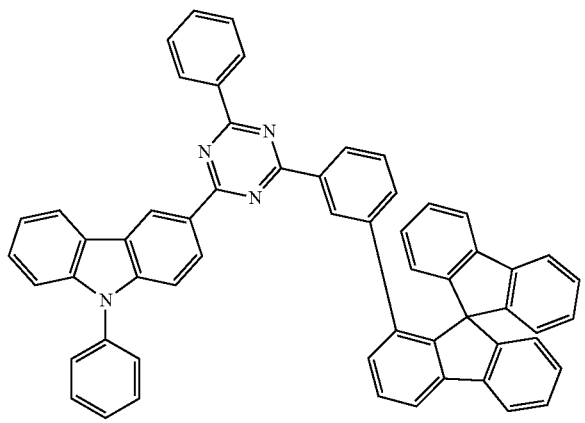
c-99
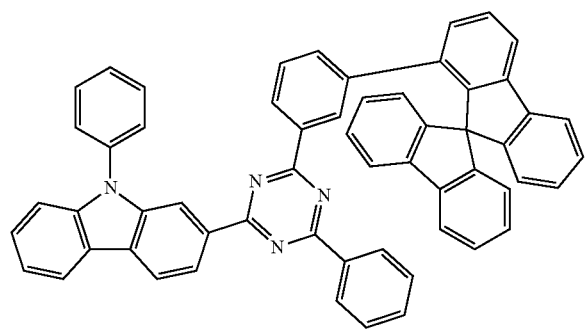
c-100
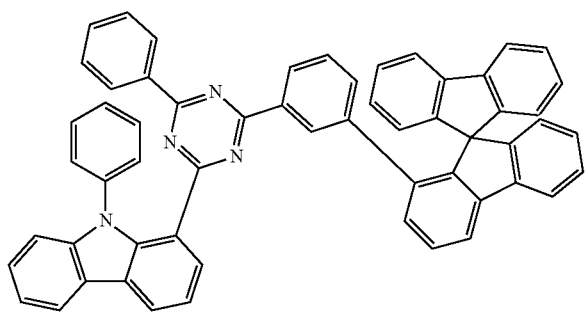

-continued
c-101
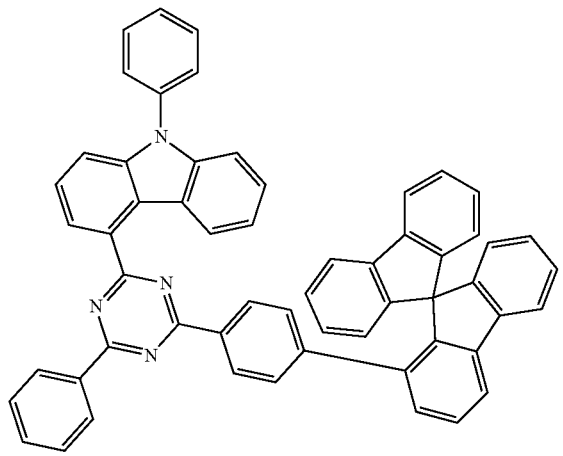
c-102
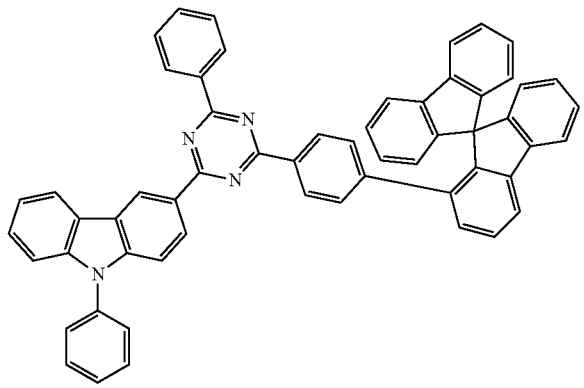
c-103
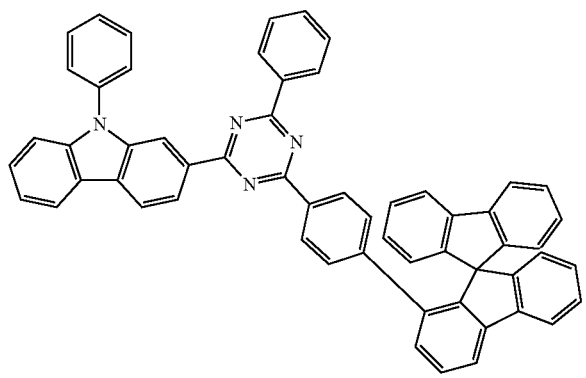
c-104
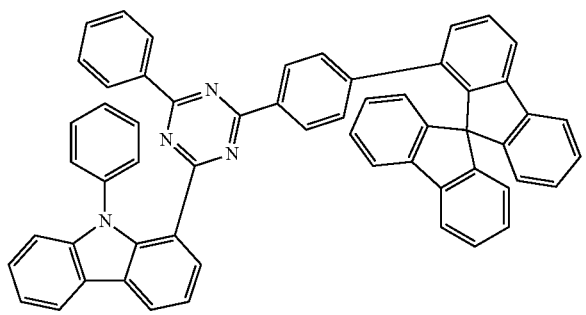
c-105
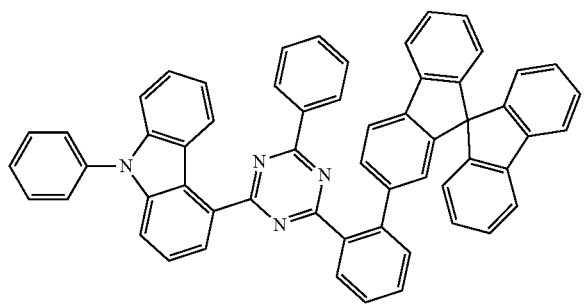
c-106
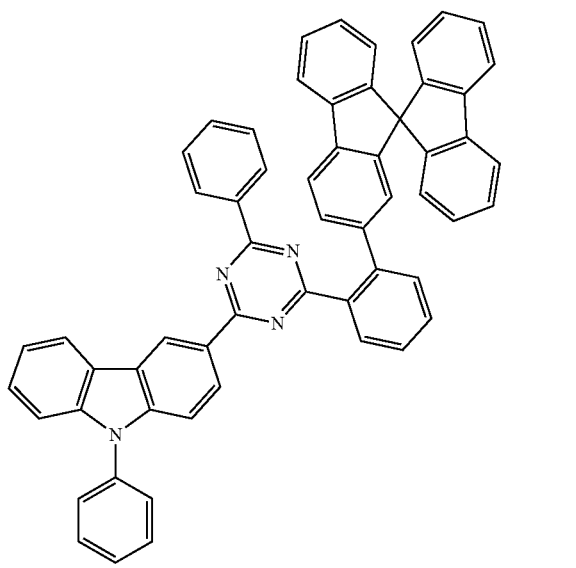

-continued
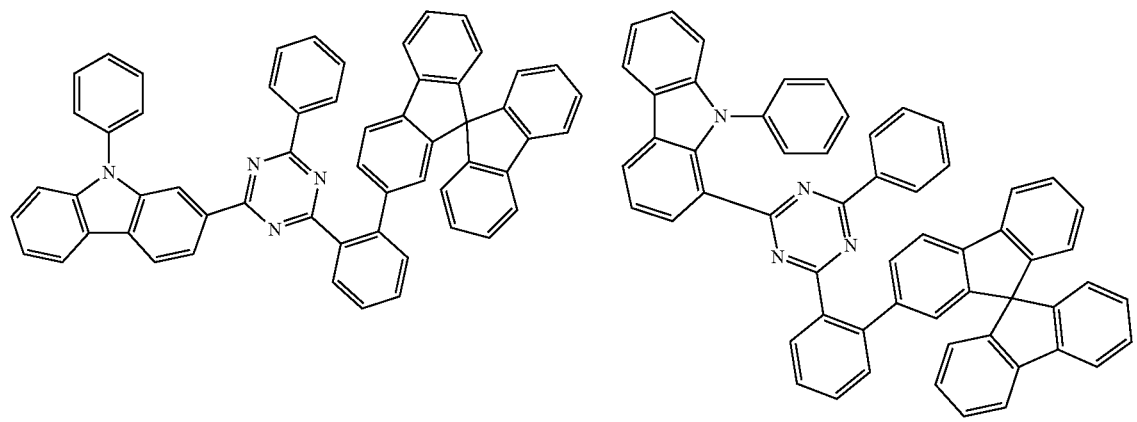
c-107
c-108
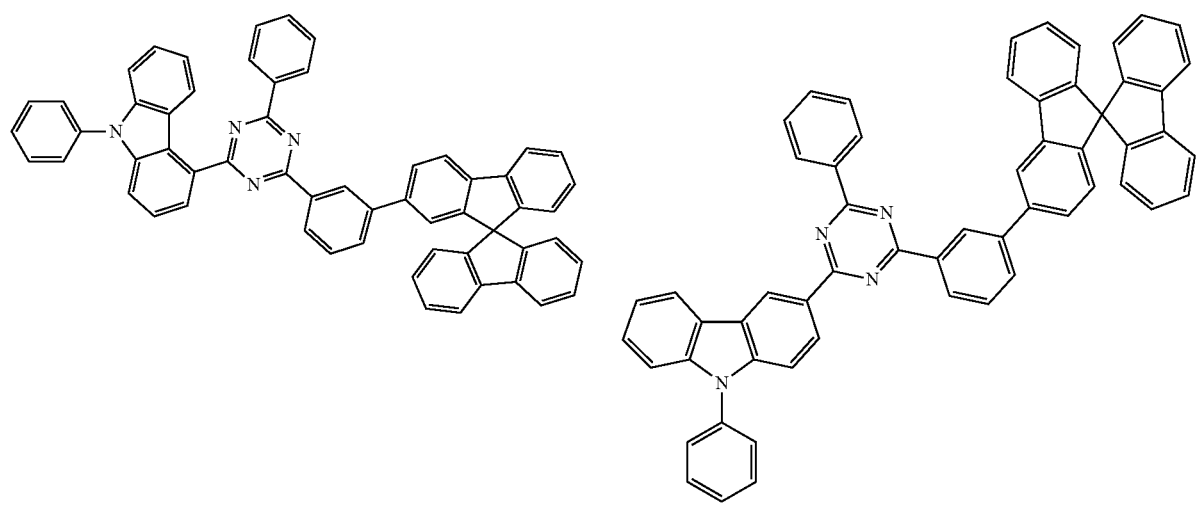
c-109
c-110
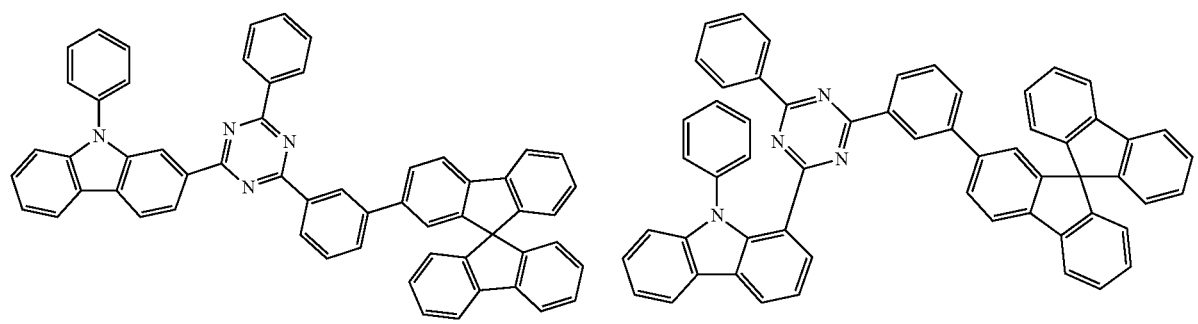
c-111
c-112

-continued
c-113
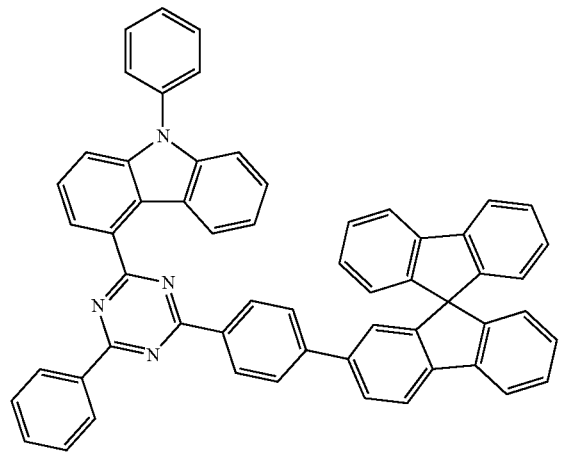
c-114
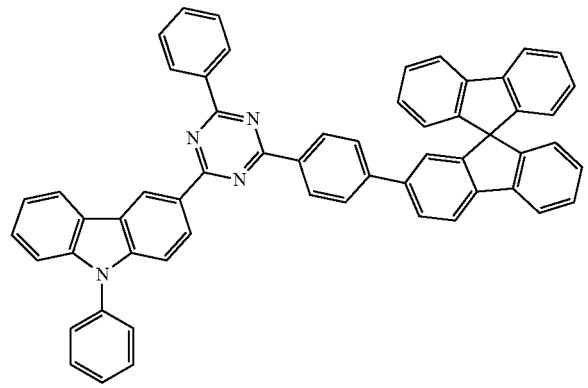
c-115
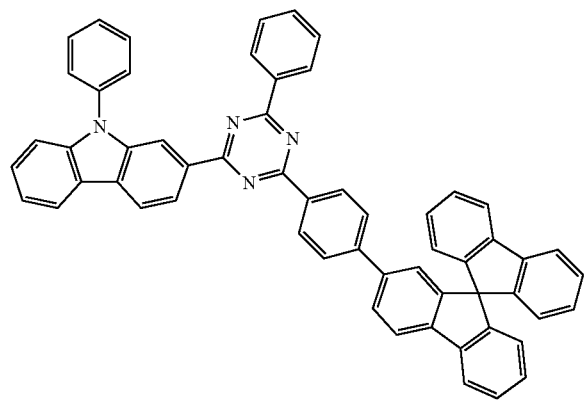
c-116
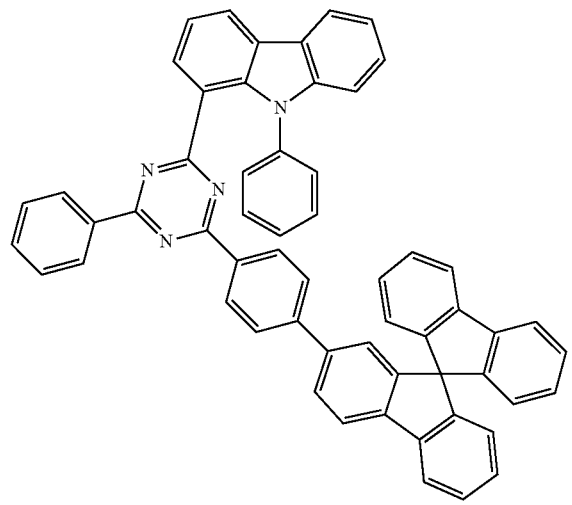
c-117
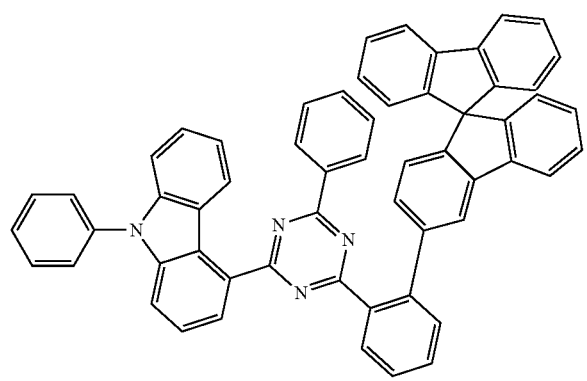
c-118
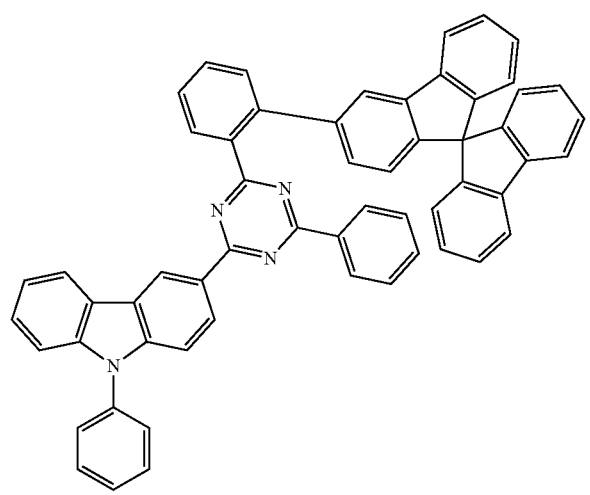

-continued
c-119
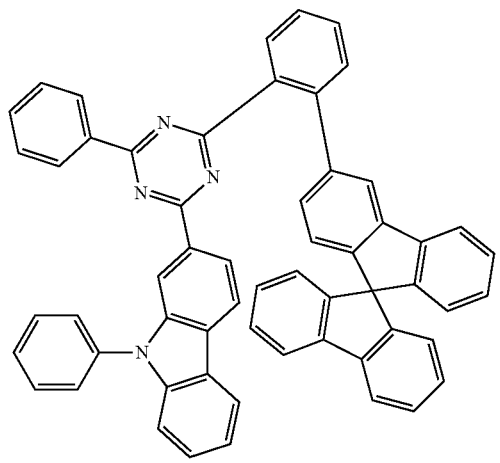
c-120
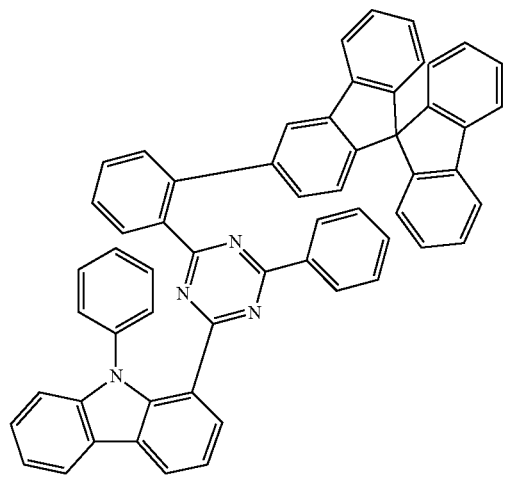
c-121
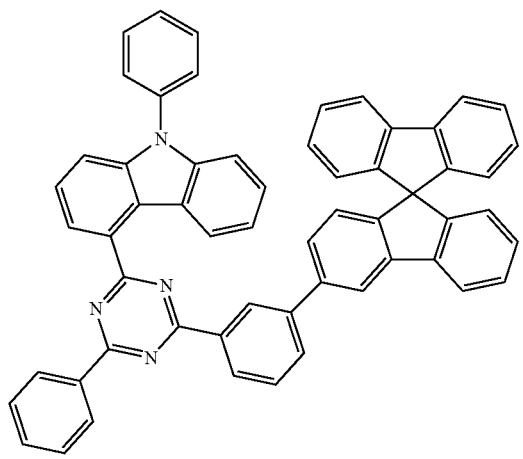
c-122
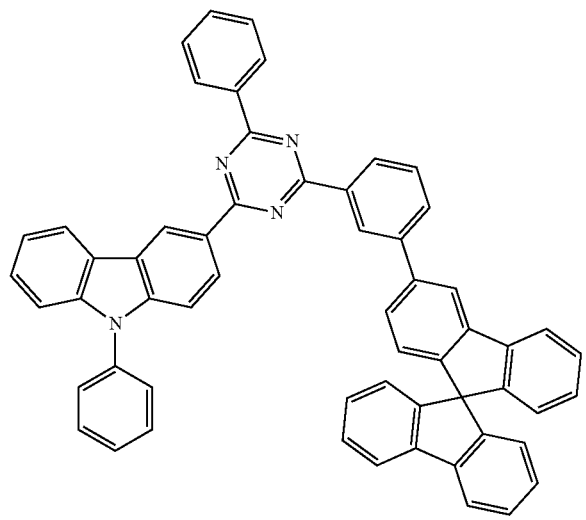
c-123
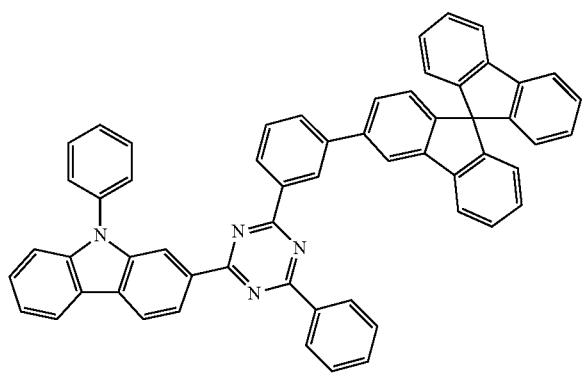
c-124
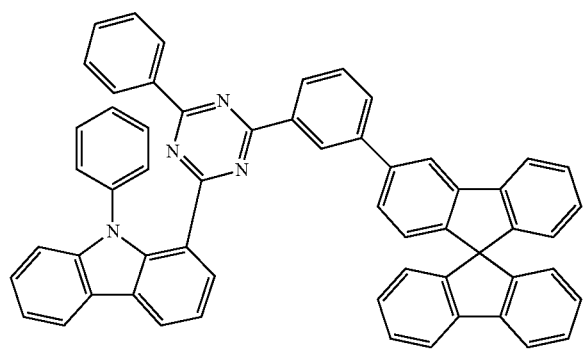

-continued
c-125
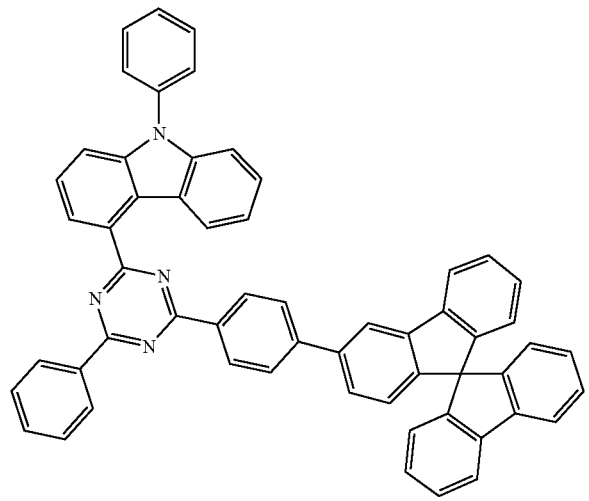
c-126
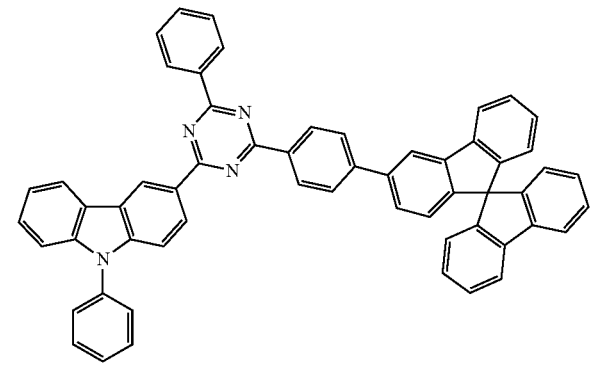
c-127
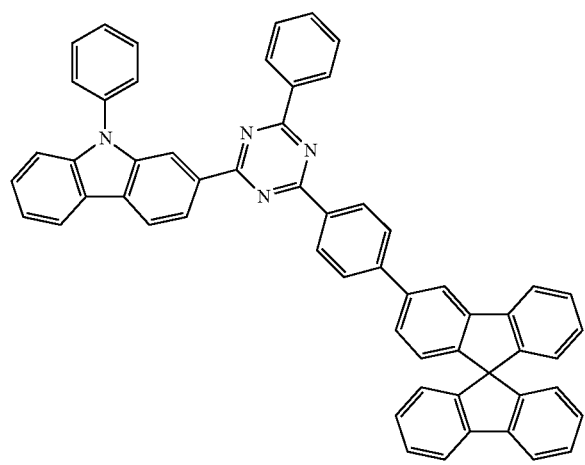
c-128
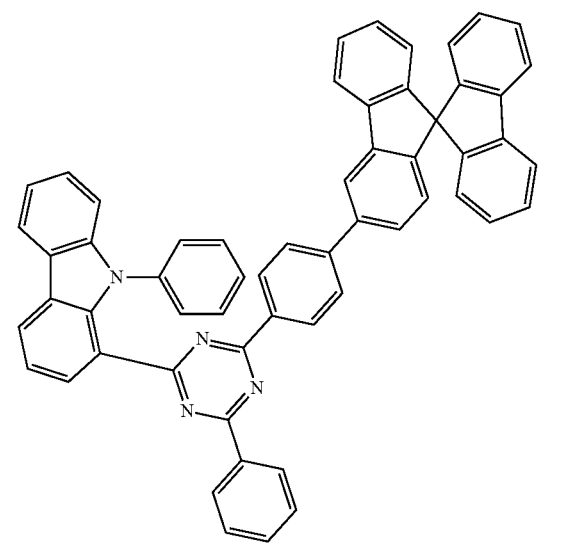
c-129
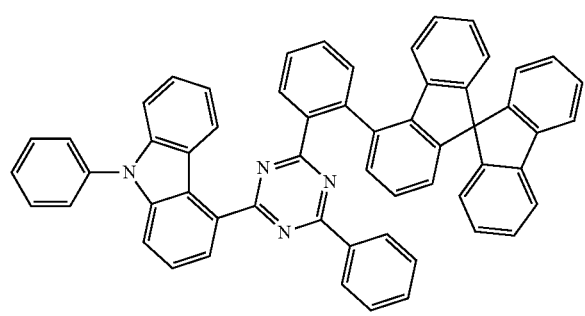
c-130
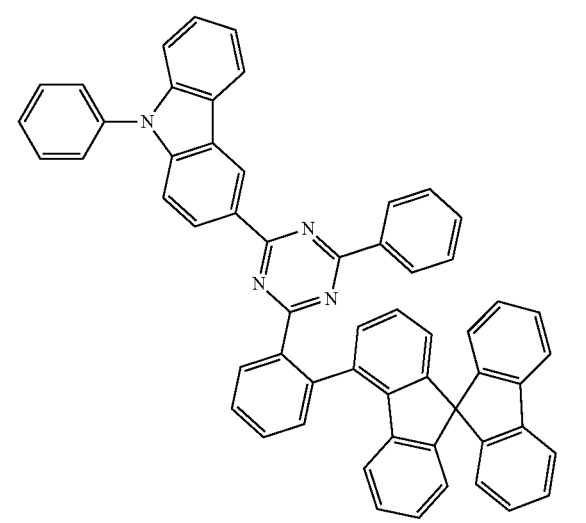

-continued
c-131
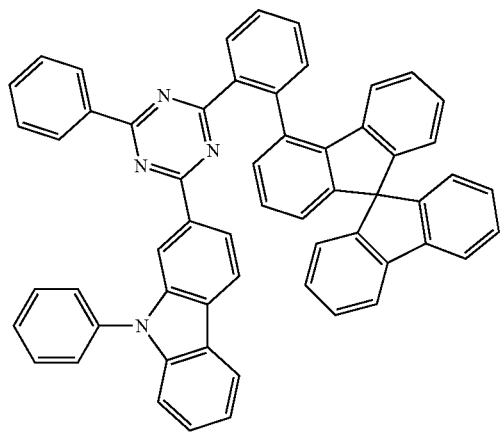
c-132
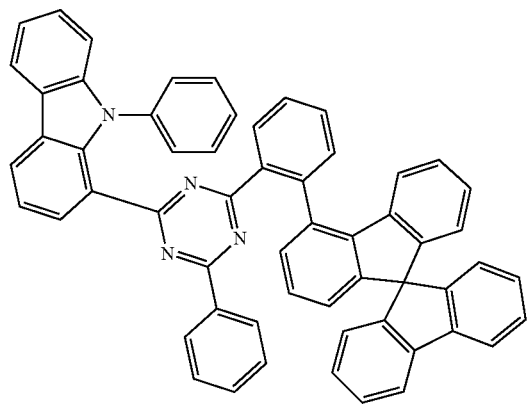
c-133
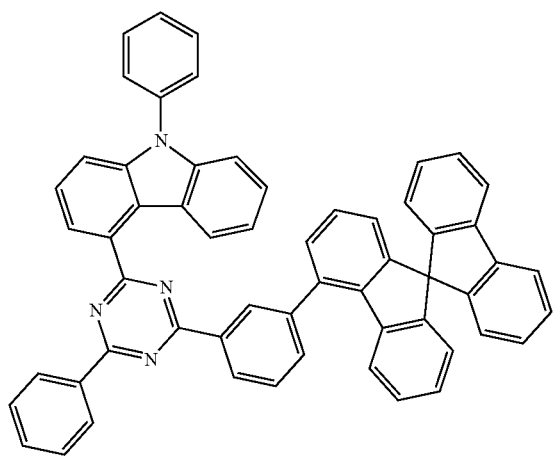
c-134
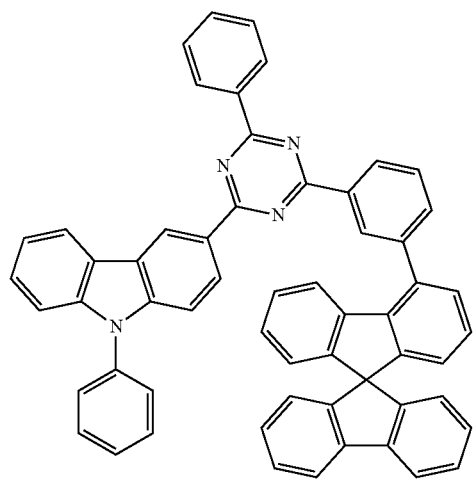
c-135
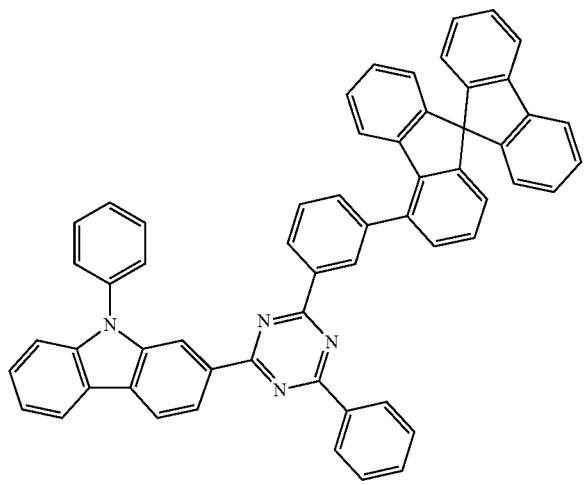
c-136
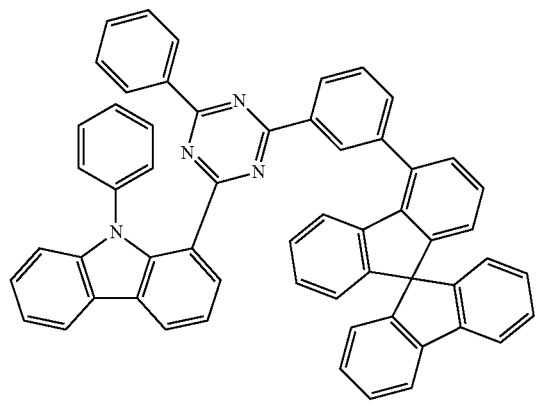

-continued
c-137
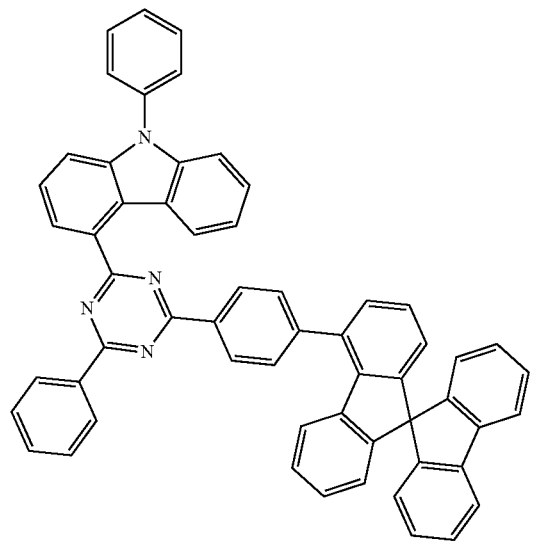
c-138
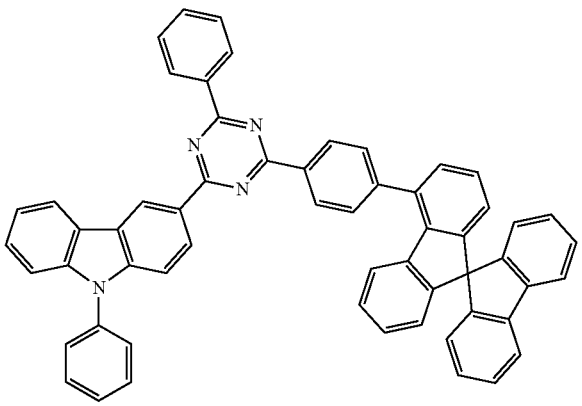
c-139
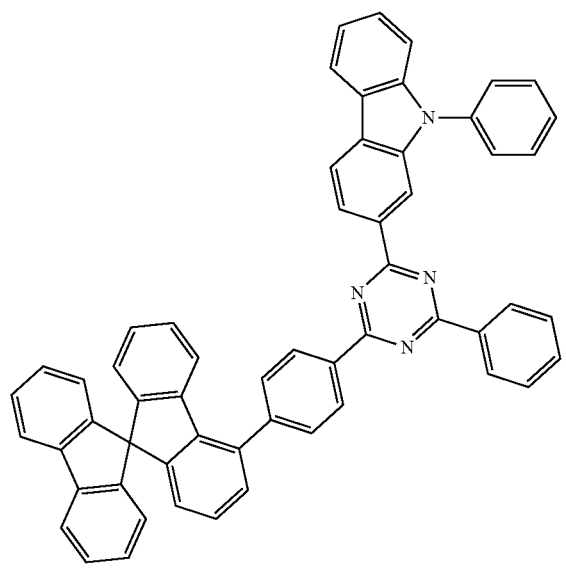
c-140
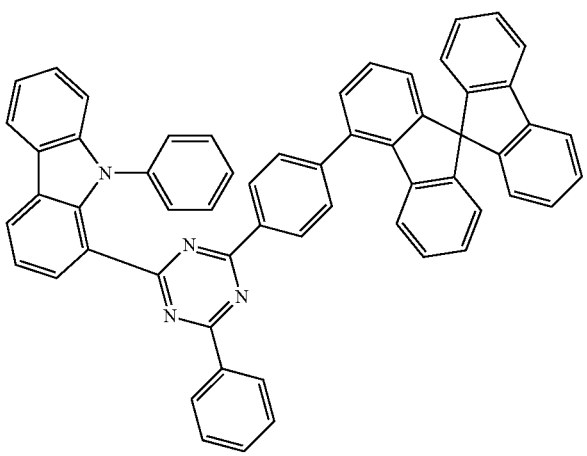
c-141
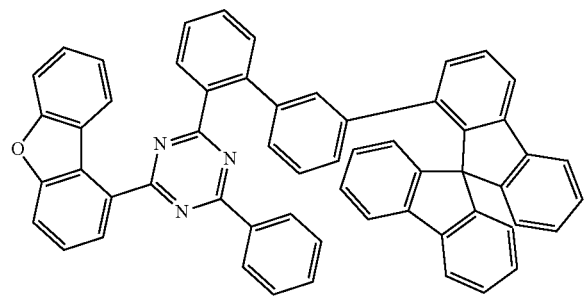
c-142
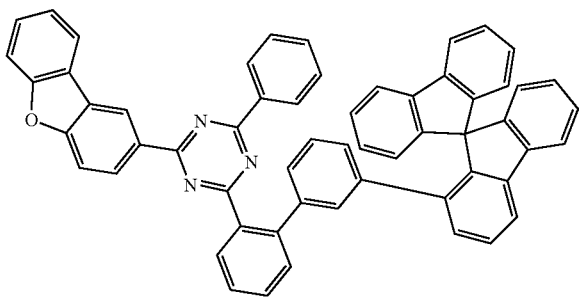

-continued
c-143
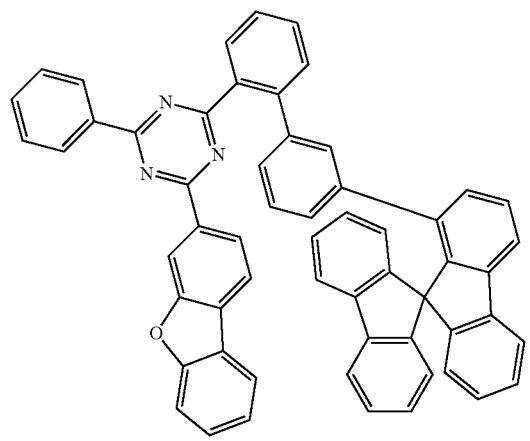
c-144
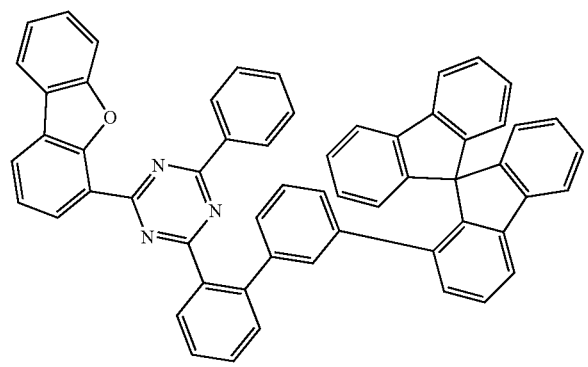
c-145
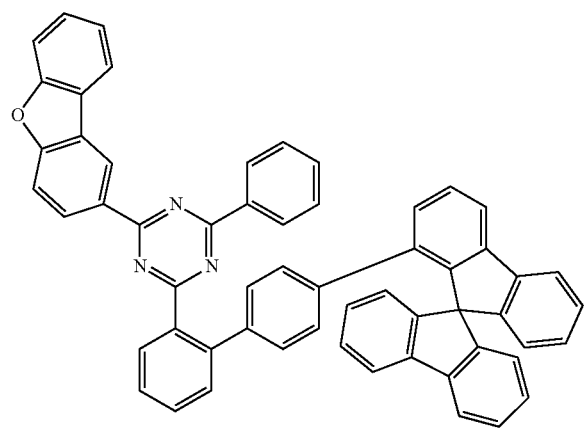
c-146
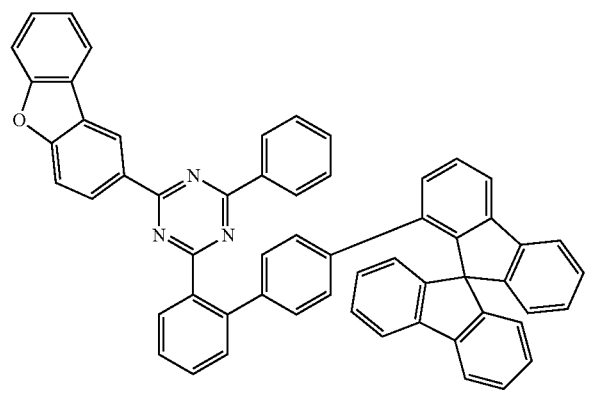
c-147
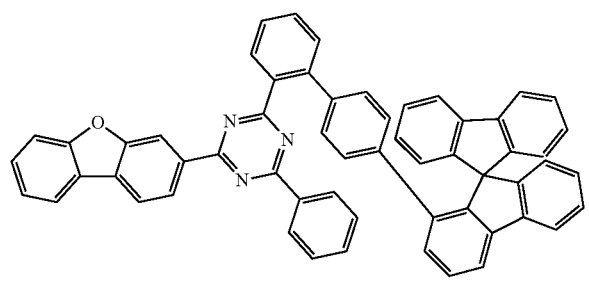
c-148
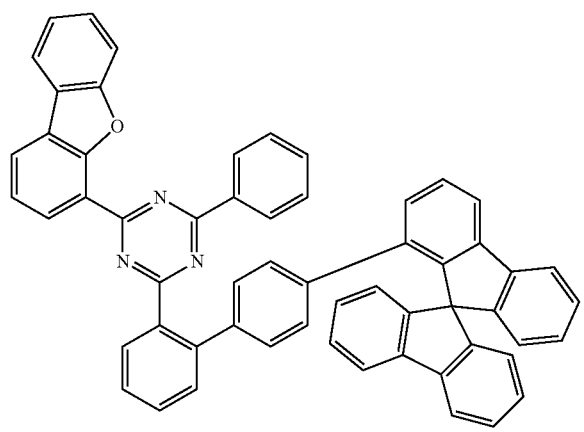

-continued
c-149
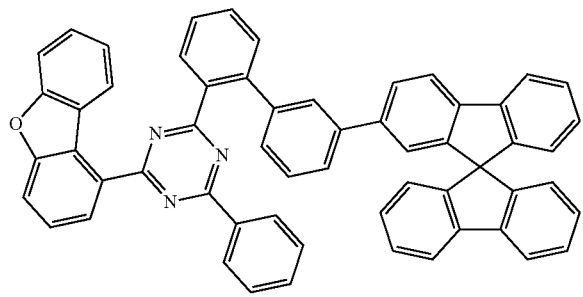
c-150
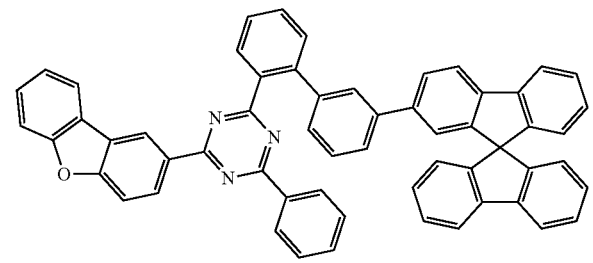
c-151
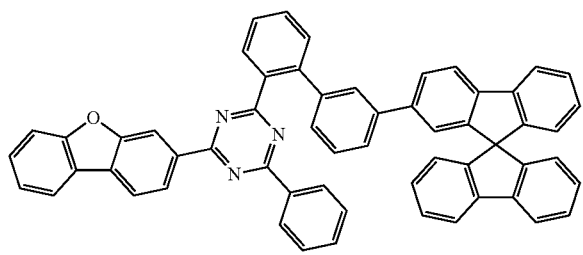
c-152
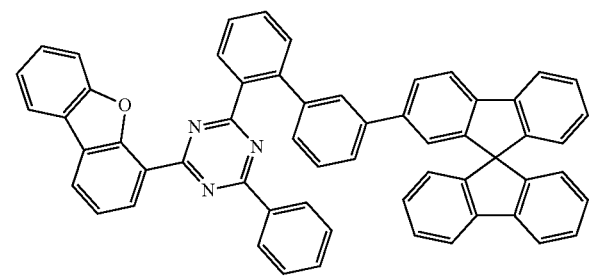
c-153
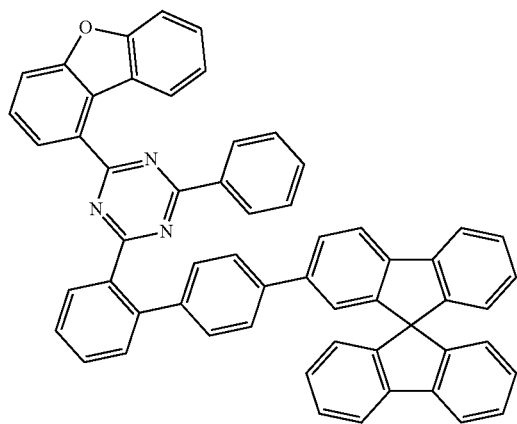
c-154
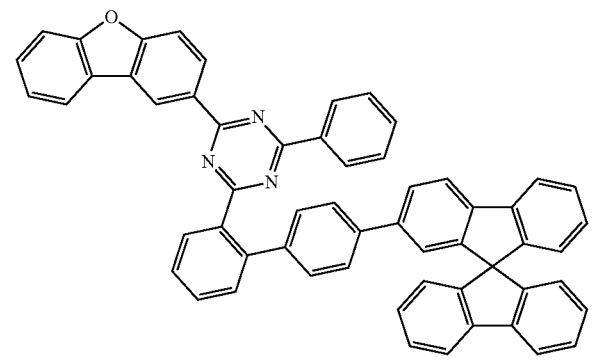
c-155
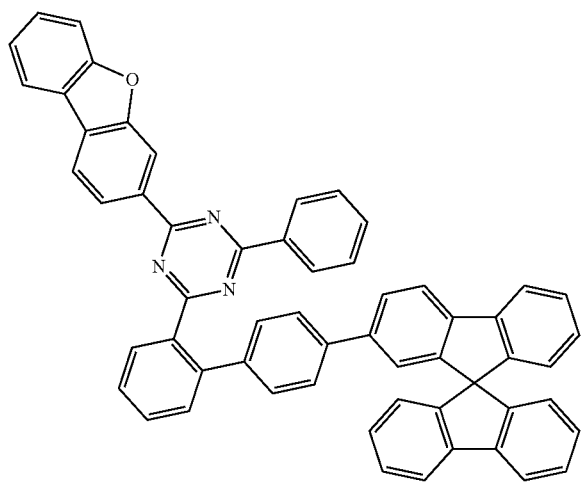
c-156
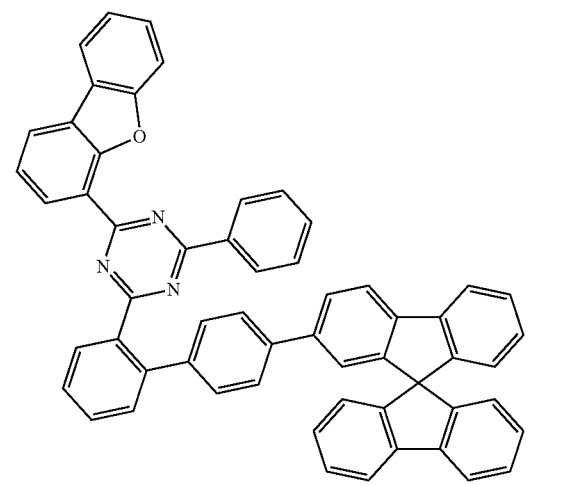

-continued
c-157
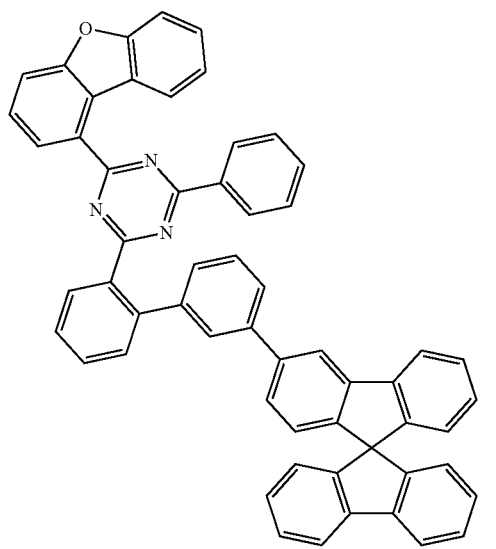
c-158
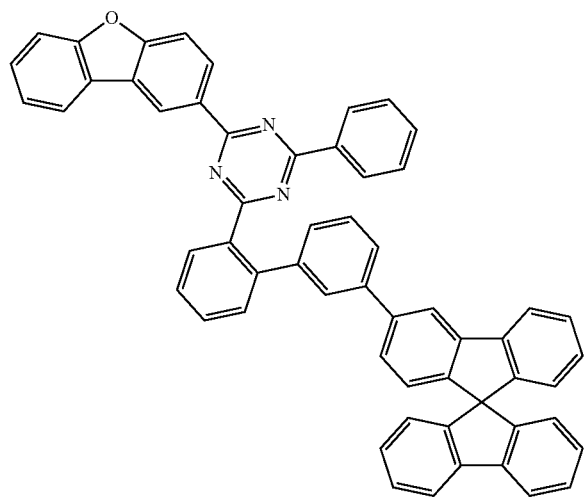
c-159
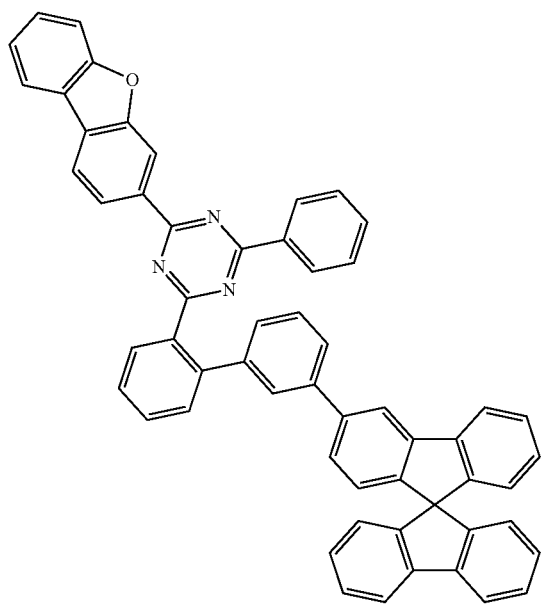
c-160
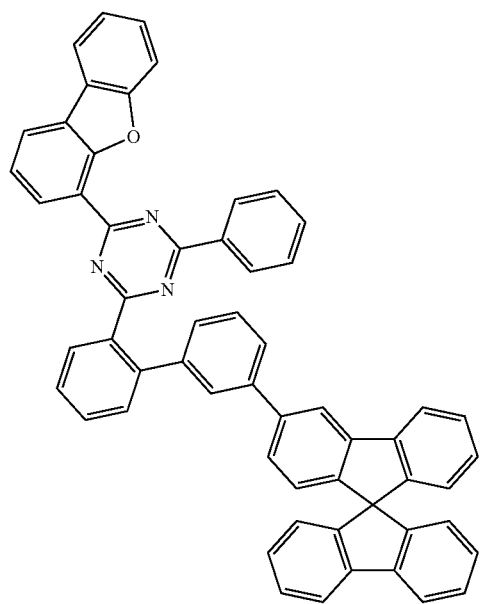

-continued
c-161
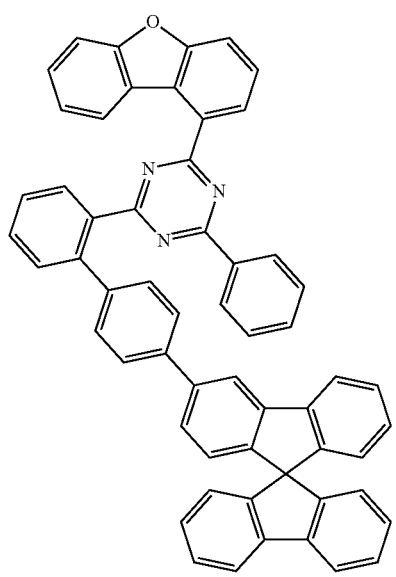
c-162
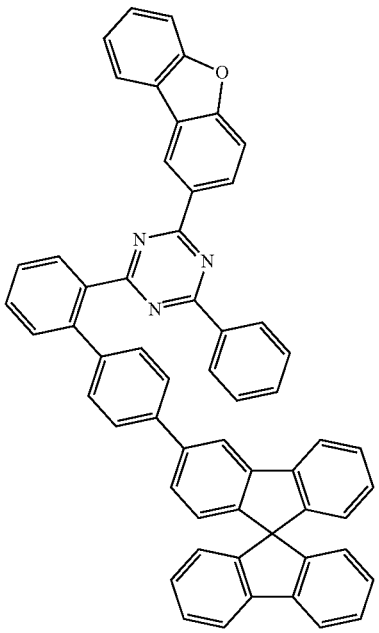
c-163
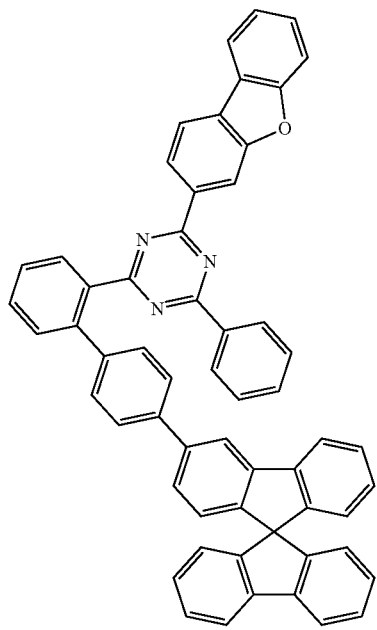
c-164
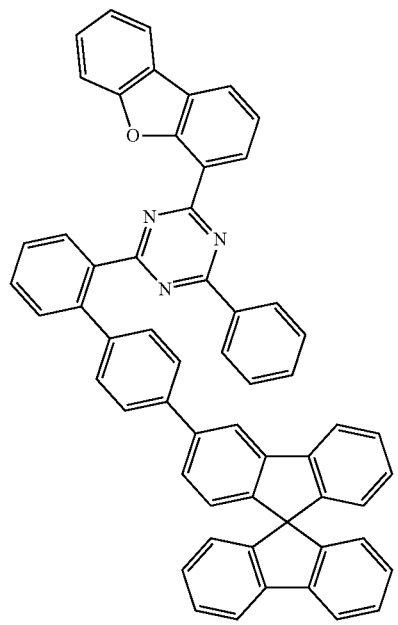
c-165
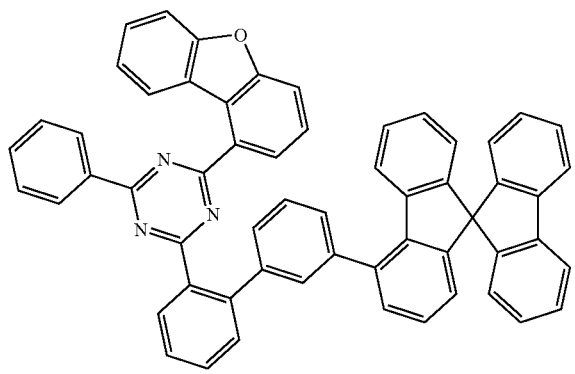
c-166
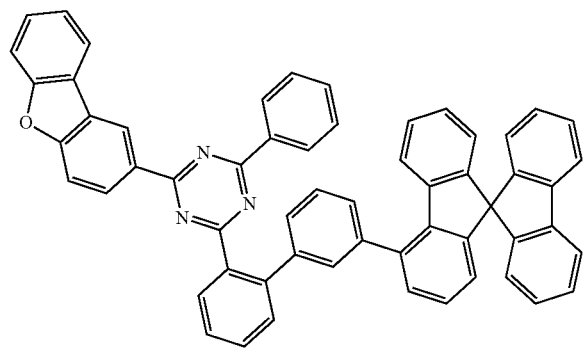

-continued
c-167
c-168
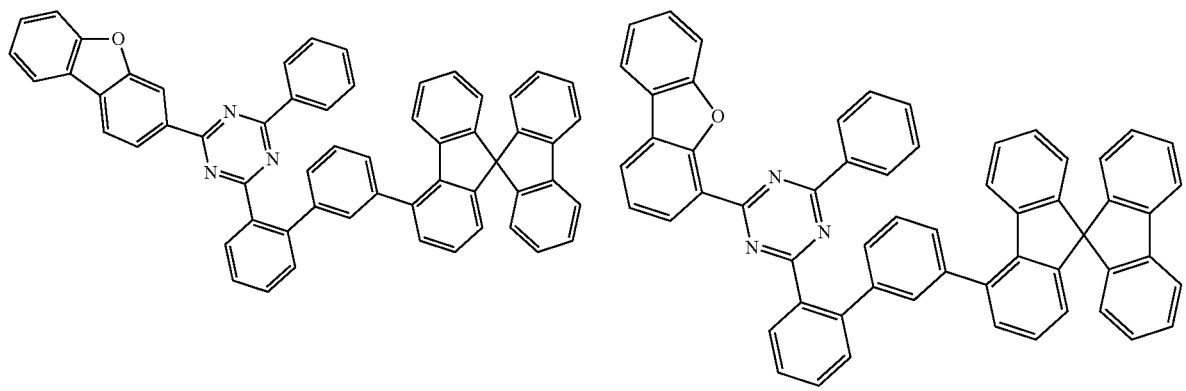
c-169
c-170
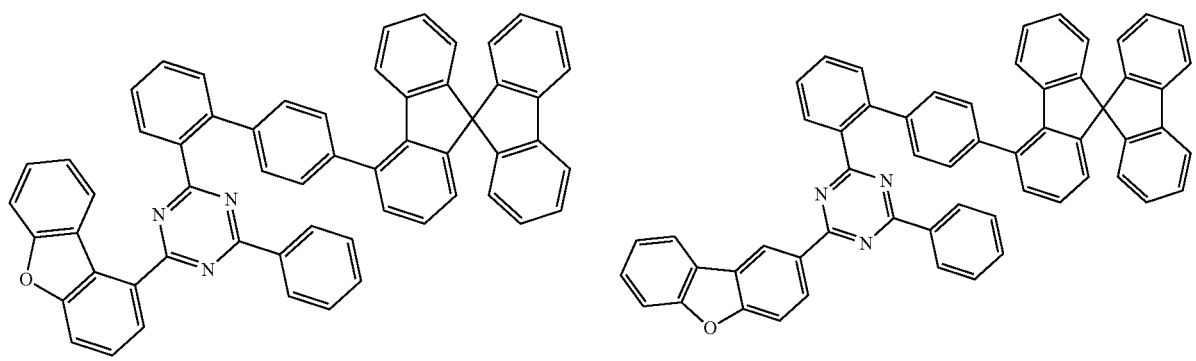
c-171
c-172

-continued
c-173
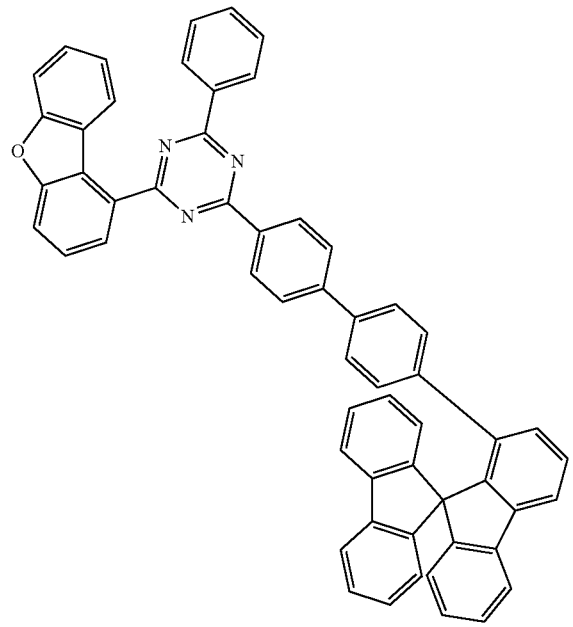
c-174
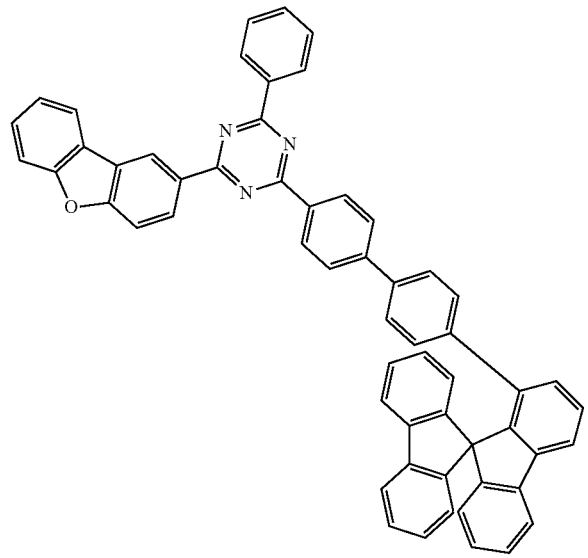
c-175
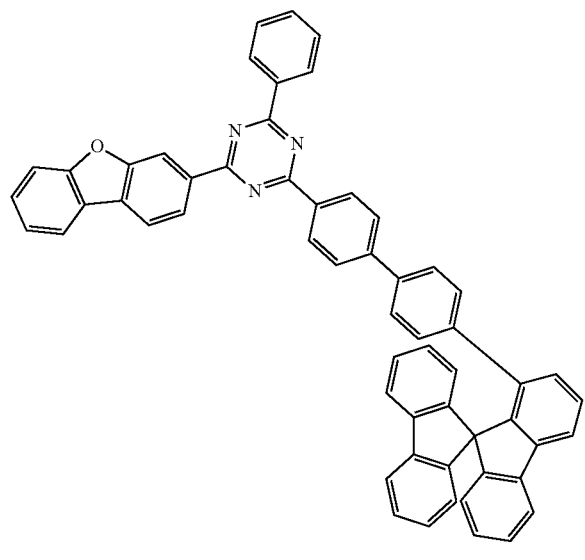
c-176
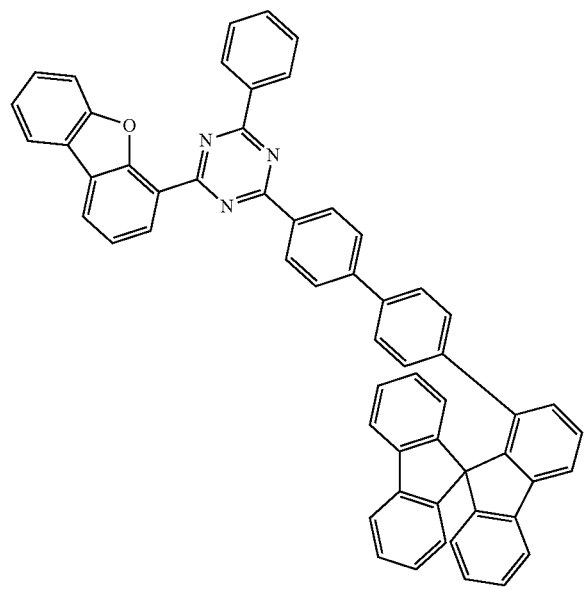

-continued
c-177
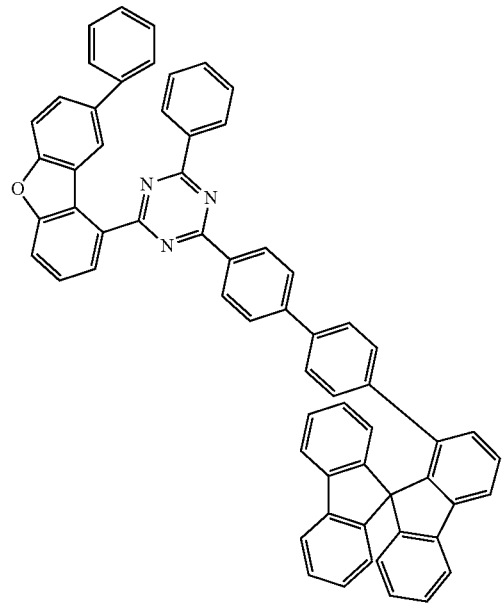
c-178
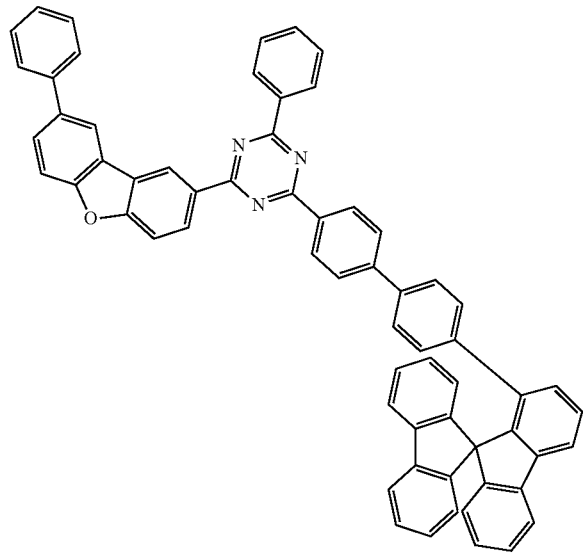
c-179
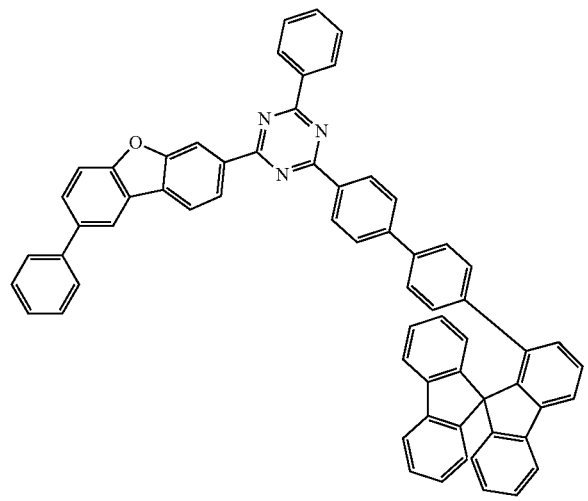
c-180
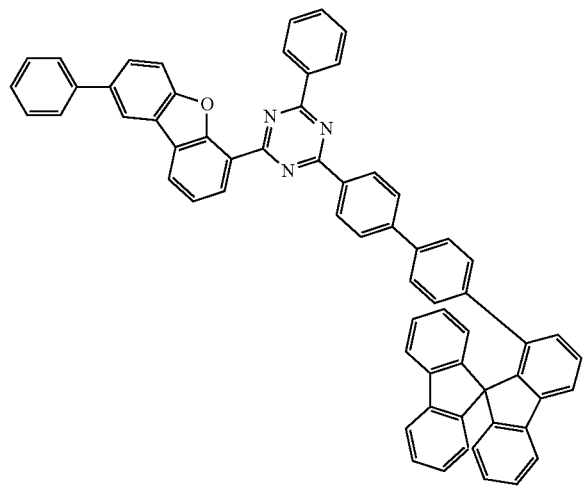
c-181
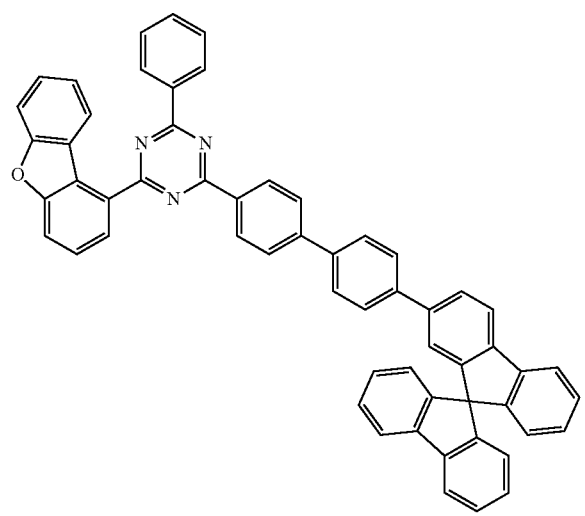
c-182
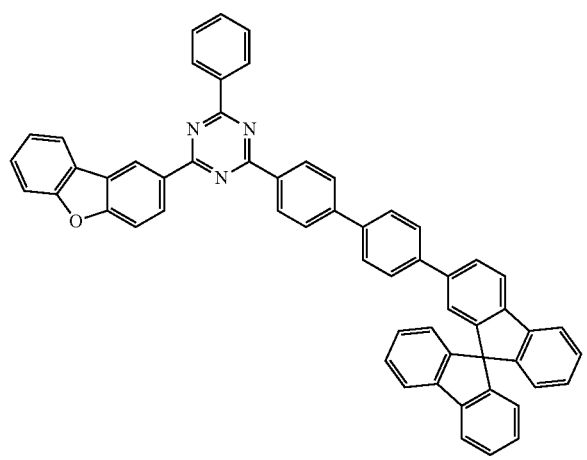

-continued
c-183
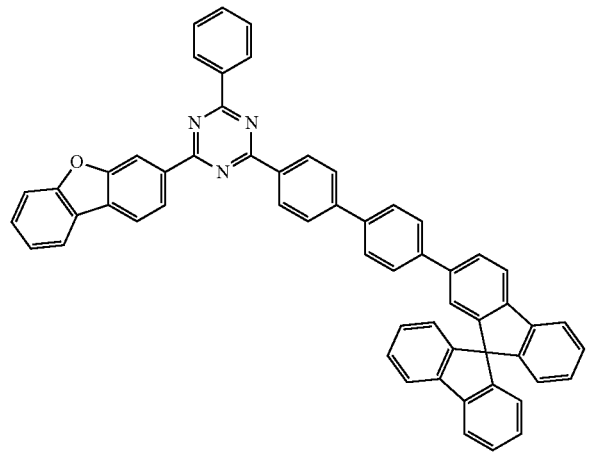
c-184
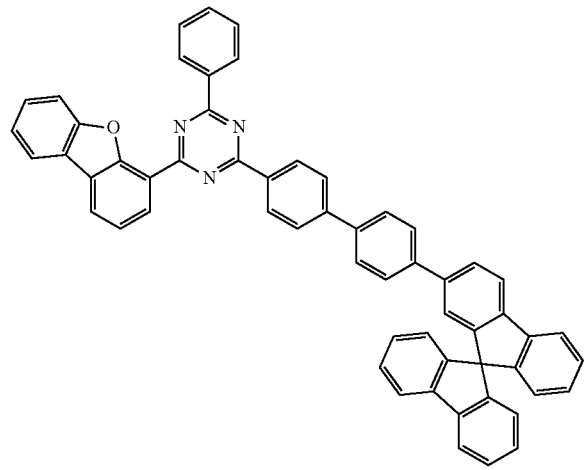
c-185
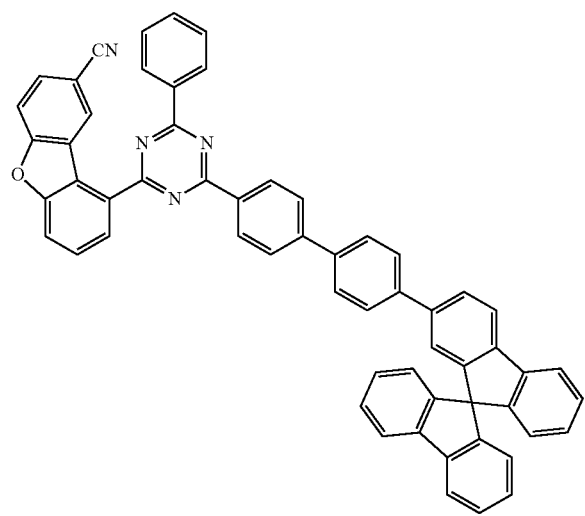
c-186
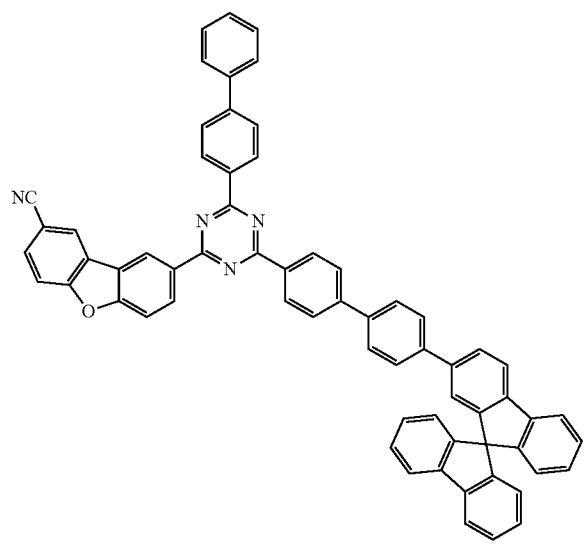

c-187
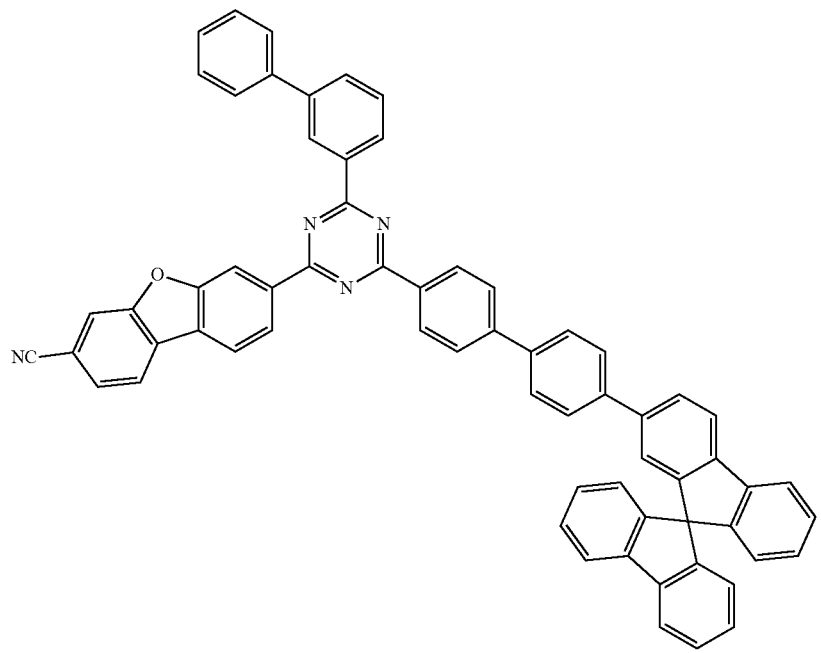
c-188
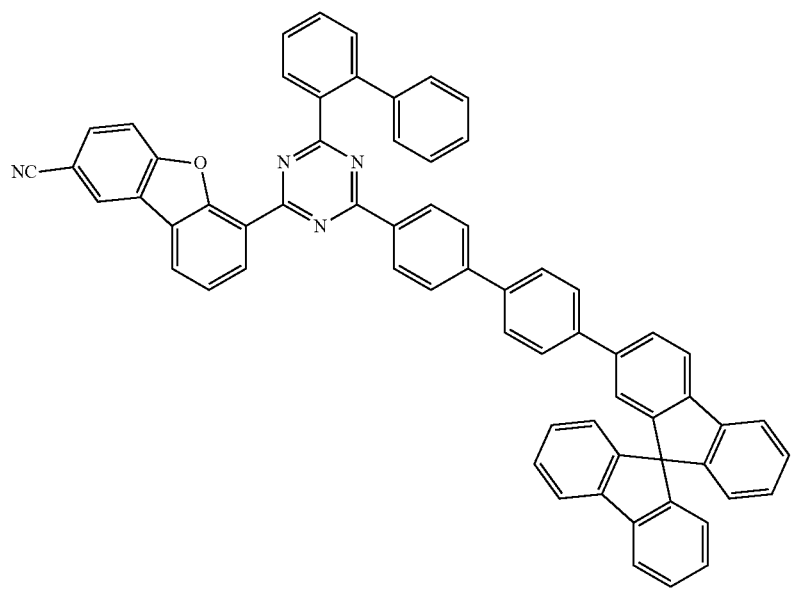

-continued
c-189
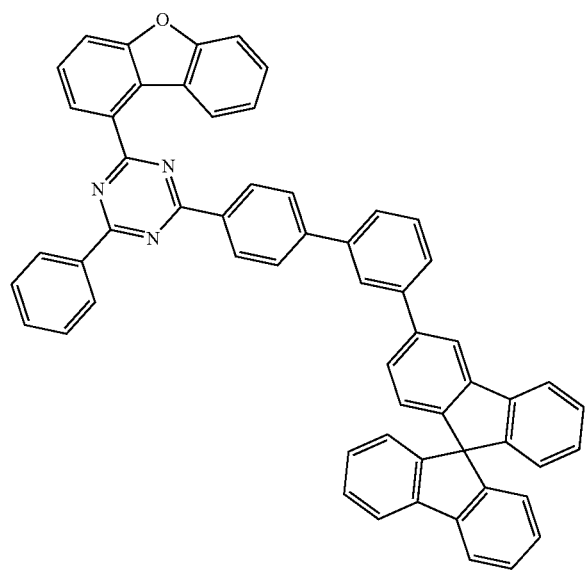
c-190
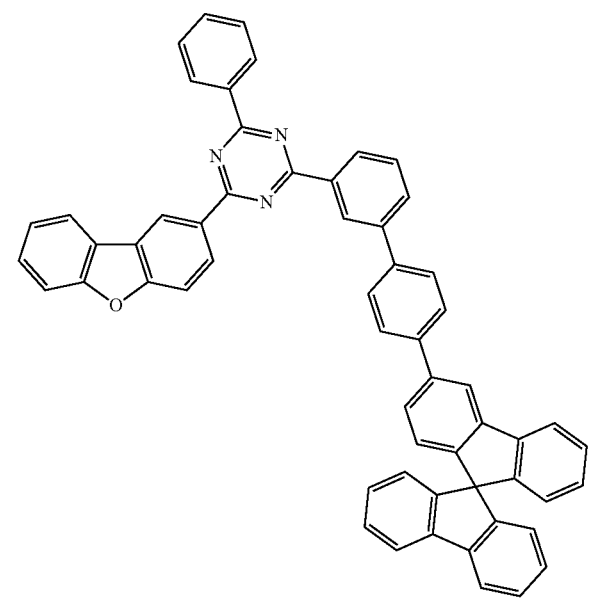
c-191
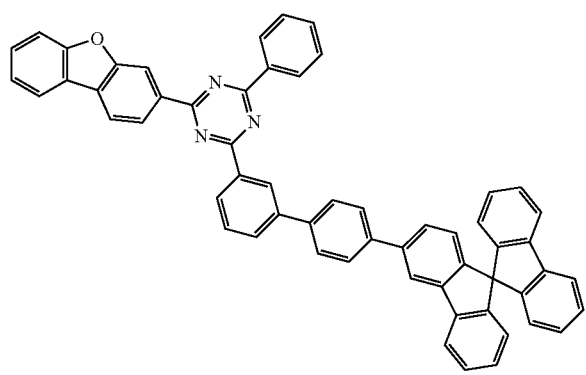
c-192
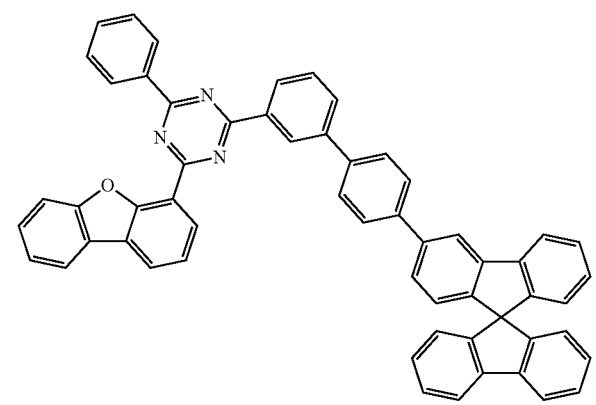
c-193
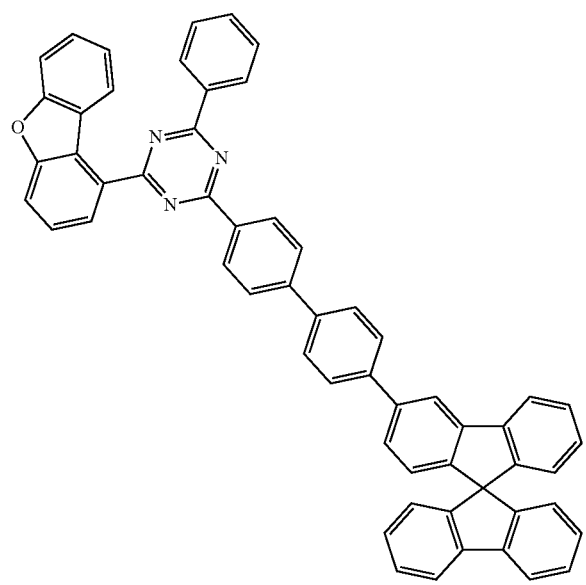
c-194
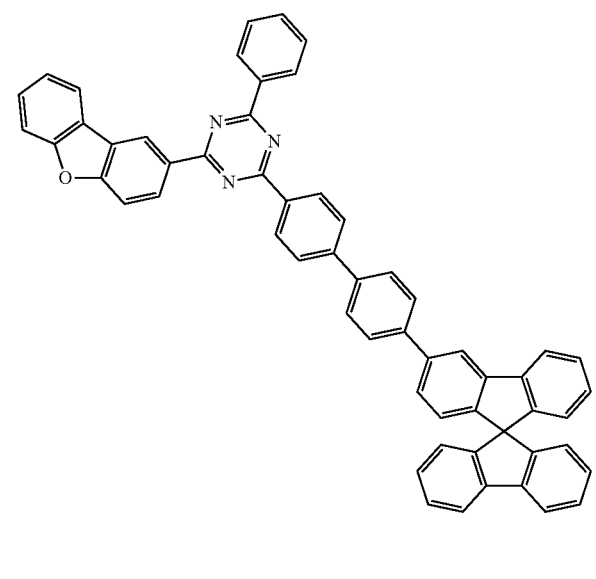

-continued
c-195
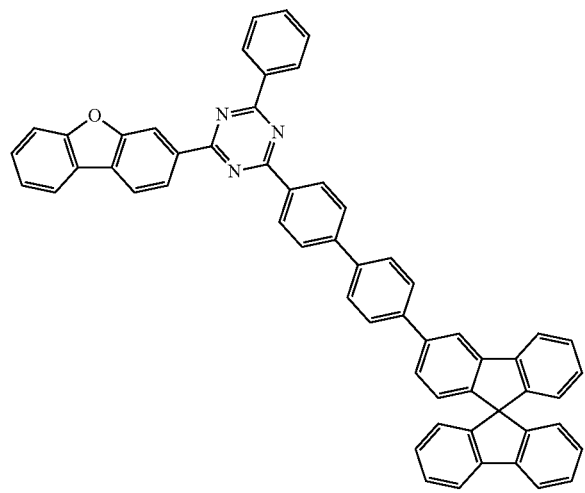
c-196
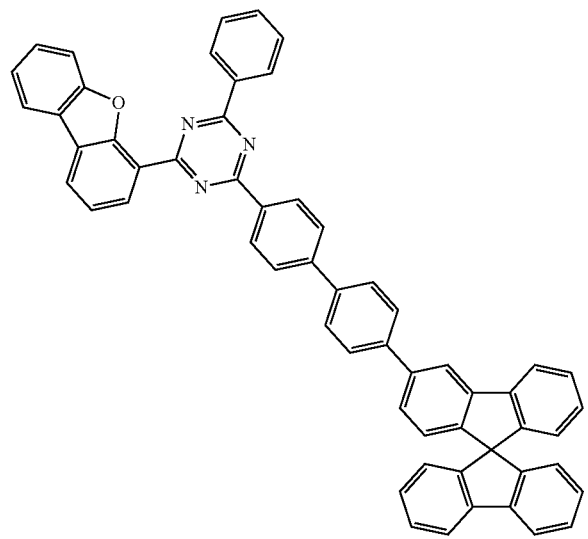
c-197
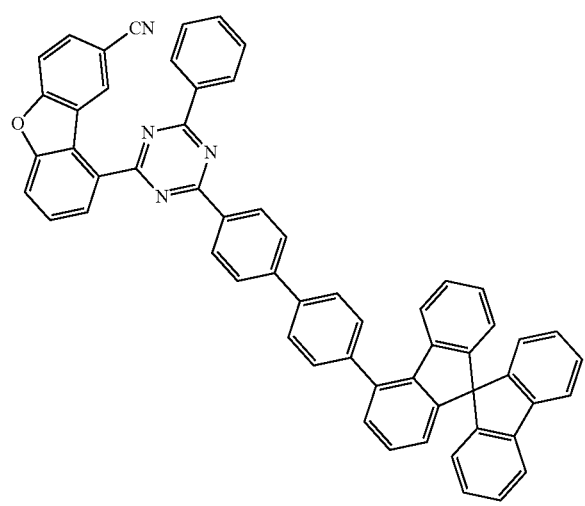
c-198
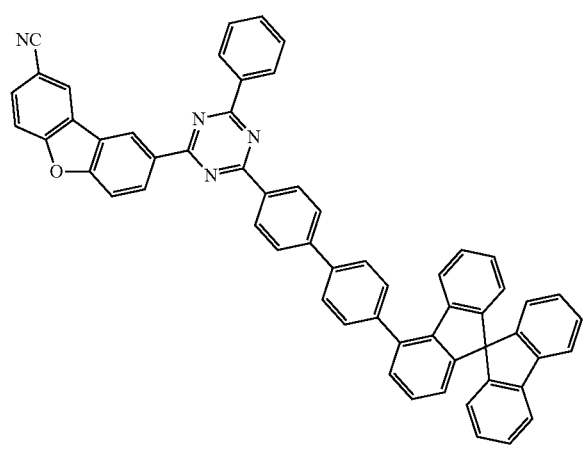
c-199
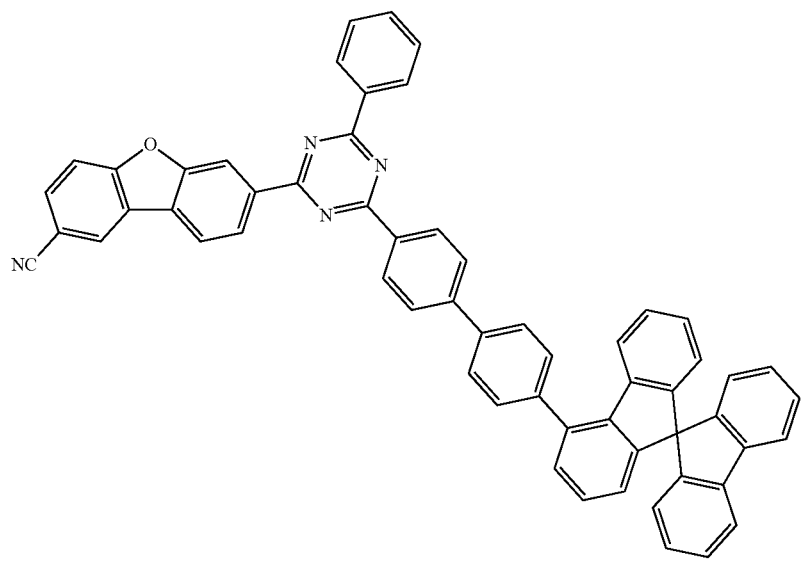

-continued
c-200
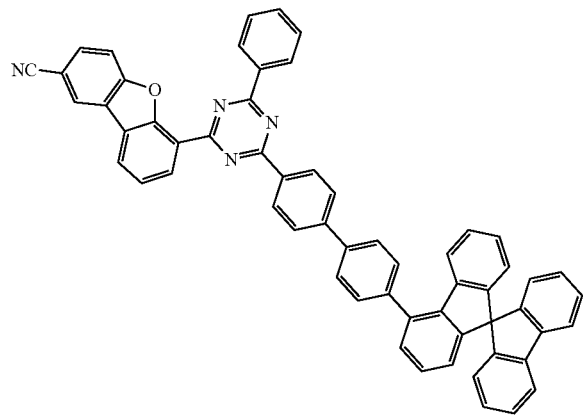
c-201
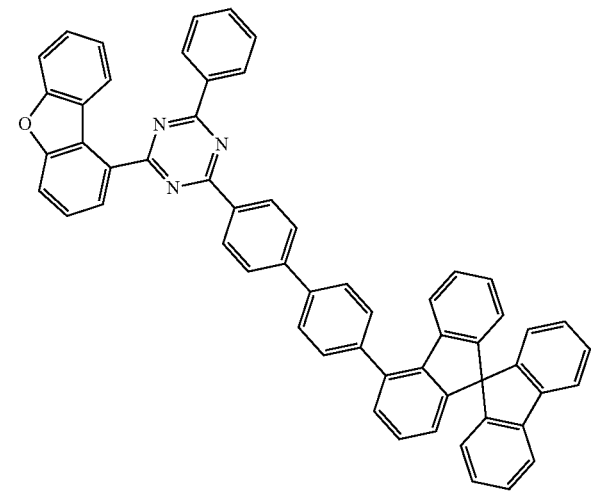
c-202
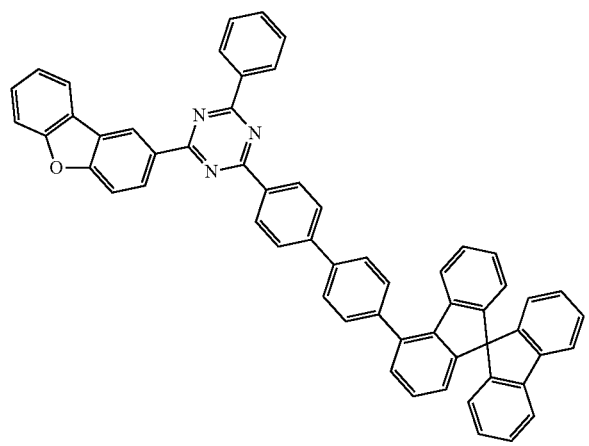
c-203
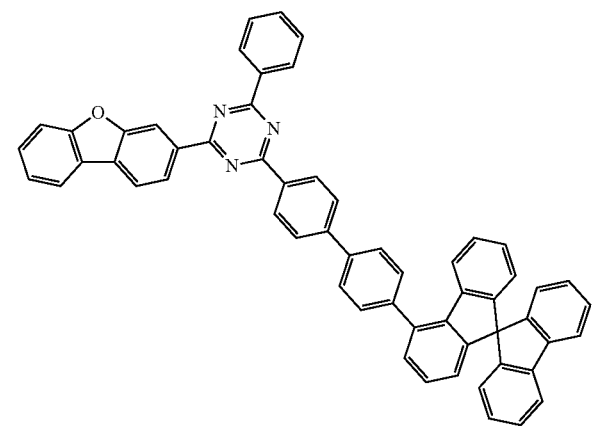
c-204
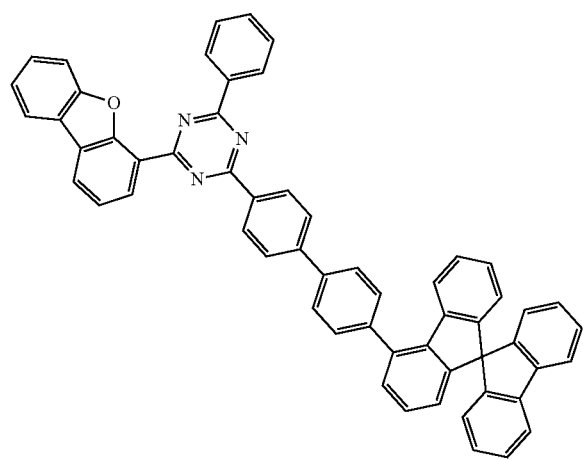
c-205
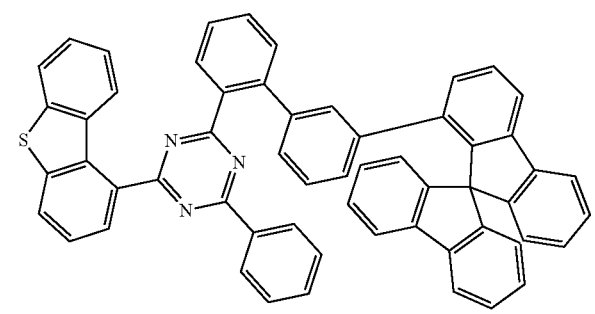

-continued
c-206
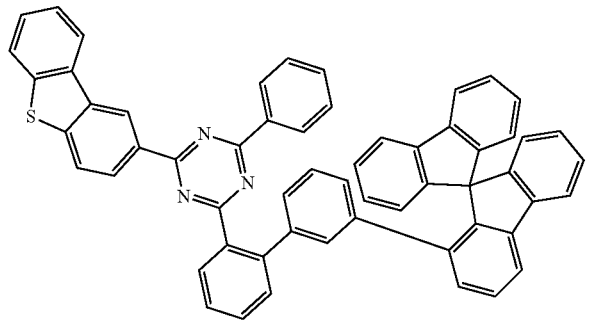
c-207
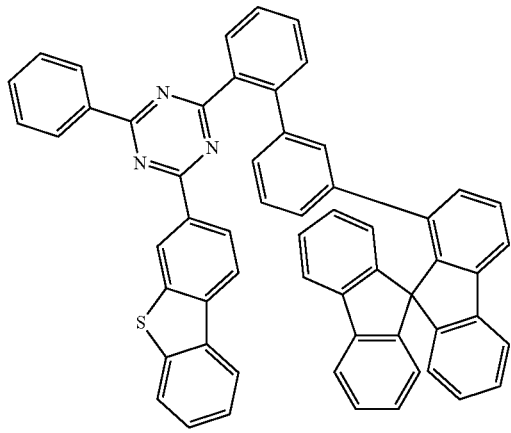
c-208
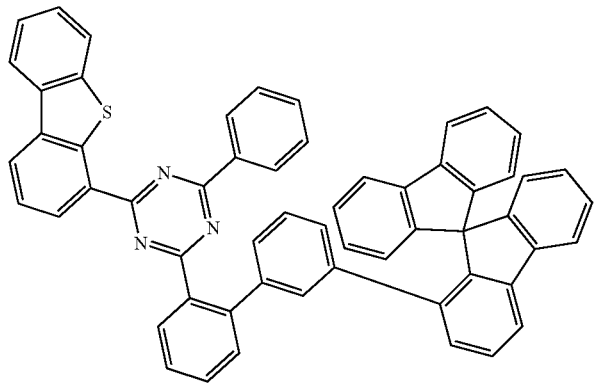
c-209
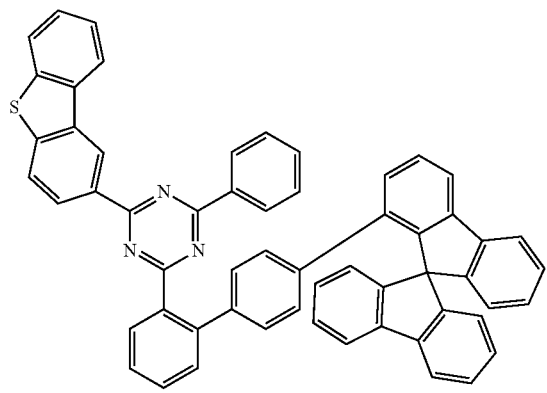
c-210
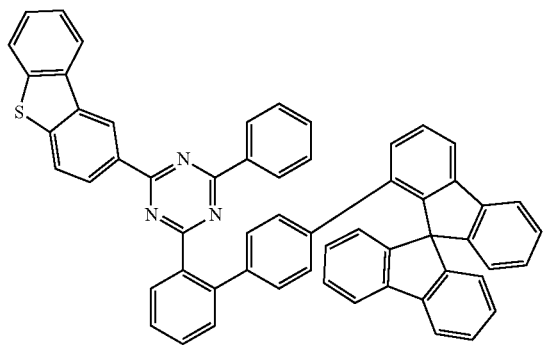

-continued
c-211
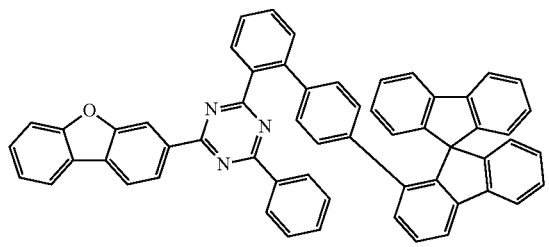
c-212
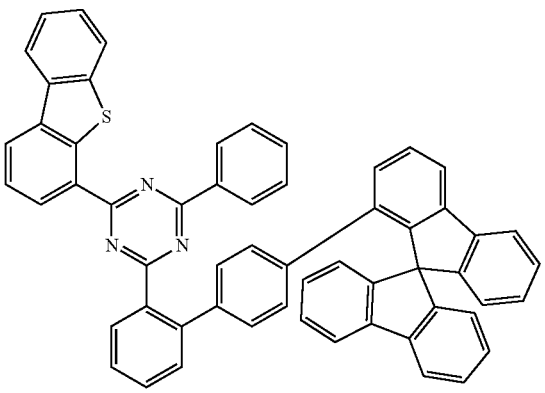
c-213
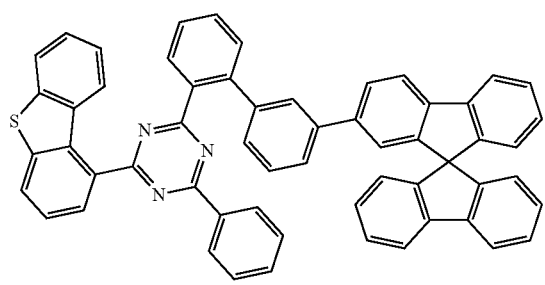
c-214
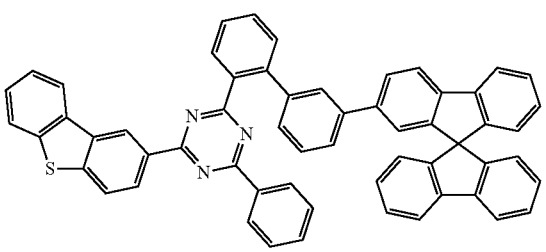
c-215
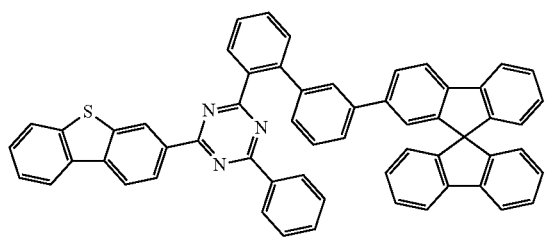
c-216
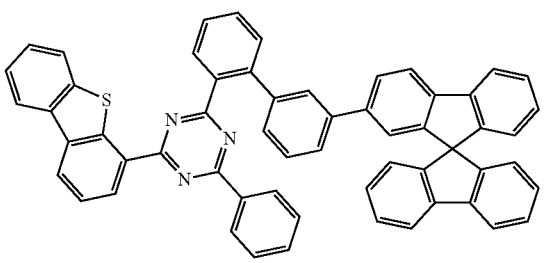
c-217
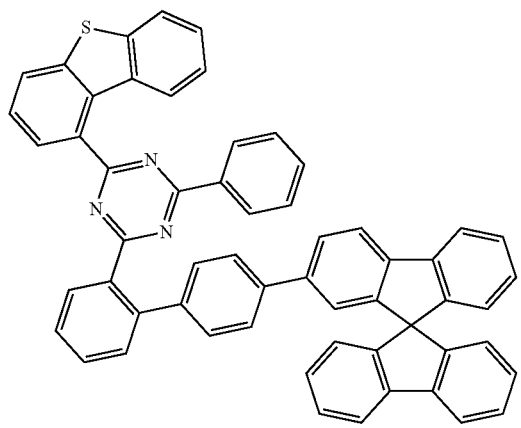
c-218
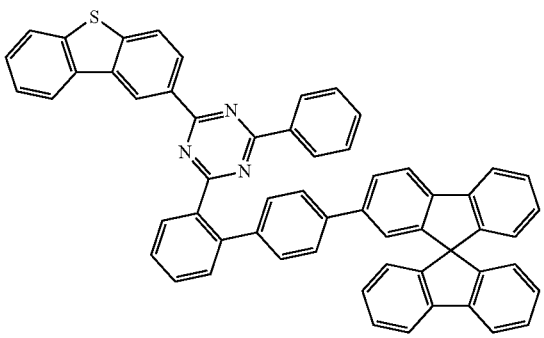

-continued
c-219
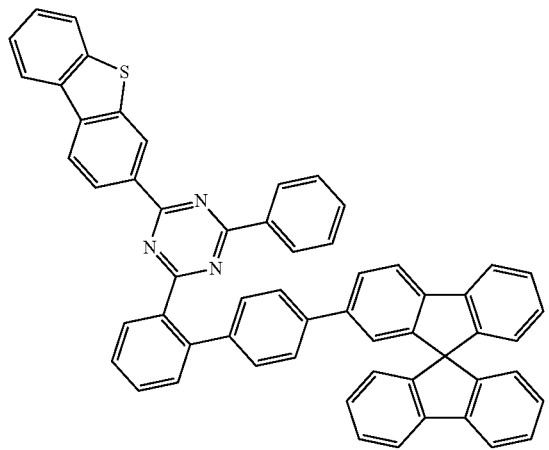
c-220
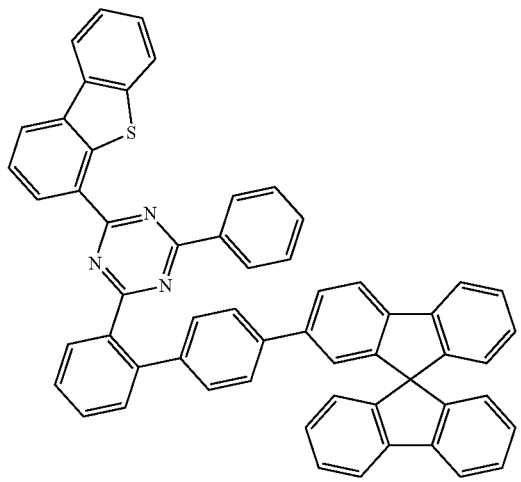
c-221
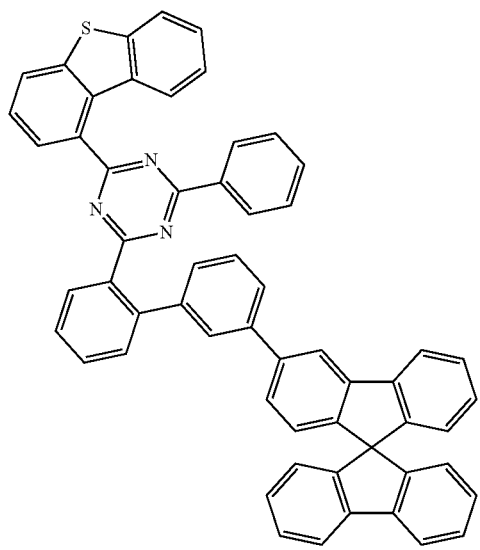
c-222
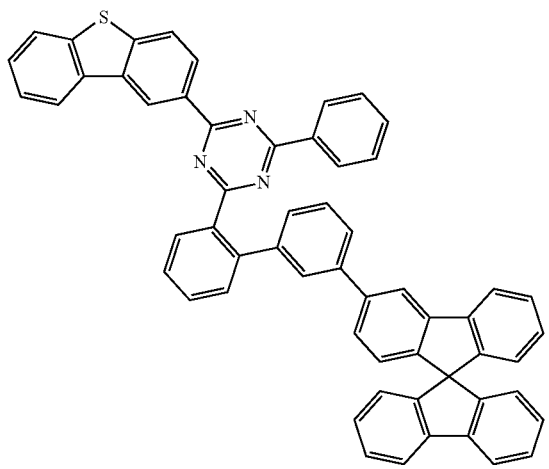

c-223
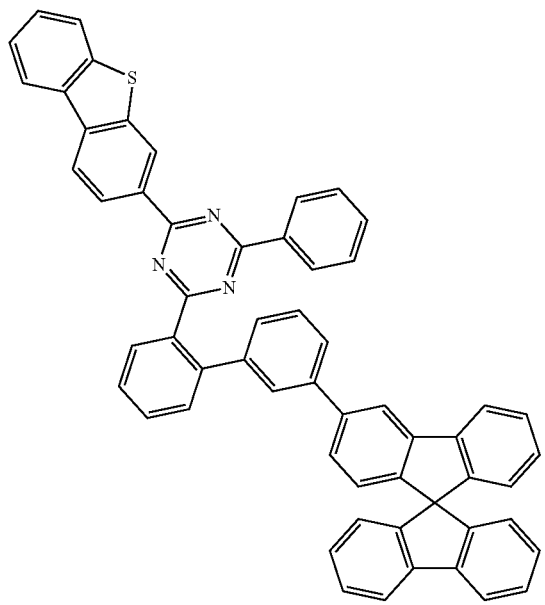
c-224
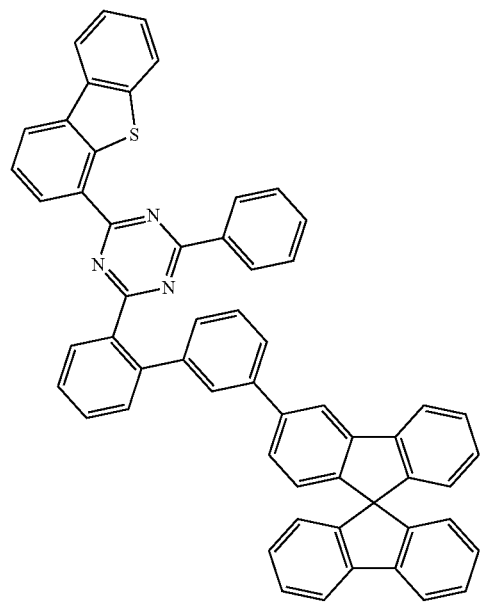
c-225
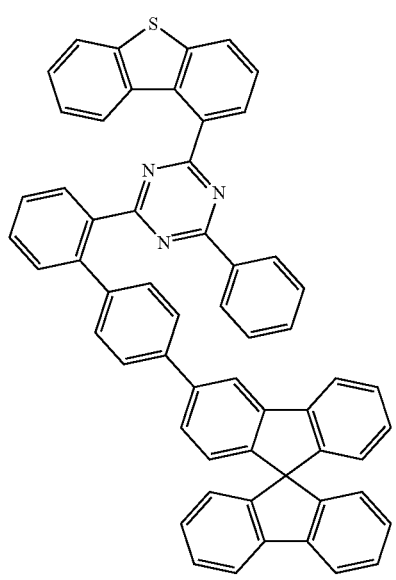
c-226
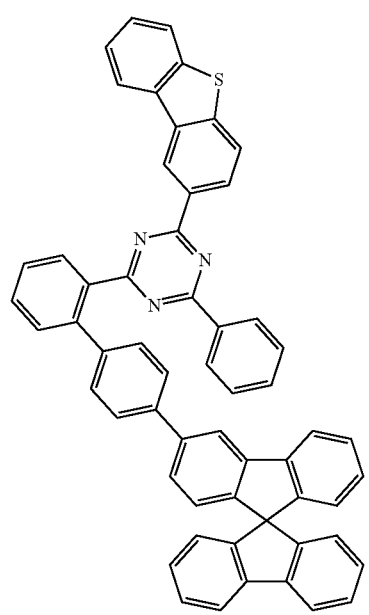

-continued
c-227
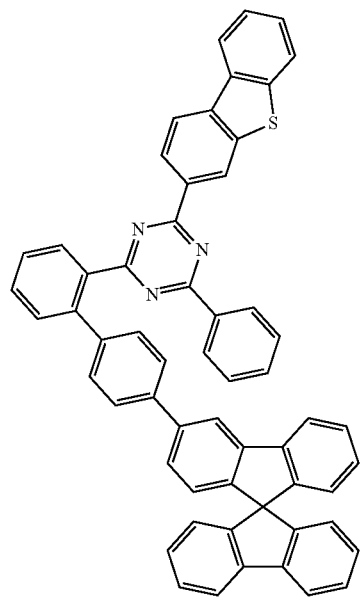
c-228
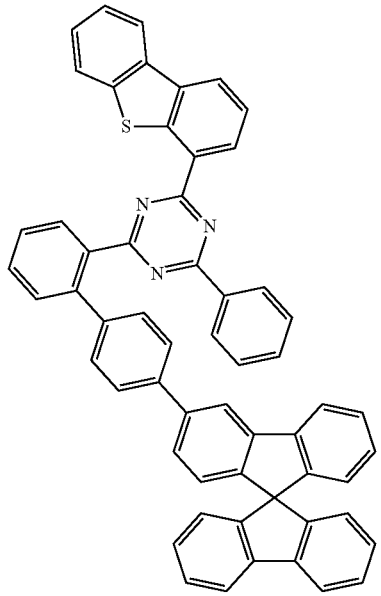
c-229
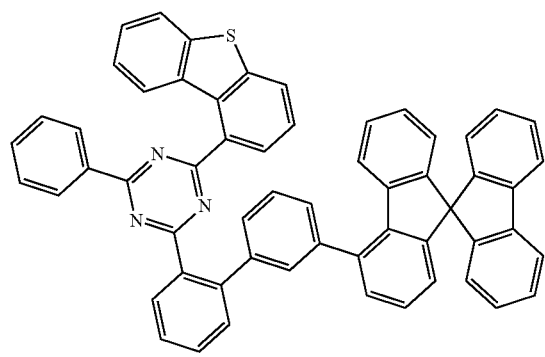
c-230
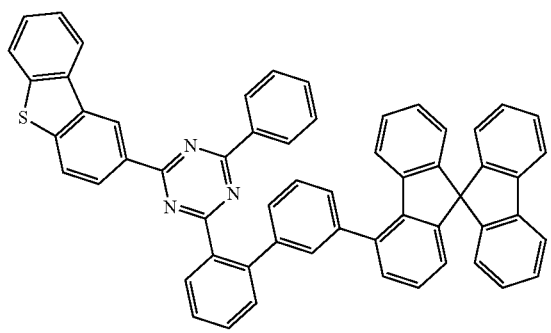
c-231
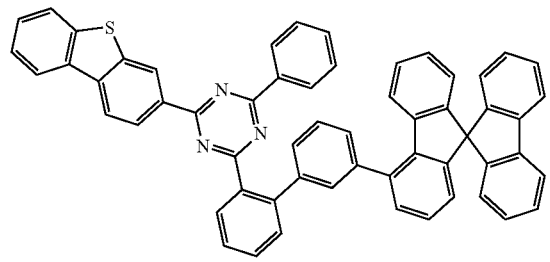
c-232
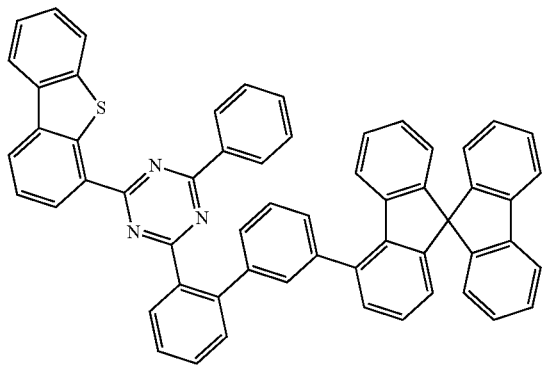

-continued
c-233
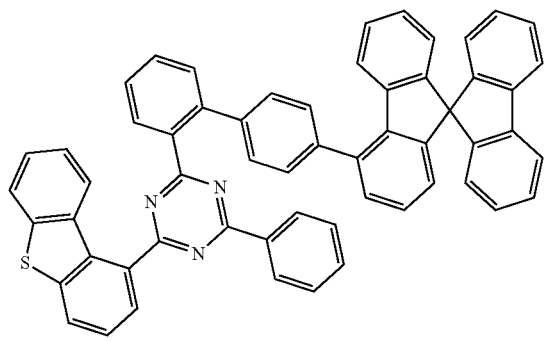
c-234
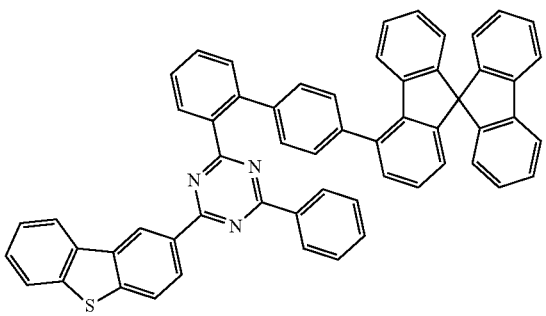
c-235
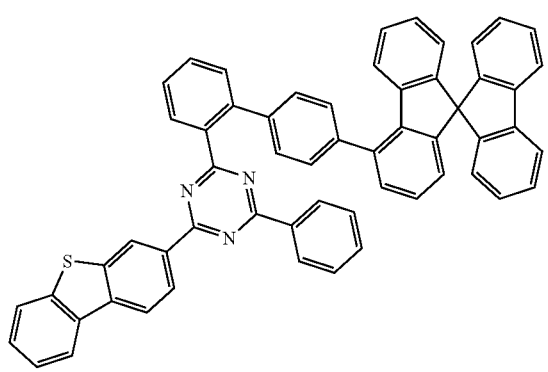
c-236
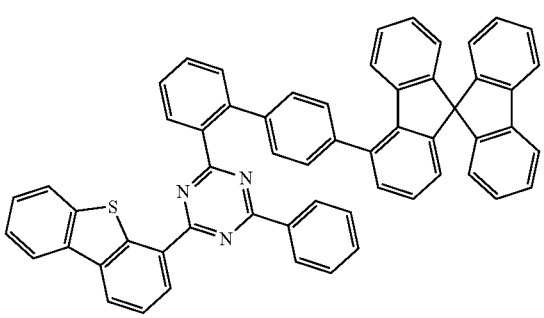
c-237
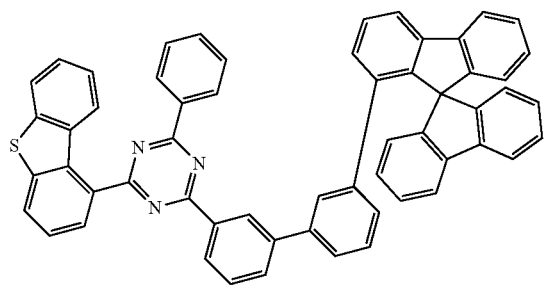
c-238
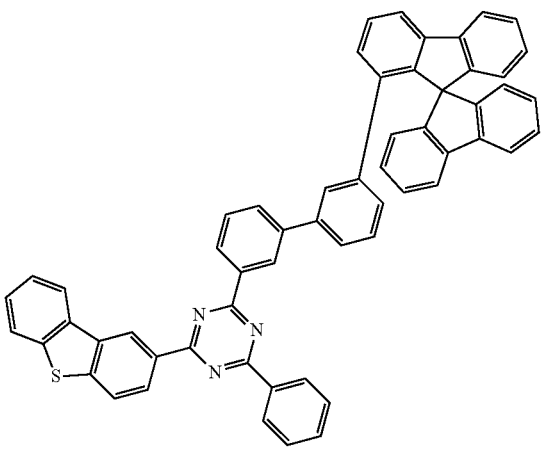
c-239
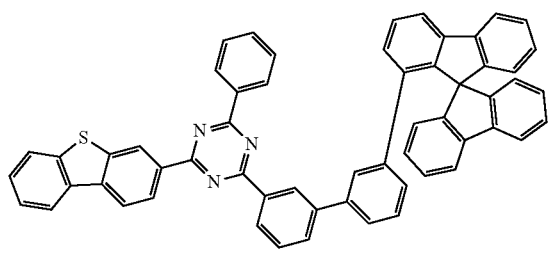
c-240
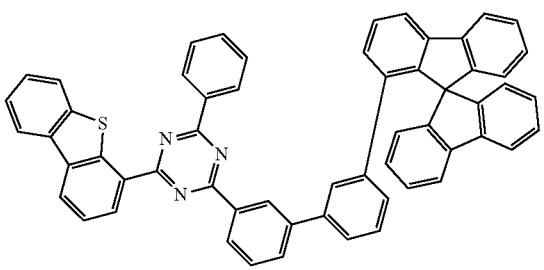

-continued
c-241
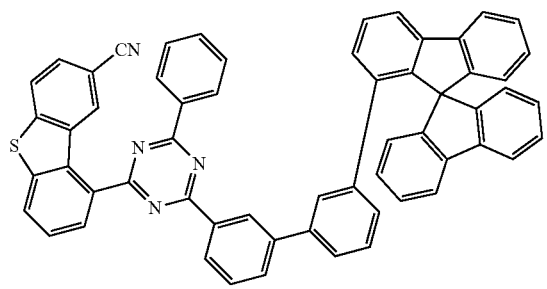
c-242
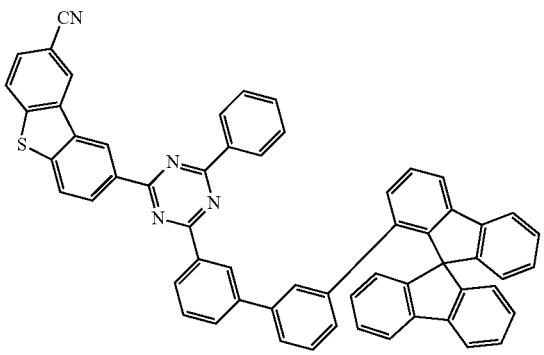
c-243
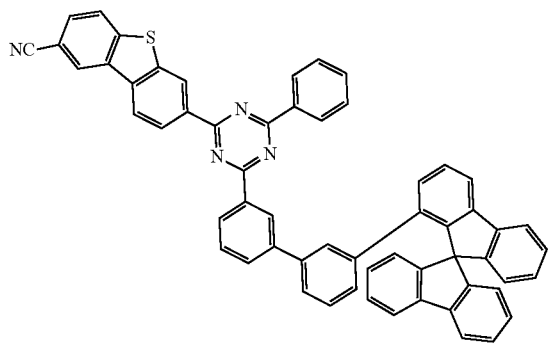
c-244
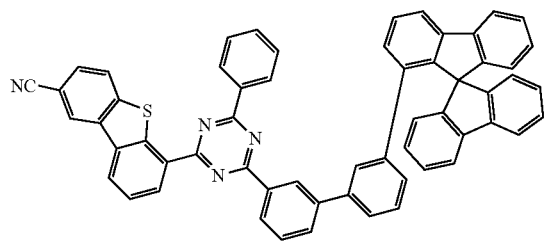
c-245
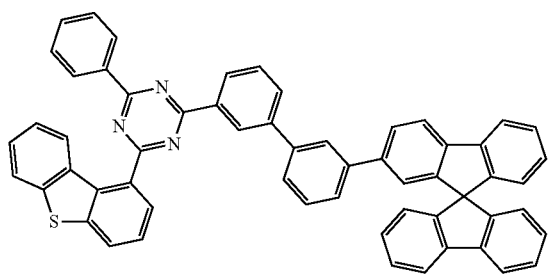
c-246
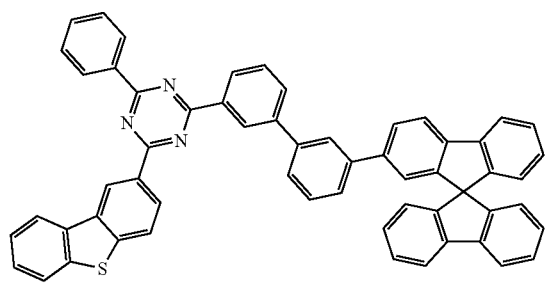
c-247
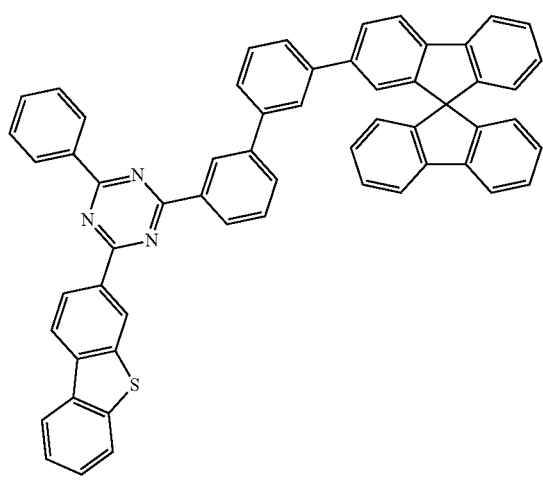
c-248
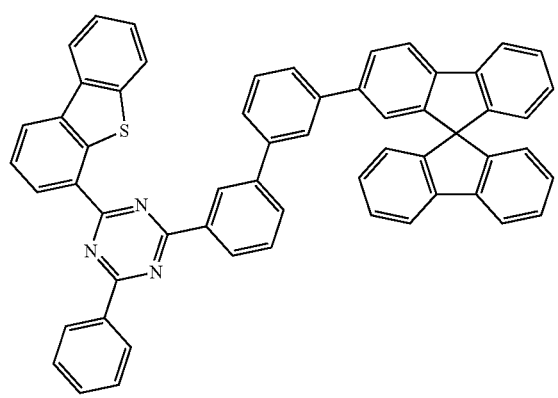

-continued
c-249
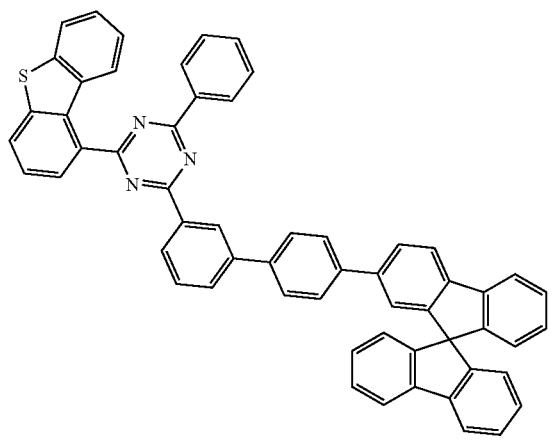
c-250
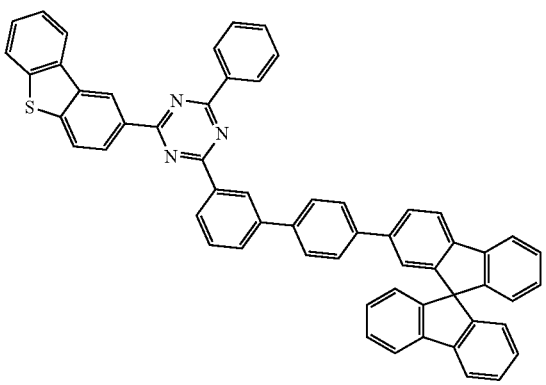
c-251
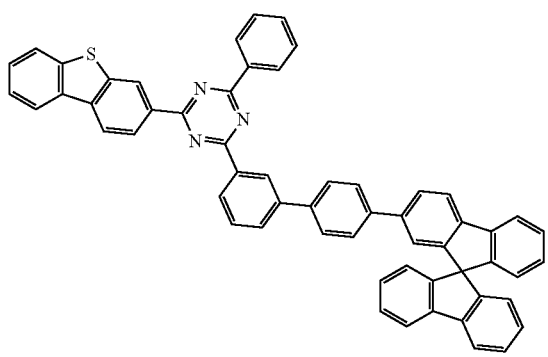
c-252
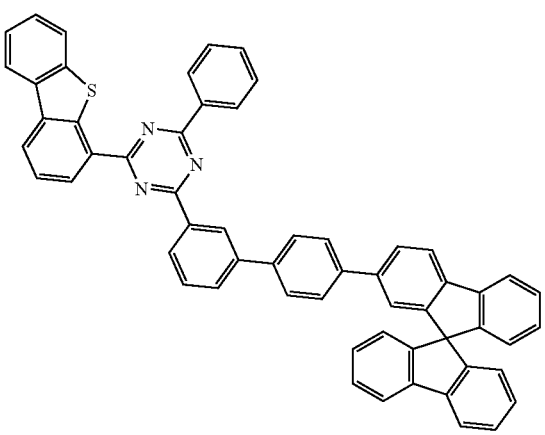
c-253
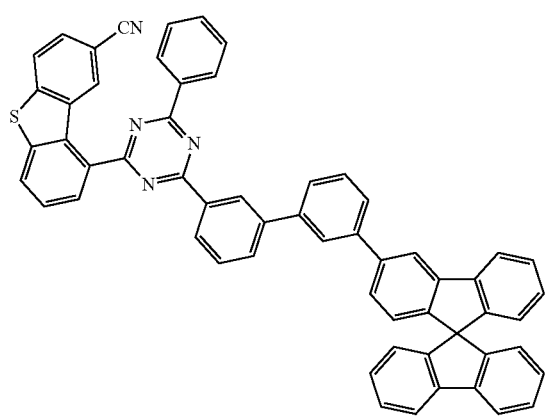
c-254
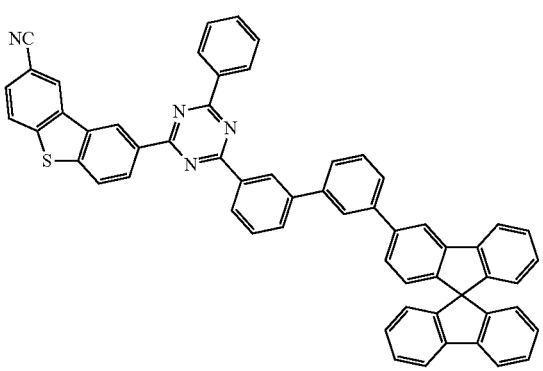

-continued
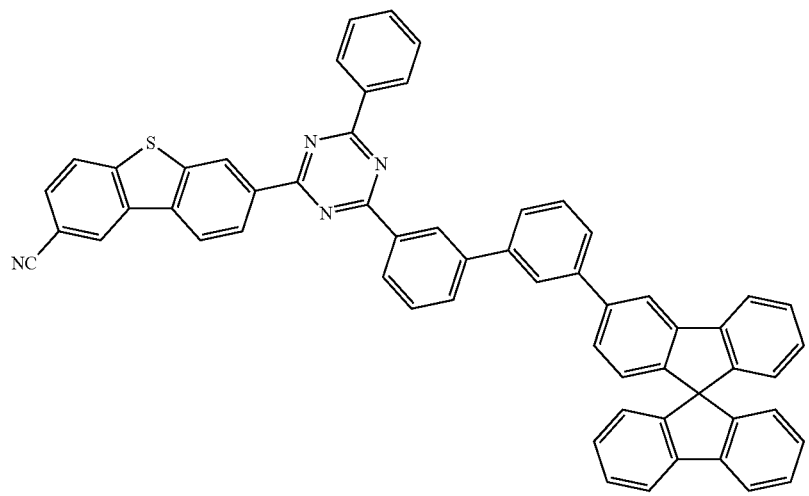
c-255
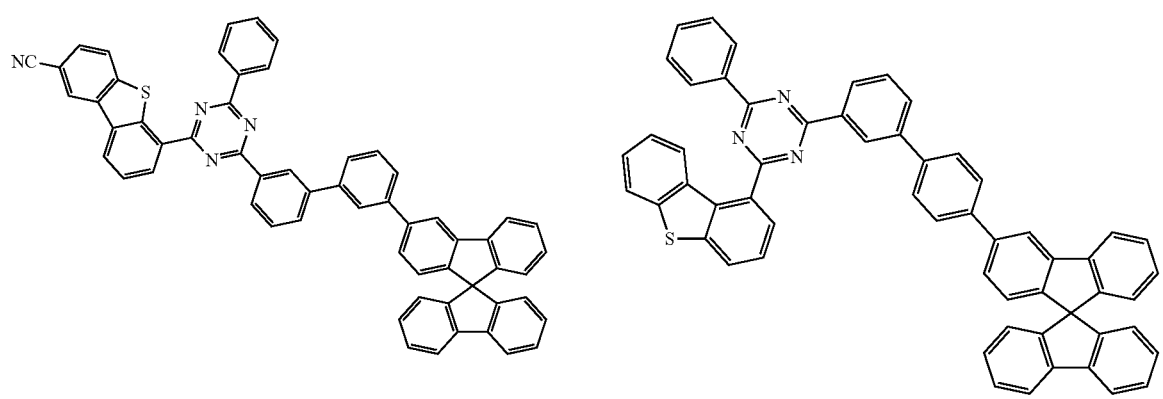
c-256 c-257
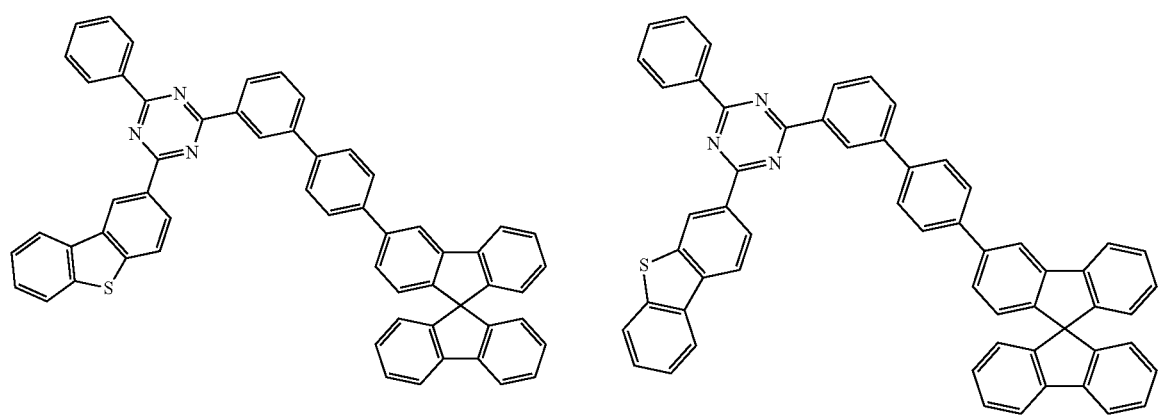
c-258 c-259

-continued
c-260
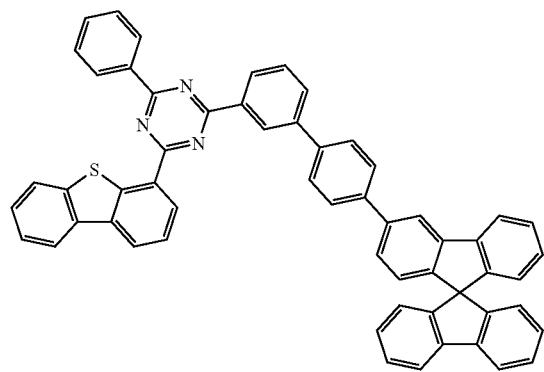
c-261
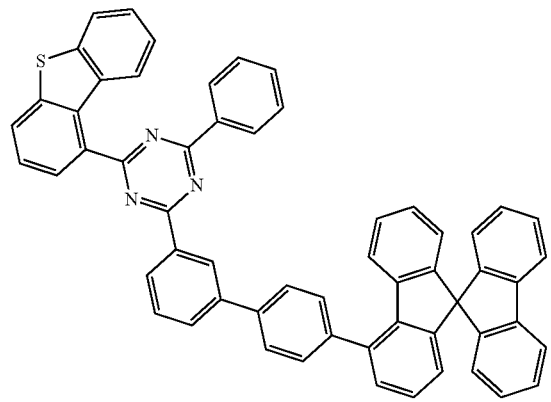
c-262
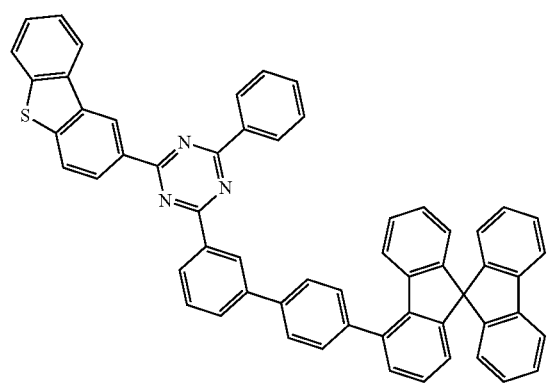
c-263
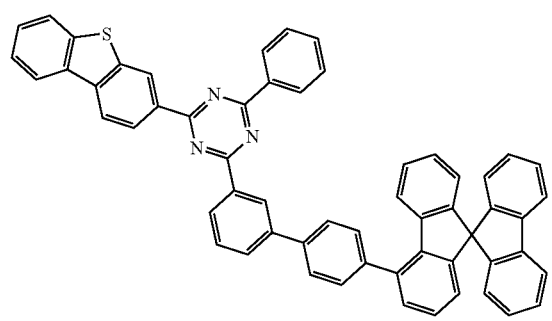
c-264
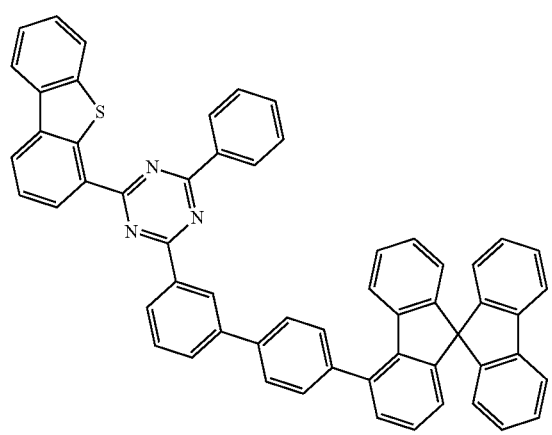
c-265
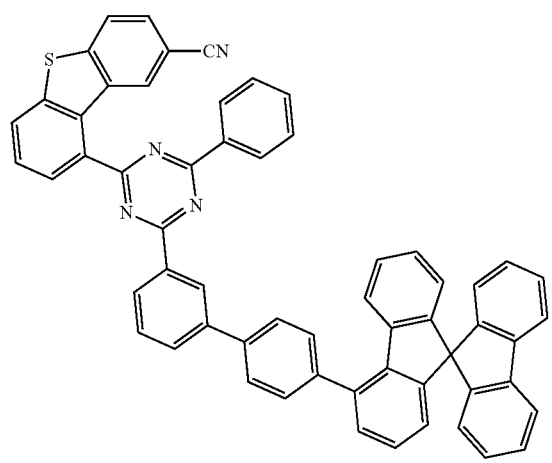

-continued
c-266
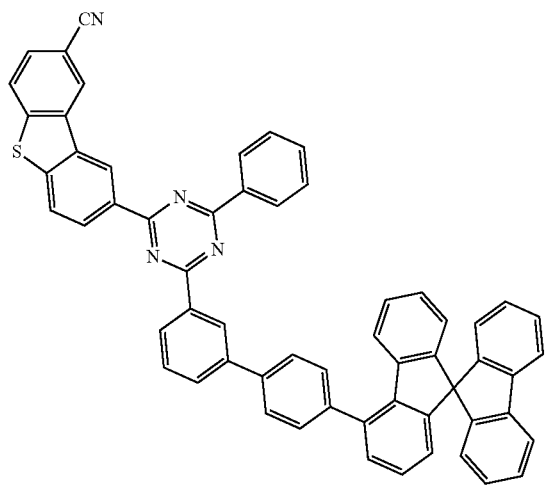
c-267
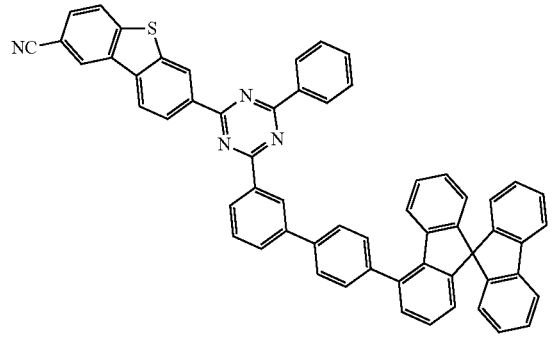
c-268
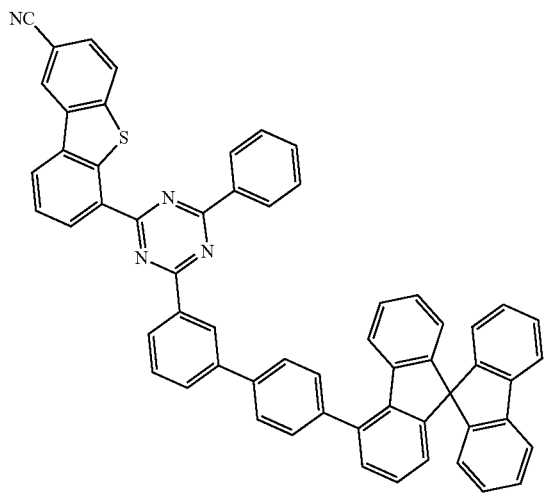
c-269
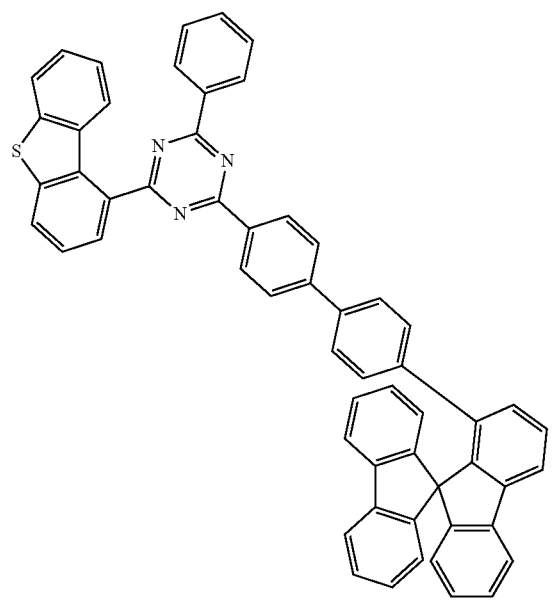
c-270
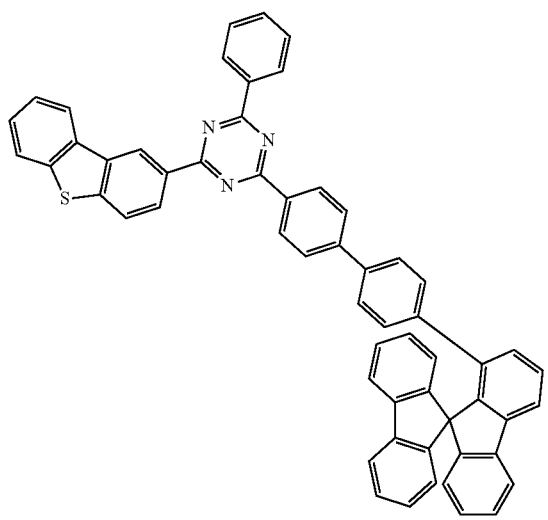
c-271
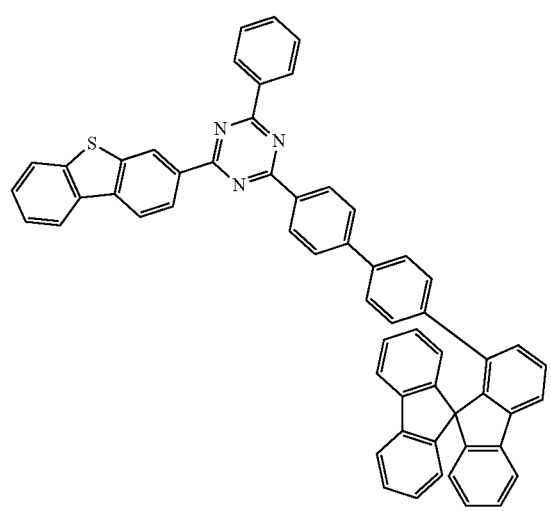

-continued
c-272
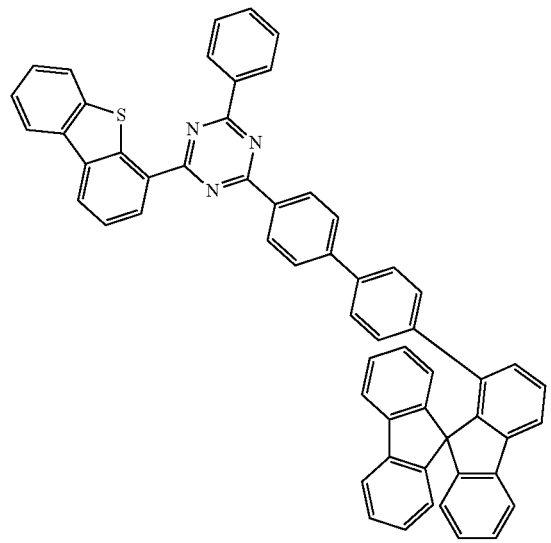
c-273
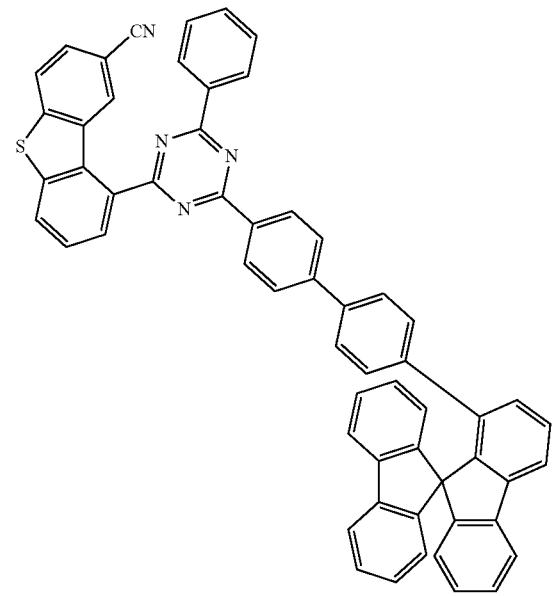
c-274
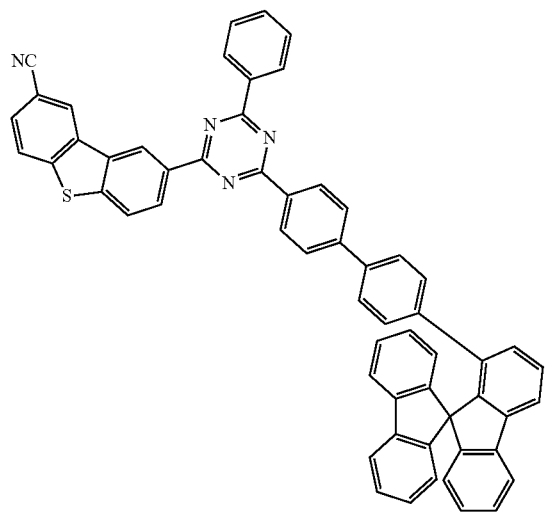
c-275
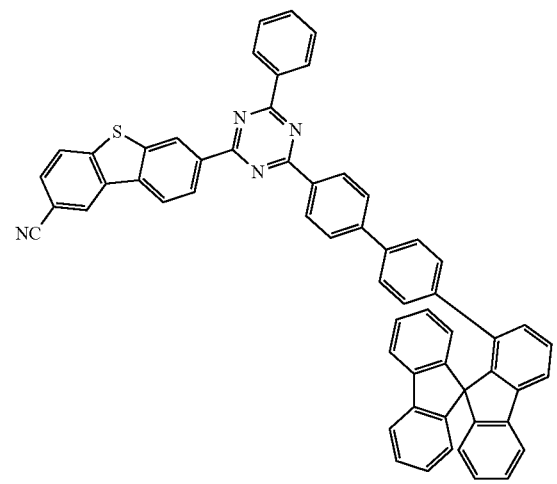
c-276
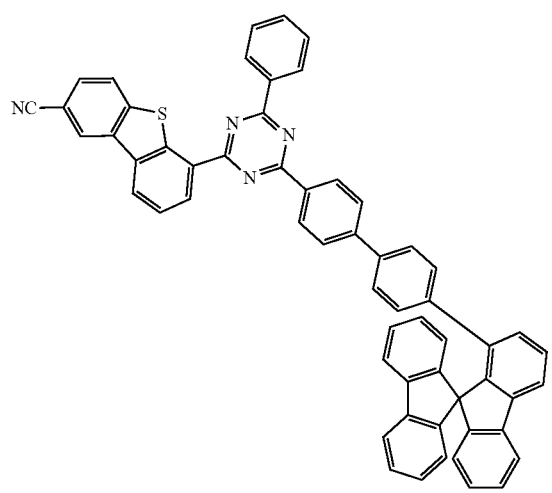
c-277
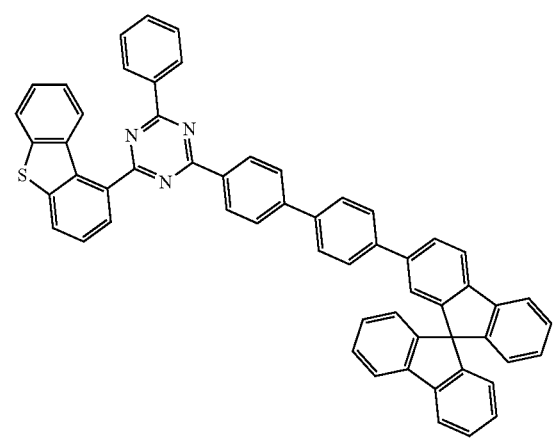

-continued
c-278
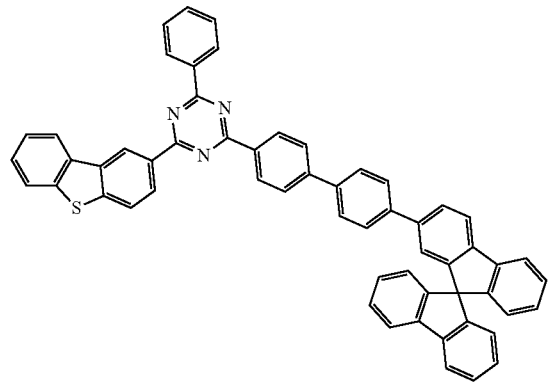
c-279
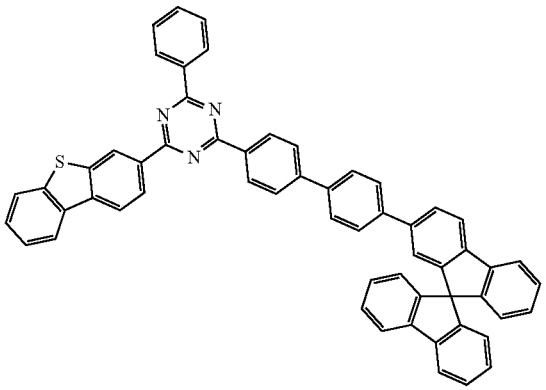
c-280
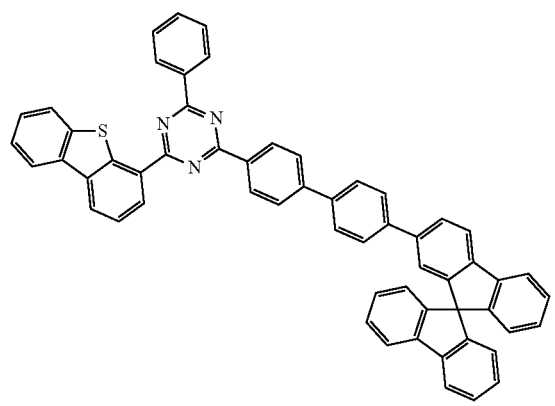
c-281
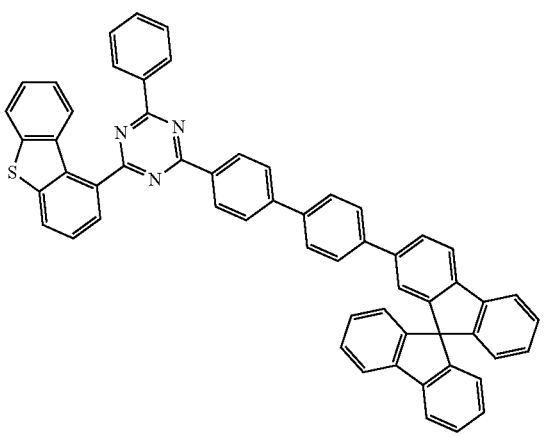
c-282
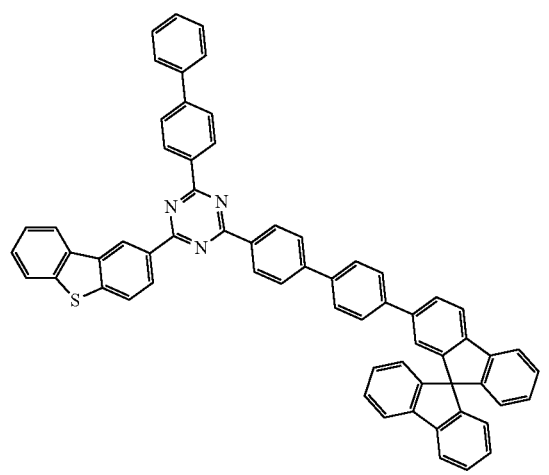
c-283
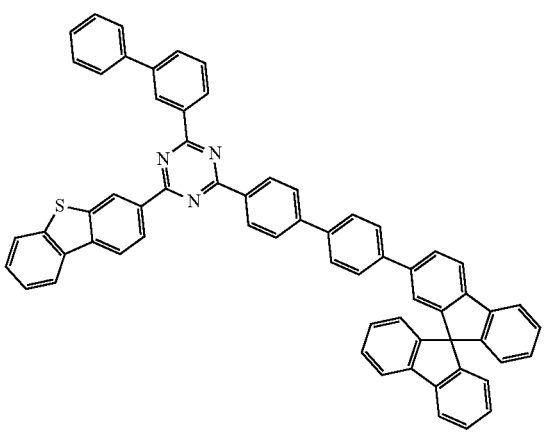

-continued
c-284
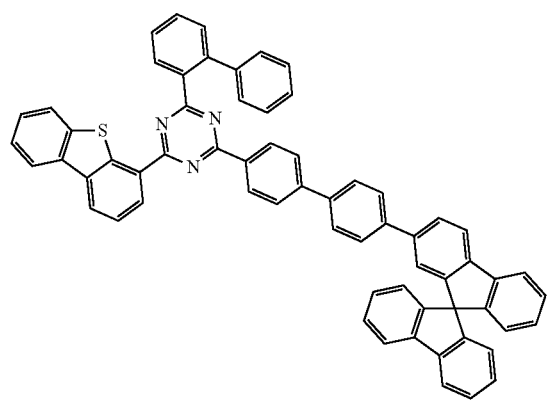
c-285
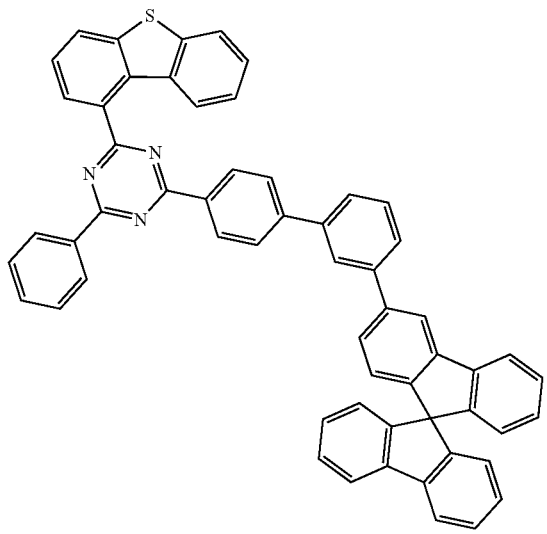
c-286
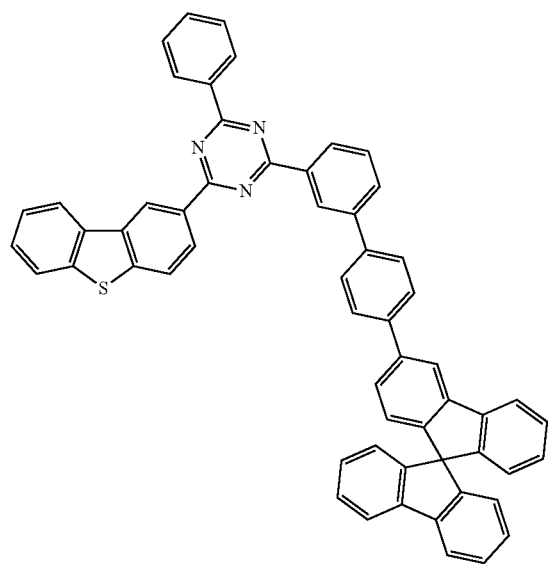
c-287
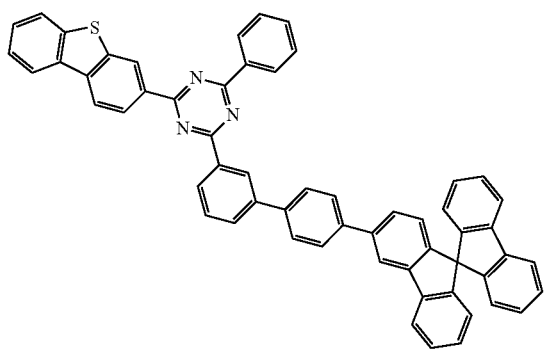

-continued
c-288
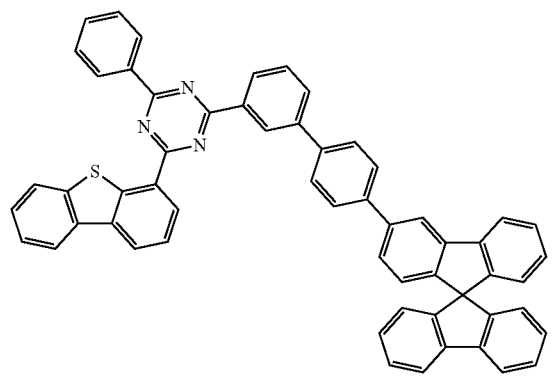
c-289
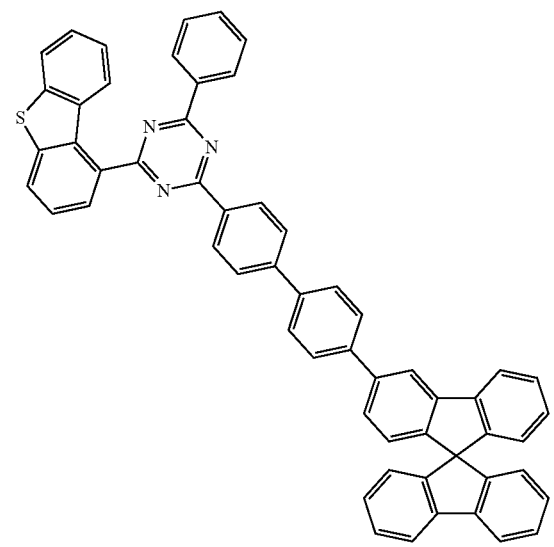
c-290
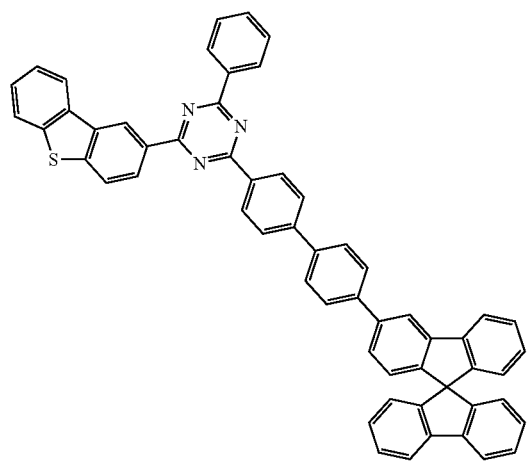
c-291
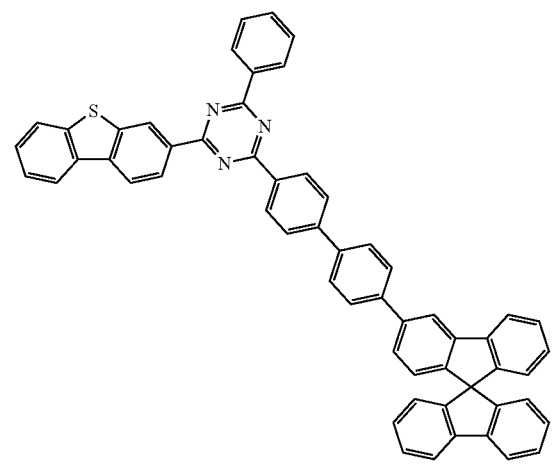
c-292
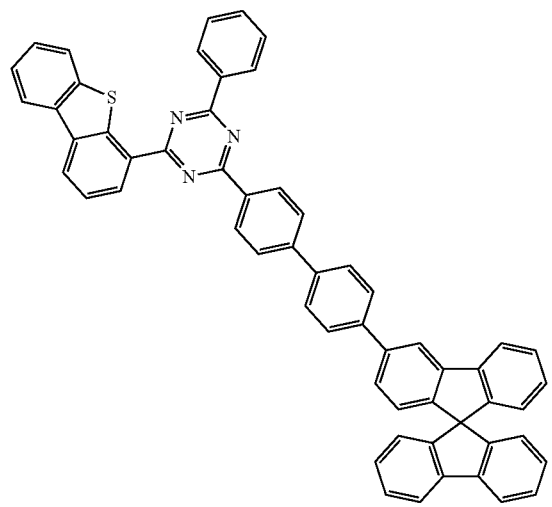
c-293
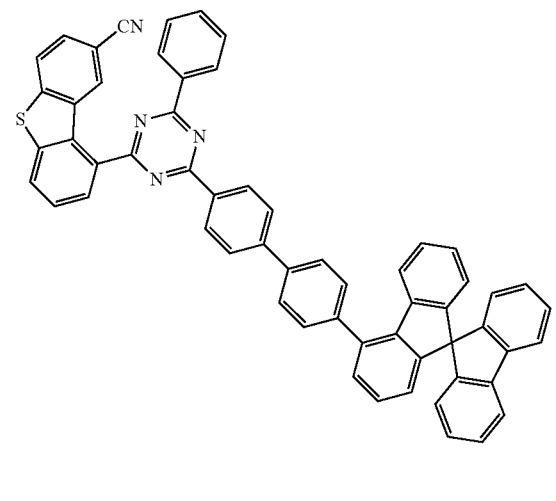

c-294
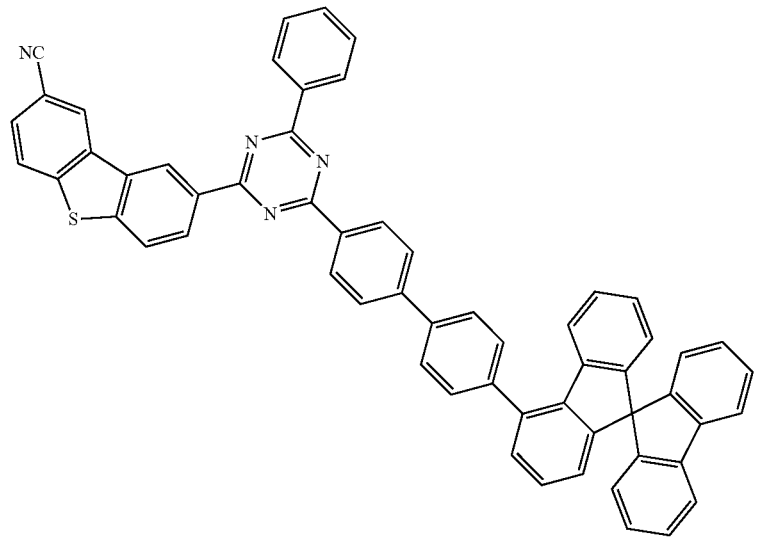
c-295
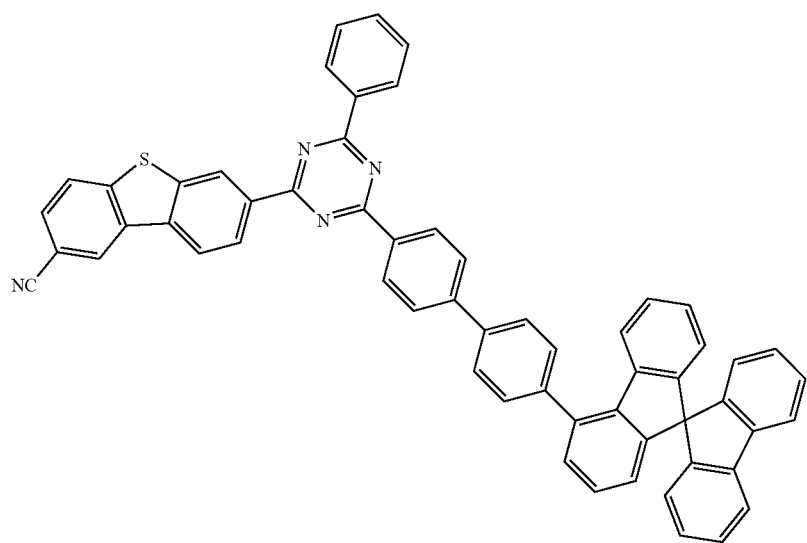
c-296
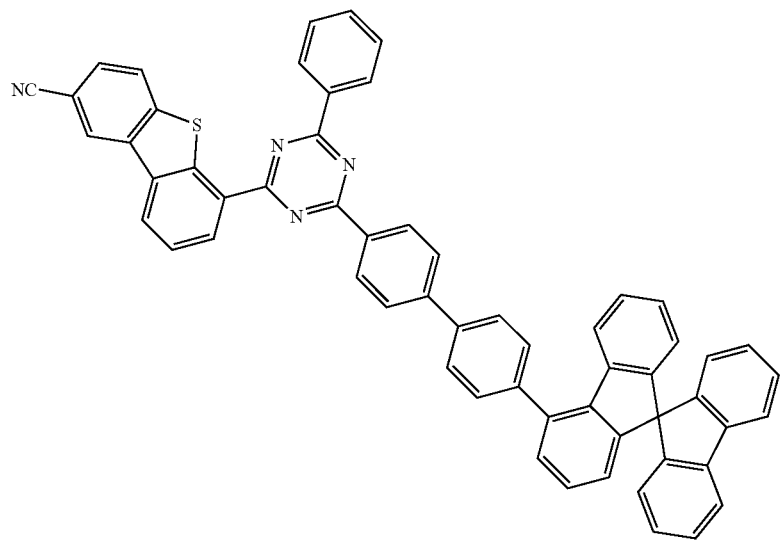

-continued
c-297
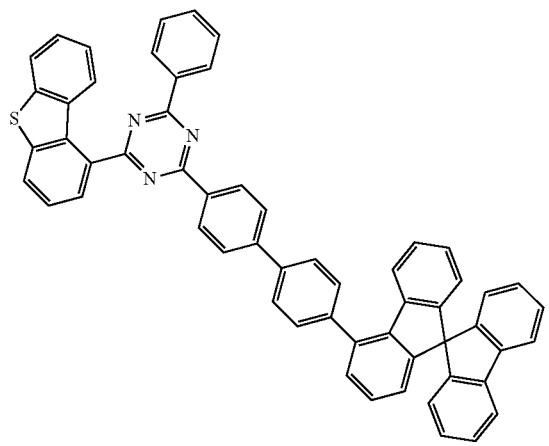
c-298
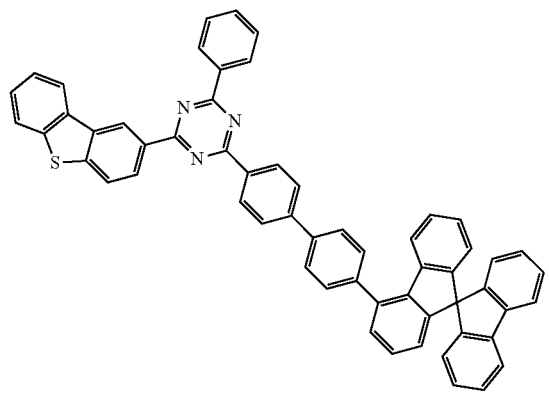
c-299
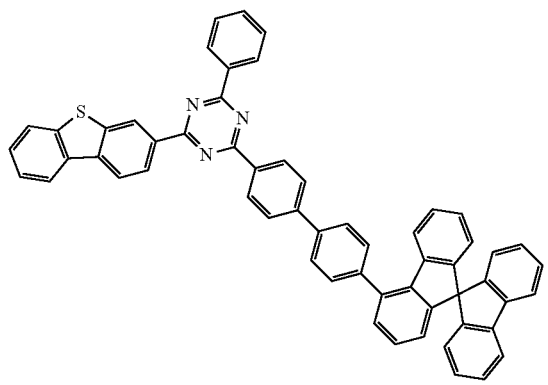
c-300
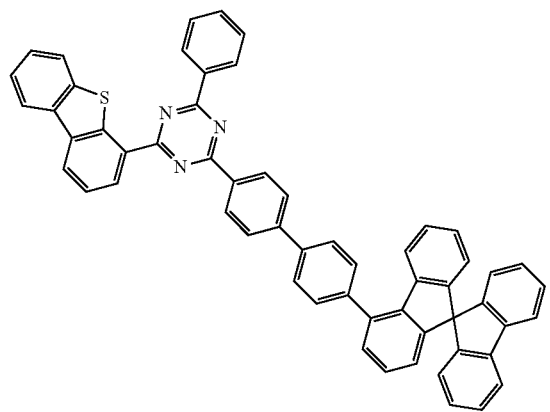
c-301
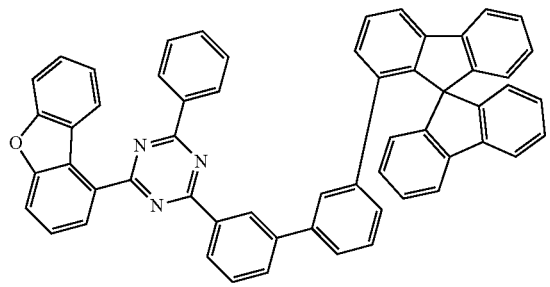
c-302
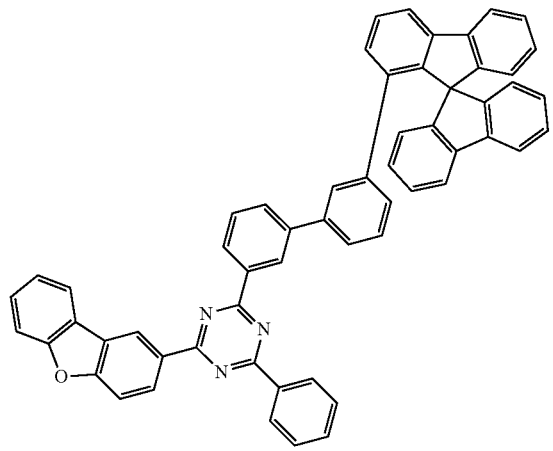
c-303
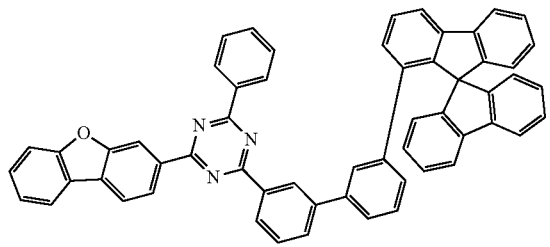
c-304
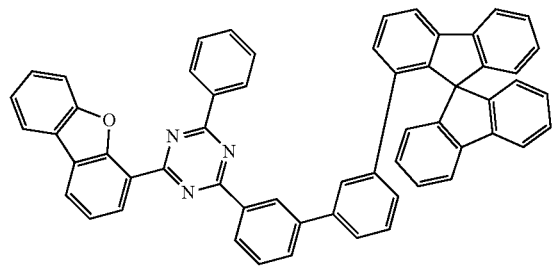

-continued
c-305
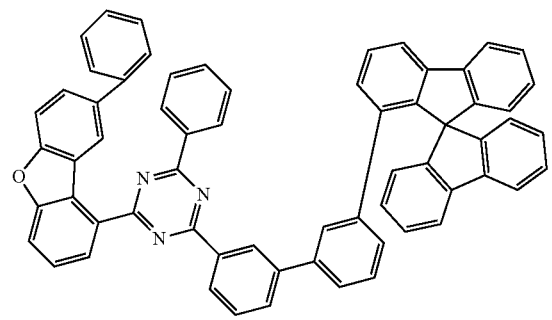
c-306
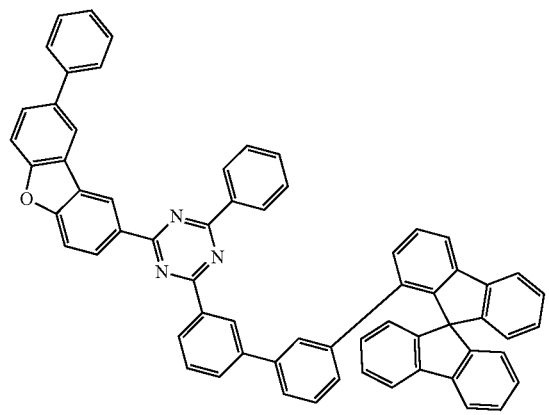
c-307
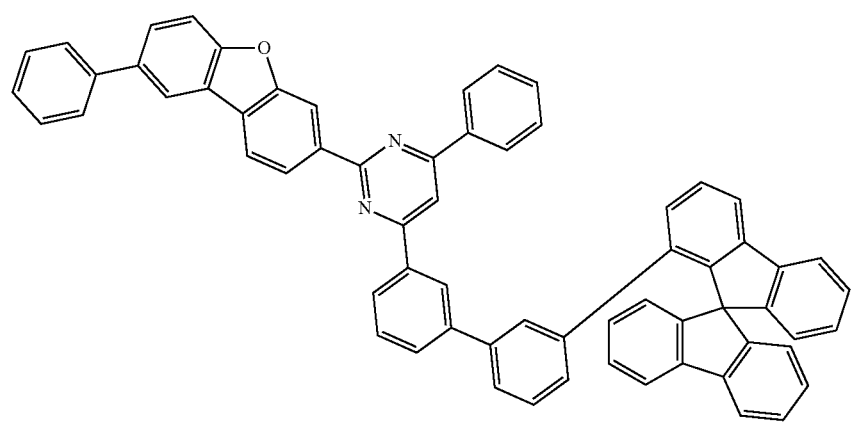
c-308
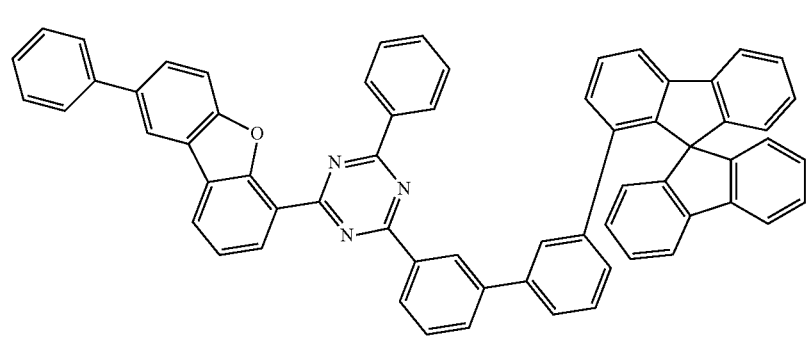
c-309
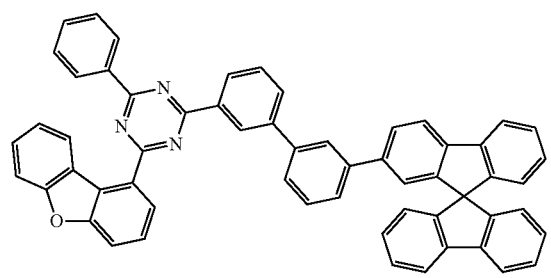
c-310
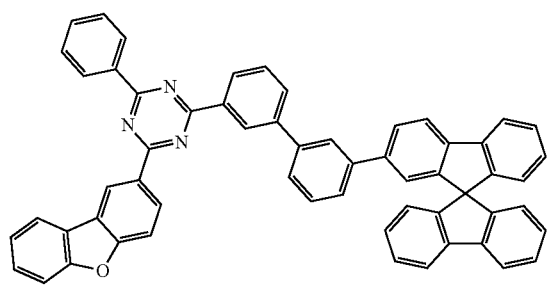

-continued
c-311
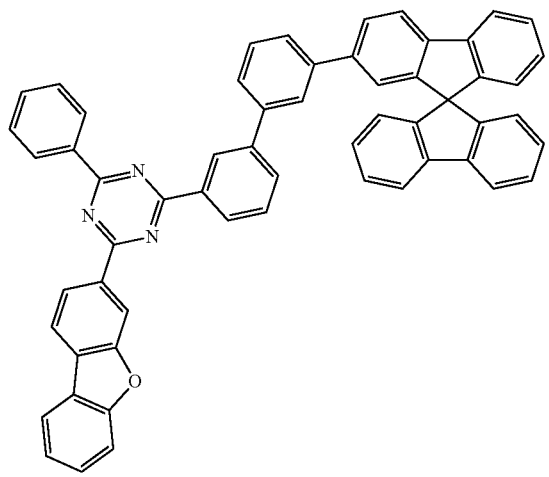
c-312
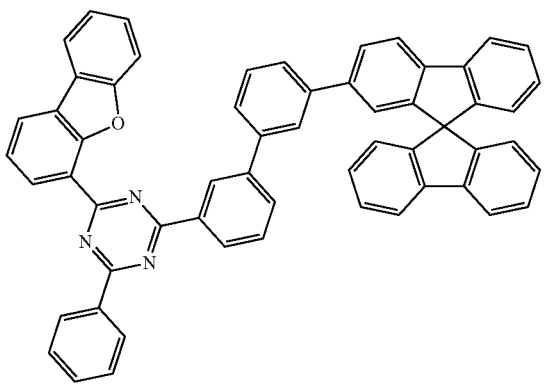
c-313
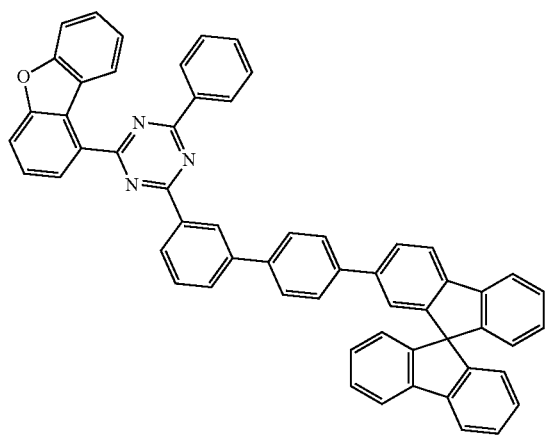
c-314
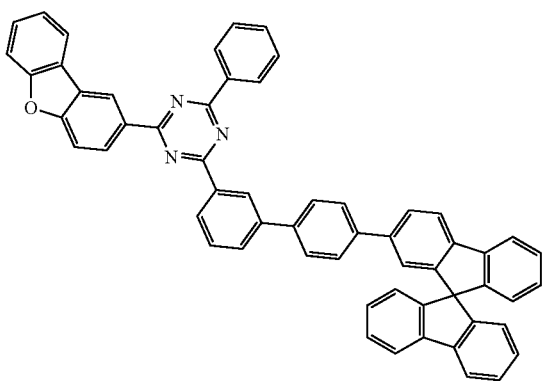
c-315
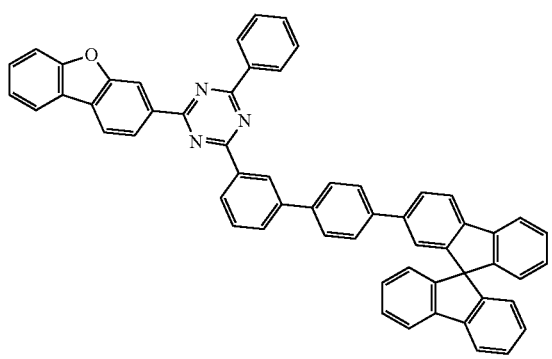
c-316
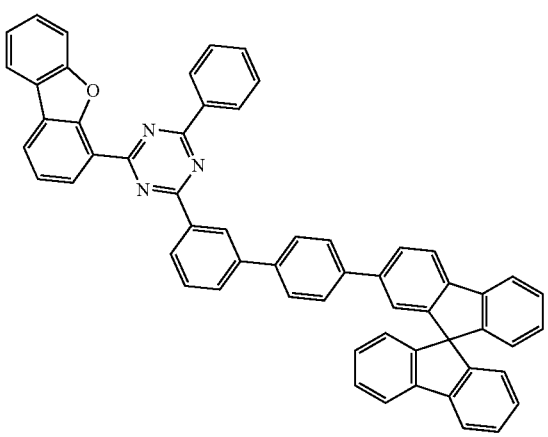

c-317
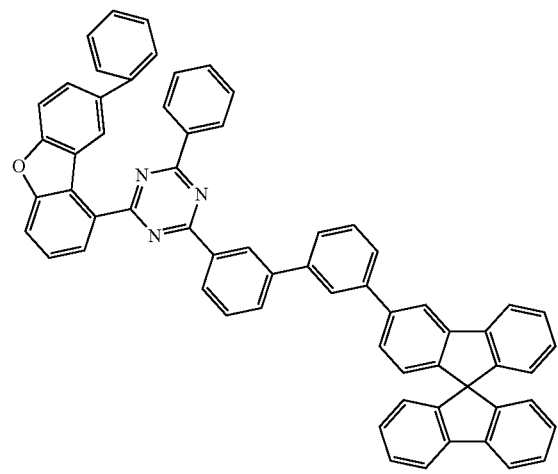
c-318
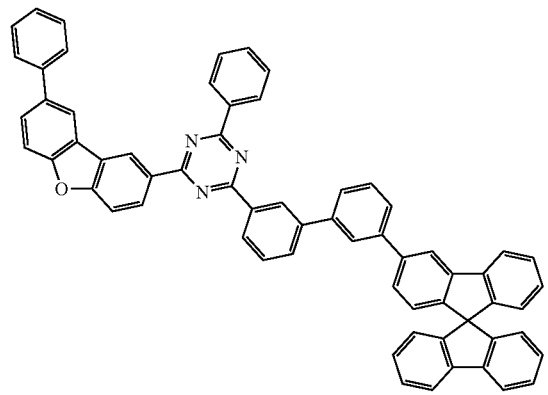
c-319
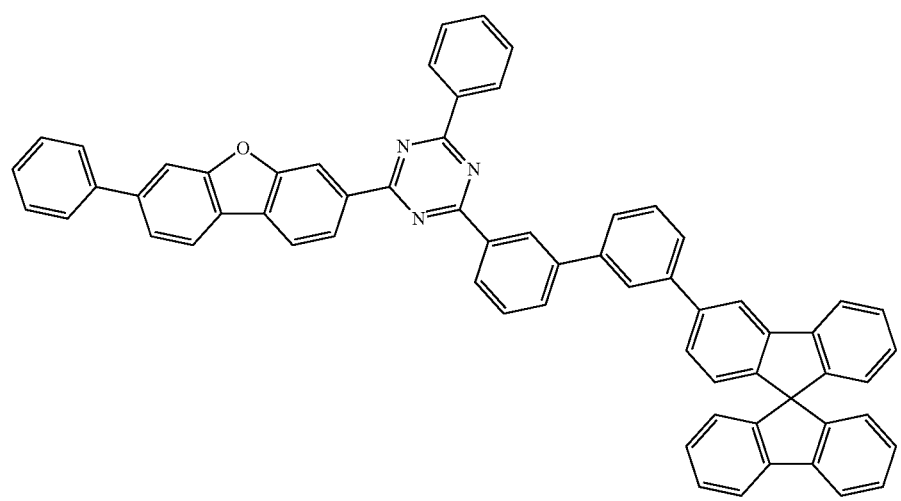
c-320
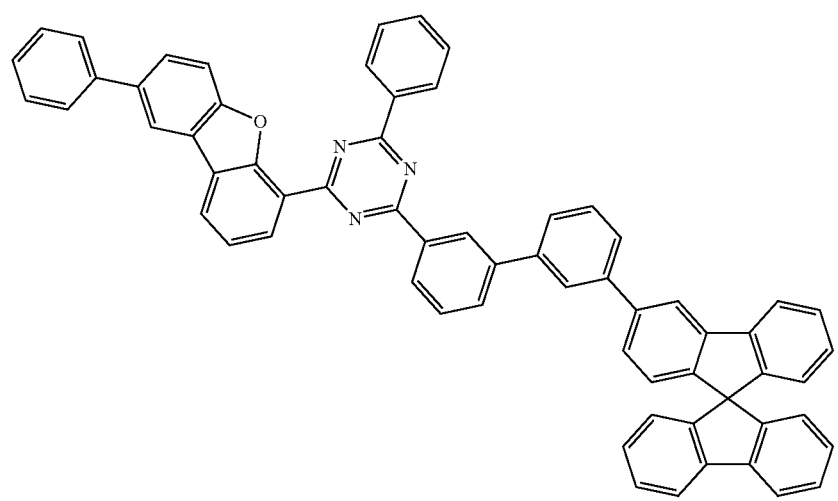

-continued
c-321
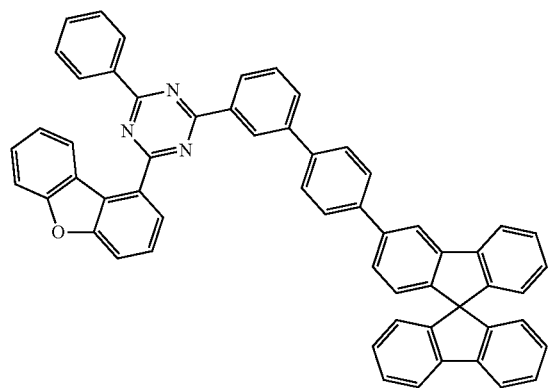
c-322
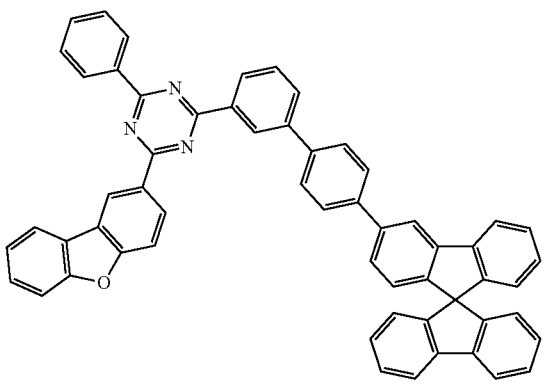
c-323
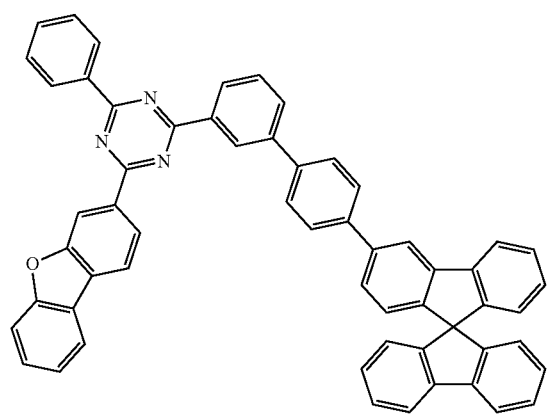
c-324
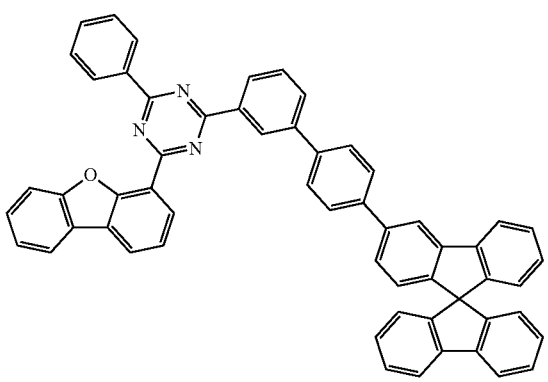
c-325
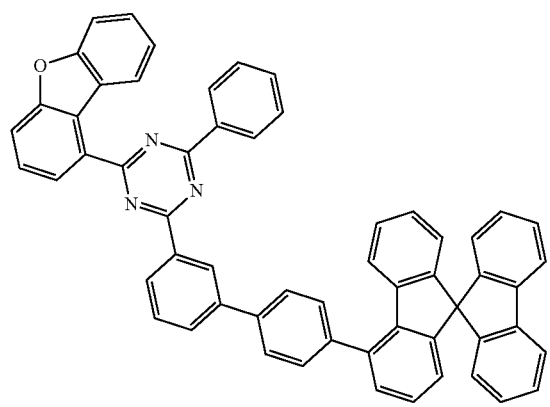
c-326
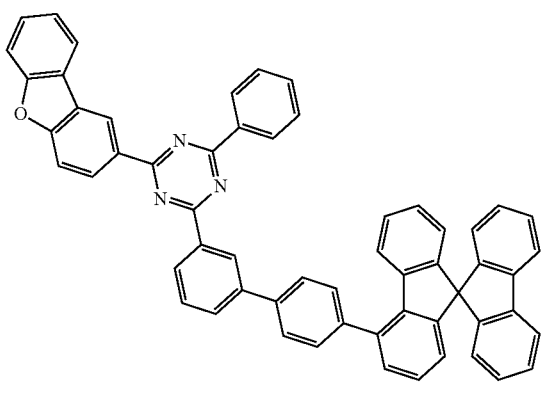

-continued
c-327
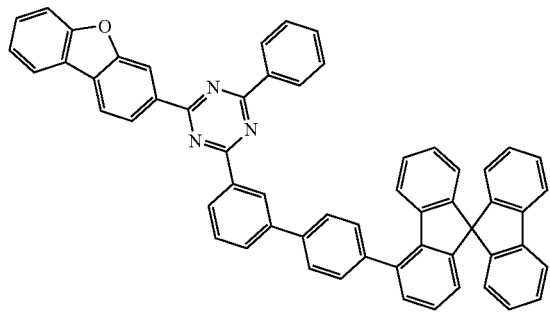
c-328
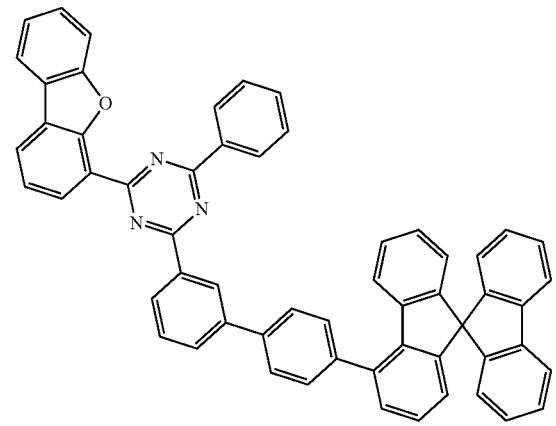
c-329
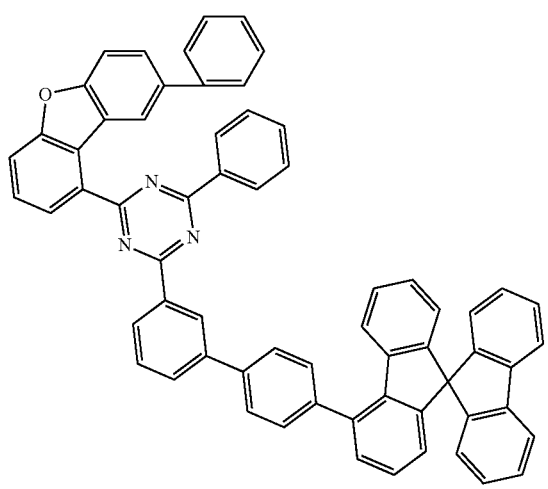
c-330
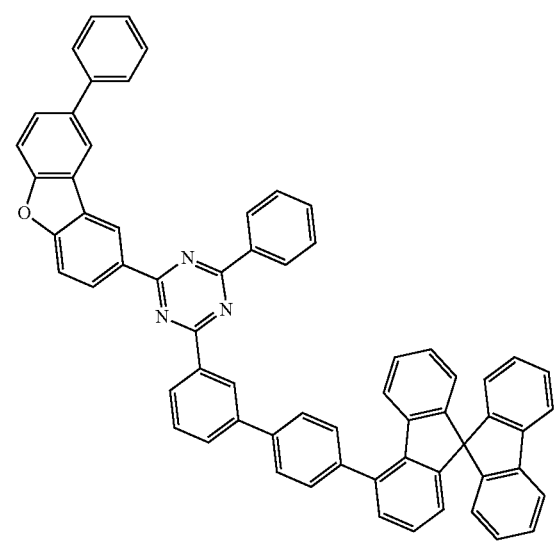
c-331
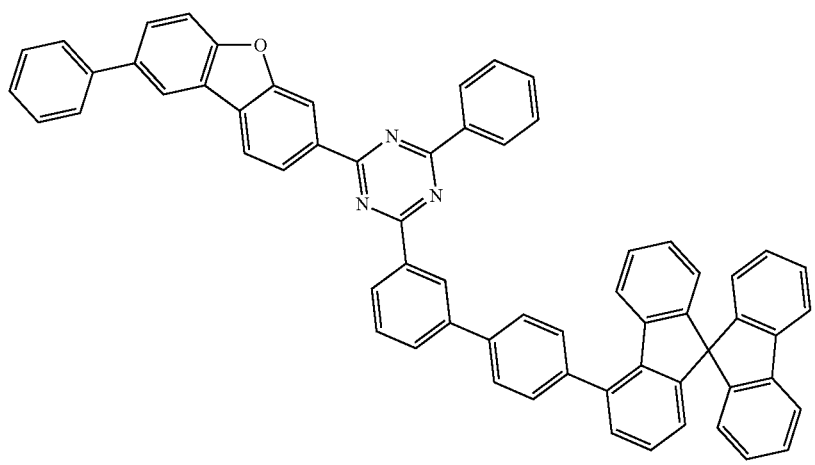

-continued
c-332
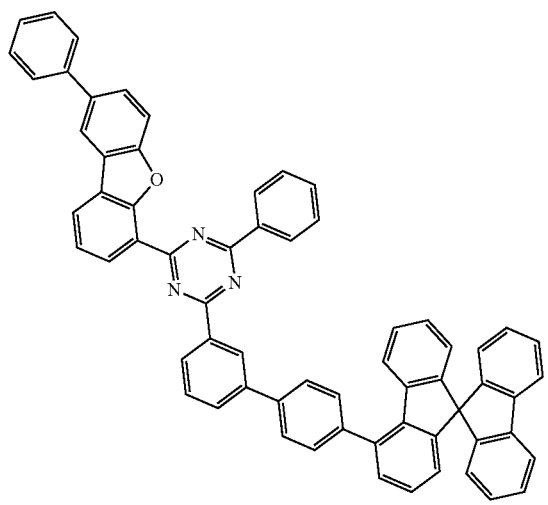
d-1
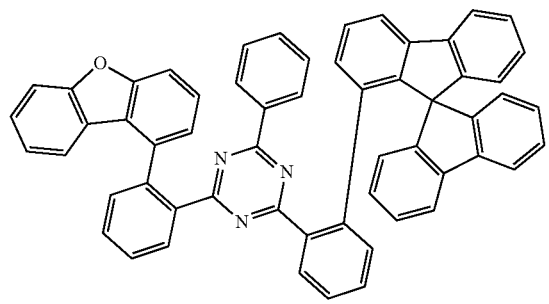
d-2
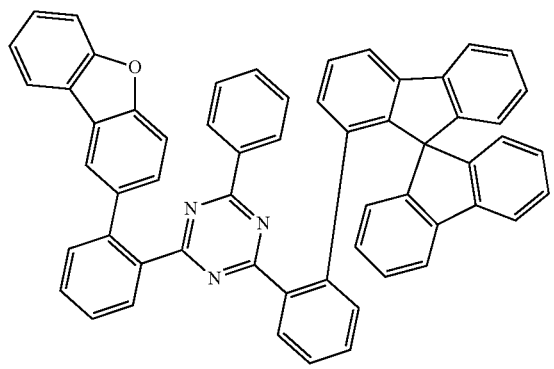
d-3
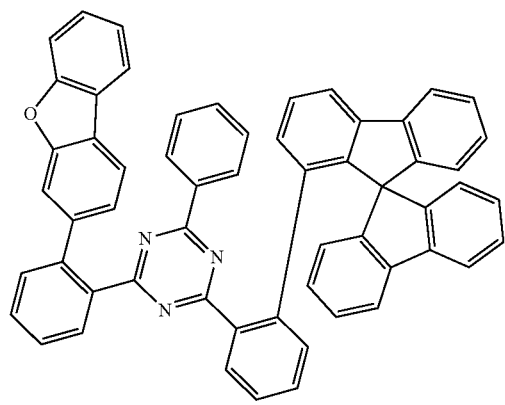
d-4
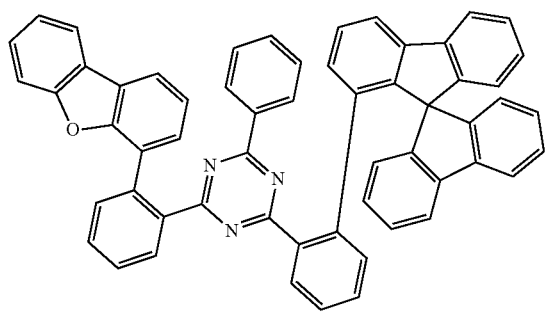
d-5
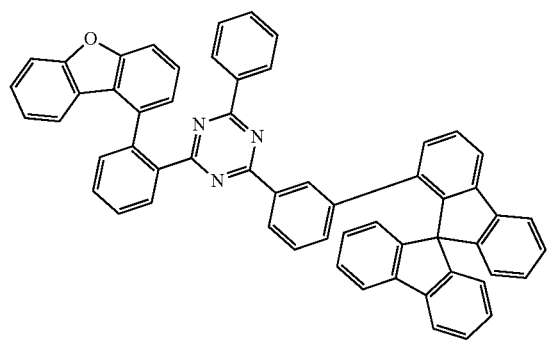

-continued
d-6
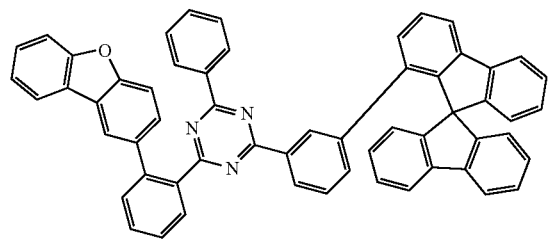
d-7
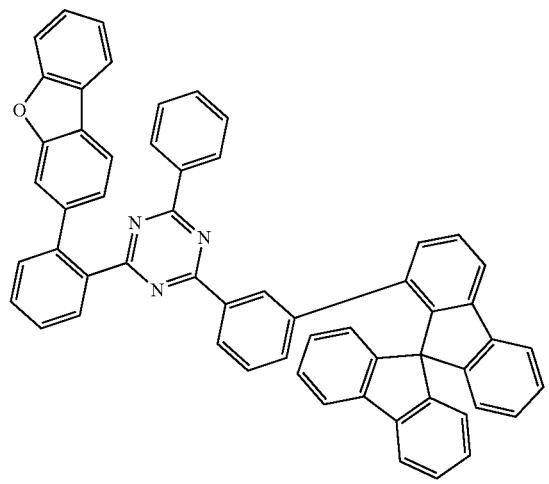
d-8
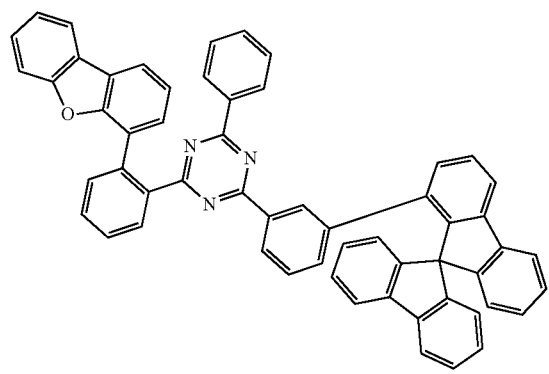
d-9
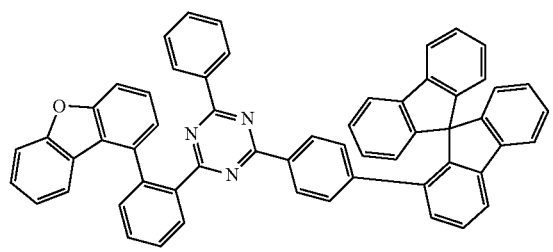
d-10
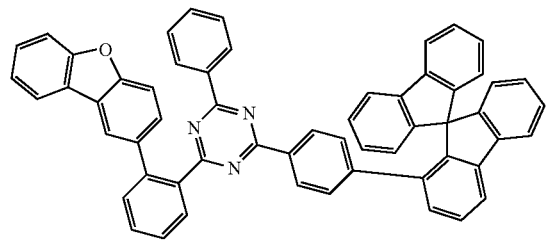
d-11
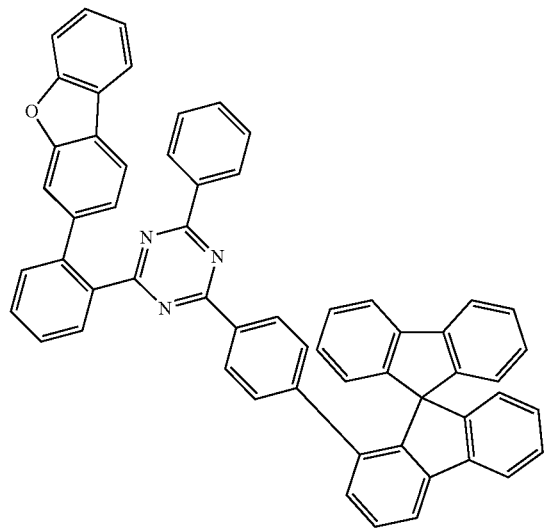

-continued
d-12
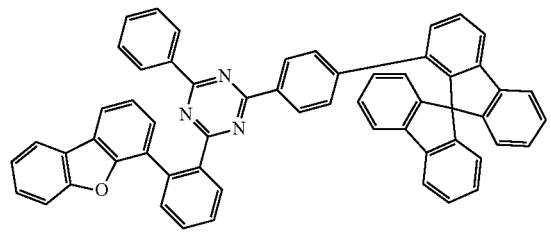
d-13
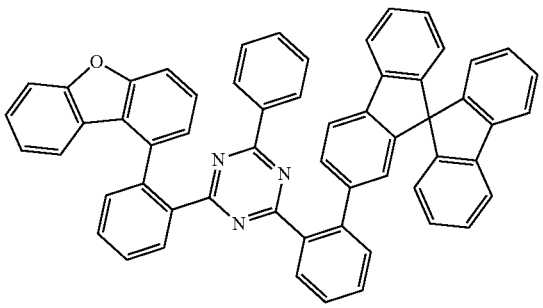
d-14
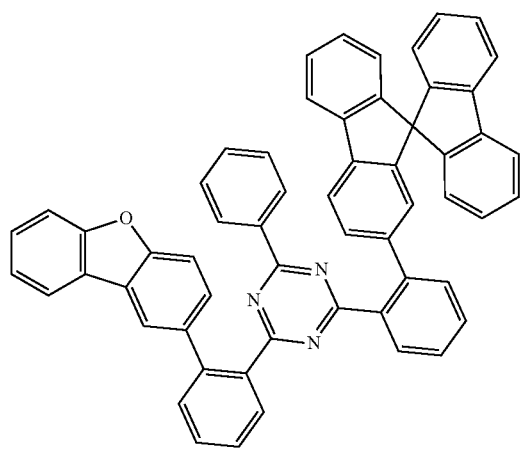
d-15
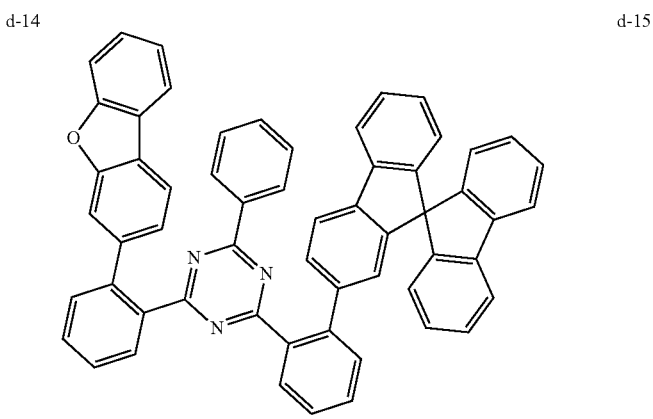
d-16
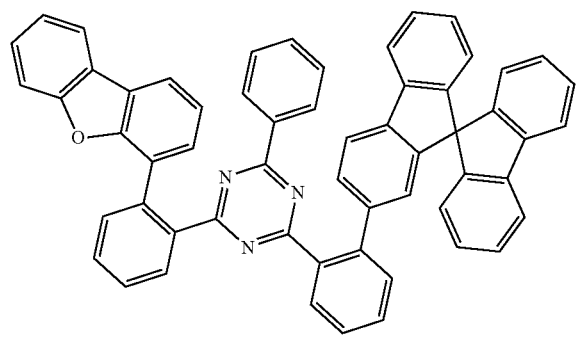
d-17
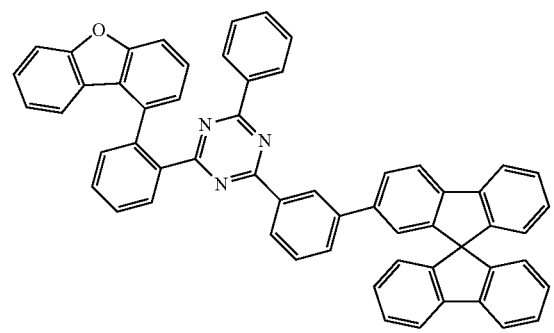
d-18
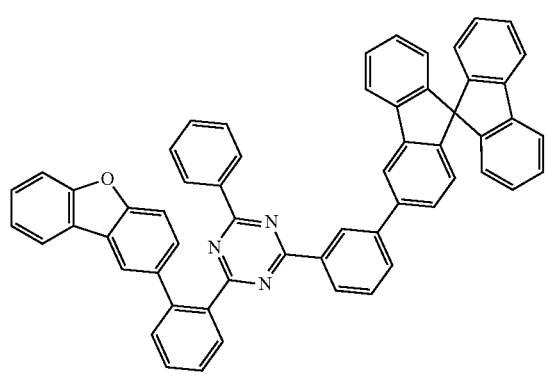
d-19
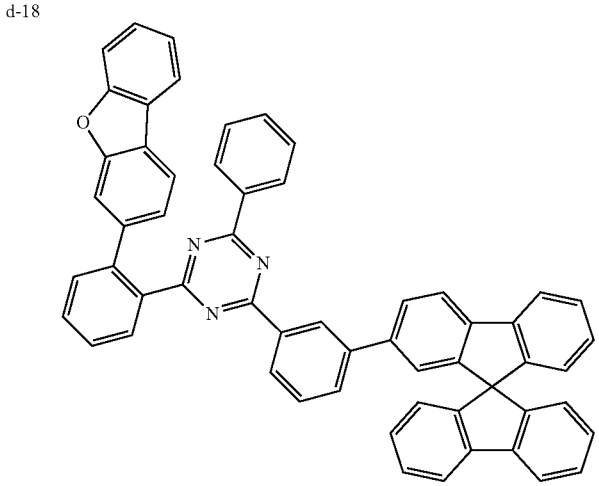

-continued
d-20
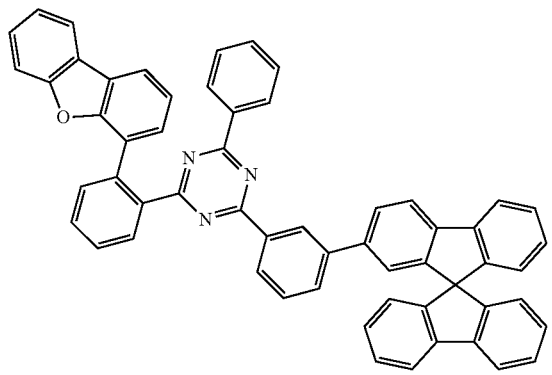
d-21
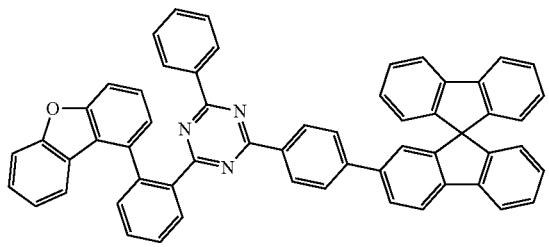
d-22
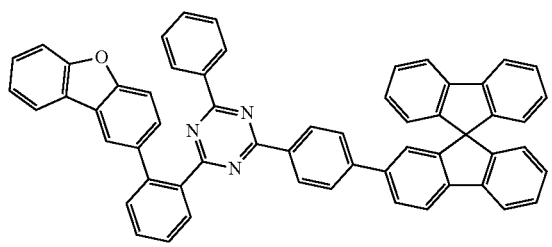
d-23
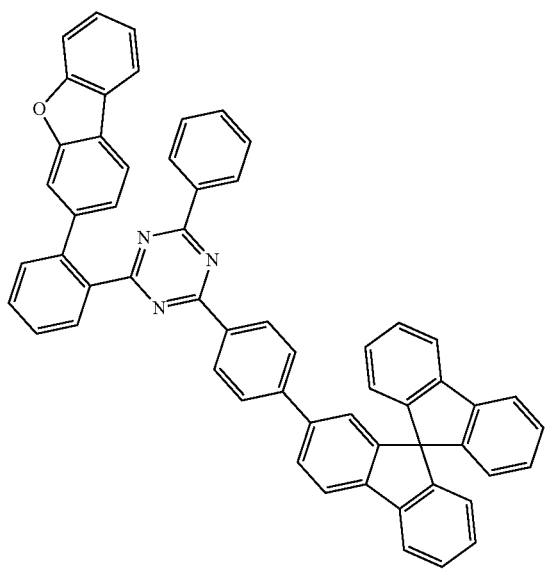
d-24
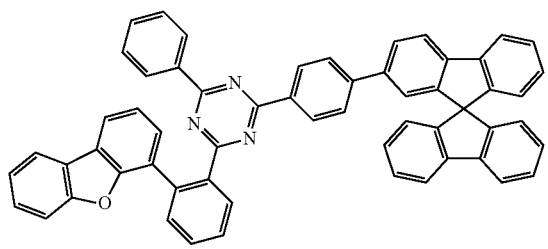
d-25
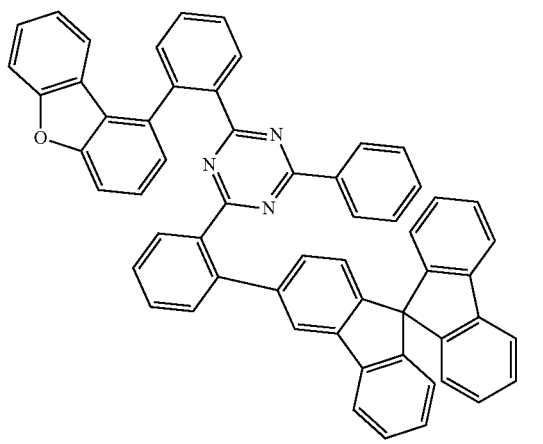

-continued
d-26
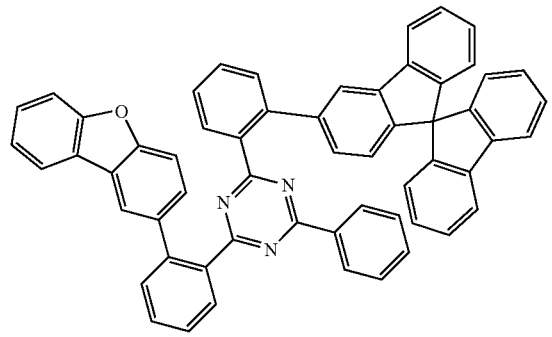
d-27
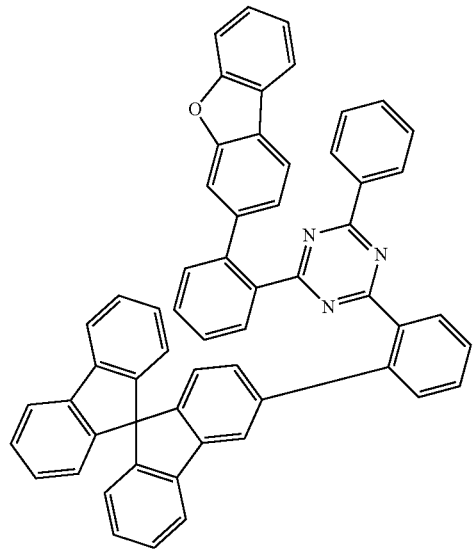
d-28
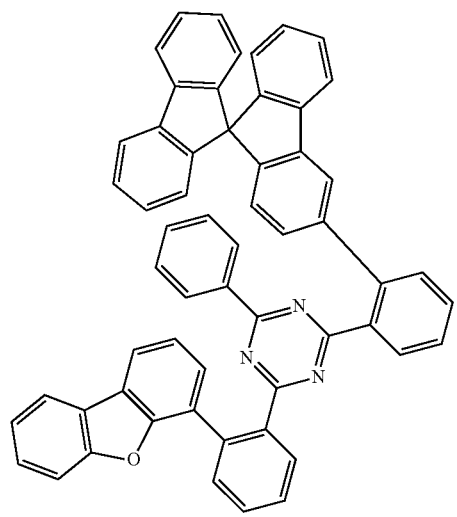
d-29
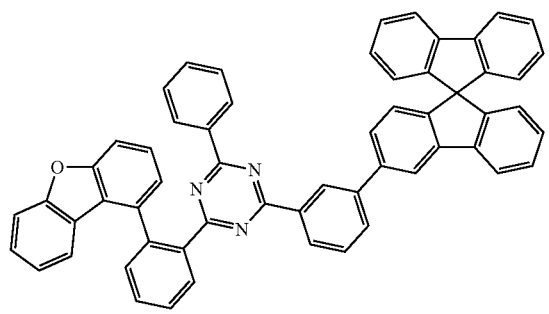
d-30
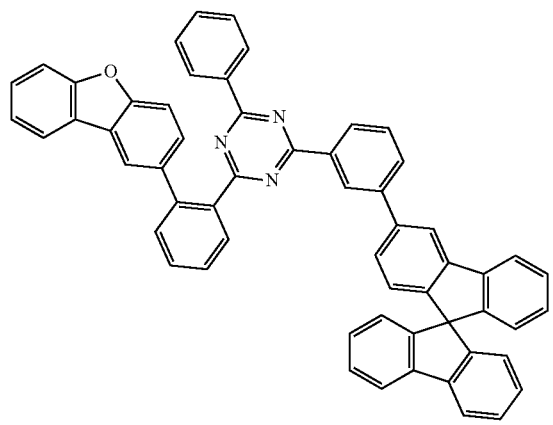
d-31
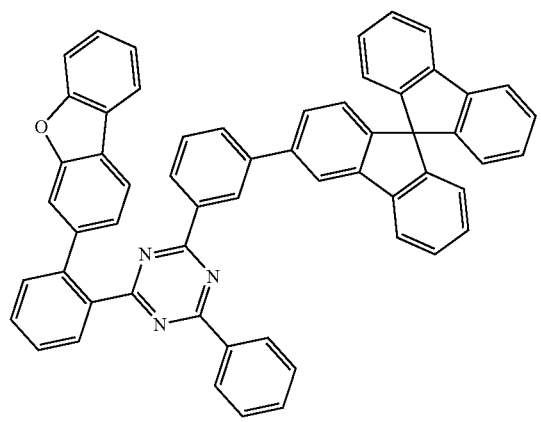

-continued
d-32
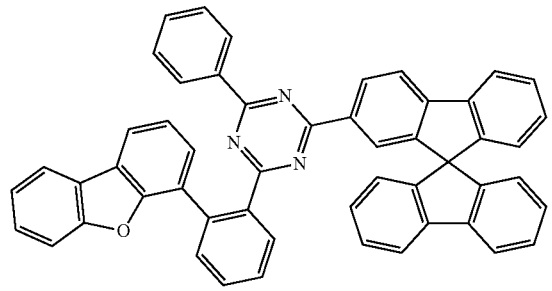
d-33
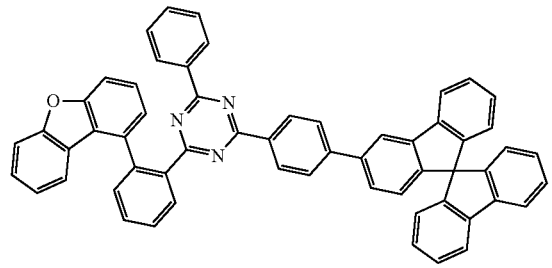
d-34
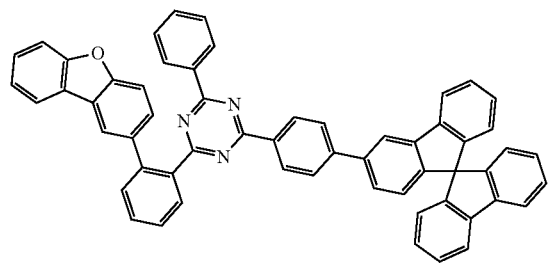
d-35
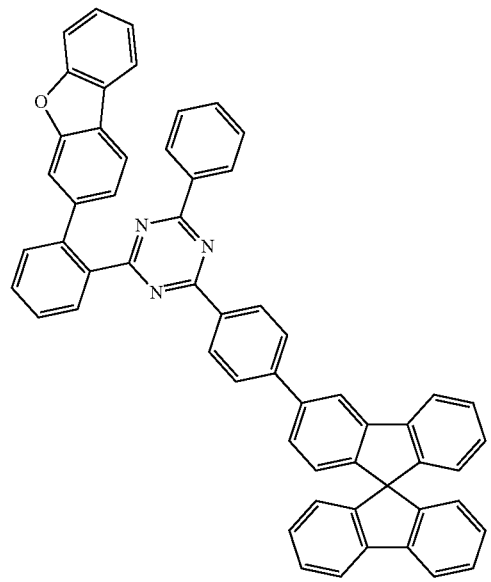
d-36
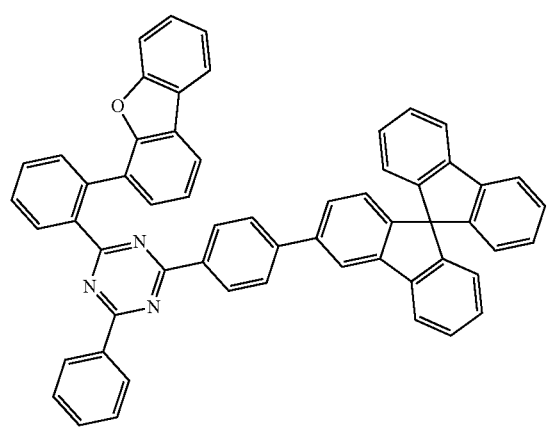
d-37
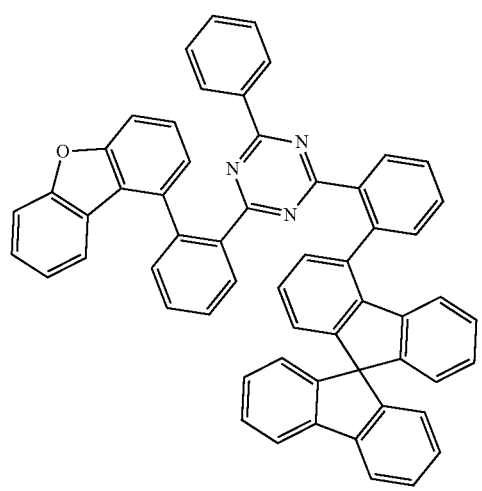

-continued
d-38
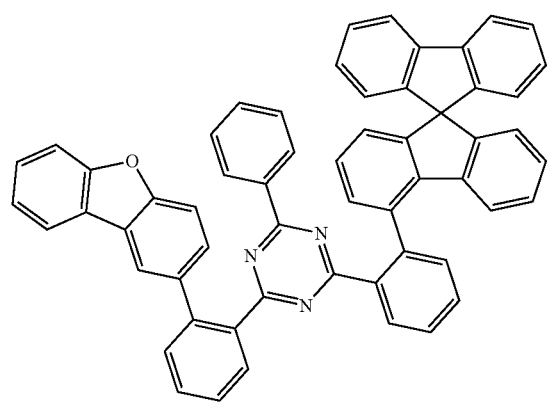
d-39
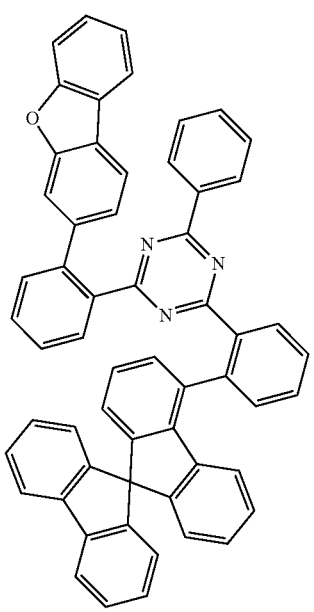
d-40
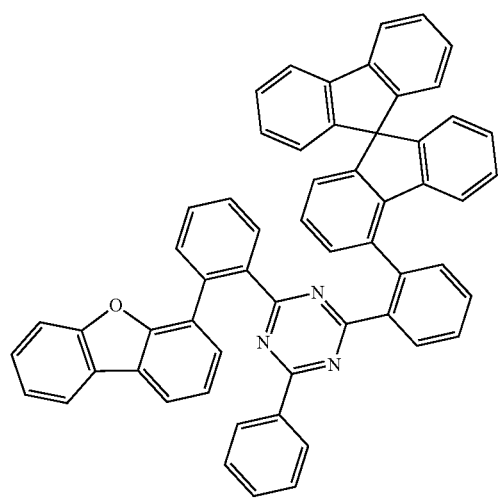
d-41
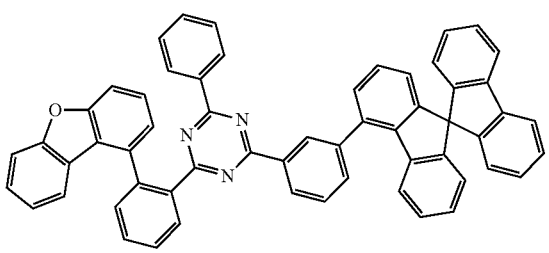
d-42
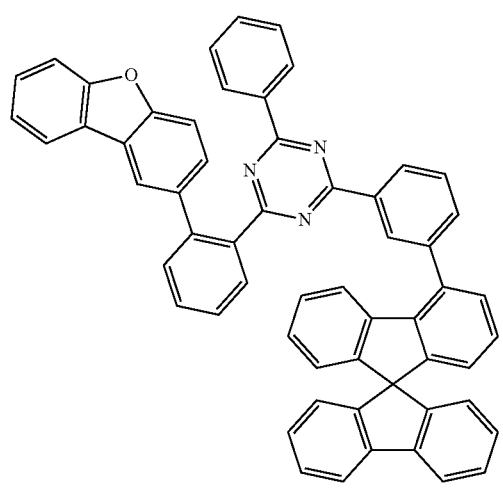
d-43
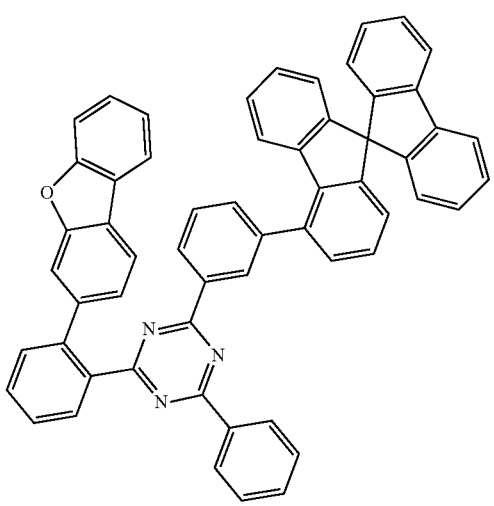

-continued
d-44
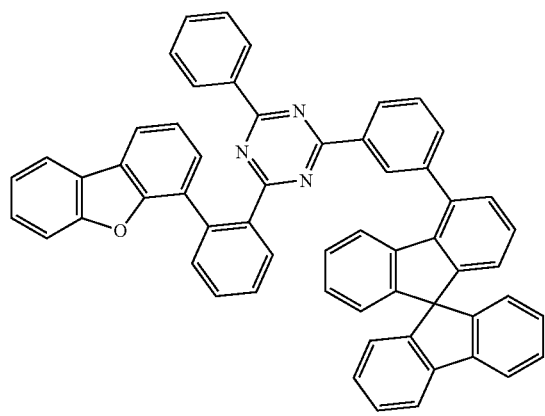
d-45
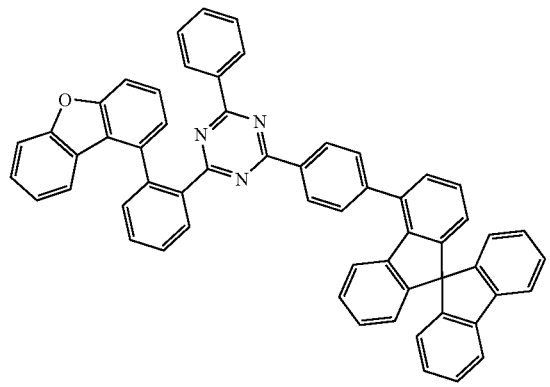
d-46
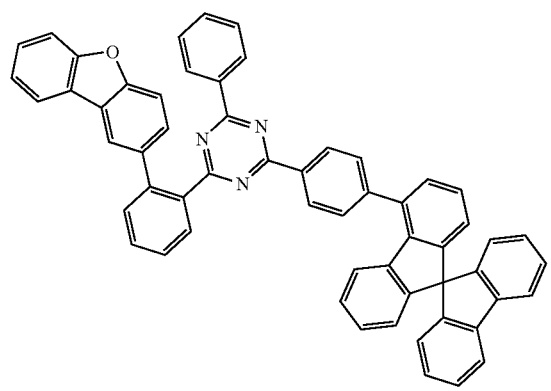
d-47
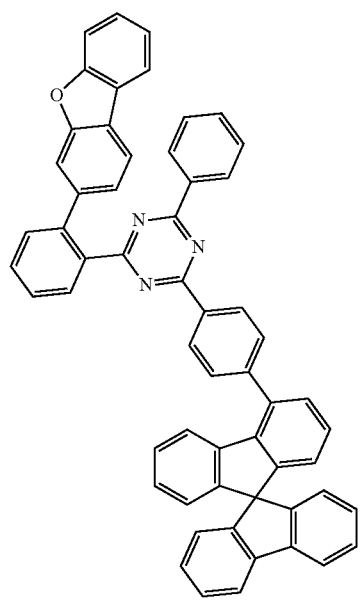
d-48
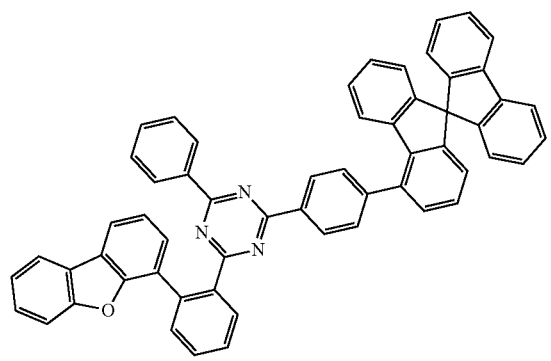
d-49
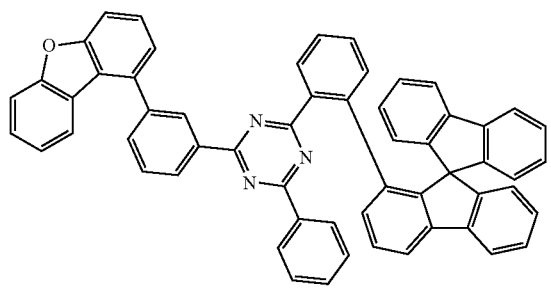

-continued
d-50
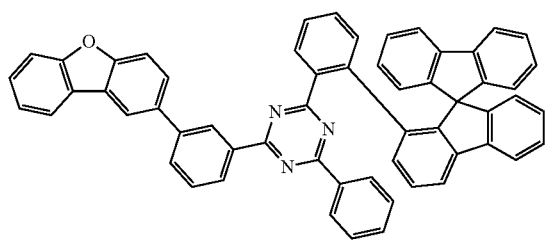
d-51
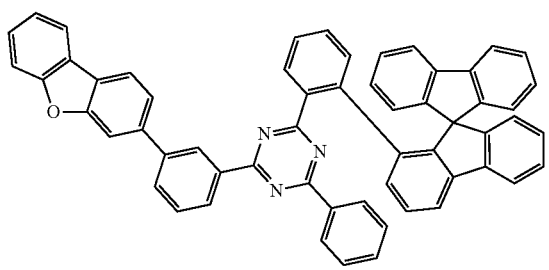
d-52
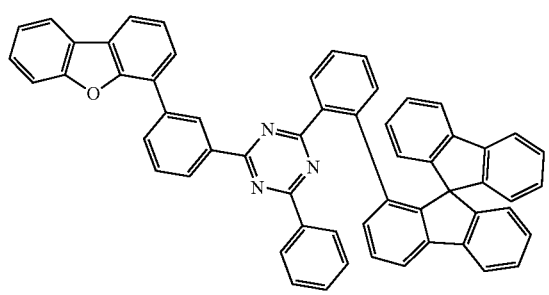
d-53
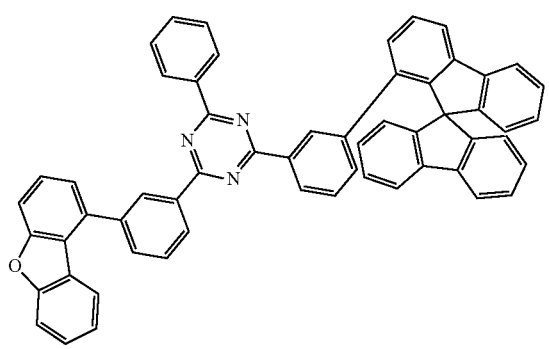
d-54
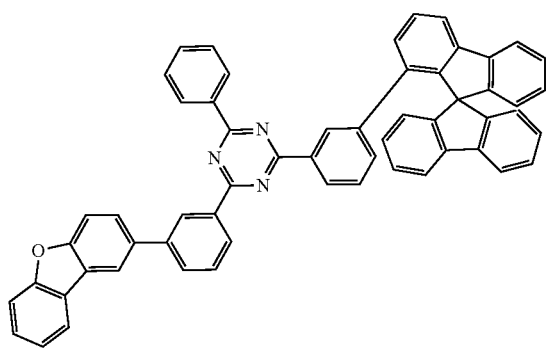
d-55
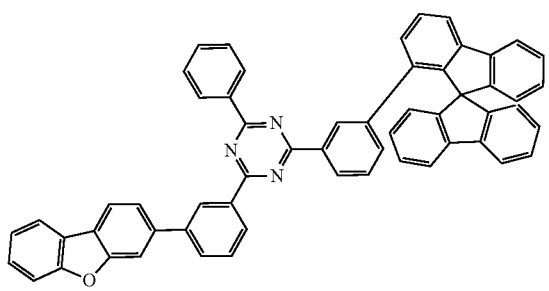
d-56
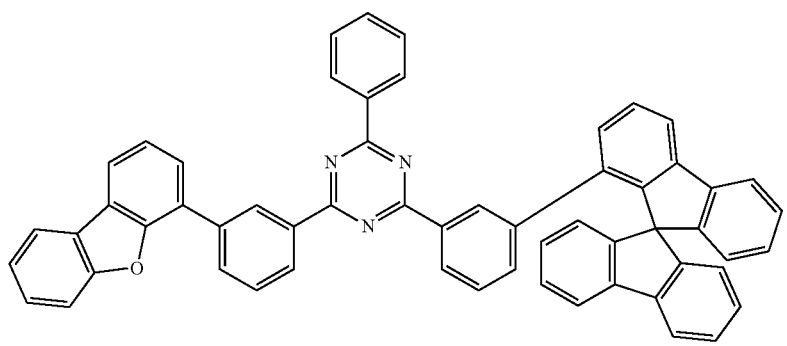

-continued
d-57
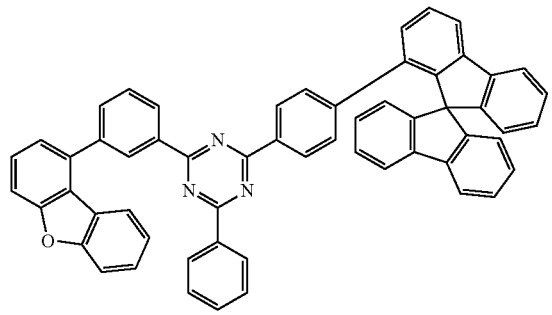
d-58
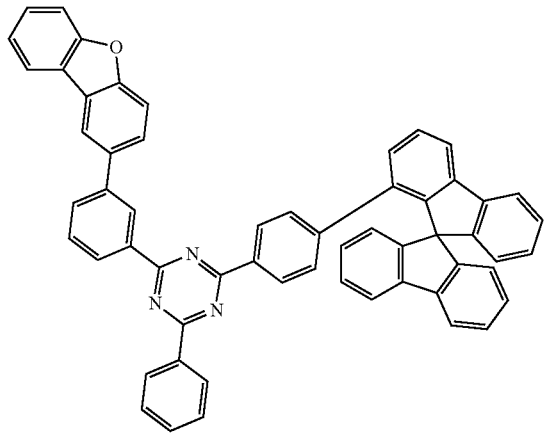
d-59
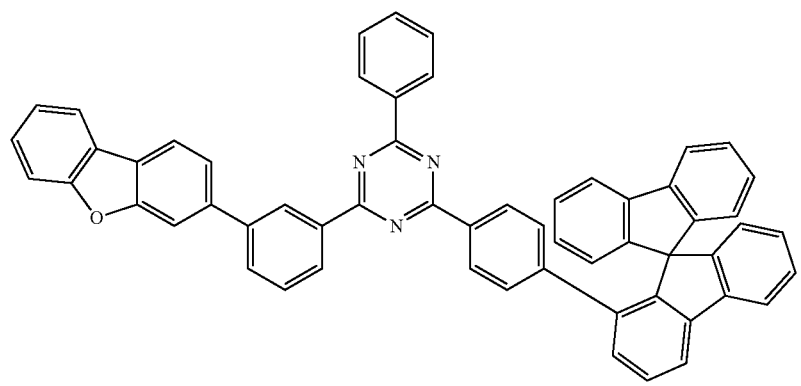
d-60
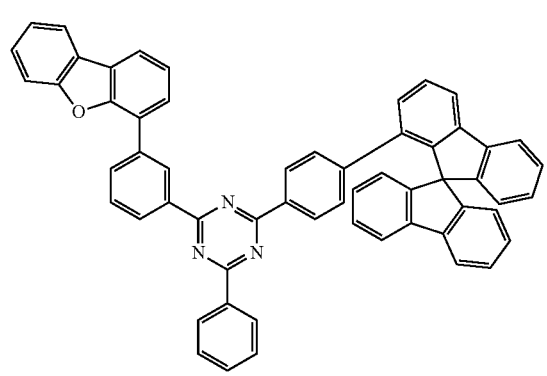
d-61
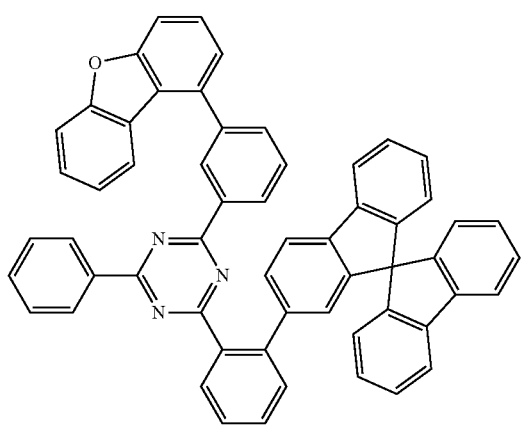

-continued
d-62
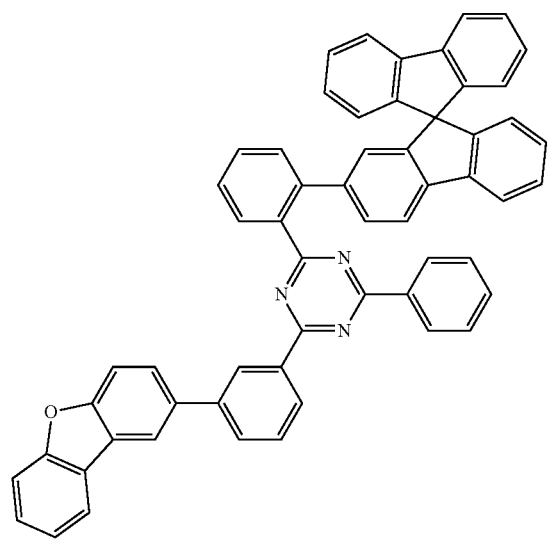
d-63
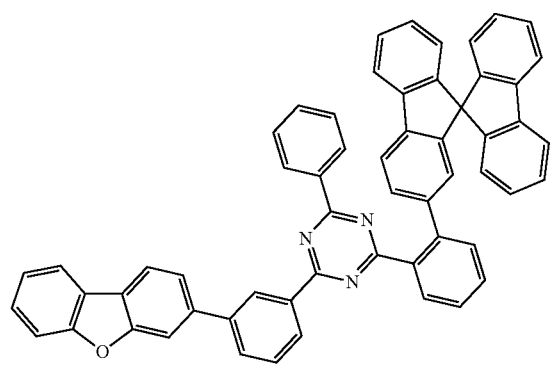
d-64
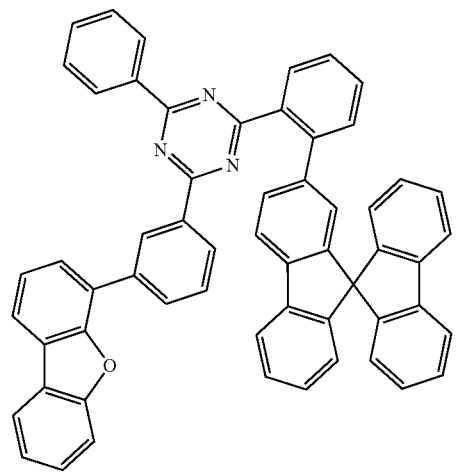
d-65
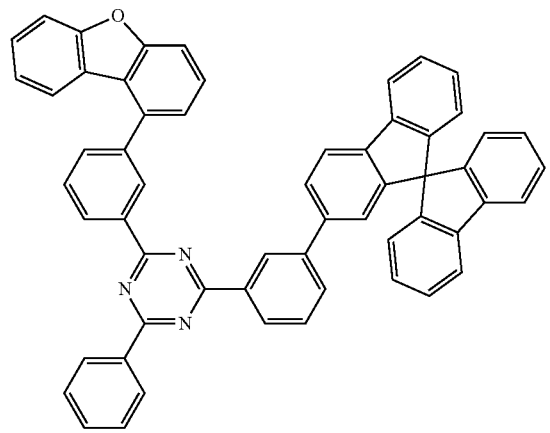
d-66
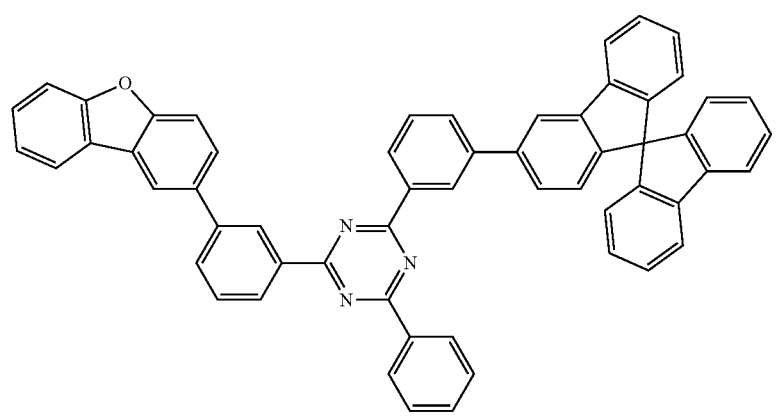

d-67
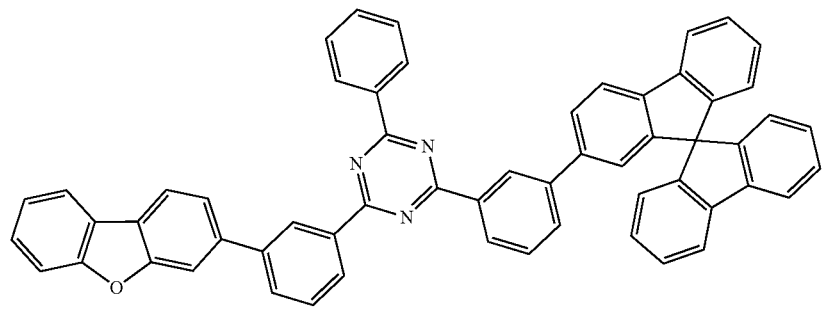
d-68
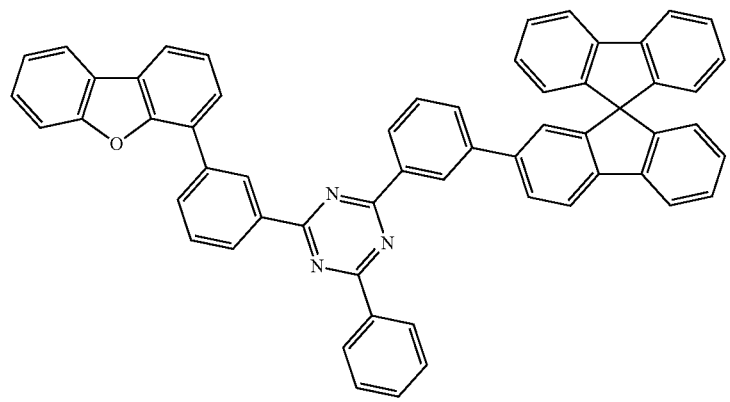
d-69
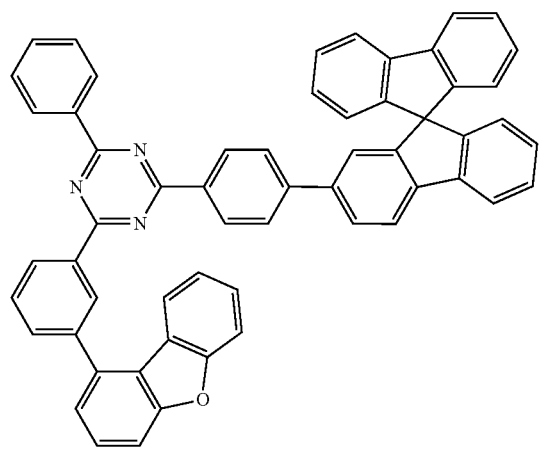
d-70
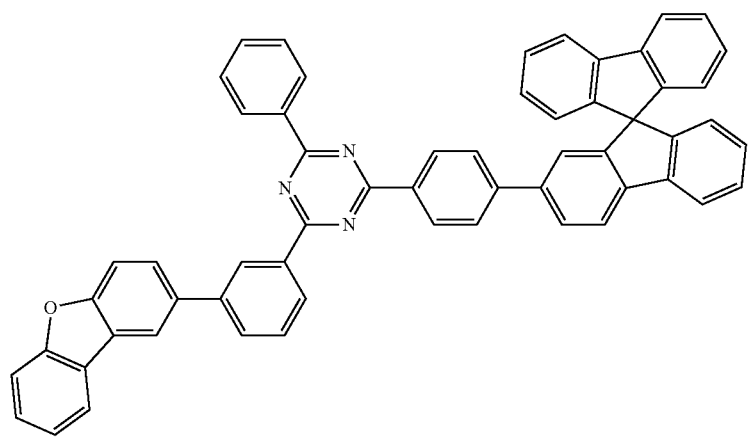

d-71
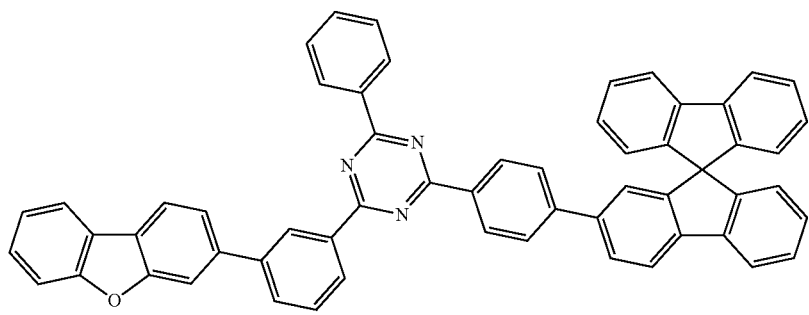
d-72
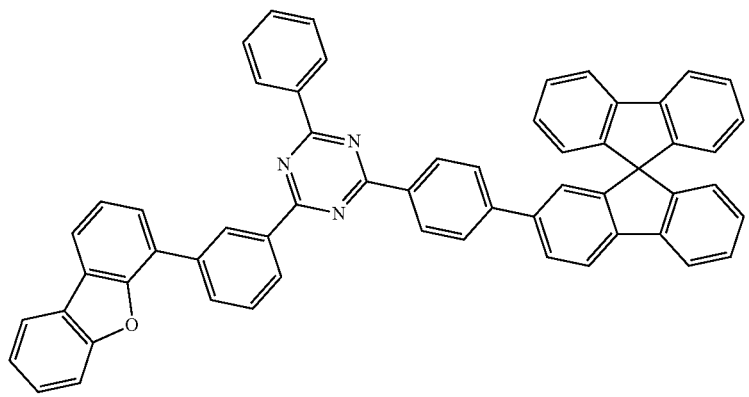
d-73
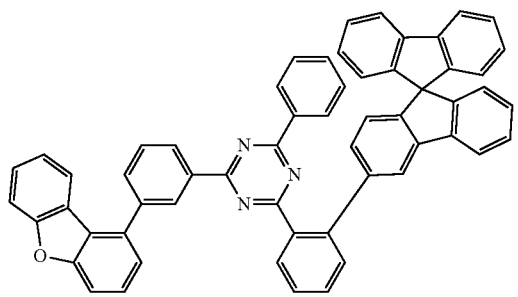
d-74
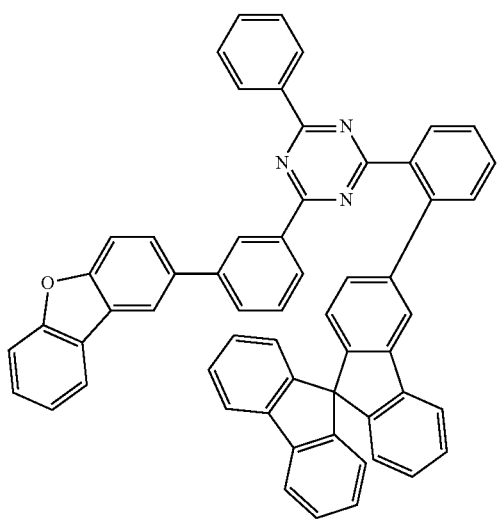

-continued
d-75
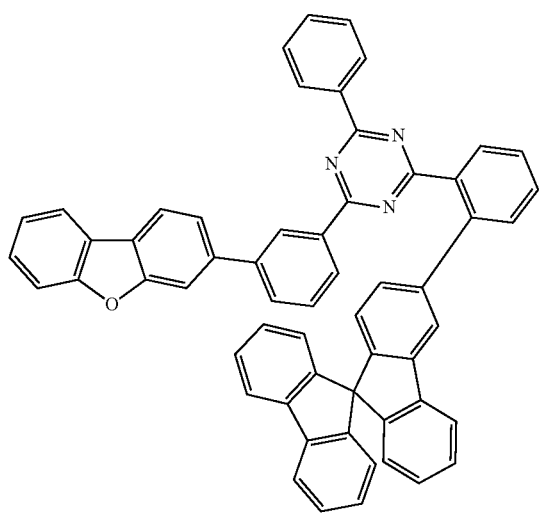
d-76
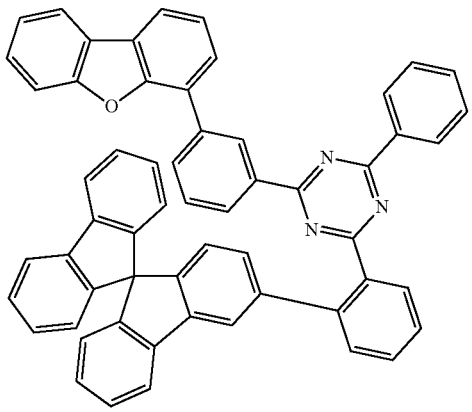
d-77
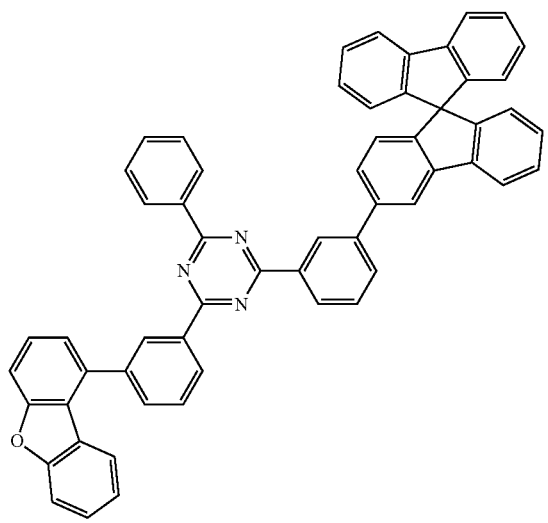
d-78
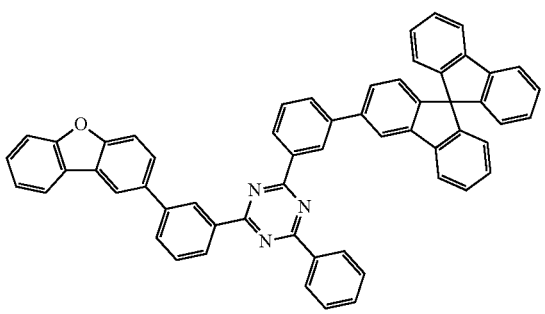
d-79
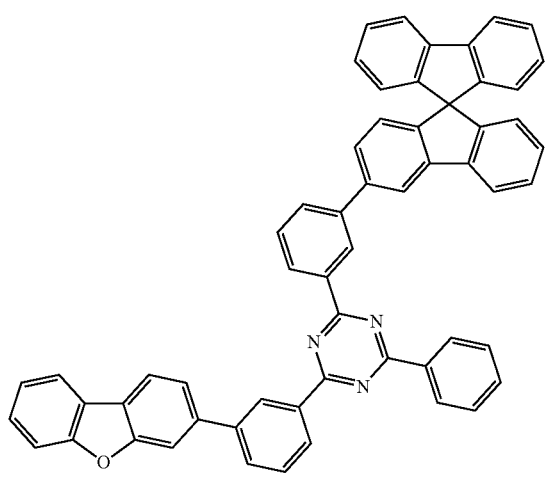
d-80
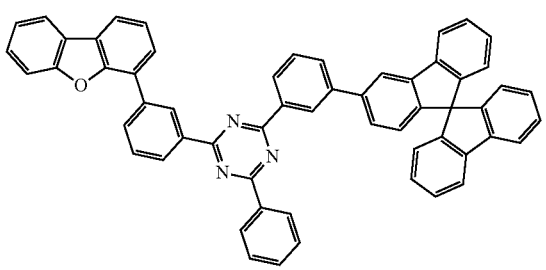

-continued
d-81
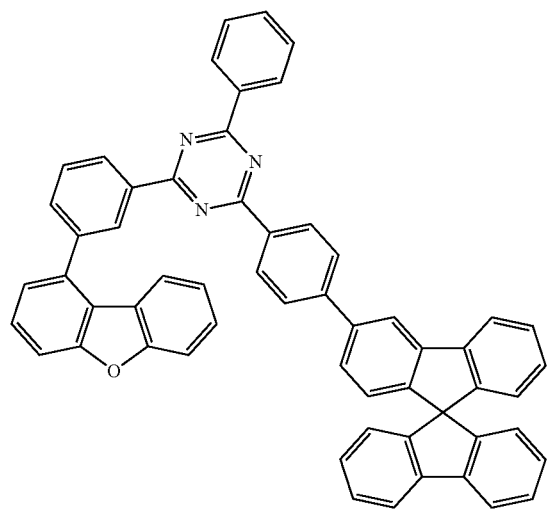
d-82
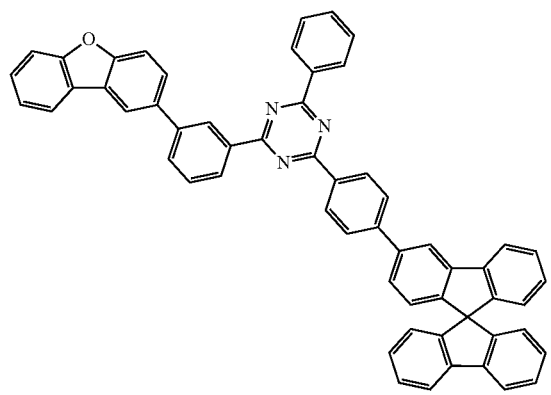
d-83
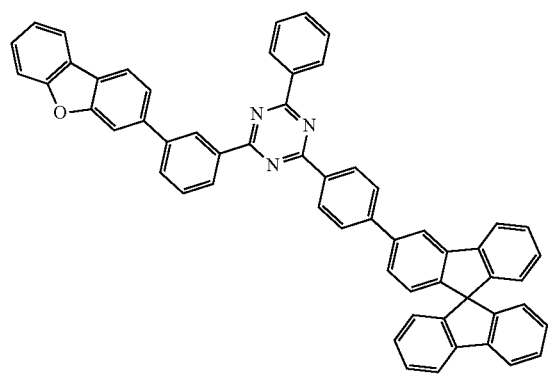
d-84
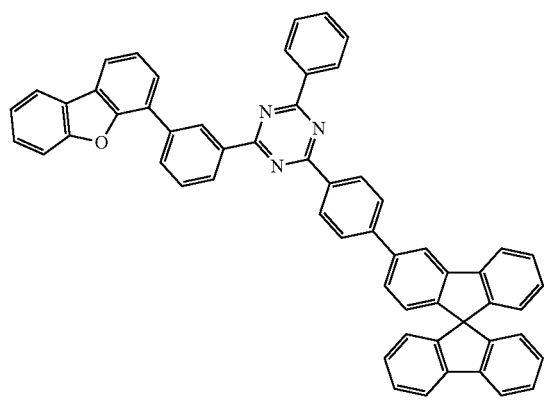
d-85
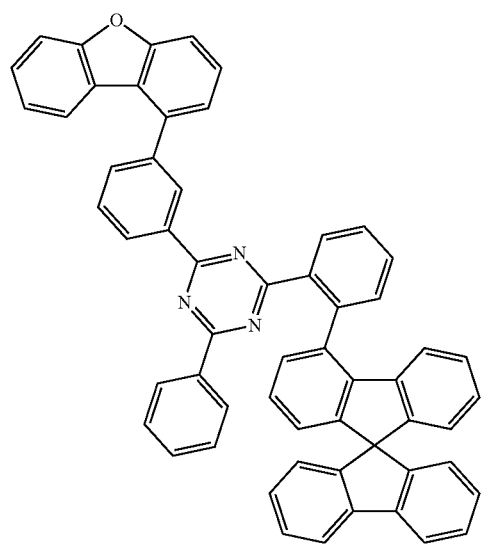
d-86
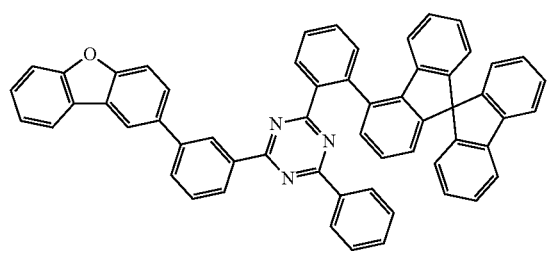

-continued
d-87
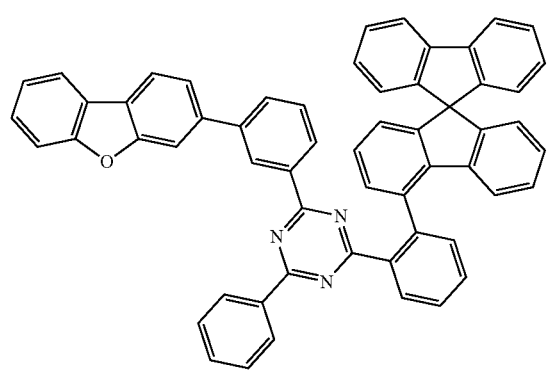
d-88
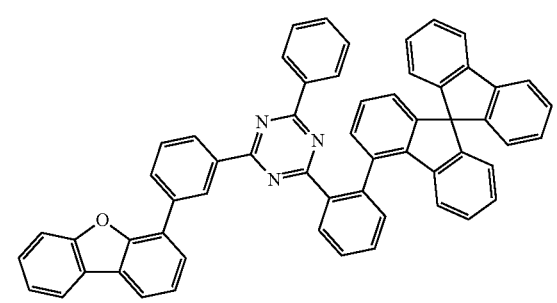
d-89
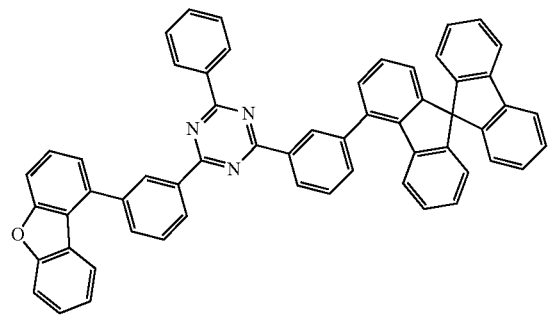
d-90
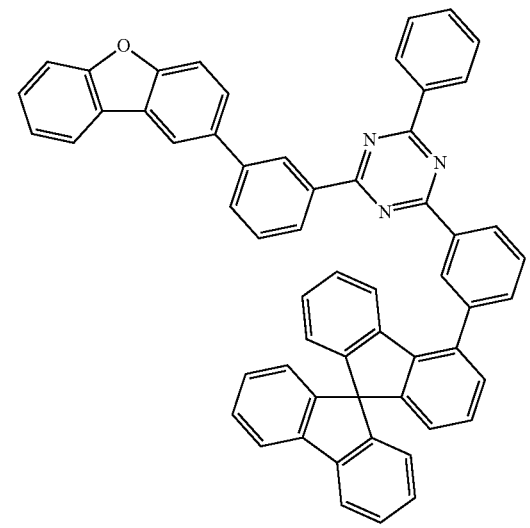
d-91
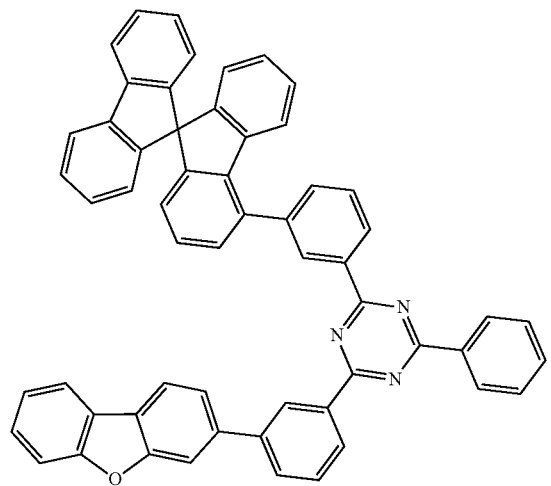
d-92
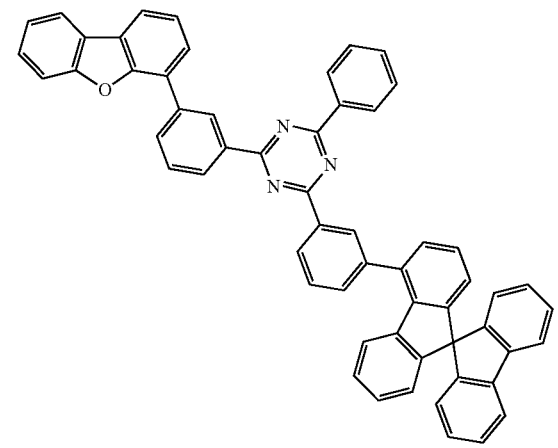

153
d-93
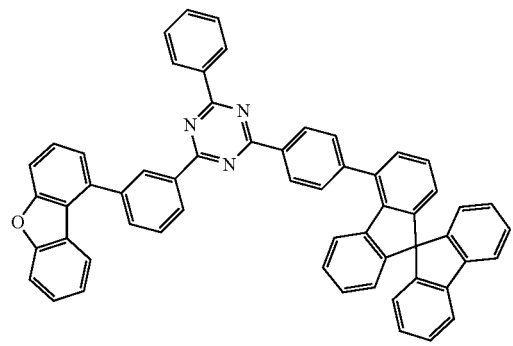
154
d-94
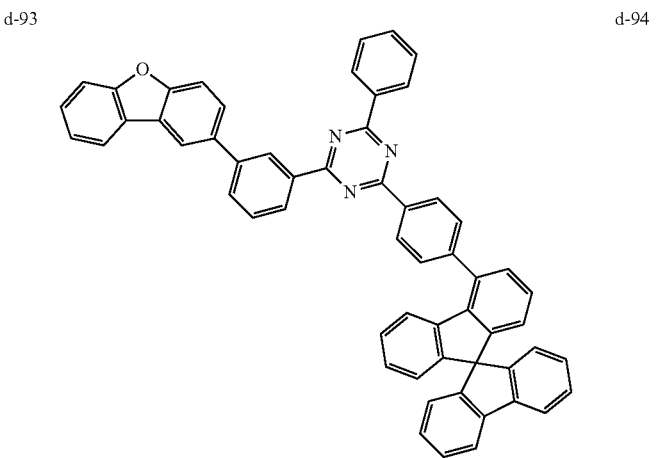
d-95
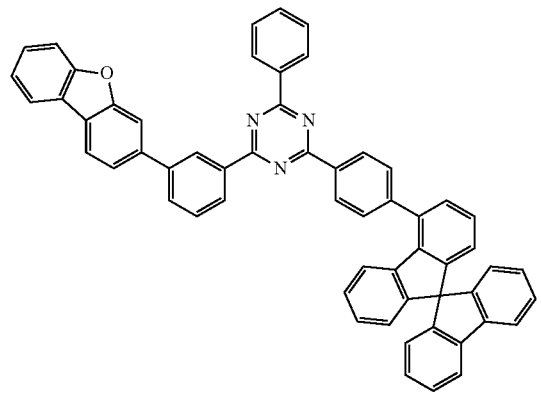
d-96
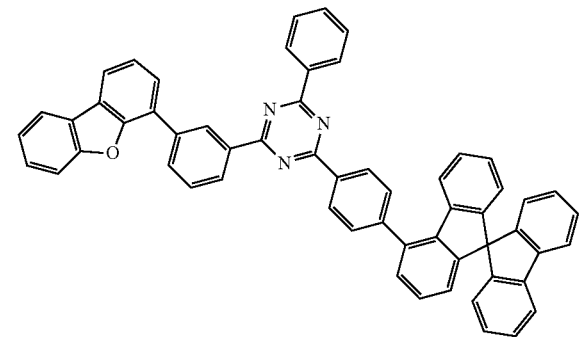
d-97
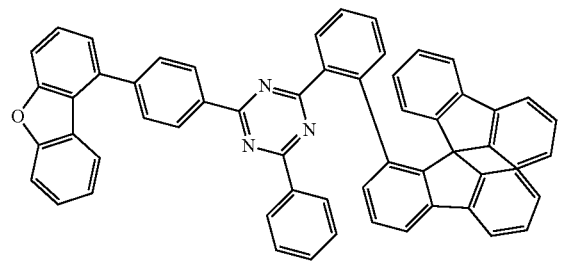
d-98
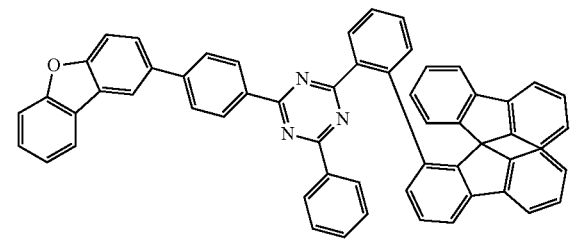
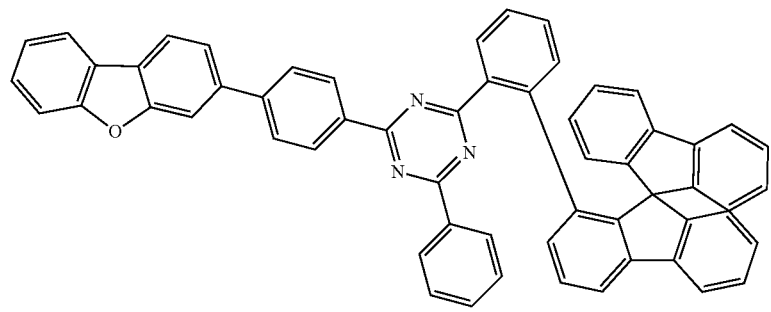

-continued
d-100
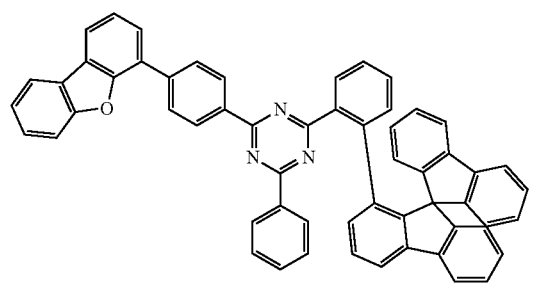
d-101
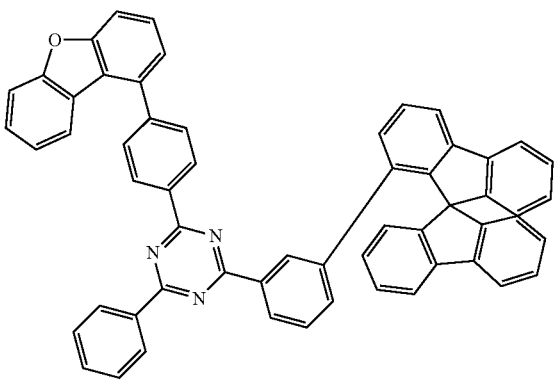
d-102
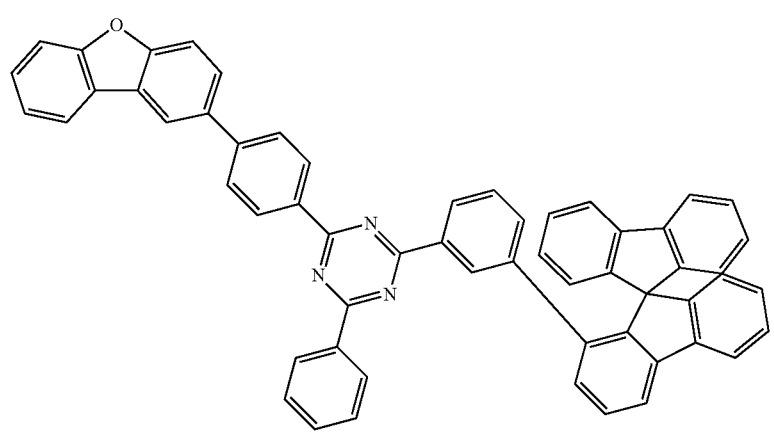
d-103
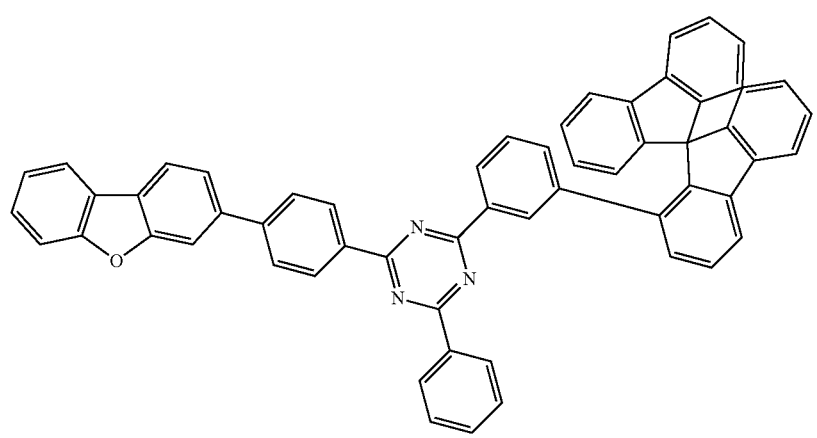

-continued
d-104
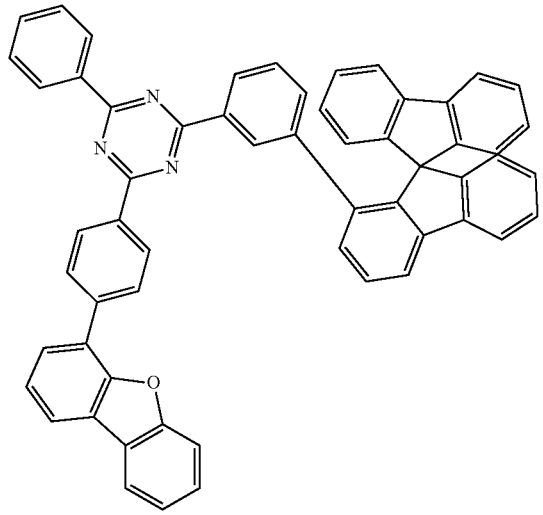
d-105
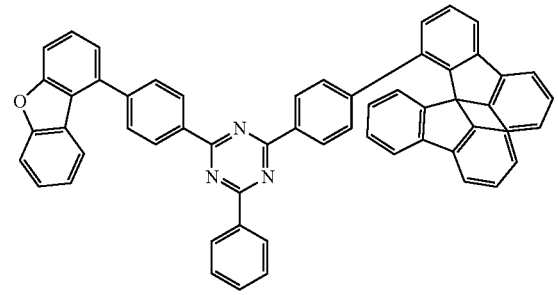
d-106
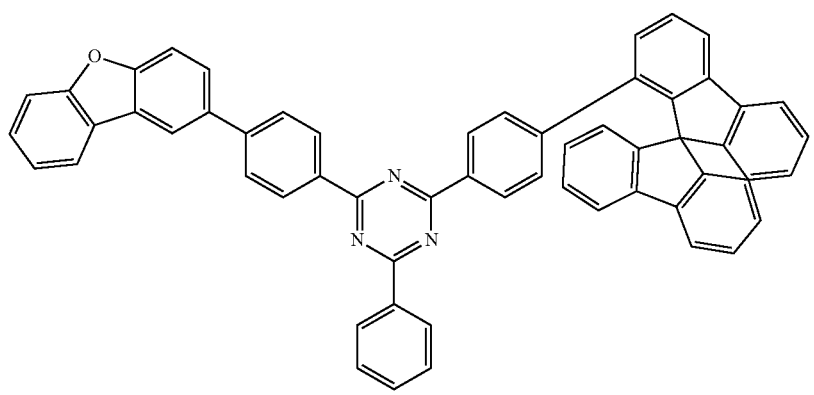
d-107
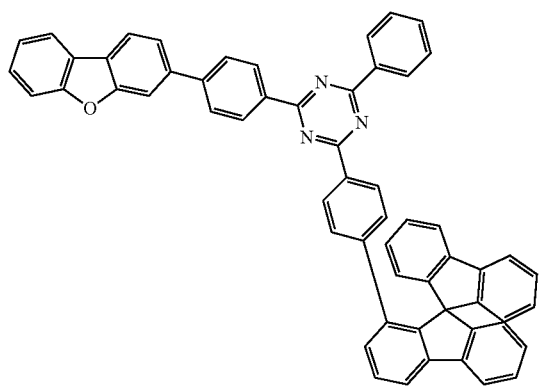
d-108
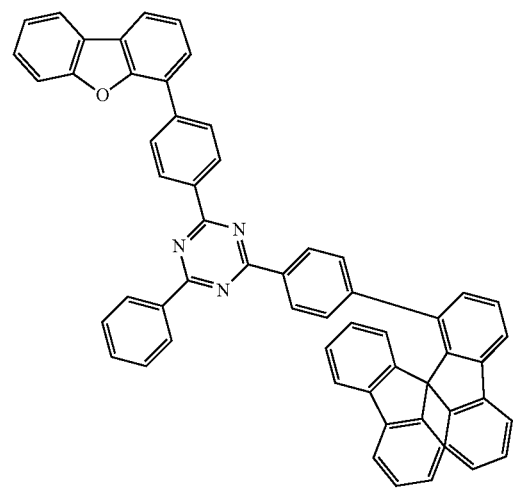

-continued
d-109
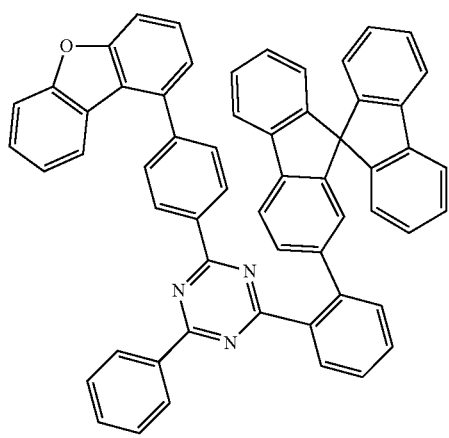
d-110
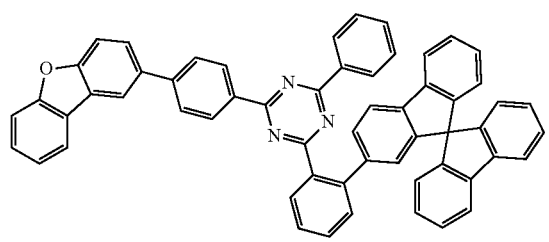
d-111
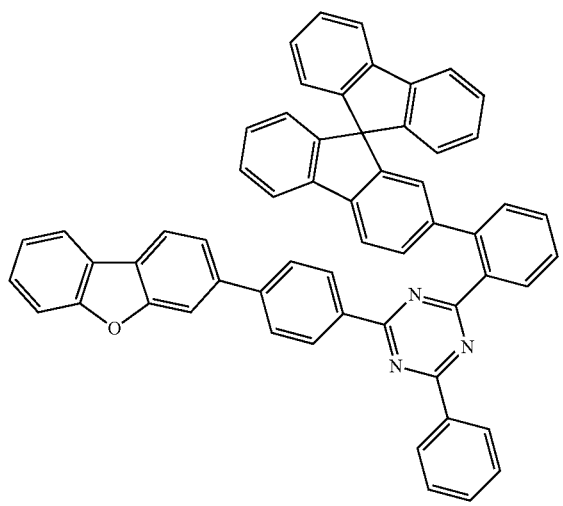
d-112
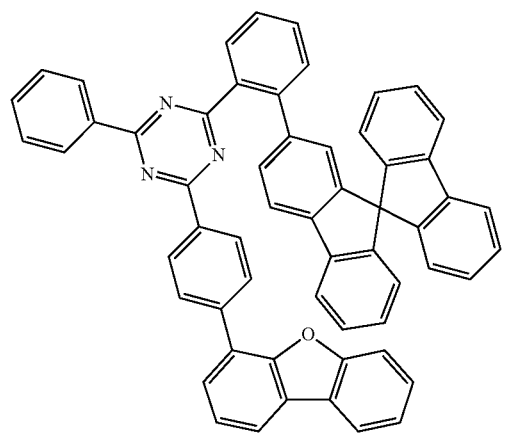
d-113
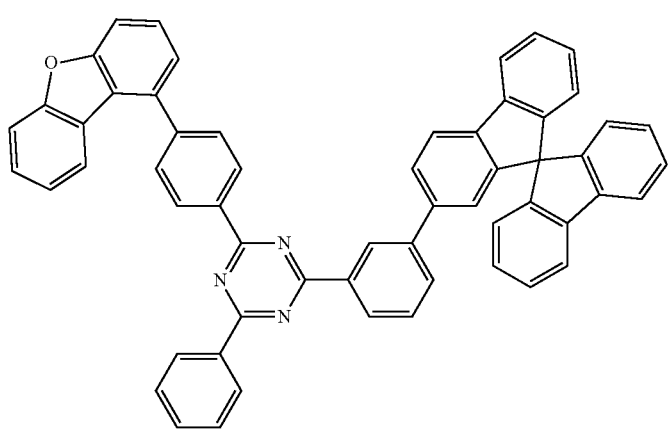

d-114
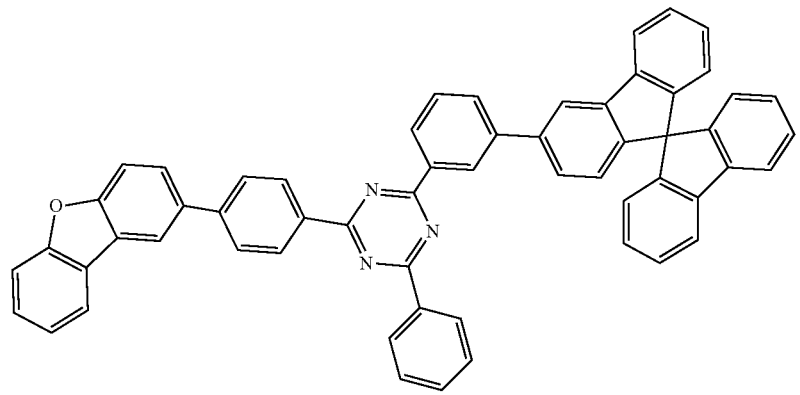
d-115
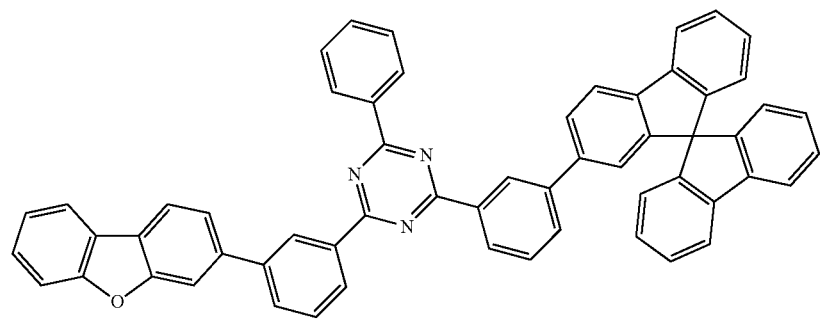
d-116
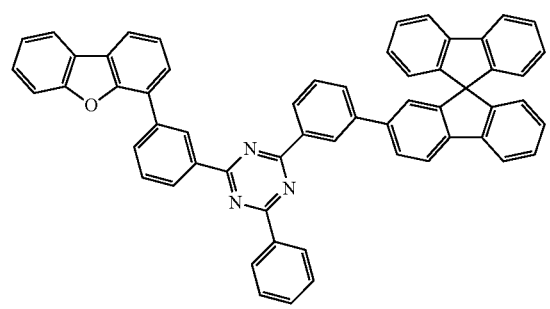
d-117
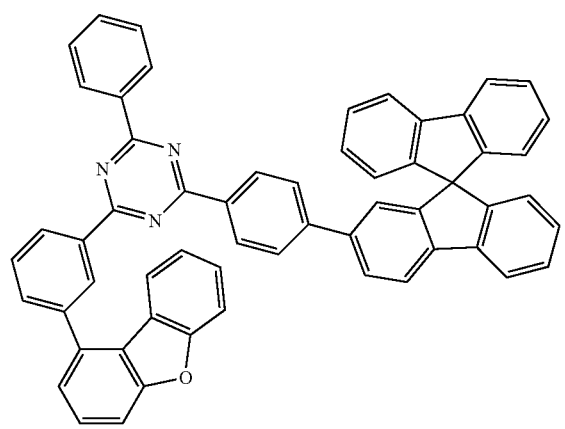
d-118
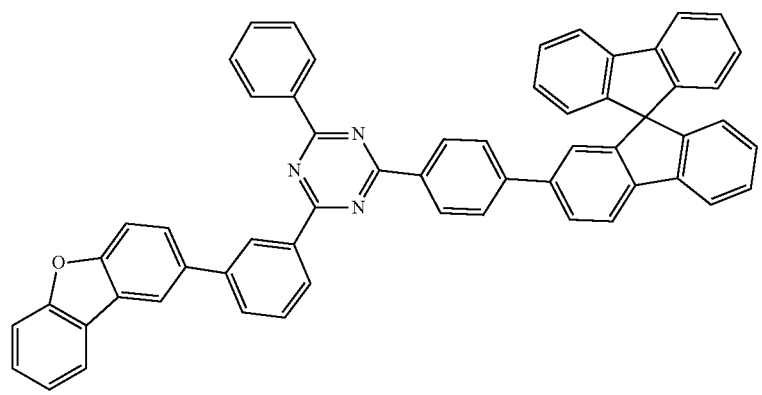

-continued
d-119
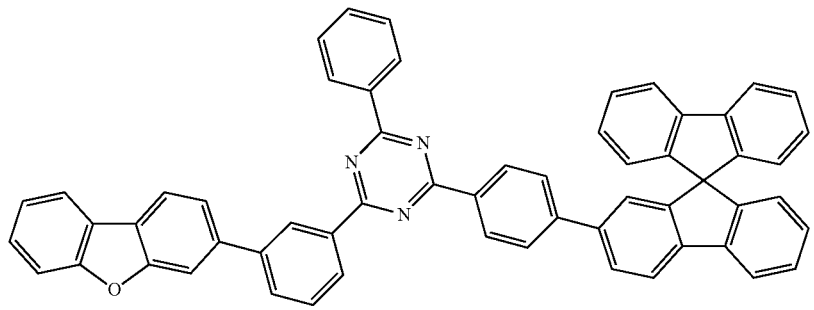
d-120
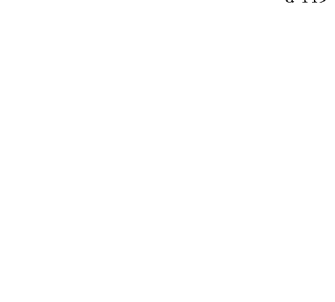
d-121
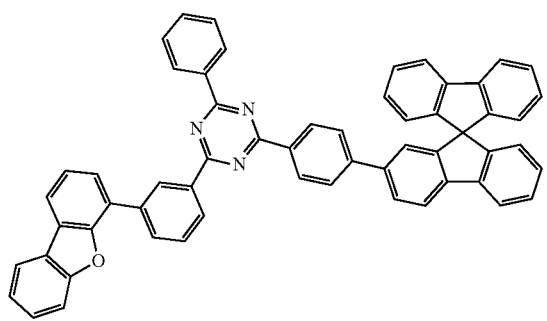
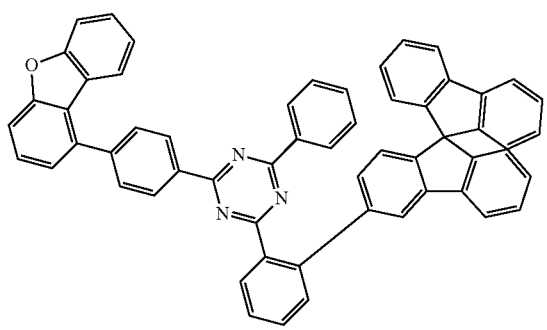
d-122
d-123
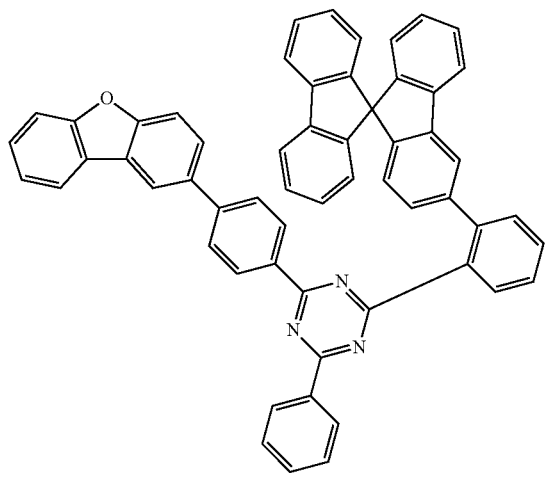
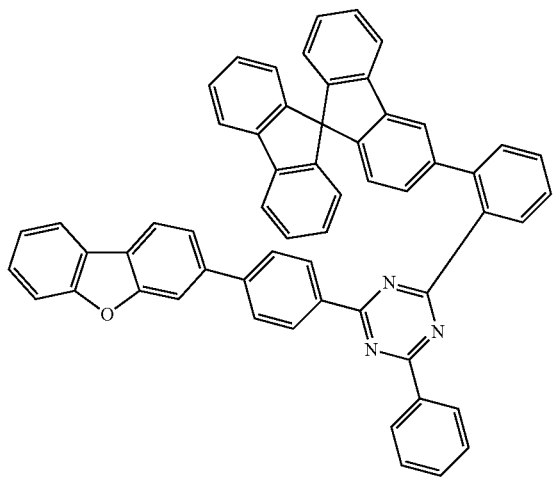
d-124
d-125
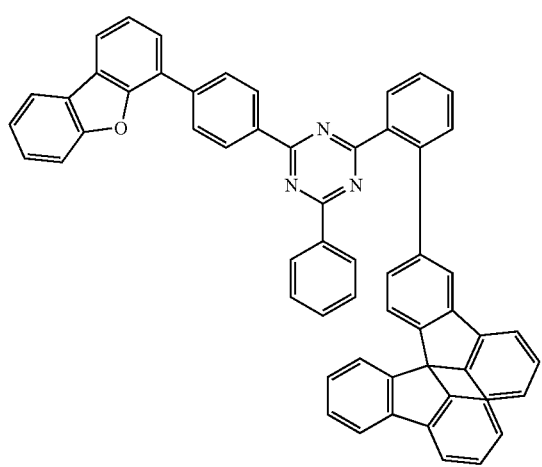
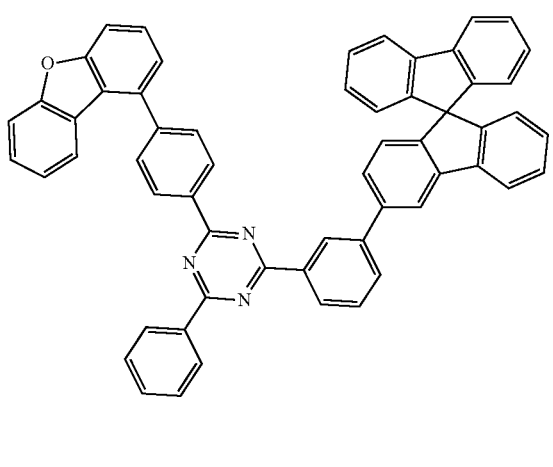

-continued
d-126
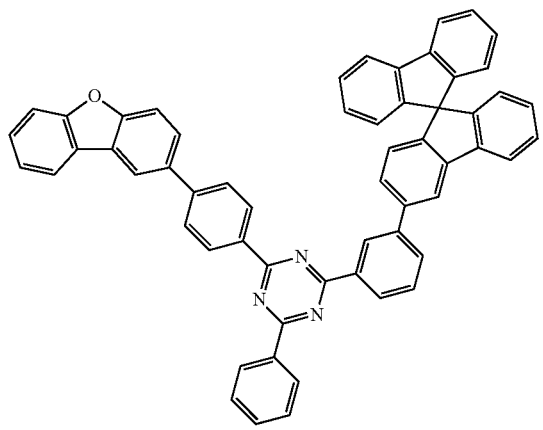
d-127
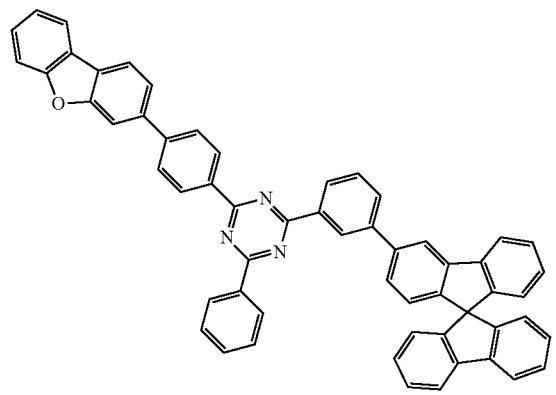
d-128
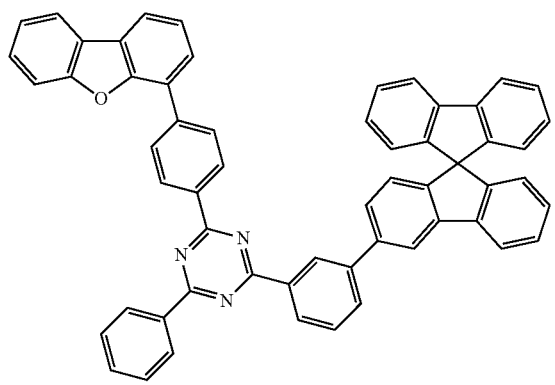
d-129
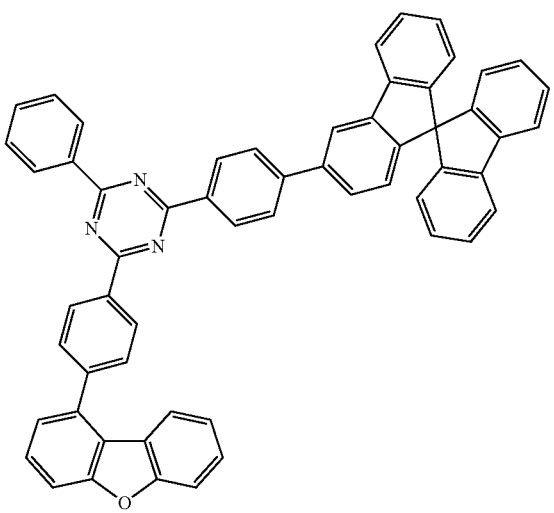
d-130
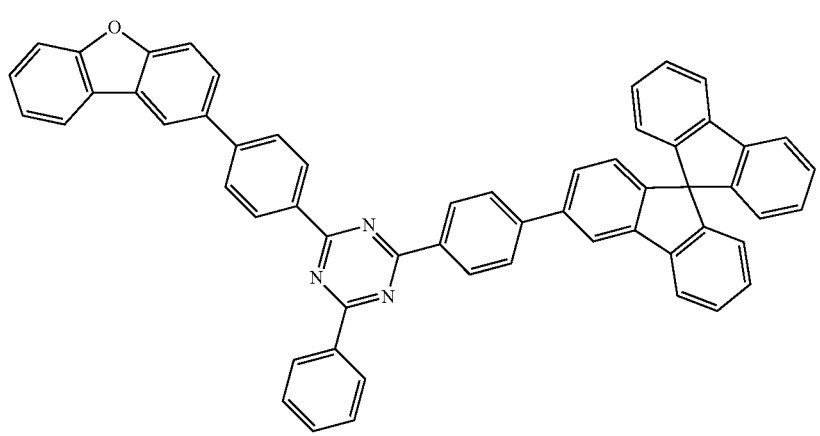

-continued
d-131
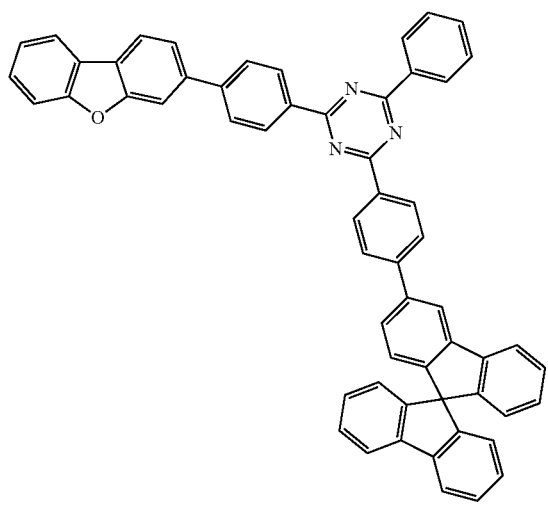
d-132
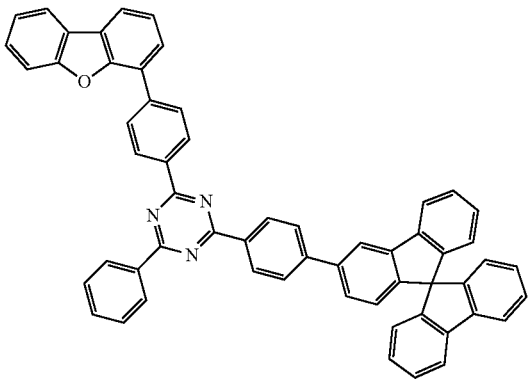
d-133
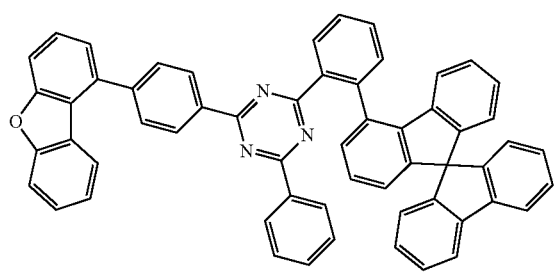
d-134
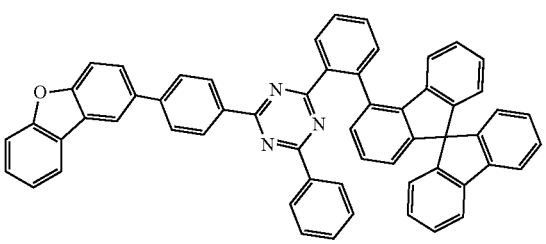
d-135
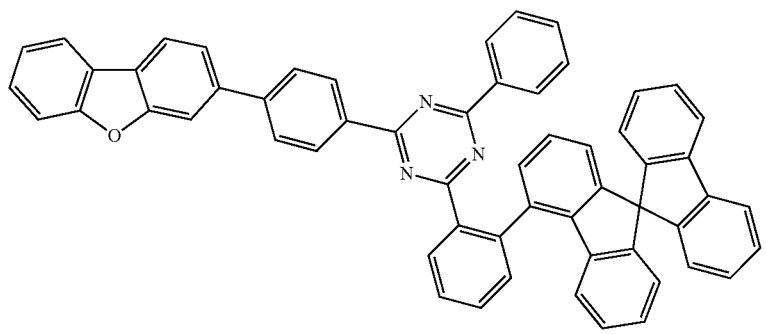
d-136
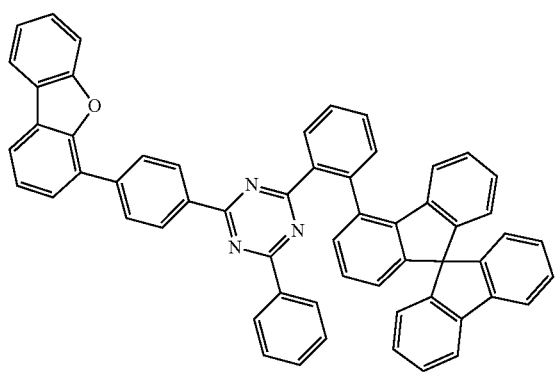
d-137
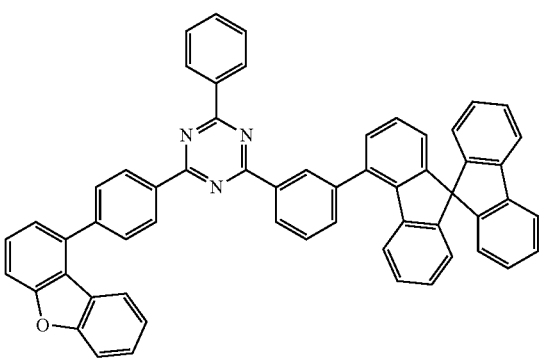

-continued
d-138
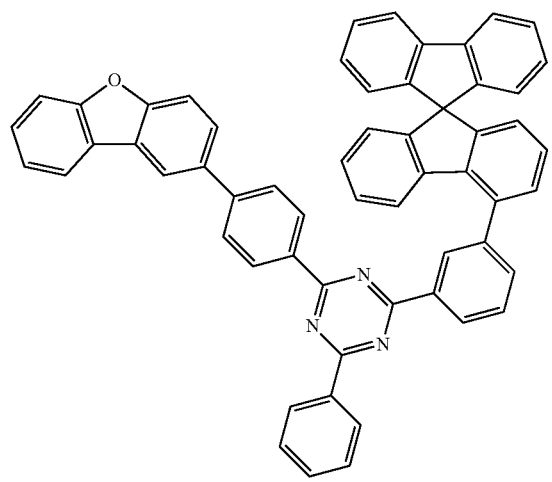
d-139
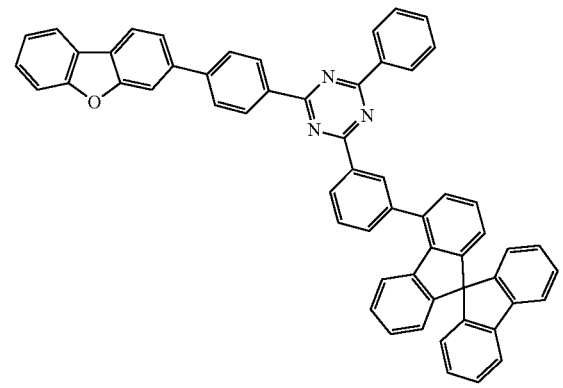
d-140
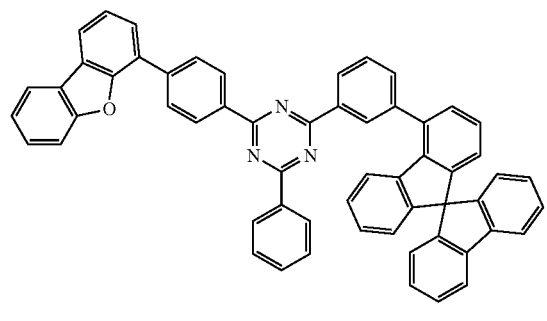
d-141
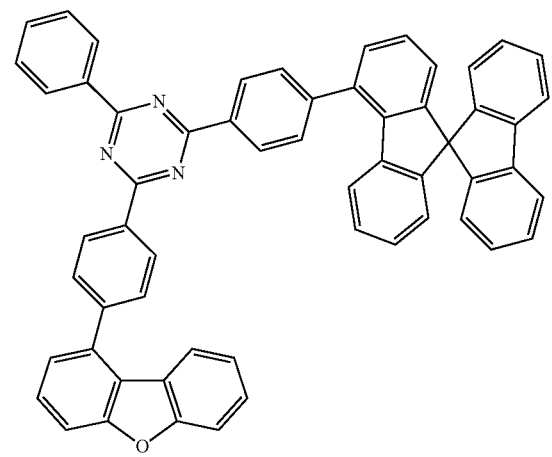
d-142
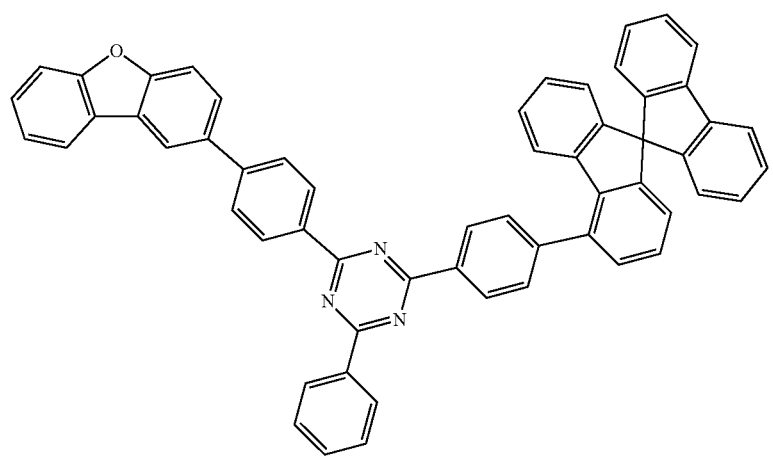

-continued
d-143
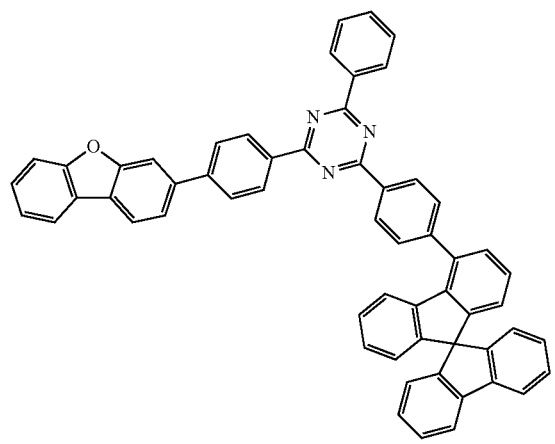
d-144
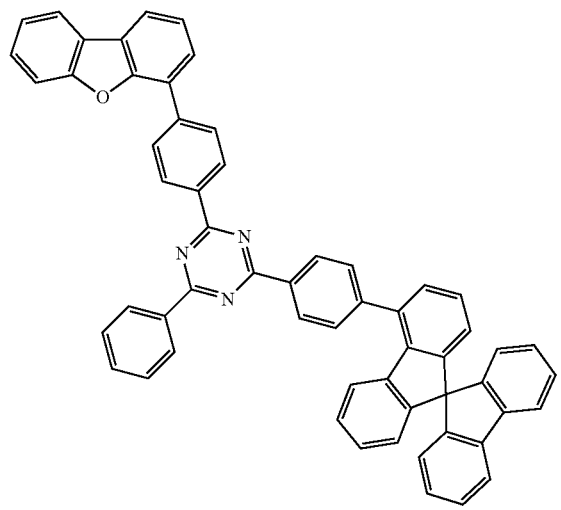
d-145
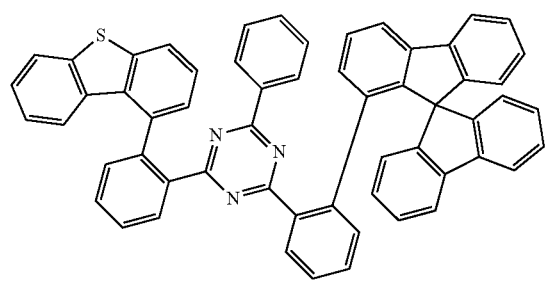
d-146
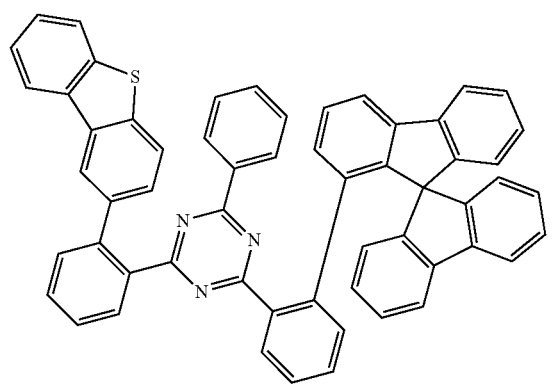
d-147
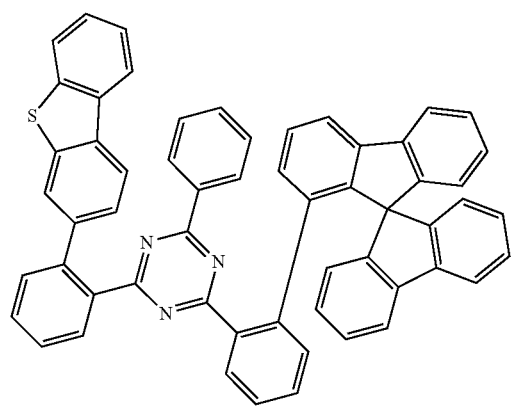
d-148
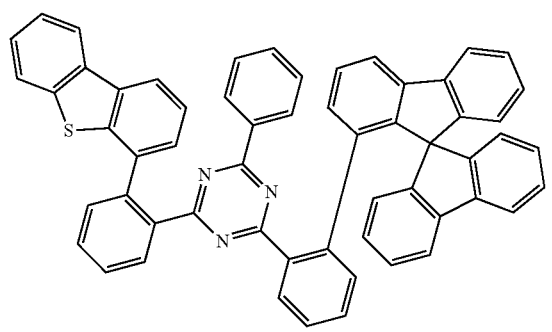

-continued
d-149
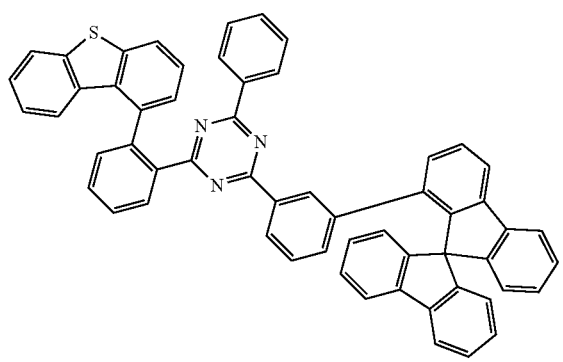
d-150
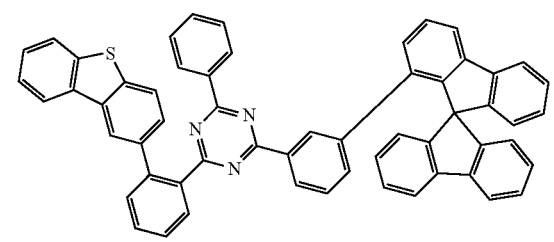
d-151
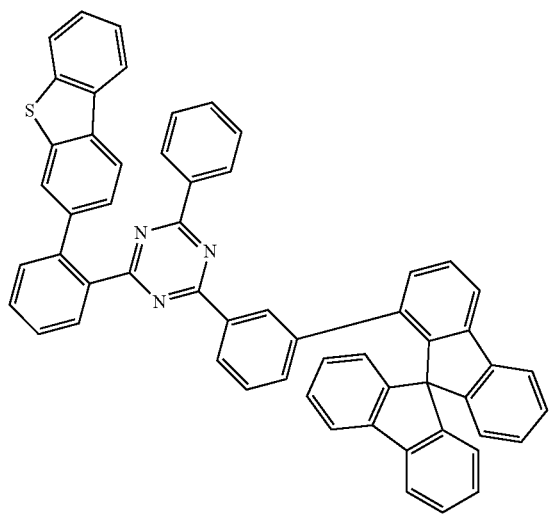
d-152
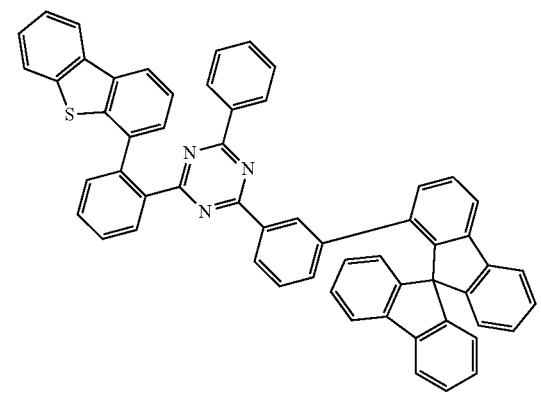
d-153
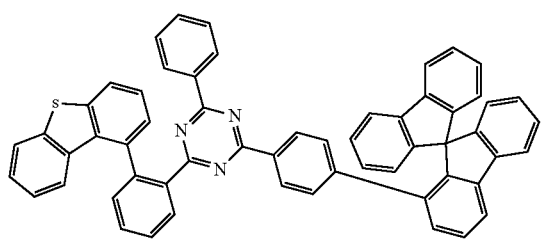
d-154
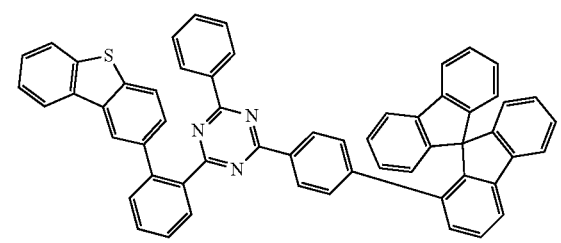

-continued
d-155
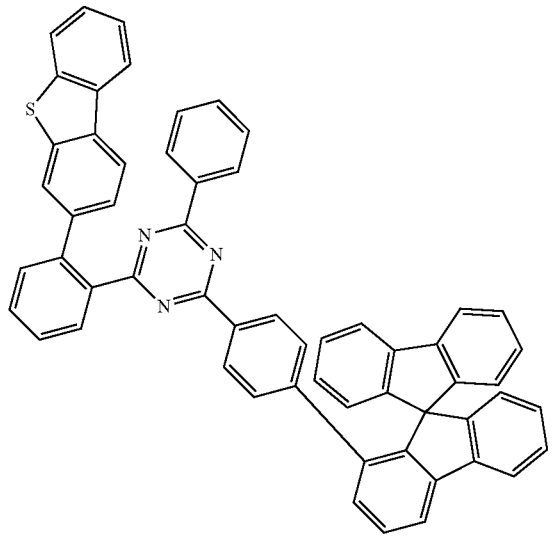
d-156
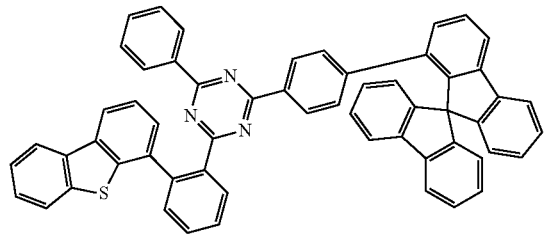
d-157
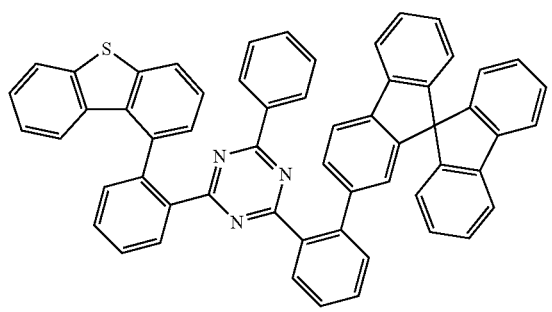
d-158
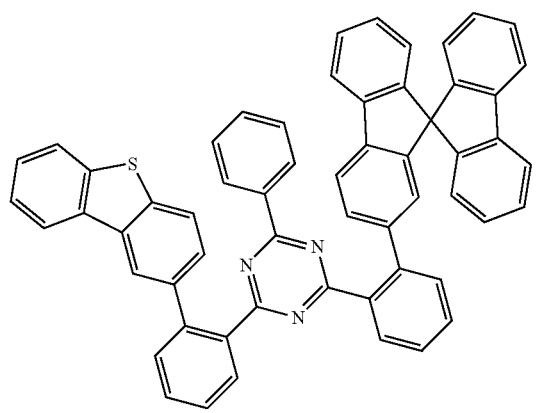
d-159
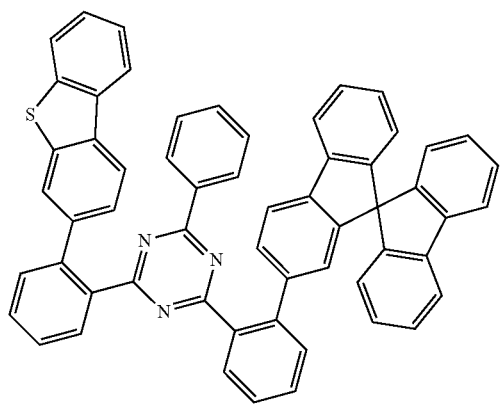
d-160
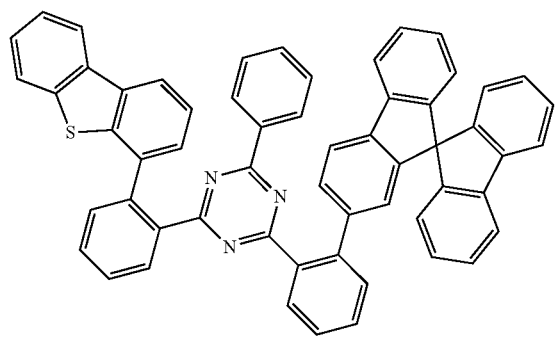

-continued
d-161
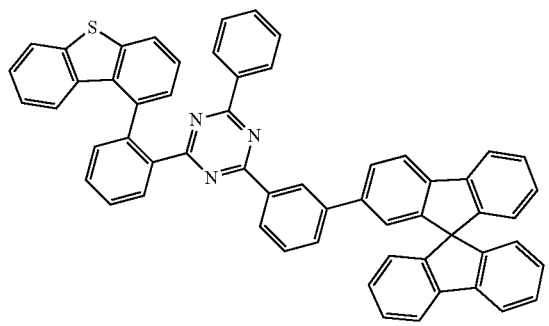
d-162
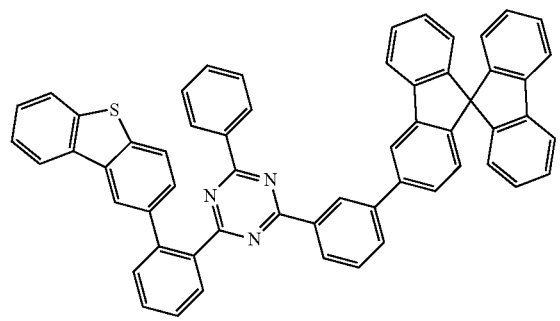
d-163
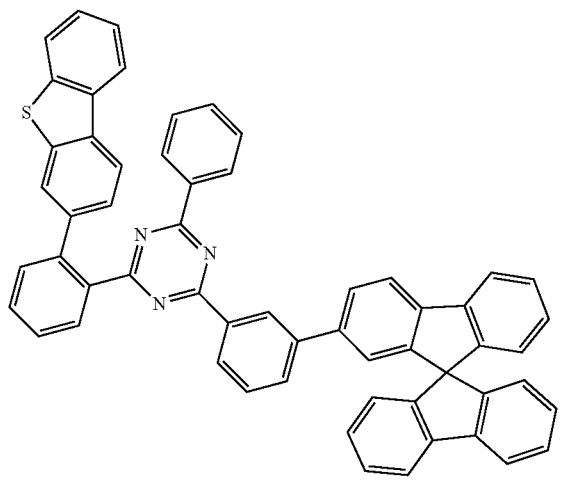
d-164
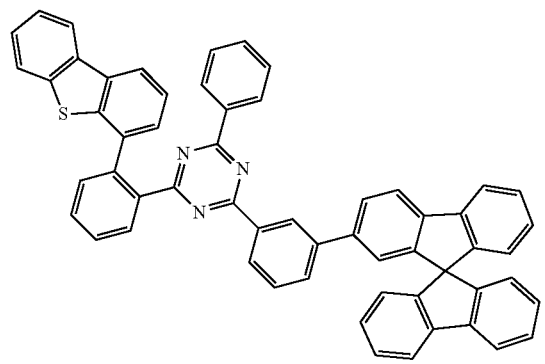
d-165
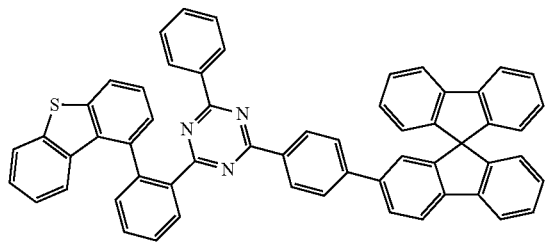
d-166
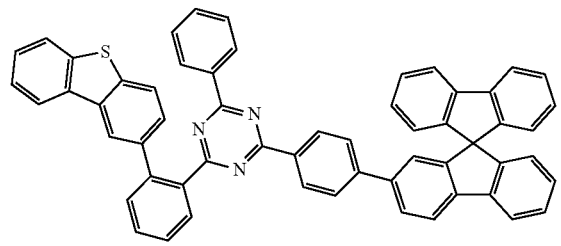

-continued
d-167
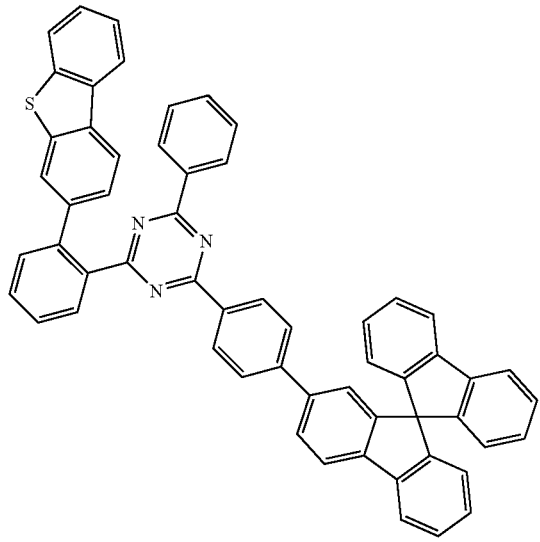
d-168
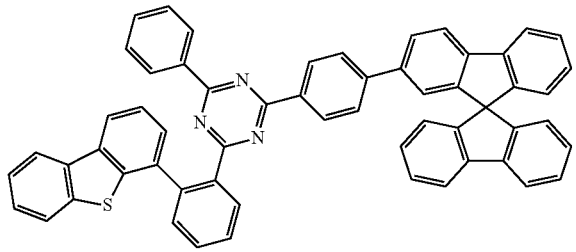
d-169
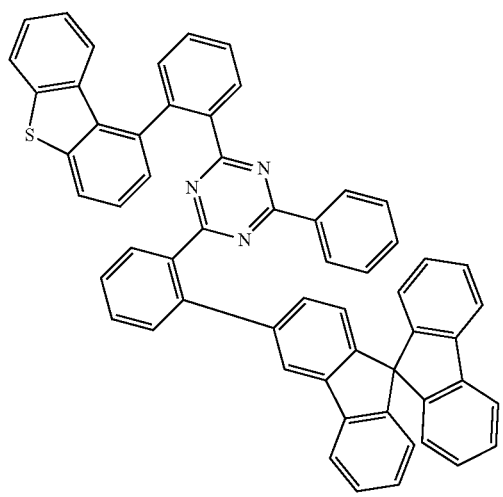
d-170
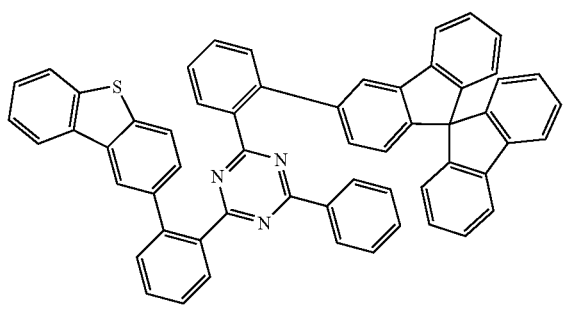
d-171
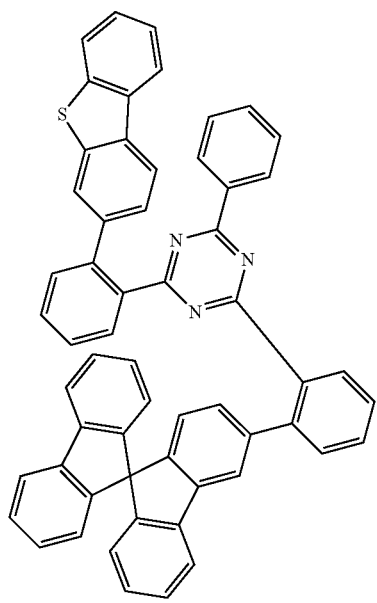
d-172
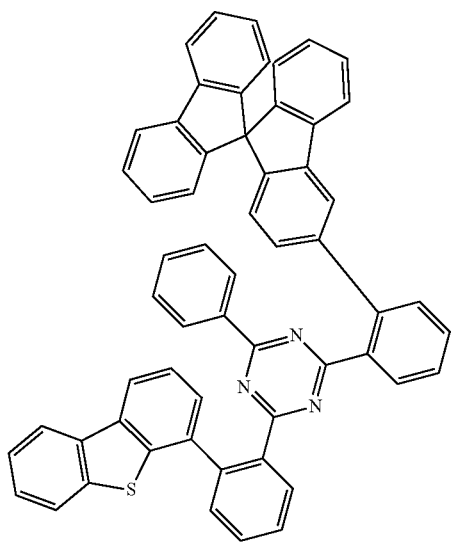

-continued
d-173
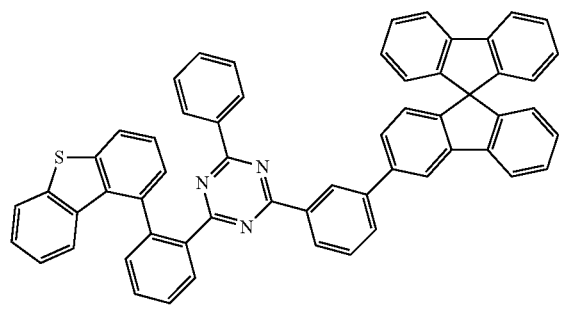
d-174
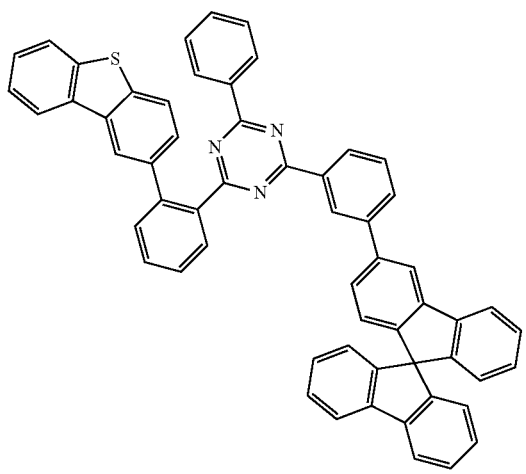
d-175
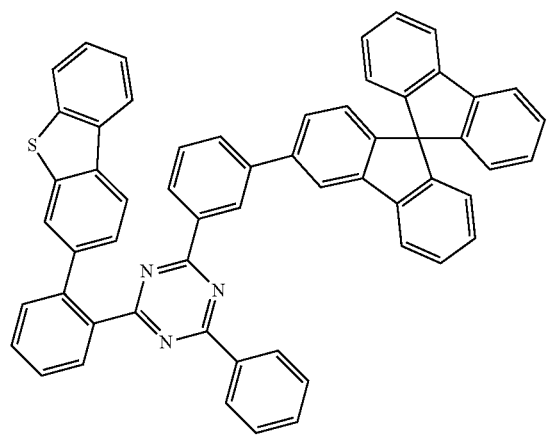
d-176
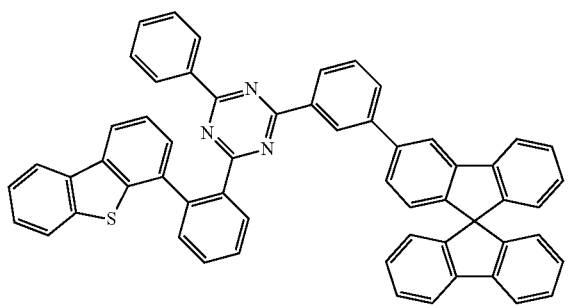
d-177
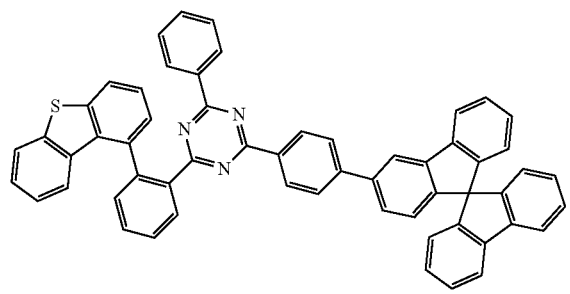
d-178
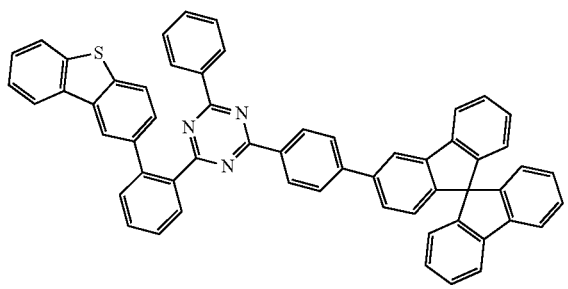

-continued
d-179
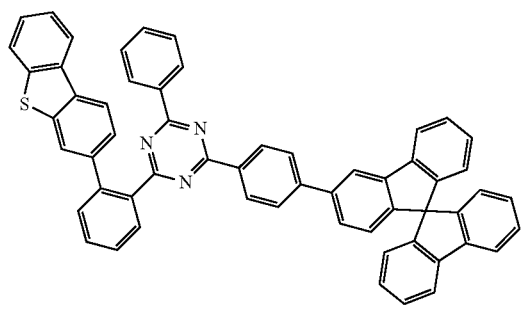
d-180
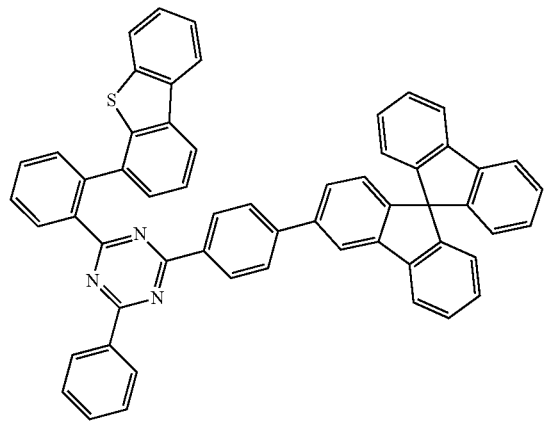
d-181
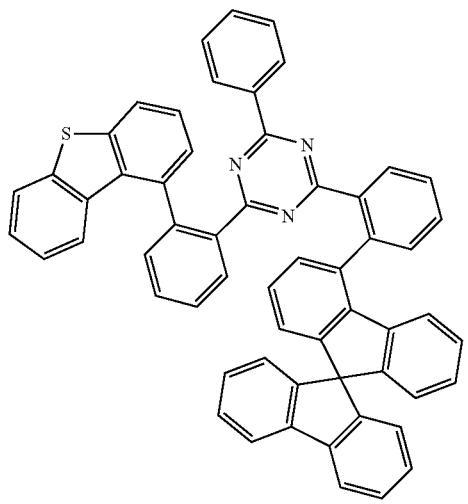
d-182
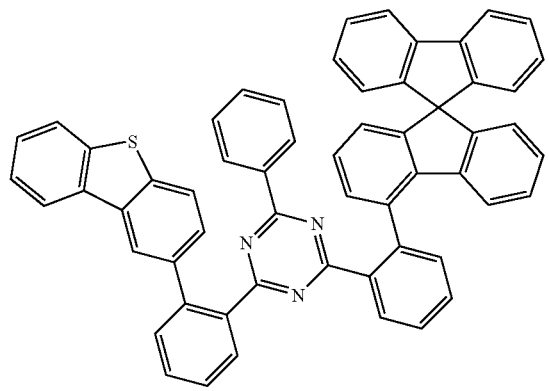
d-183
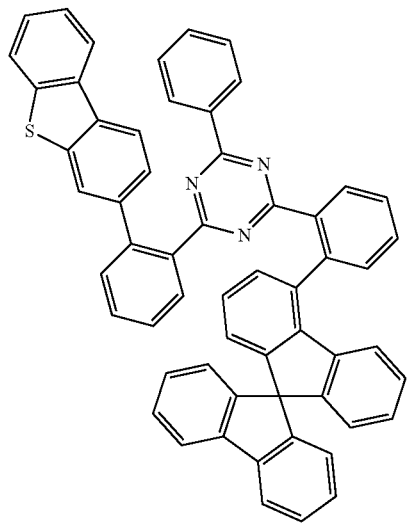
d-184
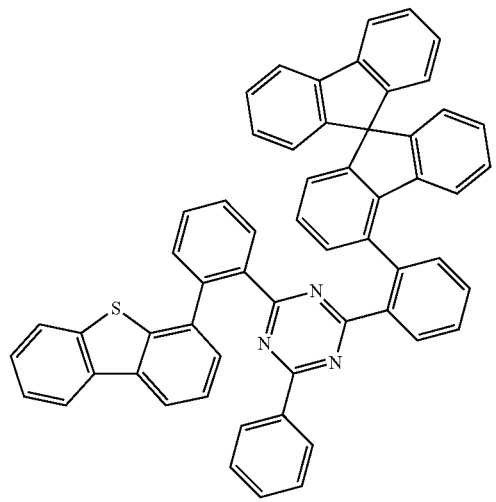

-continued
d-185
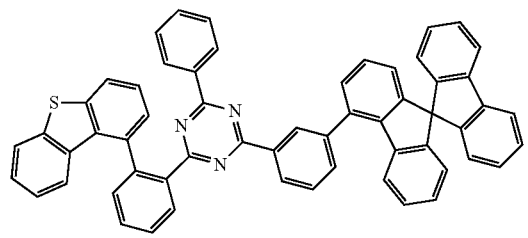
d-186
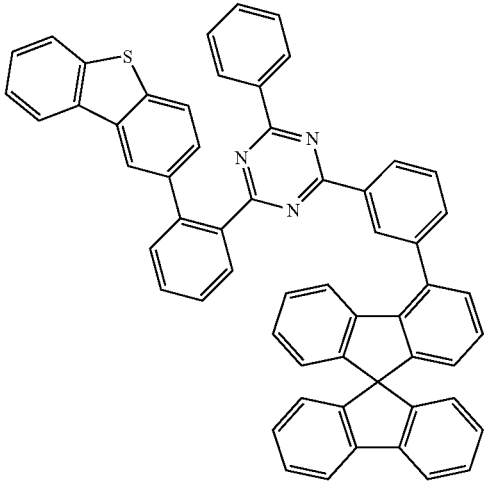
d-187
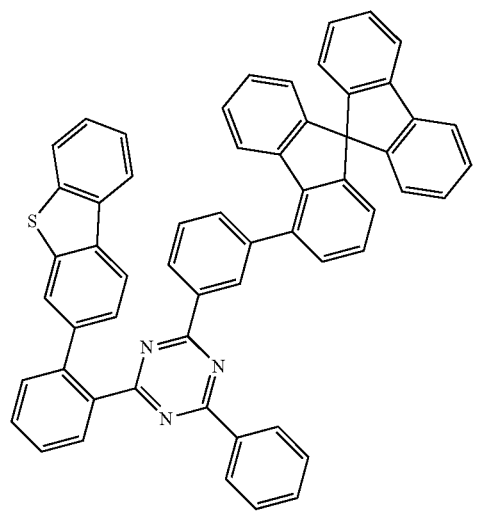
d-188
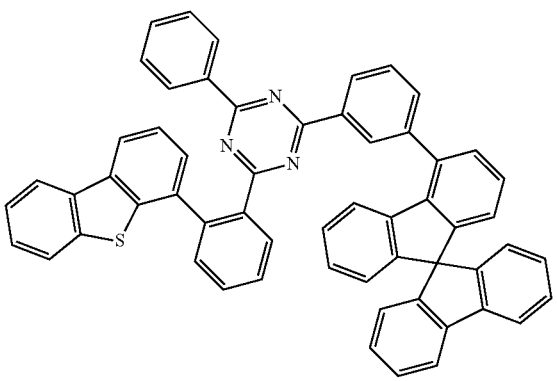
d-189
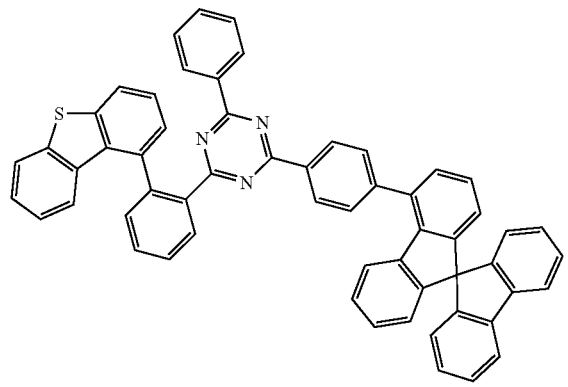
d-190
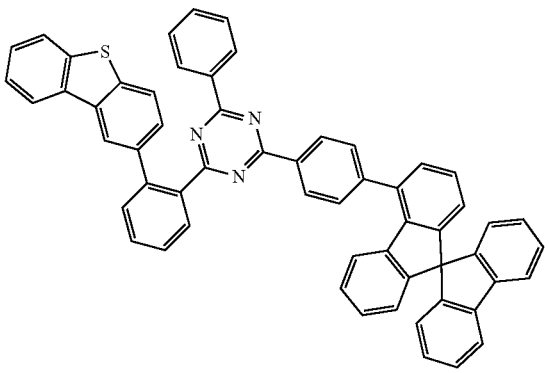

-continued
d-191
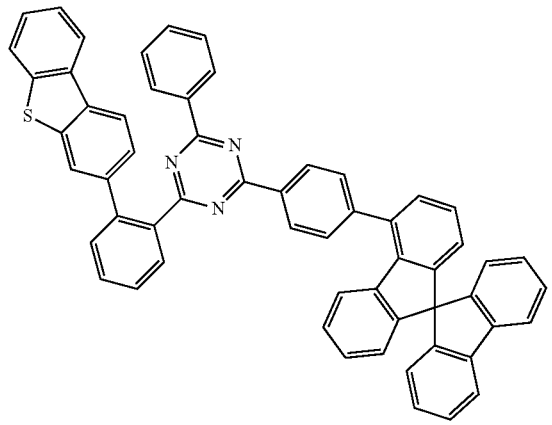
d-192
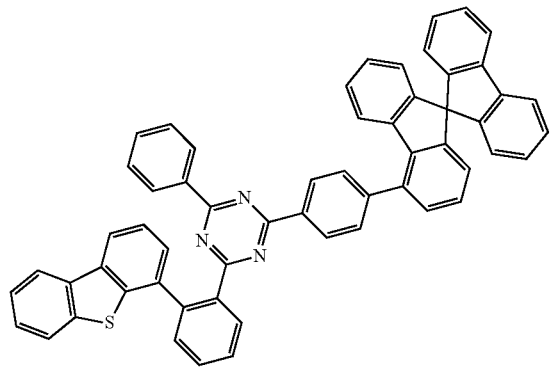
d-193
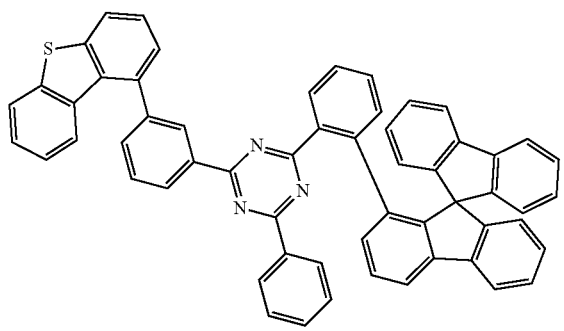
d-194
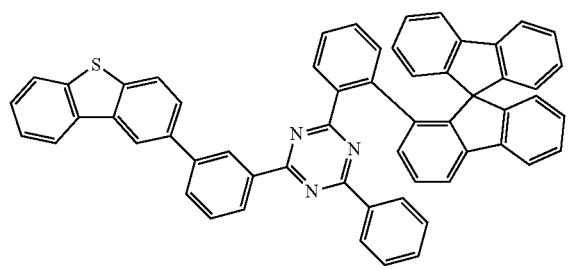
d-195
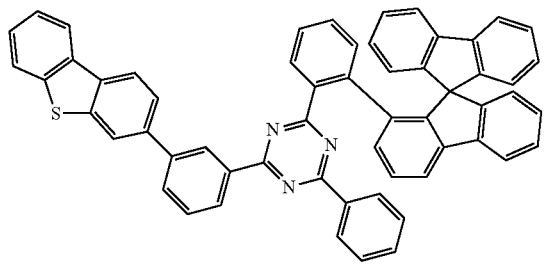
d-196
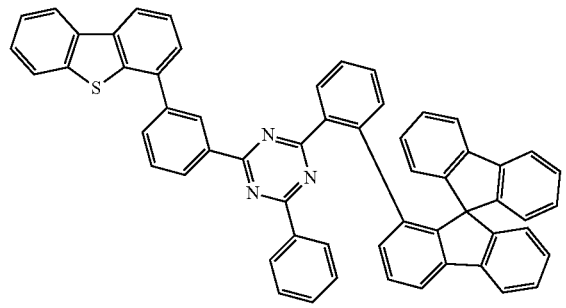
d-197
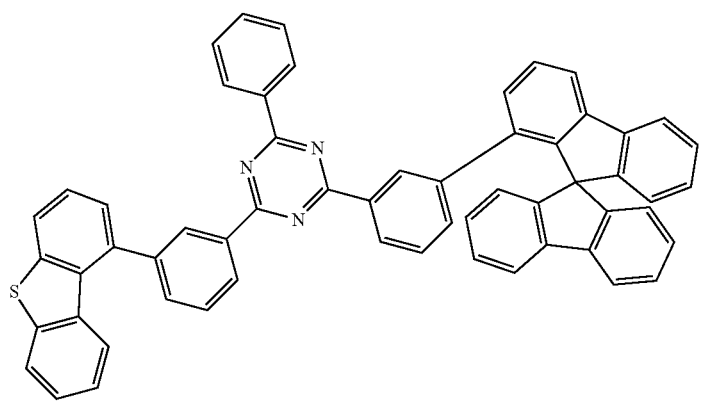

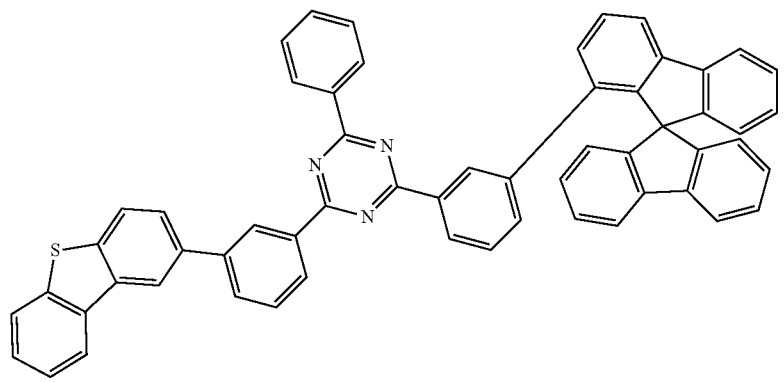
d-198
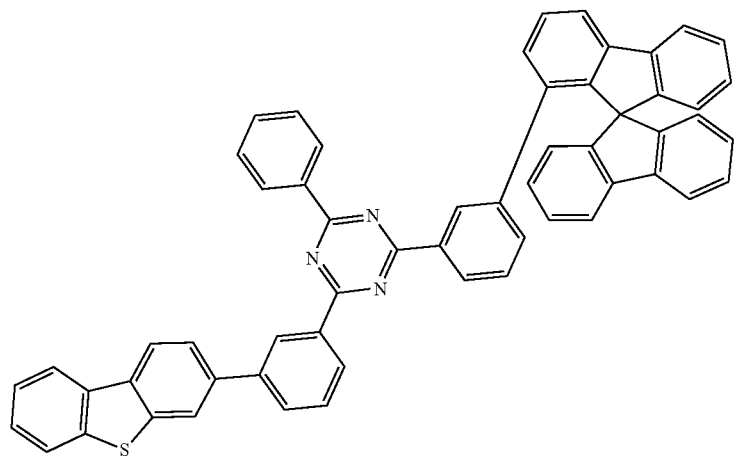
d-199
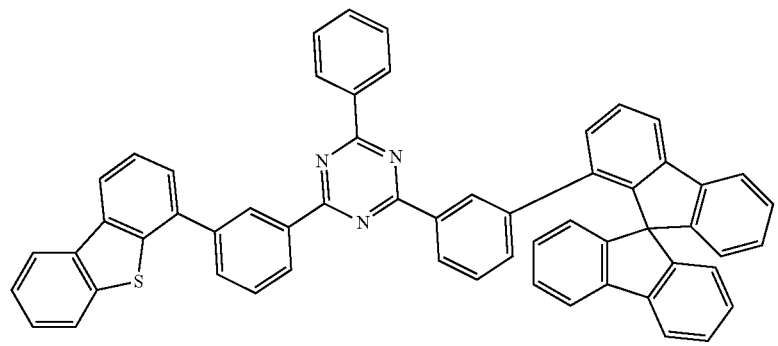
d-200
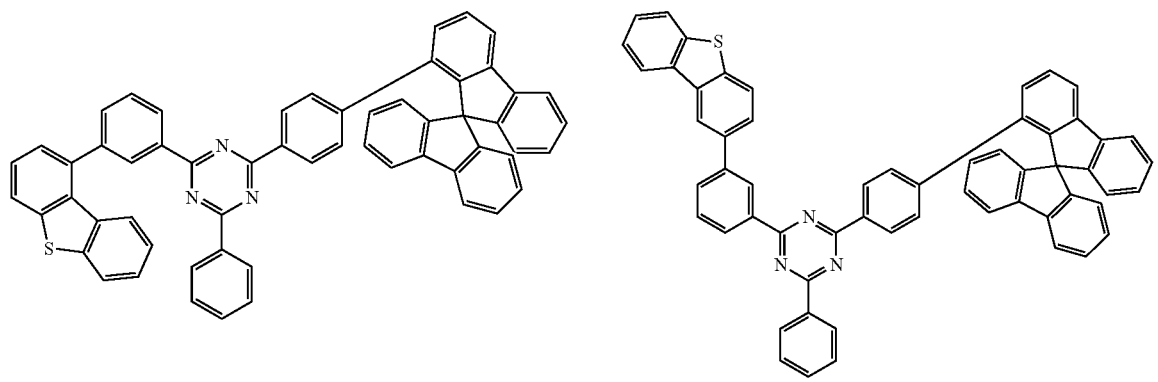
d-201        d-202

-continued
d-203
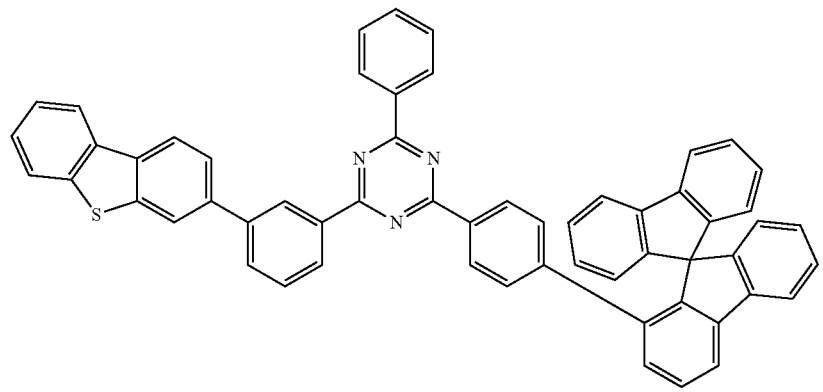
d-204
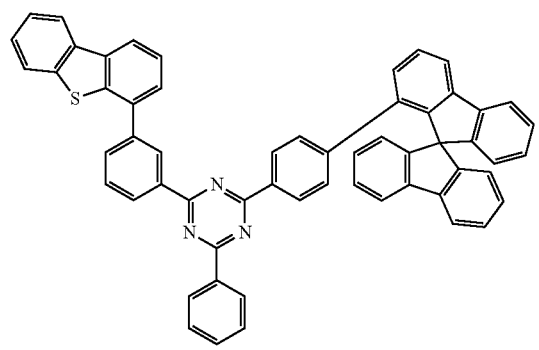
d-205
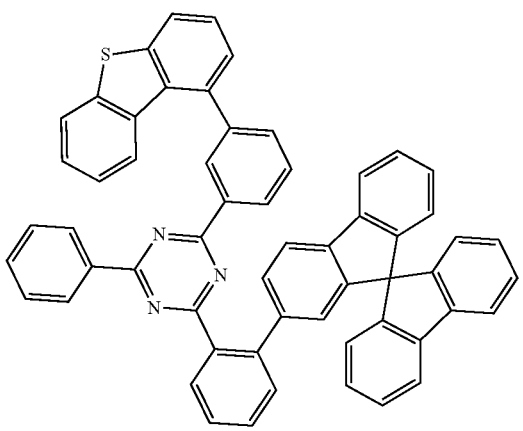
d-206
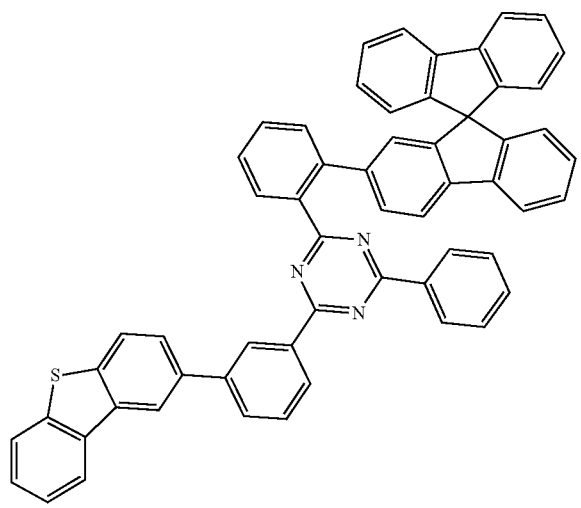
d-207
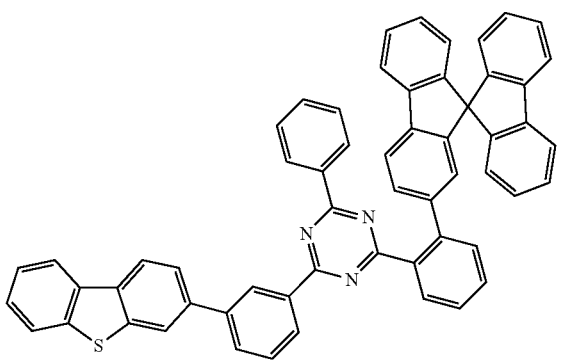

-continued
d-208
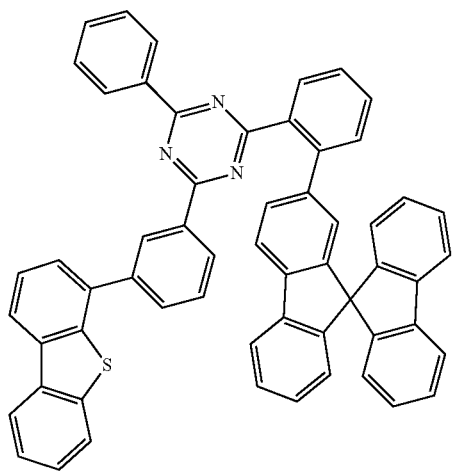
d-209
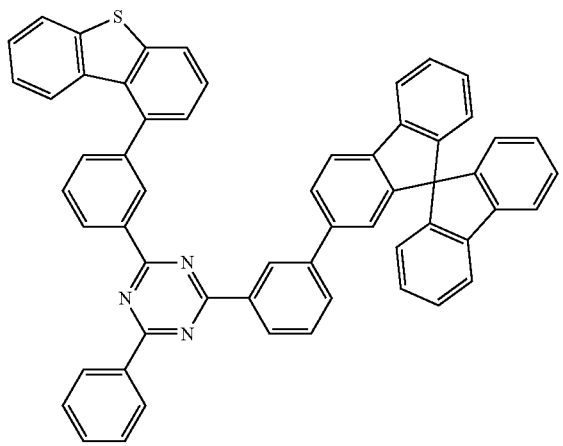
d-210
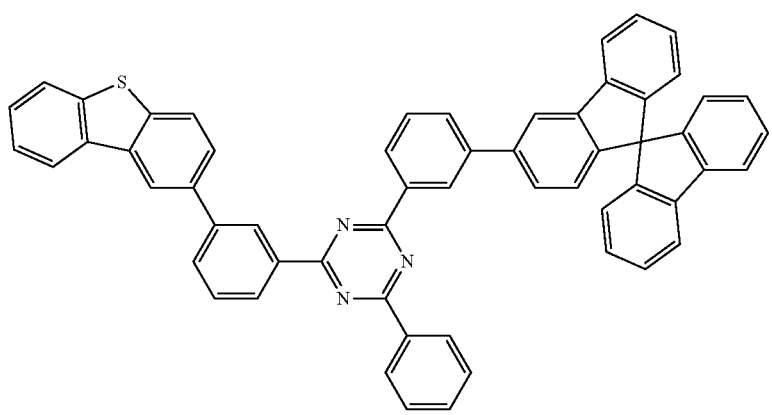
d-211
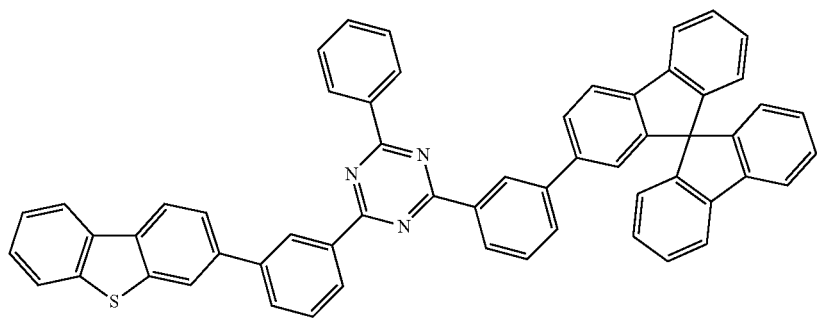
d-212
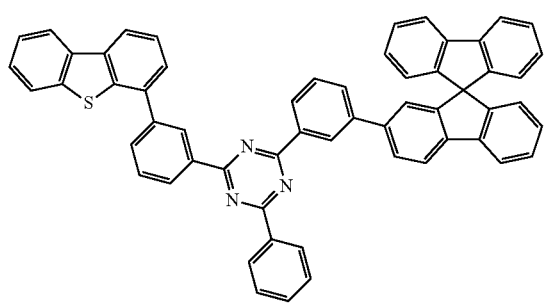
d-213
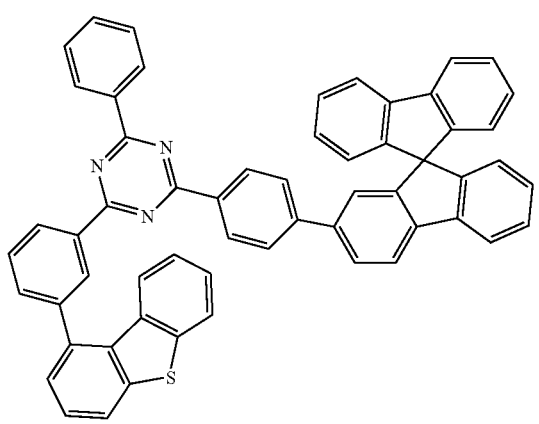

-continued
d-214
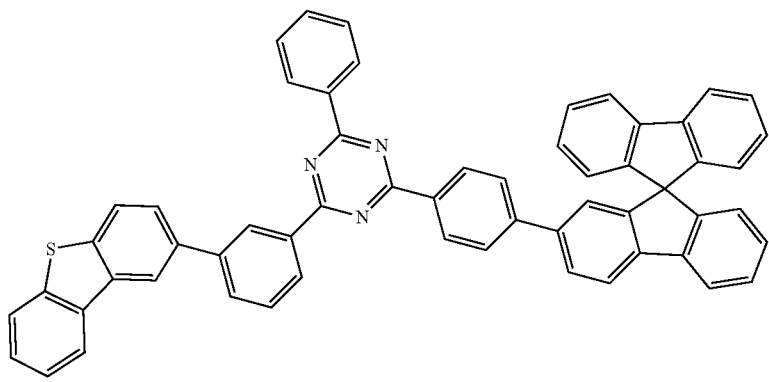
d-215
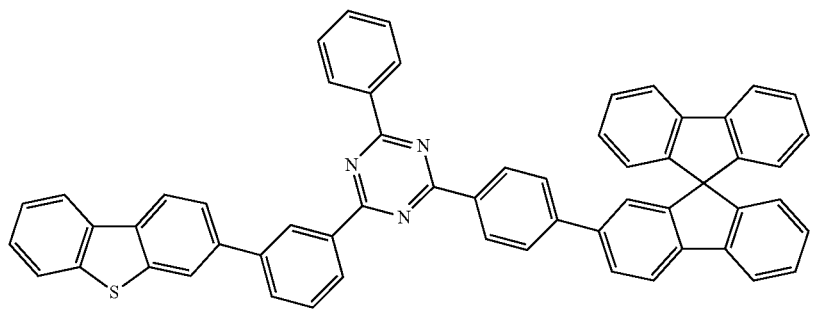
d-216
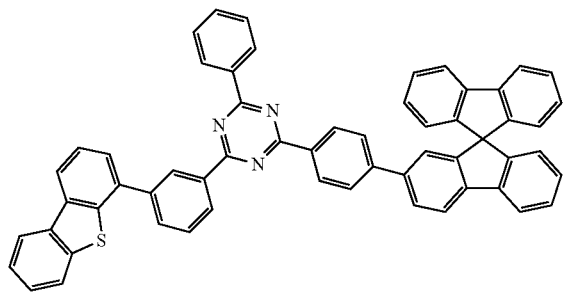
d-217
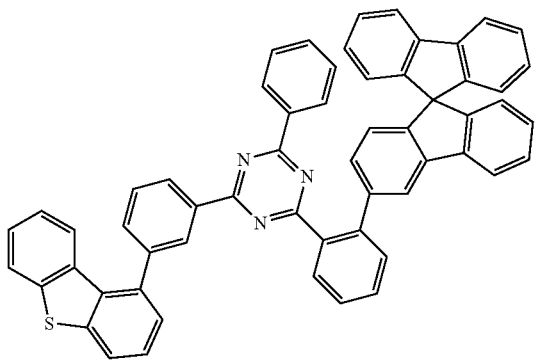
d-218
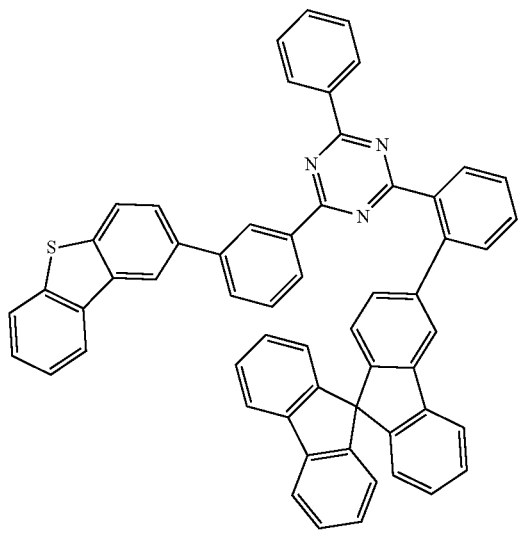
d-219
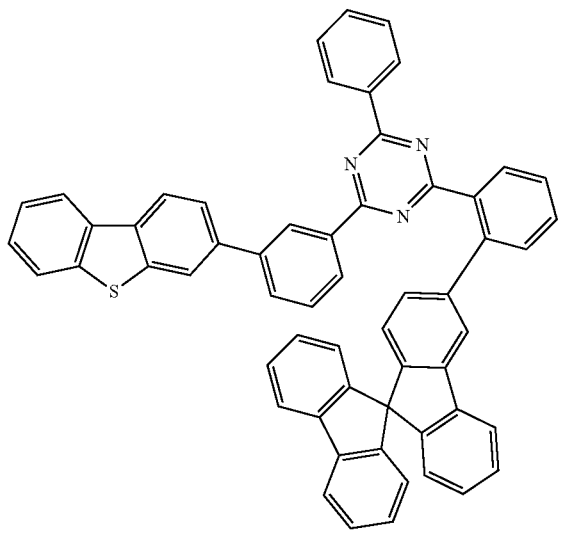

-continued
d-220
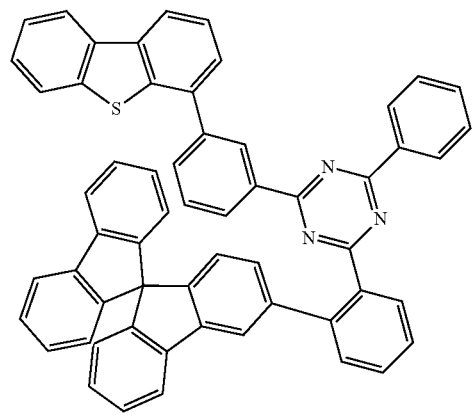
d-221
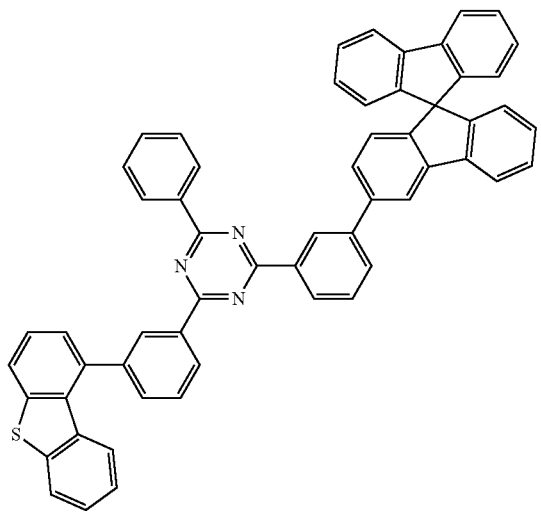
d-222
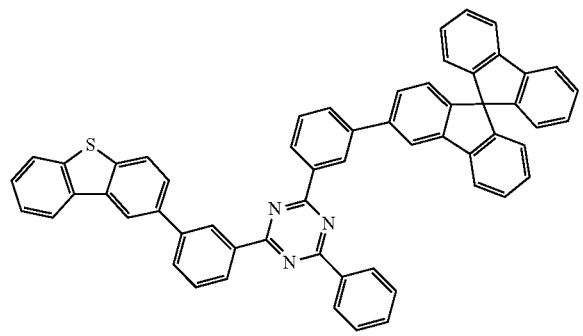
d-223
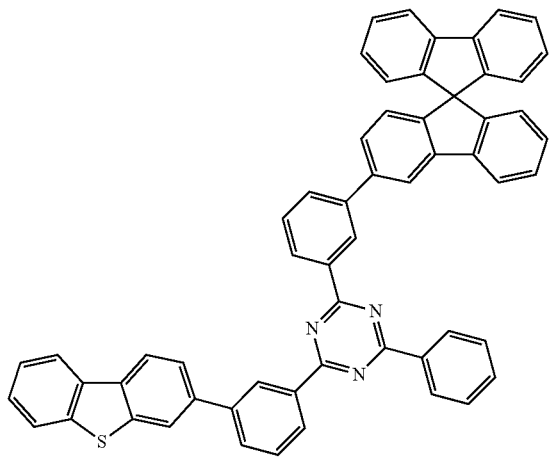
d-224
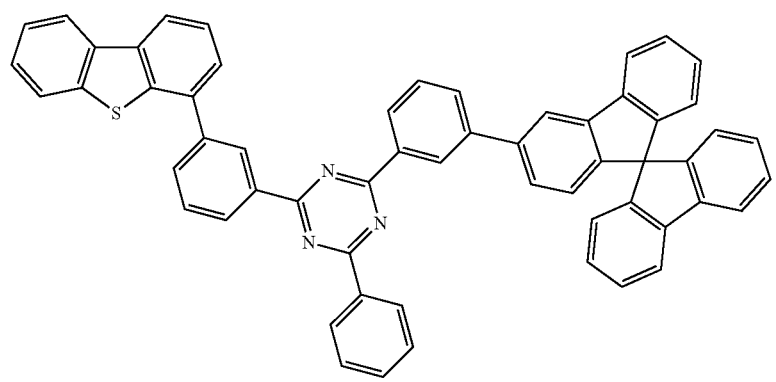

-continued
d-225
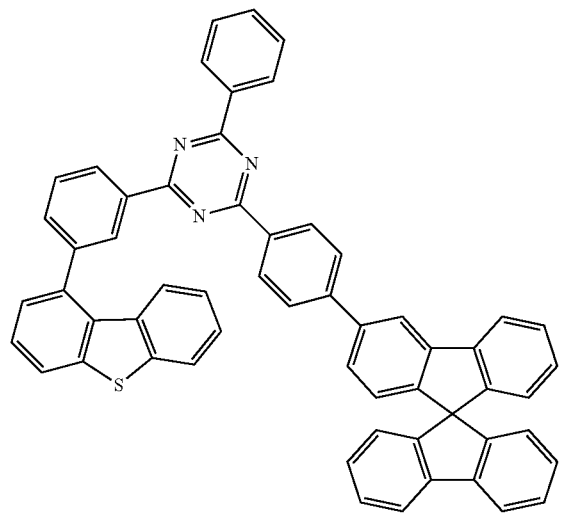
d-226
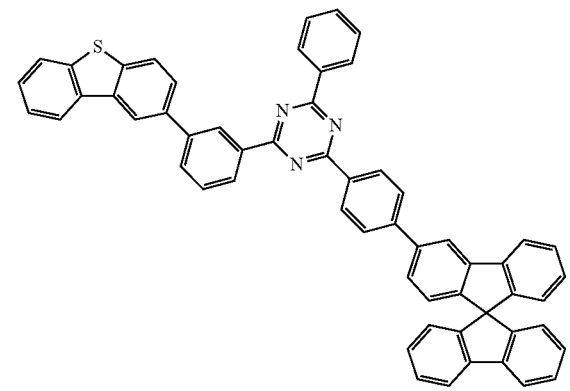
d-227
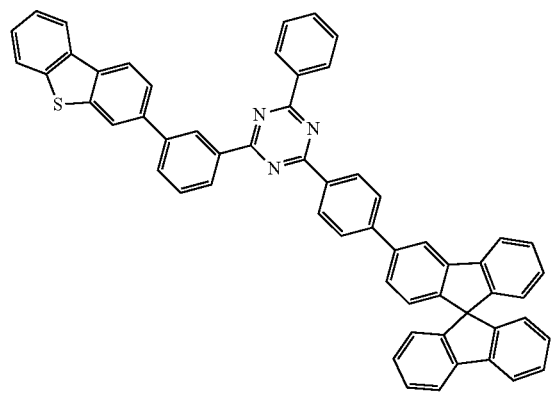
d-228
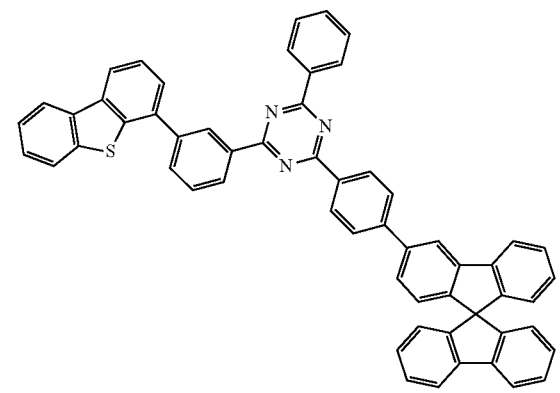
d-229
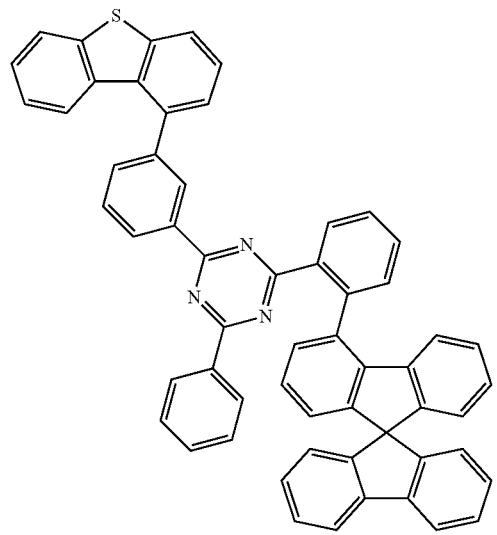
d-230
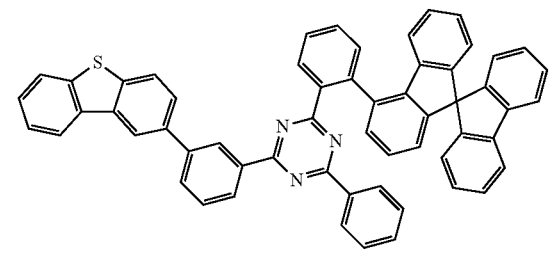

-continued
d-231
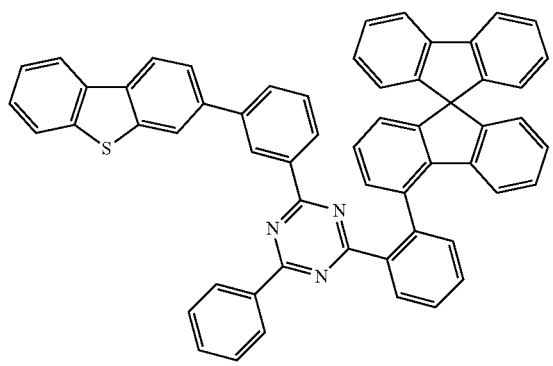
d-232
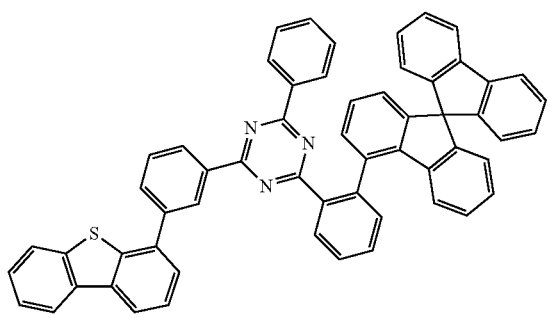
d-233
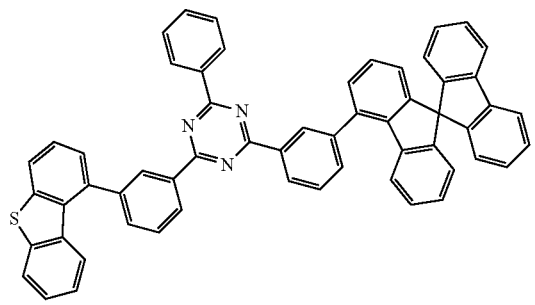
d-234
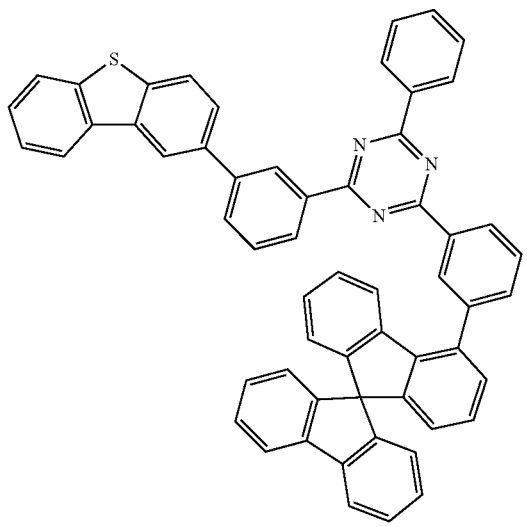
d-235
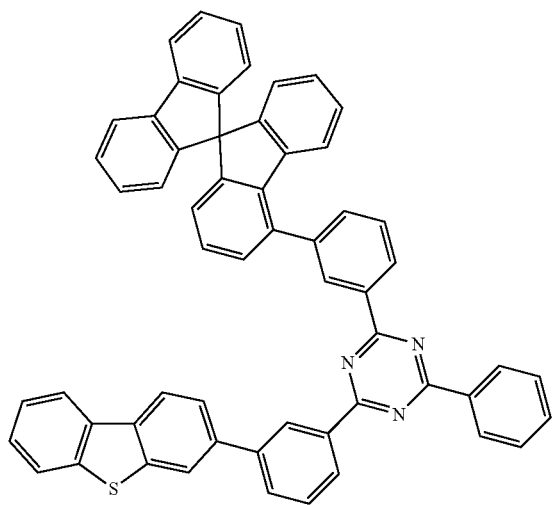
d-236
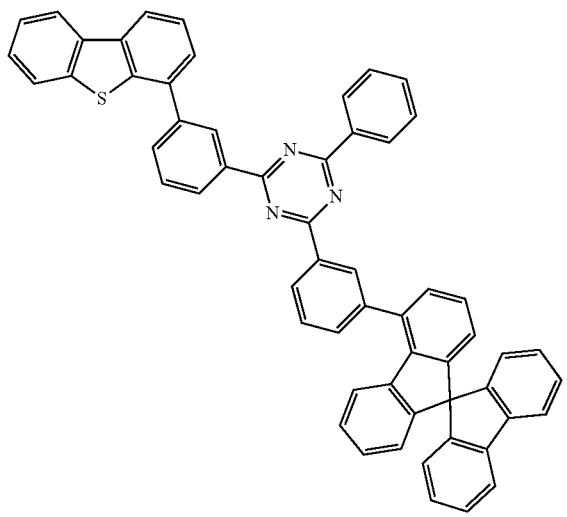

-continued
d-237
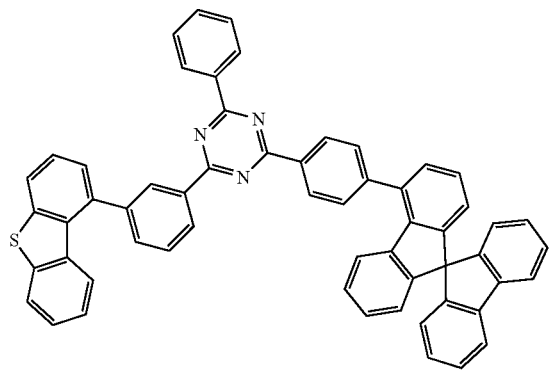
d-238
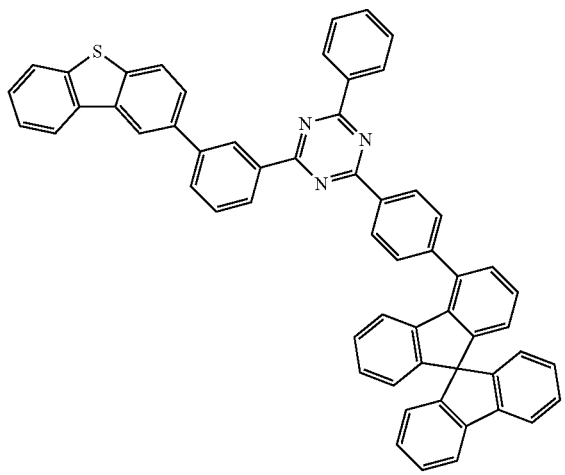
d-239
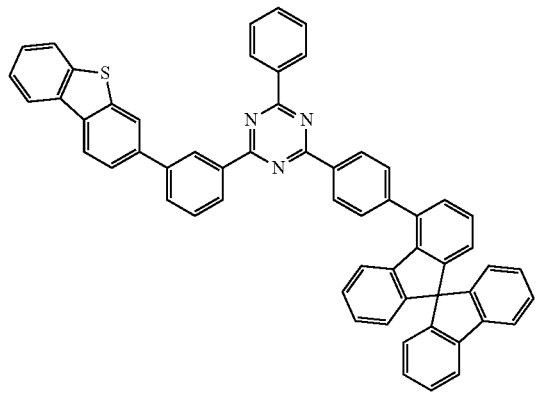
d-240
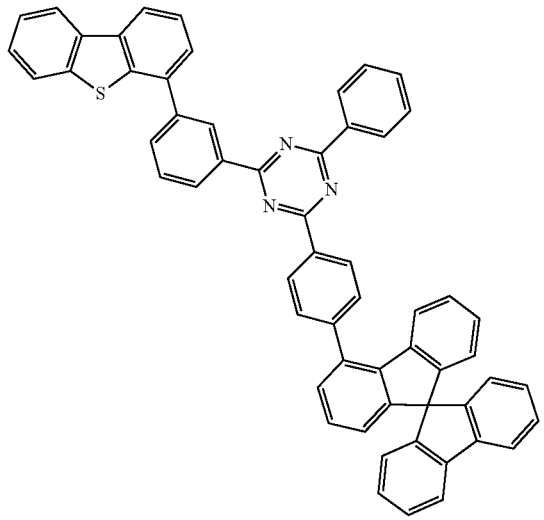
d-241
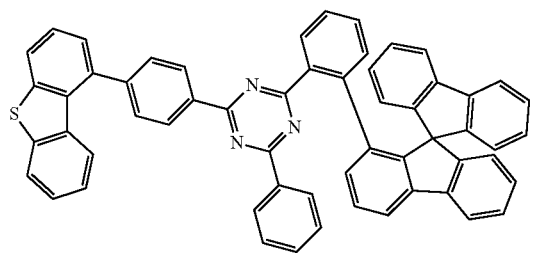
d-242
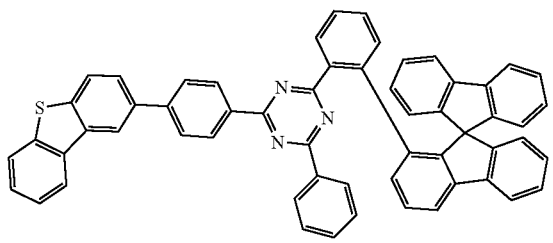
d-243
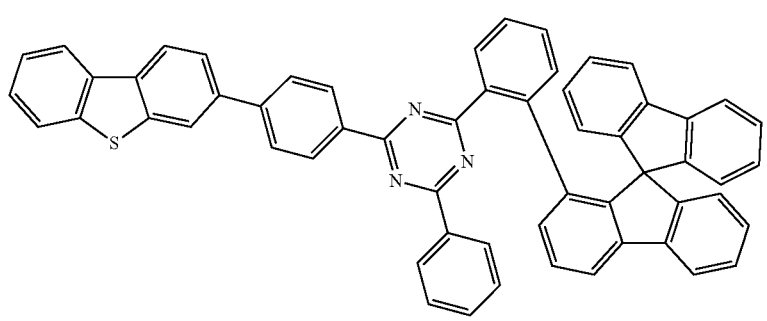

-continued
d-244
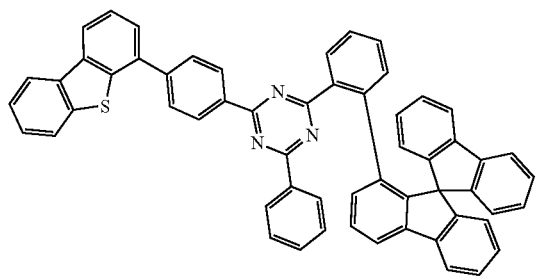
d-245
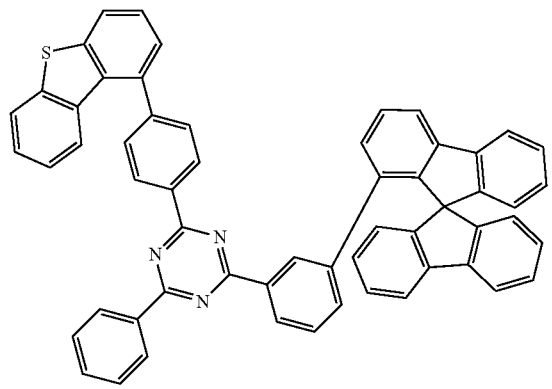
d-246
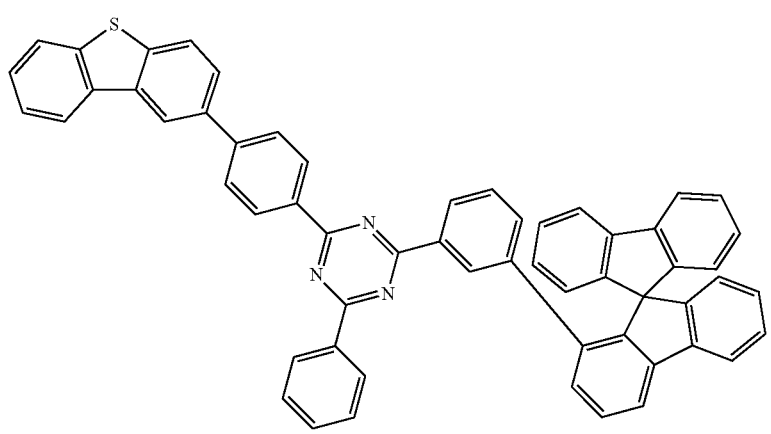
d-247
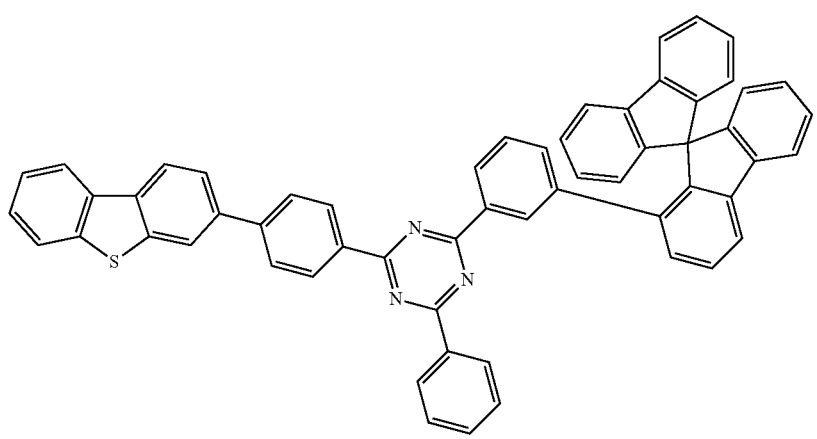

-continued
d-248
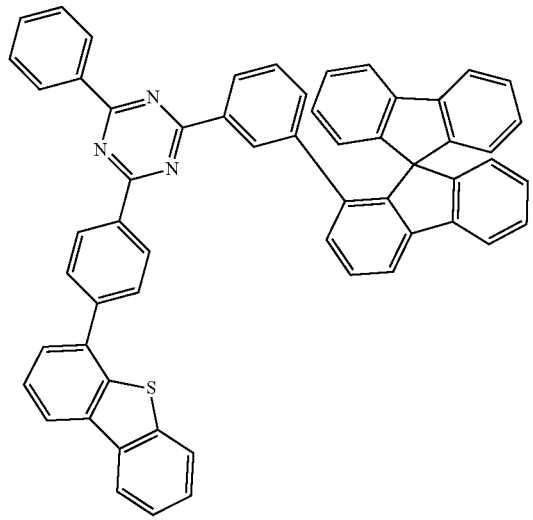
d-249
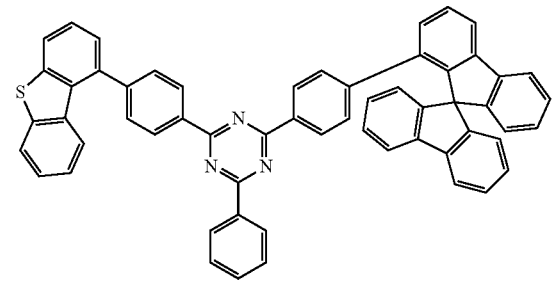
d-250
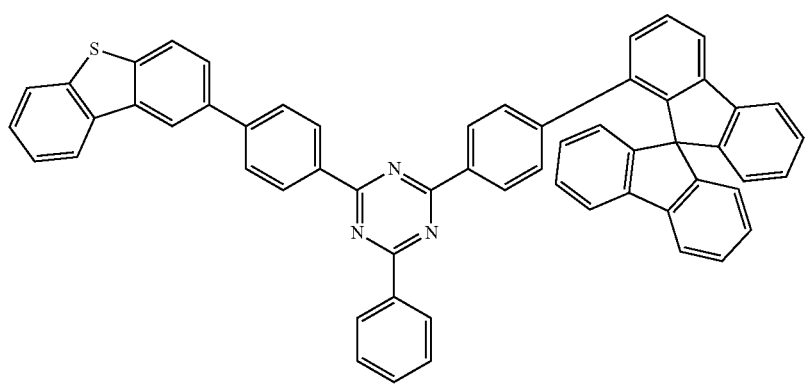
d-251
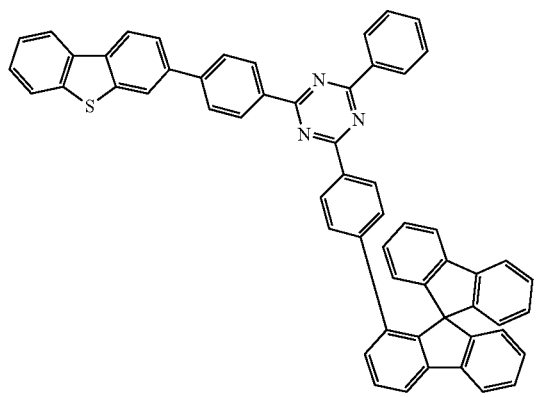
d-252
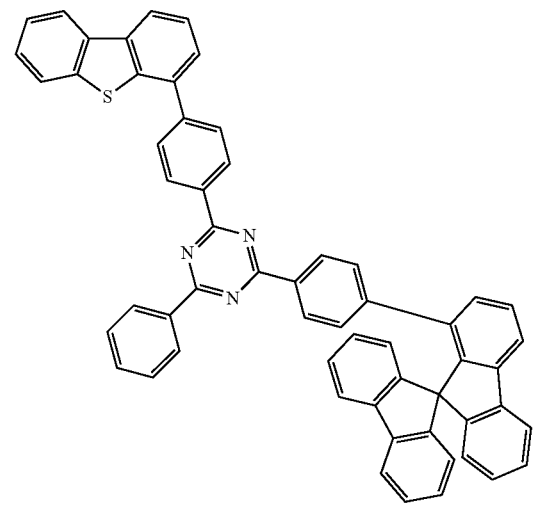

-continued
d-253
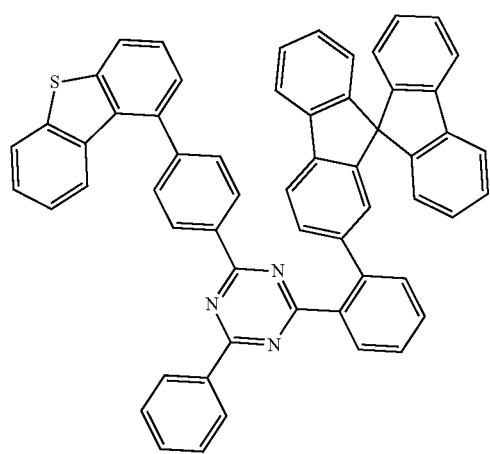
d-254
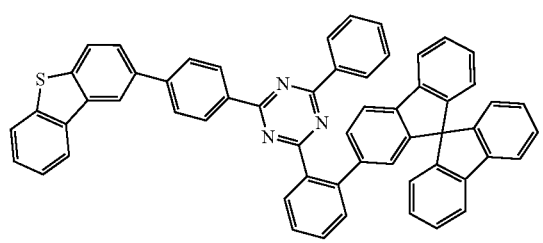
d-255
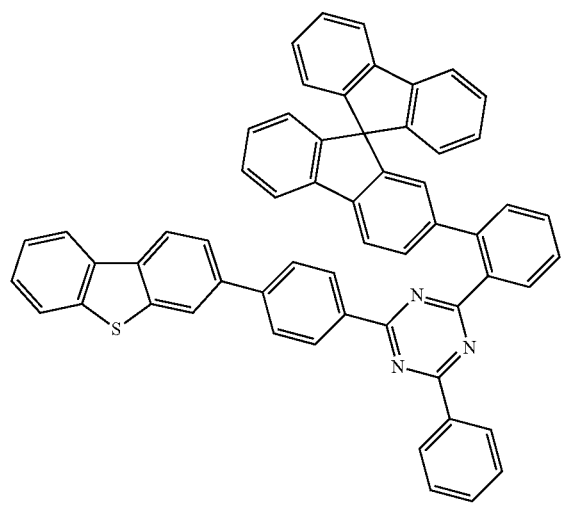
d-256
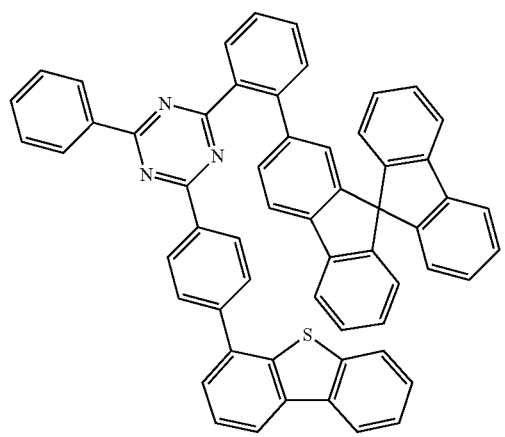
d-257
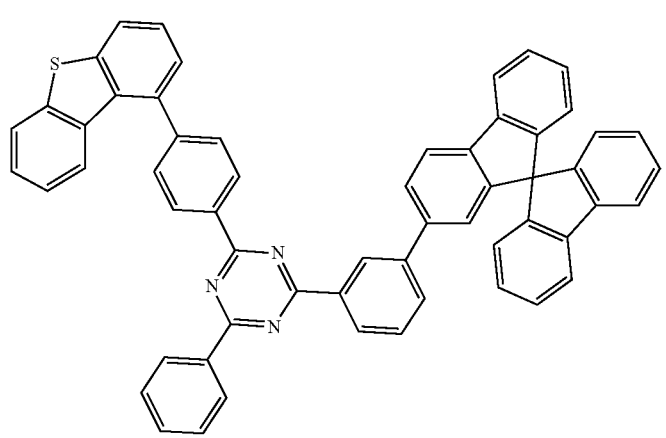

d-258
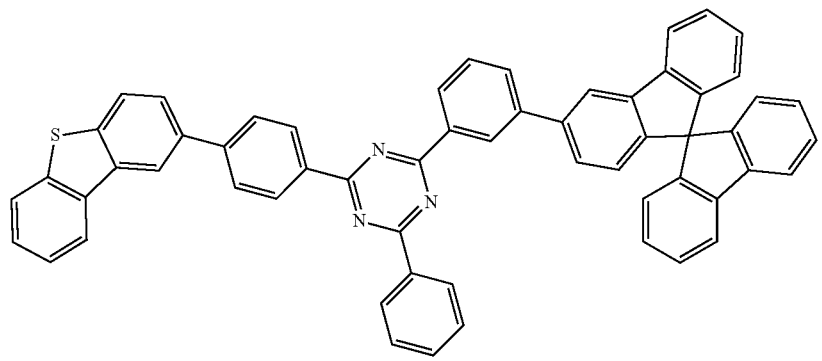
d-259
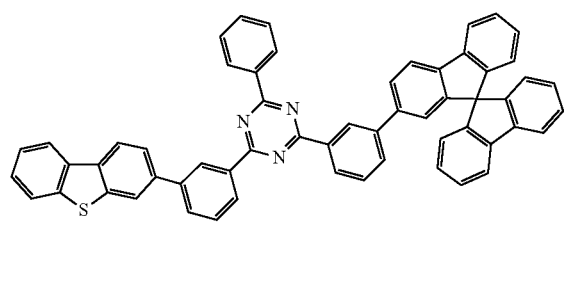
d-260
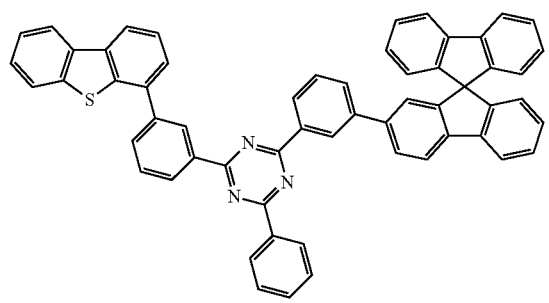
d-261
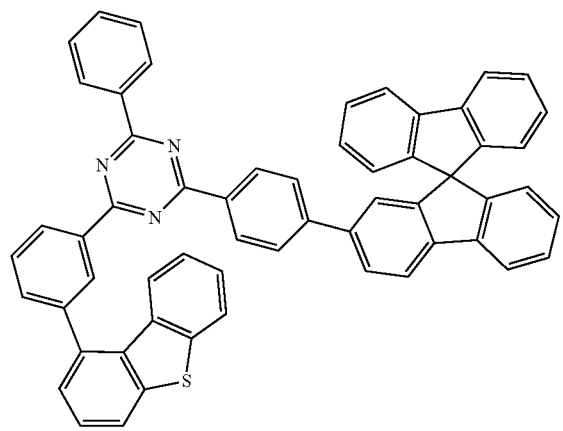
d-262
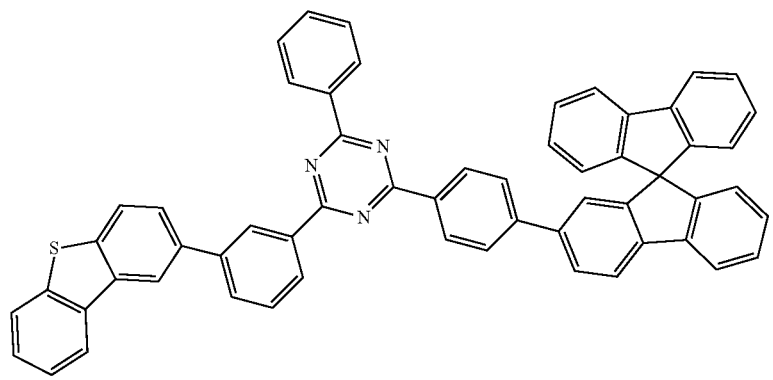

-continued
d-263
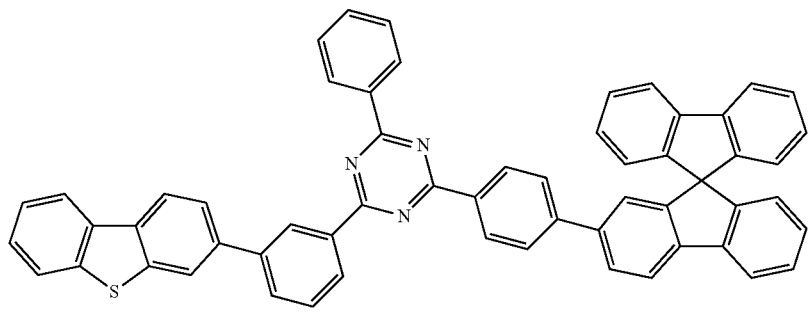
d-264
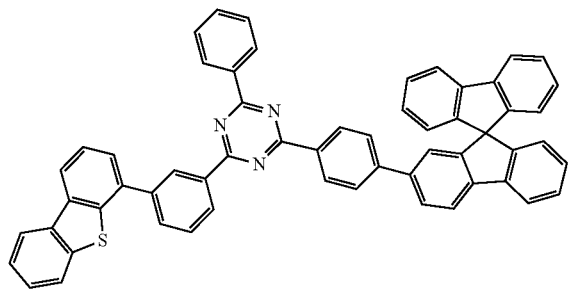
d-265
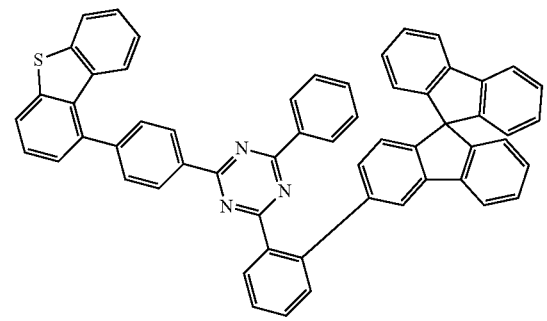
d-266
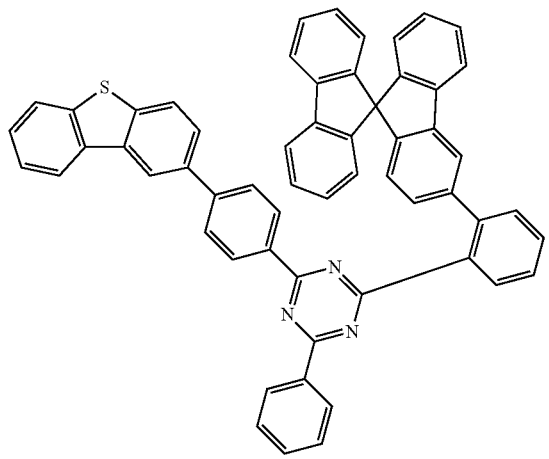
d-267
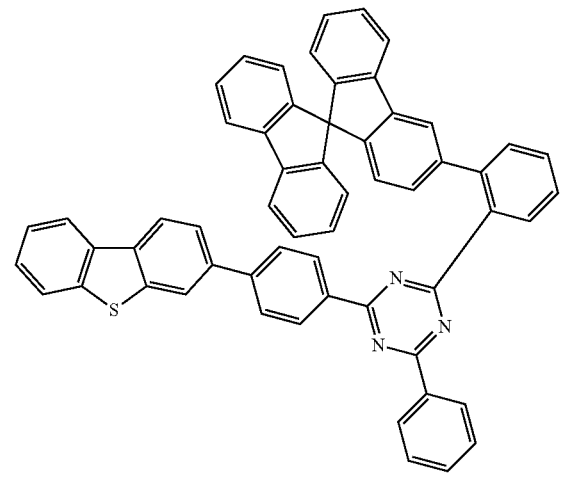
d-268
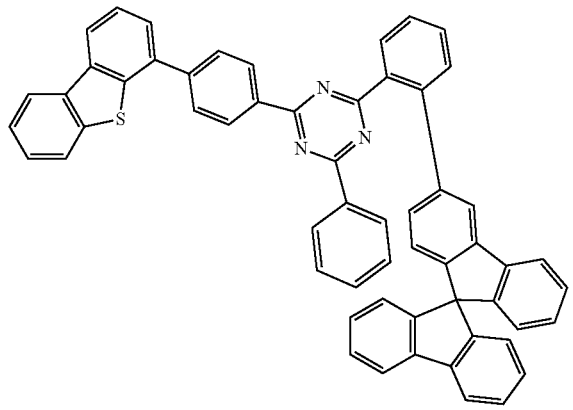
d-269
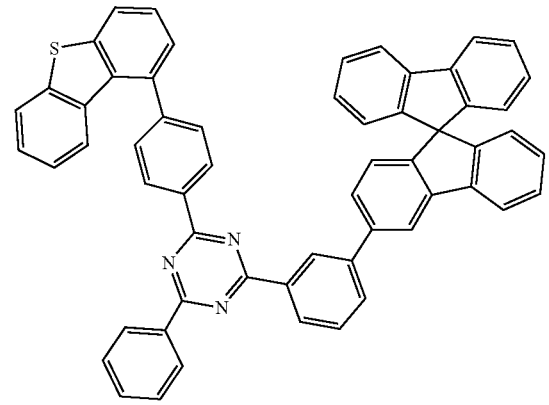

-continued
d-270
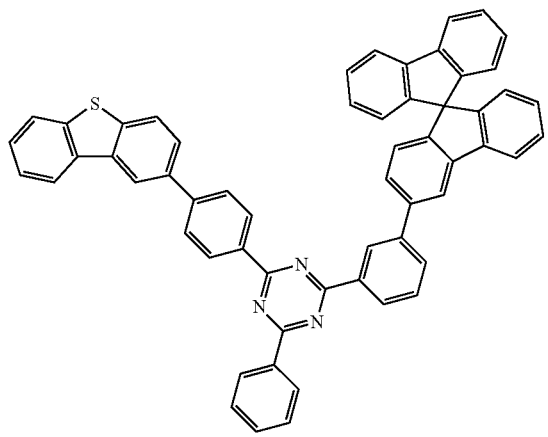
d-271
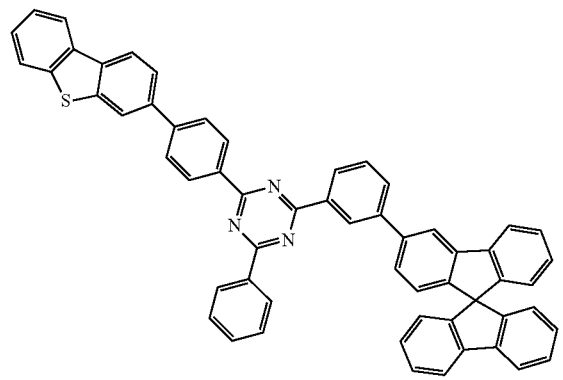
d-272
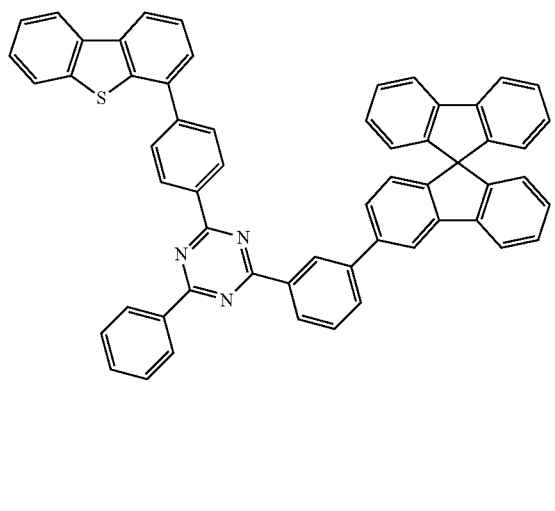
d-273
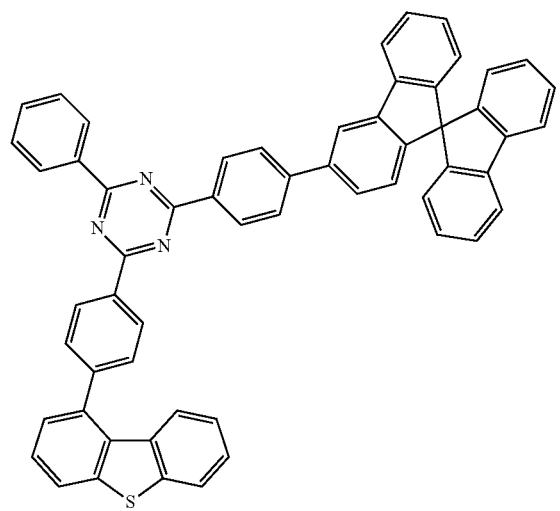
d-274
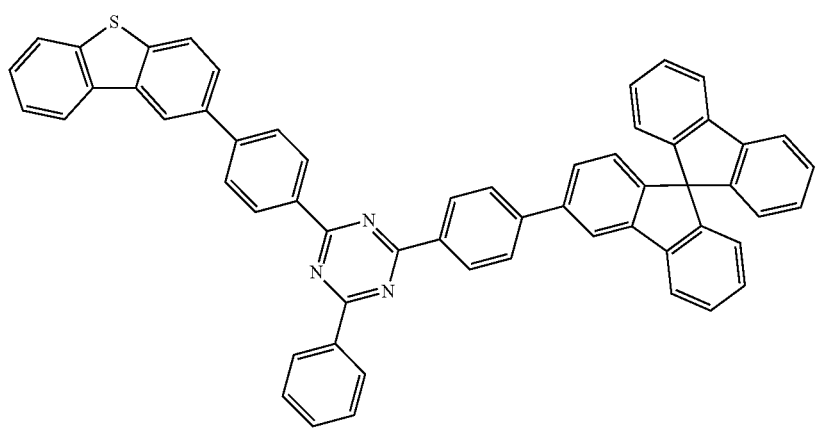

-continued
d-275
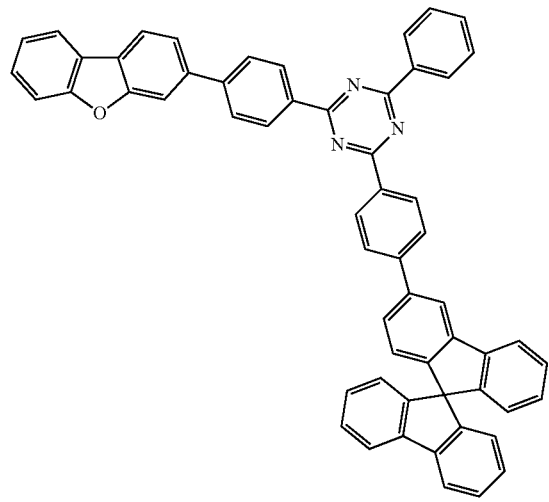
d-276
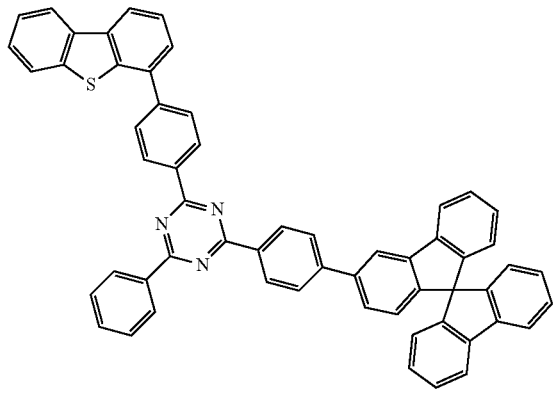
d-277
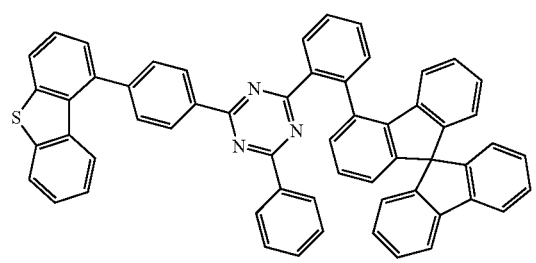
d-278
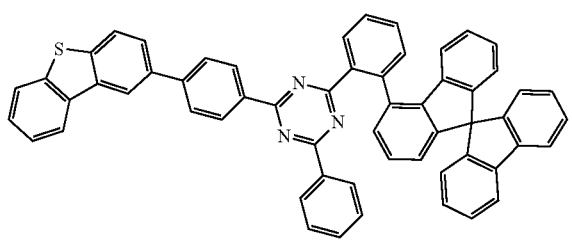
d-279
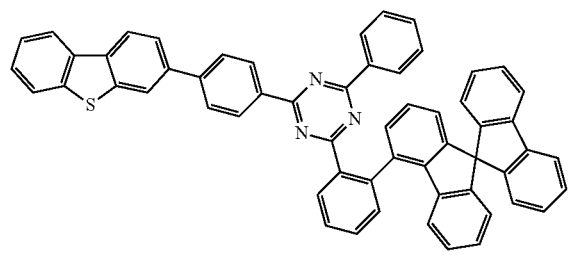
d-280
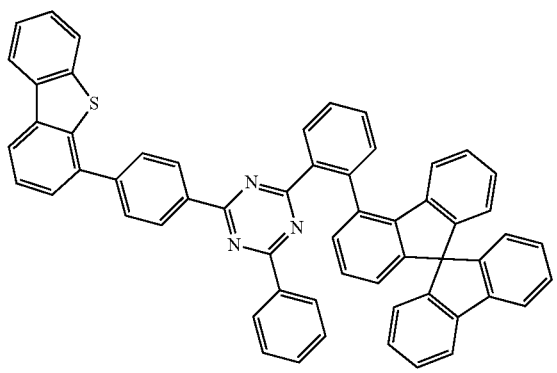

-continued
d-281
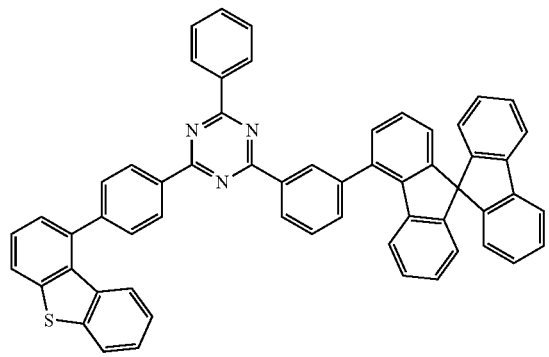
d-282
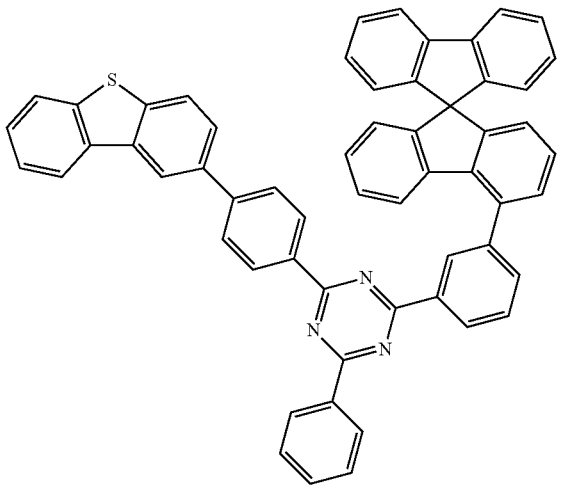
d-283
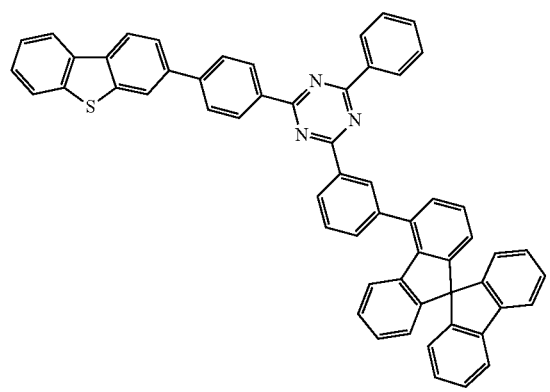
d-284
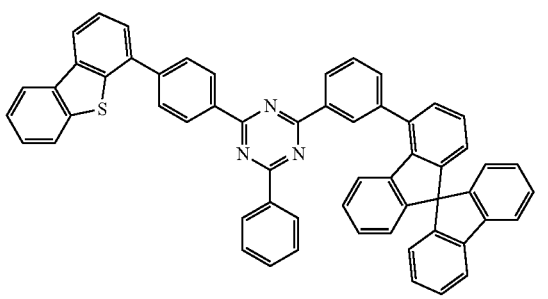
d-285
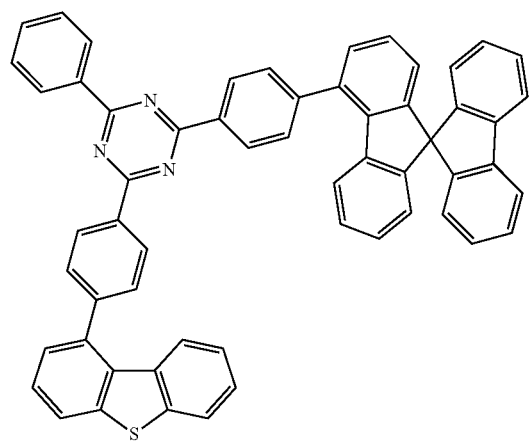
d-286
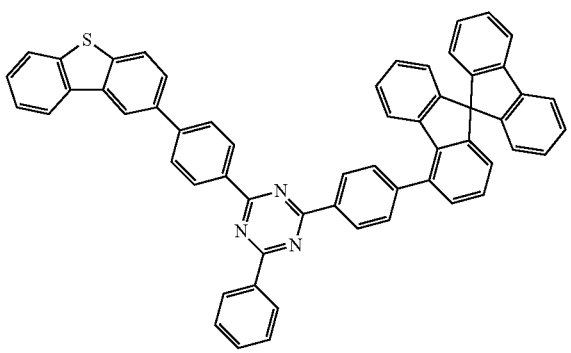

-continued
d-287
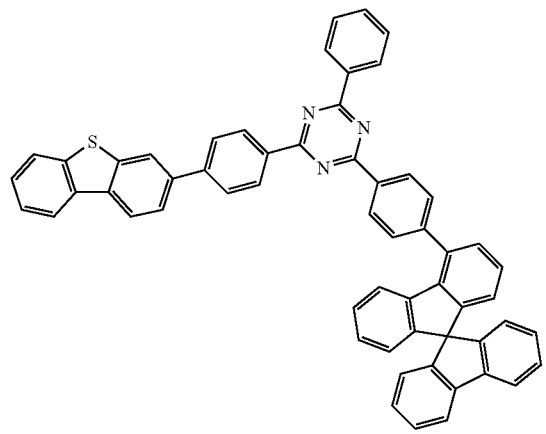
d-288
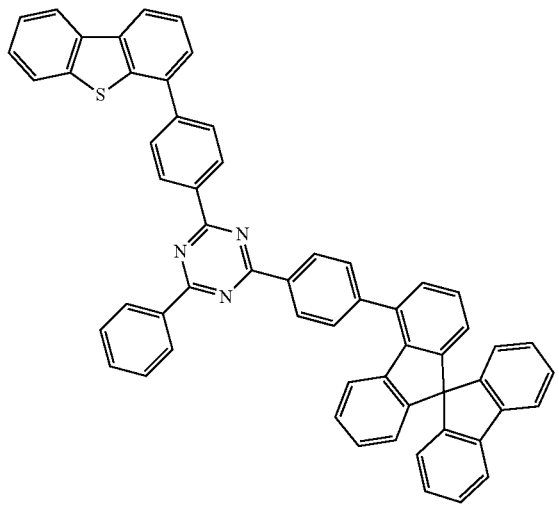
e-1
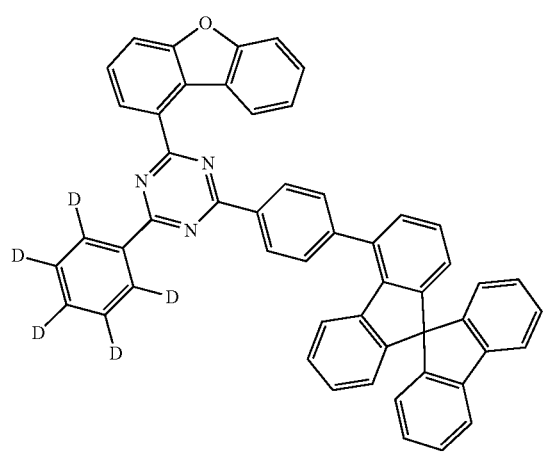
e-2
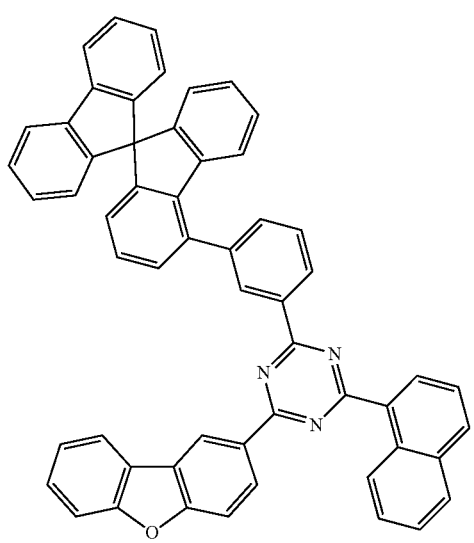
e-3
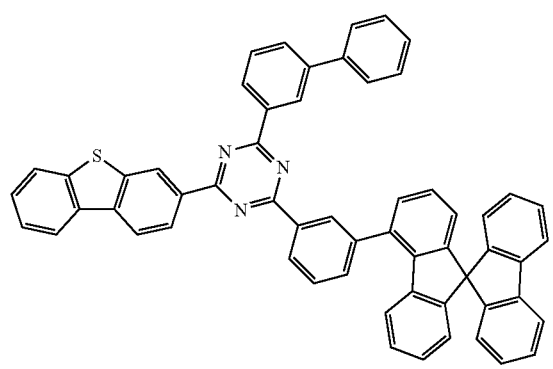
e-4
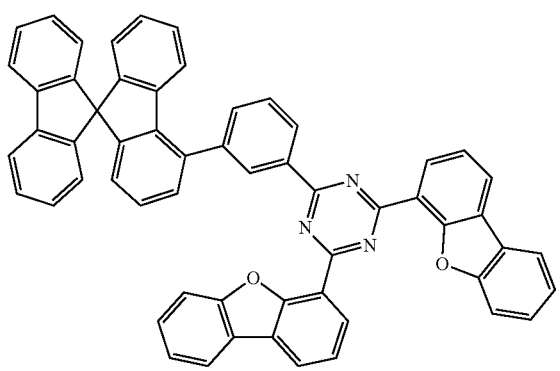

-continued
e-5
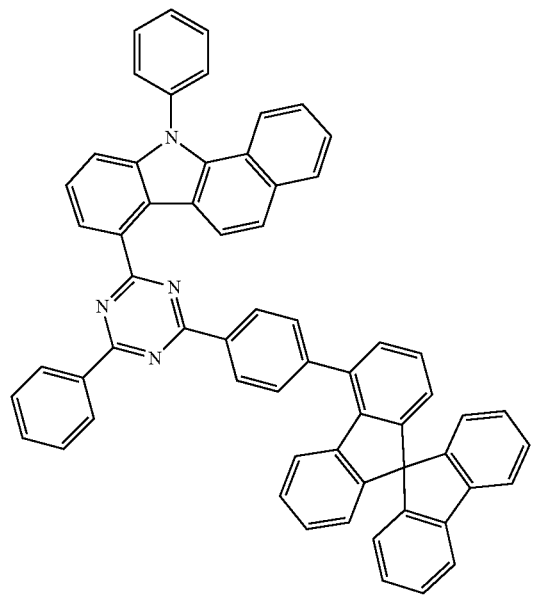
e-6
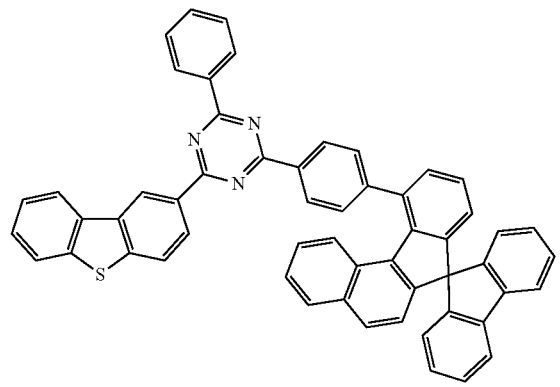
e-7
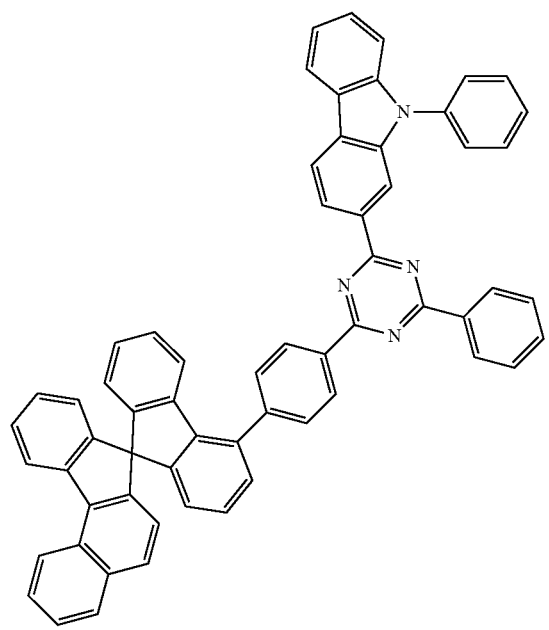
e-8
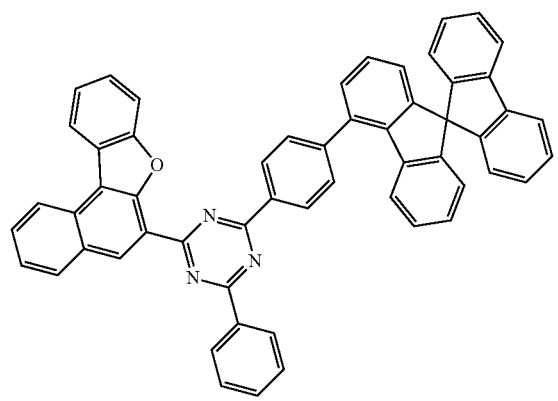
e-9
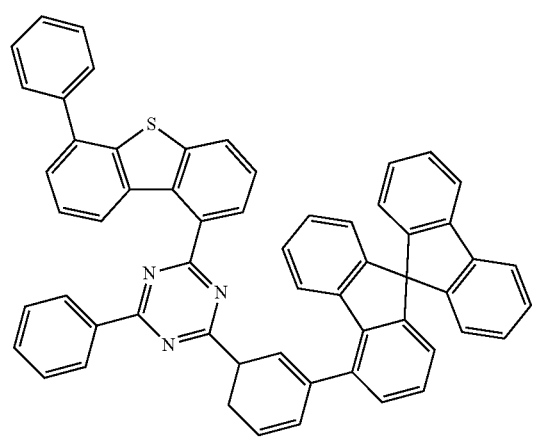
e-10
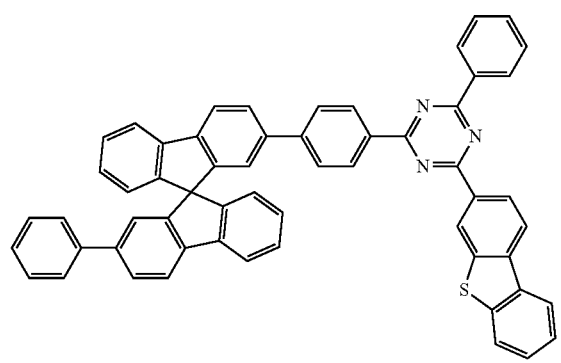

e-11

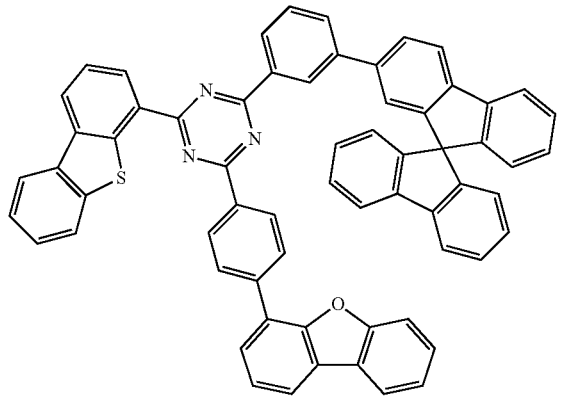

e-12

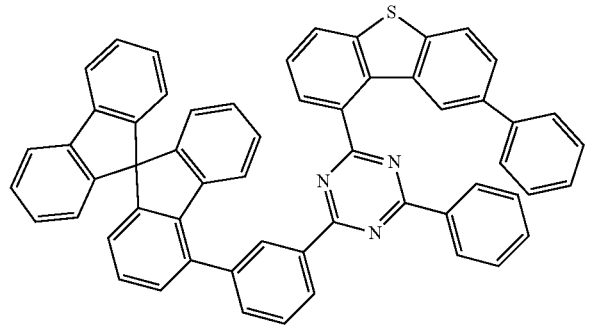

In an aspect of the present invention, the present invention provides an organic electric element comprising a first electrode, a second electrode, and an organic material layer formed between the first electrode and the second electrode, wherein the organic material layer comprises the compound represented by Formula 1 as a single compound or a mixture of two or more kinds.

The organic material layer comprises at least one of a hole injection layer, a hole transport layer, an emission-auxiliary layer, a light emitting layer, an electron transport auxiliary layer and an electron injection layer, preferably, the compound or the mixture is comprised in a light emitting layer.

In another aspect of the present invention, the present invention provides an electric device comprising a display device and a control unit for driving the display device, wherein the display device comprises the organic electric element.

Hereinafter, synthesis example of the compound represented by Formula and preparation method of an organic electric element according to one embodiment of the present invention will be described in detail by way of examples. However, the present invention is not limited to the following examples.

SYNTHESIS EXAMPLE

The compound according to the present invention can be synthesized by reacting Core and Sub as shown in Reaction Scheme 1 below, but there is no limitation thereto.

<Reaction Scheme 1>

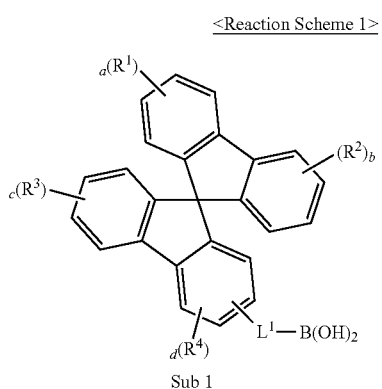

Sub 1

+

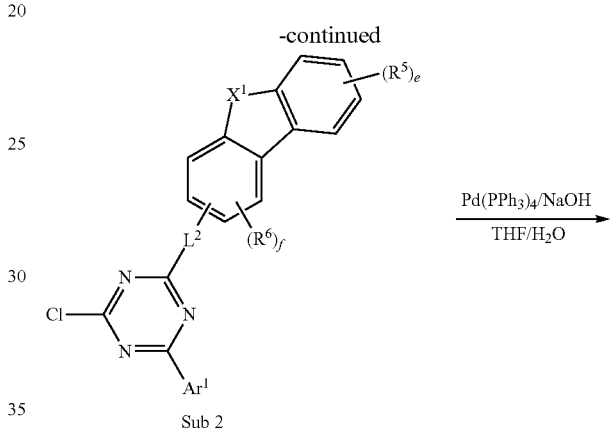

Sub 2

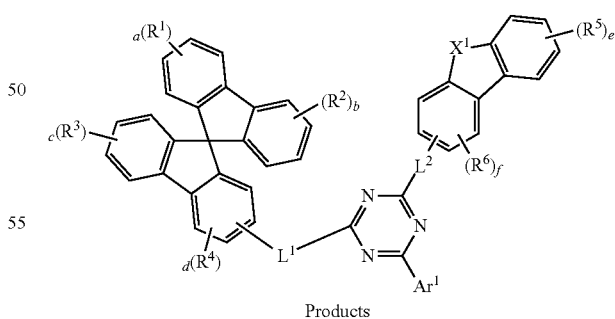

Products

Synthesis Example of Sub 1

Sub 1 of the Reaction Scheme 1 may be synthesized by the reaction route of the following Reaction Scheme 2, but there is no limitation thereto.

<Reaction Scheme 2>

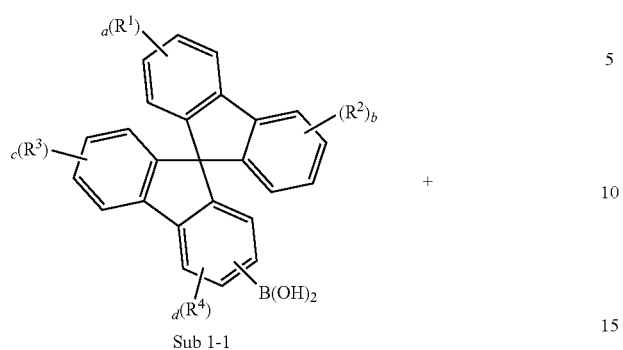

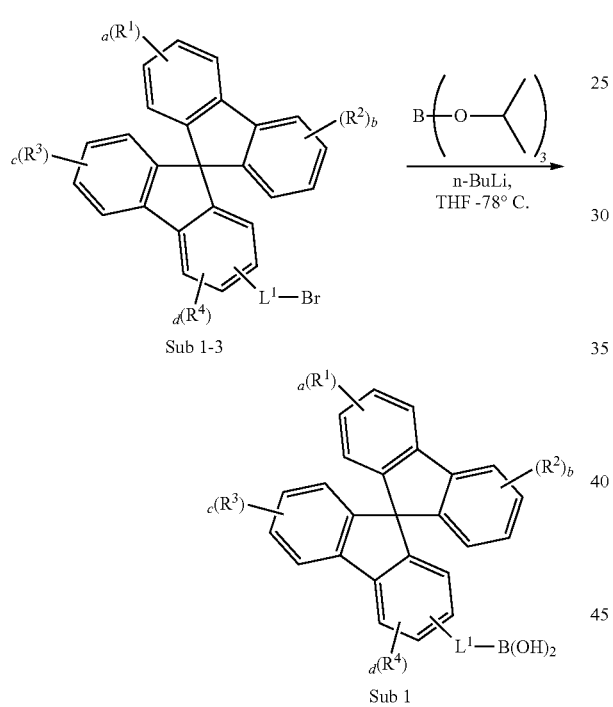

Synthesis Example of Sub 1(a-1)

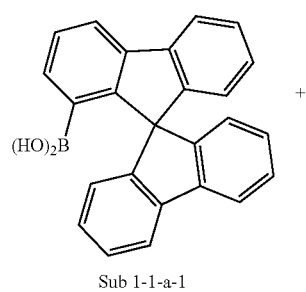

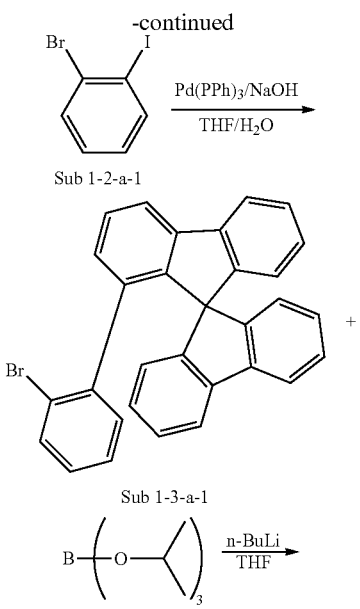

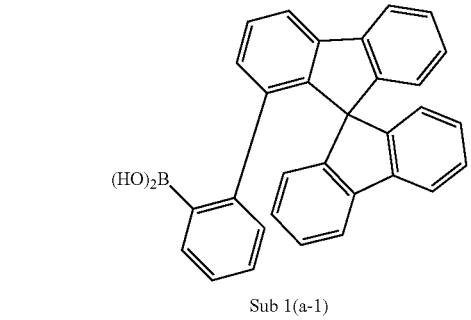

Synthesis Example of Sub 1-3-a-1

After putting Sub 1-1-a-1 (41.4 g, 115 mmol) and Sub 1-2-a-1 (32.4 g, 115 mmol), NaOH (9.2 g, 230 mmol), Pd(PPh$_3$)$_4$ (6.6 g, 5.75 mmol) into a round bottom flask, THF (800 mL) and water (200 mL) were added thereto and the mixture was dissolved. Then, the solution was refluxed at 80° C. for 12 hours. When the reaction was completed, the reaction product was cooled to room temperature, extracted with CH$_2$Cl$_2$ and washed with water. The organic layer was dried with MgSO$_4$ and concentrated. The concentrate was separated through a silica gel column to obtain Sub 1-3-a-1(36 g, 66%).

Synthesis Example of Sub 1(a-1)

After Sub 1-3-a-1 (36.3 g, 76.4 mmol) was dissolved in THF (700 mL), the temperature of the reactant was lowered to −78° C., n-BuLi (36.7 mL, 2.5M in hexane) was slowly added dropwise, and the reactant was stirred for 1 hour. After tri-isopropyl borate (26.4 mL, 114.6 mmol) was dissolved in THF, the solution was added to the reactant and the mixture was stirred for 4 hours. When the reaction was completed, water was added to the reaction product for quenching, water in the reaction product was removed and the resultant was filtered under reduced pressure. Then, the organic layer was dried with MgSO$_4$ and concentrated to obtain 21.8 g of product Sub 1(a-1) (yield: 60%).

Synthesis Example of Sub 1(a-6)

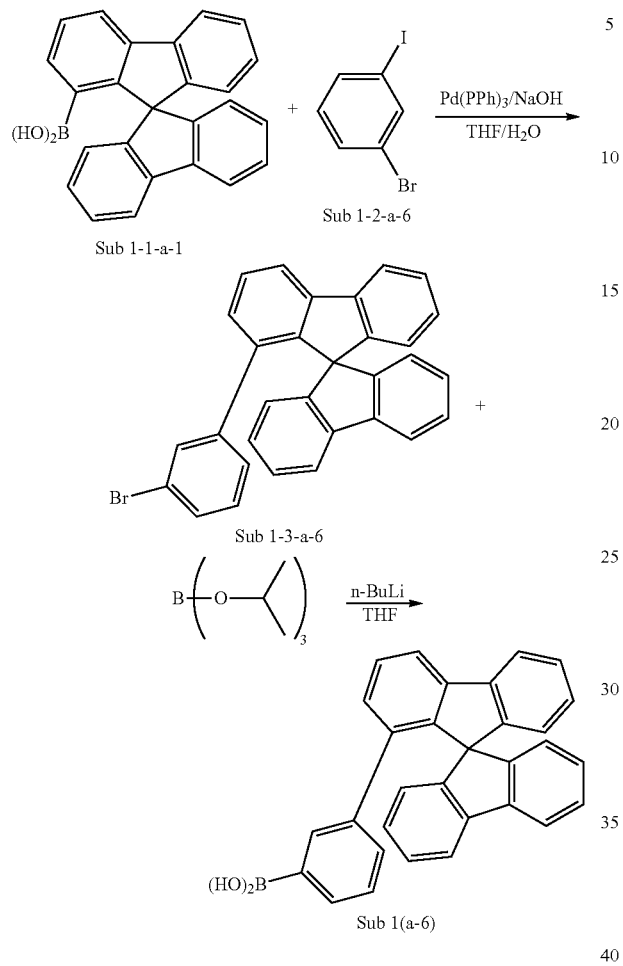

(1) Synthesis Example of Sub 1-3-a-6

Sub 1-1-a-1 (35.0 g, 97 mmol) and Sub 1-2-a-6 (27.5 g, 115 mmol) were carried out in the same manner as the synthesis method of Sub 1-3-a-1 and 22 g (yield: 59%) of the product was obtained.

(2) Synthesis Example of Sub 1(a-6)

22 g (yield: 59%) of the product was obtained in the same manner as the synthesis method of Sub 1-3-a-1 by using Sub 1-3-a-6 (22 g, 46.8 mmol) instead of Sub 1-3-a-1.

Synthesis Example of Sub 1(a-9)

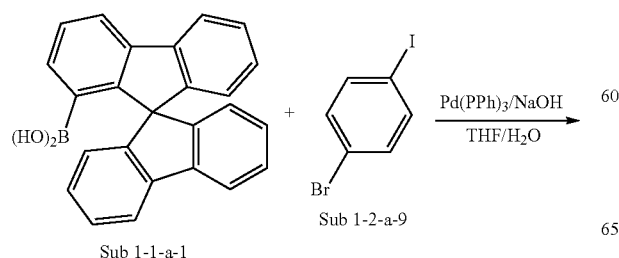

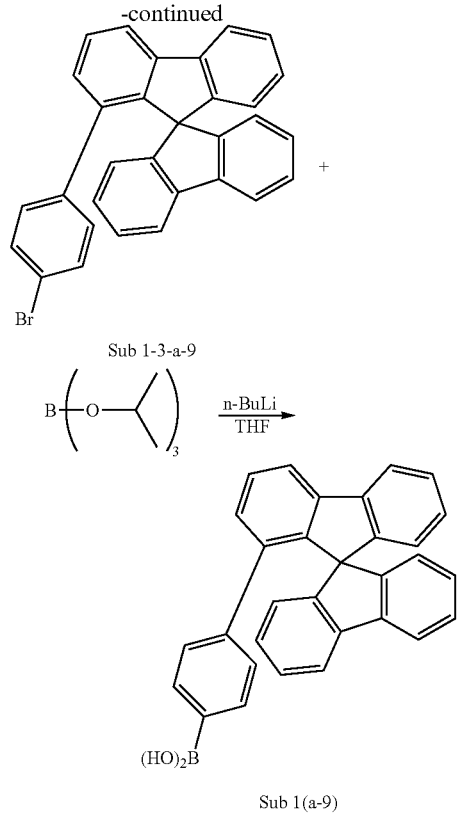

Synthesis Example of Sub 1-3-a-9

68 g (yield: 63%) of the product was obtained in the same manner as the synthesis method of Sub 1-3-a-1 by using Sub 1-1-a-1 (100 g, 228 mmol) and Sub 1-2-a-9 (78.5 g, 228 mmol).

Synthesis Example of Sub 1(a-9)

49 g (yield: 78%) of the product was obtained in the same manner as the synthesis method of Sub 1-3-a-1 by using Sub 1-3-a-9 (68 g, 144 mmol) instead of Sub 1-3-a-1.

Synthesis Example of Sub 1(a-13)

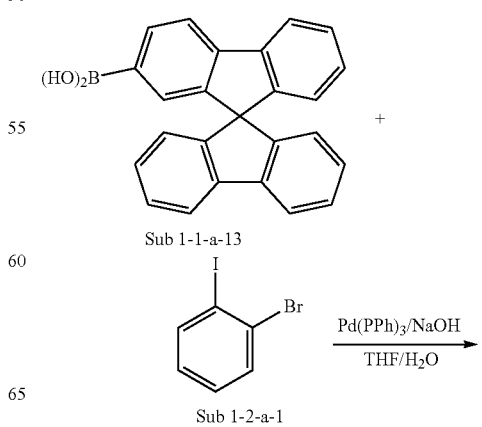

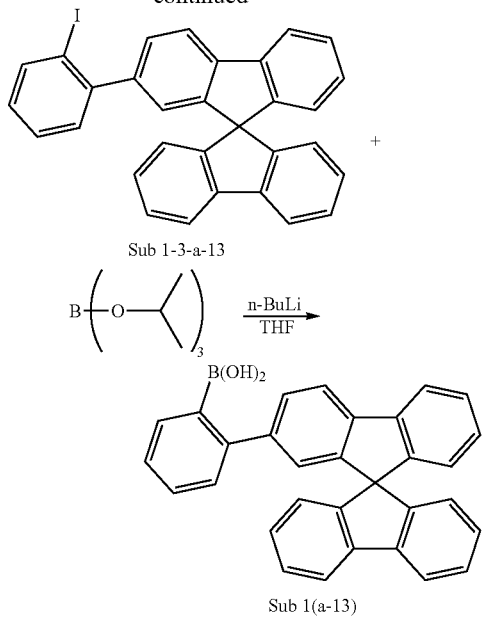

Sub 1(a-13)

Synthesis Example of Sub 1-3-a-13

72 g (yield: 67%) of the product was obtained in the same manner as the synthesis method of Sub 1-3-a-1 by using Sub 1-1-a-13 (100 g, 228 mmol) and Sub 1-2-a-1 (78.5 g, 228 mmol).

Synthesis Example of Sub 1(a-13)

55 g (yield: 82%) of the product was obtained in the same manner as the synthesis method of Sub 1-3-a-1 by using Sub 1-3-a-13 (72 g, 153 mmol) instead of Sub 1-3-a-1.

Synthesis Example of Sub 1(a-17)

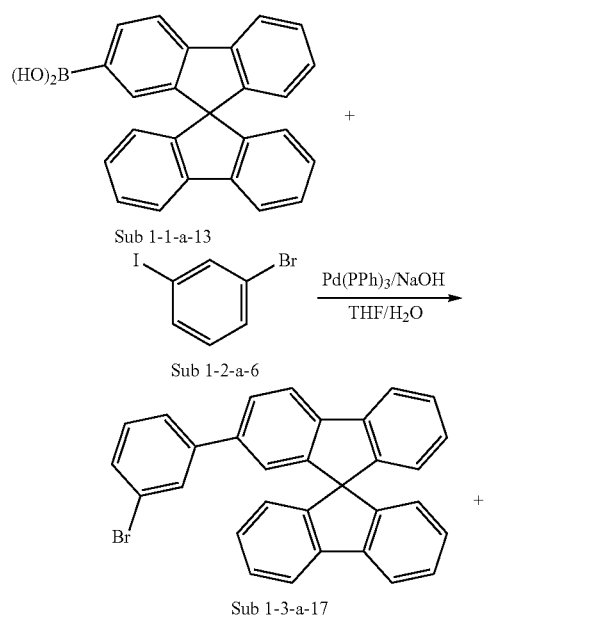

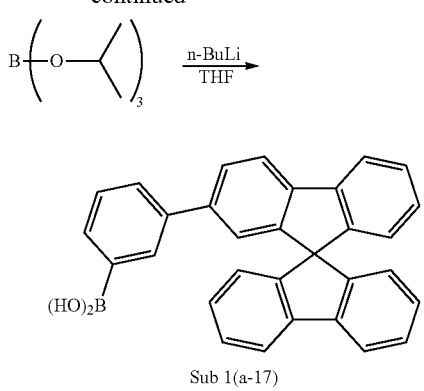

Sub 1(a-17)

Synthesis Example of Sub 1-3-a-17

77 g (yield: 72%) of the product was obtained in the same manner as the synthesis method of Sub 1-3-a-1 by using Sub 1-1-a-13 (100 g, 228 mmol) and Sub 1-2-a-6 (78.5 g, 228 mmol).

Synthesis Example of Sub 1(a-17)

60 g (yield: 84%) of the product was obtained in the same manner as the synthesis method of Sub 1-3-a-1 by using Sub 1-3-a-17 (77 g, 163 mmol) instead of Sub 1-3-a-1.

Synthesis Example of Sub 1(a-21)

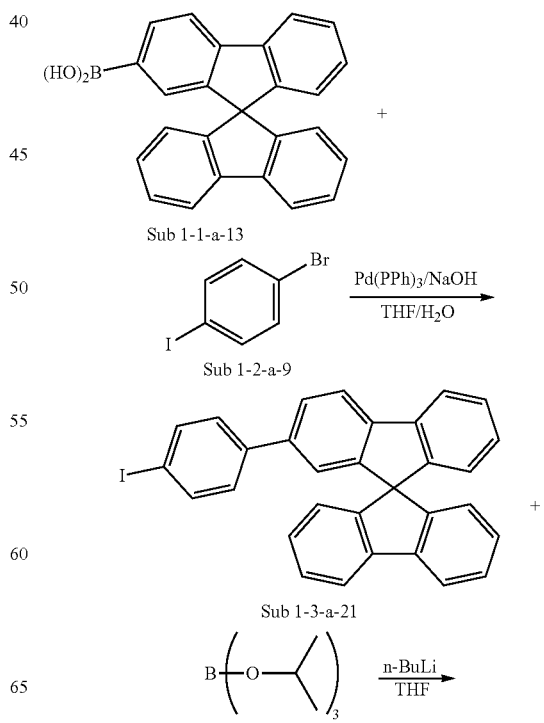

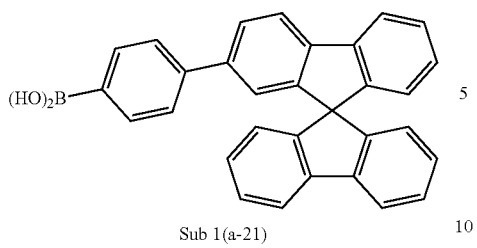

Sub 1(a-21)

Sub 1(a-25)

Synthesis Example of Sub 1-3-a-21

81 g (yield: 75%) of the product was obtained in the same manner as the synthesis method of Sub 1-3-a-1 by using Sub 1-1-a-13 (100 g, 228 mmol) and Sub 1-2-a-9 (78.5 g, 228 mmol).

Synthesis Example of Sub 1(a-21)

64 g (yield: 85%) of the product was obtained in the same manner as the synthesis method of Sub 1-3-a-1 by using Sub 1-3-a-21 (81 g, 172 mmol) instead of Sub 1-3-a-1.

Synthesis Example of Sub 1(a-25)

Synthesis Example of Sub 1-3-a-25

80 g (yield: 74%) of the product was obtained in the same manner as the synthesis method of Sub 1-3-a-1 by using Sub 1-1-a-25 (100 g, 228 mmol) and Sub 1-2-a-1 (78.5 g, 228 mmol).

Synthesis Example of Sub 1(a-25)

67 g (yield: 90%) of the product was obtained in the same manner as the synthesis method of Sub 1-3-a-1 by using Sub 1-3-a-25 (80 g, 170 mmol) instead of Sub 1-3-a-1.

Synthesis Example of Sub 1(a-29)

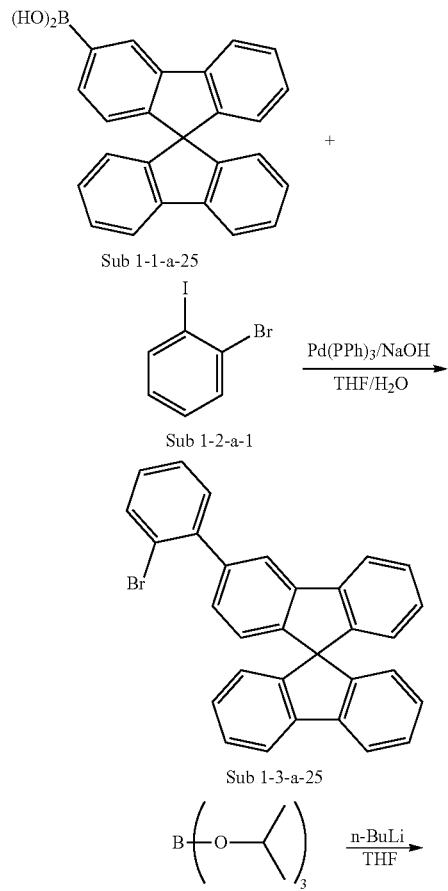

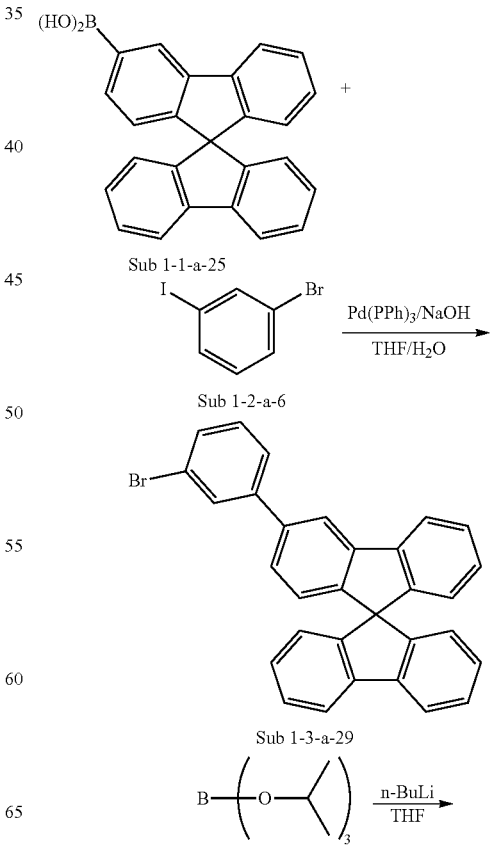

-continued

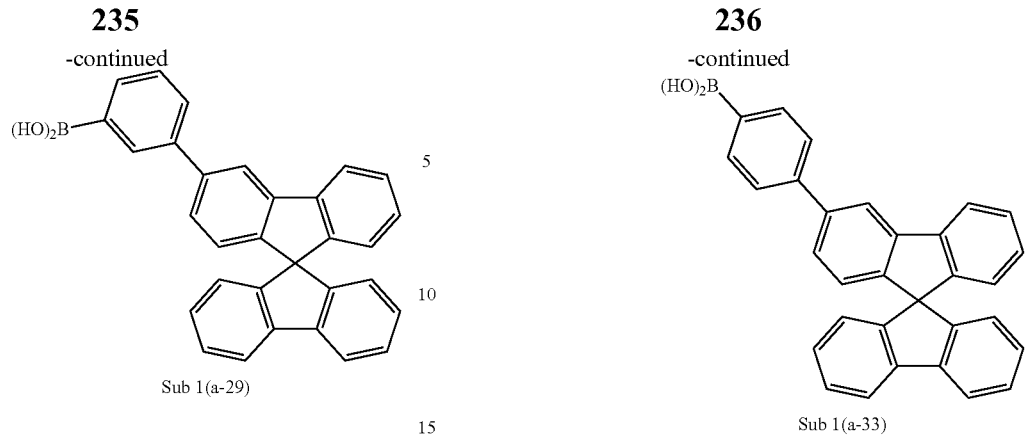

Sub 1(a-29)

Sub 1(a-33)

Synthesis Example of Sub 1-3-a-29

72 g (yield: 67%) of the product was obtained in the same manner as the synthesis method of Sub 1-3-a-1 by using Sub 1-1-a-25 (100 g, 228 mmol) and Sub 1-2-a-6 (78.5 g, 228 mmol).

Synthesis Example of Sub 1(a-29)

53 g (yield: 79%) of the product was obtained in the same manner as the synthesis method of Sub 1-3-a-1 by using Sub 1-3-a-29 (72 g, 153 mmol) instead of Sub 1-3-a-1.

Synthesis Example of Sub 1(a-33)

Synthesis Example of Sub 1-3-a-33

88 g (yield: 82%) of the product was obtained in the same manner as the synthesis method of Sub 1-3-a-1 by using Sub 1-1-a-25 (100 g, 228 mmol) and Sub 1-2-a-9 (78.5 g, 228 mmol).

Synthesis Example of Sub 1(a-33)

69 g (yield: 87%) of the product was obtained in the same manner as the synthesis method of Sub 1-3-a-1 by using Sub 1-3-a-33 (88 g, 182 mmol) instead of Sub 1-3-a-1.

Synthesis Example of Sub 1(a-37)

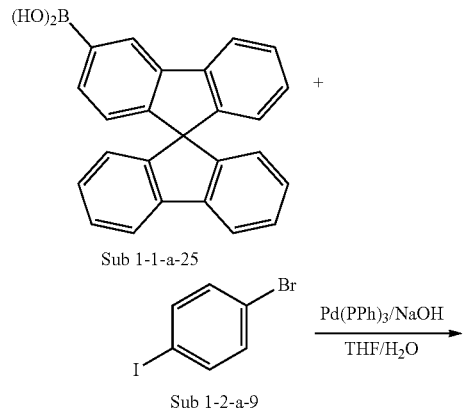

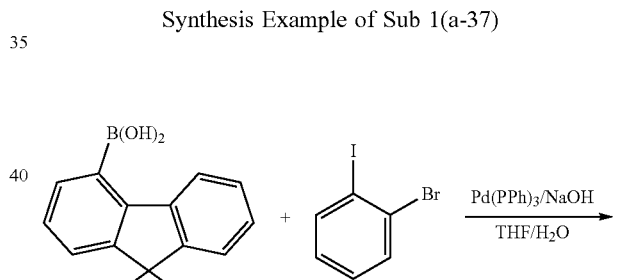

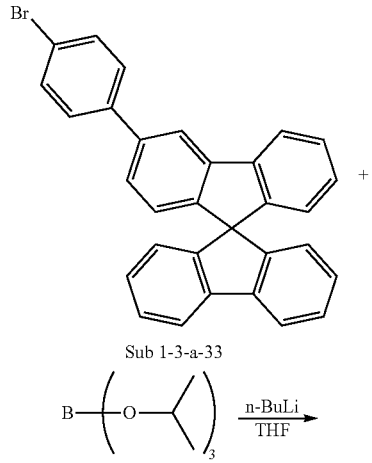

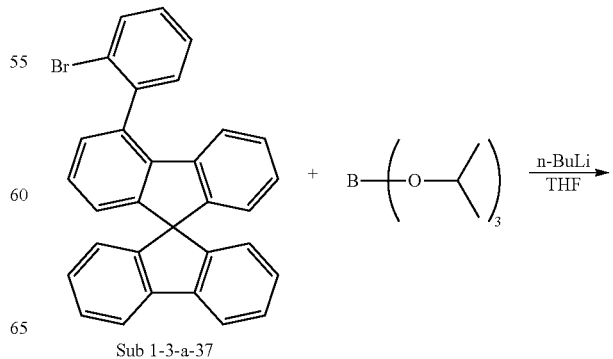

-continued

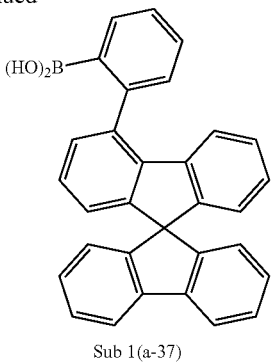

Sub 1(a-37)

Synthesis Example of Sub 1-3-a-37

66 g (yield: 62%) of the product was obtained in the same manner as the synthesis method of Sub 1-3-a-1 by using Sub 1-1-a-37 (100 g, 228 mmol) and Sub 1-2-a-1 (78.5 g, 228 mmol).

Synthesis Example of Sub 1(a-37)

47 g (yield: 77%) of the product was obtained in the same manner as the synthesis method of Sub 1-3-a-1 by using Sub 1-3-a-37 (66 g, 140 mmol) instead of Sub 1-3-a-1.

Synthesis Example of Sub 1(a-41)

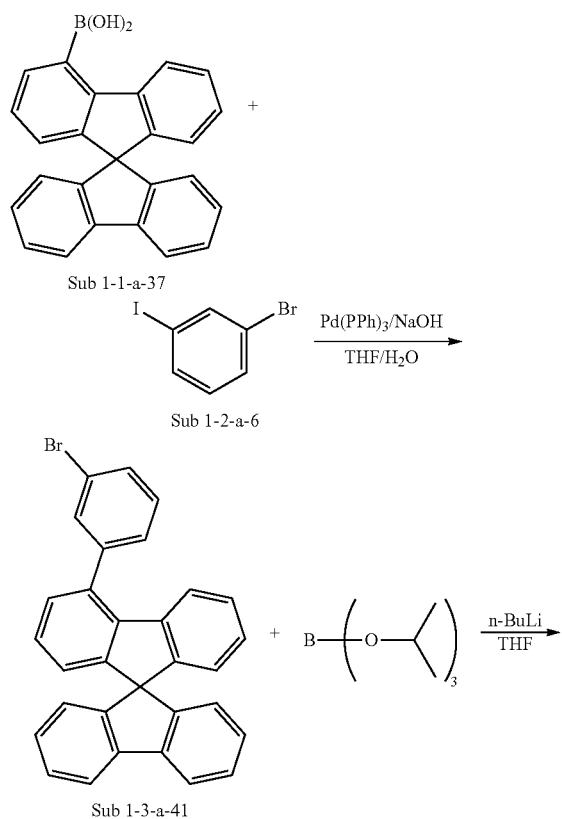

-continued

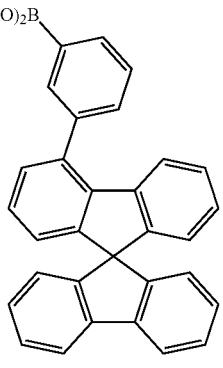

Sub 1(a-41)

Synthesis Example of Sub 1-3-a-41

77 g (yield: 72%) of the product was obtained in the same manner as the synthesis method of Sub 1-3-a-1 by using Sub 1-1-a-37 (100 g, 228 mmol) and Sub 1-2-a-6 (78.5 g, 228 mmol).

Synthesis Example of Sub 1(a-41)

54 g (yield: 75%) of the product was obtained in the same manner as the synthesis method of Sub 1-3-a-1 by using Sub 1-3-a-41 (77 g, 164 mmol) instead of Sub 1-3-a-1.

Synthesis Example of Sub 1(a-45)

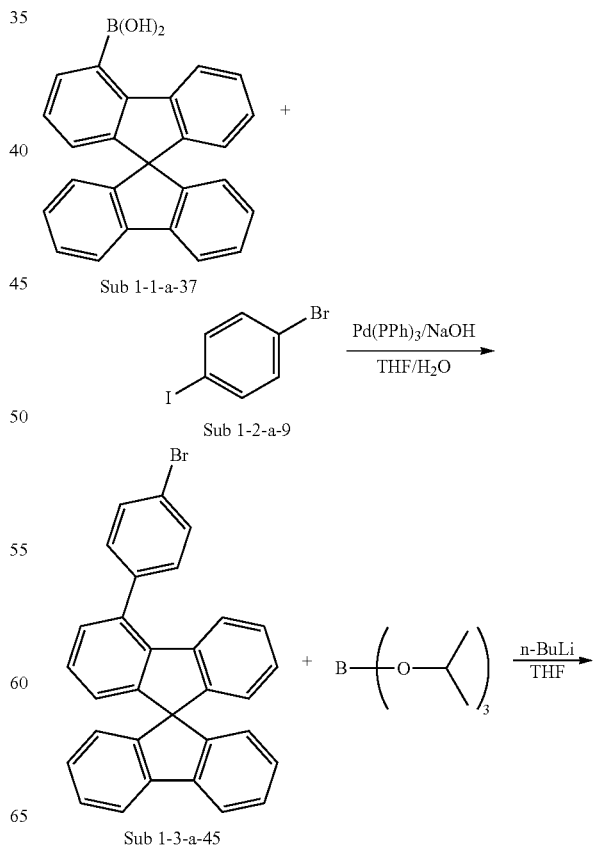

-continued

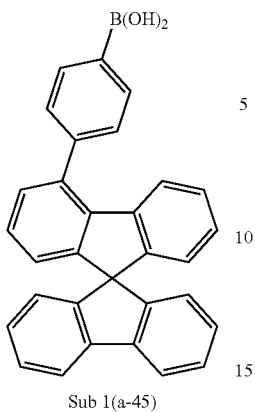
Sub 1(a-45)

Synthesis Example of Sub 1-3-a-45

79 g (yield: 74%) of the product was obtained in the same manner as the synthesis method of Sub 1-3-a-1 by using Sub 1-1-a-37 (100 g, 228 mmol) and Sub 1-2-a-9 (78.5 g, 228 mmol).

Synthesis Example of Sub 1(a-45)

53 g (yield: 72%) of the product was obtained in the same manner as the synthesis method of Sub 1-3-a-1 by using Sub 1-3-a-45 (79 g, 168 mmol) instead of Sub 1-3-a-1.

Example of Sub 1

The example compounds of Sub 1 may be, but not limited to, the following compounds, and Table 1 shows the FD-MS values of the following compounds.

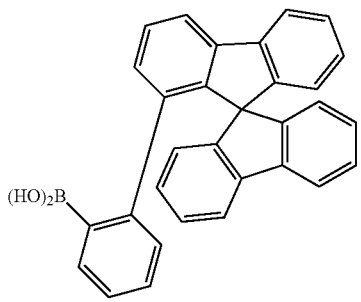
Sub 1(a-1)

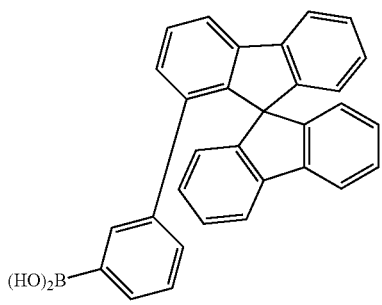
Sub 1(a-6)

-continued

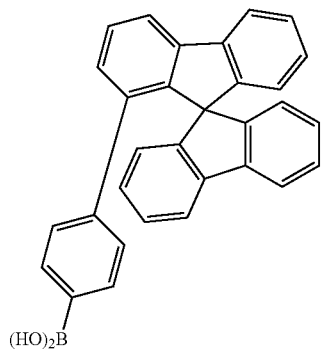
Sub 1(a-9)

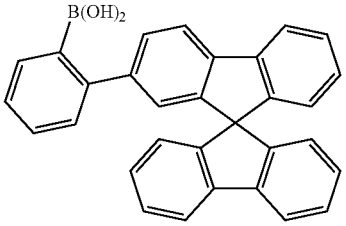
Sub 1(a-13)

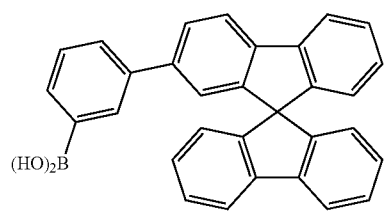
Sub 1(a-17)

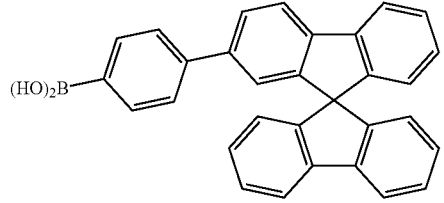
Sub 1(a-21)

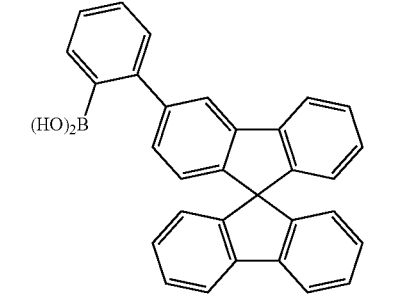
Sub 1(a-25)

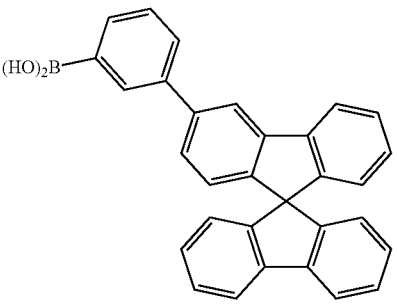
Sub 1(a-29)

-continued

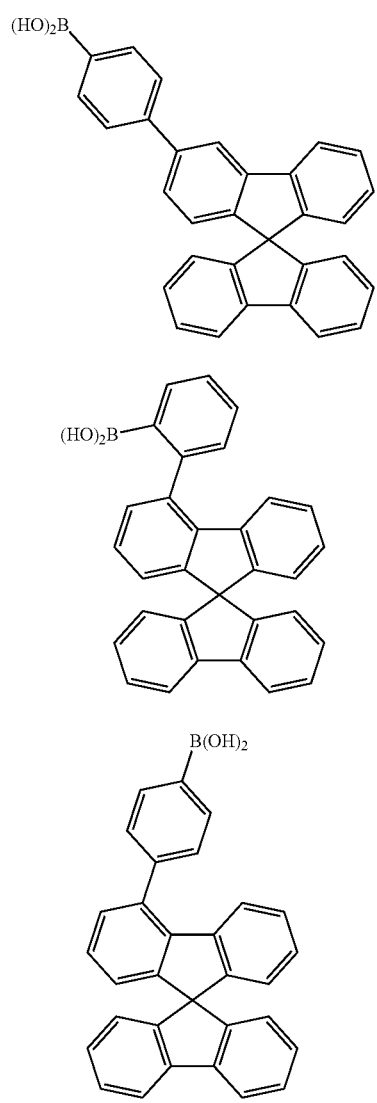

Sub 1(a-33)

Sub 1(a-37)

Sub 1(a-45)

TABLE 1

| Compound | FD-MS |
| --- | --- |
| Sub 1(a-1) | m/z = 436.16($C_{31}H_{22}BO_2$ = 437.16) |
| Sub 1(a-6) | m/z = 436.16($C_{31}H_{22}BO_2$ = 437.16) |
| Sub 1(a-9) | m/z = 436.16($C_{31}H_{22}BO_2$ = 437.16) |
| Sub 1(a-13) | m/z = 436.16($C_{31}H_{22}BO_2$ = 437.16) |
| Sub 1(a-17) | m/z = 436.16($C_{31}H_{22}BO_2$ = 437.16) |
| Sub 1(a-21) | m/z = 436.16($C_{31}H_{22}BO_2$ = 437.16) |
| Sub 1(a-25) | m/z = 436.16($C_{31}H_{22}BO_2$ = 437.16) |
| Sub 1(a-29) | m/z = 436.16($C_{31}H_{22}BO_2$ = 437.16) |
| Sub 1(a-33) | m/z = 436.16($C_{31}H_{22}BO_2$ = 437.16) |
| Sub 1(a-37) | m/z = 436.16($C_{31}H_{22}BO_2$ = 437.16) |
| Sub 1(a-41) | m/z = 436.16($C_{31}H_{22}BO_2$ = 437.16) |
| Sub 1(a-45) | m/z = 436.16($C_{31}H_{22}BO_2$ = 437.16) |

Example of Sub 2

Example of Sub 2 may be, but not limited to, the following compounds, and Table 2 shows the FD-MS values of the following compounds.

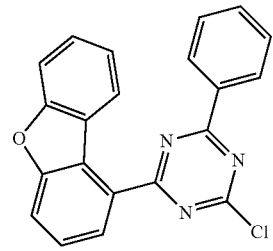

Sub 2 (c-1)

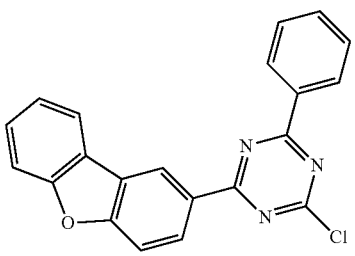

Sub 2 (c-2)

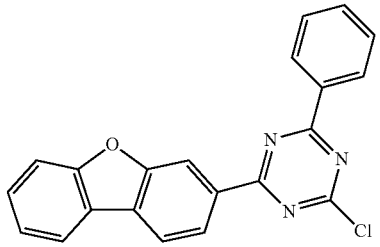

Sub 2 (c-3)

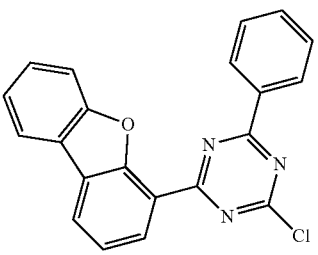

Sub 2 (c-4)

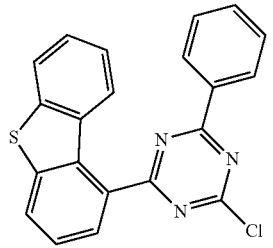

Sub 2 (c-49)

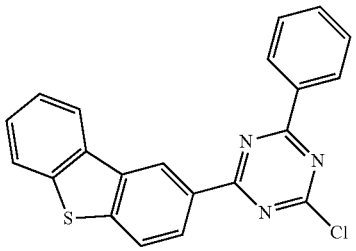

Sub 2 (c-50)

Sub 2 (c-51)
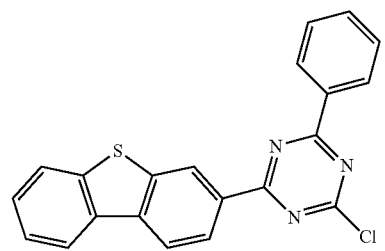
Sub 2 (c-52)
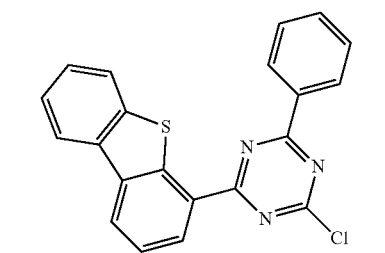
Sub 2 (c-93)
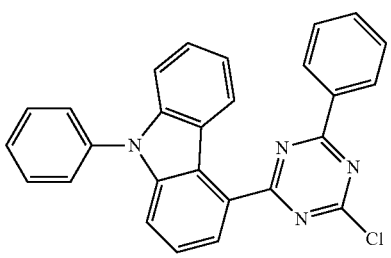
Sub 2 (c-94)
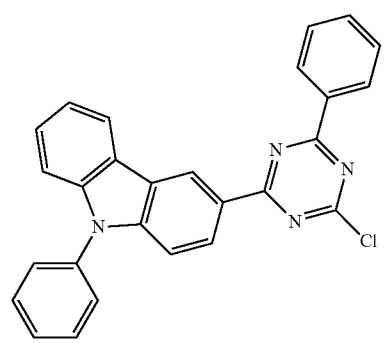
Sub 2 (c-95)
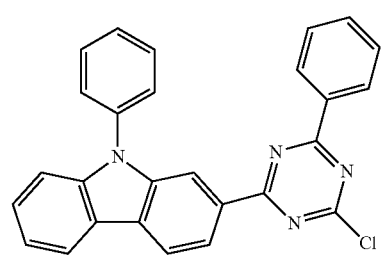
Sub 2 (c-96)
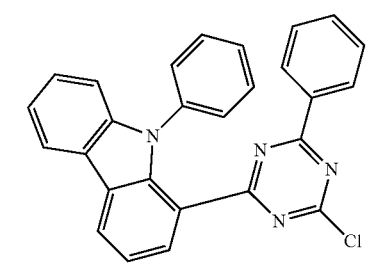
Sub 2 (d-49)
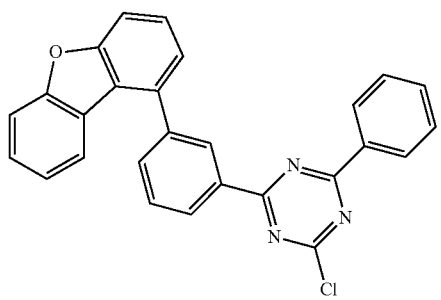
Sub 2 (d-50)
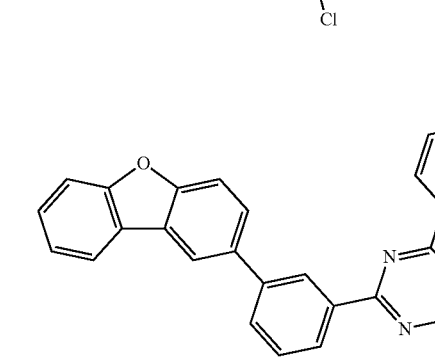
Sub 2 (d-51)
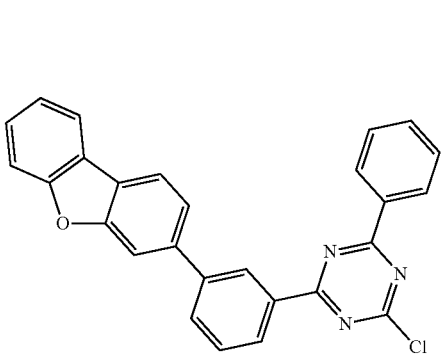
Sub 2 (d-52)
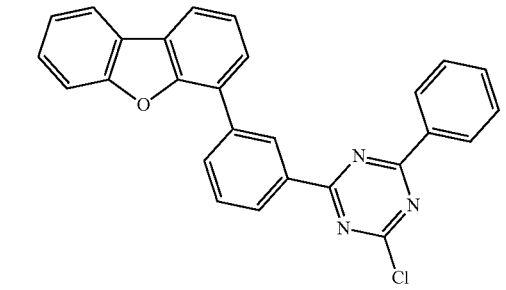
Sub 2 (d-97)
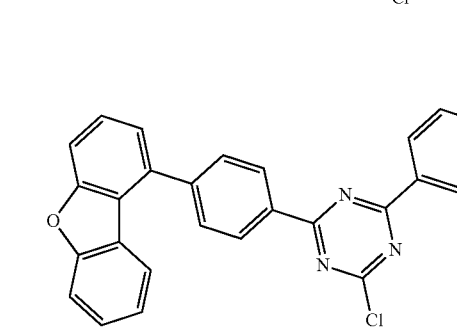

Sub 2 (d-98)
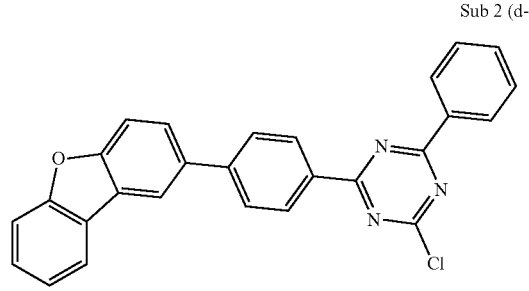
Sub 2 (d-99)
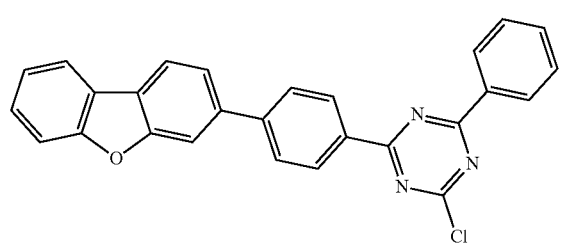
Sub 2 (d-100)
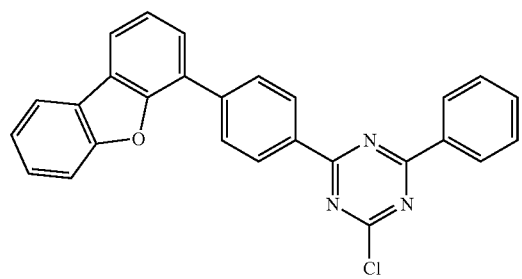
Sub 2 (d-193)
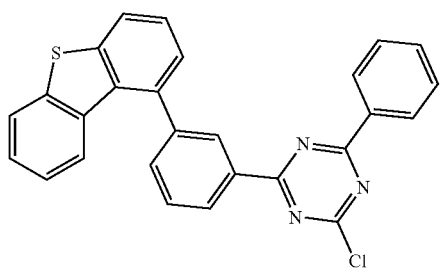
Sub 2 (d-194)
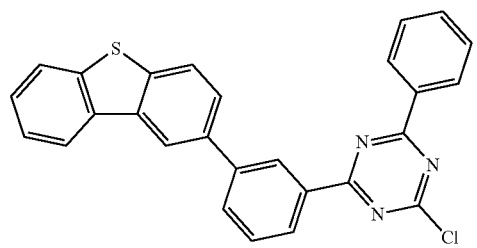
Sub 2 (d-195)
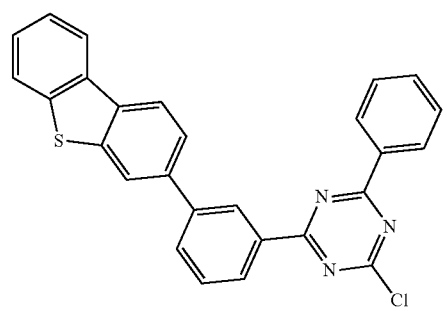
Sub 2 (d-196)
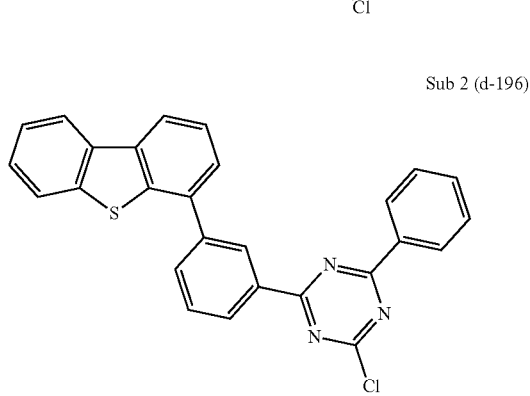
Sub 2 (d-241)
Sub 2 (d-242)
Sub 2 (d-243)
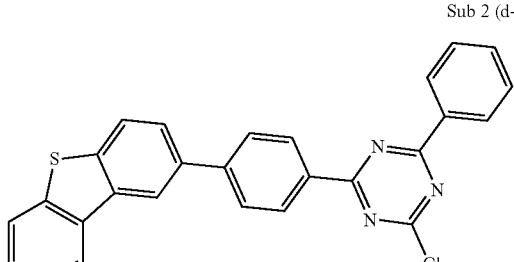

Sub 2 (d-244)

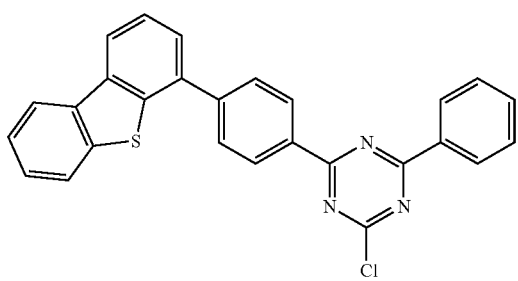

Sub 2(c-51)

TABLE 2

| Compound | FD-MS |
|---|---|
| Sub 2(c-1) | m/z = 357.07($C_{21}H_{12}ClN_3O$ = 358.07) |
| Sub 2(c-2) | m/z = 357.07($C_{21}H_{12}ClN_3O$ = 358.07) |
| Sub 2(c-3) | m/z = 357.07($C_{21}H_{12}ClN_3O$ = 358.07) |
| Sub 2(c-4) | m/z = 357.07($C_{21}H_{12}ClN_3O$ = 358.07) |
| Sub 2(c-49) | m/z = 373.04($C_{21}H_{12}ClN_3O$ = 374.04) |
| Sub 2(c-50) | m/z = 373.04($C_{21}H_{12}ClN_3O$ = 374.04) |
| Sub 2(c-51) | m/z = 373.04($C_{21}H_{12}ClN_3O$ = 374.04) |
| Sub 2(c-52) | m/z = 373.04($C_{21}H_{12}ClN_3O$ = 374.04) |
| Sub 2(c-93) | m/z = 432.11($C_{27}H_{17}ClN_4$ = 433.11) |
| Sub 2(c-94) | m/z = 432.11($C_{27}H_{17}ClN_4$ = 433.11) |
| Sub 2(d-99) | m/z = 433.10($C_{27}H_{16}ClN_3O$ = 434.10) |
| Sub 2(d-100) | m/z = 433.10($C_{27}H_{16}ClN_3O$ = 434.10) |
| Sub 2(d-193) | m/z = 449.08($C_{27}H_{16}ClN_3S$ = 450.08) |
| Sub 2(d-194) | m/z = 449.08($C_{27}H_{16}ClN_3S$ = 450.08) |
| Sub 2(d-195) | m/z = 449.08($C_{27}H_{16}ClN_3S$ = 450.08) |
| Sub 2(d-196) | m/z = 449.08($C_{27}H_{16}ClN_3S$ = 450.08) |
| Sub 2(d-241) | m/z = 449.08($C_{27}H_{16}ClN_3S$ = 450.08) |
| Sub 2(d-242) | m/z = 449.08($C_{27}H_{16}ClN_3S$ = 450.08) |
| Sub 2(d-243) | m/z = 449.08($C_{27}H_{16}ClN_3S$ = 450.08) |
| Sub 2(d-244) | m/z = 449.08($C_{27}H_{16}ClN_3S$ = 450.08) |

Synthesis Example of Final Product

Synthesis Example of c-95

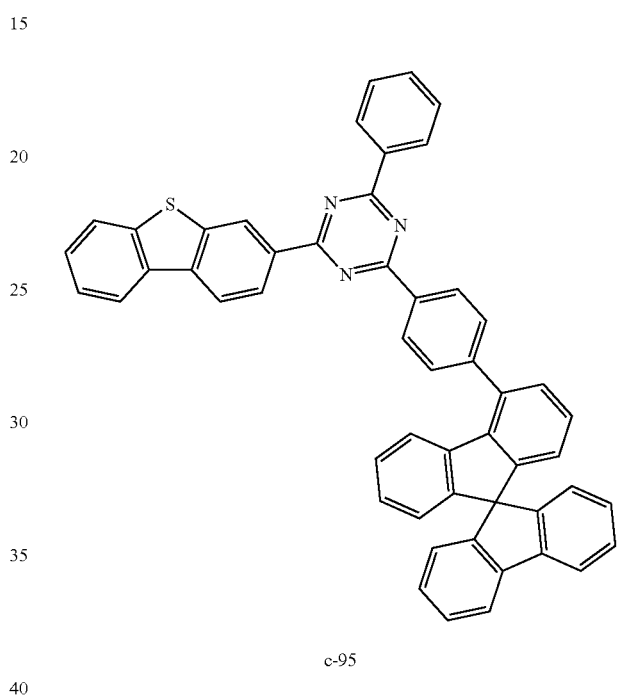

c-95 c-95 (7.2 g, 49%) of the product was obtained in the same manner as the synthesis method of Sub 1-3-a-1 by using Sub 1(a-41) (10.0 g, 22.9 mmol) and Sub 2(c-51) (7.48 g, 20.0 mmol).

Synthesis Example of c-96

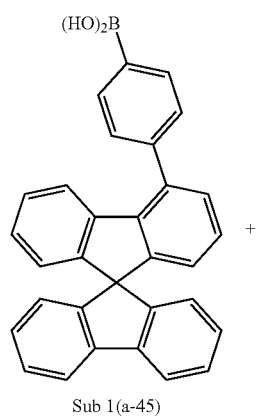

Sub 1(a-45)

+

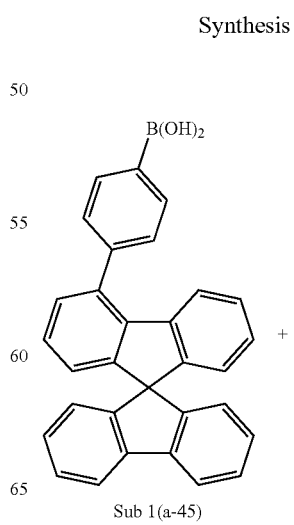

Sub 1(a-45)

+

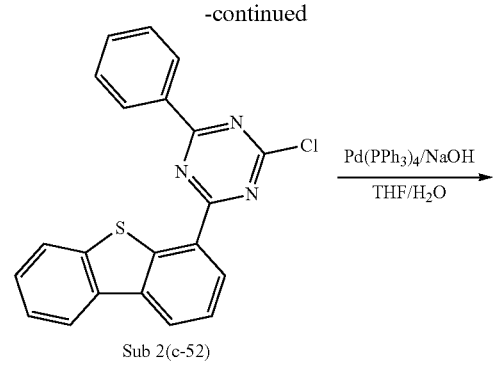
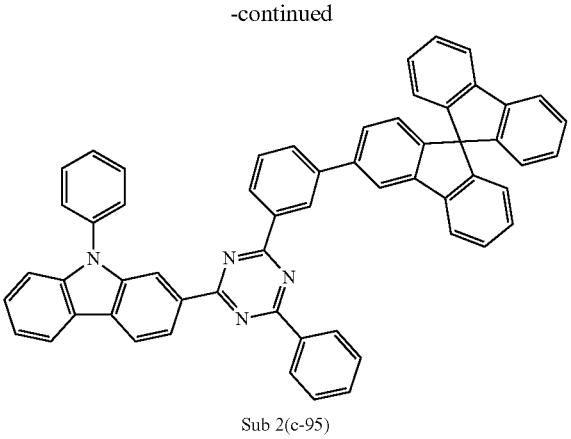
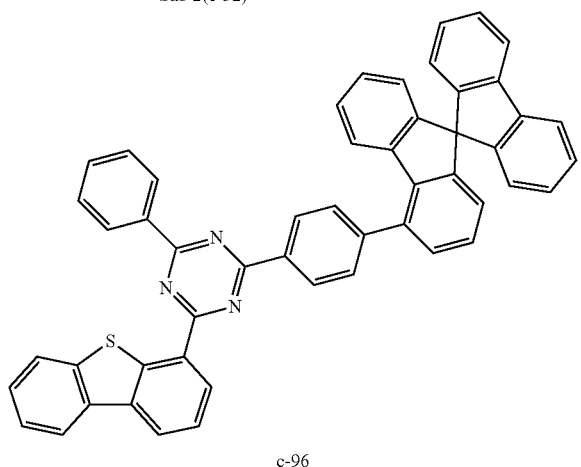
c-96 (8.9 g, 61%) of the product was obtained in the same manner as the synthesis method of Sub 1-3-a-1 by using Sub 1(a-45) (10.0 g, 22.9 mmol) and Sub 2(c-52) (7.48 g, 20.0 mmol).
Synthesis Example of c-123
c-123 (10.6 g, 67%) of the product was obtained in the same manner as the synthesis method of Sub 1-3-a-1 by using Sub 1(a-29) (10.0 g, 22.9 mmol) and Sub 2(c-95) (8.66 g, 20.0 mmol).
Synthesis Example of c-126
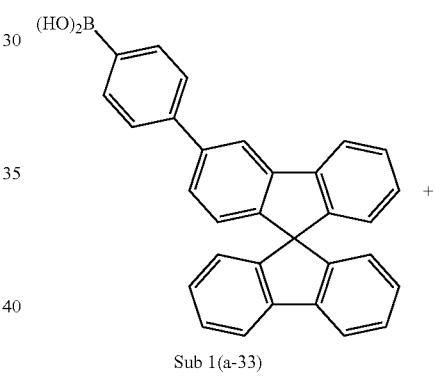
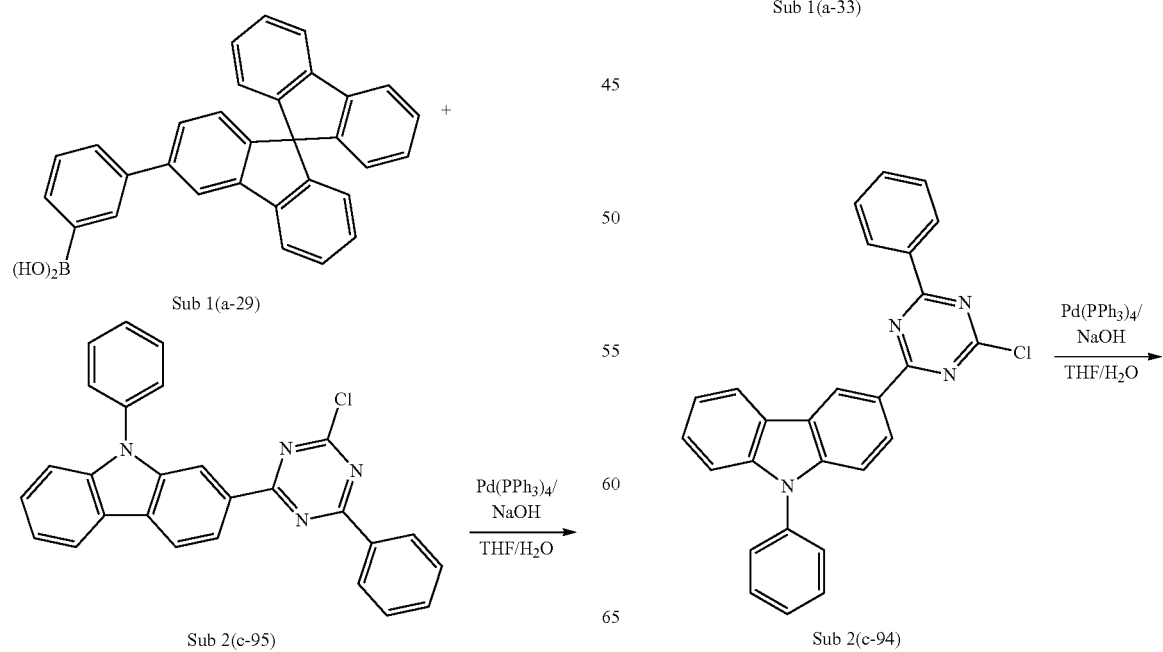

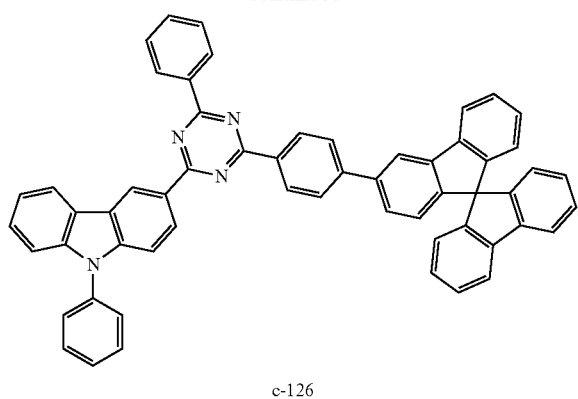
c-126
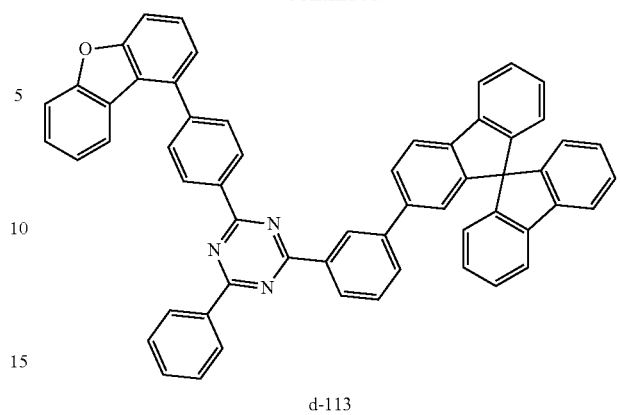
d-113
c-126 (9.0 g, 57%) of the product was obtained in the same manner as the synthesis method of Sub 1-3-a-1 by using Sub 1(a-33) (10.0 g, 22.9 mmol) and Sub 2(c-94) (8.66 g, 20.0 mmol).
d-113 (7.4 g, 47%) of the product was obtained in the same manner as the synthesis method of Sub 1-3-a-1 by using Sub 1(a-17) (10.0 g, 22.9 mmol) and Sub 2(d-97) (8.68 g, 20.0 mmol).
Synthesis Example of d-113
Synthesis Example of d-139
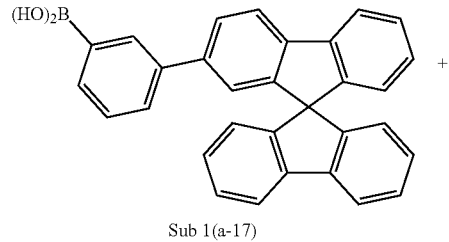
Sub 1(a-17)
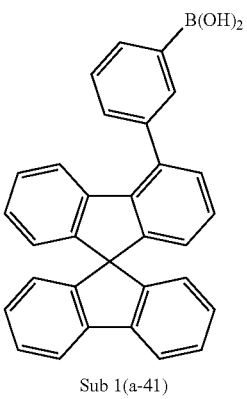
Sub 1(a-41)
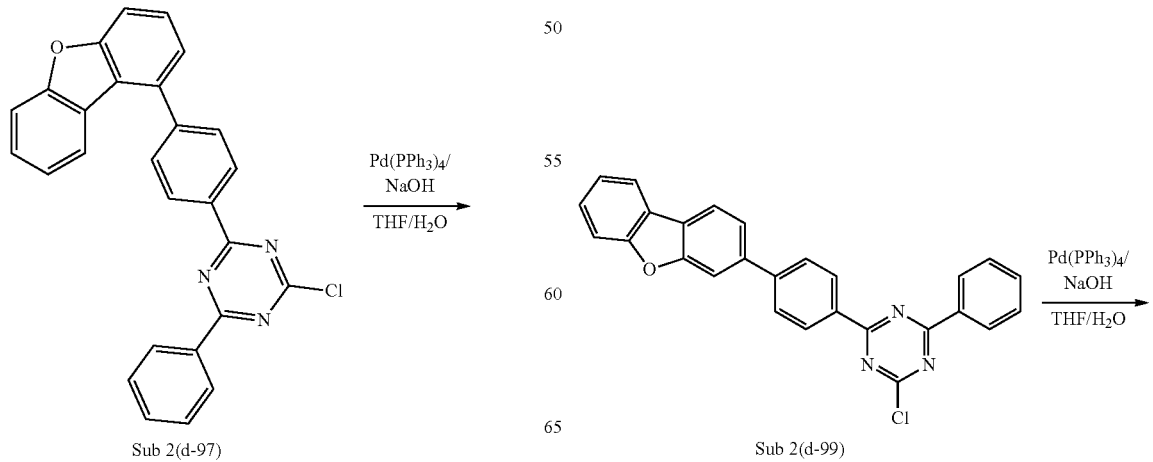
Sub 2(d-97)
Sub 2(d-99)

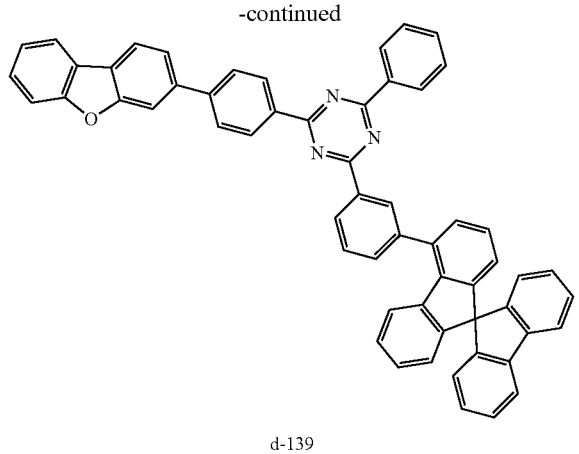

d-139 d-139 (8.8 g, 56%) of the product was obtained in the same manner as the synthesis method of Sub 1-3-a-1 by using Sub 1(a-41) (10.0 g, 22.9 mmol) and Sub 2(d-99) (8.68 g, 20.0 mmol).

Synthesis Example of d-212

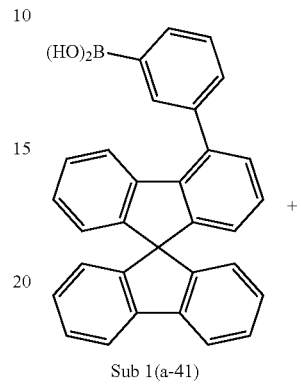

Sub 1(a-17)

d-212 d-212 (11.2 g, 70%) of the product was obtained in the same manner as the synthesis method of Sub 1-3-a-1 by using Sub 1(a-17) (10.0 g, 22.9 mmol) and Sub 2(d-196) (9.00 g, 20.0 mmol).

Synthesis Example of d-284

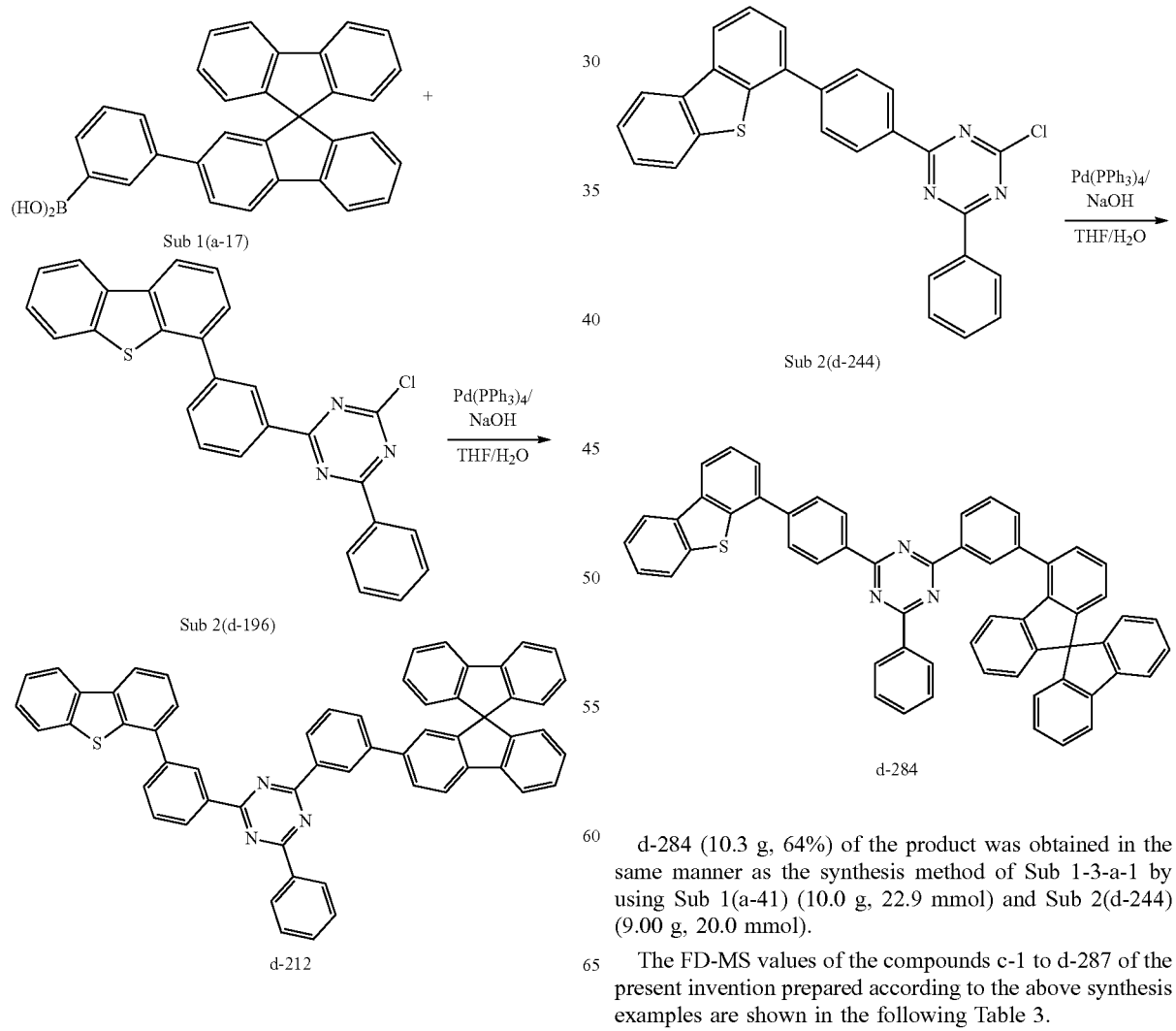

d-284 d-284 (10.3 g, 64%) of the product was obtained in the same manner as the synthesis method of Sub 1-3-a-1 by using Sub 1(a-41) (10.0 g, 22.9 mmol) and Sub 2(d-244) (9.00 g, 20.0 mmol).

The FD-MS values of the compounds c-1 to d-287 of the present invention prepared according to the above synthesis examples are shown in the following Table 3.

TABLE 3

| Compound | FD-MS | Compound | FD-MS |
|---|---|---|---|
| c-1 | m/z = 713.25(C$_{52}$H$_{31}$N$_3$O = 714.84) | c-2 | m/z = 713.25(C$_{52}$H$_{31}$N$_3$O = 714.84) |
| c-3 | m/z = 713.25(C$_{52}$H$_{31}$N$_3$O = 714.84) | c-4 | m/z = 713.25(C$_{52}$H$_{31}$N$_3$O = 714.84) |
| c-5 | m/z = 713.25(C$_{52}$H$_{31}$N$_3$O = 714.84) | c-6 | m/z = 713.25(C$_{52}$H$_{31}$N$_3$O = 714.84) |
| c-7 | m/z = 713.25(C$_{52}$H$_{31}$N$_3$O = 714.84) | c-8 | m/z = 713.25(C$_{52}$H$_{31}$N$_3$O = 714.84) |
| c-9 | m/z = 713.25(C$_{52}$H$_{31}$N$_3$O = 714.84) | c-44 | m/z = 713.25(C$_{52}$H$_{31}$N$_3$O = 714.84) |
| c-10 | m/z = 713.25(C$_{52}$H$_{31}$N$_3$O = 714.84) | c-45 | m/z = 713.25(C$_{52}$H$_{31}$N$_3$O = 714.84) |
| c-11 | m/z = 713.25(C$_{52}$H$_{31}$N$_3$O = 714.84) | c-46 | m/z = 713.25(C$_{52}$H$_{31}$N$_3$O = 714.84) |
| c-12 | m/z = 713.25(C$_{52}$H$_{31}$N$_3$O = 714.84) | c-47 | m/z = 713.25(C$_{52}$H$_{31}$N$_3$O = 714.84) |
| c-13 | m/z = 713.25(C$_{52}$H$_{31}$N$_3$O = 714.84) | c-48 | m/z = 713.25(C$_{52}$H$_{31}$N$_3$O = 714.84) |
| c-14 | m/z = 713.25(C$_{52}$H$_{31}$N$_3$O = 714.84) | c-49 | m/z = 729.22(C$_{52}$H$_{31}$N$_3$S = 730.90) |
| c-15 | m/z = 713.25(C$_{52}$H$_{31}$N$_3$O = 714.84) | c-50 | m/z = 729.22(C$_{52}$H$_{31}$N$_3$S = 730.90) |
| c-16 | m/z = 713.25(C$_{52}$H$_{31}$N$_3$O = 714.84) | c-51 | m/z = 729.22(C$_{52}$H$_{31}$N$_3$S = 730.90) |
| c-17 | m/z = 713.25(C$_{52}$H$_{31}$N$_3$O = 714.84) | c-52 | m/z = 729.22(C$_{52}$H$_{31}$N$_3$S = 730.90) |
| c-18 | m/z = 713.25(C$_{52}$H$_{31}$N$_3$O = 714.84) | c-53 | m/z = 729.22(C$_{52}$H$_{31}$N$_3$S = 730.90) |
| c-19 | m/z = 713.25(C$_{52}$H$_{31}$N$_3$O = 714.84) | c-54 | m/z = 729.22(C$_{52}$H$_{31}$N$_3$S = 730.90) |
| c-20 | m/z = 713.25(C$_{52}$H$_{31}$N$_3$O = 714.84) | c-55 | m/z = 729.22(C$_{52}$H$_{31}$N$_3$S = 730.90) |
| c-21 | m/z = 713.25(C$_{52}$H$_{31}$N$_3$O = 714.84) | c-56 | m/z = 729.22(C$_{52}$H$_{31}$N$_3$S = 730.90) |
| c-22 | m/z = 713.25(C$_{52}$H$_{31}$N$_3$O = 714.84) | c-57 | m/z = 729.22(C$_{52}$H$_{31}$N$_3$S = 730.90) |
| c-23 | m/z = 713.25(C$_{52}$H$_{31}$N$_3$O = 714.84) | c-58 | m/z = 729.22(C$_{52}$H$_{31}$N$_3$S = 730.90) |
| c-24 | m/z = 713.25(C$_{52}$H$_{31}$N$_3$O = 714.84) | c-59 | m/z = 729.22(C$_{52}$H$_{31}$N$_3$S = 730.90) |
| c-25 | m/z = 713.25(C$_{52}$H$_{31}$N$_3$O = 714.84) | c-60 | m/z = 729.22(C$_{52}$H$_{31}$N$_3$S = 730.90) |
| c-26 | m/z = 713.25(C$_{52}$H$_{31}$N$_3$O = 714.84) | c-61 | m/z = 729.22(C$_{52}$H$_{31}$N$_3$S = 730.90) |
| c-27 | m/z = 713.25(C$_{52}$H$_{31}$N$_3$O = 714.84) | c-62 | m/z = 729.22(C$_{52}$H$_{31}$N$_3$S = 730.90) |
| c-28 | m/z = 713.25(C$_{52}$H$_{31}$N$_3$O = 714.84) | c-63 | m/z = 729.22(C$_{52}$H$_{31}$N$_3$S = 730.90) |
| c-29 | m/z = 713.25(C$_{52}$H$_{31}$N$_3$O = 714.84) | c-64 | m/z = 729.22(C$_{52}$H$_{31}$N$_3$S = 730.90) |
| c-30 | m/z = 713.25(C$_{52}$H$_{31}$N$_3$O = 714.84) | c-65 | m/z = 729.22(C$_{52}$H$_{31}$N$_3$S = 730.90) |
| c-31 | m/z = 713.25(C$_{52}$H$_{31}$N$_3$O = 714.84) | c-66 | m/z = 729.22(C$_{52}$H$_{31}$N$_3$S = 730.90) |
| c-32 | m/z = 713.25(C$_{52}$H$_{31}$N$_3$O = 714.84) | c-67 | m/z = 729.22(C$_{52}$H$_{31}$N$_3$S = 730.90) |
| c-33 | m/z = 713.25(C$_{52}$H$_{31}$N$_3$O = 714.84) | c-68 | m/z = 729.22(C$_{52}$H$_{31}$N$_3$S = 730.90) |
| c-34 | m/z = 713.25(C$_{52}$H$_{31}$N$_3$O = 714.84) | c-69 | m/z = 729.22(C$_{52}$H$_{31}$N$_3$S = 730.90) |
| c-35 | m/z = 713.25(C$_{52}$H$_{31}$N$_3$O = 714.84) | c-70 | m/z = 729.22(C$_{52}$H$_{31}$N$_3$S = 730.90) |
| c-36 | m/z = 713.25(C$_{52}$H$_{31}$N$_3$O = 714.84) | c-71 | m/z = 729.22(C$_{52}$H$_{31}$N$_3$S = 730.90) |
| c-37 | m/z = 713.25(C$_{52}$H$_{31}$N$_3$O = 714.84) | c-72 | m/z = 729.22(C$_{52}$H$_{31}$N$_3$S = 730.90) |
| c-38 | m/z = 713.25(C$_{52}$H$_{31}$N$_3$O = 714.84) | c-73 | m/z = 729.22(C$_{52}$H$_{31}$N$_3$S = 730.90) |
| c-39 | m/z = 713.25(C$_{52}$H$_{31}$N$_3$O = 714.84) | c-74 | m/z = 729.22(C$_{52}$H$_{31}$N$_3$S = 730.90) |
| c-40 | m/z = 713.25(C$_{52}$H$_{31}$N$_3$O = 714.84) | c-75 | m/z = 729.22(C$_{52}$H$_{31}$N$_3$S = 730.90) |
| c-41 | m/z = 713.25(C$_{52}$H$_{31}$N$_3$O = 714.84) | c-76 | m/z = 729.22(C$_{52}$H$_{31}$N$_3$S = 730.90) |
| c-42 | m/z = 713.25(C$_{52}$H$_{31}$N$_3$O = 714.84) | c-77 | m/z = 729.22(C$_{52}$H$_{31}$N$_3$S = 730.90) |
| c-43 | m/z = 713.25(C$_{52}$H$_{31}$N$_3$O = 714.84) | c-78 | m/z = 729.22(C$_{52}$H$_{31}$N$_3$S = 730.90) |
| c-79 | m/z = 729.22(C$_{52}$H$_{31}$N$_3$S = 730.90) | c-110 | m/z = 788.29(C$_{58}$H$_{36}$N$_4$ = 789.95) |
| c-80 | m/z = 729.22(C$_{52}$H$_{31}$N$_3$S = 730.90) | c-111 | m/z = 788.29(C$_{58}$H$_{36}$N$_4$ = 789.95) |
| c-81 | m/z = 729.22(C$_{52}$H$_{31}$N$_3$S = 730.90) | c-112 | m/z = 788.29(C$_{58}$H$_{36}$N$_4$ = 789.95) |
| c-82 | m/z = 729.22(C$_{52}$H$_{31}$N$_3$S = 730.90) | c-113 | m/z = 788.29(C$_{58}$H$_{36}$N$_4$ = 789.95) |
| c-79 | m/z = 729.22(C$_{52}$H$_{31}$N$_3$S = 730.90) | c-114 | m/z = 788.29(C$_{58}$H$_{36}$N$_4$ = 789.95) |
| c-80 | m/z = 729.22(C$_{52}$H$_{31}$N$_3$S = 730.90) | c-115 | m/z = 788.29(C$_{58}$H$_{36}$N$_4$ = 789.95) |
| c-81 | m/z = 729.22(C$_{52}$H$_{31}$N$_3$S = 730.90) | c-116 | m/z = 788.29(C$_{58}$H$_{36}$N$_4$ = 789.95) |
| c-82 | m/z = 729.22(C$_{52}$H$_{31}$N$_3$S = 730.90) | c-117 | m/z = 788.29(C$_{58}$H$_{36}$N$_4$ = 789.95) |
| c-83 | m/z = 729.22(C$_{52}$H$_{31}$N$_3$S = 730.90) | c-118 | m/z = 788.29(C$_{58}$H$_{36}$N$_4$ = 789.95) |
| c-84 | m/z = 729.22(C$_{52}$H$_{31}$N$_3$S = 730.90) | c-119 | m/z = 788.29(C$_{58}$H$_{36}$N$_4$ = 789.95) |
| c-85 | m/z = 729.22(C$_{52}$H$_{31}$N$_3$S = 730.90) | c-120 | m/z = 788.29(C$_{58}$H$_{36}$N$_4$ = 789.95) |
| c-86 | m/z = 729.22(C$_{52}$H$_{31}$N$_3$S = 730.90) | c-121 | m/z = 788.29(C$_{58}$H$_{36}$N$_4$ = 789.95) |
| c-87 | m/z = 729.22(C$_{52}$H$_{31}$N$_3$S = 730.90) | c-122 | m/z = 788.29(C$_{58}$H$_{36}$N$_4$ = 789.95) |
| c-88 | m/z = 729.22(C$_{52}$H$_{31}$N$_3$S = 730.90) | c-123 | m/z = 788.29(C$_{58}$H$_{36}$N$_4$ = 789.95) |
| c-89 | m/z = 729.22(C$_{52}$H$_{31}$N$_3$S = 730.90) | c-124 | m/z = 788.29(C$_{58}$H$_{36}$N$_4$ = 789.95) |
| c-90 | m/z = 729.22(C$_{52}$H$_{31}$N$_3$S = 730.90) | c-125 | m/z = 788.29(C$_{58}$H$_{36}$N$_4$ = 789.95) |
| c-91 | m/z = 729.22(C$_{52}$H$_{31}$N$_3$S = 730.90) | c-126 | m/z = 788.29(C$_{58}$H$_{36}$N$_4$ = 789.95) |
| c-92 | m/z = 729.22(C$_{52}$H$_{31}$N$_3$S = 730.90) | c-127 | m/z = 788.29(C$_{58}$H$_{36}$N$_4$ = 789.95) |
| c-93 | m/z = 729.22(C$_{52}$H$_{31}$N$_3$S = 730.90) | c-128 | m/z = 788.29(C$_{58}$H$_{36}$N$_4$ = 789.95) |
| c-94 | m/z = 729.22(C$_{52}$H$_{31}$N$_3$S = 730.90) | c-129 | m/z = 788.29(C$_{58}$H$_{36}$N$_4$ = 789.95) |
| c-95 | m/z = 729.22(C$_{52}$H$_{31}$N$_3$S = 730.90) | c-130 | m/z = 788.29(C$_{58}$H$_{36}$N$_4$ = 789.95) |
| c-96 | m/z = 729.22(C$_{52}$H$_{31}$N$_3$S = 730.90) | c-131 | m/z = 788.29(C$_{58}$H$_{36}$N$_4$ = 789.95) |
| c-97 | m/z = 788.29(C$_{58}$H$_{36}$N$_4$ = 789.95) | c-132 | m/z = 788.29(C$_{58}$H$_{36}$N$_4$ = 789.95) |
| c-98 | m/z = 788.29(C$_{58}$H$_{36}$N$_4$ = 789.95) | c-133 | m/z = 788.29(C$_{58}$H$_{36}$N$_4$ = 789.95) |
| c-99 | m/z = 788.29(C$_{58}$H$_{36}$N$_4$ = 789.95) | c-134 | m/z = 788.29(C$_{58}$H$_{36}$N$_4$ = 789.95) |
| c-100 | m/z = 788.29(C$_{58}$H$_{36}$N$_4$ = 789.95) | c-135 | m/z = 788.29(C$_{58}$H$_{36}$N$_4$ = 789.95) |
| c-101 | m/z = 788.29(C$_{58}$H$_{36}$N$_4$ = 789.95) | c-136 | m/z = 788.29(C$_{58}$H$_{36}$N$_4$ = 789.95) |
| c-102 | m/z = 788.29(C$_{58}$H$_{36}$N$_4$ = 789.95) | c-137 | m/z = 788.29(C$_{58}$H$_{36}$N$_4$ = 789.95) |
| c-103 | m/z = 788.29(C$_{58}$H$_{36}$N$_4$ = 789.95) | c-138 | m/z = 788.29(C$_{58}$H$_{36}$N$_4$ = 789.95) |
| c-104 | m/z = 788.29(C$_{58}$H$_{36}$N$_4$ = 789.95) | c-139 | m/z = 788.29(C$_{58}$H$_{36}$N$_4$ = 789.95) |
| c-105 | m/z = 788.29(C$_{58}$H$_{36}$N$_4$ = 789.95) | c-140 | m/z = 788.29(C$_{58}$H$_{36}$N$_4$ = 789.95) |
| c-106 | m/z = 788.29(C$_{58}$H$_{36}$N$_4$ = 789.95) | d-1 | m/z = 789.28(C$_{58}$H$_{35}$N$_3$O = 790.94) |
| c-107 | m/z = 788.29(C$_{58}$H$_{36}$N$_4$ = 789.95) | d-2 | m/z = 789.28(C$_{58}$H$_{35}$N$_3$O = 790.94) |
| c-108 | m/z = 788.29(C$_{58}$H$_{36}$N$_4$ = 789.95) | d-3 | m/z = 789.28(C$_{58}$H$_{35}$N$_3$O = 790.94) |
| c-109 | m/z = 788.29(C$_{58}$H$_{36}$N$_4$ = 789.95) | d-4 | m/z = 789.28(C$_{58}$H$_{35}$N$_3$O = 790.94) |
| d-5 | m/z = 789.28(C$_{58}$H$_{35}$N$_3$O = 790.94) | d-38 | m/z = 789.28(C$_{58}$H$_{35}$N$_3$O = 790.94) |
| d-6 | m/z = 789.28(C$_{58}$H$_{35}$N$_3$O = 790.94) | d-39 | m/z = 789.28(C$_{58}$H$_{35}$N$_3$O = 790.94) |
| d-7 | m/z = 789.28(C$_{58}$H$_{35}$N$_3$O = 790.94) | d-40 | m/z = 789.28(C$_{58}$H$_{35}$N$_3$O = 790.94) |
| d-8 | m/z = 789.28(C$_{58}$H$_{35}$N$_3$O = 790.94) | d-41 | m/z = 789.28(C$_{58}$H$_{35}$N$_3$O = 790.94) |

TABLE 3-continued

| Compound | FD-MS | Compound | FD-MS |
|---|---|---|---|
| d-9 | m/z = 789.28($C_{58}H_{35}N_3O$ = 790.94) | d-42 | m/z = 789.28($C_{58}H_{35}N_3O$ = 790.94) |
| d-10 | m/z = 789.28($C_{58}H_{35}N_3O$ = 790.94) | d-43 | m/z = 789.28($C_{58}H_{35}N_3O$ = 790.94) |
| d-11 | m/z = 789.28($C_{58}H_{35}N_3O$ = 790.94) | d-44 | m/z = 789.28($C_{58}H_{35}N_3O$ = 790.94) |
| d-12 | m/z = 789.28($C_{58}H_{35}N_3O$ = 790.94) | d-45 | m/z = 789.28($C_{58}H_{35}N_3O$ = 790.94) |
| d-13 | m/z = 789.28($C_{58}H_{35}N_3O$ = 790.94) | d-46 | m/z = 789.28($C_{58}H_{35}N_3O$ = 790.94) |
| d-14 | m/z = 789.28($C_{58}H_{35}N_3O$ = 790.94) | d-47 | m/z = 789.28($C_{58}H_{35}N_3O$ = 790.94) |
| d-15 | m/z = 789.28($C_{58}H_{35}N_3O$ = 790.94) | d-48 | m/z = 789.28($C_{58}H_{35}N_3O$ = 790.94) |
| d-16 | m/z = 789.28($C_{58}H_{35}N_3O$ = 790.94) | d-49 | m/z = 789.28($C_{58}H_{35}N_3O$ = 790.94) |
| d-17 | m/z = 789.28($C_{58}H_{35}N_3O$ = 790.94) | d-50 | m/z = 789.28($C_{58}H_{35}N_3O$ = 790.94) |
| d-18 | m/z = 789.28($C_{58}H_{35}N_3O$ = 790.94) | d-51 | m/z = 789.28($C_{58}H_{35}N_3O$ = 790.94) |
| d-19 | m/z = 789.28($C_{58}H_{35}N_3O$ = 790.94) | d-52 | m/z = 789.28($C_{58}H_{35}N_3O$ = 790.94) |
| d-20 | m/z = 789.28($C_{58}H_{35}N_3O$ = 790.94) | d-53 | m/z = 789.28($C_{58}H_{35}N_3O$ = 790.94) |
| d-21 | m/z = 789.28($C_{58}H_{35}N_3O$ = 790.94) | d-54 | m/z = 789.28($C_{58}H_{35}N_3O$ = 790.94) |
| d-22 | m/z = 789.28($C_{58}H_{35}N_3O$ = 790.94) | d-55 | m/z = 789.28($C_{58}H_{35}N_3O$ = 790.94) |
| d-23 | m/z = 789.28($C_{58}H_{35}N_3O$ = 790.94) | d-56 | m/z = 789.28($C_{58}H_{35}N_3O$ = 790.94) |
| d-24 | m/z = 789.28($C_{58}H_{35}N_3O$ = 790.94) | d-57 | m/z = 789.28($C_{58}H_{35}N_3O$ = 790.94) |
| d-25 | m/z = 789.28($C_{58}H_{35}N_3O$ = 790.94) | d-58 | m/z = 789.28($C_{58}H_{35}N_3O$ = 790.94) |
| d-26 | m/z = 789.28($C_{58}H_{35}N_3O$ = 790.94) | d-59 | m/z = 789.28($C_{58}H_{35}N_3O$ = 790.94) |
| d-27 | m/z = 789.28($C_{58}H_{35}N_3O$ = 790.94) | d-60 | m/z = 789.28($C_{58}H_{35}N_3O$ = 790.94) |
| d-28 | m/z = 789.28($C_{58}H_{35}N_3O$ = 790.94) | d-61 | m/z = 789.28($C_{58}H_{35}N_3O$ = 790.94) |
| d-29 | m/z = 789.28($C_{58}H_{35}N_3O$ = 790.94) | d-62 | m/z = 789.28($C_{58}H_{35}N_3O$ = 790.94) |
| d-30 | m/z = 789.28($C_{58}H_{35}N_3O$ = 790.94) | d-63 | m/z = 789.28($C_{58}H_{35}N_3O$ = 790.94) |
| d-31 | m/z = 789.28($C_{58}H_{35}N_3O$ = 790.94) | d-64 | m/z = 789.28($C_{58}H_{35}N_3O$ = 790.94) |
| d-32 | m/z = 789.28($C_{58}H_{35}N_3O$ = 790.94) | d-65 | m/z = 789.28($C_{58}H_{35}N_3O$ = 790.94) |
| d-33 | m/z = 789.28($C_{58}H_{35}N_3O$ = 790.94) | d-66 | m/z = 789.28($C_{58}H_{35}N_3O$ = 790.94) |
| d-34 | m/z = 789.28($C_{58}H_{35}N_3O$ = 790.94) | d-67 | m/z = 789.28($C_{58}H_{35}N_3O$ = 790.94) |
| d-35 | m/z = 789.28($C_{58}H_{35}N_3O$ = 790.94) | d-68 | m/z = 789.28($C_{58}H_{35}N_3O$ = 790.94) |
| d-36 | m/z = 789.28($C_{58}H_{35}N_3O$ = 790.94) | d-69 | m/z = 789.28($C_{58}H_{35}N_3O$ = 790.94) |
| d-37 | m/z = 789.28($C_{58}H_{35}N_3O$ = 790.94) | d-70 | m/z = 789.28($C_{58}H_{35}N_3O$ = 790.94) |
| d-71 | m/z = 789.28($C_{58}H_{35}N_3O$ = 790.94) | d-115 | m/z = 789.28($C_{58}H_{35}N_3O$ = 790.94) |
| d-72 | m/z = 789.28($C_{58}H_{35}N_3O$ = 790.94) | d-116 | m/z = 789.28($C_{58}H_{35}N_3O$ = 790.94) |
| d-73 | m/z = 789.28($C_{58}H_{35}N_3O$ = 790.94) | d-117 | m/z = 789.28($C_{58}H_{35}N_3O$ = 790.94) |
| d-74 | m/z = 789.28($C_{58}H_{35}N_3O$ = 790.94) | d-118 | m/z = 789.28($C_{58}H_{35}N_3O$ = 790.94) |
| d-75 | m/z = 789.28($C_{58}H_{35}N_3O$ = 790.94) | d-119 | m/z = 789.28($C_{58}H_{35}N_3O$ = 790.94) |
| d-76 | m/z = 789.28($C_{58}H_{35}N_3O$ = 790.94) | d-120 | m/z = 789.28($C_{58}H_{35}N_3O$ = 790.94) |
| d-77 | m/z = 789.28($C_{58}H_{35}N_3O$ = 790.94) | d-121 | m/z = 789.28($C_{58}H_{35}N_3O$ = 790.94) |
| d-78 | m/z = 789.28($C_{58}H_{35}N_3O$ = 790.94) | d-122 | m/z = 789.28($C_{58}H_{35}N_3O$ = 790.94) |
| d-79 | m/z = 789.28($C_{58}H_{35}N_3O$ = 790.94) | d-123 | m/z = 789.28($C_{58}H_{35}N_3O$ = 790.94) |
| d-80 | m/z = 789.28($C_{58}H_{35}N_3O$ = 790.94) | d-124 | m/z = 789.28($C_{58}H_{35}N_3O$ = 790.94) |
| d-81 | m/z = 789.28($C_{58}H_{35}N_3O$ = 790.94) | d-125 | m/z = 789.28($C_{58}H_{35}N_3O$ = 790.94) |
| d-82 | m/z = 789.28($C_{58}H_{35}N_3O$ = 790.94) | d-126 | m/z = 789.28($C_{58}H_{35}N_3O$ = 790.94) |
| d-83 | m/z = 789.28($C_{58}H_{35}N_3O$ = 790.94) | d-127 | m/z = 789.28($C_{58}H_{35}N_3O$ = 790.94) |
| d-84 | m/z = 789.28($C_{58}H_{35}N_3O$ = 790.94) | d-128 | m/z = 789.28($C_{58}H_{35}N_3O$ = 790.94) |
| d-85 | m/z = 789.28($C_{58}H_{35}N_3O$ = 790.94) | d-129 | m/z = 789.28($C_{58}H_{35}N_3O$ = 790.94) |
| d-86 | m/z = 789.28($C_{58}H_{35}N_3O$ = 790.94) | d-130 | m/z = 789.28($C_{58}H_{35}N_3O$ = 790.94) |
| d-87 | m/z = 789.28($C_{58}H_{35}N_3O$ = 790.94) | d-131 | m/z = 789.28($C_{58}H_{35}N_3O$ = 790.94) |
| d-88 | m/z = 789.28($C_{58}H_{35}N_3O$ = 790.94) | d-132 | m/z = 789.28($C_{58}H_{35}N_3O$ = 790.94) |
| d-89 | m/z = 789.28($C_{58}H_{35}N_3O$ = 790.94) | d-133 | m/z = 789.28($C_{58}H_{35}N_3O$ = 790.94) |
| d-90 | m/z = 789.28($C_{58}H_{35}N_3O$ = 790.94) | d-134 | m/z = 789.28($C_{58}H_{35}N_3O$ = 790.94) |
| d-91 | m/z = 789.28($C_{58}H_{35}N_3O$ = 790.94) | d-135 | m/z = 789.28($C_{58}H_{35}N_3O$ = 790.94) |
| d-91 | m/z = 789.28($C_{58}H_{35}N_3O$ = 790.94) | d-136 | m/z = 789.28($C_{58}H_{35}N_3O$ = 790.94) |
| d-92 | m/z = 789.28($C_{58}H_{35}N_3O$ = 790.94) | d-137 | m/z = 789.28($C_{58}H_{35}N_3O$ = 790.94) |
| d-93 | m/z = 789.28($C_{58}H_{35}N_3O$ = 790.94) | d-138 | m/z = 789.28($C_{58}H_{35}N_3O$ = 790.94) |
| d-94 | m/z = 789.28($C_{58}H_{35}N_3O$ = 790.94) | d-139 | m/z = 789.28($C_{58}H_{35}N_3O$ = 790.94) |
| d-95 | m/z = 789.28($C_{58}H_{35}N_3O$ = 790.94) | d-140 | m/z = 789.28($C_{58}H_{35}N_3O$ = 790.94) |
| d-96 | m/z = 789.28($C_{58}H_{35}N_3O$ = 790.94) | d-141 | m/z = 789.28($C_{58}H_{35}N_3O$ = 790.94) |
| d-97 | m/z = 789.28($C_{58}H_{35}N_3O$ = 790.94) | d-142 | m/z = 789.28($C_{58}H_{35}N_3O$ = 790.94) |
| d-98 | m/z = 789.28($C_{58}H_{35}N_3O$ = 790.94) | d-143 | m/z = 789.28($C_{58}H_{35}N_3O$ = 790.94) |
| d-99 | m/z = 789.28($C_{58}H_{35}N_3O$ = 790.94) | d-144 | m/z = 789.28($C_{58}H_{35}N_3O$ = 790.94) |
| d-110 | m/z = 789.28($C_{58}H_{35}N_3O$ = 790.94) | d-145 | m/z = 805.26($C_{58}H_{35}N_3S$ = 807.00) |
| d-111 | m/z = 789.28($C_{58}H_{35}N_3O$ = 790.94) | d-146 | m/z = 805.26($C_{58}H_{35}N_3S$ = 807.00) |
| d-112 | m/z = 789.28($C_{58}H_{35}N_3O$ = 790.94) | d-147 | m/z = 805.26($C_{58}H_{35}N_3S$ = 807.00) |
| d-113 | m/z = 789.28($C_{58}H_{35}N_3O$ = 790.94) | d-148 | m/z = 805.26($C_{58}H_{35}N_3S$ = 807.00) |
| d-114 | m/z = 789.28($C_{58}H_{35}N_3O$ = 790.94) | d-149 | m/z = 805.26($C_{58}H_{35}N_3S$ = 807.00) |
| d-150 | m/z = 805.26($C_{58}H_{35}N_3S$ = 807.00) | d-185 | m/z = 805.26($C_{58}H_{35}N_3S$ = 807.00) |
| d-151 | m/z = 805.26($C_{58}H_{35}N_3S$ = 807.00) | d-186 | m/z = 805.26($C_{58}H_{35}N_3S$ = 807.00) |
| d-152 | m/z = 805.26($C_{58}H_{35}N_3S$ = 807.00) | d-187 | m/z = 805.26($C_{58}H_{35}N_3S$ = 807.00) |
| d-153 | m/z = 805.26($C_{58}H_{35}N_3S$ = 807.00) | d-188 | m/z = 805.26($C_{58}H_{35}N_3S$ = 807.00) |
| d-154 | m/z = 805.26($C_{58}H_{35}N_3S$ = 807.00) | d-189 | m/z = 805.26($C_{58}H_{35}N_3S$ = 807.00) |
| d-155 | m/z = 805.26($C_{58}H_{35}N_3S$ = 807.00) | d-190 | m/z = 805.26($C_{58}H_{35}N_3S$ = 807.00) |
| d-156 | m/z = 805.26($C_{58}H_{35}N_3S$ = 807.00) | d-191 | m/z = 805.26($C_{58}H_{35}N_3S$ = 807.00) |
| d-157 | m/z = 805.26($C_{58}H_{35}N_3S$ = 807.00) | d-192 | m/z = 805.26($C_{58}H_{35}N_3S$ = 807.00) |
| d-158 | m/z = 805.26($C_{58}H_{35}N_3S$ = 807.00) | d-193 | m/z = 805.26($C_{58}H_{35}N_3S$ = 807.00) |
| d-159 | m/z = 805.26($C_{58}H_{35}N_3S$ = 807.00) | d-194 | m/z = 805.26($C_{58}H_{35}N_3S$ = 807.00) |
| d-160 | m/z = 805.26($C_{58}H_{35}N_3S$ = 807.00) | d-195 | m/z = 805.26($C_{58}H_{35}N_3S$ = 807.00) |
| d-161 | m/z = 805.26($C_{58}H_{35}N_3S$ = 807.00) | d-196 | m/z = 805.26($C_{58}H_{35}N_3S$ = 807.00) |
| d-162 | m/z = 805.26($C_{58}H_{35}N_3S$ = 807.00) | d-197 | m/z = 805.26($C_{58}H_{35}N_3S$ = 807.00) |
| d-163 | m/z = 805.26($C_{58}H_{35}N_3S$ = 807.00) | d-198 | m/z = 805.26($C_{58}H_{35}N_3S$ = 807.00) |

TABLE 3-continued

| Compound | FD-MS | Compound | FD-MS |
|---|---|---|---|
| d-164 | m/z = 805.26($C_{58}H_{35}N_3S$ = 807.00) | d-199 | m/z = 805.26($C_{58}H_{35}N_3S$ = 807.00) |
| d-165 | m/z = 805.26($C_{58}H_{35}N_3S$ = 807.00) | d-200 | m/z = 805.26($C_{58}H_{35}N_3S$ = 807.00) |
| d-166 | m/z = 805.26($C_{58}H_{35}N_3S$ = 807.00) | d-201 | m/z = 805.26($C_{58}H_{35}N_3S$ = 807.00) |
| d-167 | m/z = 805.26($C_{58}H_{35}N_3S$ = 807.00) | d-202 | m/z = 805.26($C_{58}H_{35}N_3S$ = 807.00) |
| d-168 | m/z = 805.26($C_{58}H_{35}N_3S$ = 807.00) | d-203 | m/z = 805.26($C_{58}H_{35}N_3S$ = 807.00) |
| d-169 | m/z = 805.26($C_{58}H_{35}N_3S$ = 807.00) | d-204 | m/z = 805.26($C_{58}H_{35}N_3S$ = 807.00) |
| d-170 | m/z = 805.26($C_{58}H_{35}N_3S$ = 807.00) | d-205 | m/z = 805.26($C_{58}H_{35}N_3S$ = 807.00) |
| d-171 | m/z = 805.26($C_{58}H_{35}N_3S$ = 807.00) | d-206 | m/z = 805.26($C_{58}H_{35}N_3S$ = 807.00) |
| d-172 | m/z = 805.26($C_{58}H_{35}N_3S$ = 807.00) | d-207 | m/z = 805.26($C_{58}H_{35}N_3S$ = 807.00) |
| d-173 | m/z = 805.26($C_{58}H_{35}N_3S$ = 807.00) | d-208 | m/z = 805.26($C_{58}H_{35}N_3S$ = 807.00) |
| d-174 | m/z = 805.26($C_{58}H_{35}N_3S$ = 807.00) | d-209 | m/z = 805.26($C_{58}H_{35}N_3S$ = 807.00) |
| d-175 | m/z = 805.26($C_{58}H_{35}N_3S$ = 807.00) | d-210 | m/z = 805.26($C_{58}H_{35}N_3S$ = 807.00) |
| d-176 | m/z = 805.26($C_{58}H_{35}N_3S$ = 807.00) | d-211 | m/z = 805.26($C_{58}H_{35}N_3S$ = 807.00) |
| d-177 | m/z = 805.26($C_{58}H_{35}N_3S$ = 807.00) | d-212 | m/z = 805.26($C_{58}H_{35}N_3S$ = 807.00) |
| d-178 | m/z = 805.26($C_{58}H_{35}N_3S$ = 807.00) | d-213 | m/z = 805.26($C_{58}H_{35}N_3S$ = 807.00) |
| d-179 | m/z = 805.26($C_{58}H_{35}N_3S$ = 807.00) | d-214 | m/z = 805.26($C_{58}H_{35}N_3S$ = 807.00) |
| d-180 | m/z = 805.26($C_{58}H_{35}N_3S$ = 807.00) | d-215 | m/z = 805.26($C_{58}H_{35}N_3S$ = 807.00) |
| d-181 | m/z = 805.26($C_{58}H_{35}N_3S$ = 807.00) | d-216 | m/z = 805.26($C_{58}H_{35}N_3S$ = 807.00) |
| d-182 | m/z = 805.26($C_{58}H_{35}N_3S$ = 807.00) | d-217 | m/z = 805.26($C_{58}H_{35}N_3S$ = 807.00) |
| d-183 | m/z = 805.26($C_{58}H_{35}N_3S$ = 807.00) | d-218 | m/z = 805.26($C_{58}H_{35}N_3S$ = 807.00) |
| d-184 | m/z = 805.26($C_{58}H_{35}N_3S$ = 807.00) | d-219 | m/z = 805.26($C_{58}H_{35}N_3S$ = 807.00) |
| d-219 | m/z = 805.26($C_{58}H_{35}N_3S$ = 807.00) | d-253 | m/z = 805.26($C_{58}H_{35}N_3S$ = 807.00) |
| d-220 | m/z = 805.26($C_{58}H_{35}N_3S$ = 807.00) | d-254 | m/z = 805.26($C_{58}H_{35}N_3S$ = 807.00) |
| d-221 | m/z = 805.26($C_{58}H_{35}N_3S$ = 807.00) | d-255 | m/z = 805.26($C_{58}H_{35}N_3S$ = 807.00) |
| d-222 | m/z = 805.26($C_{58}H_{35}N_3S$ = 807.00) | d-256 | m/z = 805.26($C_{58}H_{35}N_3S$ = 807.00) |
| d-223 | m/z = 805.26($C_{58}H_{35}N_3S$ = 807.00) | d-257 | m/z = 805.26($C_{58}H_{35}N_3S$ = 807.00) |
| d-224 | m/z = 805.26($C_{58}H_{35}N_3S$ = 807.00) | d-258 | m/z = 805.26($C_{58}H_{35}N_3S$ = 807.00) |
| d-225 | m/z = 805.26($C_{58}H_{35}N_3S$ = 807.00) | d-259 | m/z = 805.26($C_{58}H_{35}N_3S$ = 807.00) |
| d-226 | m/z = 805.26($C_{58}H_{35}N_3S$ = 807.00) | d-260 | m/z = 805.26($C_{58}H_{35}N_3S$ = 807.00) |
| d-227 | m/z = 805.26($C_{58}H_{35}N_3S$ = 807.00) | d-261 | m/z = 805.26($C_{58}H_{35}N_3S$ = 807.00) |
| d-228 | m/z = 805.26($C_{58}H_{35}N_3S$ = 807.00) | d-262 | m/z = 805.26($C_{58}H_{35}N_3S$ = 807.00) |
| d-229 | m/z = 805.26($C_{58}H_{35}N_3S$ = 807.00) | d-263 | m/z = 805.26($C_{58}H_{35}N_3S$ = 807.00) |
| d-233 | m/z = 805.26($C_{58}H_{35}N_3S$ = 807.00) | d-264 | m/z = 805.26($C_{58}H_{35}N_3S$ = 807.00) |
| d-231 | m/z = 805.26($C_{58}H_{35}N_3S$ = 807.00) | d-265 | m/z = 805.26($C_{58}H_{35}N_3S$ = 807.00) |
| d-232 | m/z = 805.26($C_{58}H_{35}N_3S$ = 807.00) | d-266 | m/z = 805.26($C_{58}H_{35}N_3S$ = 807.00) |
| d-233 | m/z = 805.26($C_{58}H_{35}N_3S$ = 807.00) | d-267 | m/z = 805.26($C_{58}H_{35}N_3S$ = 807.00) |
| d-234 | m/z = 805.26($C_{58}H_{35}N_3S$ = 807.00) | d-268 | m/z = 805.26($C_{58}H_{35}N_3S$ = 807.00) |
| d-235 | m/z = 805.26($C_{58}H_{35}N_3S$ = 807.00) | d-269 | m/z = 805.26($C_{58}H_{35}N_3S$ = 807.00) |
| d-236 | m/z = 805.26($C_{58}H_{35}N_3S$ = 807.00) | d-270 | m/z = 805.26($C_{58}H_{35}N_3S$ = 807.00) |
| d-237 | m/z = 805.26($C_{58}H_{35}N_3S$ = 807.00) | d-271 | m/z = 805.26($C_{58}H_{35}N_3S$ = 807.00) |
| d-238 | m/z = 805.26($C_{58}H_{35}N_3S$ = 807.00) | d-272 | m/z = 805.26($C_{58}H_{35}N_3S$ = 807.00) |
| d-239 | m/z = 805.26($C_{58}H_{35}N_3S$ = 807.00) | d-273 | m/z = 805.26($C_{58}H_{35}N_3S$ = 807.00) |
| d-240 | m/z = 805.26($C_{58}H_{35}N_3S$ = 807.00) | d-274 | m/z = 805.26($C_{58}H_{35}N_3S$ = 807.00) |
| d-241 | m/z = 805.26($C_{58}H_{35}N_3S$ = 807.00) | d-275 | m/z = 805.26($C_{58}H_{35}N_3S$ = 807.00) |
| d-242 | m/z = 805.26($C_{58}H_{35}N_3S$ = 807.00) | d-276 | m/z = 805.26($C_{58}H_{35}N_3S$ = 807.00) |
| d-243 | m/z = 805.26($C_{58}H_{35}N_3S$ = 807.00) | d-277 | m/z = 805.26($C_{58}H_{35}N_3S$ = 807.00) |
| d-244 | m/z = 805.26($C_{58}H_{35}N_3S$ = 807.00) | d-278 | m/z = 805.26($C_{58}H_{35}N_3S$ = 807.00) |
| d-245 | m/z = 805.26($C_{58}H_{35}N_3S$ = 807.00) | d-279 | m/z = 805.26($C_{58}H_{35}N_3S$ = 807.00) |
| d-246 | m/z = 805.26($C_{58}H_{35}N_3S$ = 807.00) | d-280 | m/z = 805.26($C_{58}H_{35}N_3S$ = 807.00) |
| d-247 | m/z = 805.26($C_{58}H_{35}N_3S$ = 807.00) | d-281 | m/z = 805.26($C_{58}H_{35}N_3S$ = 807.00) |
| d-248 | m/z = 805.26($C_{58}H_{35}N_3S$ = 807.00) | d-282 | m/z = 805.26($C_{58}H_{35}N_3S$ = 807.00) |
| d-249 | m/z = 805.26($C_{58}H_{35}N_3S$ = 807.00) | d-283 | m/z = 805.26($C_{58}H_{35}N_3S$ = 807.00) |
| d-250 | m/z = 805.26($C_{58}H_{35}N_3S$ = 807.00) | d-284 | m/z = 805.26($C_{58}H_{35}N_3S$ = 807.00) |
| d-250 | m/z = 805.26($C_{58}H_{35}N_3S$ = 807.00) | d-285 | m/z = 805.26($C_{58}H_{35}N_3S$ = 807.00) |
| d-251 | m/z = 805.26($C_{58}H_{35}N_3S$ = 807.00) | d-286 | m/z = 805.26($C_{58}H_{35}N_3S$ = 807.00) |
| d-252 | m/z = 805.26($C_{58}H_{35}N_3S$ = 807.00) | d-287 | m/z = 805.26($C_{58}H_{35}N_3S$ = 807.00) |

Fabrication and Evaluation of Organic Electroluminescent Element

[Example 1] Green OLED

After vacuum-depositing $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") on an ITO layer (anode) formed on a glass substrate to form a hole injection layer with a thickness of 60 nm, a hole transport layer with a thickness of 60 nm was formed by vacuum-depositing 4,4-bis[N-(1-naphthyl)-N-phenylamino]bipheny (hereinafter, "NPD") on the hole injection layer.

Next, the compound c-1 of the present invention as a host material and tris(2-phenylpyridine)-iridium (hereinafter, "Ir(ppy)$_3$") as a dopant material in a weight ratio of 95:5 were deposited on the hole transport layer to form a light emitting layer with a thickness of 30 nm.

Subsequently, (1,1'-bisphenyl-4-olato)bis(2-methyl-8-quinolinolato)aluminum (hereinafter, "BAlq") was vacuum-deposited to a thickness of 10 nm on the light emitting layer to form a hole blocking layer, and tris(8-quinolinolato)aluminum (hereinafter, "Alq$_3$") was vacuum-deposited to a thickness of 40 nm on the hole blocking layer to form a an electron transport layer.

Next, LiF was deposited to a thickness of 0.2 nm to form an electron injection layer, and then Al was deposited to a thickness of 150 to form a cathode.

[Example 2] to [Example 19]

The OLEDs were fabricated in the same manner as described in Example 1 except that the compound of the present invention described in the following Table 4, instead of the compound c-1 of the present invention, was used as host material of a light emitting layer.

[Comparative Example 1] to [Comparative Example 4]

The OLEDs were fabricated in the same manner as described in Example 1 except that one of the following Comparative compound A, Comparative compound B, Comparative compound C, Comparative compound D, instead of the compound c-1 of the present invention, was used as host material of a light emitting layer.

<Comp. Compd A> <Comp. Compd B> <Comp. Compd C> <Comp. Compd D>

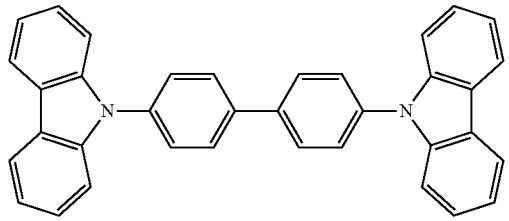

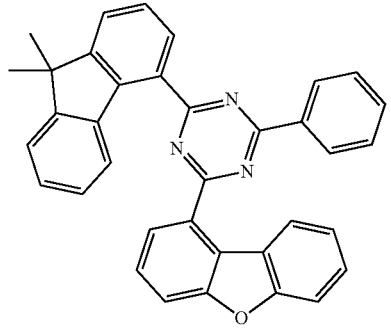

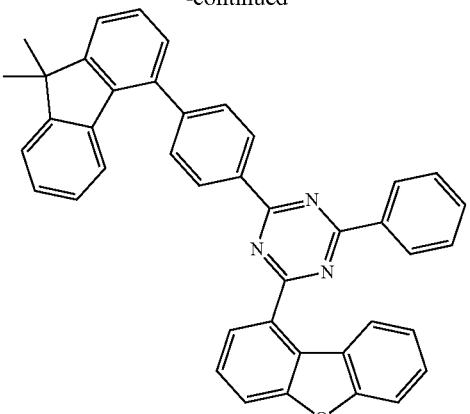

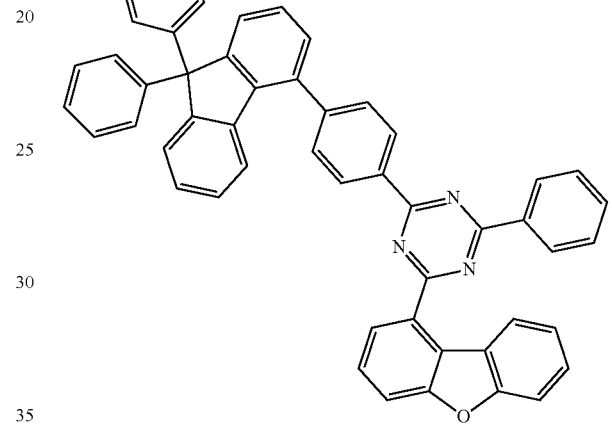

Electroluminescence (EL) characteristics were measured with a PR-650 (Photoresearch) by applying a forward bias DC voltage to the OLEDs prepared in Examples 1 to 19 of the present invention and Comparative Examples 1 to 4. And, the T95 life time was measured using a life time measuring apparatus manufactured by ms science Inc. at reference brightness of 2500 cd/m². The measurement results are shown in Tables 4 below.

TABLE 4

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp.Ex(1) | comp.Com A | 5.9 | 21.2 | 5000.0 | 23.6 | 56.1 | 0.31 | 0.60 |
| comp.Ex(2) | comp.Com B | 5.6 | 18.2 | 5000.0 | 27.5 | 63.2 | 0.32 | 0.63 |
| comp.Ex(3) | comp.Com C | 5.4 | 16.7 | 5000.0 | 29.9 | 68.6 | 0.30 | 0.62 |
| comp.Ex(4) | comp.Com D | 5.3 | 16.0 | 5000.0 | 31.2 | 70.2 | 0.31 | 0.61 |
| Ex.(1) | c-1 | 4.9 | 13.0 | 5000.0 | 38.4 | 83.0 | 0.33 | 0.65 |
| Ex.(2) | c-45 | 4.2 | 12.3 | 5000.0 | 40.5 | 96.4 | 0.35 | 0.60 |
| Ex.(3) | c-62 | 4.7 | 12.5 | 5000.0 | 39.9 | 92.7 | 0.33 | 0.63 |
| Ex.(4) | c-89 | 4.3 | 12.2 | 5000.0 | 40.8 | 95.8 | 0.32 | 0.61 |
| Ex.(5) | c-127 | 4.9 | 13.0 | 5000.0 | 38.3 | 87.5 | 0.35 | 0.62 |
| Ex.(6) | c-133 | 4.4 | 12.3 | 5000.0 | 40.5 | 95.8 | 0.35 | 0.65 |
| Ex.(7) | c-168 | 4.4 | 12.4 | 5000.0 | 40.5 | 97.5 | 0.33 | 0.60 |
| Ex.(8) | c-201 | 4.4 | 12.4 | 5000.0 | 40.4 | 97.2 | 0.32 | 0.63 |
| Ex.(9) | c-248 | 4.8 | 12.7 | 5000.0 | 39.2 | 94.8 | 0.31 | 0.65 |
| Ex.(10) | c-283 | 5.0 | 13.3 | 5000.0 | 37.5 | 87.5 | 0.30 | 0.63 |
| Ex.(11) | d-29 | 5.1 | 13.4 | 5000.0 | 37.3 | 83.0 | 0.31 | 0.63 |
| Ex.(12) | d-116 | 4.7 | 12.7 | 5000.0 | 39.4 | 93.9 | 0.32 | 0.61 |
| Ex.(13) | d-154 | 5.0 | 13.2 | 5000.0 | 37.8 | 82.9 | 0.33 | 0.61 |
| Ex.(14) | d-192 | 4.5 | 12.4 | 5000.0 | 40.3 | 98.8 | 0.30 | 0.64 |
| Ex.(15) | d-240 | 4.5 | 12.4 | 5000.0 | 40.4 | 98.9 | 0.31 | 0.62 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex.(16) | e-1 | 4.2 | 12.3 | 5000.0 | 40.7 | 96.4 | 0.30 | 0.64 |
| Ex.(17) | e-2 | 4.2 | 12.3 | 5000.0 | 40.5 | 99.5 | 0.34 | 0.64 |
| Ex.(18) | e-4 | 5.2 | 13.6 | 5000.0 | 36.8 | 98.1 | 0.33 | 0.60 |
| Ex.(19) | e-9 | 4.3 | 12.3 | 5000.0 | 40.8 | 97.7 | 0.35 | 0.63 |

From the results of Table 4, it is confirmed that the luminous efficiency and life of the organic electroluminescent element can be significantly improved and the driving voltage can be lowered when the material for an organic electroluminescent element of the present invention is used as a phosphorescent host.

Compared to CBP (Comparative Compound A), which is generally used as a host material, when Comparative Compounds B to D, which are substituted with dimethyl fluorene or diphenylfluorene in triazine, as a phosphorescent host material, the results of element are improved, and the driving voltage, efficiency, and lifetime of the organic electroluminescent element all exhibit remarkably excellent results when the compound of the present invention, which is similar to Comparative Compounds B to D and is substituted with spirofluorene in triazine, is used as a phosphorescent host material.

Looking at Comparative Compound B and Comparative Compound C, although they have similar structures, the difference is that dimethylfluorene is directly bonded to the triazine in Comparative Compound B, whereas dimethylfluorene is bonded to the triazine via phenyl. In addition, when comparing Comparative Compound C and Comparative Compound D, they have similar structures to each other, but the difference is that dimethyl fluorene is bonded to the linking group phenyl in Comparative Compound C, while diphenyl fluorine is bonded to the linking group phenyl in Comparative Compound D.

On the other hand, referring to Table 4, it can be seen that when using the compound of the present invention as a phosphorescent host material rather than Comparative Compound D, Comparative Compound D rather than Comparative Compound C, and Comparative Compound C rather than Comparative Compound B, the characteristics of element are further improved. The compound of the present invention is similar to comparative compound D, but differs in that spyrobifluorene is bonded to the linking group phenyl rather than diphenylfluorene.

This is because the compound in which the spirofluorene is bonded to the linking group is different from the compound in which dimethylfluorene or diphenylfluorene is bonded to the linking group, in properties such as HOMO, LUMO, and T1 and above all, has significantly improved thermal stability.

Therefore, chemical and physical properties can be significantly different depending on whether a linker exists between fluorenes and triazines, and what kind of fluorene is attached to the linker, and it suggests that this difference can act as a major factor in device properties.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

[Formula 1]

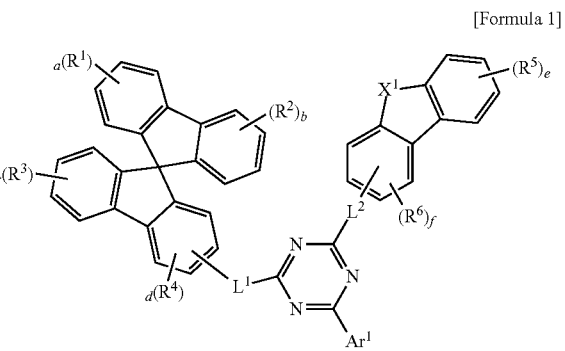

wherein:
X¹ is S, O or N(Ar'),
R¹ to R⁴ are each independently selected from the group consisting of hydrogen, deuterium, halogen, a cyano group, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups together may be bonded to each other to form a ring, wherein the ring is selected from the group consisting of a $C_2$-$C_{60}$ heterocyclic ring, a $C_3$-$C_{60}$ aliphatic ring and a combination thereof,
R⁵ and R⁶ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups together may be bonded to each other to form a ring, wherein the ring is selected from the group consisting of a $C_6$-$C_{60}$ aromatic hydrocarbon, a $C_2$-$C_{60}$ heterocyclic ring, a $C_3$-$C_{60}$ aliphatic ring and a combination thereof, a, b, c and e are each represent an integer of 0-4, d and f are each represent an integer of 0-3, and when each of these is an integer of 2 or more, each of $R^1$s, each of $R^2$s, each of $R^3$s, each of $R^4$s, each of $R^5$s or each of $R^6$s may be the same or different from each other, $L^1$ is selected from the group consisting of a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof, $L^2$ is selected from the group consisting of a single bond, a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof, Ar' is selected from the group consisting of a $C_6$-$C_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), $Ar^1$ is selected from the group consisting of a $C_6$-$C_{60}$ aryl group, a fluorenyl group, a $C_2$-$C_{60}$ heterocyclic group containing at least one heteroatom of O, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), L' is selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, $R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, $R^1$ to $R^6$, $Ar^1$, $L^1$, $L^2$, L', $R_a$, $R_b$, a ring formed by adjacent $R^1$ groups, adjacent $R^2$ groups, adjacent $R^3$ groups, adjacent $R^4$ groups, adjacent $R^5$ groups and adjacent $R^6$ groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a $C_7$-$C_{20}$ arylalkyl group and a $C_8$-$C_{20}$ arylalkenyl group, and the $Ar^1$ may be optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, S, Si, and P, a $C_3$-$C_{20}$ cycloalkyl group, a $C_7$-$C_{20}$ arylalkyl group and a $C_8$-$C_{20}$ arylalkenyl group.

2. The compound of claim 1, wherein Formula 1 is represented by one of Formula 2 to Formula 5:

<Formula 2>

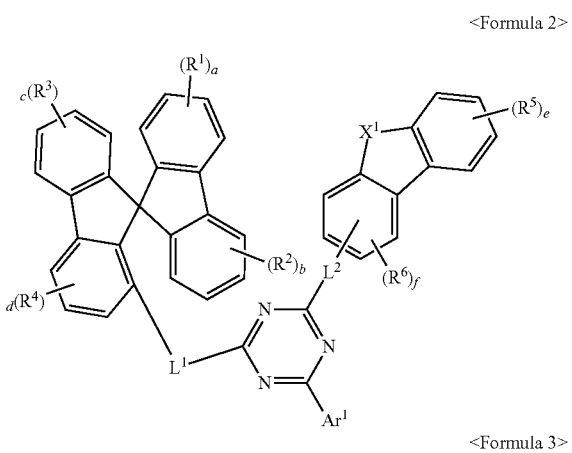

<Formula 3>

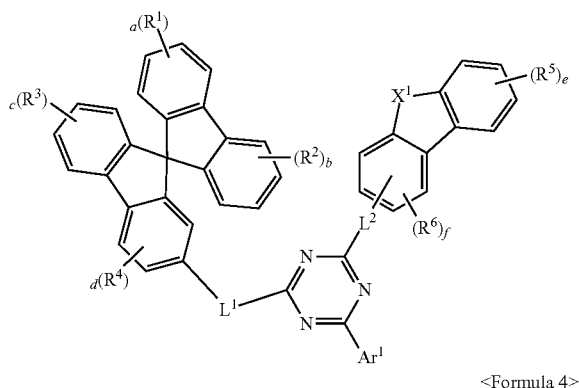

<Formula 4>

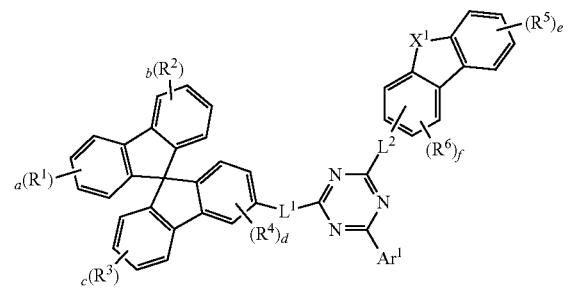

<Formula 5>

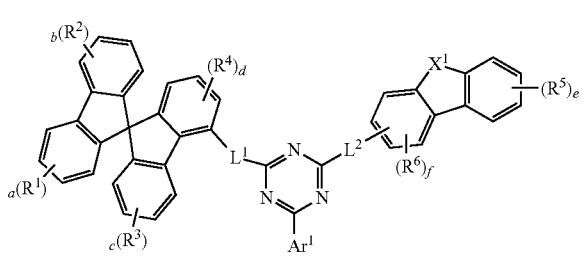

wherein $X^1$, $R^1$ to $R^6$, a, b, c, e, d, f, $L^1$, $L^2$ and $Ar^1$ are the same as defined in claim 1.

3. The compound of claim 1, wherein Formula 1 is represented by one of Formula 6 to Formula 9:
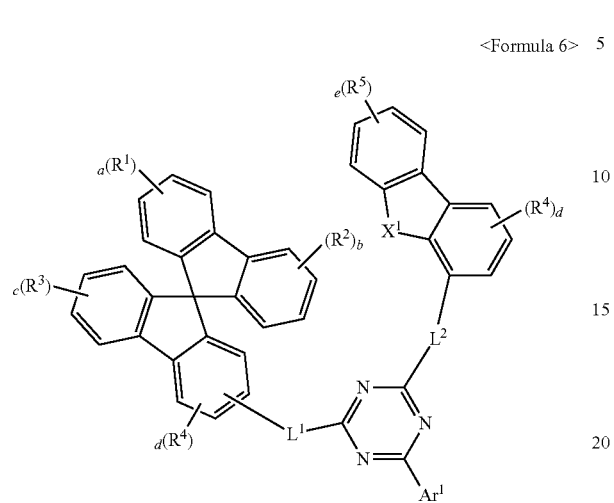
<Formula 6>
<Formula 7>
<Formula 8>
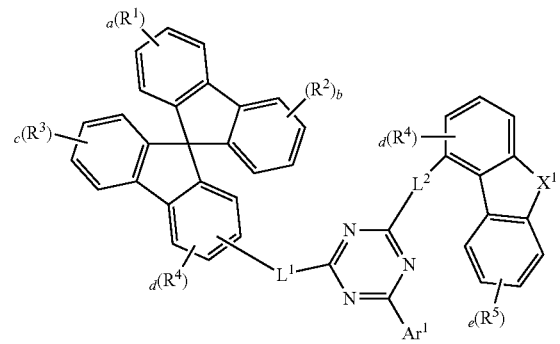
<Formula 9>
wherein $X^1$, $R^1$ to $R^6$, a, b, c, e, d, f, $L^1$, $L^2$ and $Ar^1$ are the same as defined in claim 1.
4. The compound of claim 1, wherein the compound represented by Formula 1 is one of the following compounds:
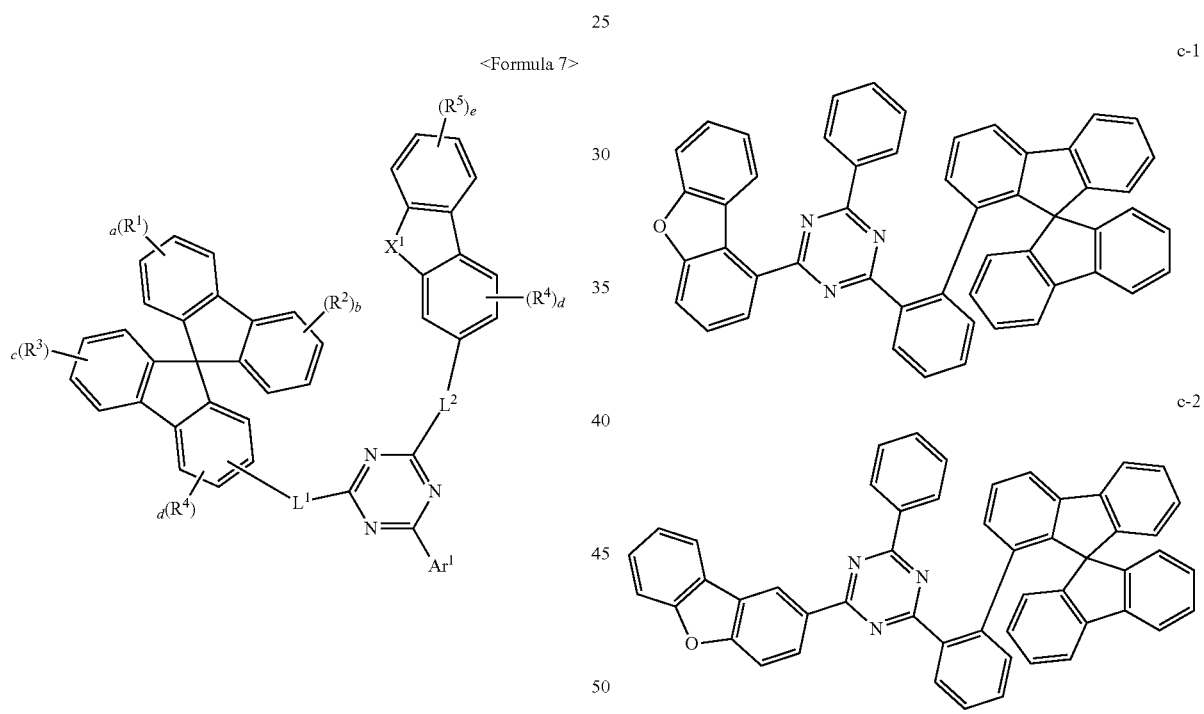
c-1
c-2
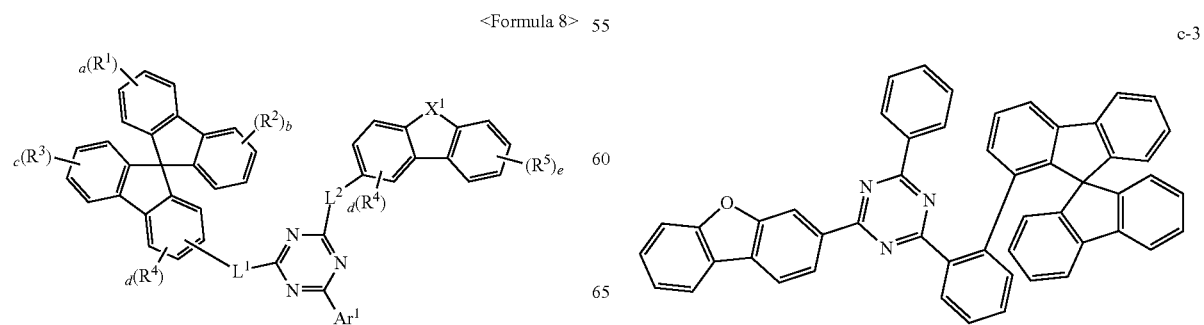
c-3

-continued
c-4
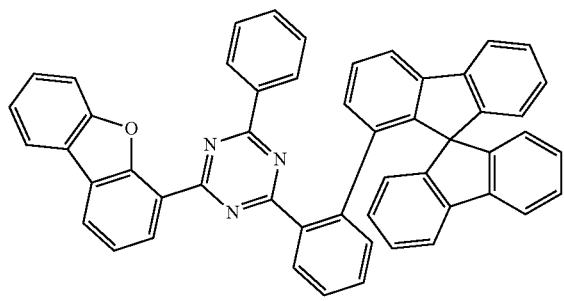
c-5
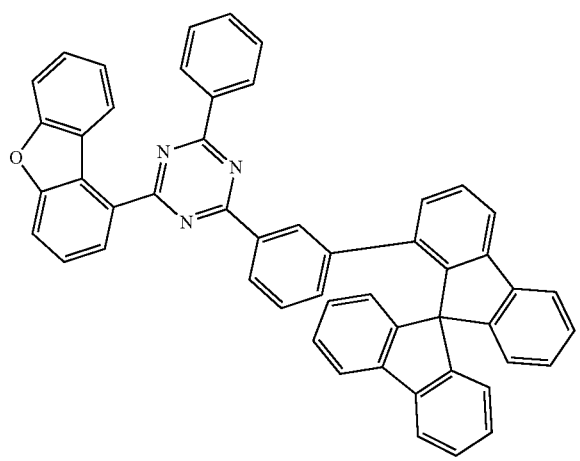
c-6
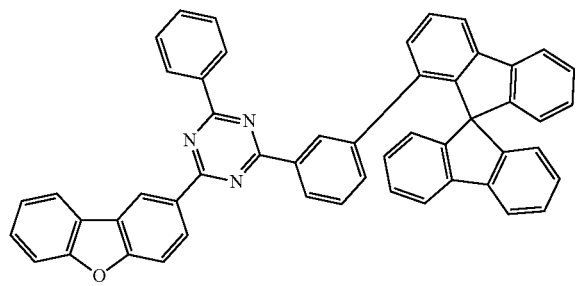
c-7
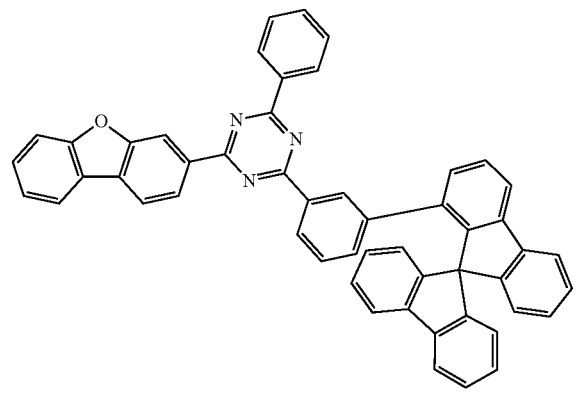
-continued
c-8
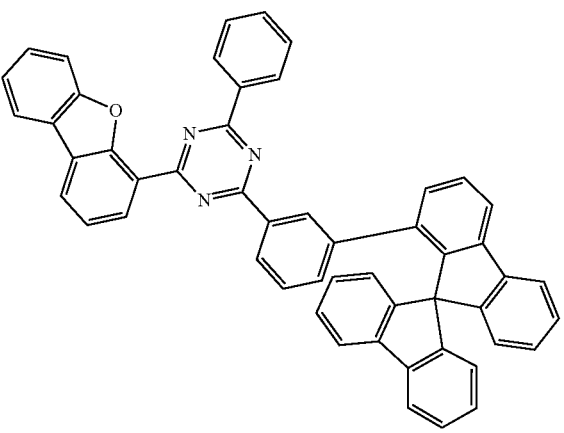
c-9
c-10
c-11
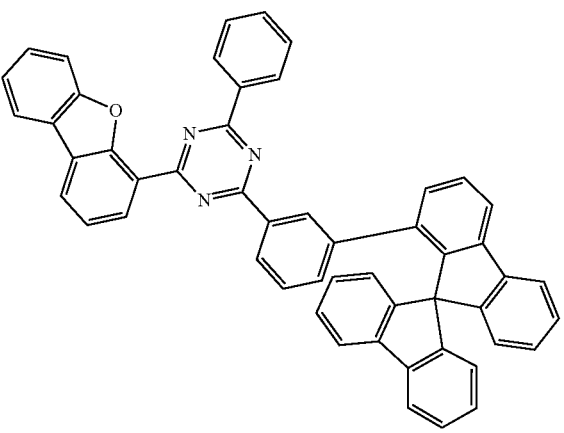

c-12
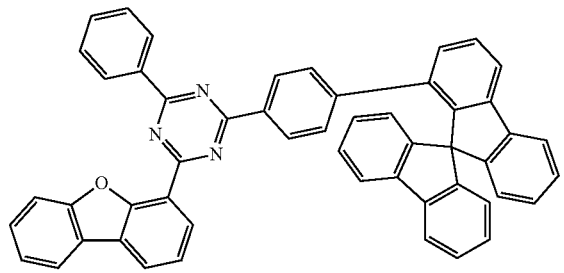
c-16
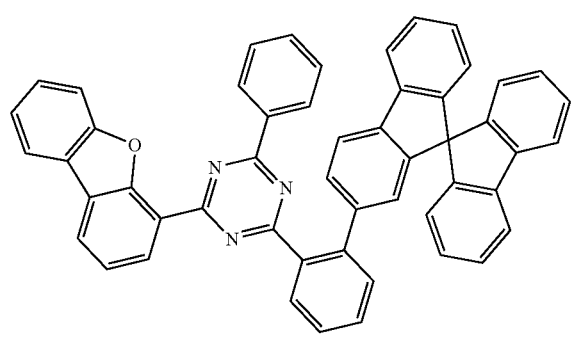
c-13
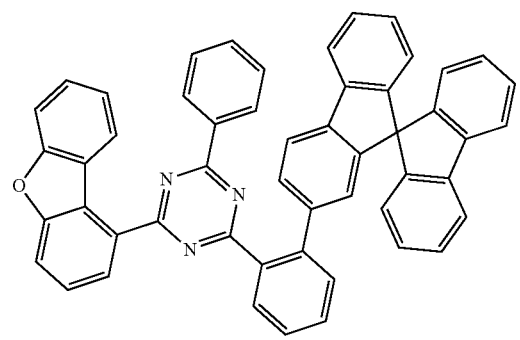
c-17
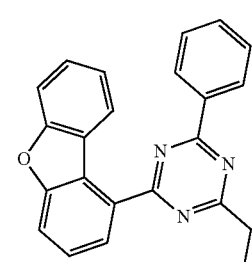
c-14
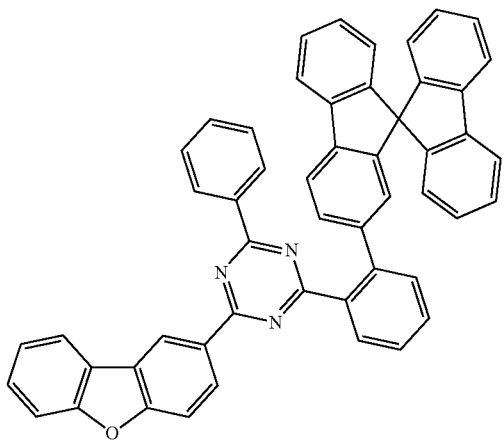
c-18
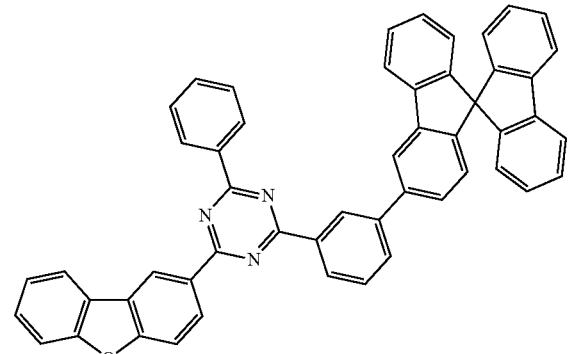
c-15
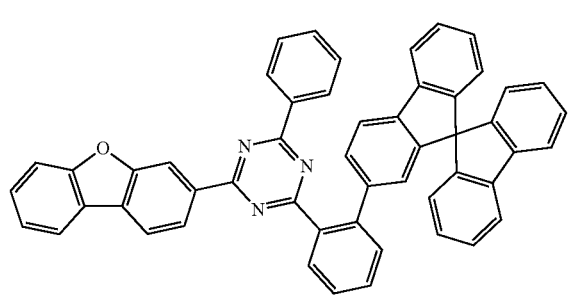
c-19
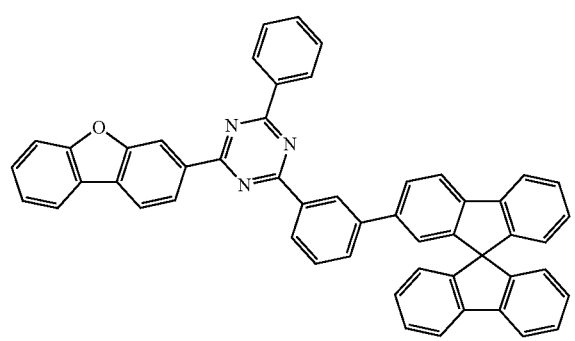

c-20
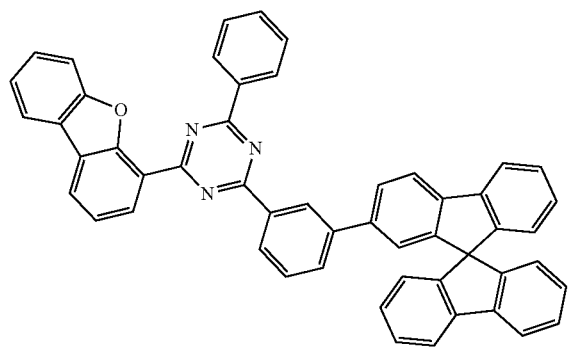
c-21
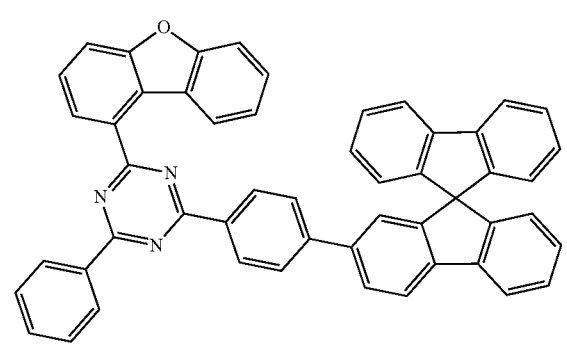
c-22
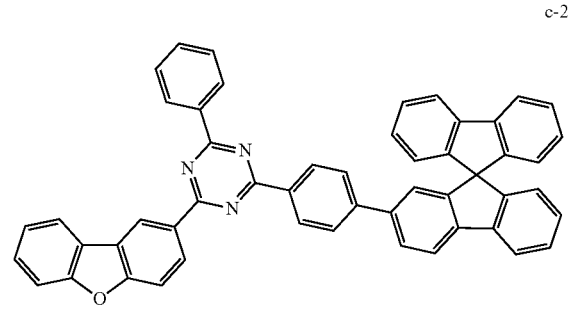
c-23
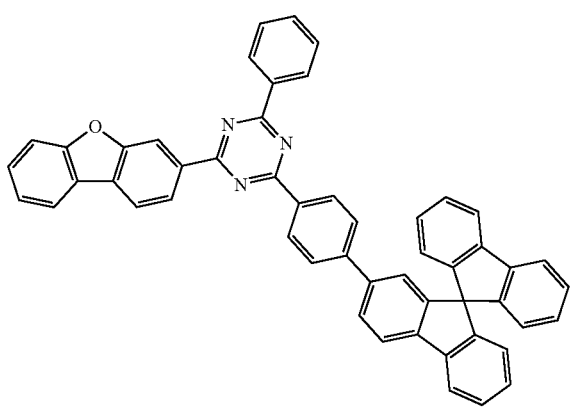
c-24
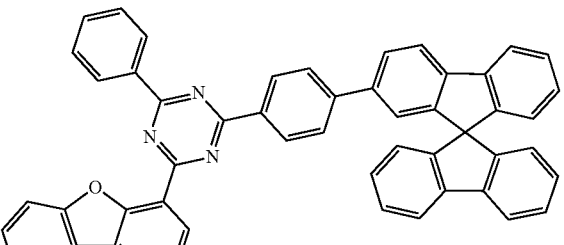
c-25
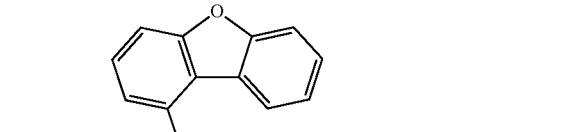
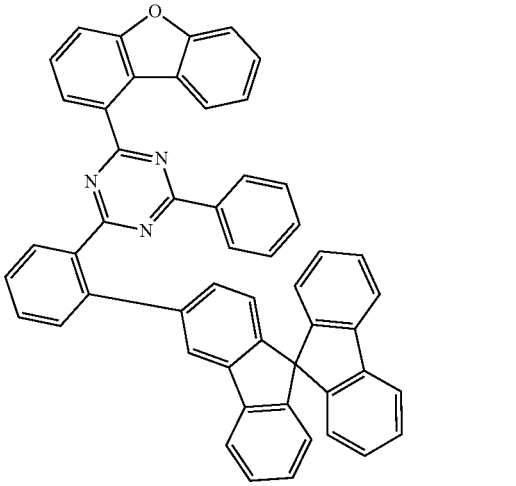
c-26
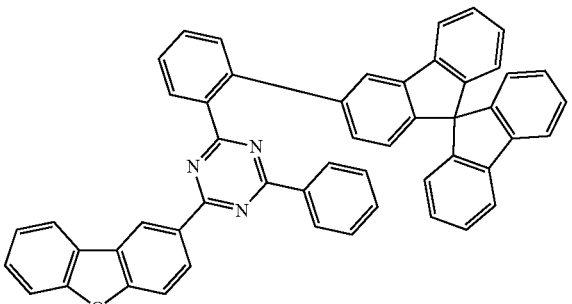
c-27
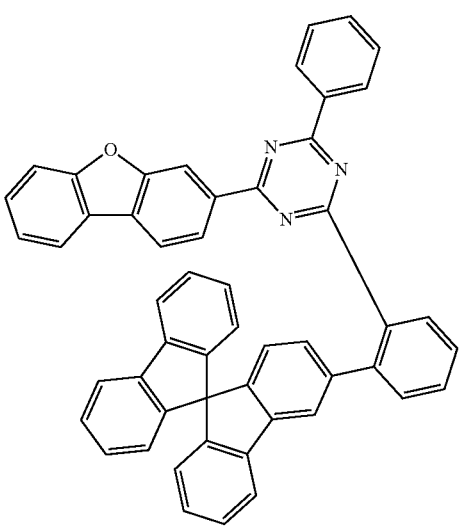

c-28
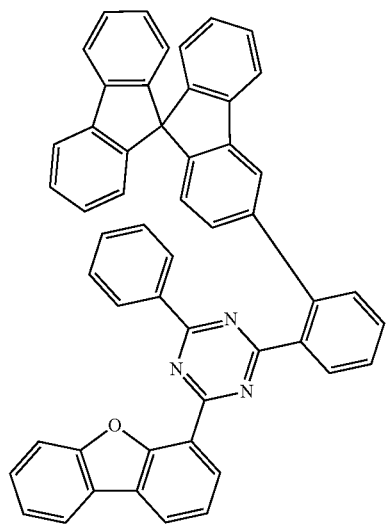
c-31
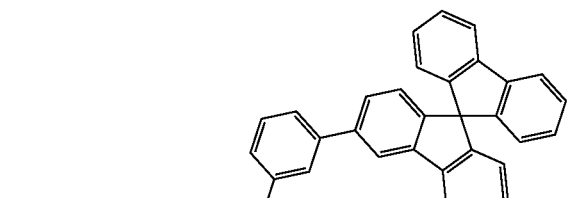
c-29
c-32
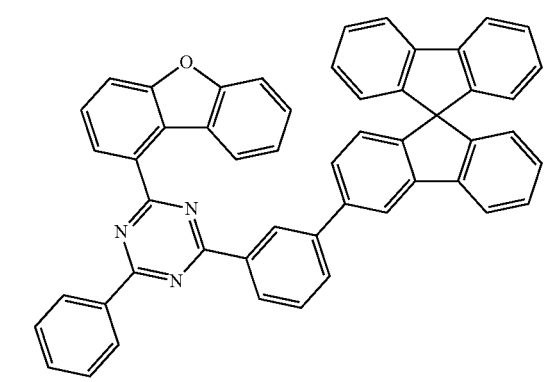
c-30
c-33
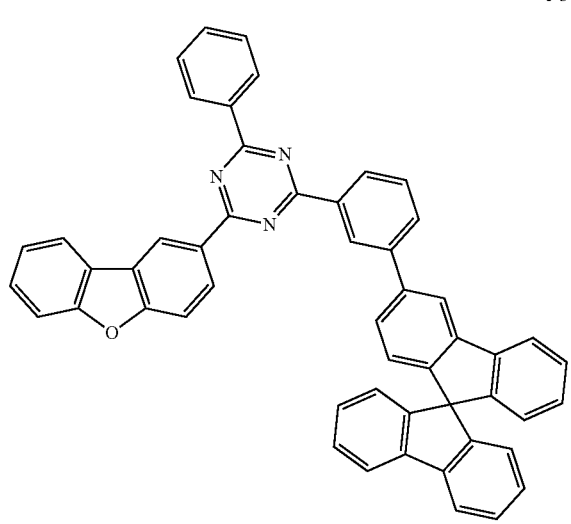
c-34
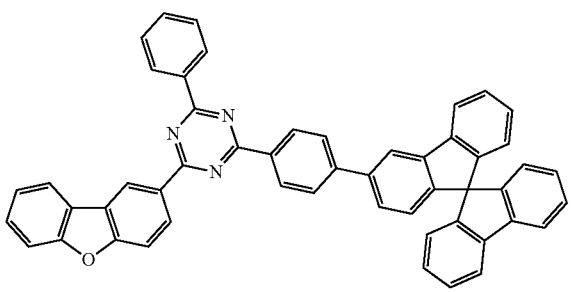

c-35
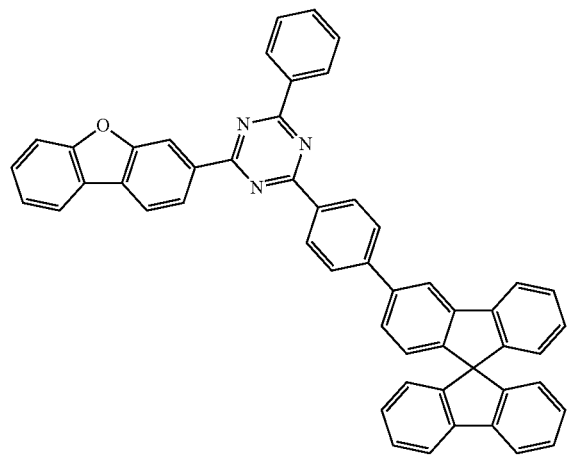
c-36
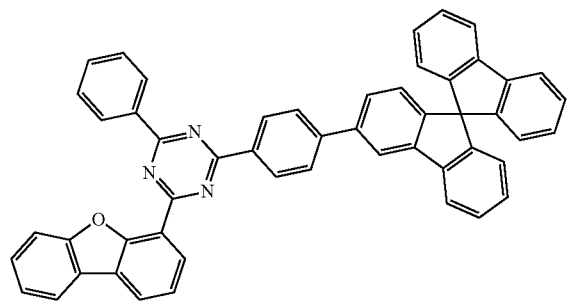
c-37
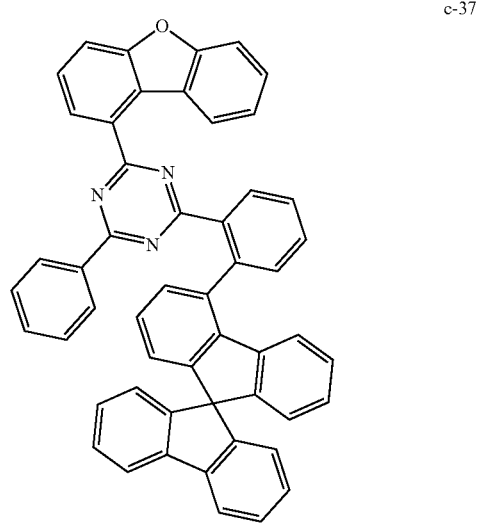
c-38
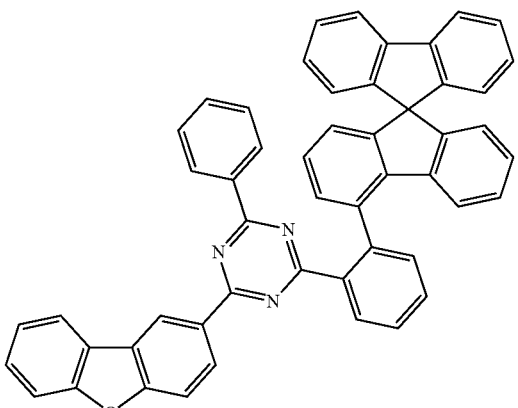
c-39
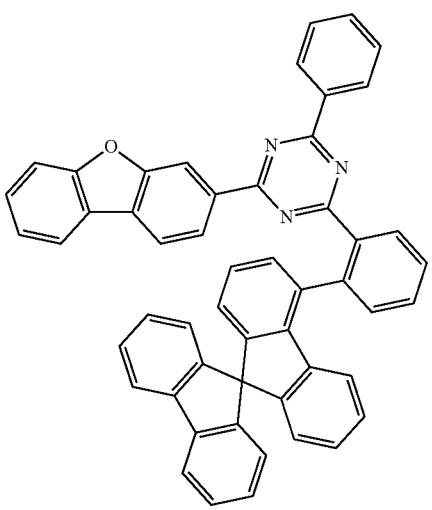
c-40
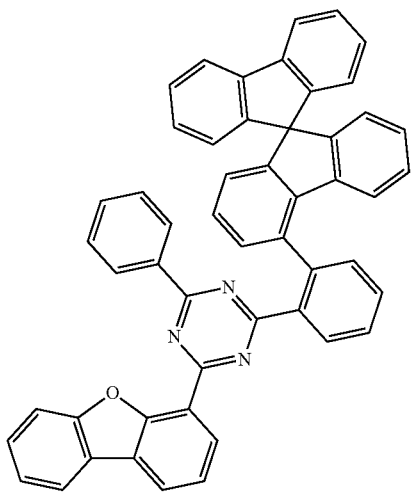

c-41
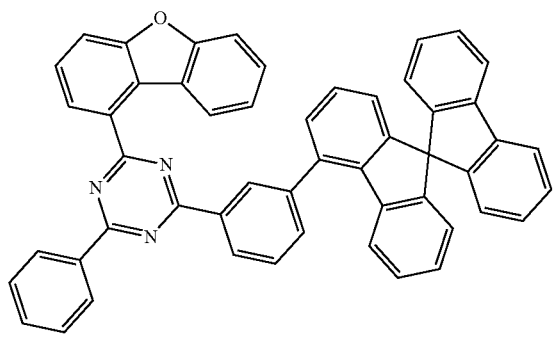
c-42
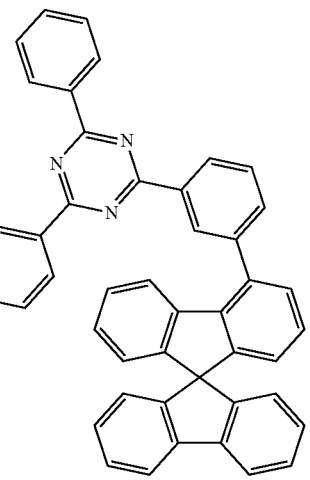
c-43
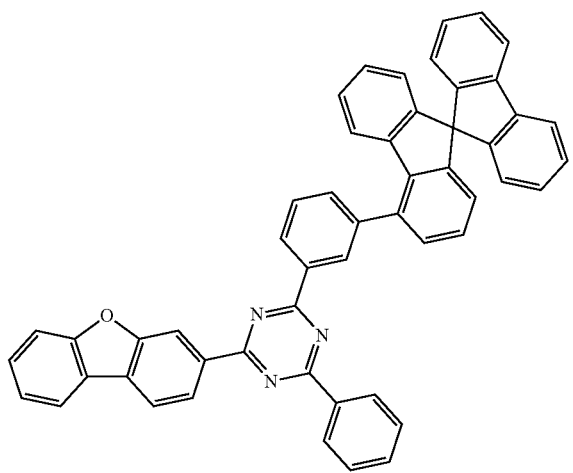
c-44
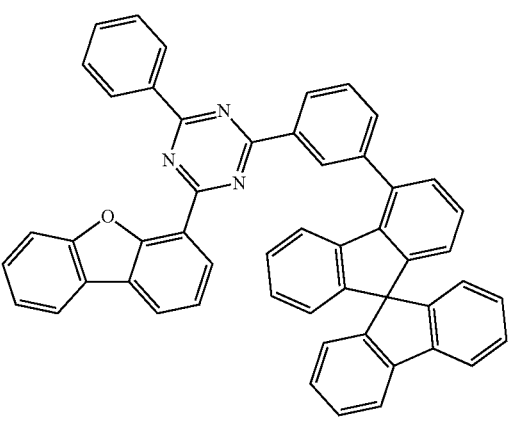
c-45
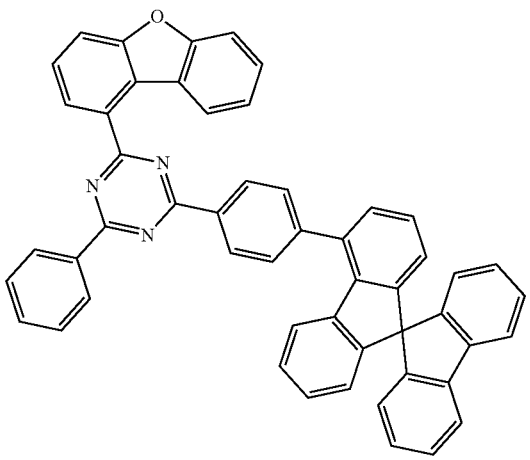
c-46
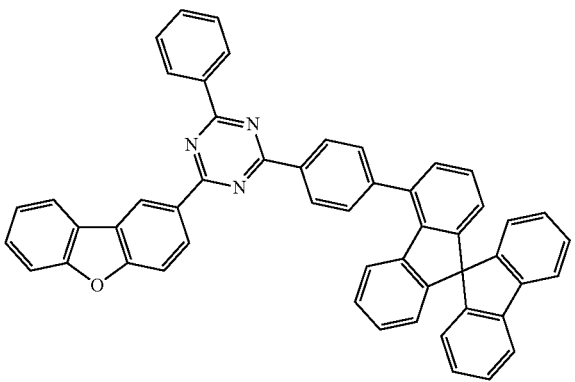

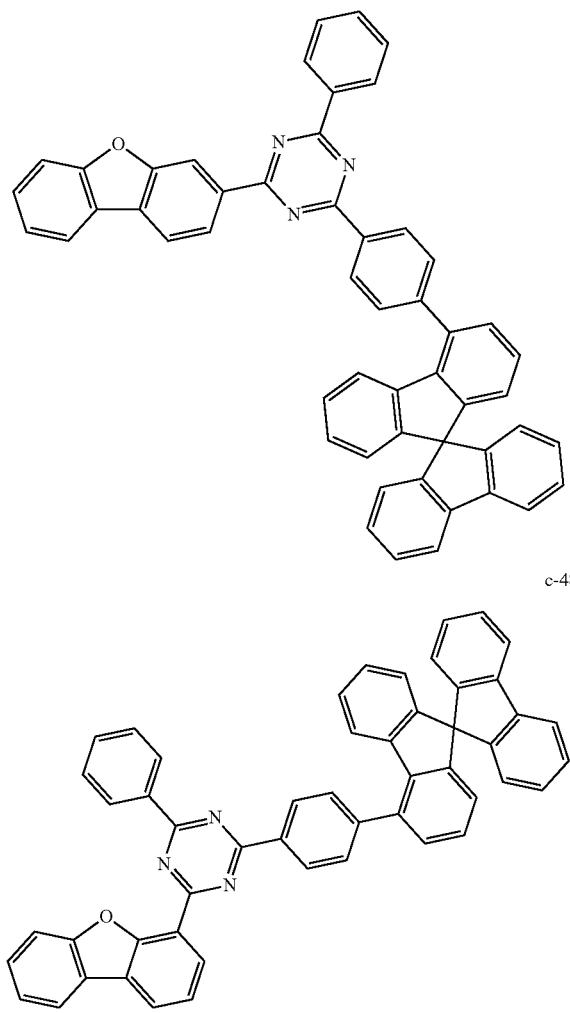
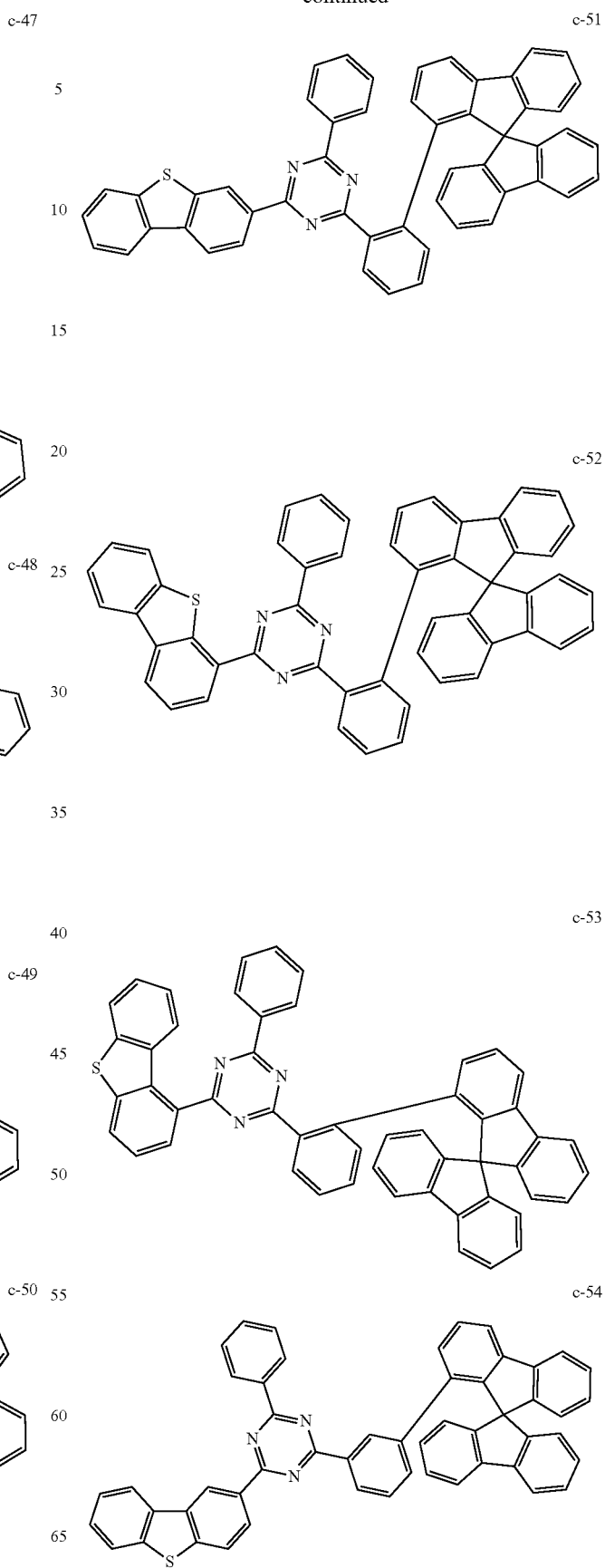

c-55
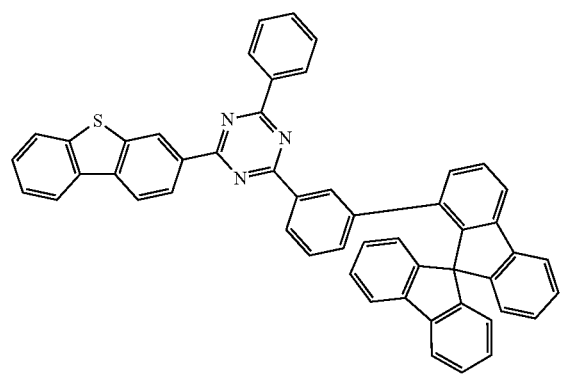
c-56
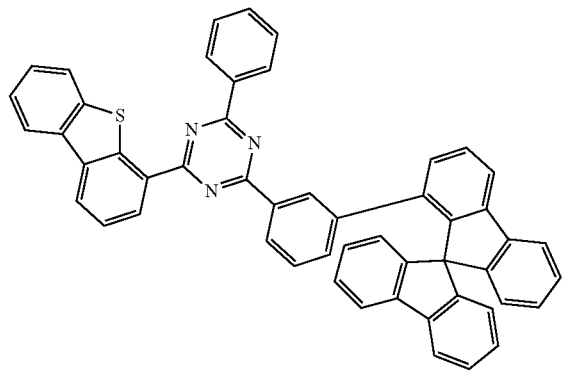
c-57
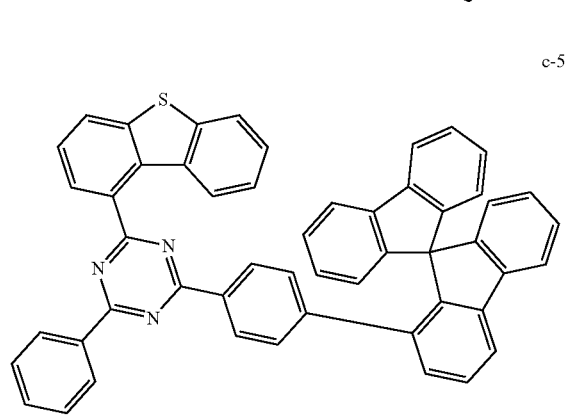
c-58
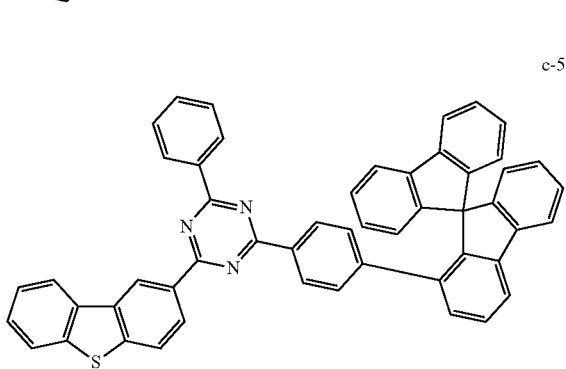
c-59
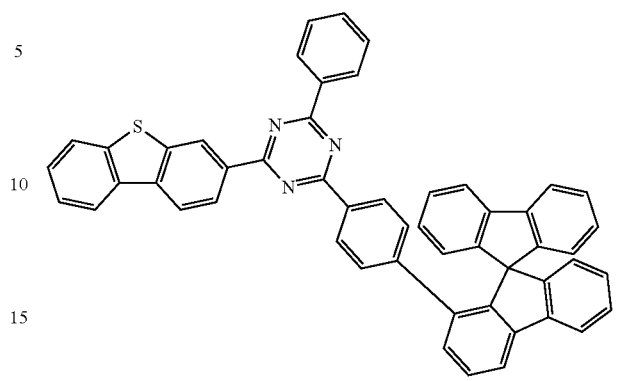
c-60
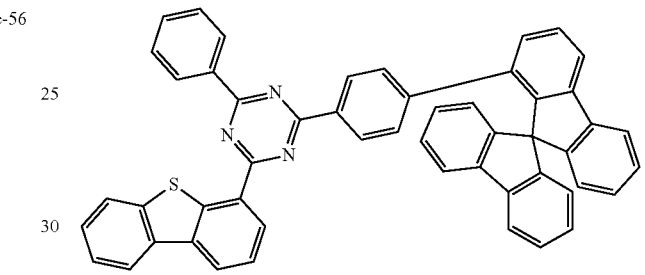
c-61
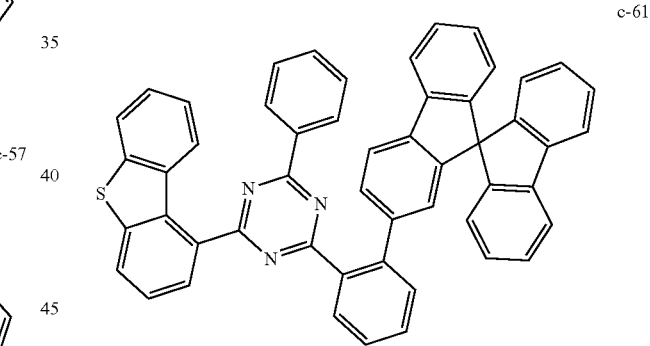
c-62
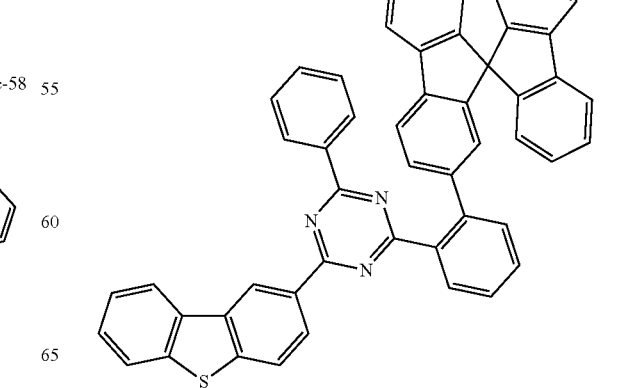

c-63
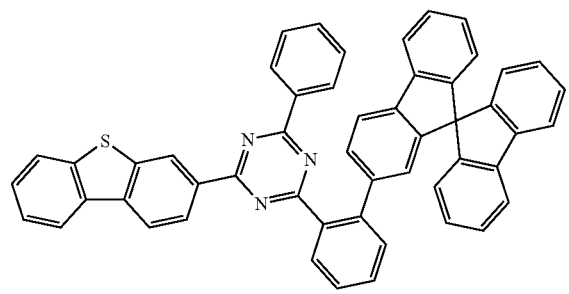
c-64
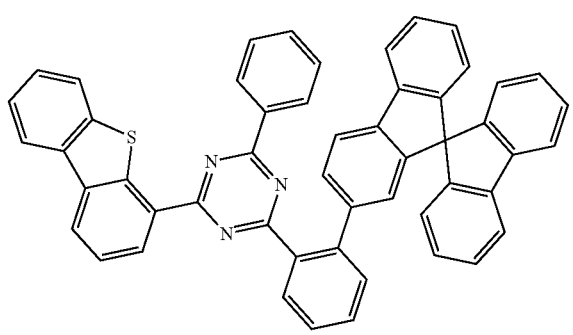
c-65
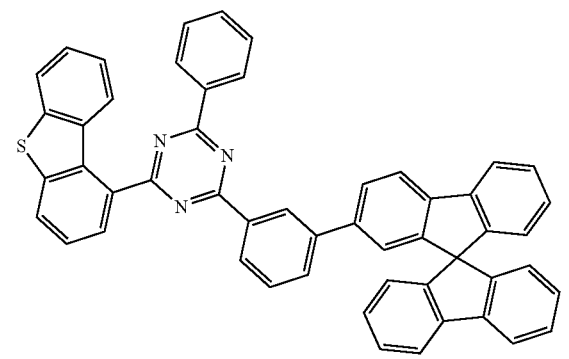
c-66
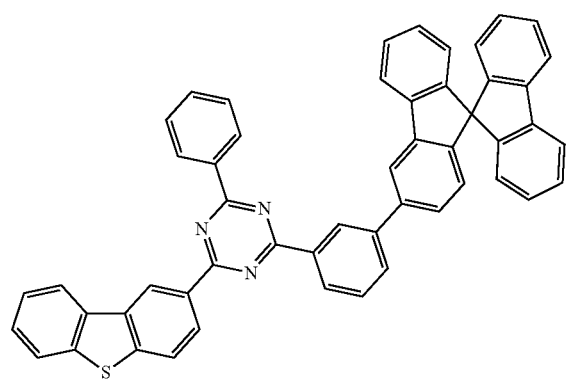
c-67
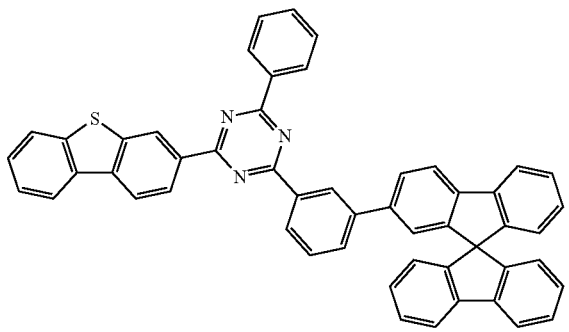
c-68
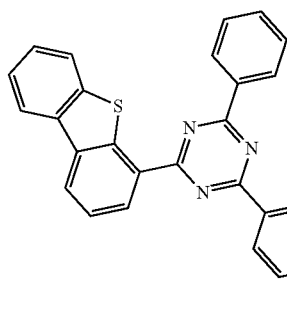
c-69
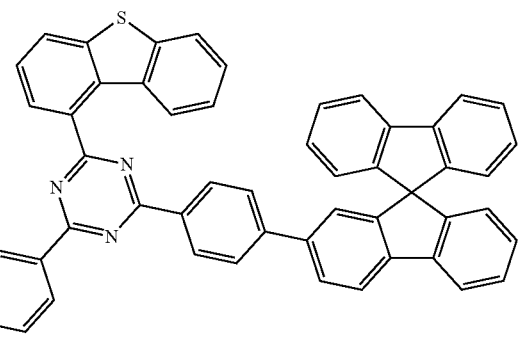
c-70
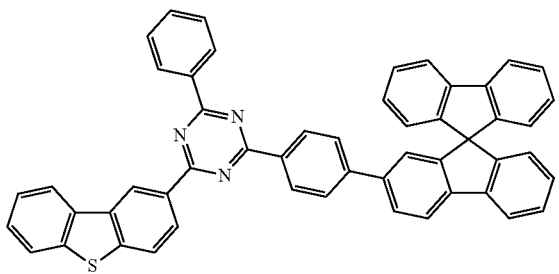

c-71
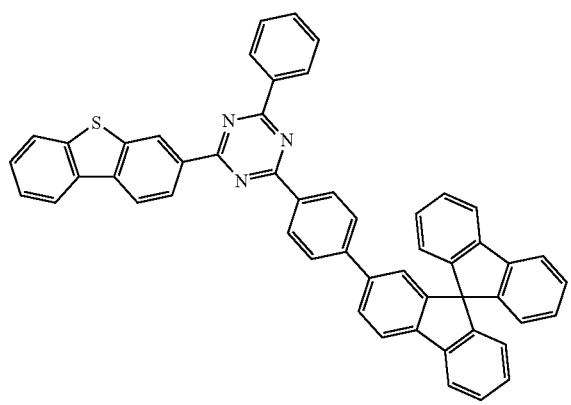
c-72
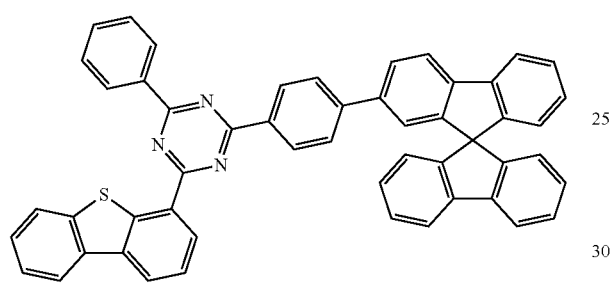
c-73
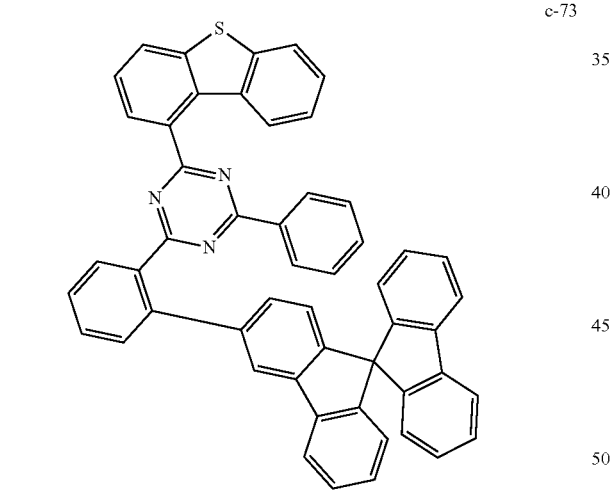
c-74
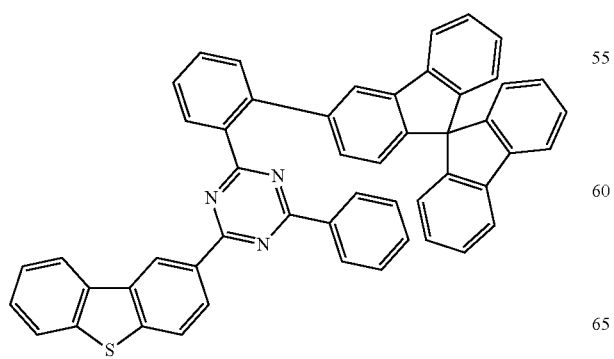
c-75
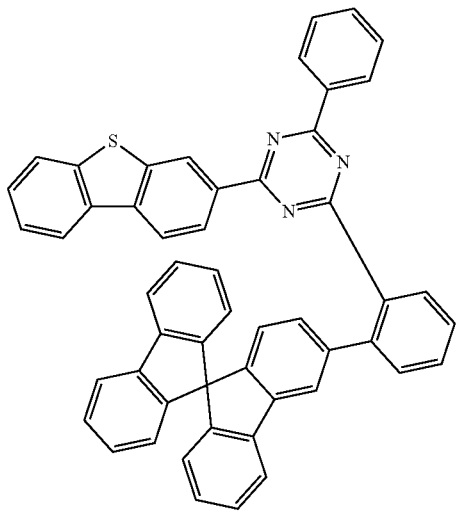
c-76
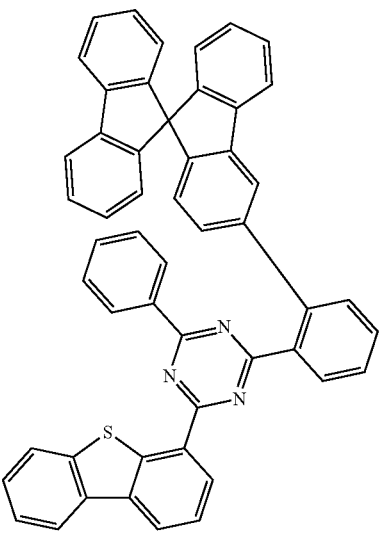
c-77
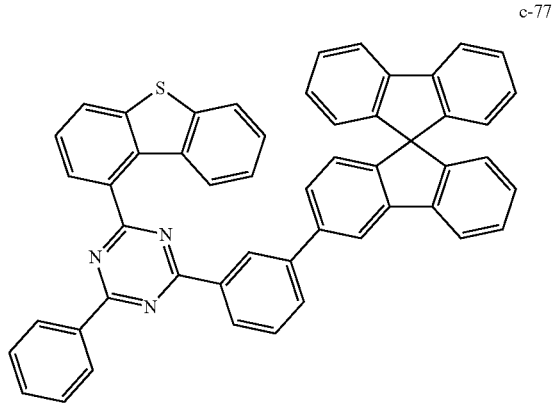

c-78
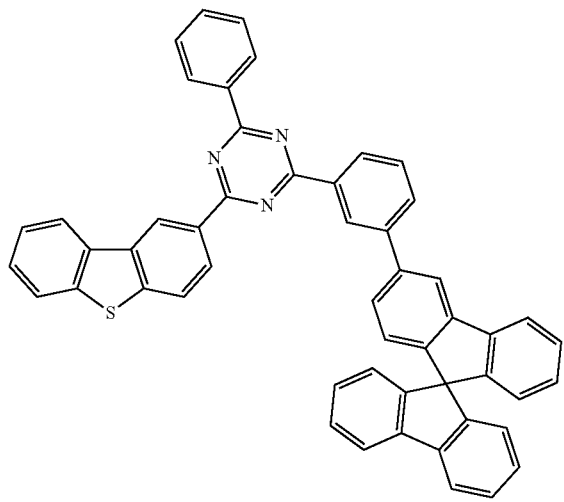
c-79
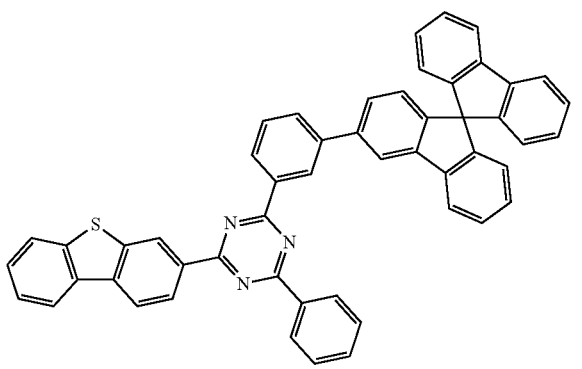
c-80
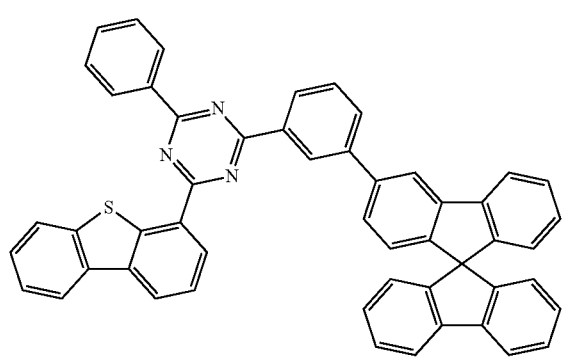
c-81
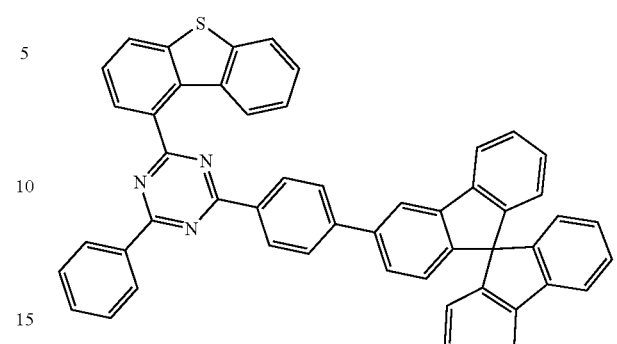
c-82
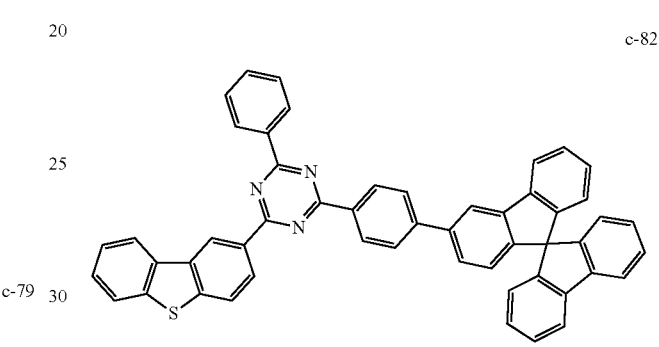
c-83
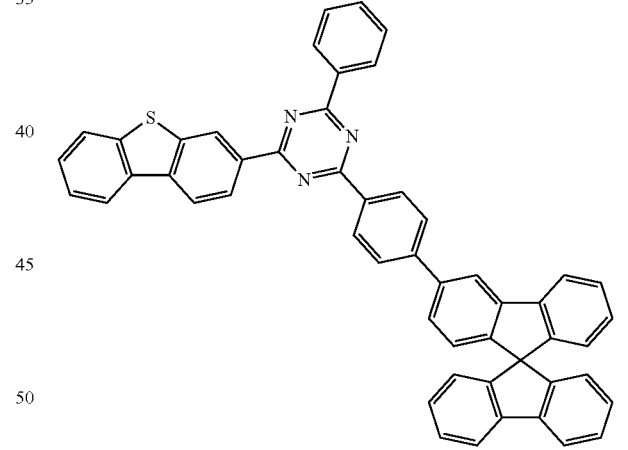
c-84
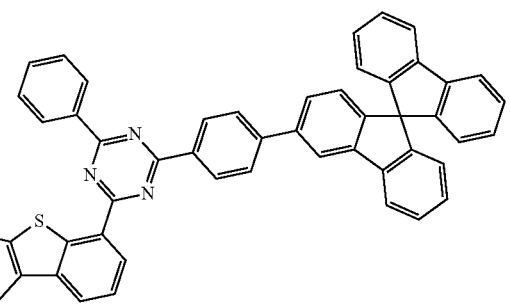

c-85
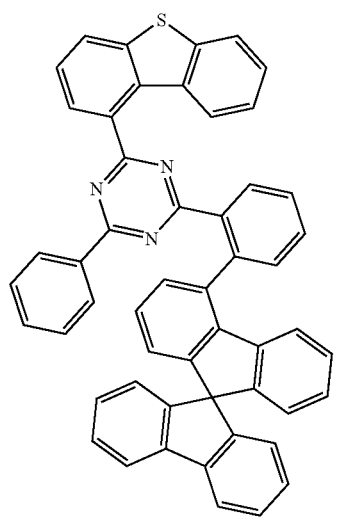
c-86
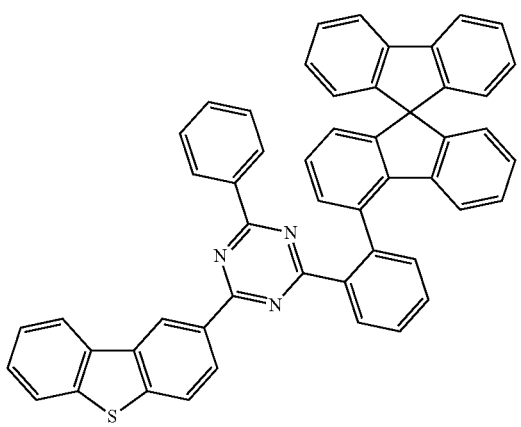
c-87
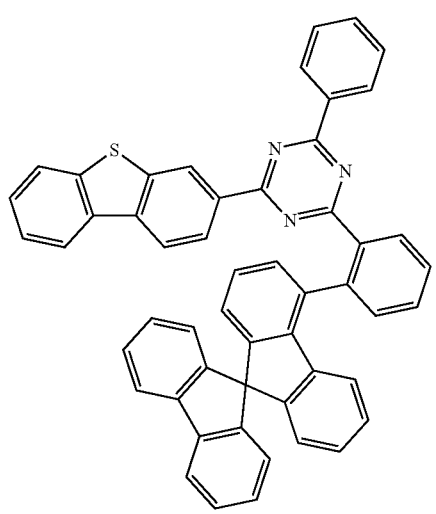
c-88
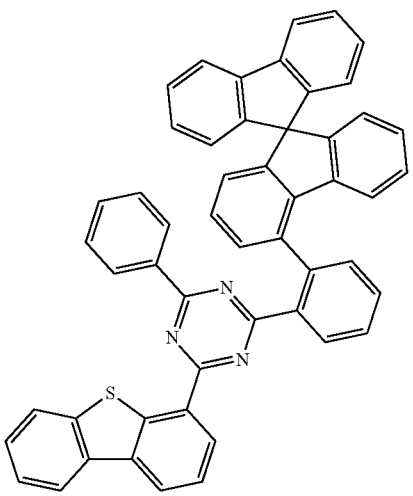
c-89
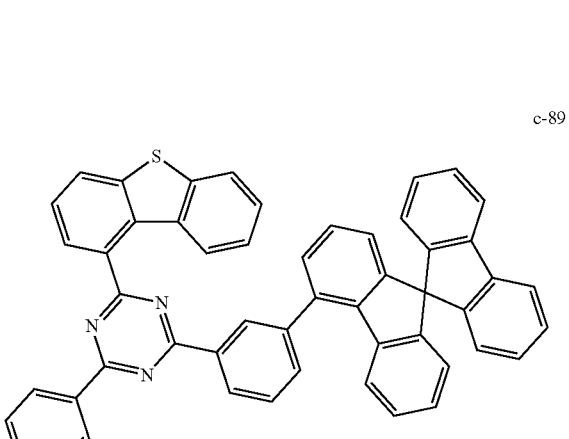
c-90
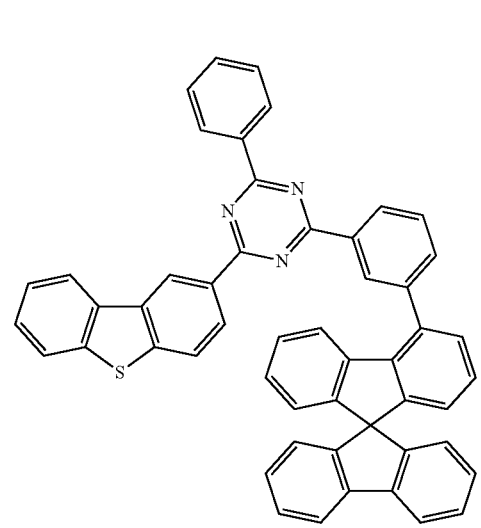

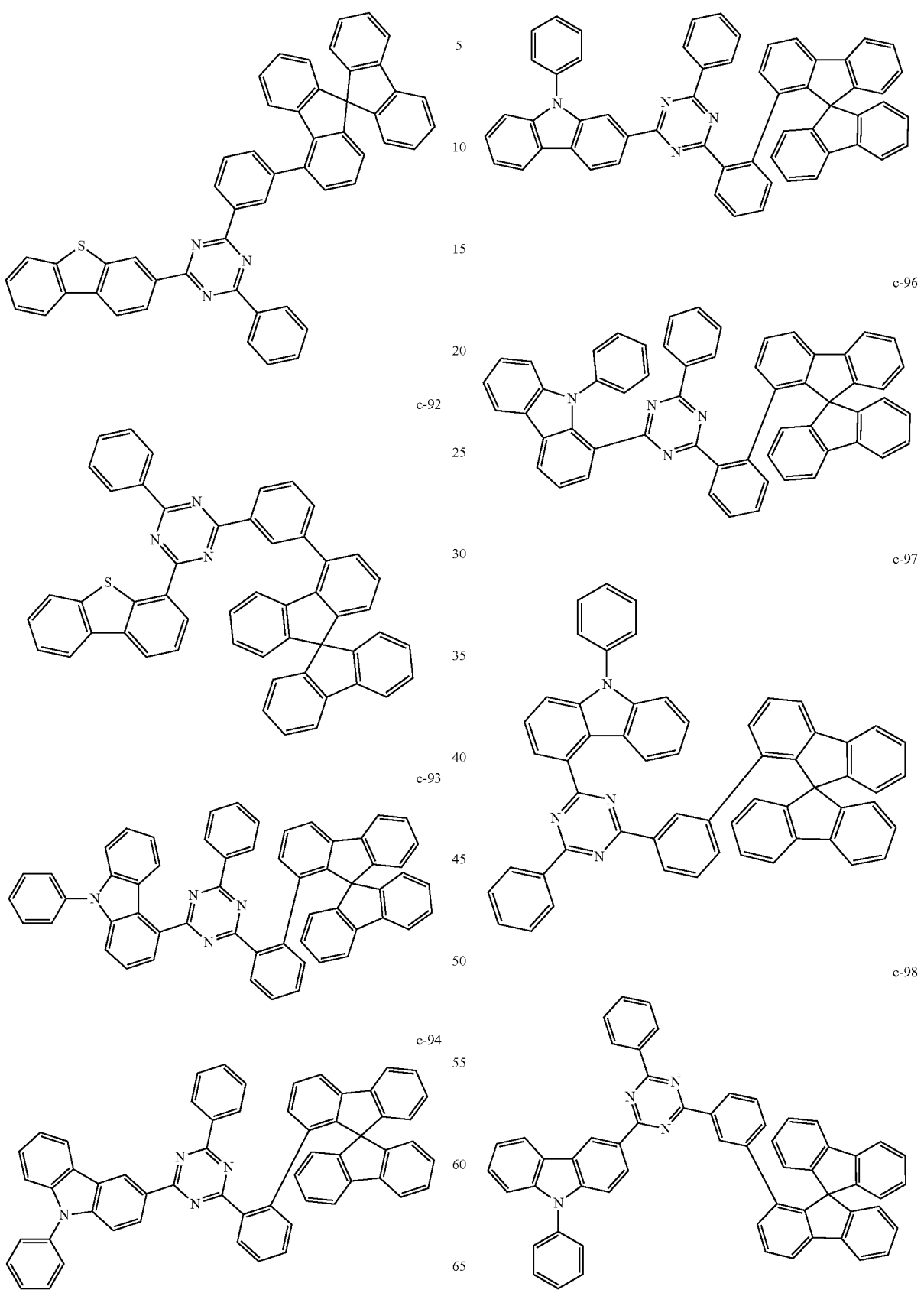

c-99
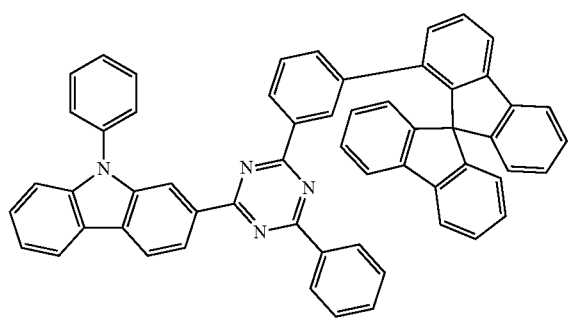
c-100
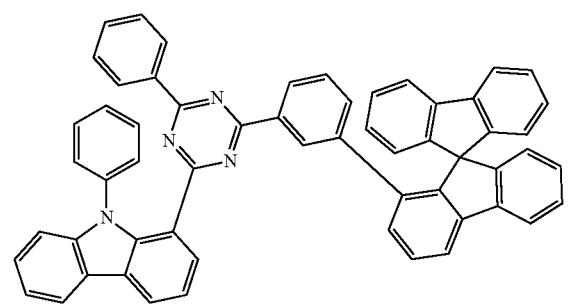
c-101
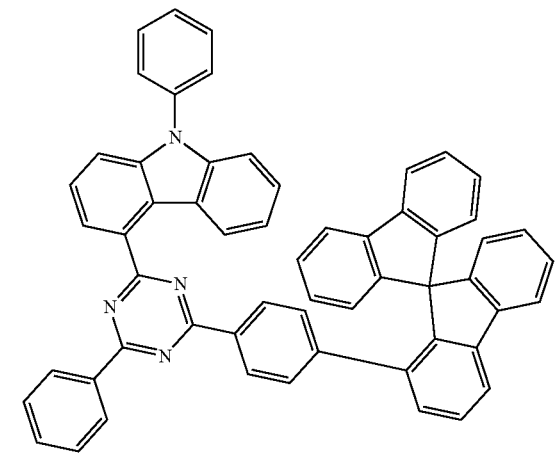
c-102
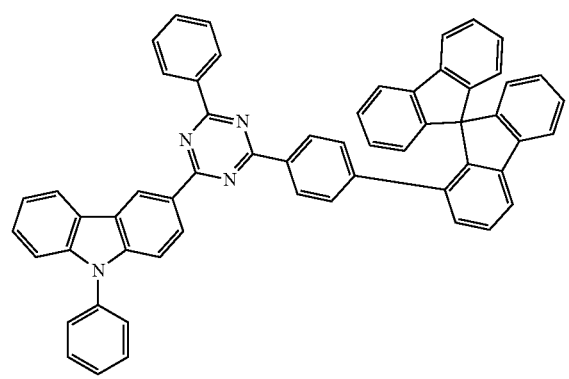
c-103
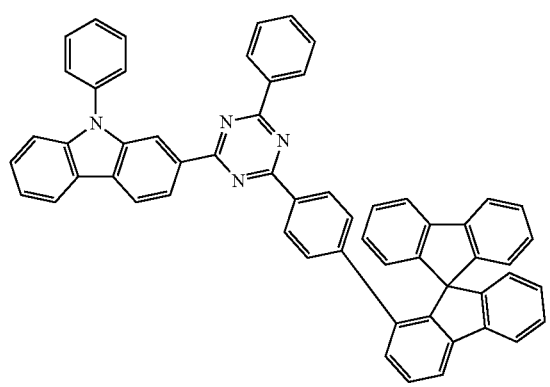
c-104
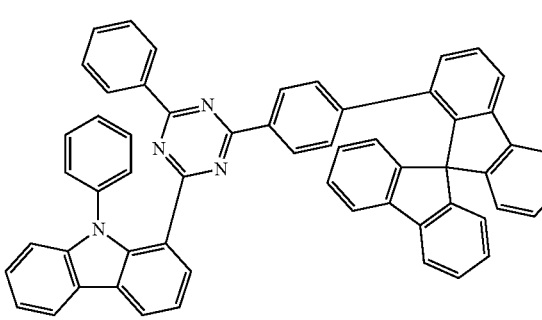
c-105
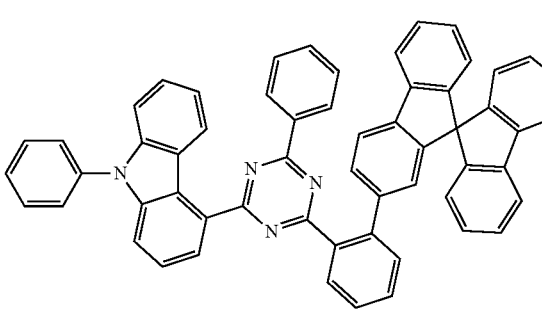
c-106
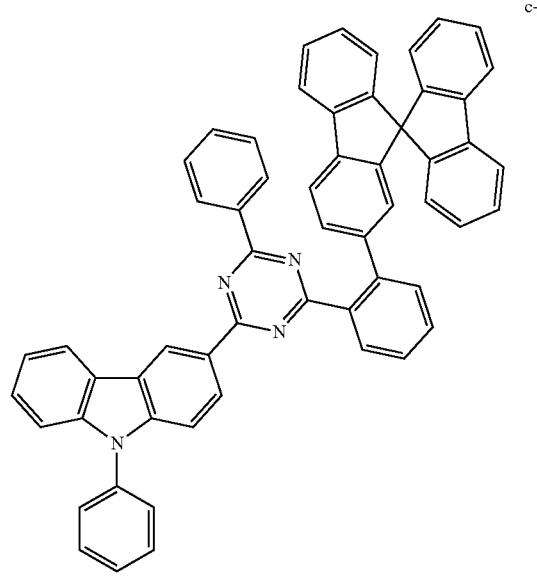

c-107
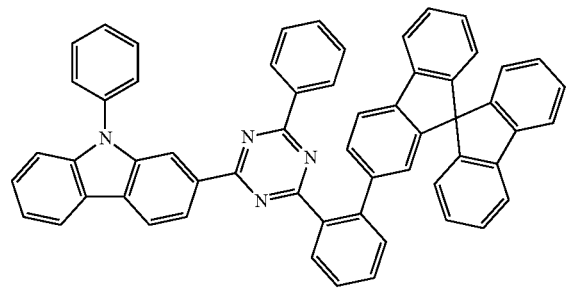
c-108
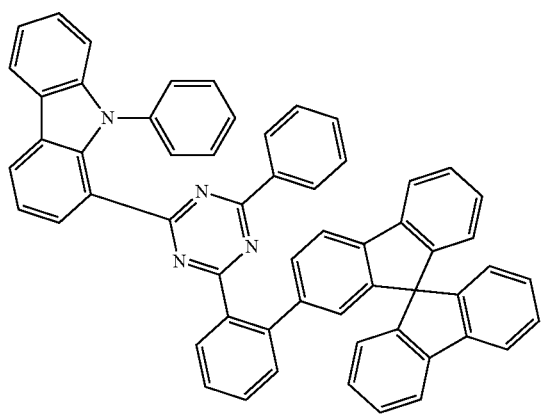
c-109
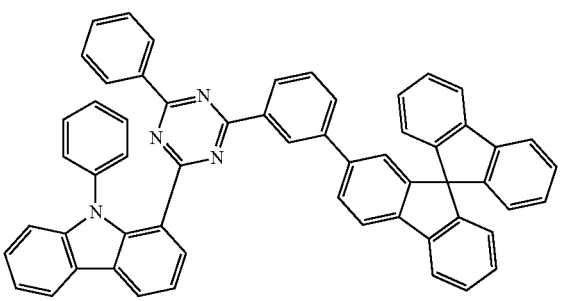
c-110
c-111
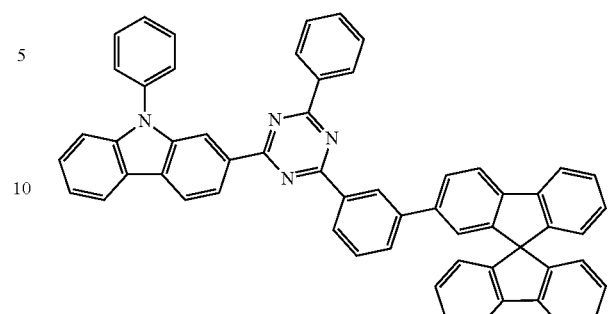
c-112
c-113
c-114
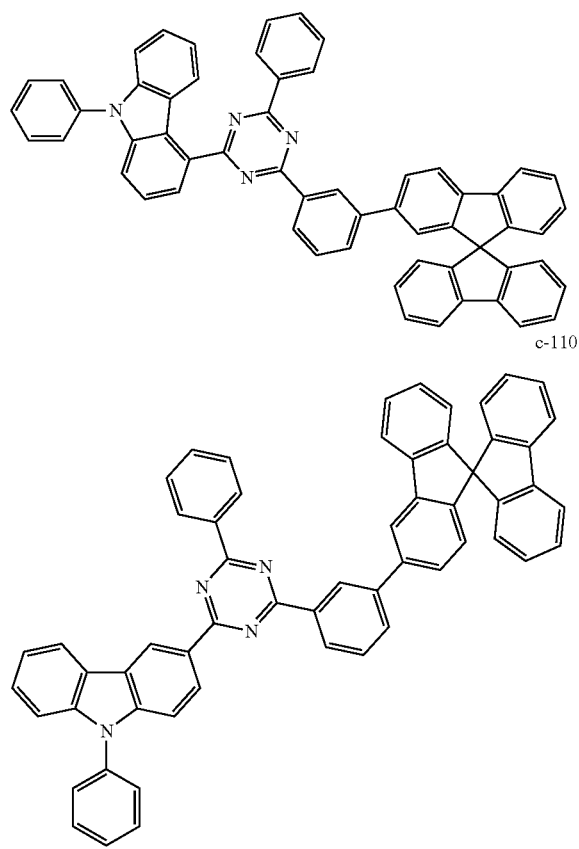

-continued
c-115
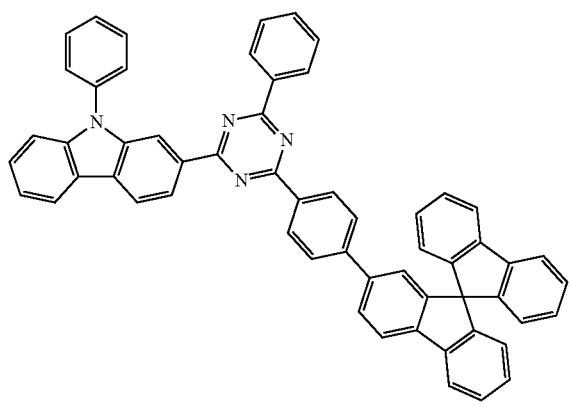
c-116
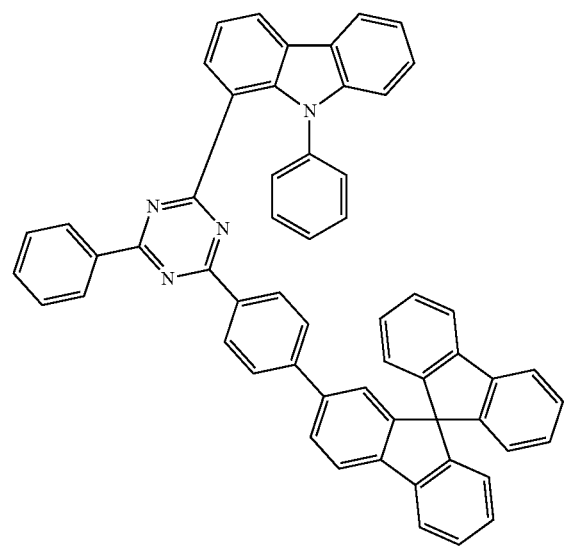
c-117
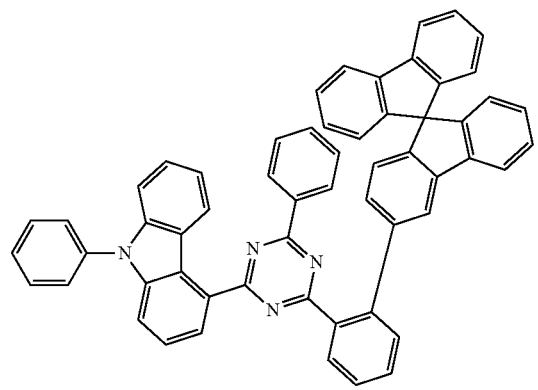
-continued
c-118
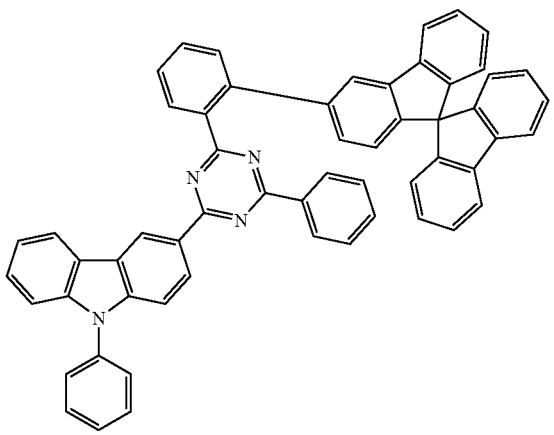
c-119
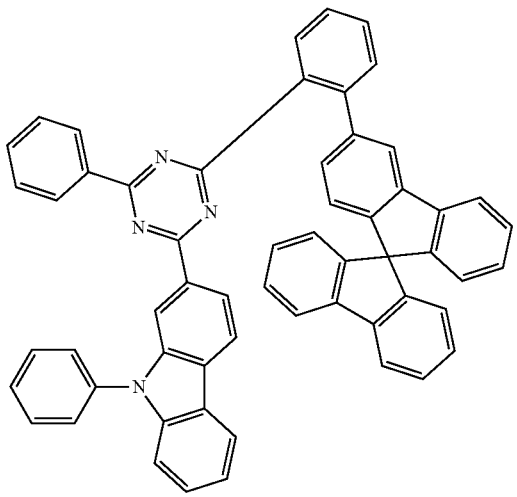
c-120
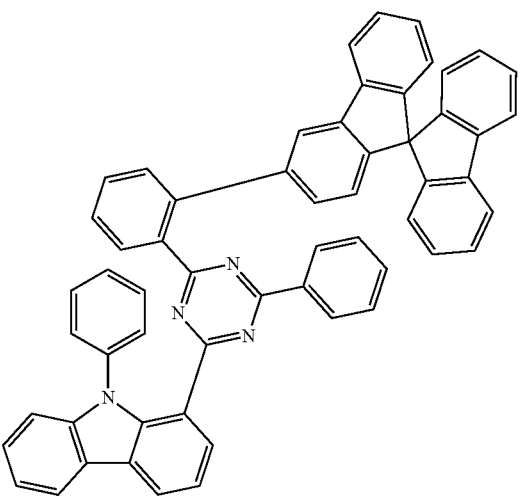

c-121
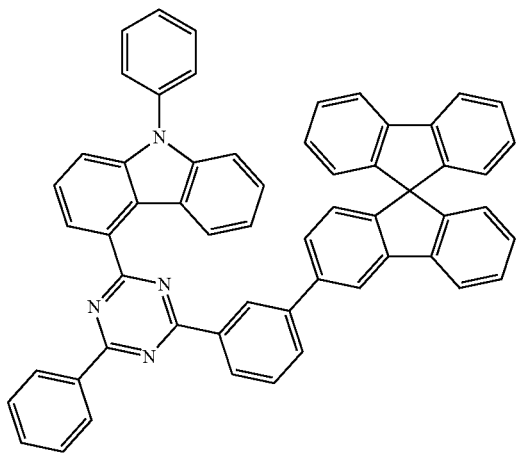
c-124
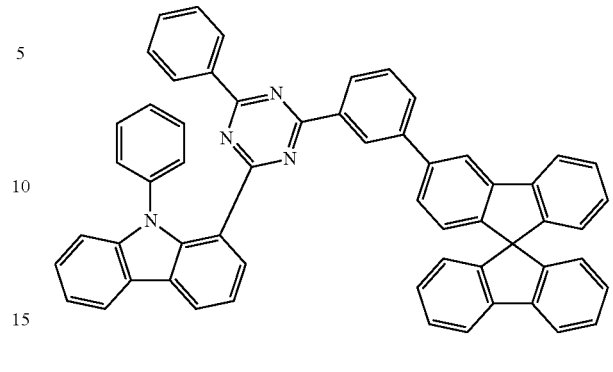
c-122
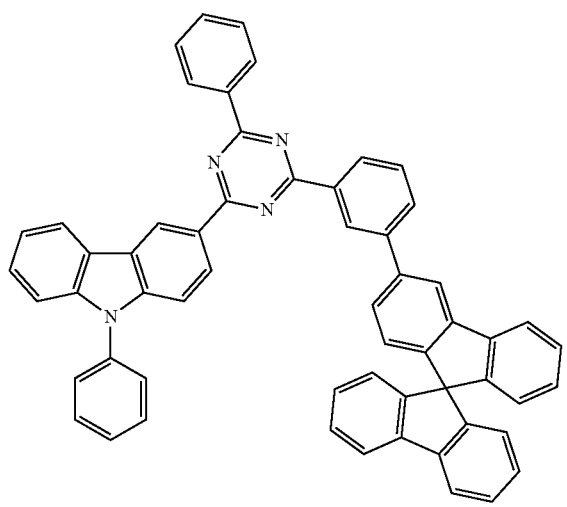
c-125
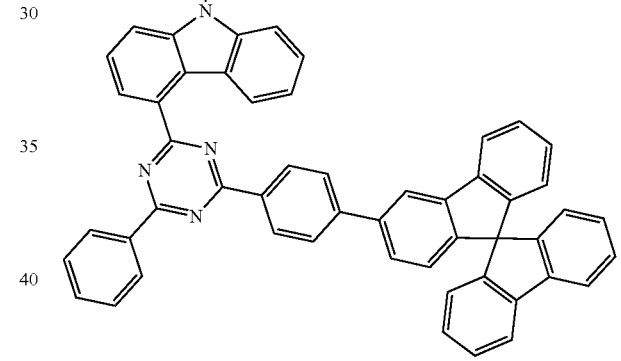
c-123
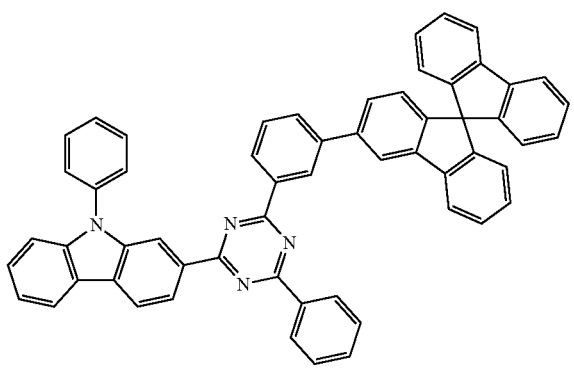
c-126
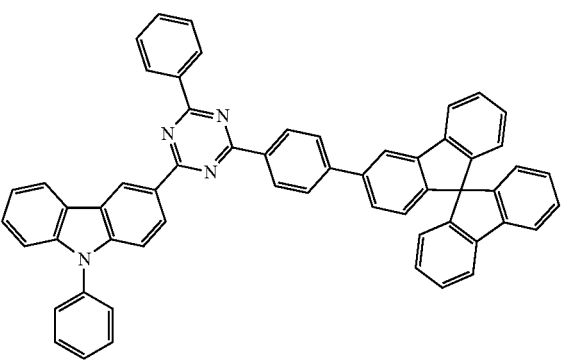

c-127
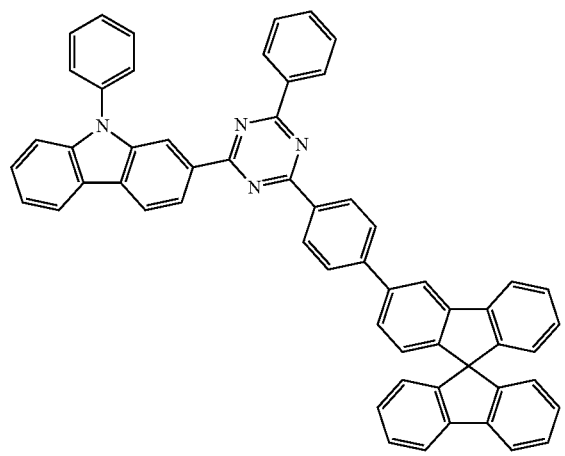
c-128
c-129
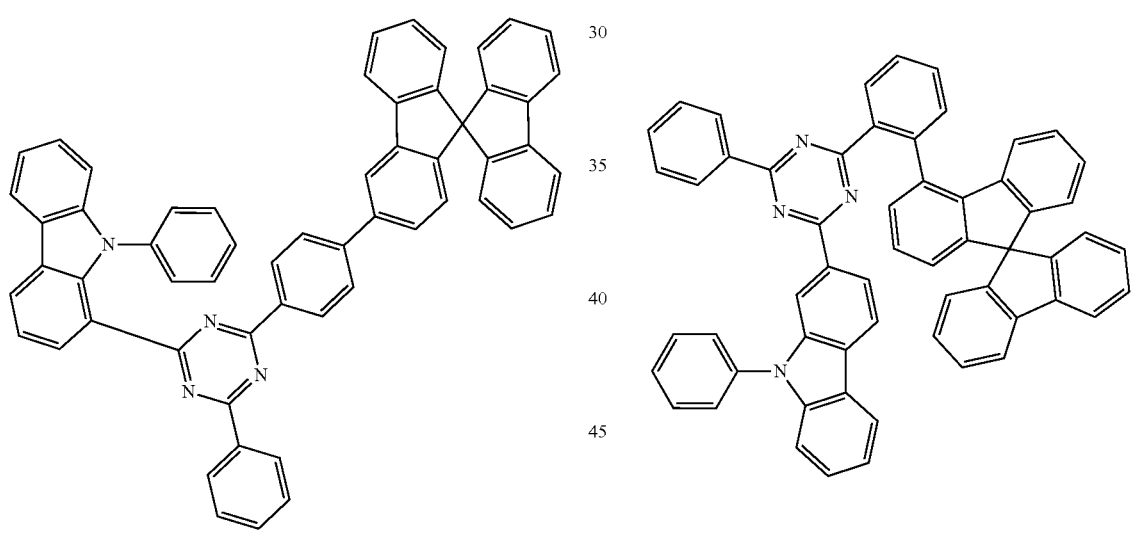
c-130
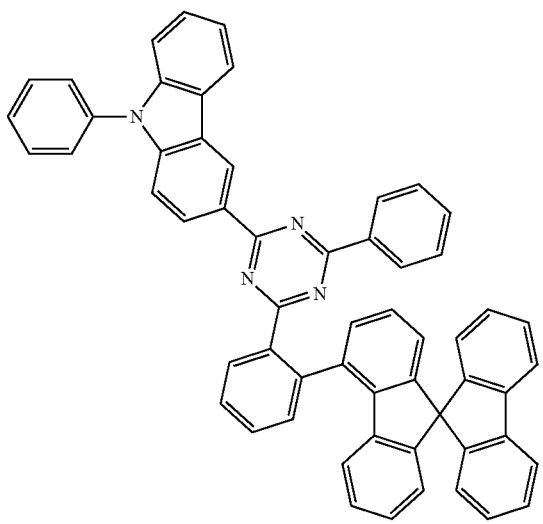
c-131
c-132
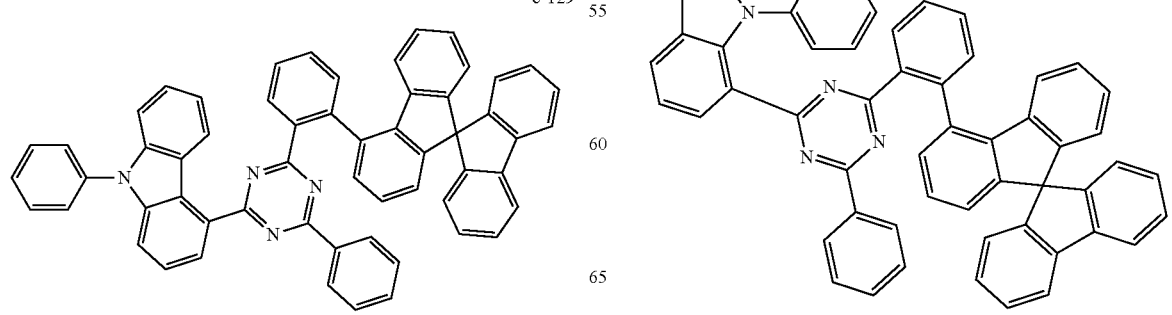

-continued
c-133
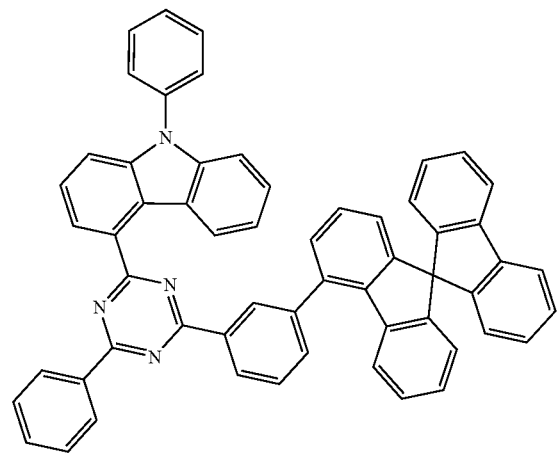
c-134
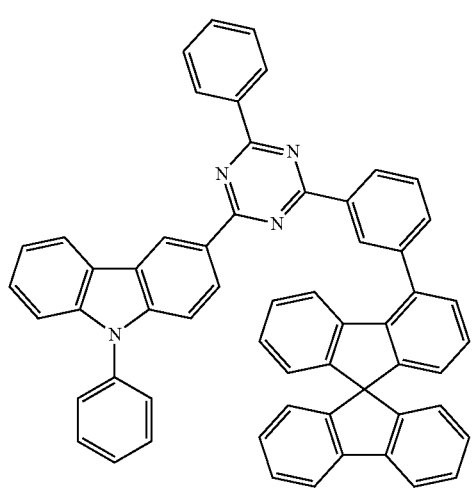
c-135
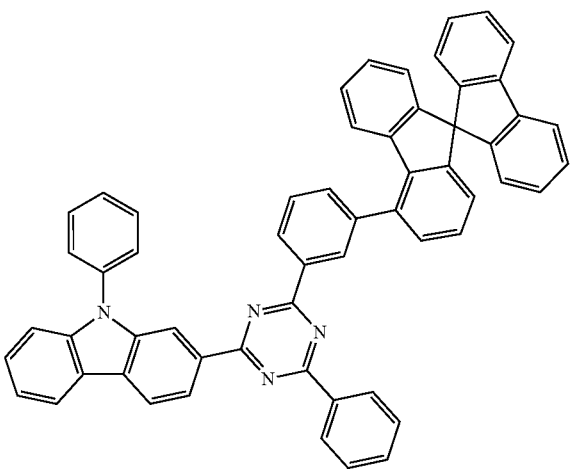
c-136
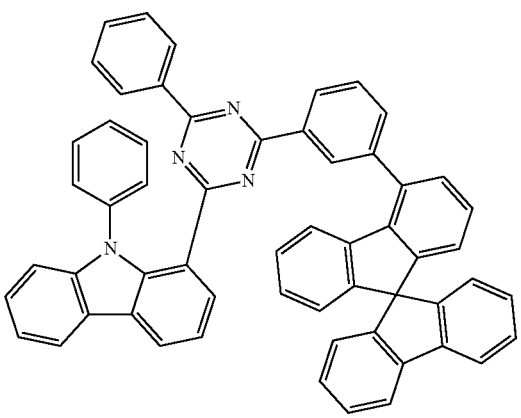
c-137
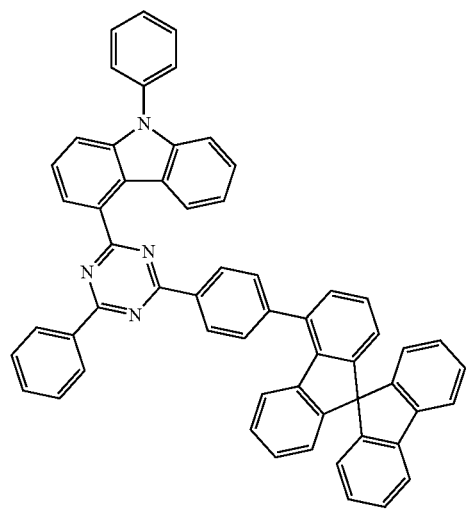
c-138
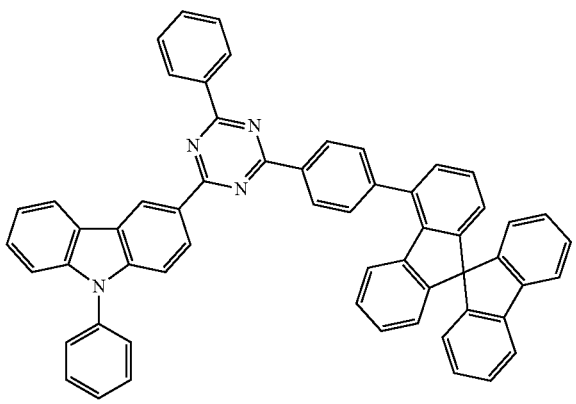

-continued
c-139
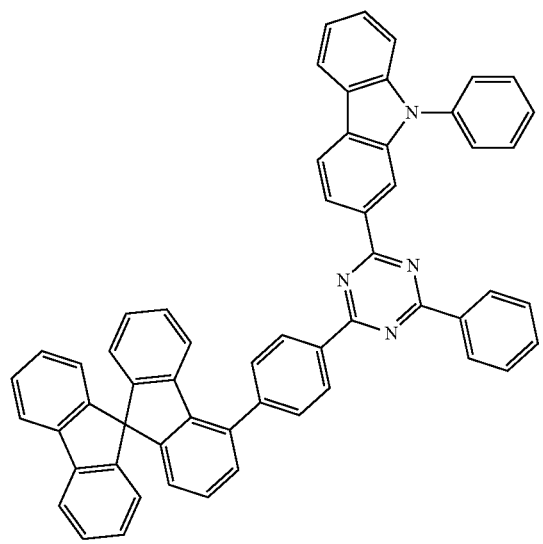
c-140
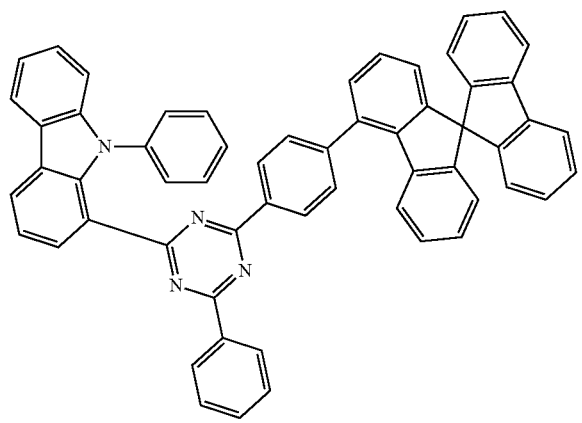
c-141
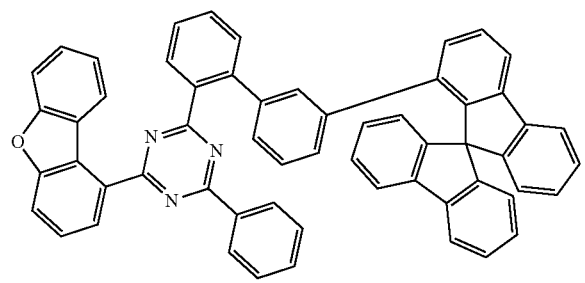
c-142
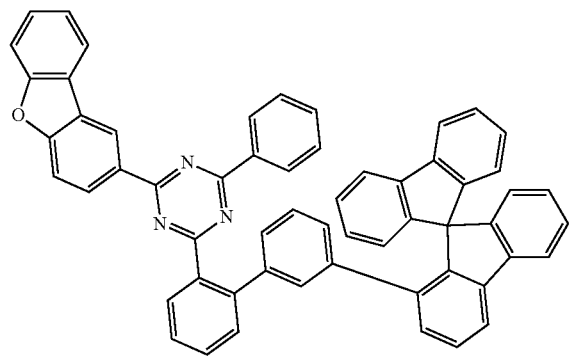
c-143
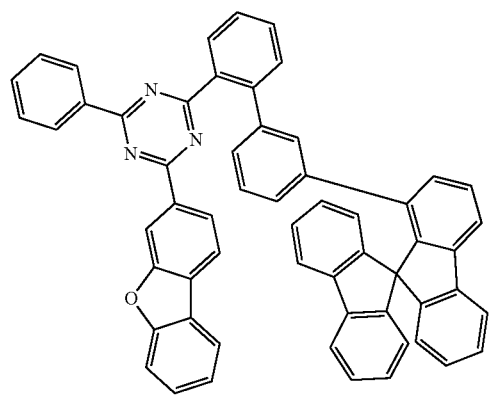
c-144
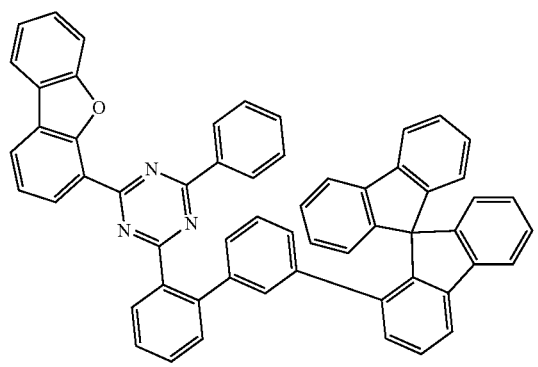

-continued
c-145
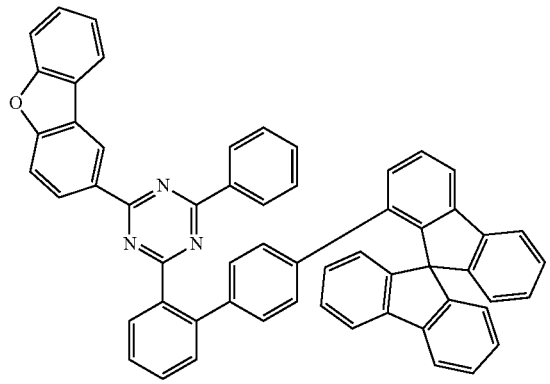
c-146
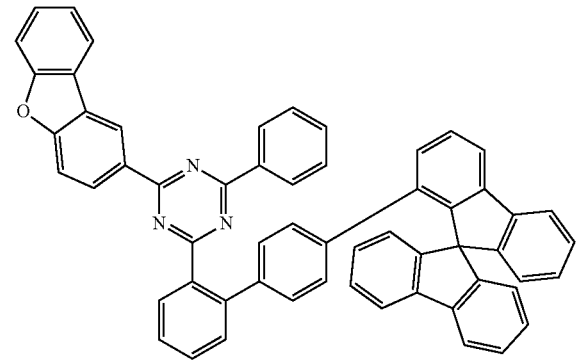
c-147
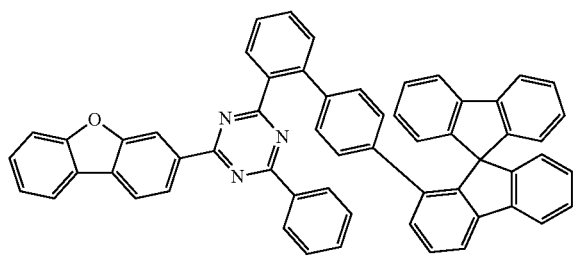
c-148
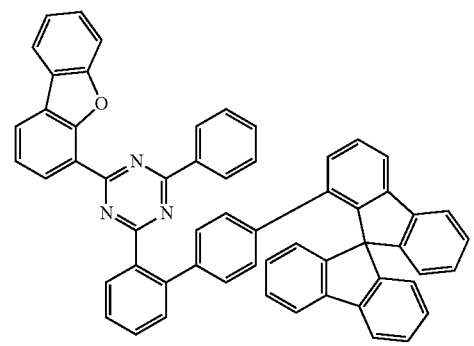
c-149
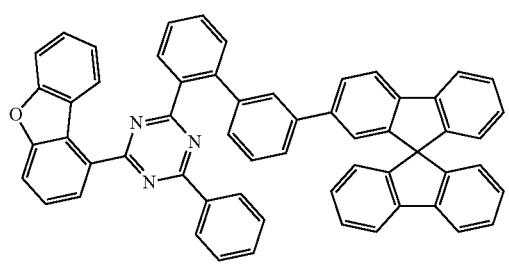
c-150
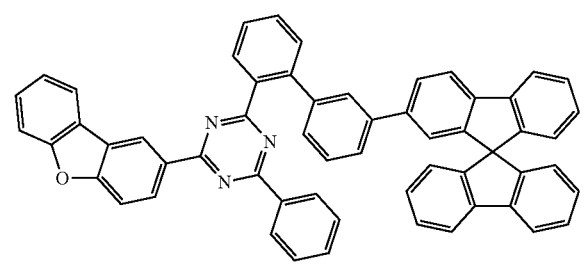
c-151
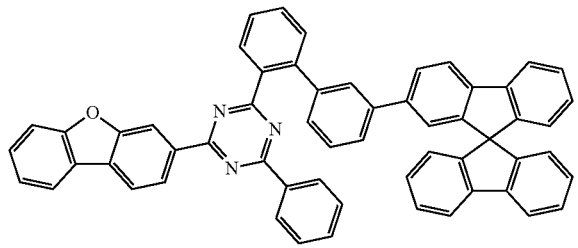
c-152
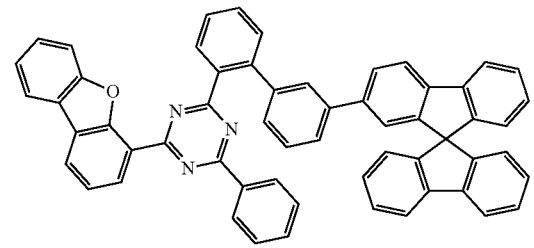

-continued
c-153
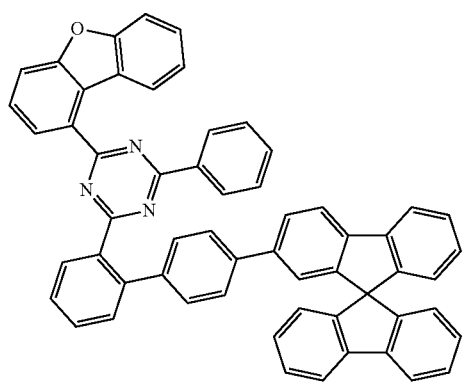
c-154
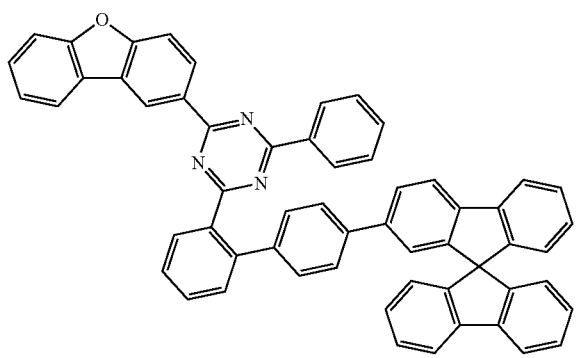
c-155
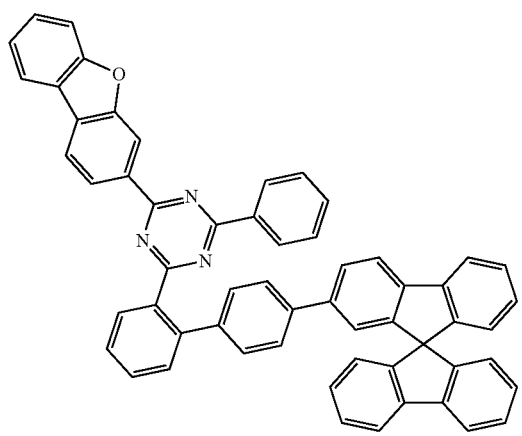
c-156
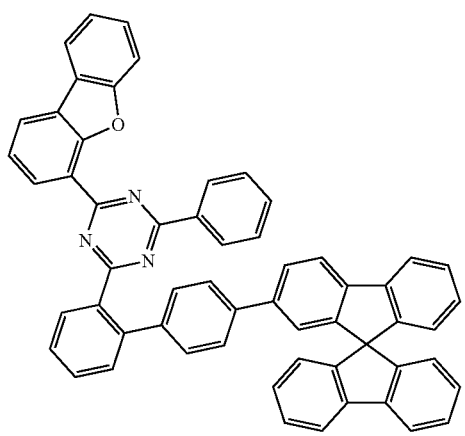
c-157
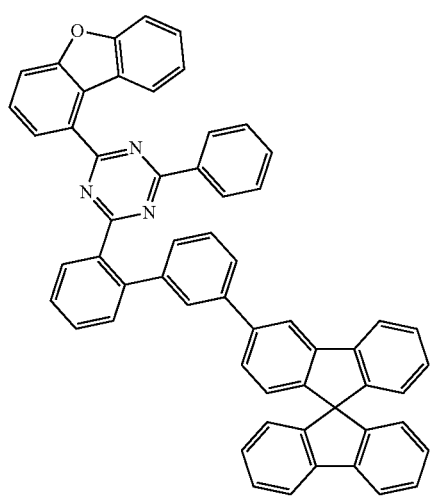
c-158
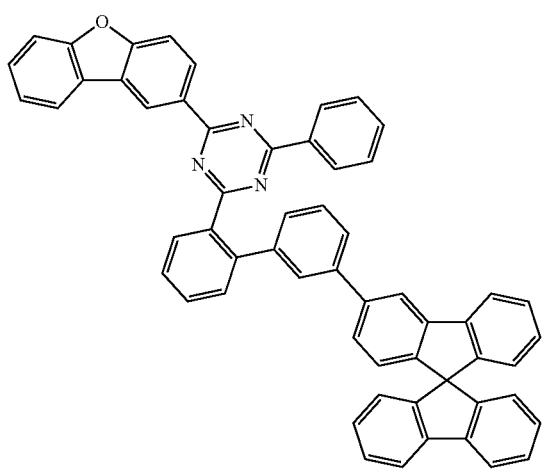

c-159
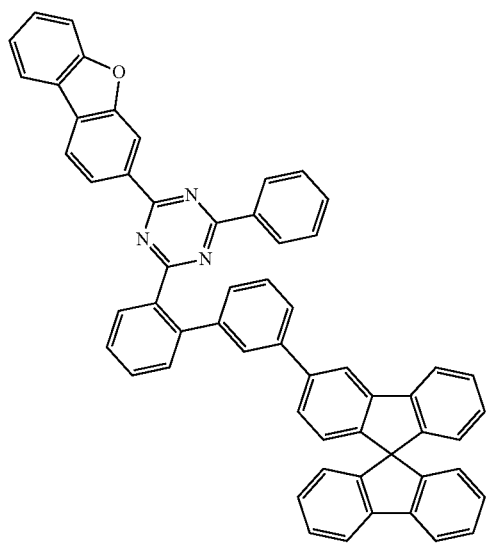
c-160
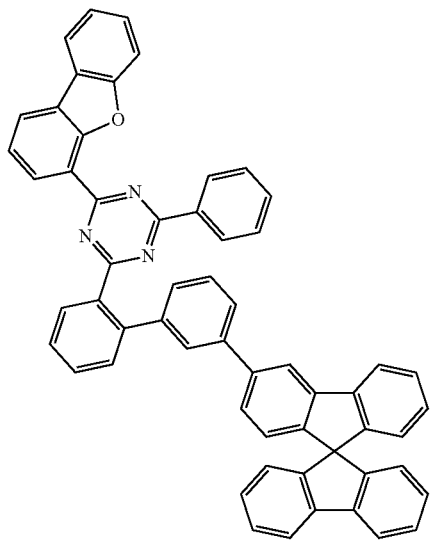
c-161
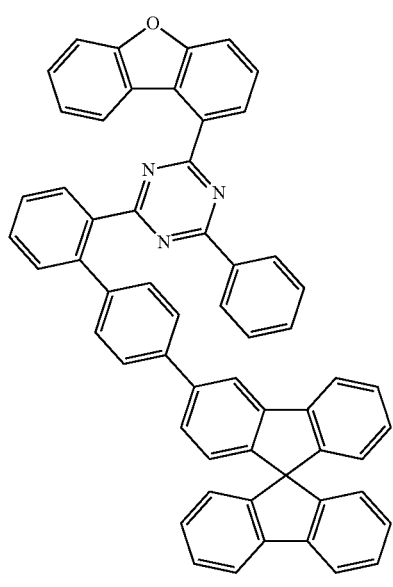
c-162
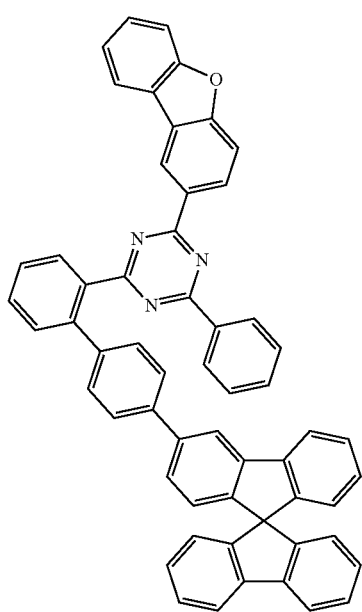

-continued
c-163
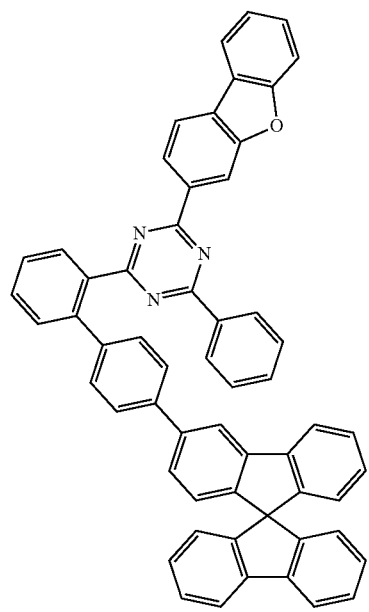
c-164
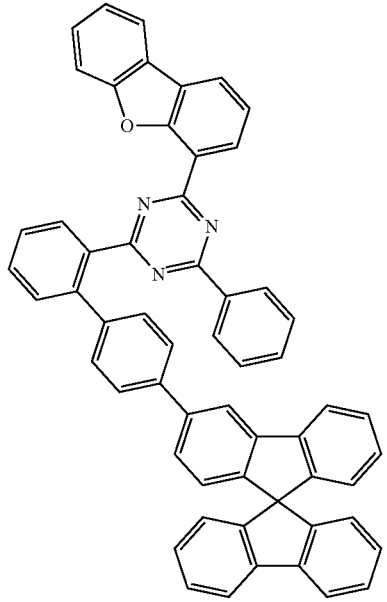
c-165
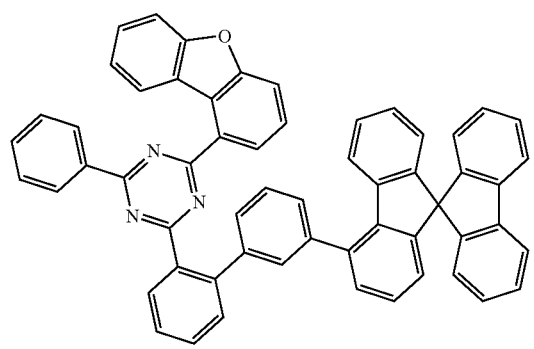
c-166
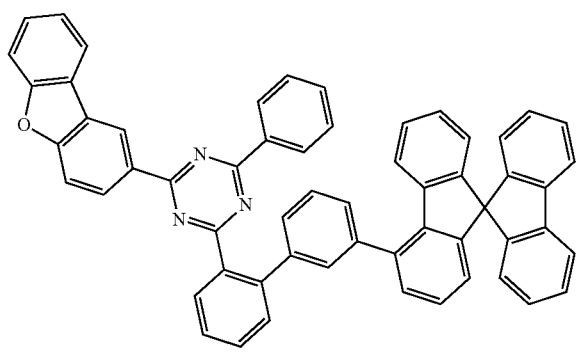
c-167
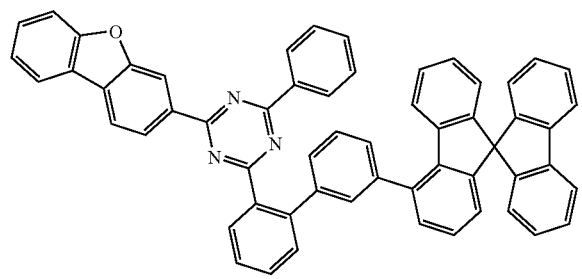
c-168
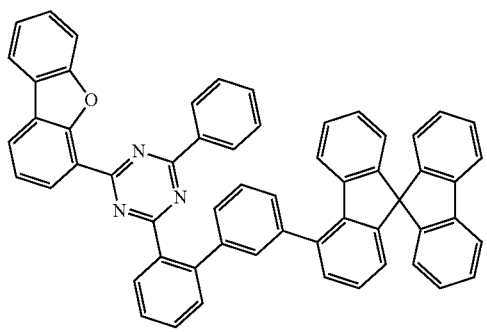

-continued
c-169
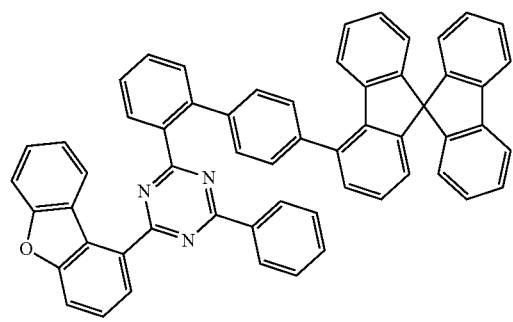
c-170
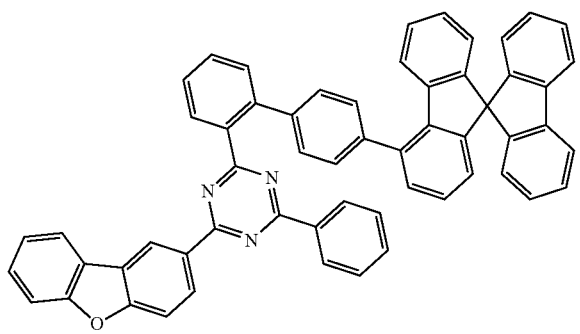
c-171
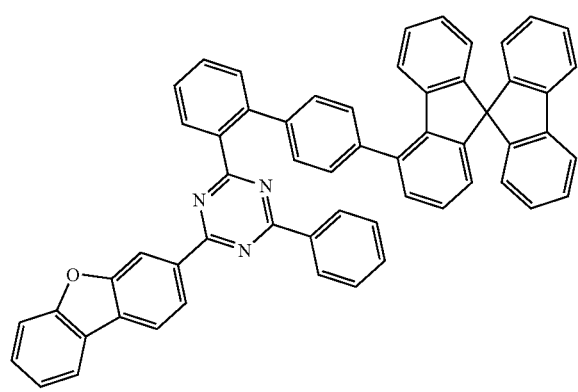
c-172
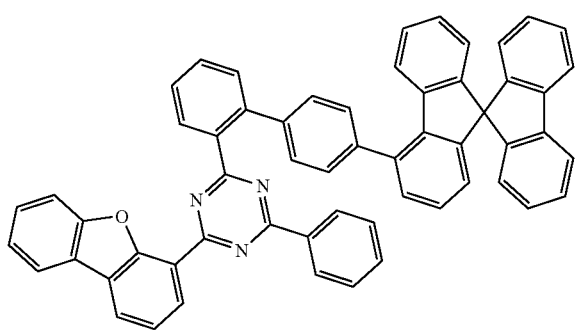
c-173
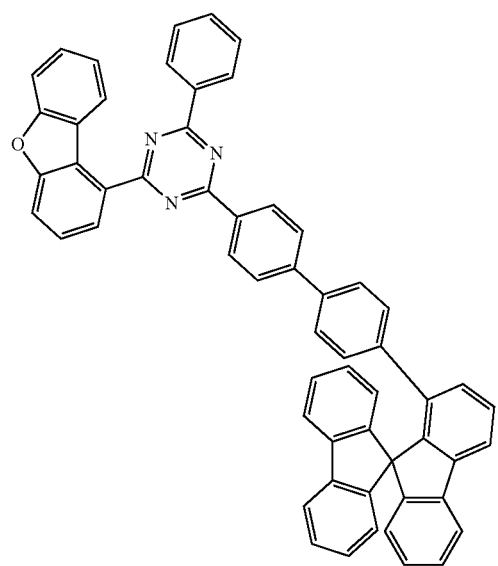
c-174
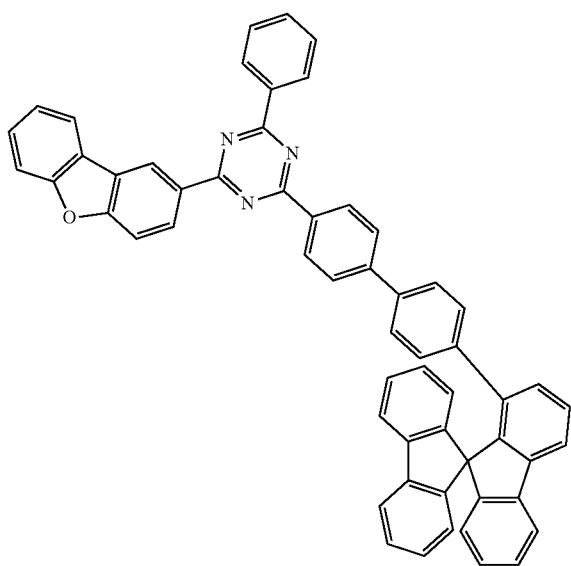

-continued
c-175
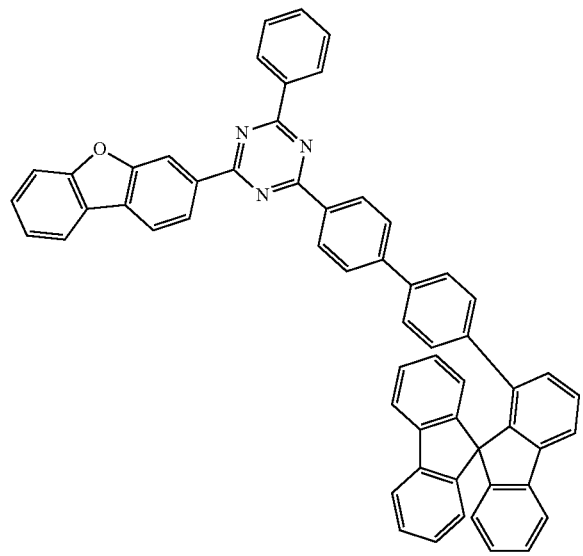
c-176
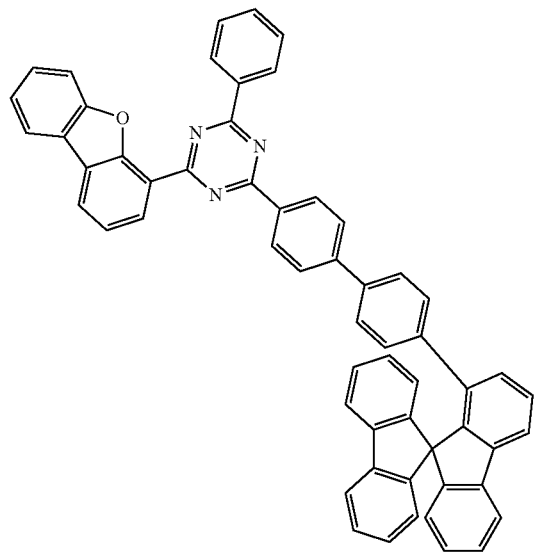
c-177
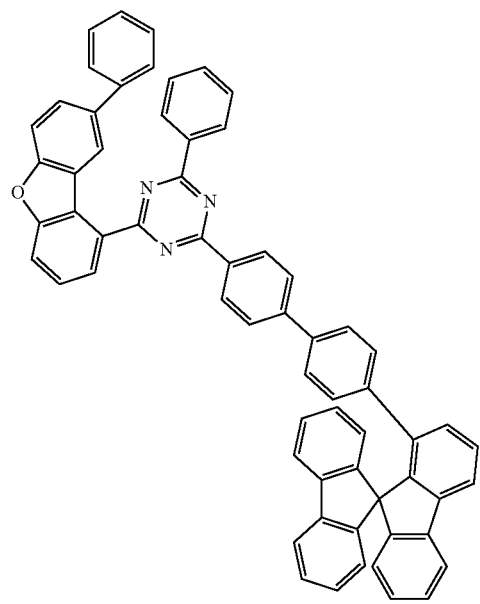
c-178
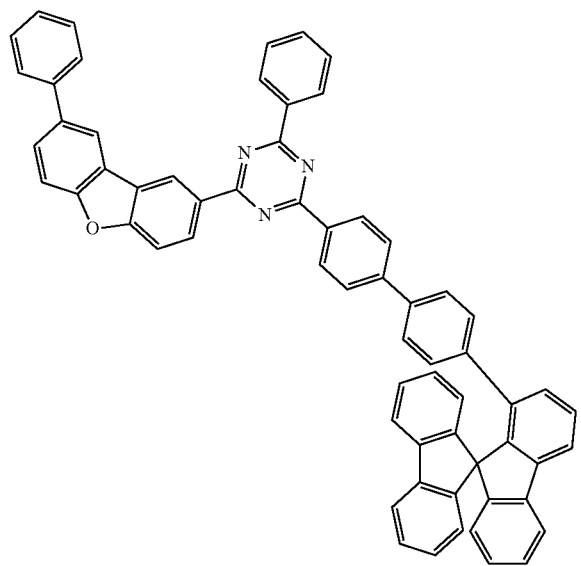

-continued
c-179
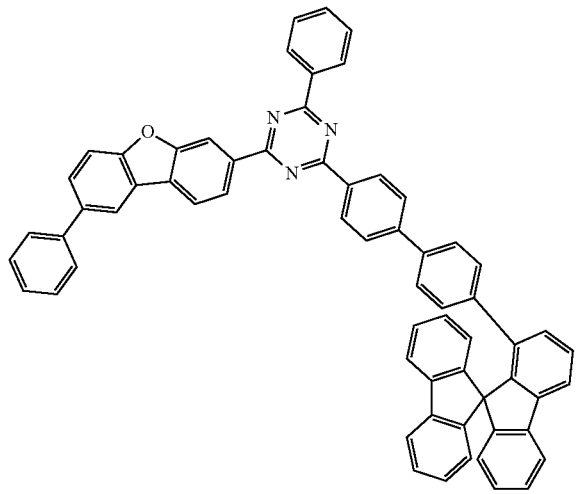
c-180
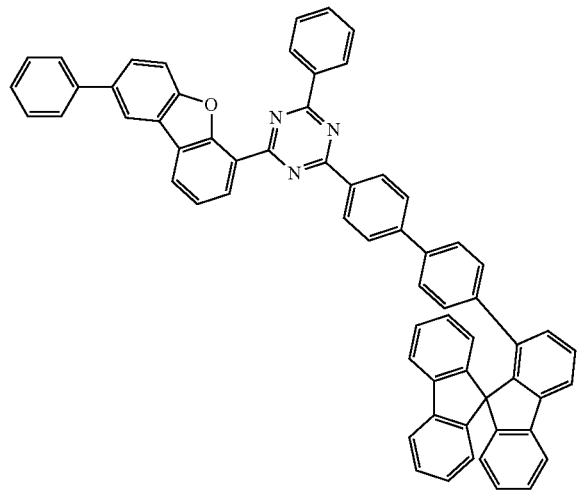
c-181
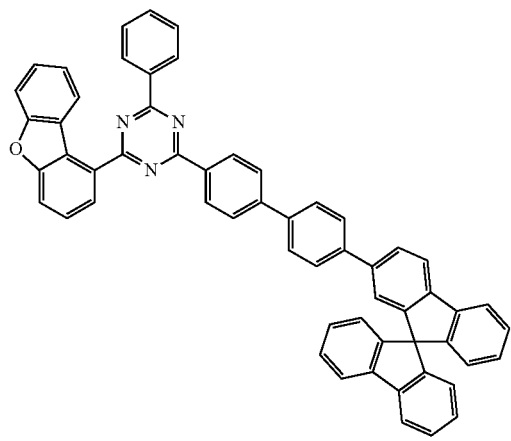
c-182
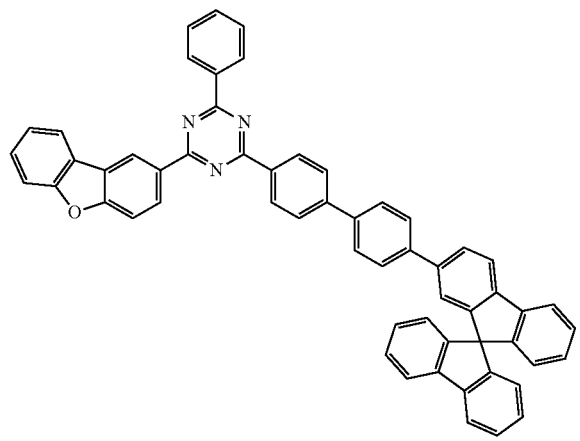
c-183
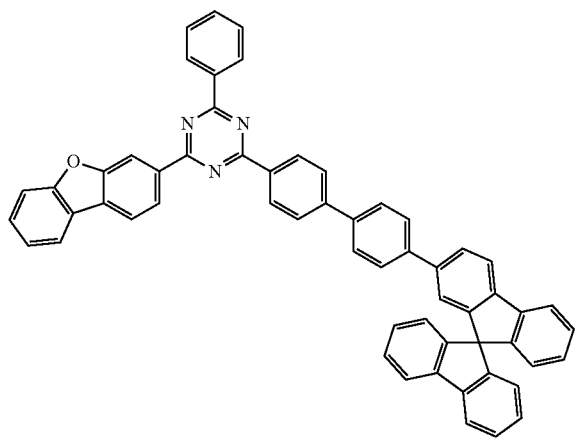
c-184
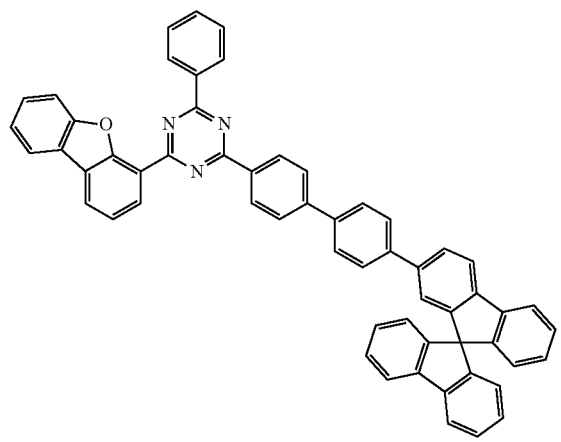

-continued
c-185
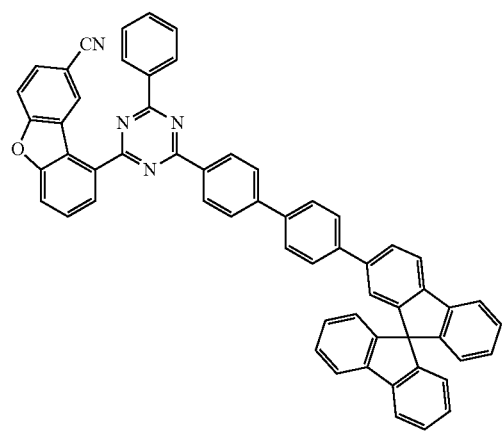
c-186
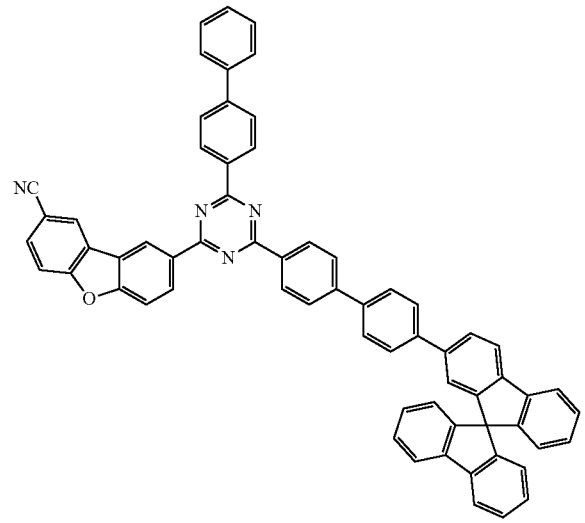
c-187
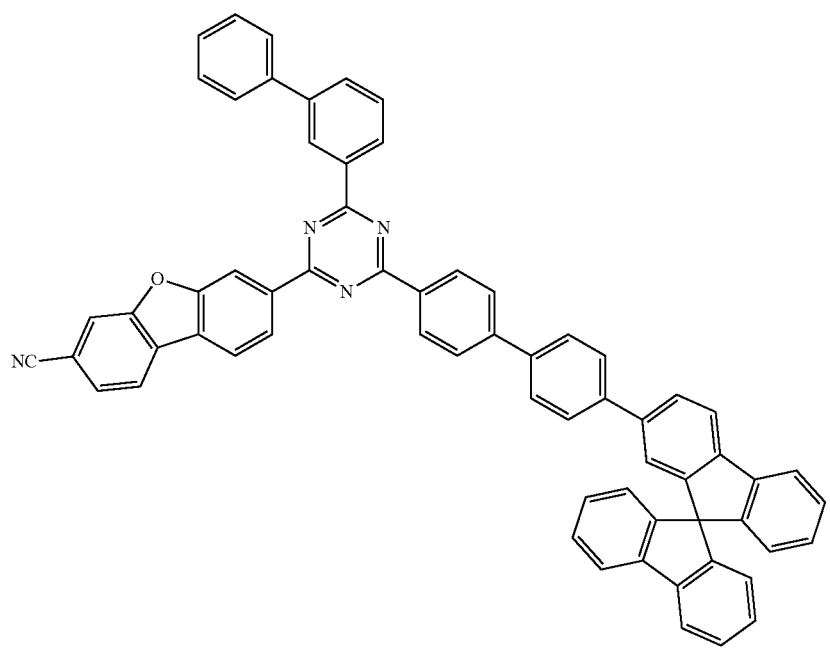

-continued
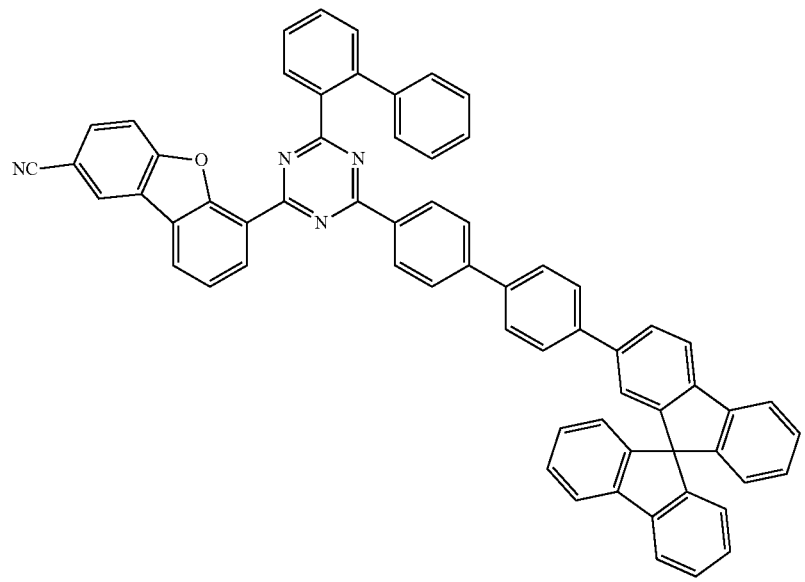
c-188
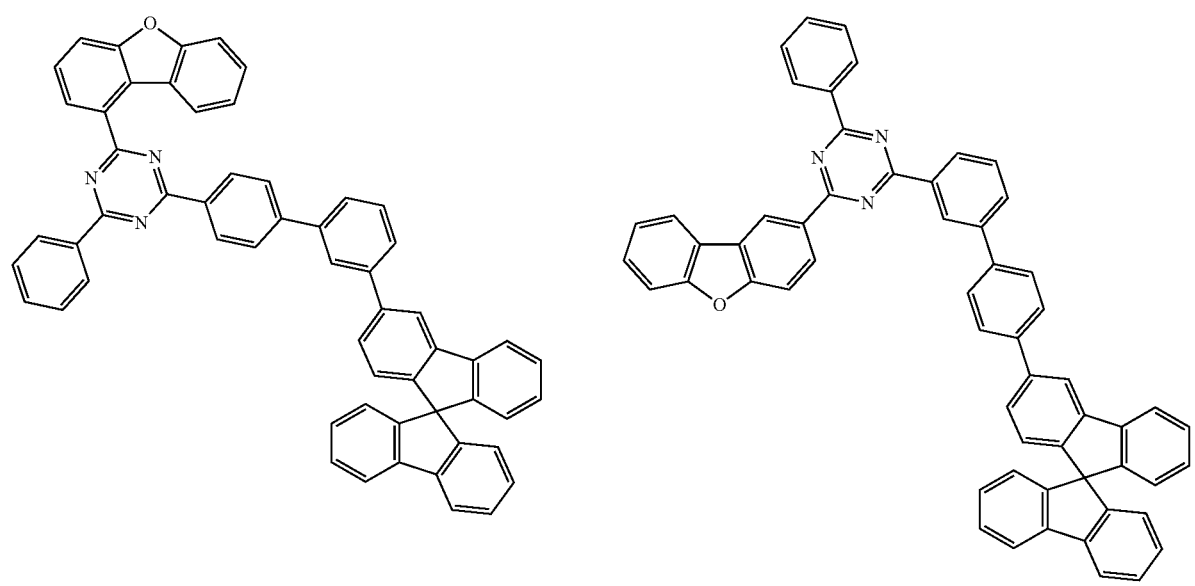
c-189
c-190
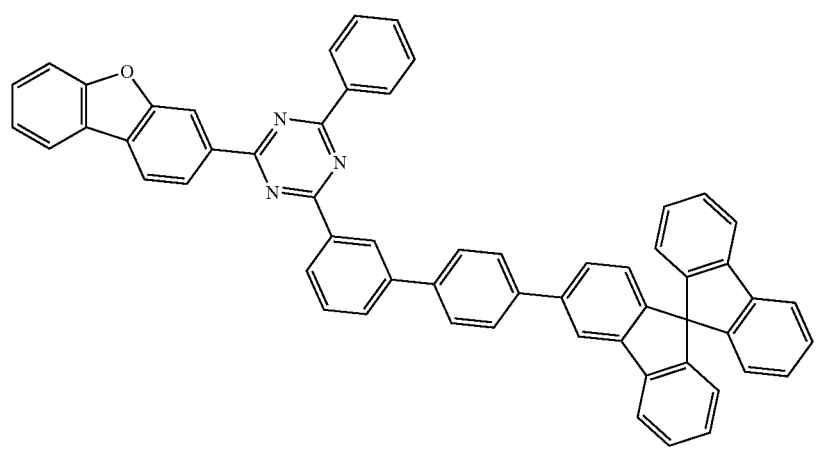
c-191

-continued
c-192
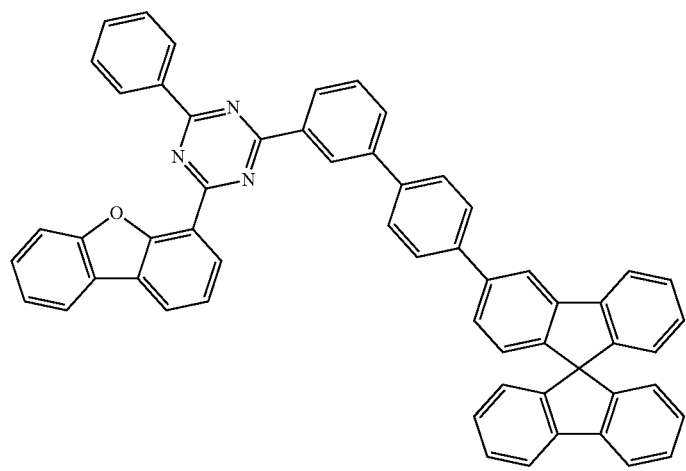
c-193
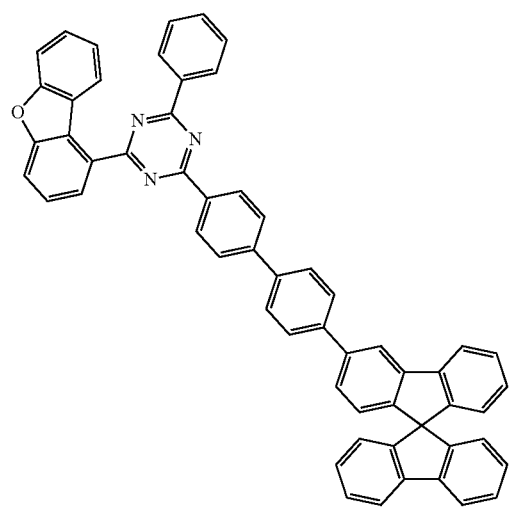
C-194
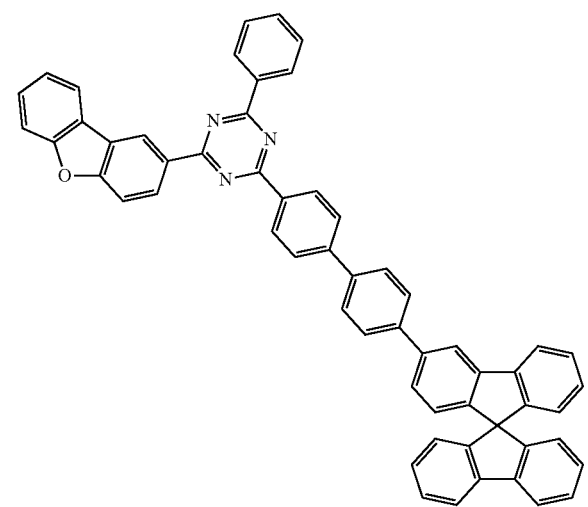
c-195
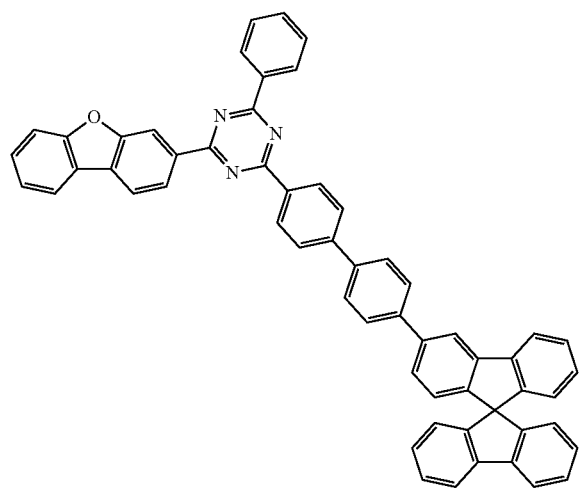
c-196
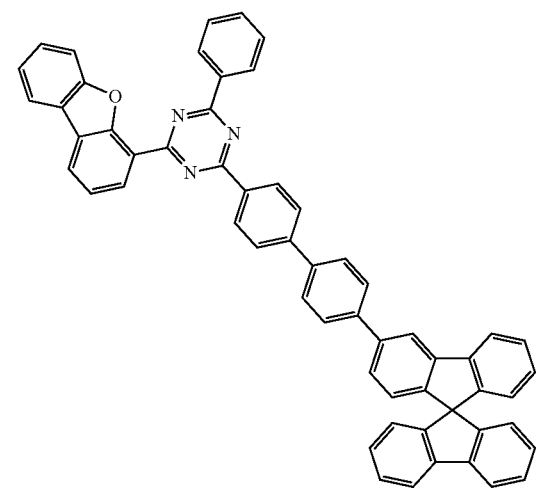

-continued
c-197
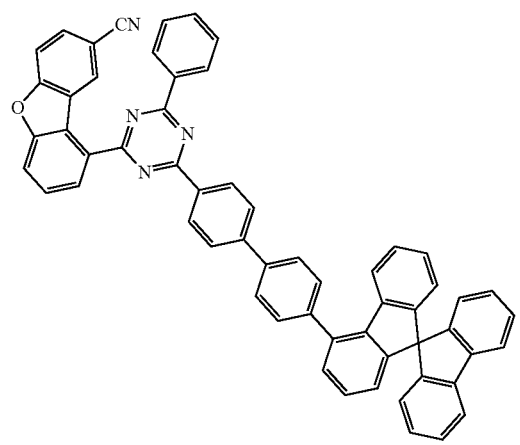
c-198
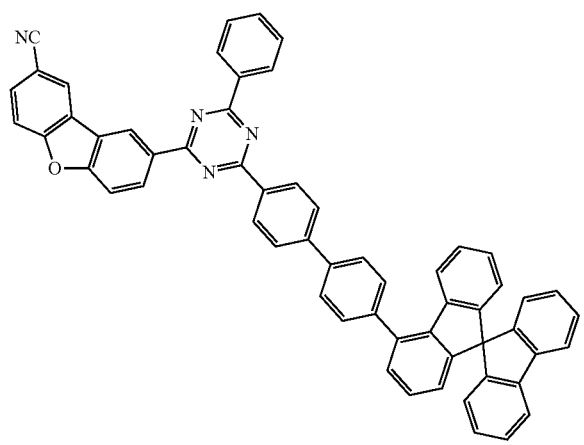
c-199
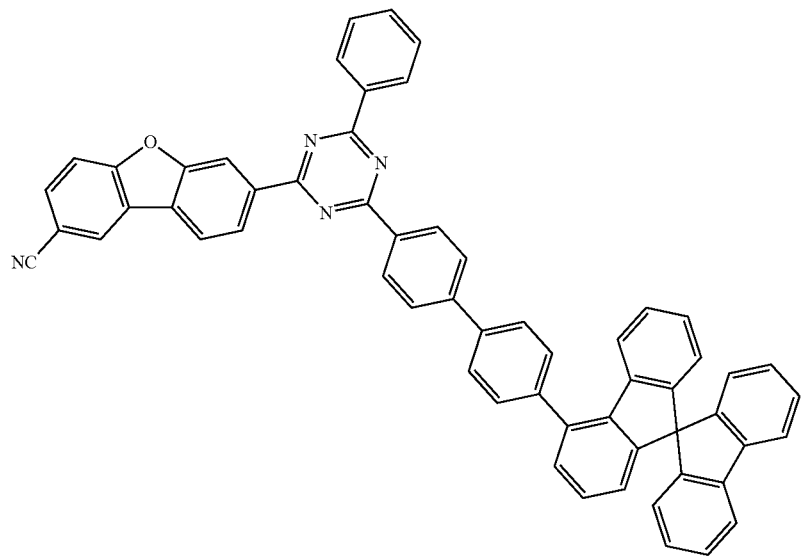
c-200
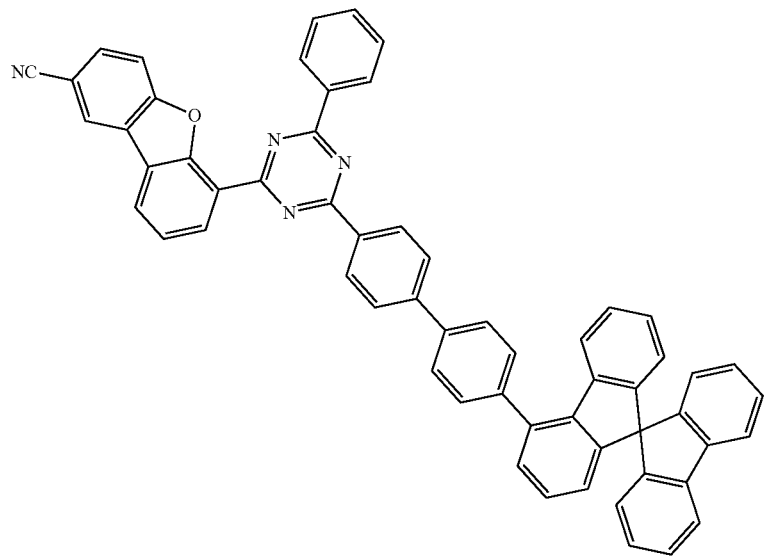

-continued
c-201
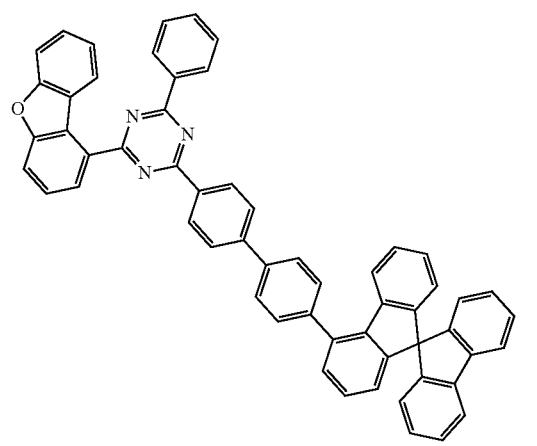
c-202
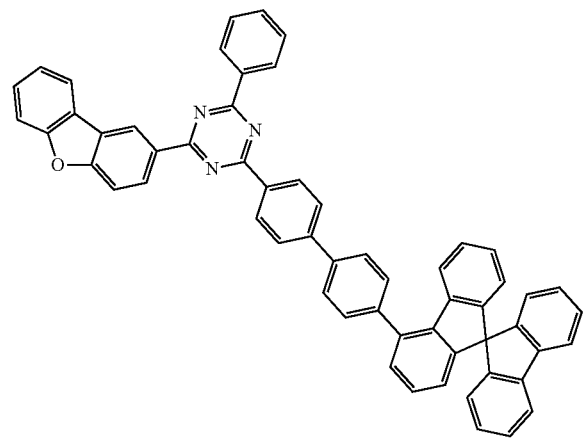
c-203
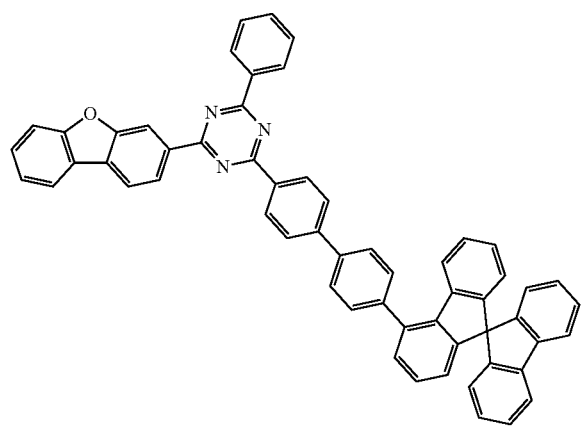
c-204
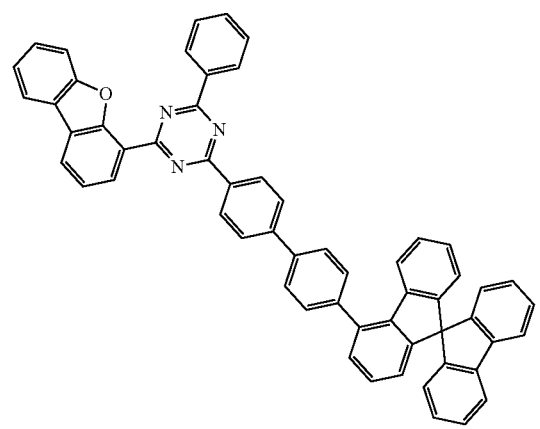
c-205
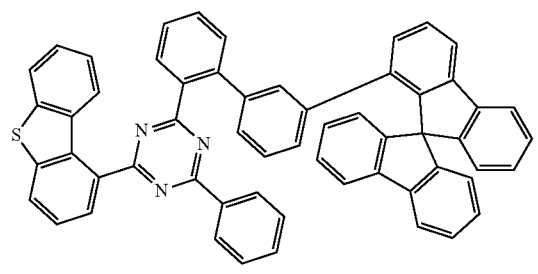
c-206
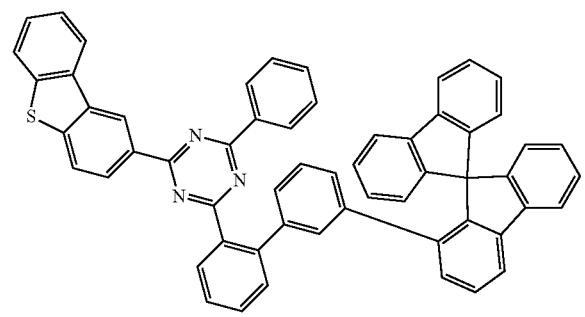

-continued
c-207
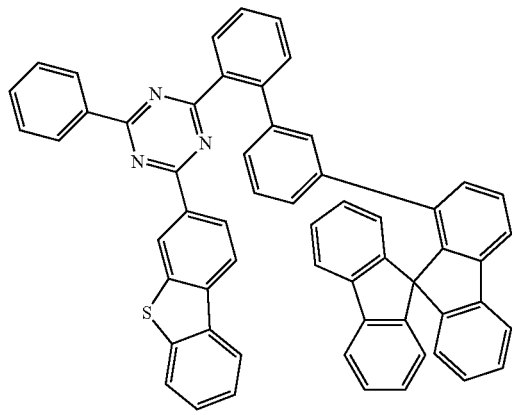
c-208
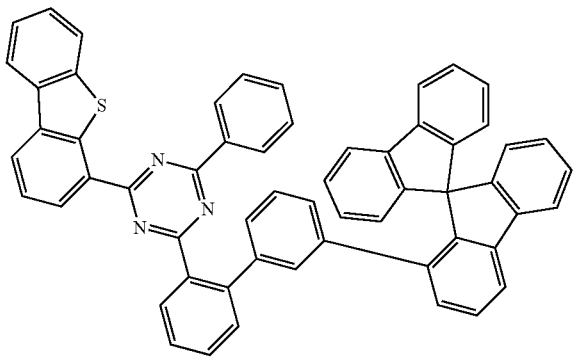
c-209
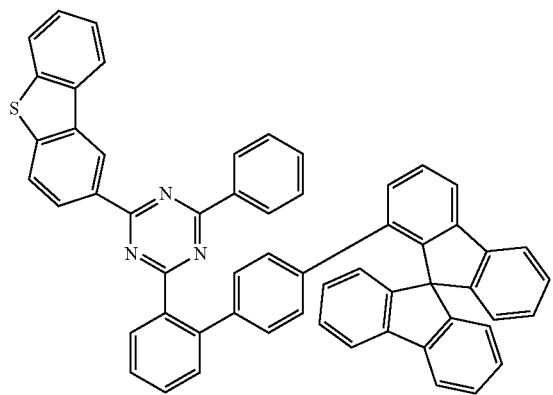
c-210
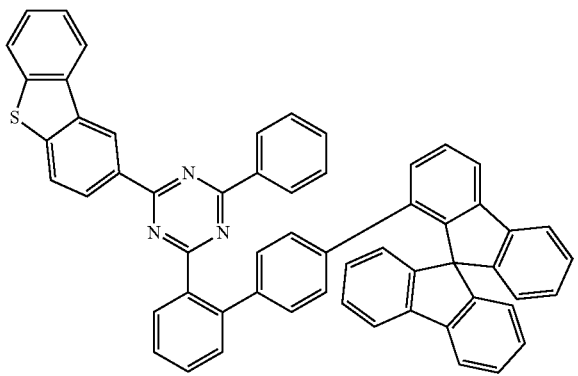
c-211
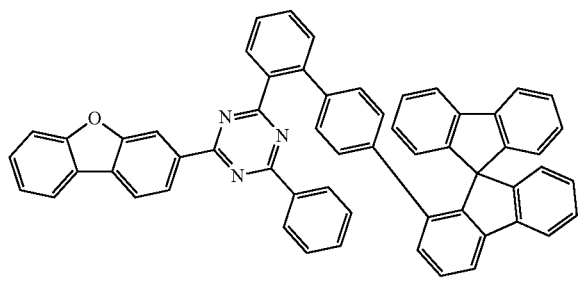
c-212
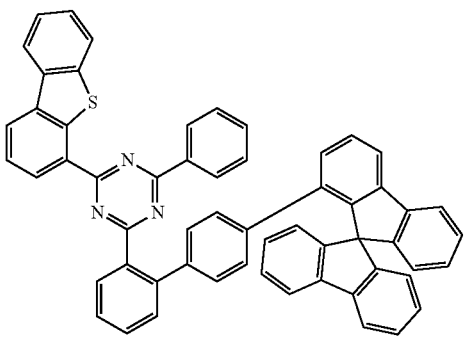
c-213
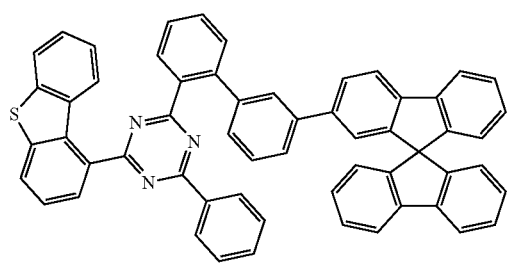
c-214
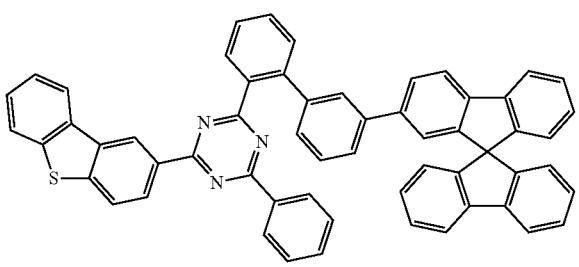

-continued
c-215
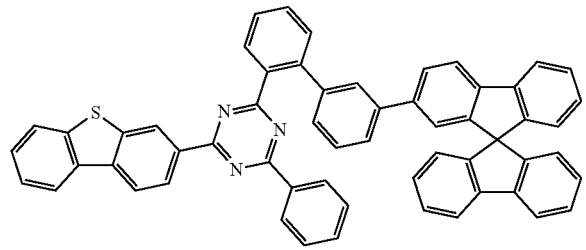
c-216
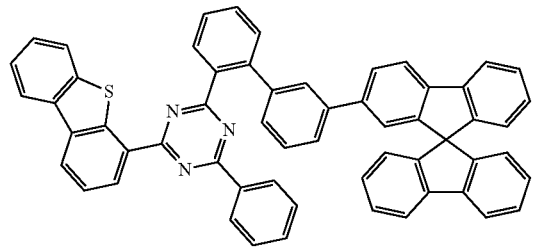
c-217
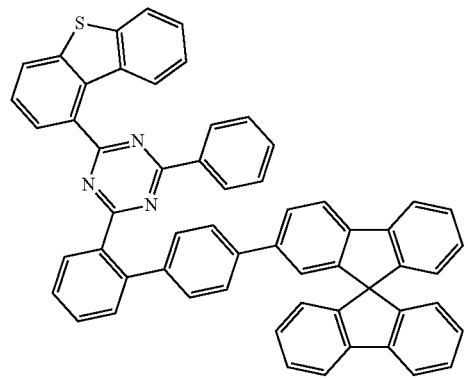
c-218
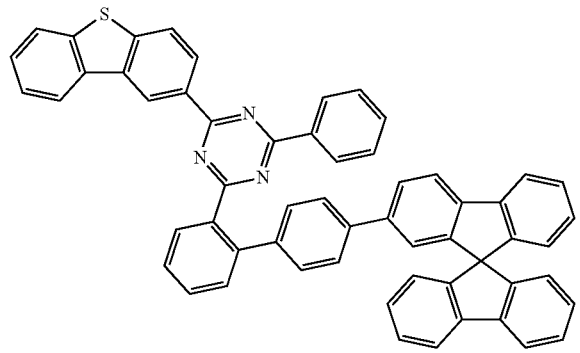
c-219
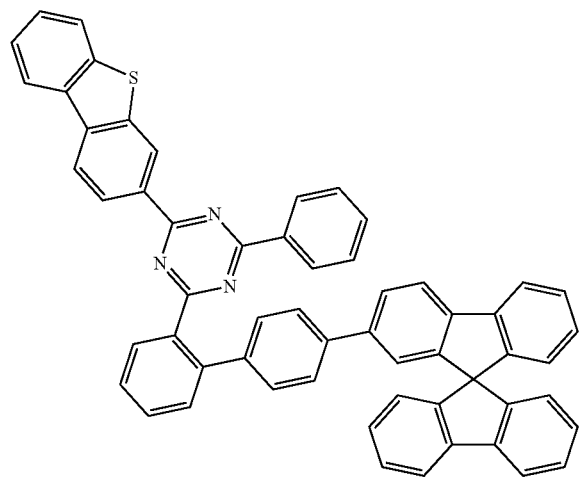
c-220
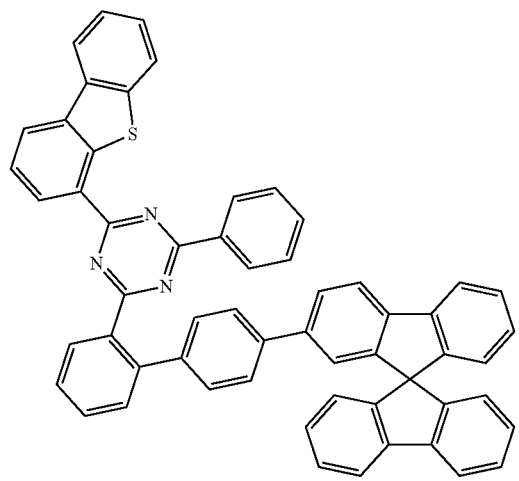

-continued
c-221
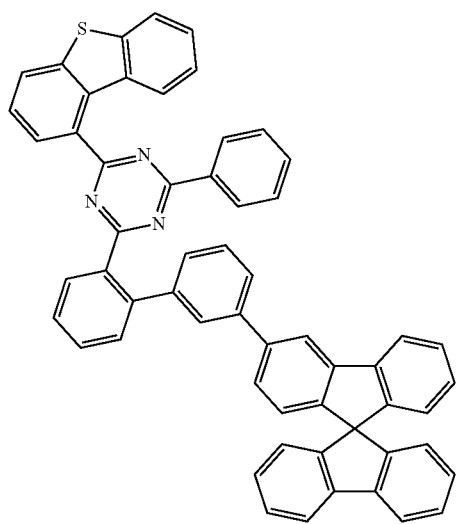
c-222
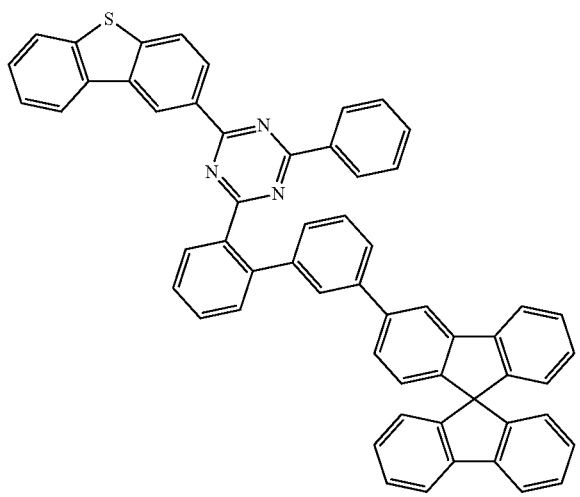
c-223
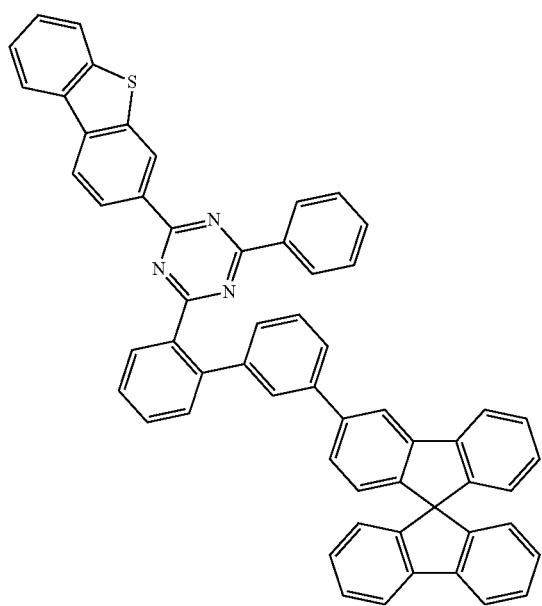
c-224
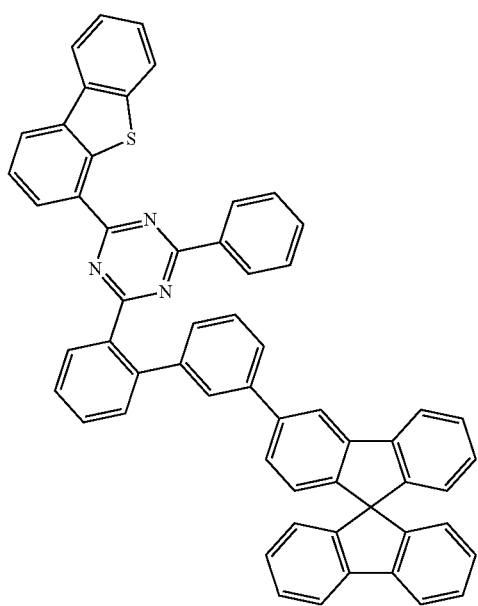

-continued
c-225
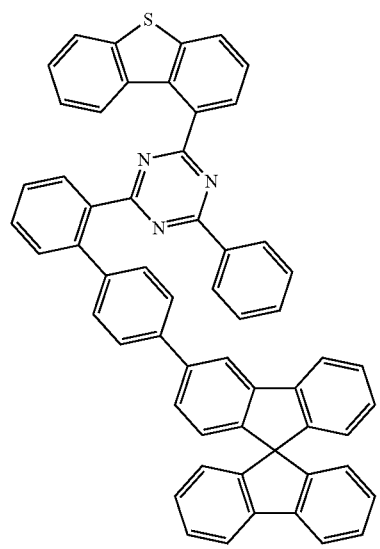
c-226
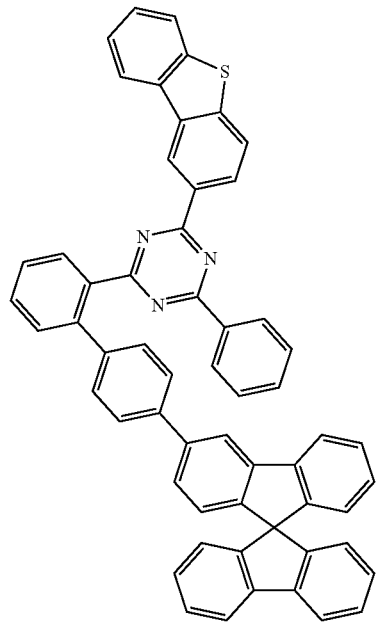
c-227
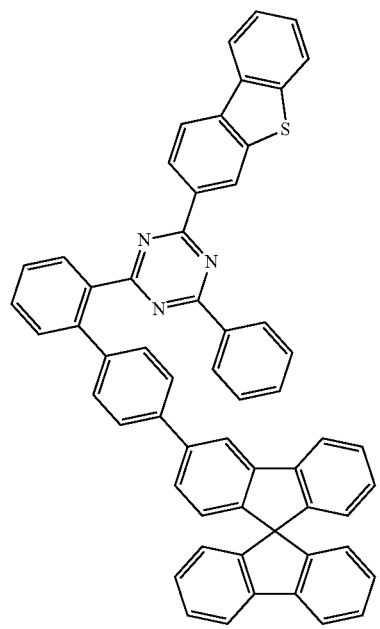
c-228
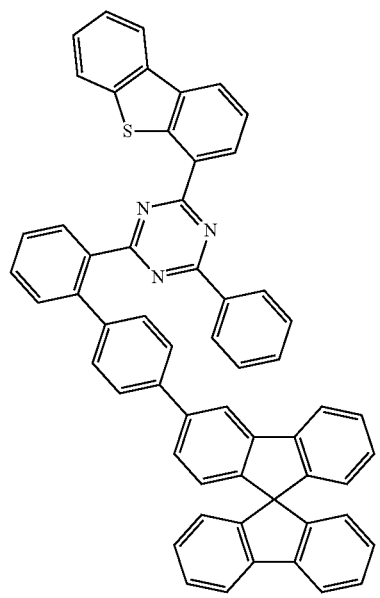
c-229
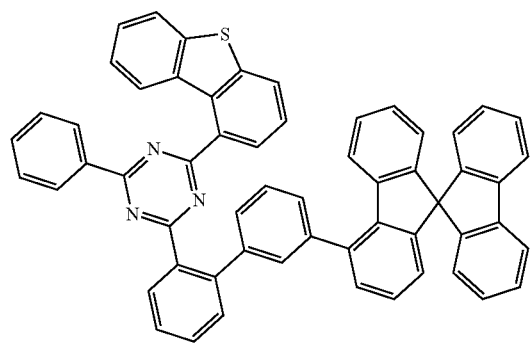
c-230
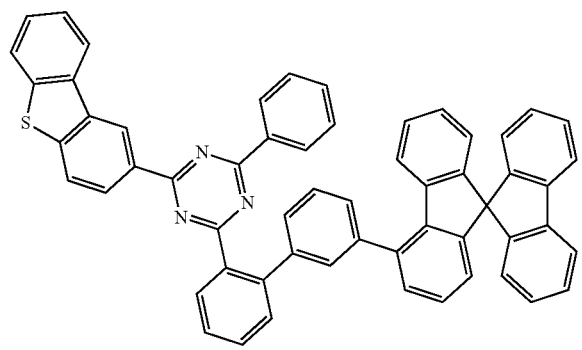

-continued
c-231
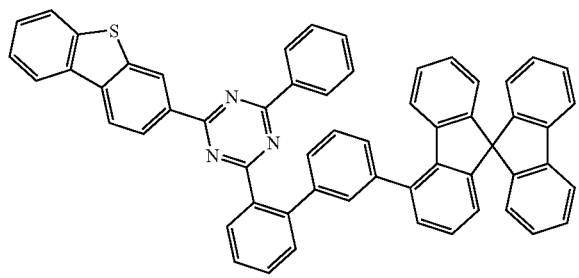
c-232
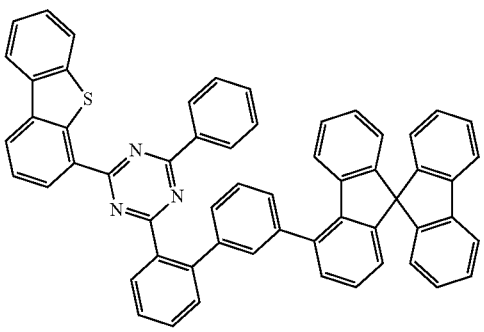
c-233
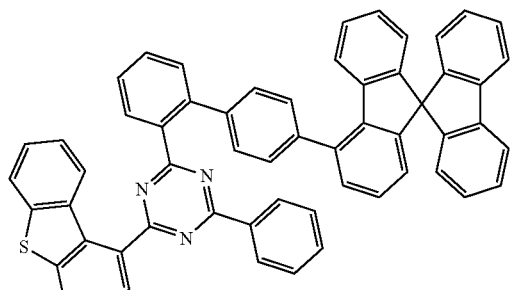
c-234
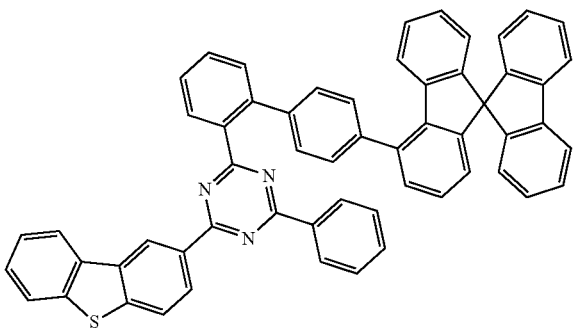
c-235
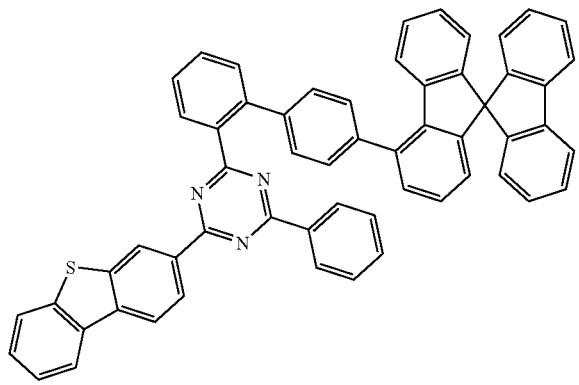
c-236
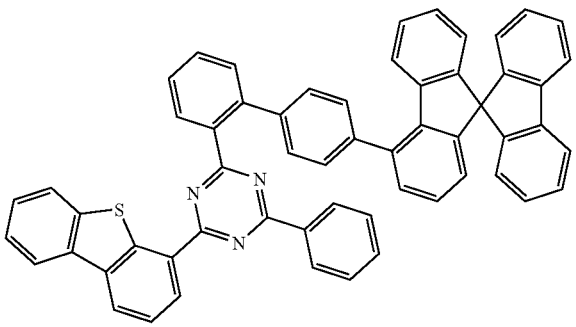
c-237
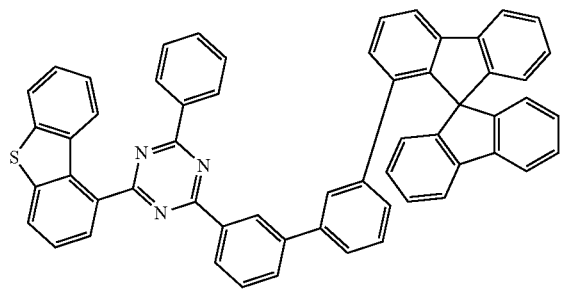
c-238
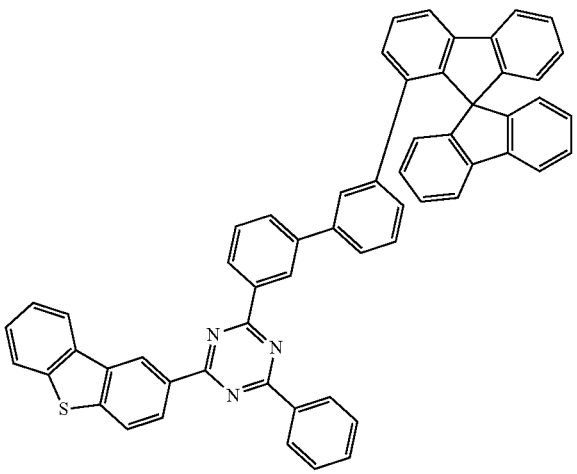

-continued
c-239
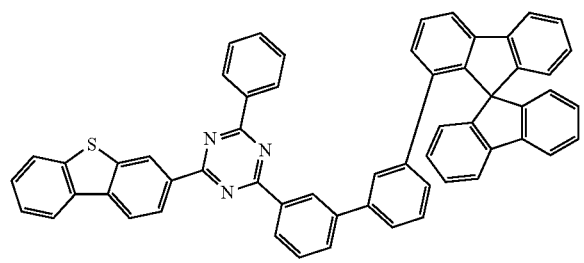
c-240
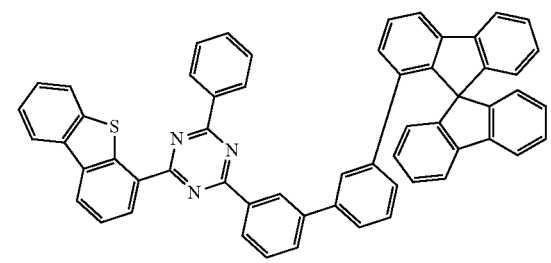
c-241
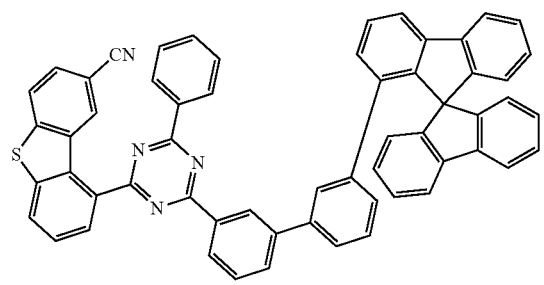
c-242
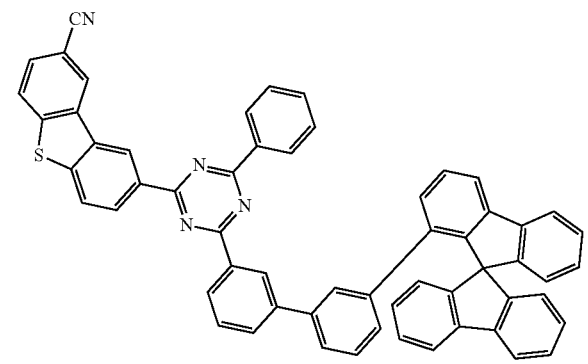
c-243
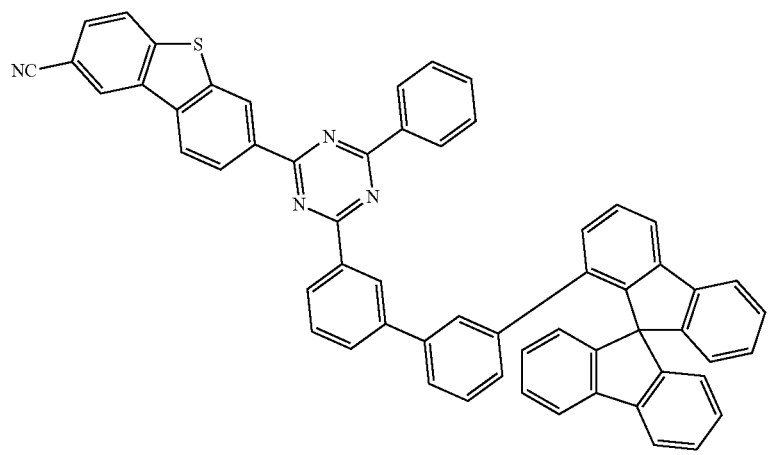
c-244
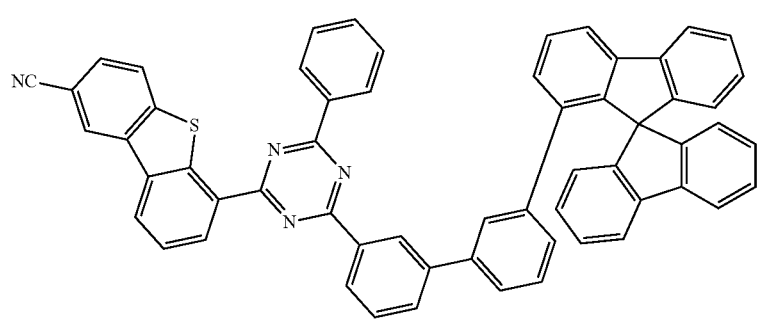

-continued
c-245
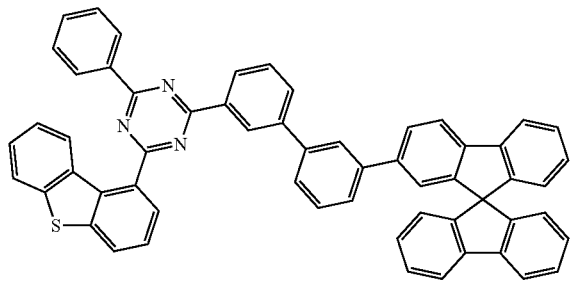
c-246
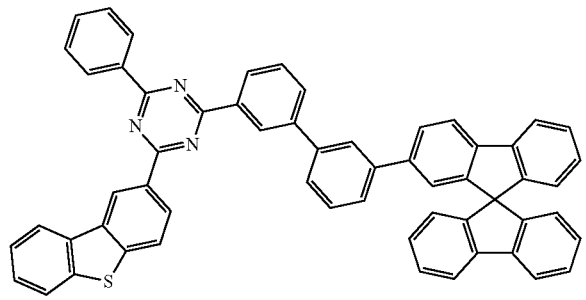
c-247
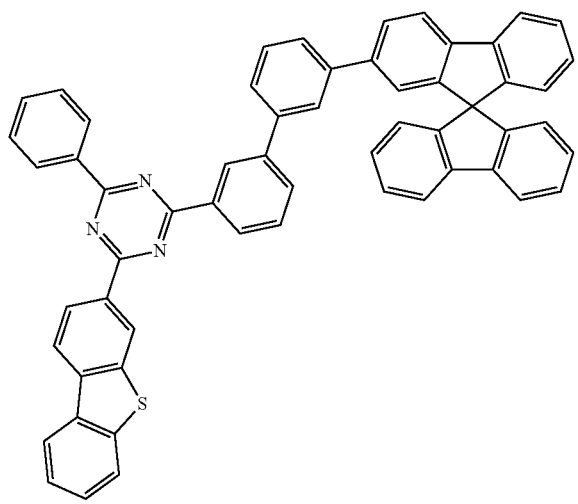
c-248
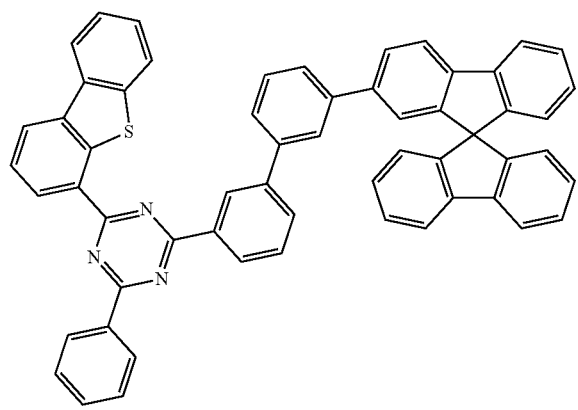
c-249
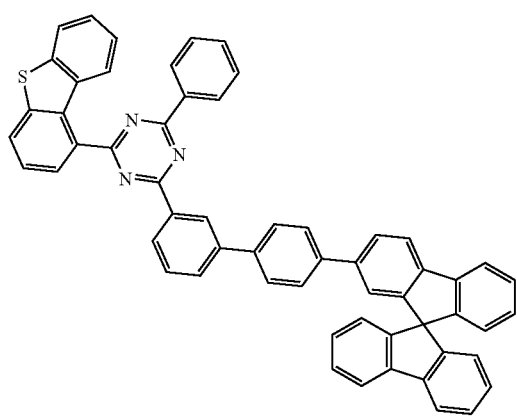
c-250
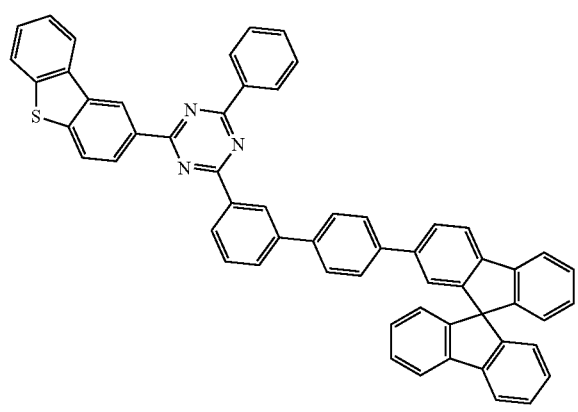

-continued
c-251
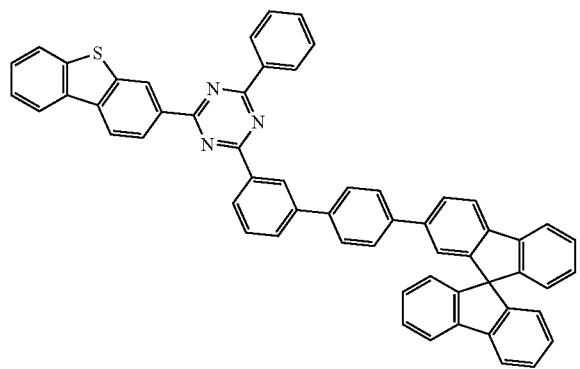
c-252
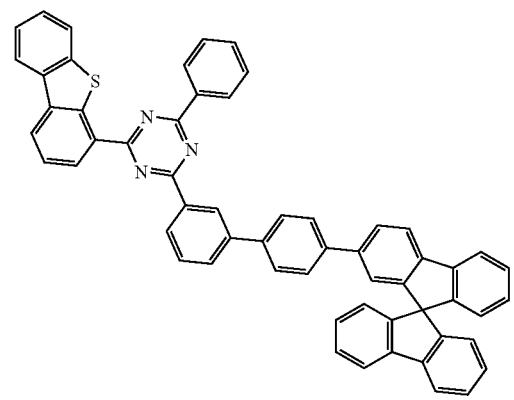
c-253
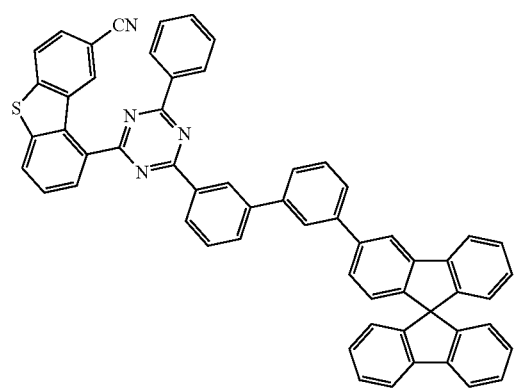
c-254
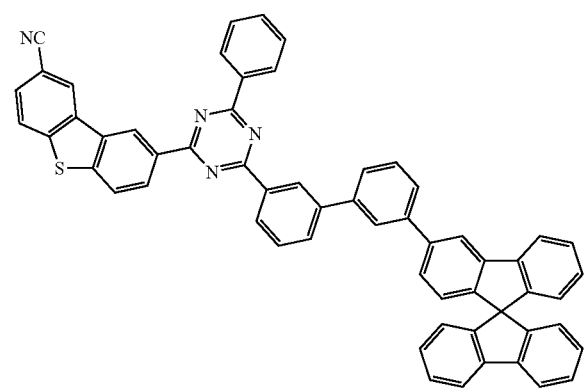
c-255
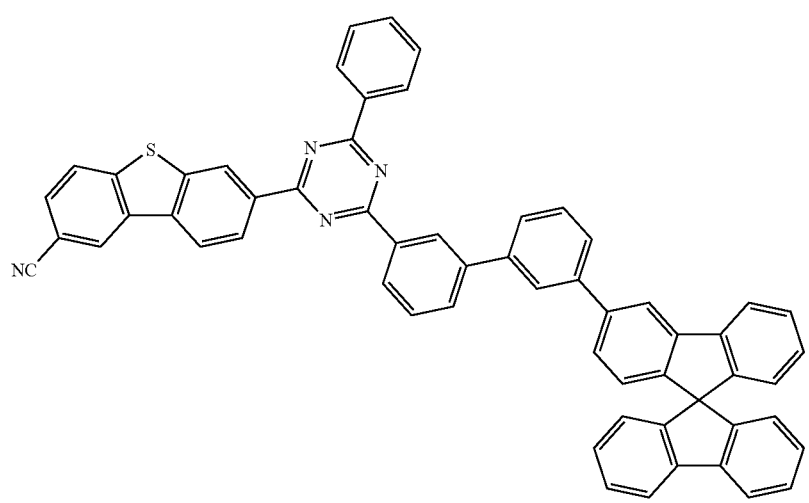

-continued
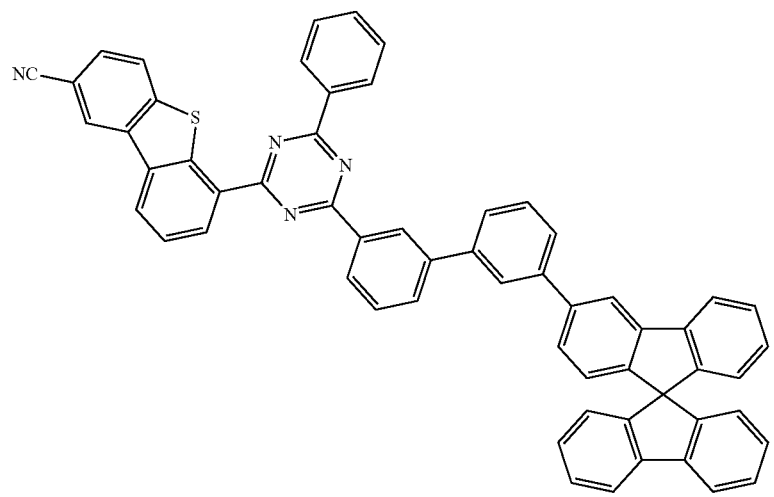
c-256
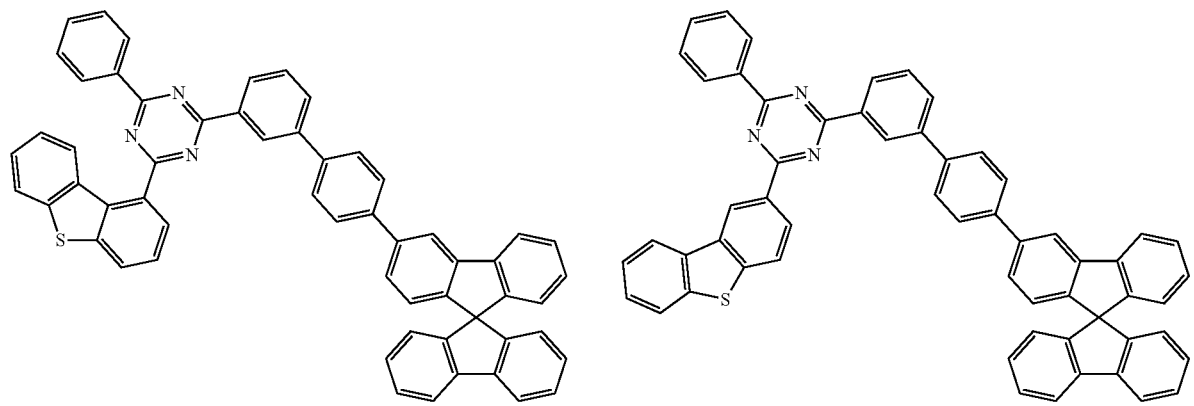
c-257    c-258
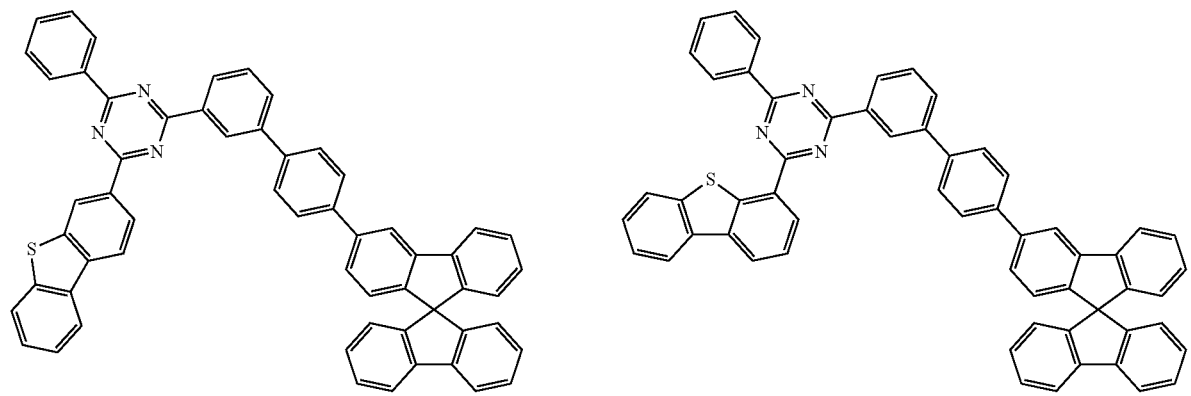
c-259    c-260

-continued
c-261
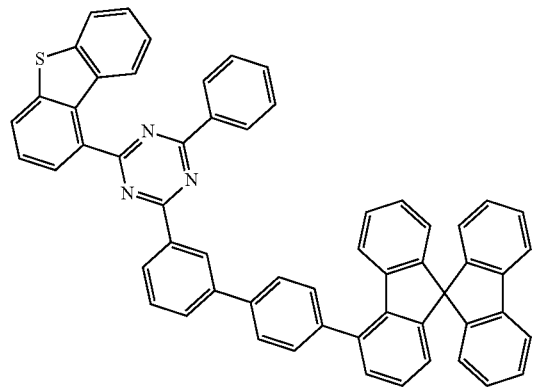
c-262
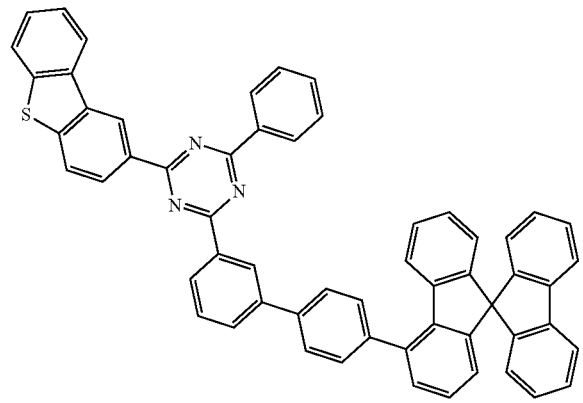
c-263
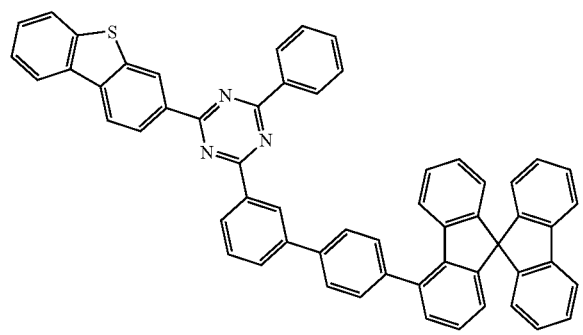
c-264
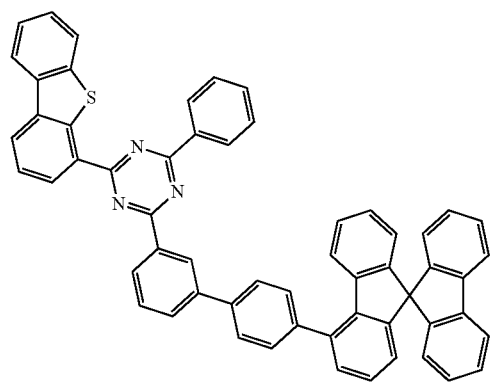
c-265
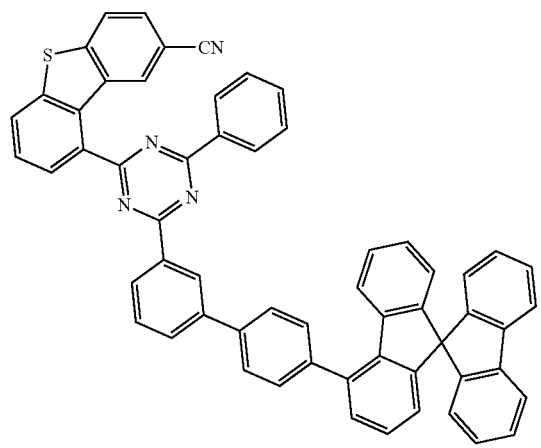
c-266
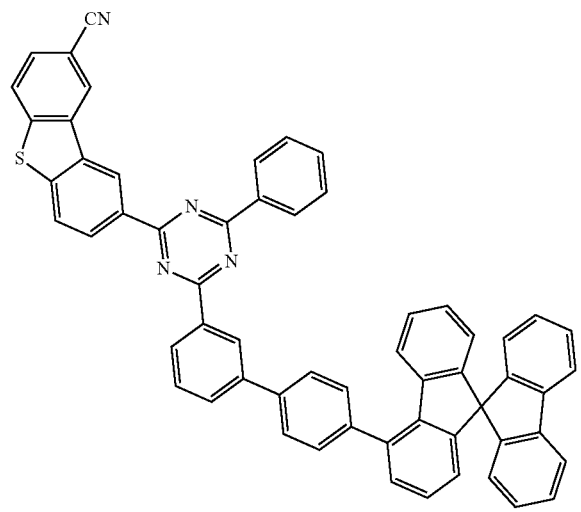

-continued
c-267
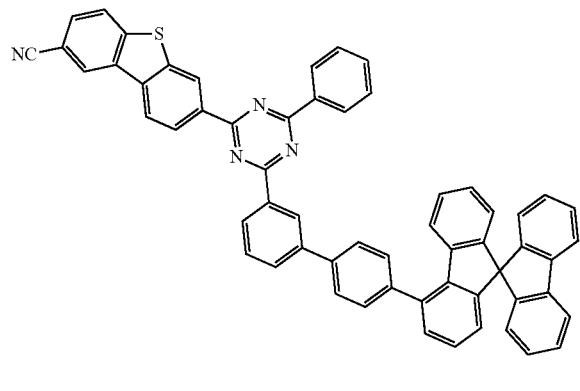
c-268
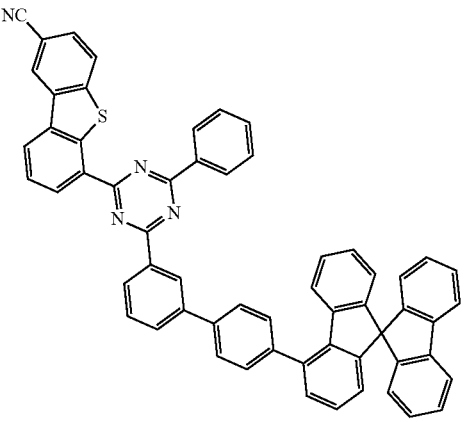
c-269
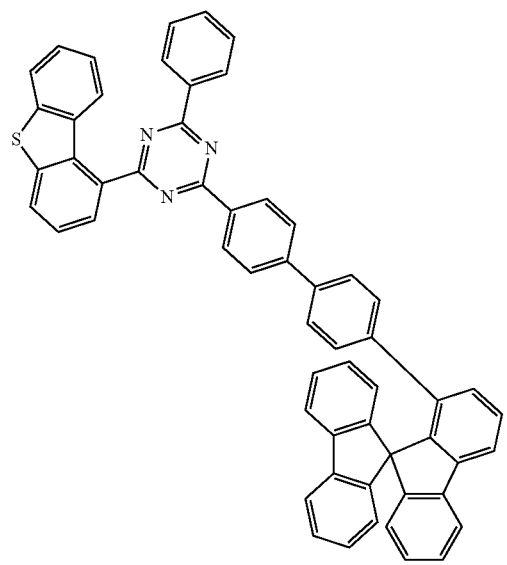
c-270
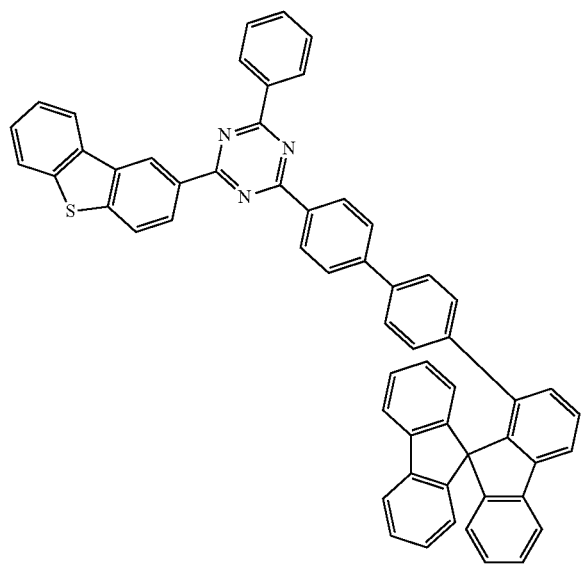
c-271
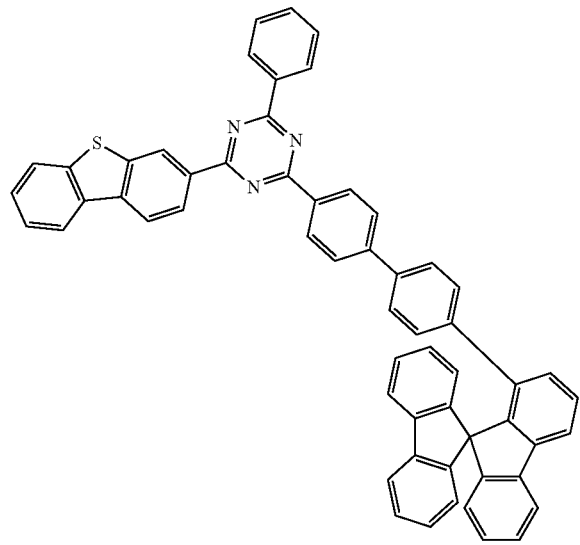
c-272
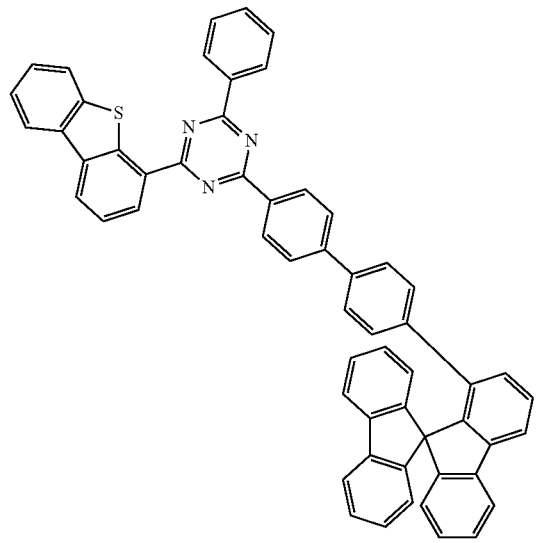

-continued
c-273
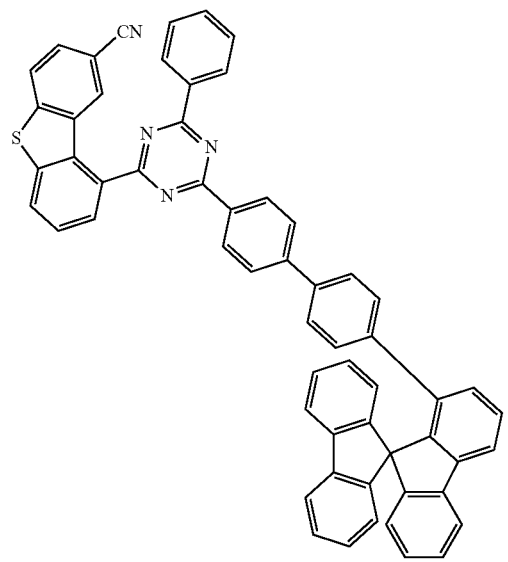
c-274
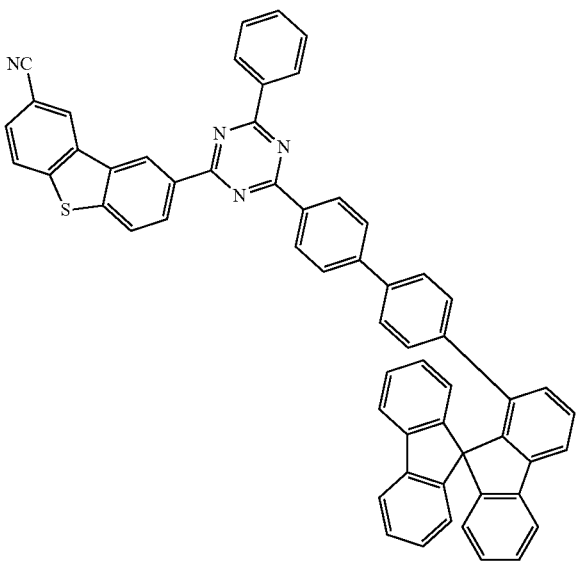
c-275
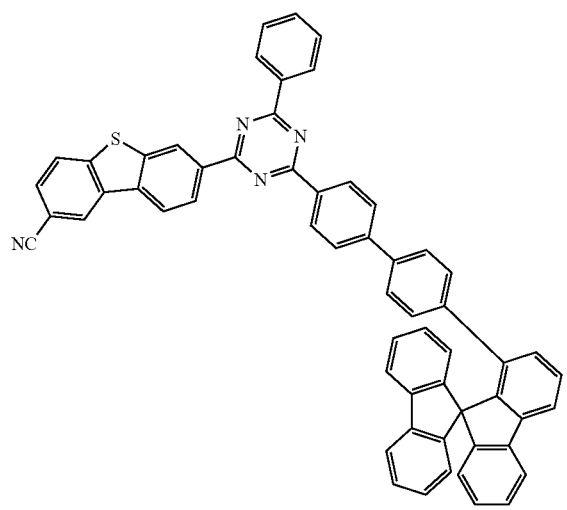
c-276
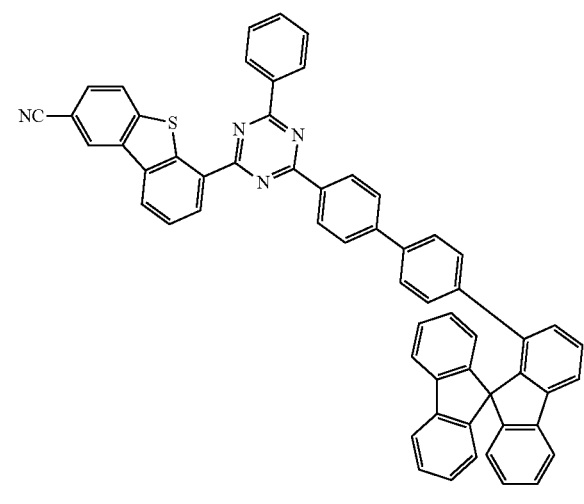
c-277
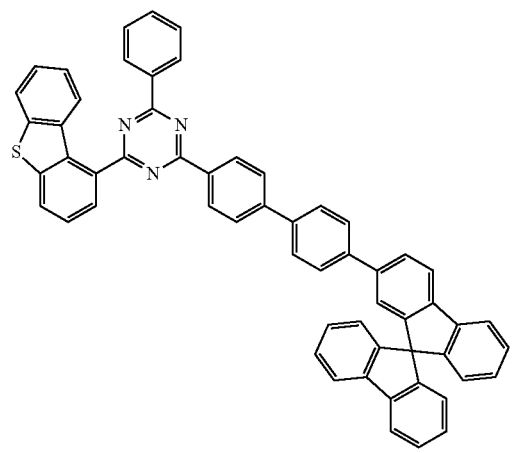
c-278
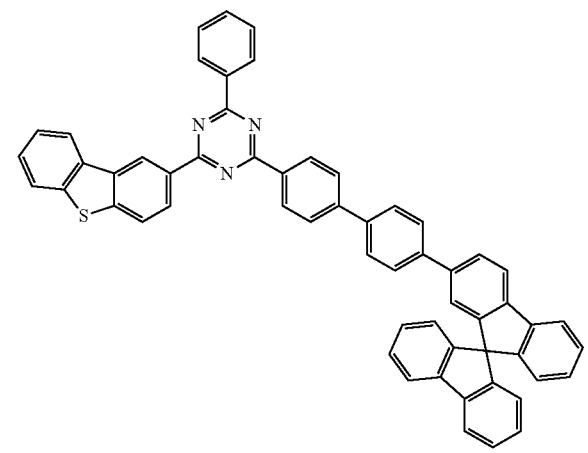

-continued
c-279
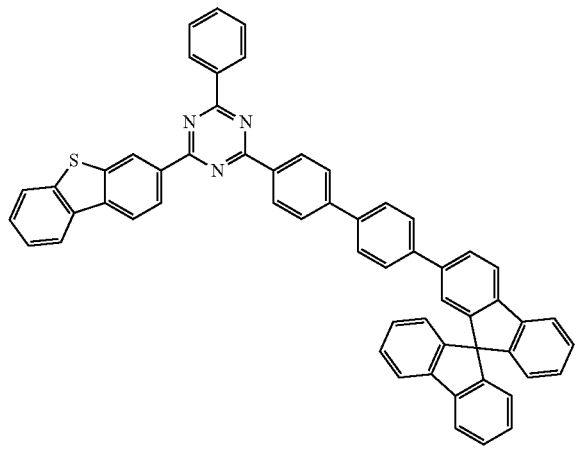
c-280
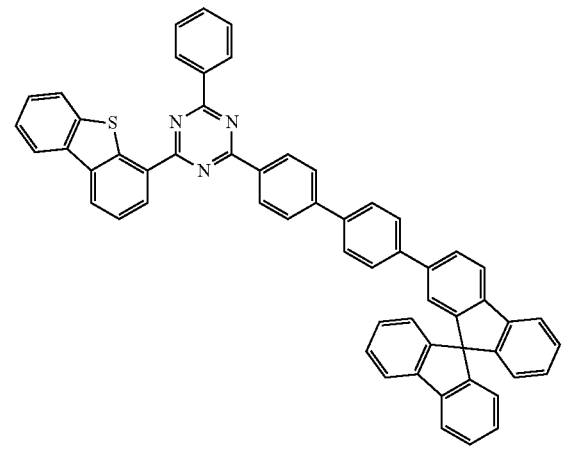
c-281
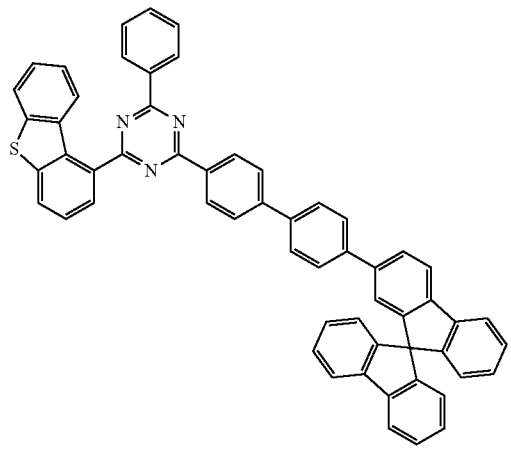
c-282
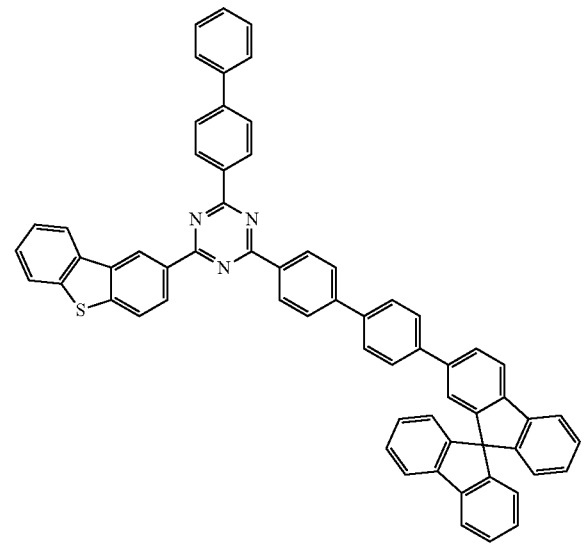
c-283
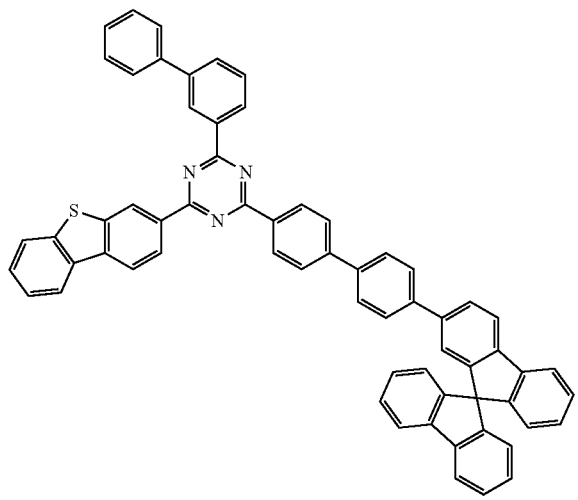
c-284
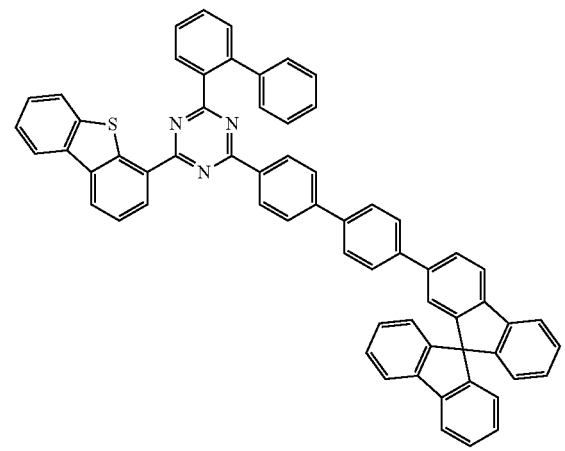

-continued
c-285
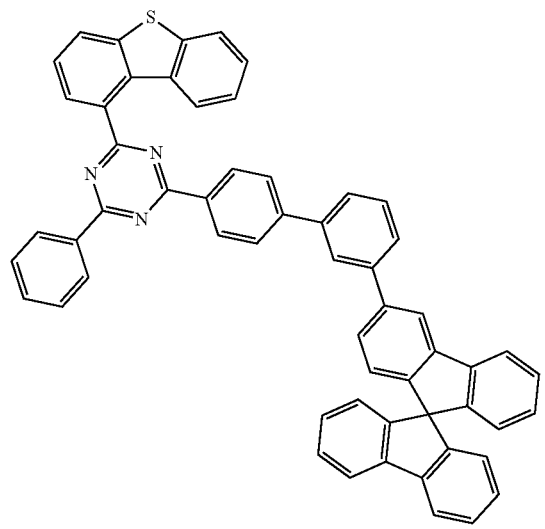
c-286
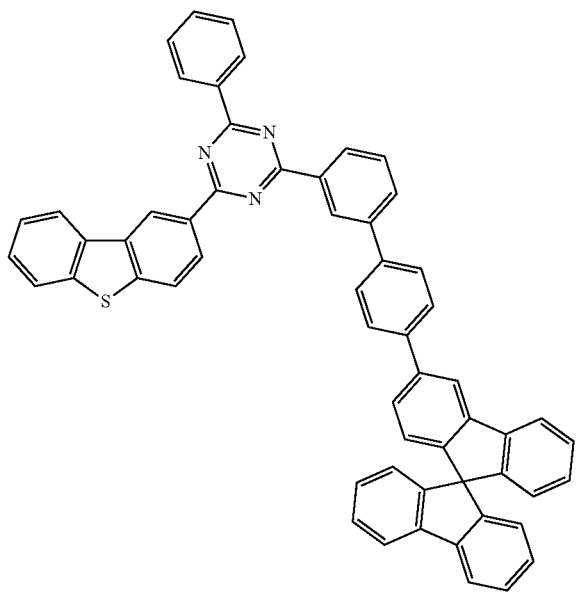
c-287
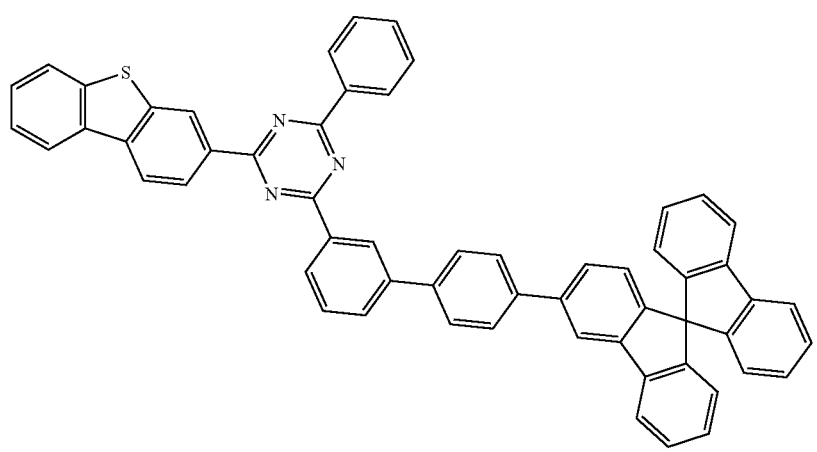
c-288
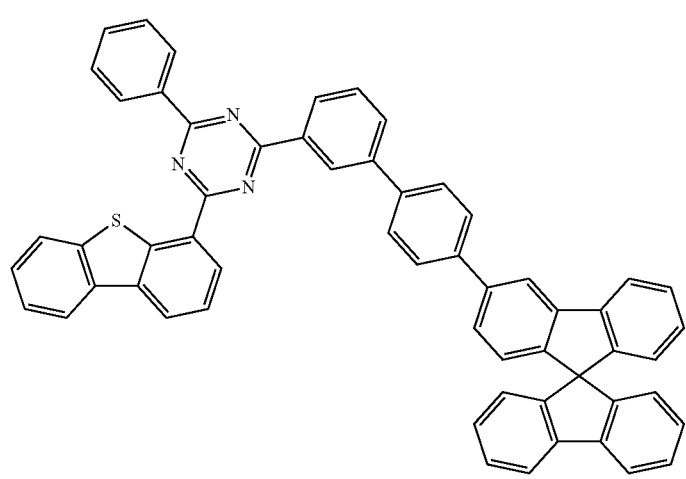

-continued
c-289
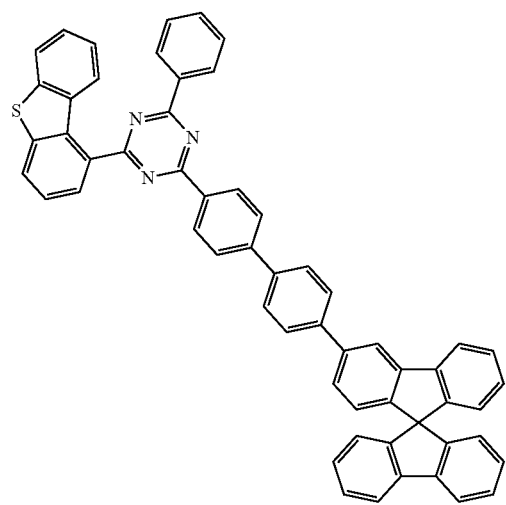
c-290
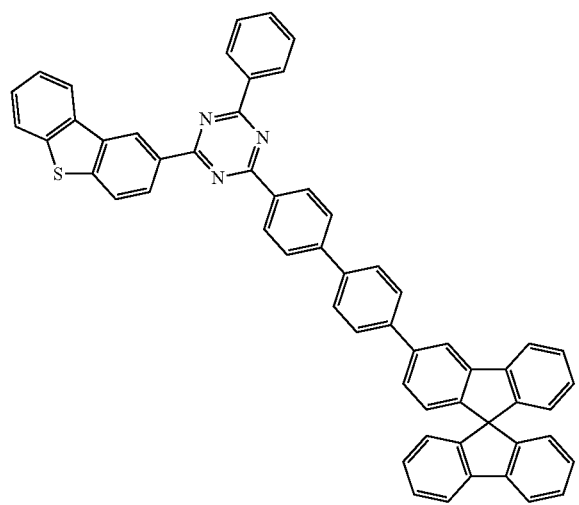
c-291
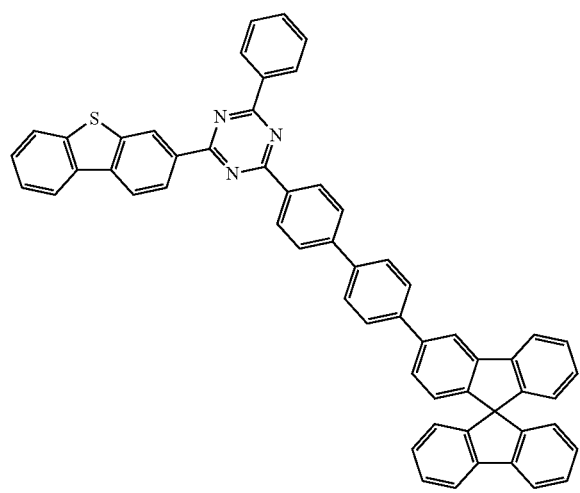
c-292
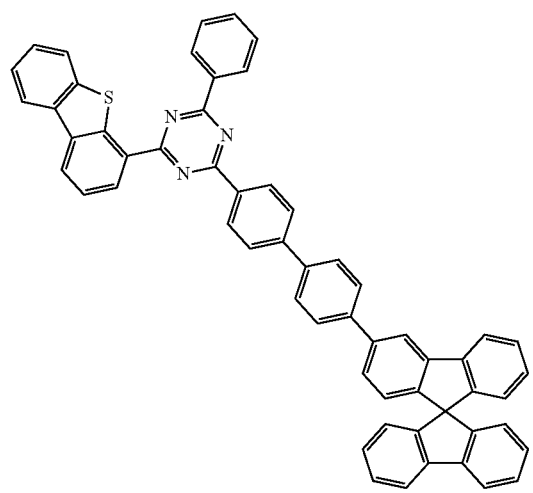
c-293
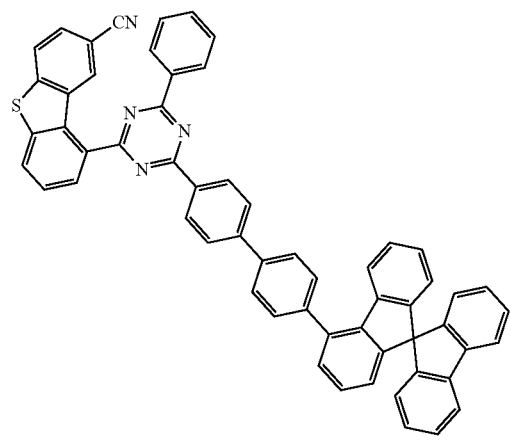
c-294
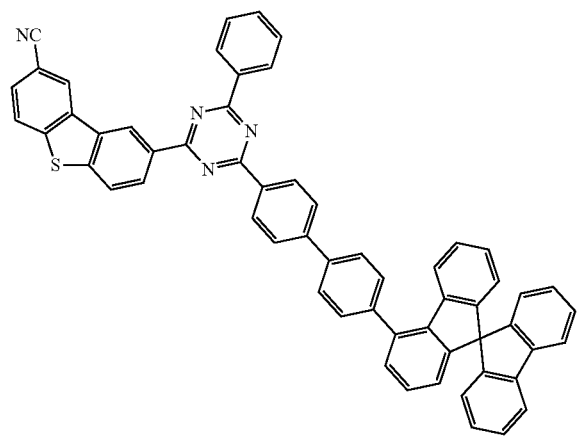

-continued
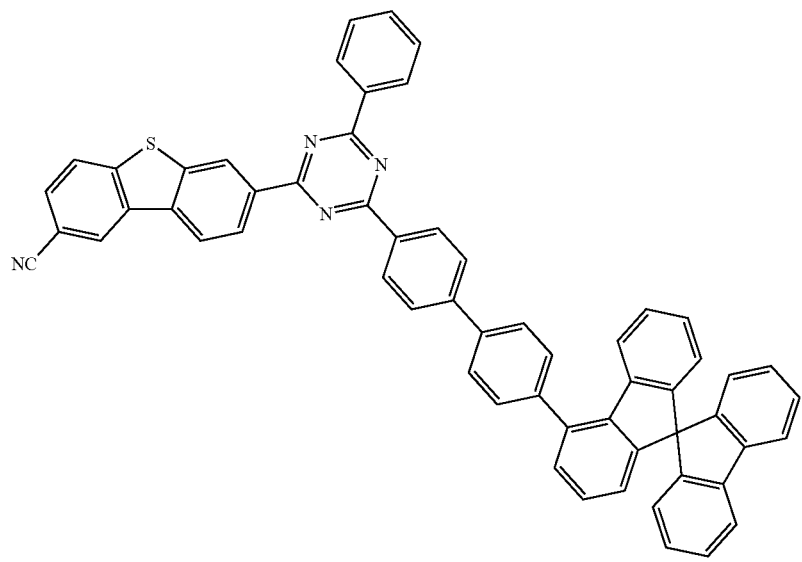
c-295
c-296
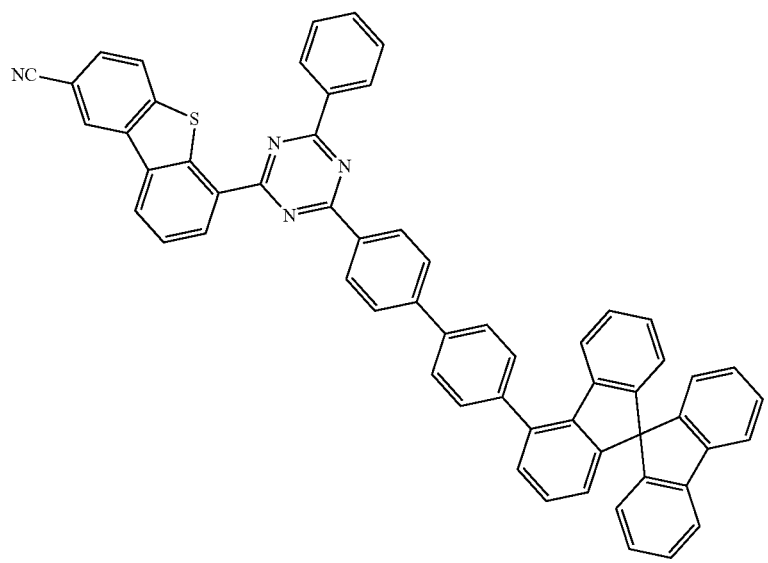
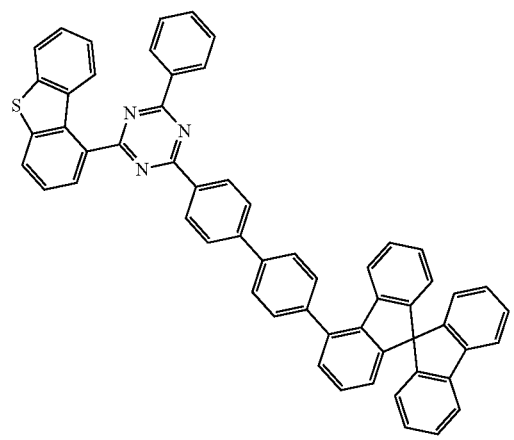
c-297
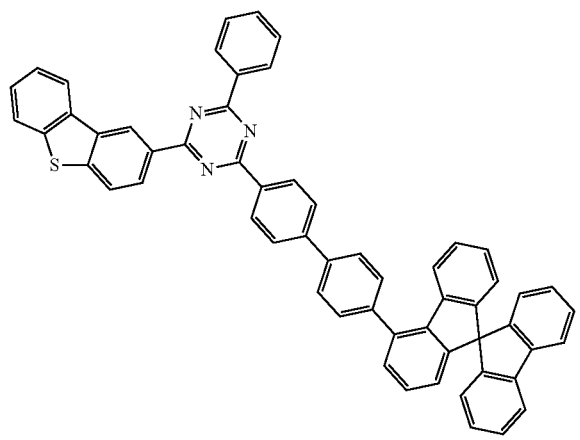
c-298

-continued
c-299
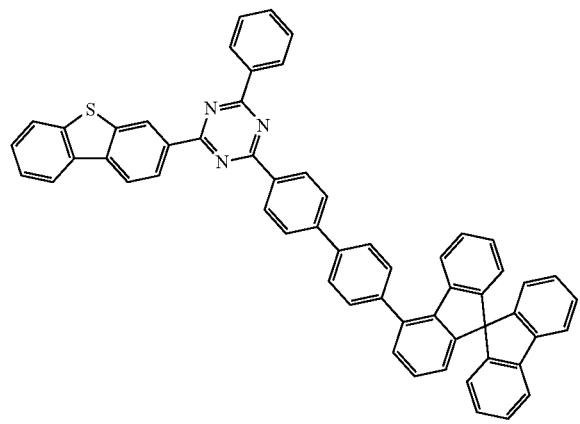
c-300
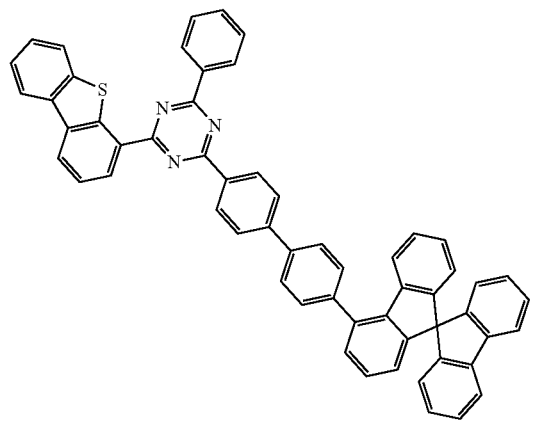
c-301
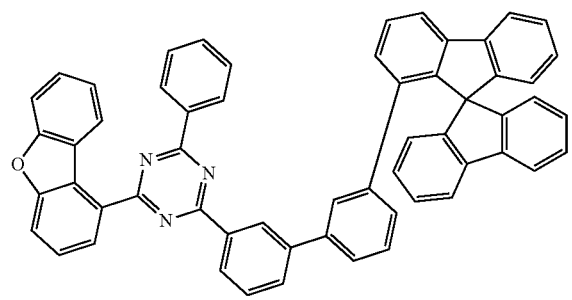
c-302
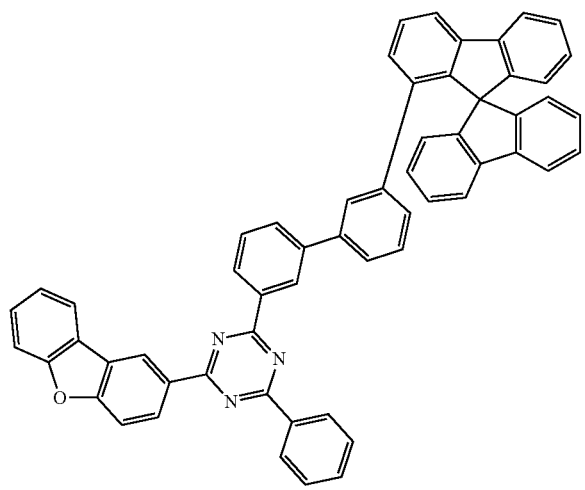
c-303
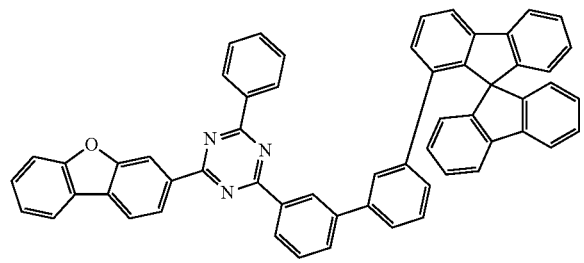
c-304
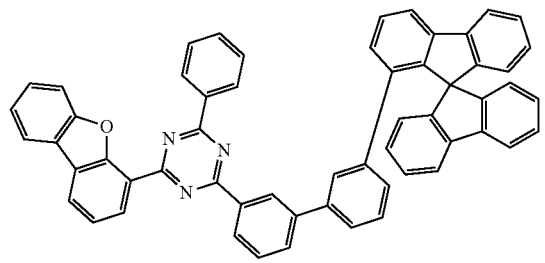
c-305
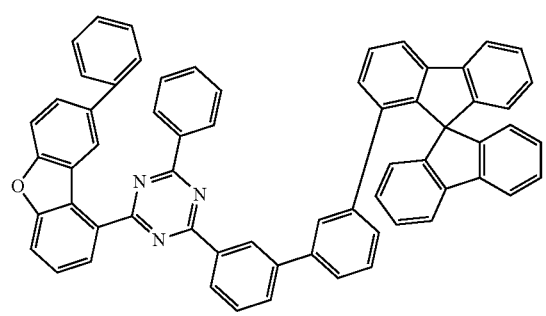
c-306
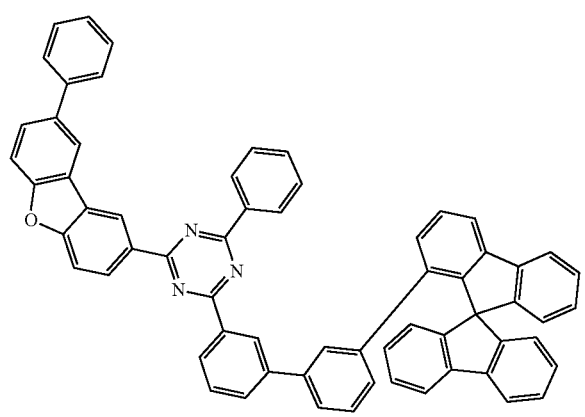

-continued
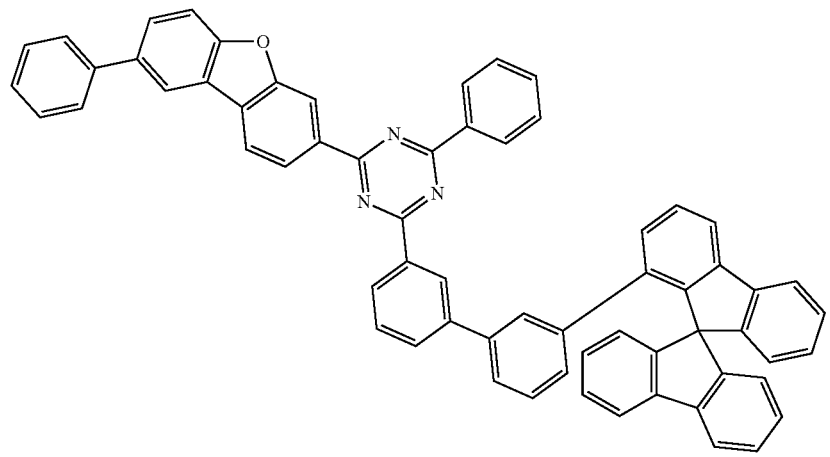
c-307
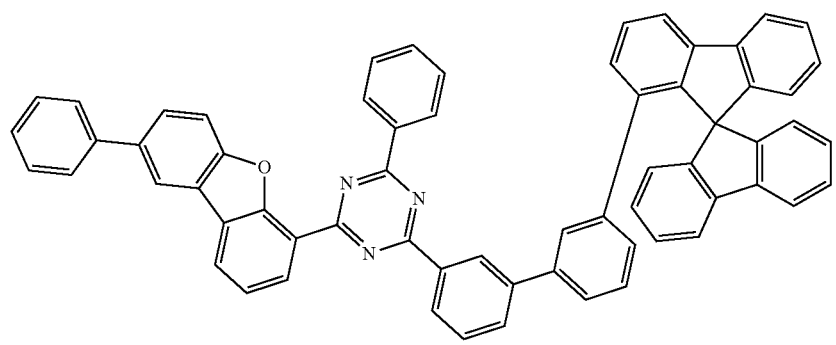
c-308
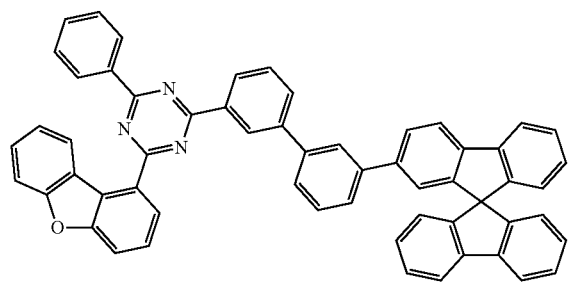
c-309
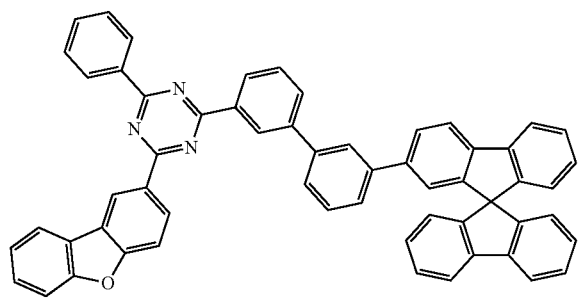
c-310
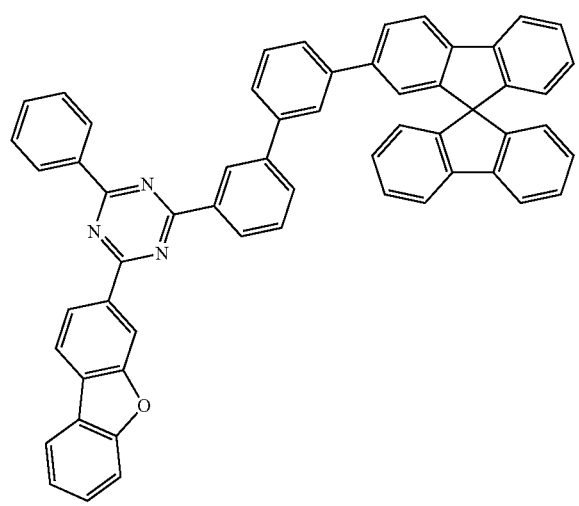
c-311
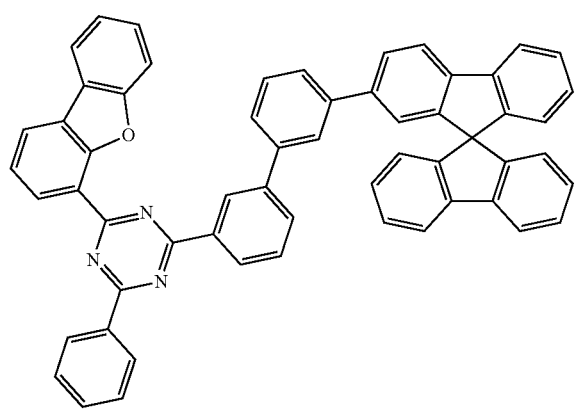
c-312

-continued
c-313
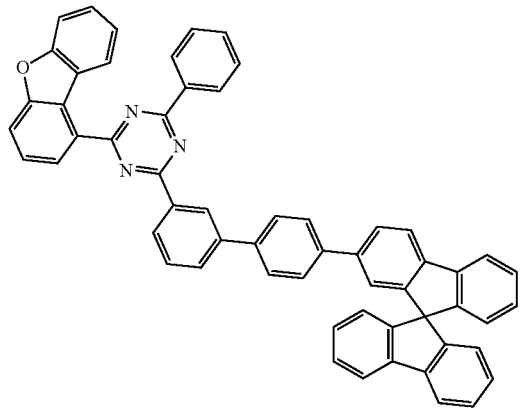
c-314
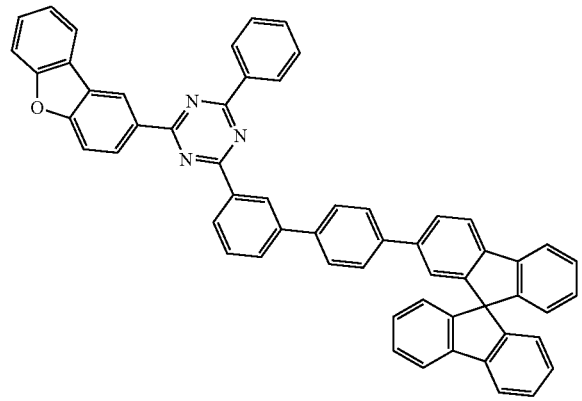
c-315
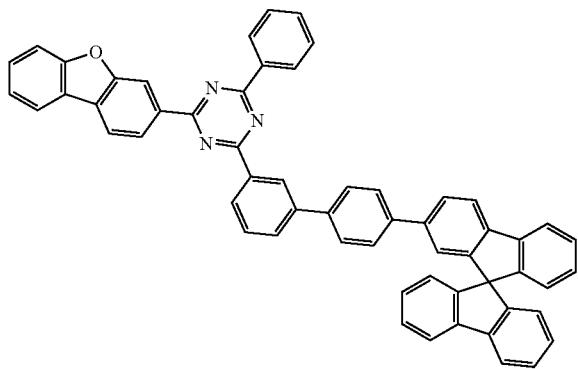
c-316
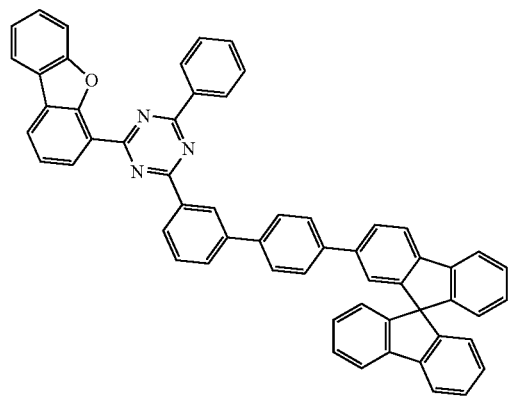
c-317
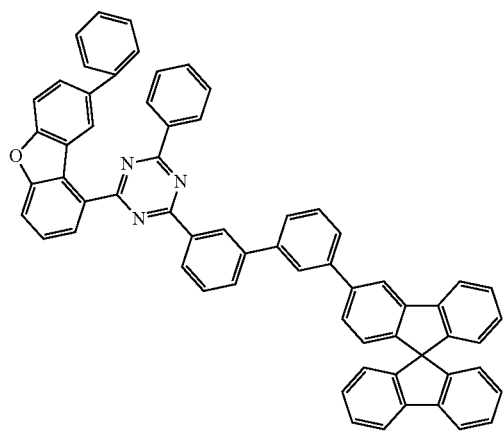
c-318
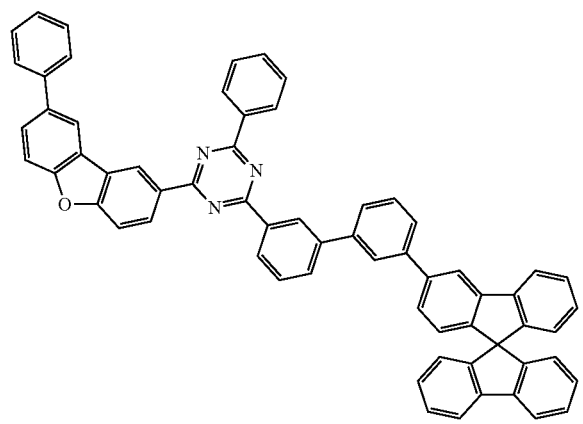

-continued
c-319
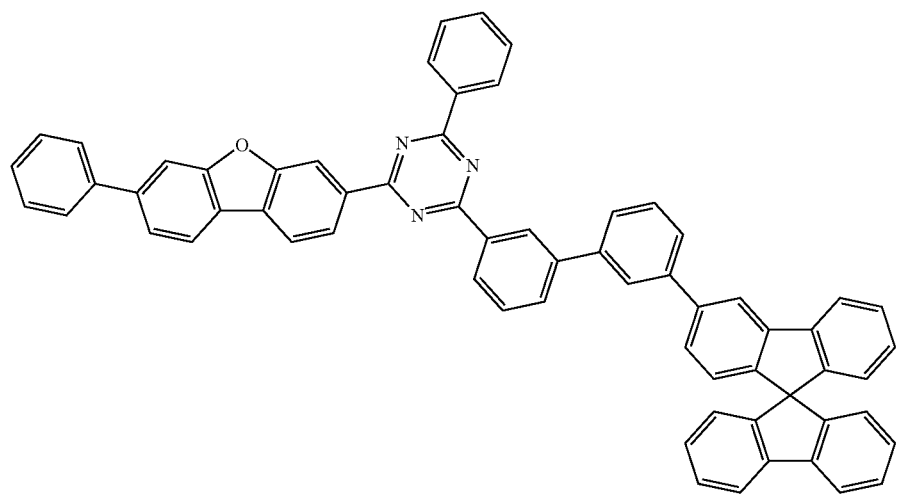
c-320
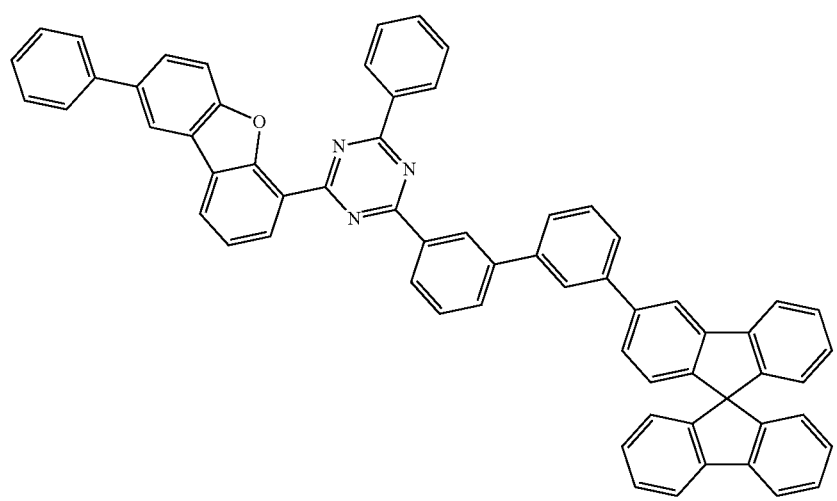
c-321 c-322
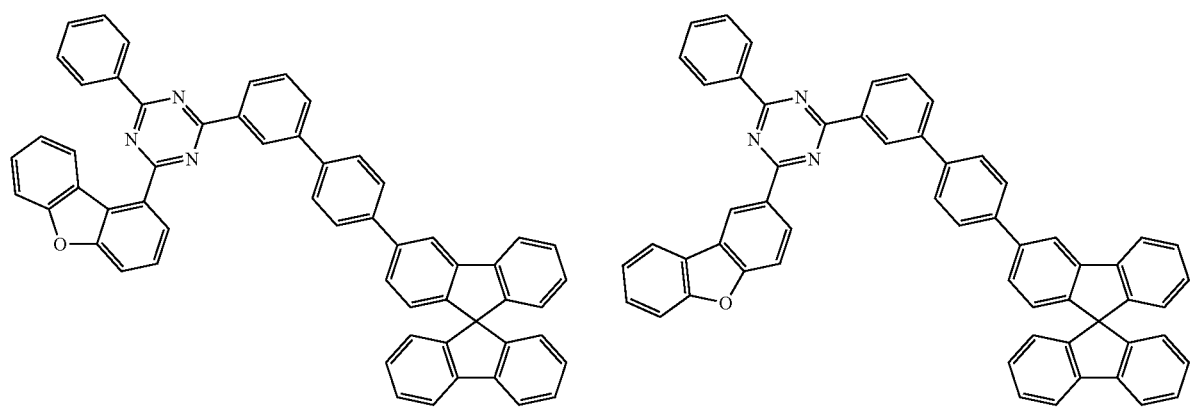

-continued
c-323
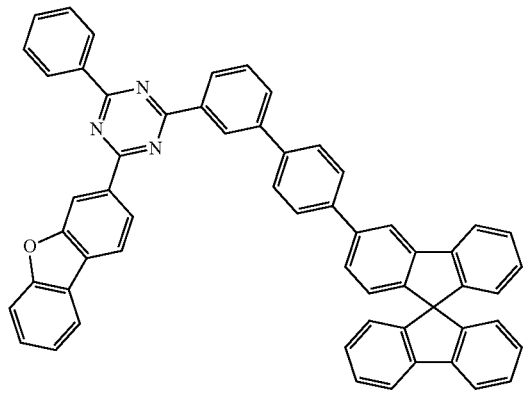
c-324
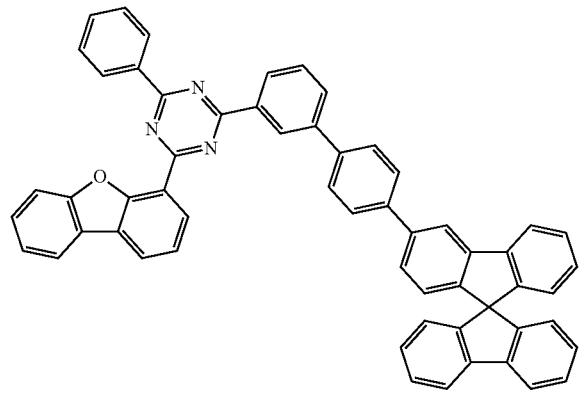
c-325
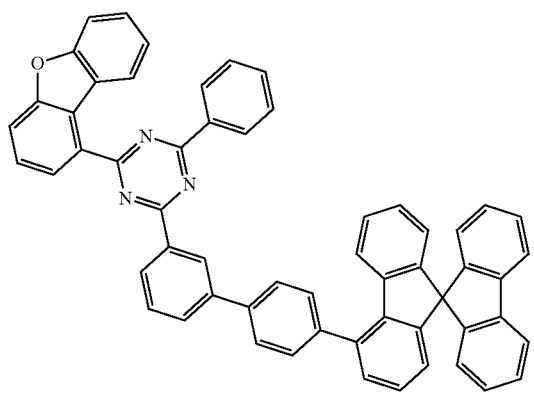
c-326
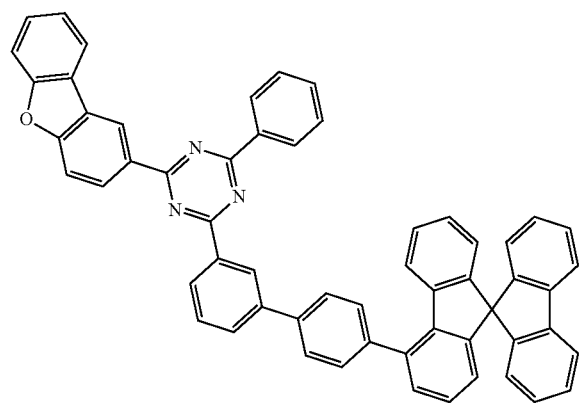
c-327
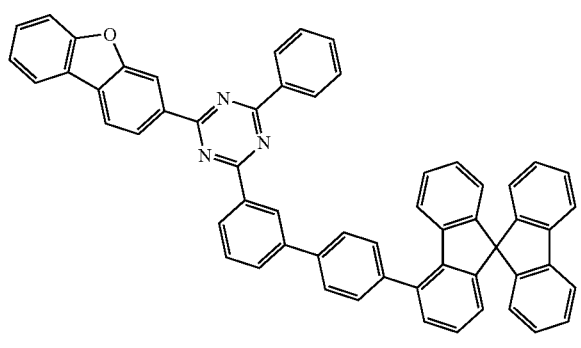
c-328
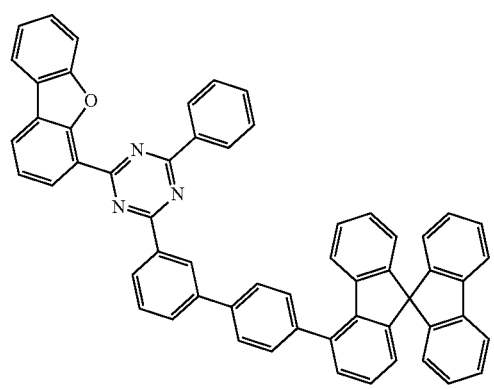

-continued
c-329
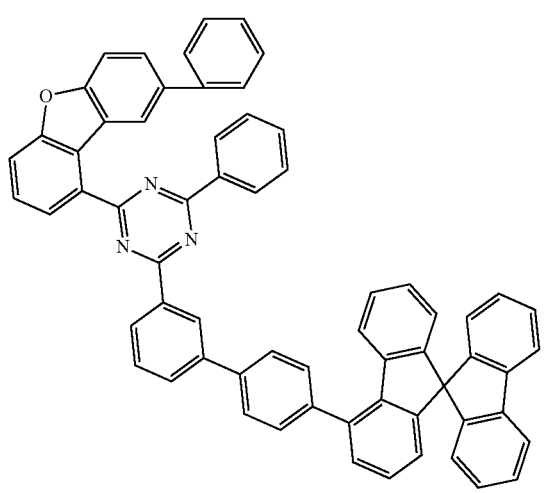
c-330
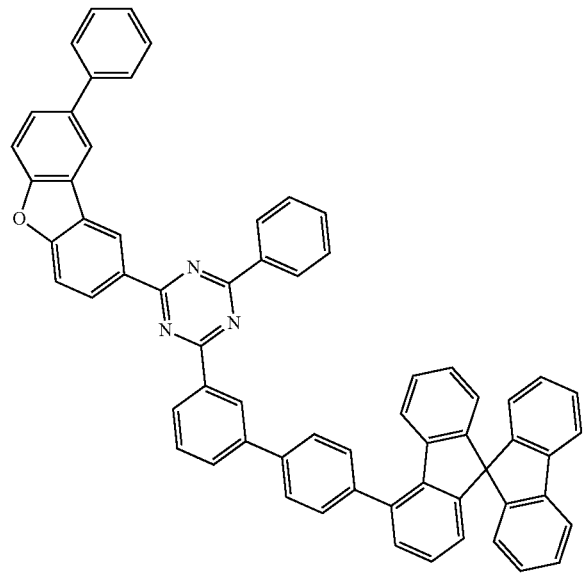
c-331
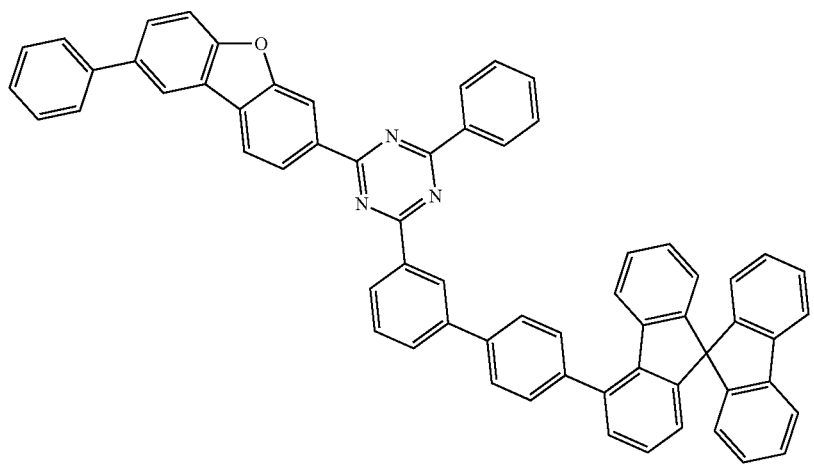

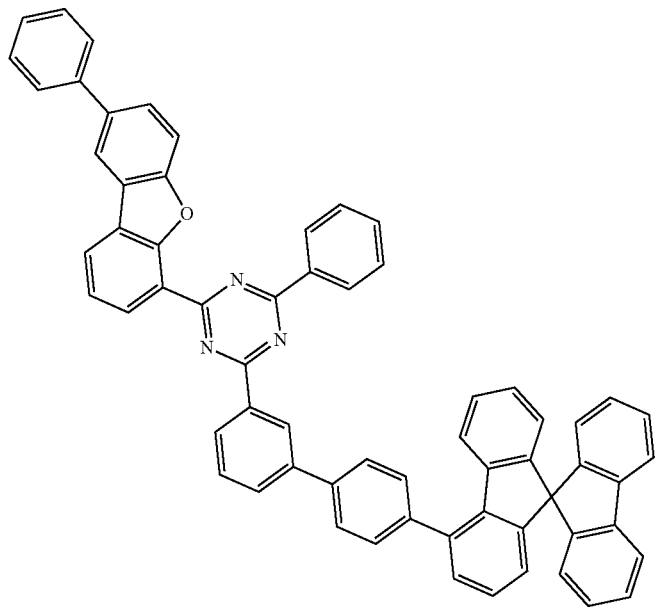
c-332
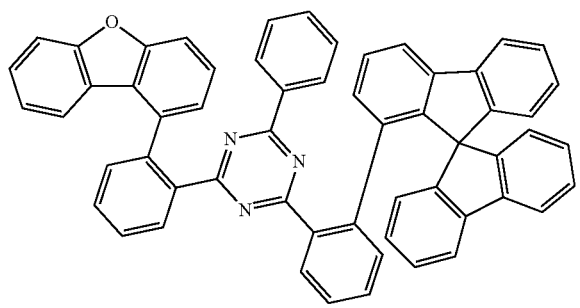
d-1
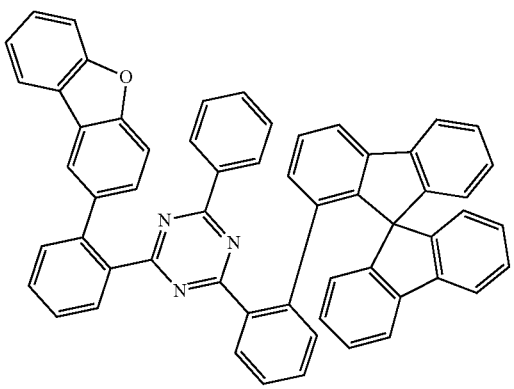
d-2
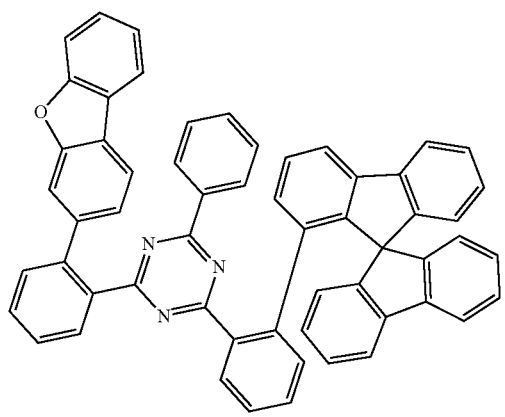
d-3
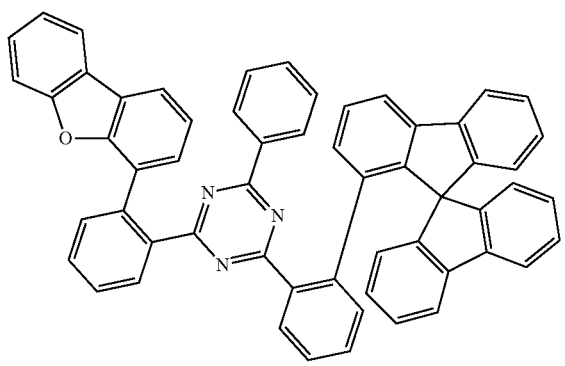
d-4

-continued
d-5
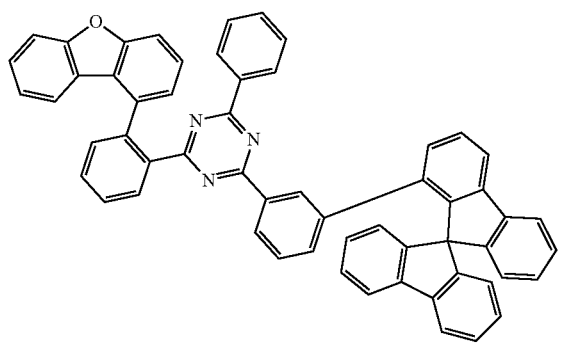
d-6
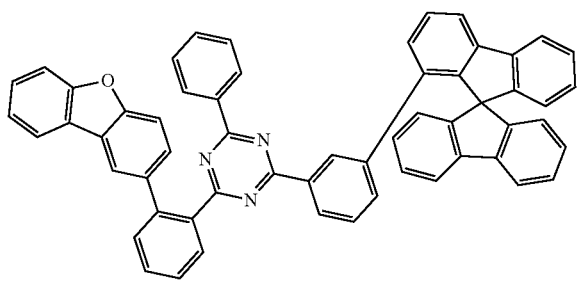
d-7
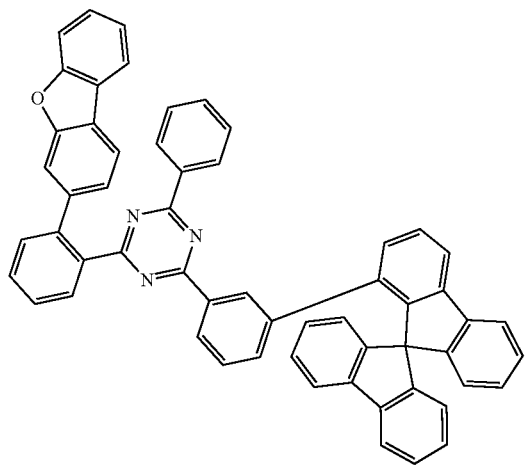
d-8
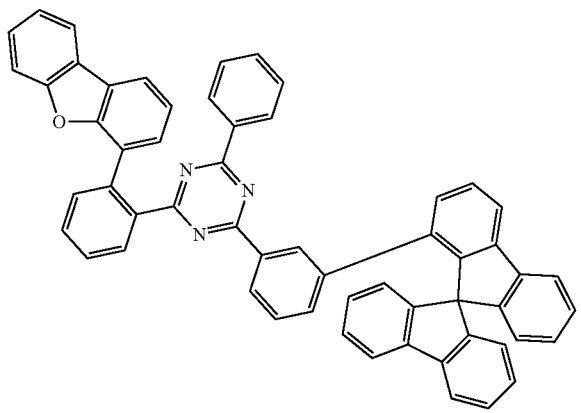
d-9
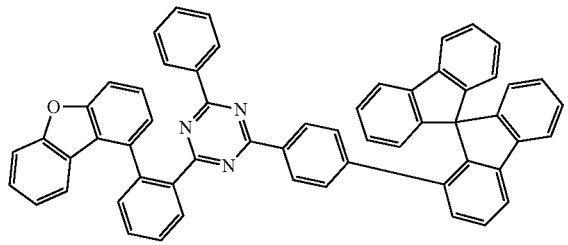
d-10
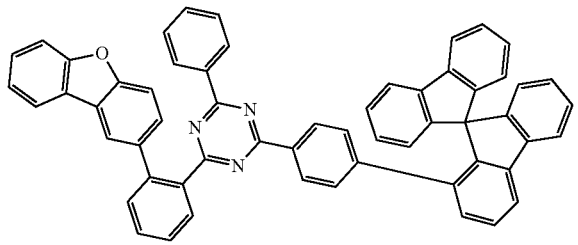
d-11
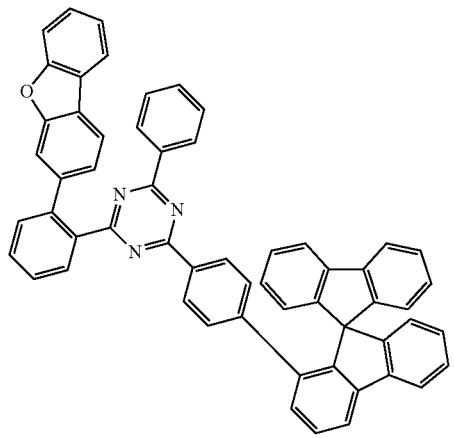
d-12
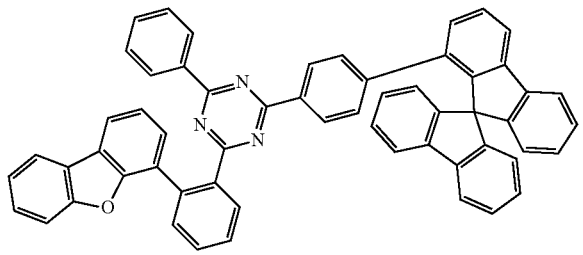

-continued
d-13
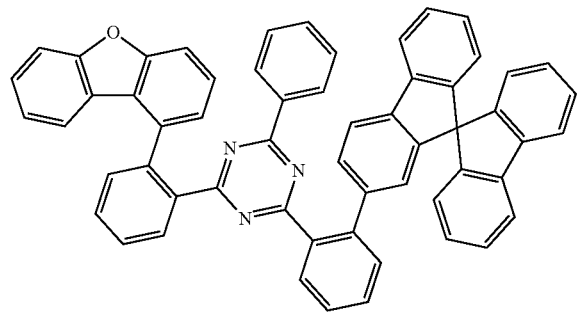
d-14
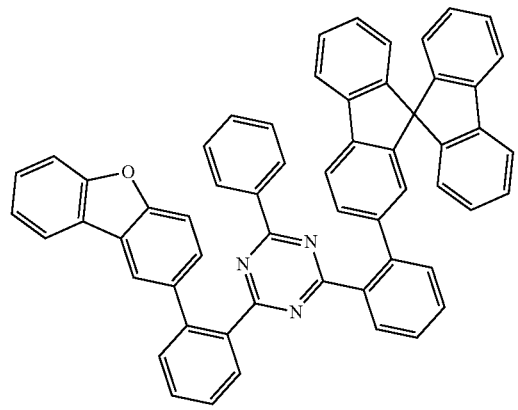
d-15
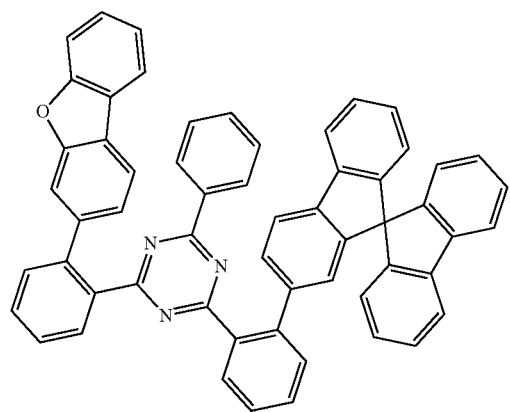
d-16
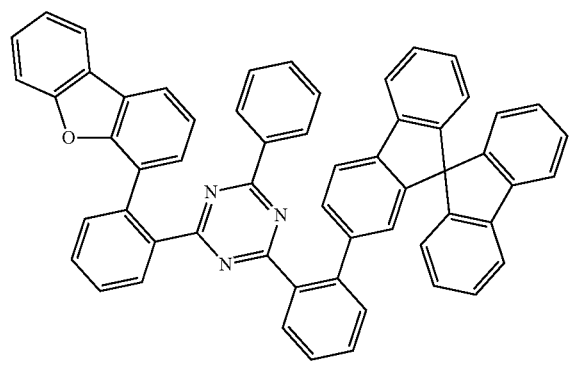
d-17
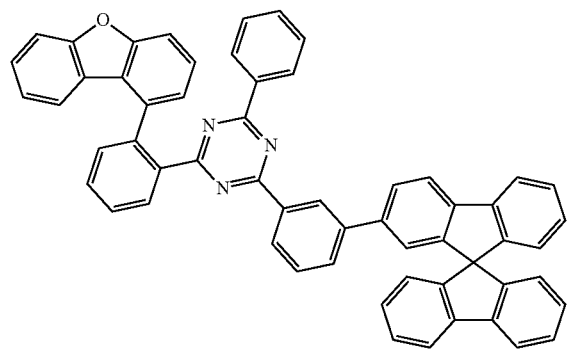
d-18
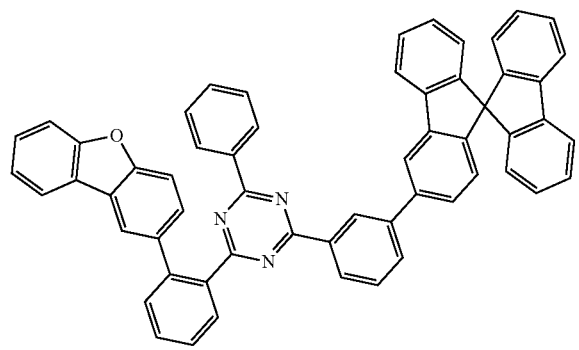

-continued
d-19
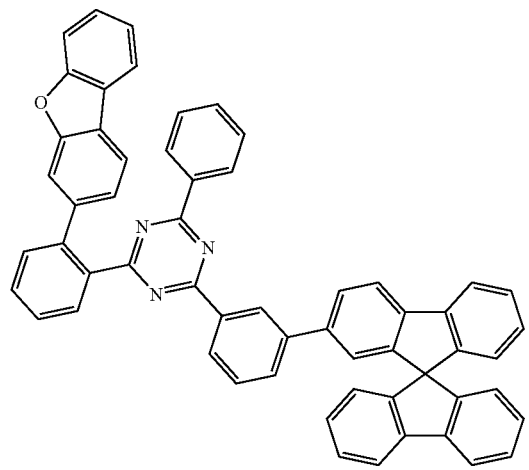
d-20
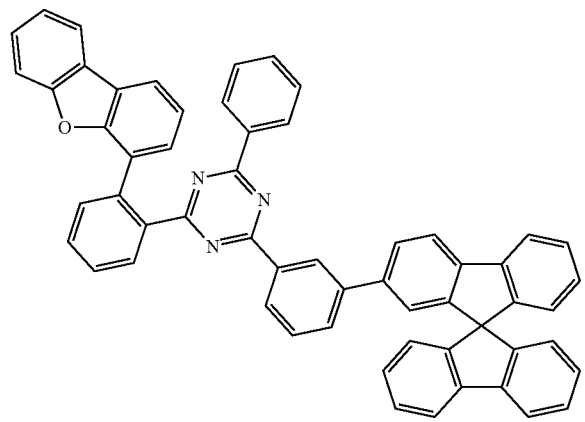
d-21
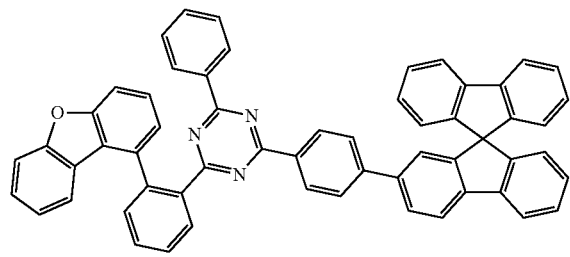
d-22
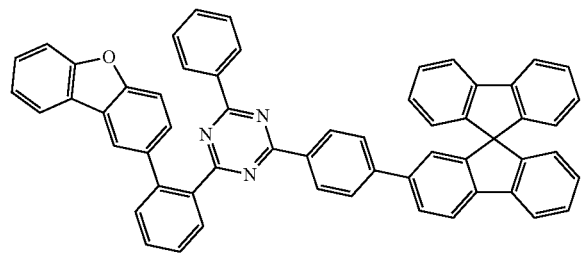
d-23
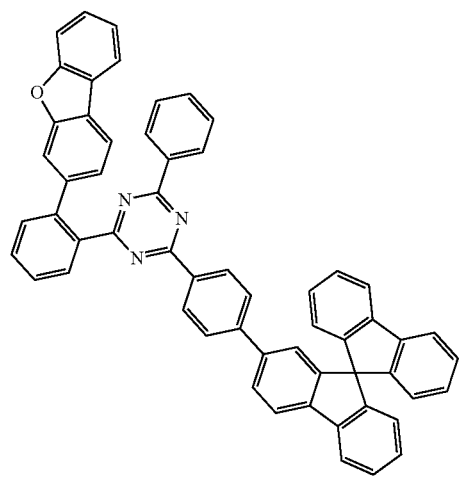
d-24
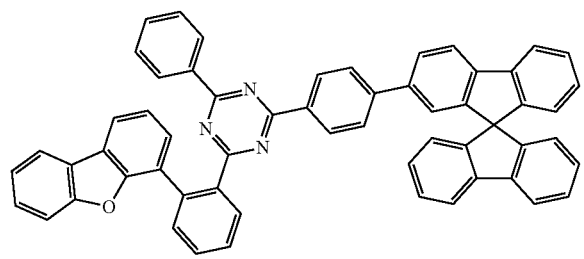

d-25 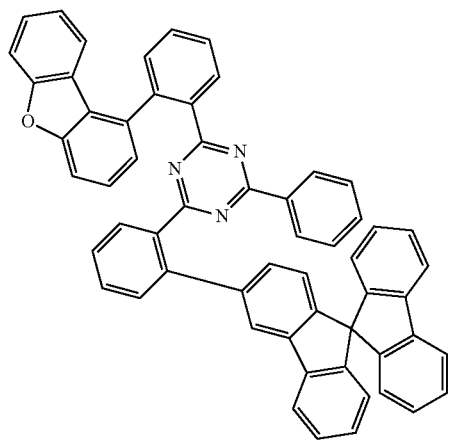
d-26 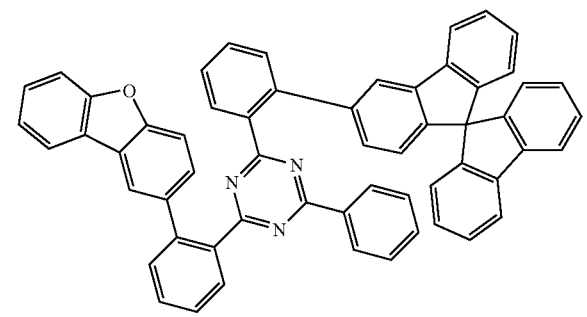
d-27 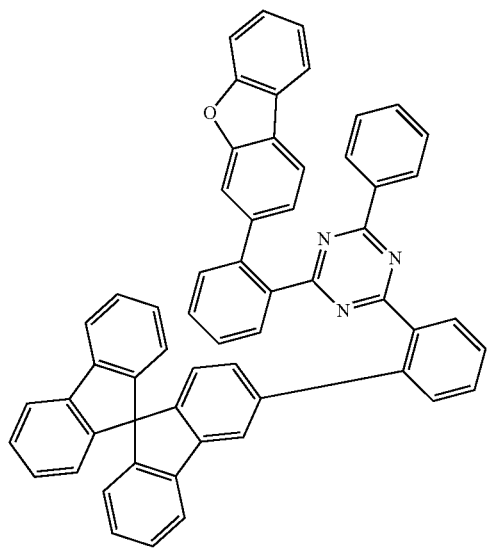
d-28 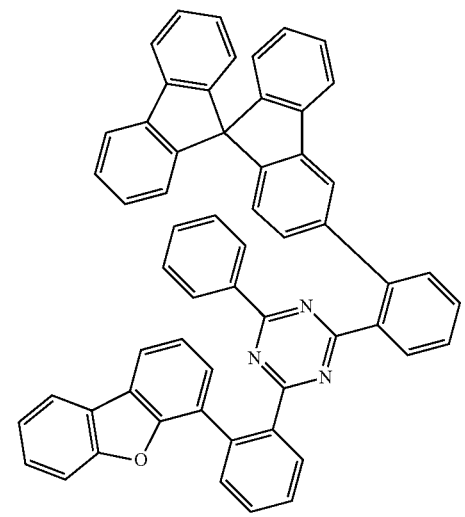
d-29 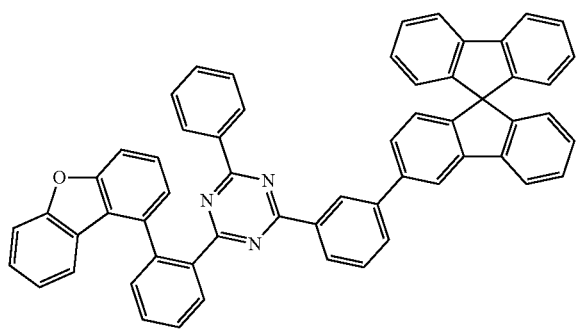
d-30 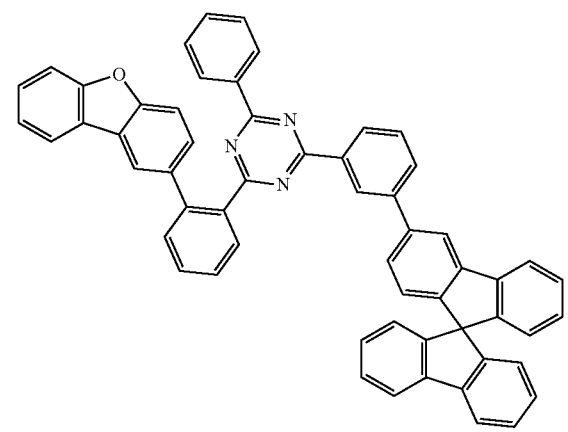

-continued
d-31
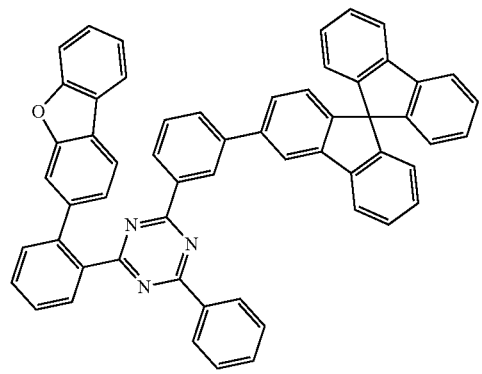
d-32
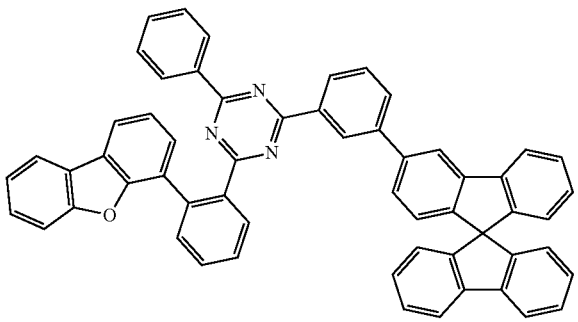
d-33
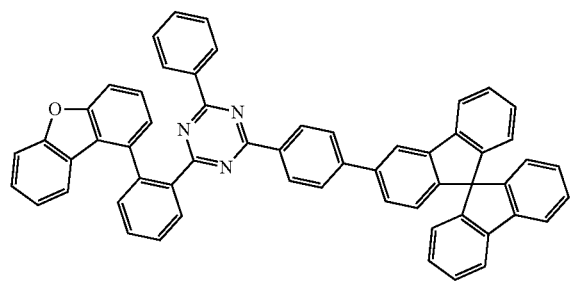
d-34
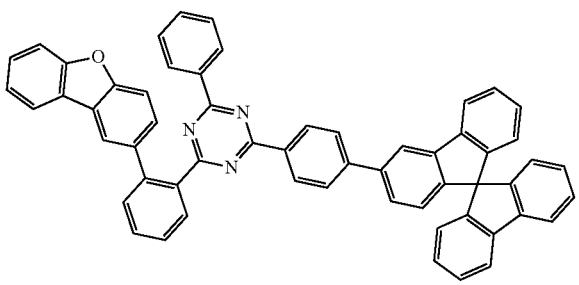
d-35
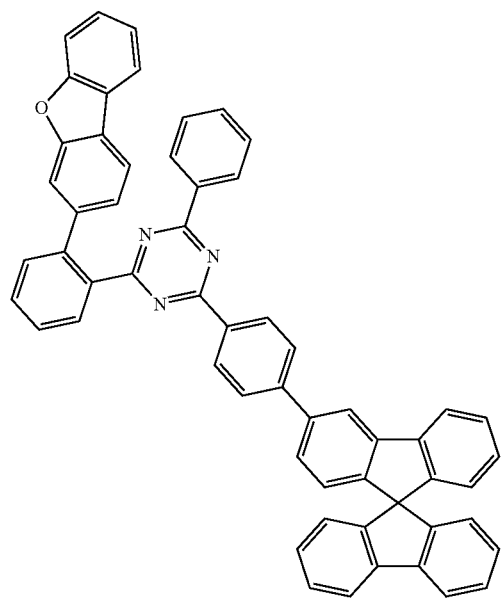
d-36
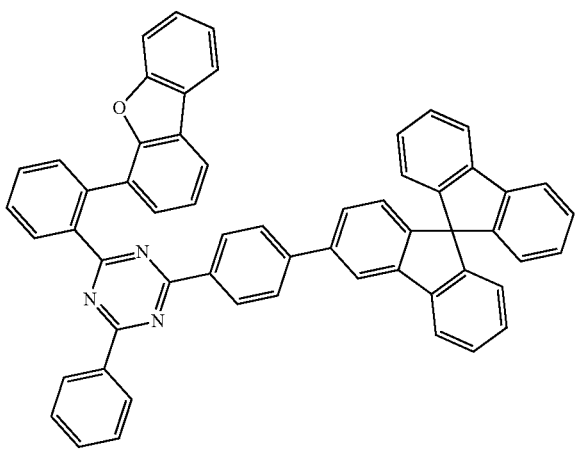

-continued
d-37
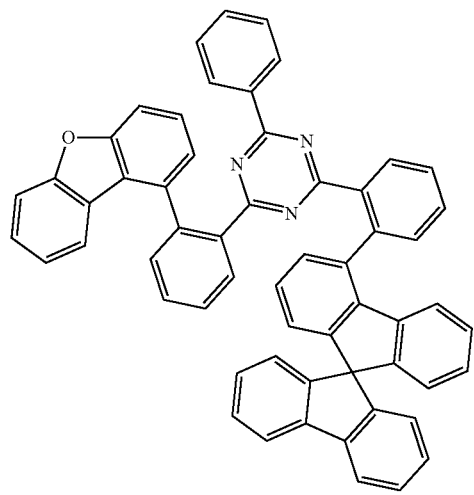
d-38
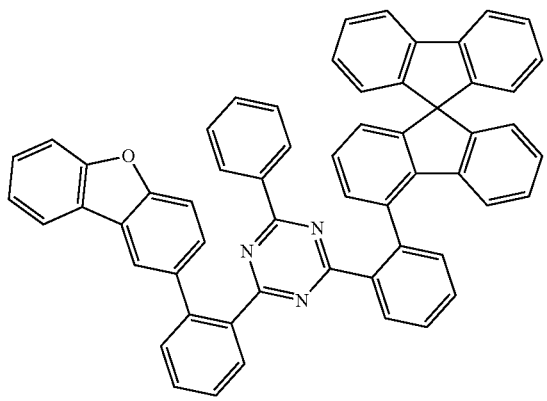
d-39
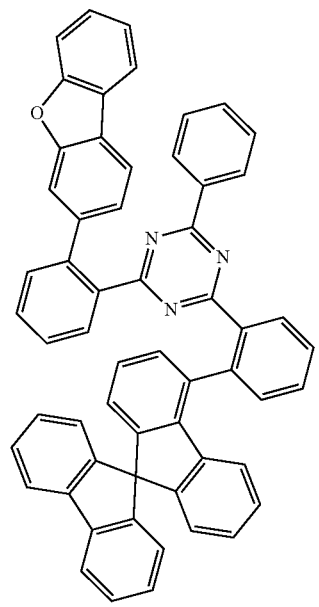
d-40
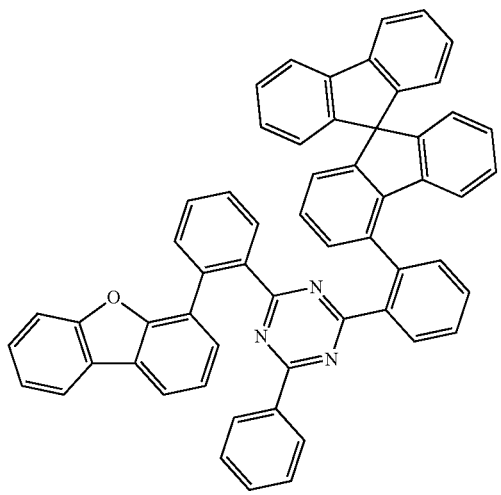
d-41
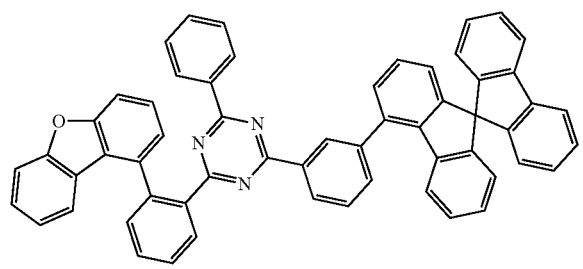
d-42
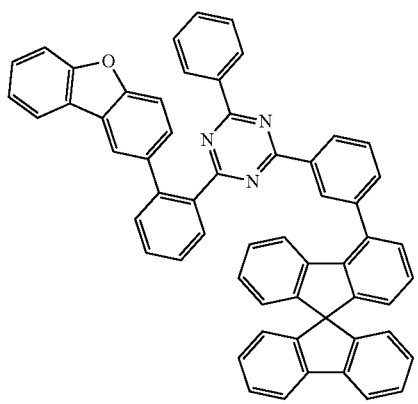

-continued
d-43
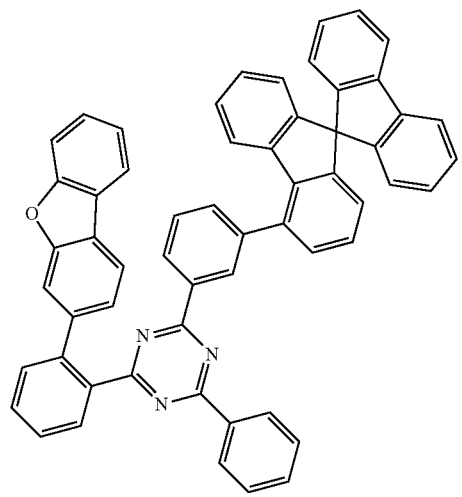
d-44
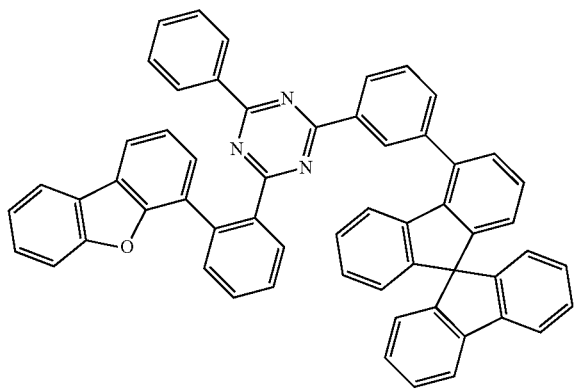
d-45
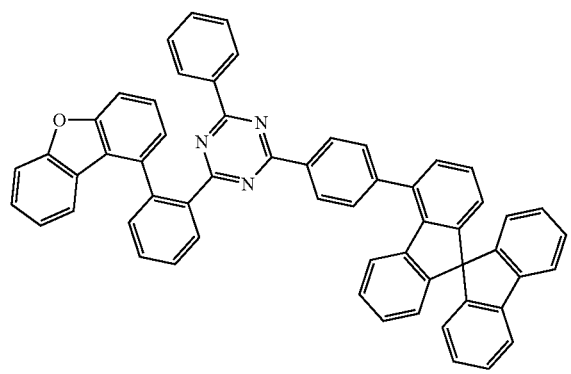
d-46
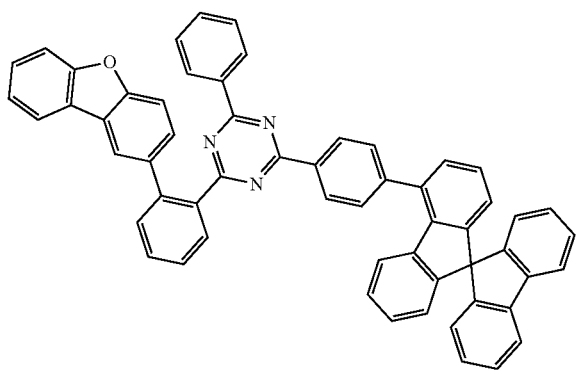
d-47
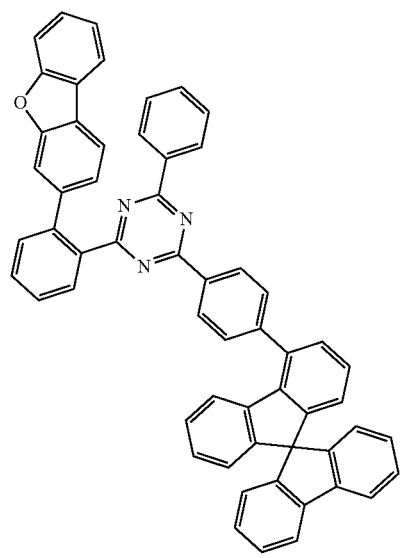
d-48
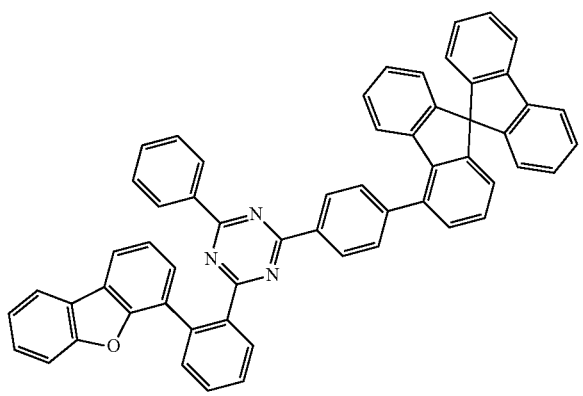

-continued
d-49
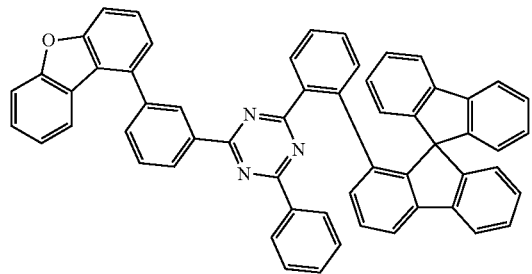
d-50
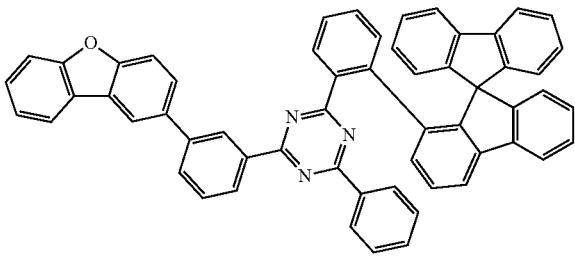
d-51
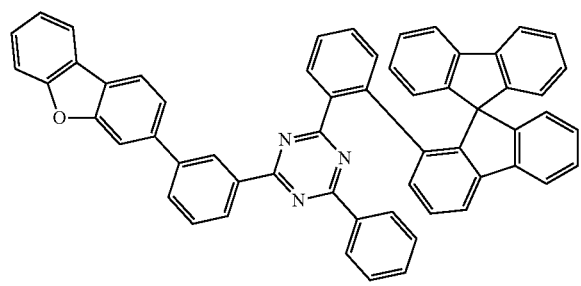
d-52
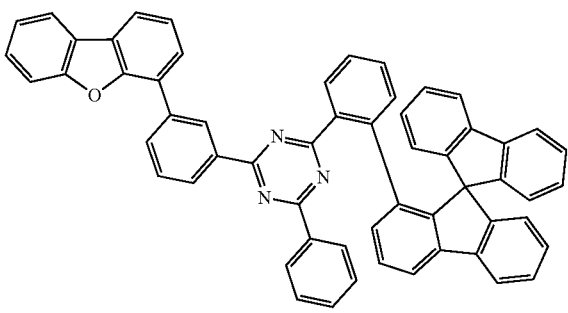
d-53
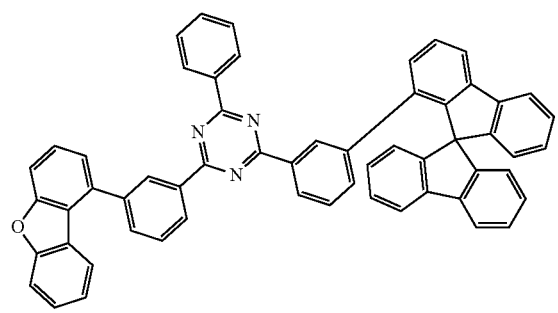
d-54
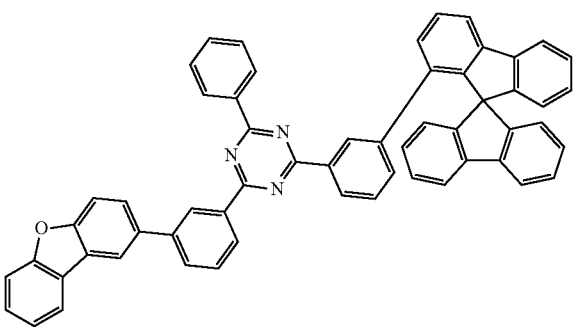
d-55
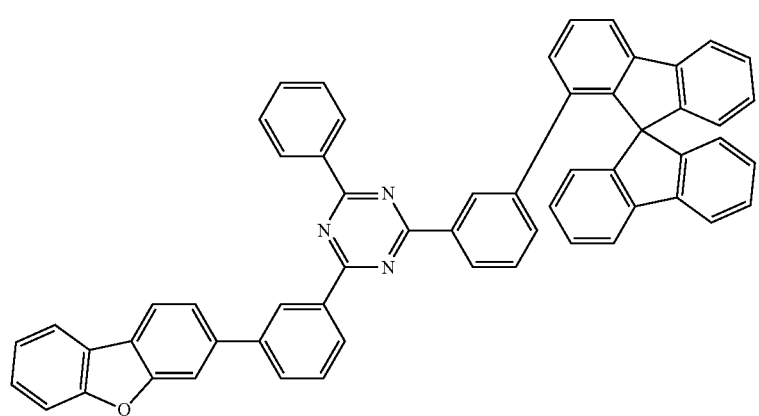

d-56
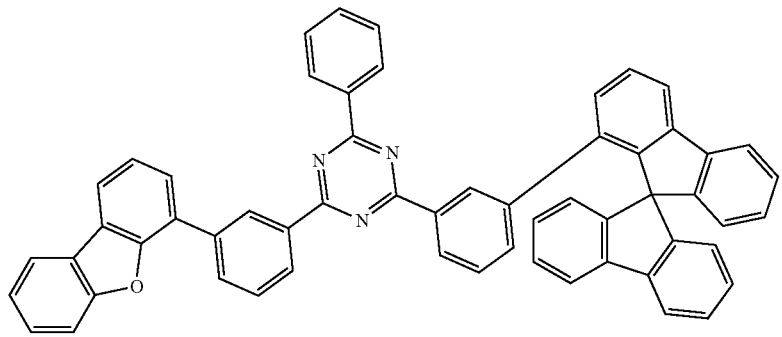
d-57
d-58
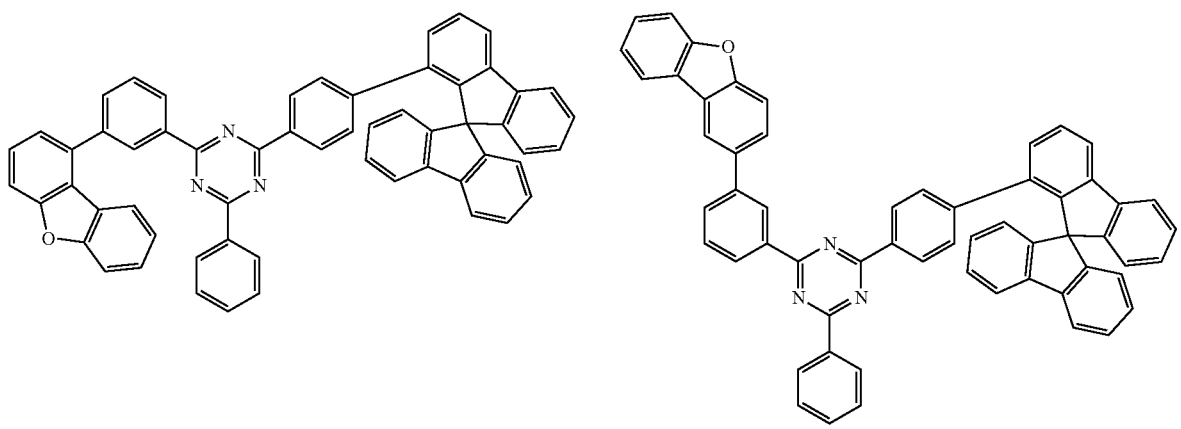
d-59
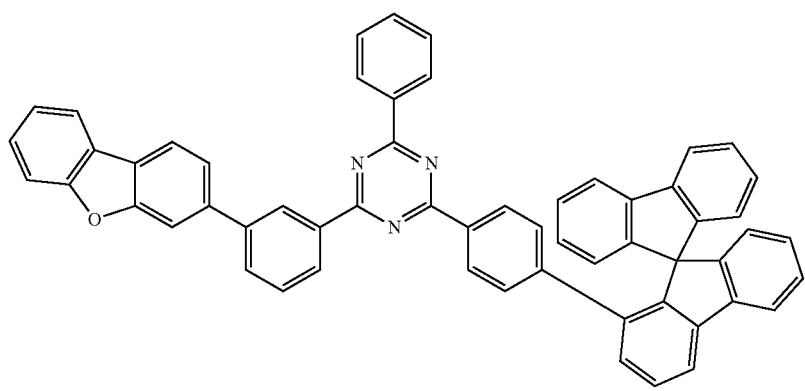
d-60
d-61
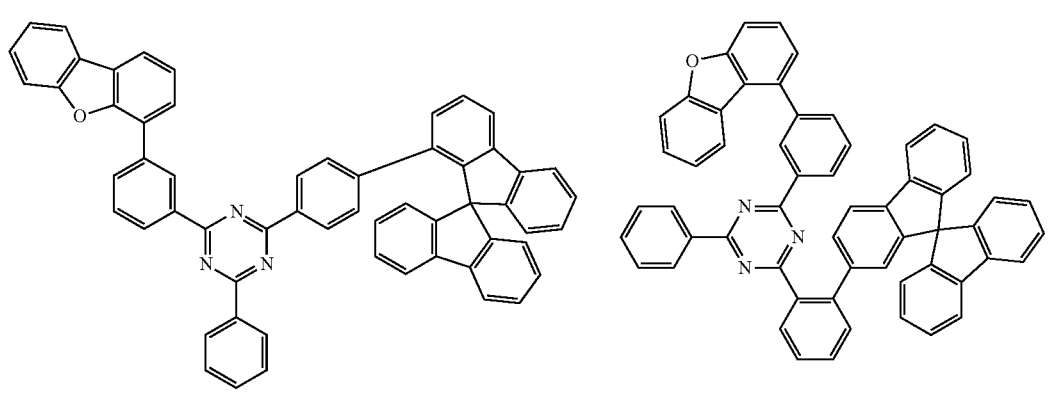

-continued
d-62
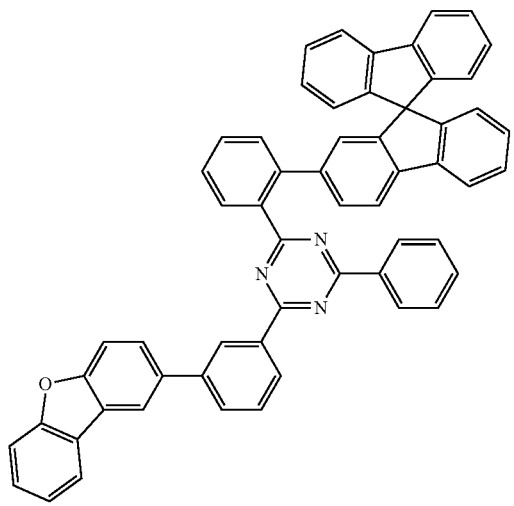
d-63
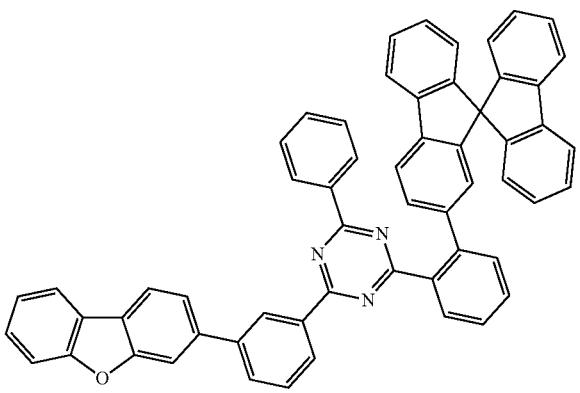
d-64
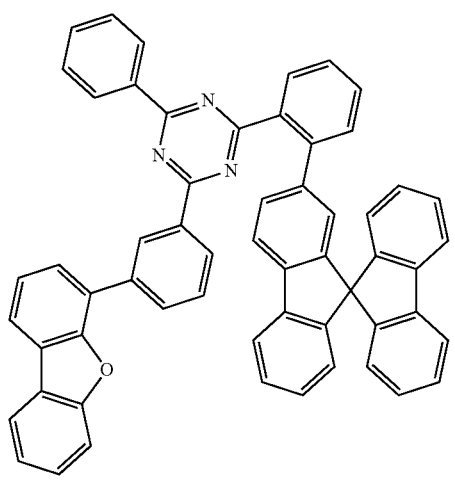
d-65
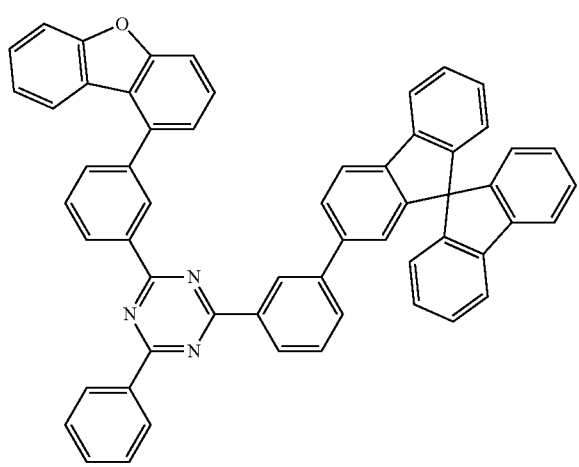

-continued
d-66
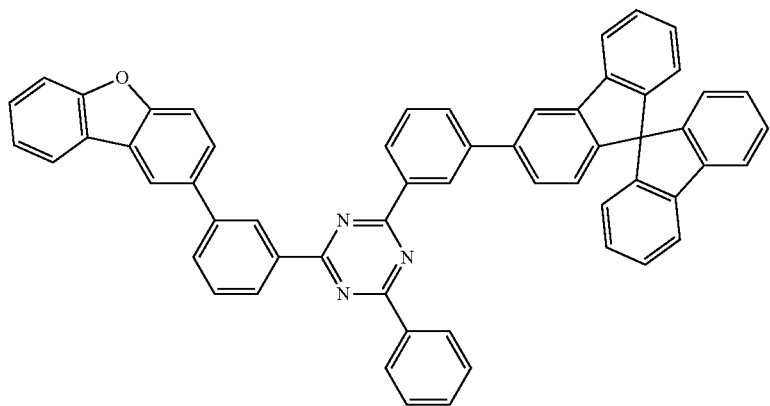
d-67
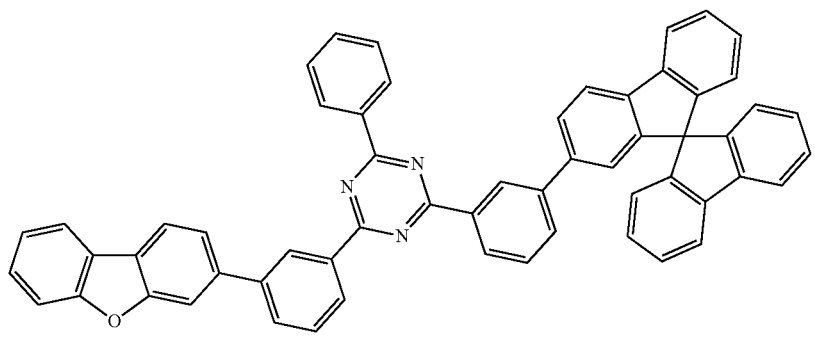
d-68
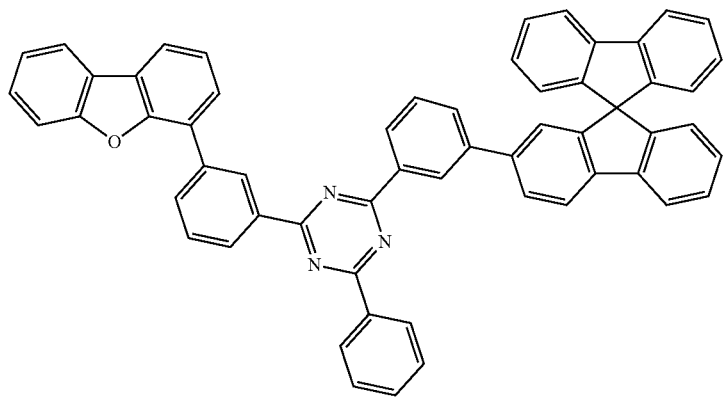
d-69
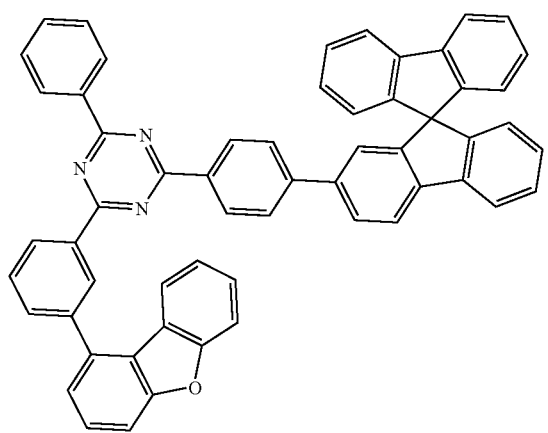
d-70
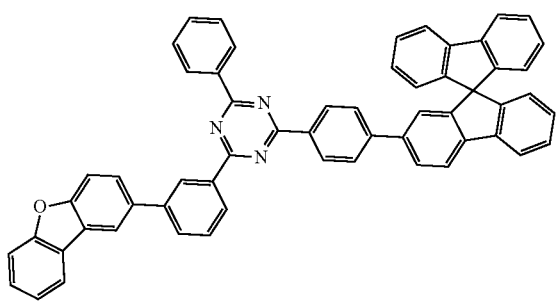

-continued
d-71
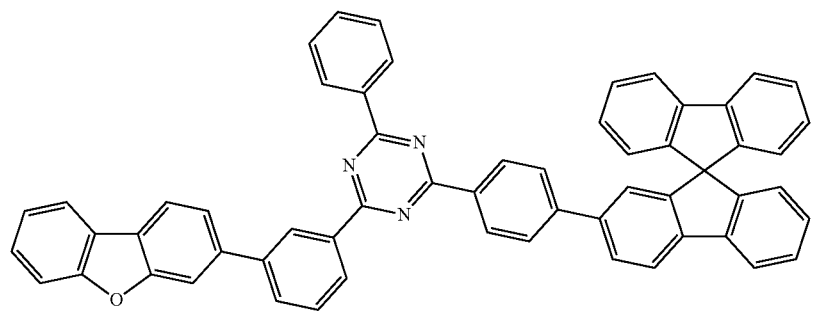
d-72
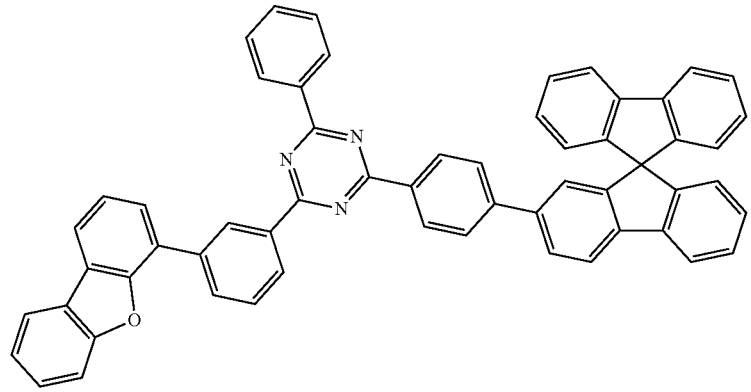
d-73
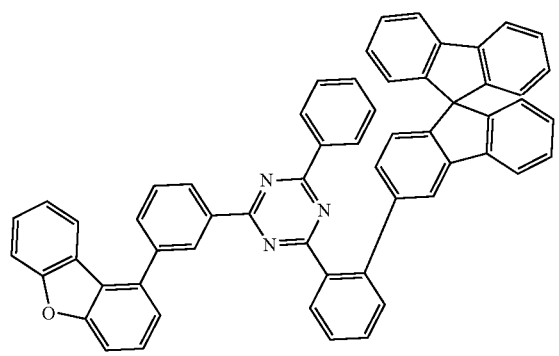
d-74
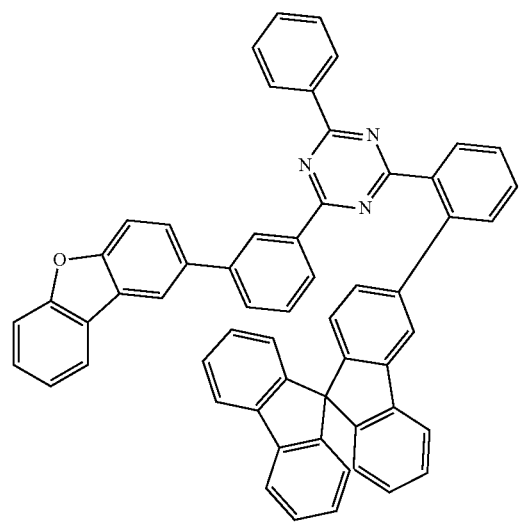

-continued
d-75
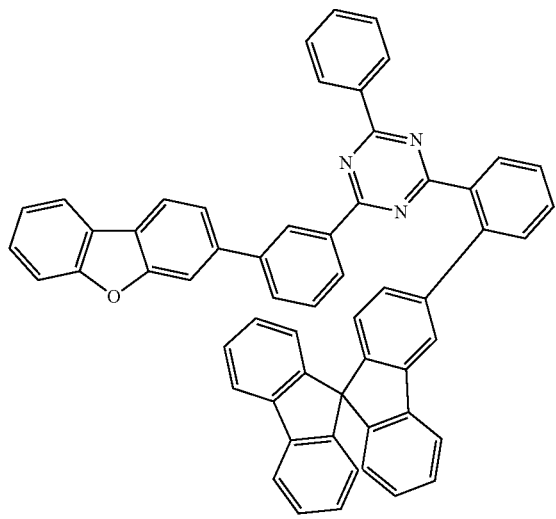
d-76
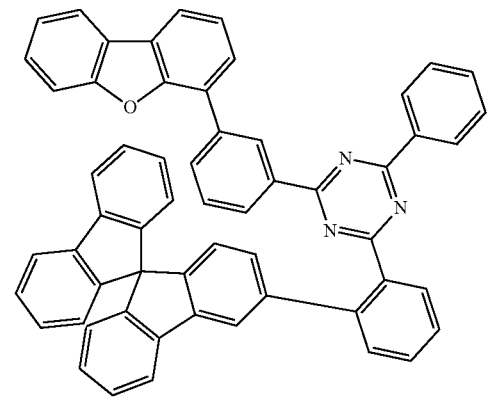
d-77
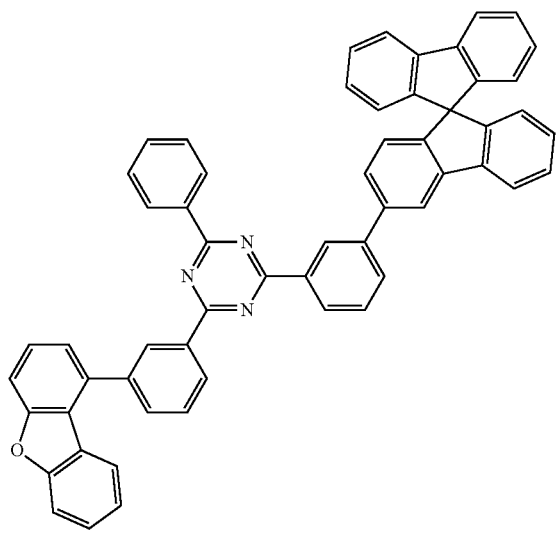
d-78
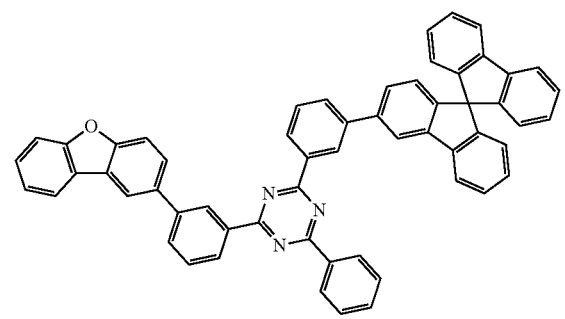
d-79
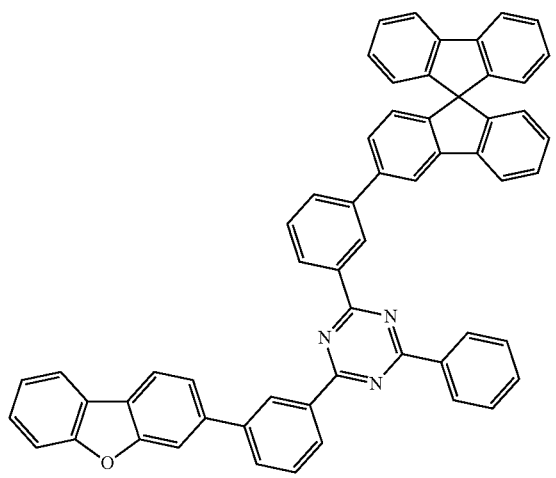
d-80
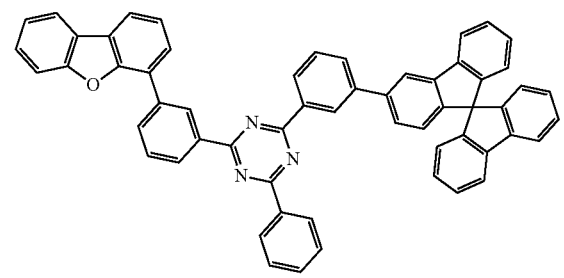

-continued
d-81
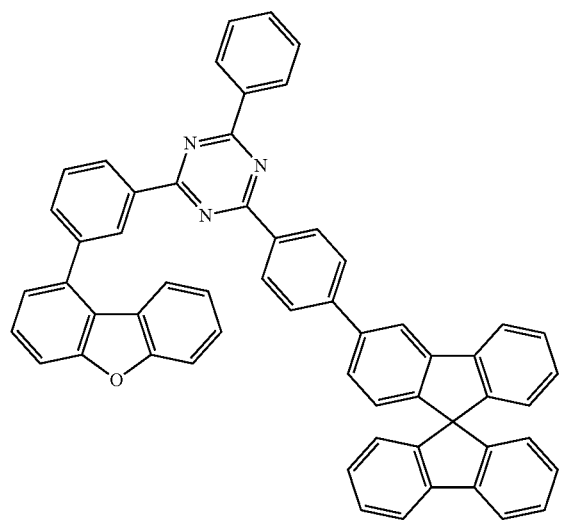
d-82
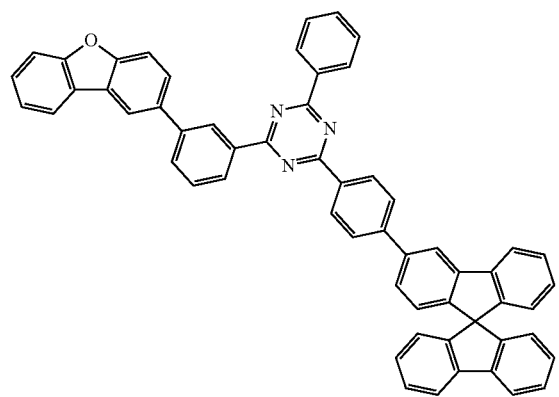
d-83
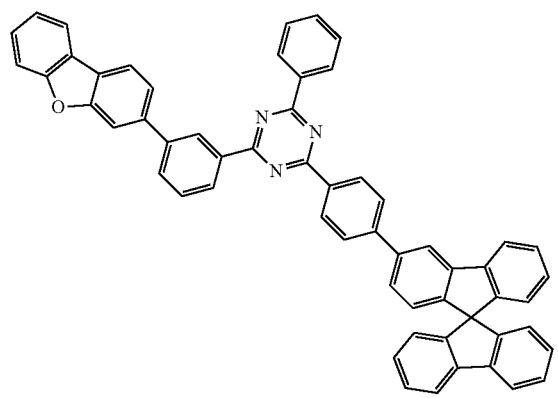
d-84
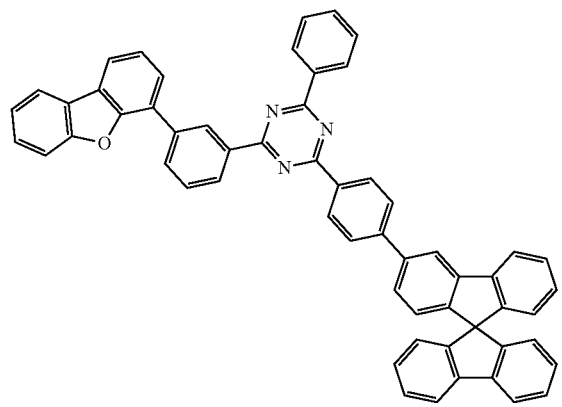
d-85
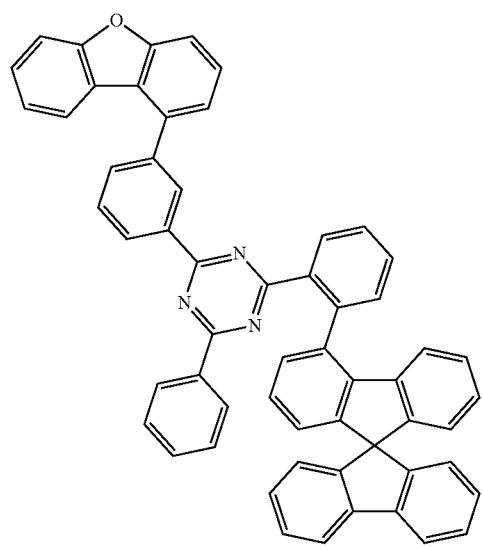
d-86
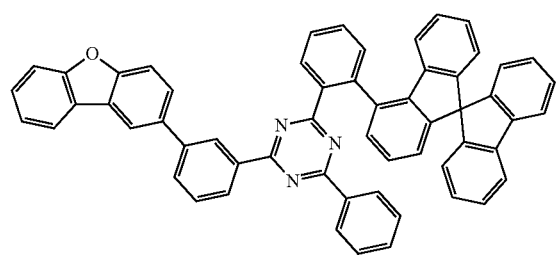

-continued
d-87
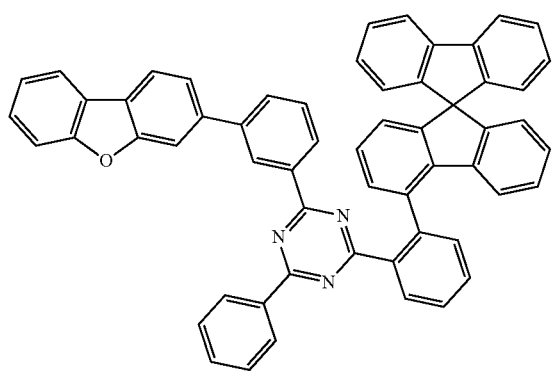
d-88
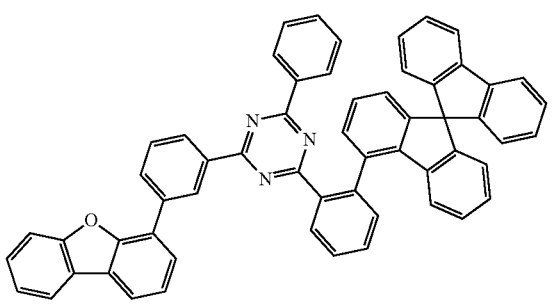
d-89
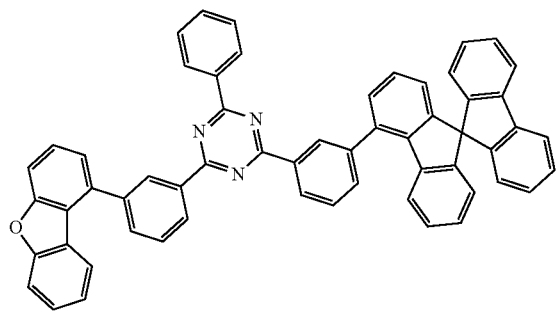
d-90
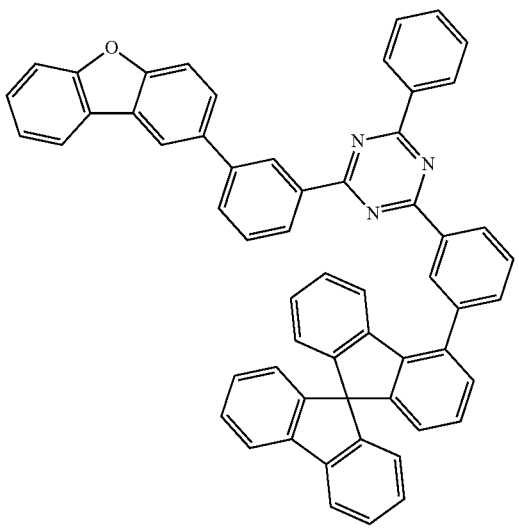
d-91
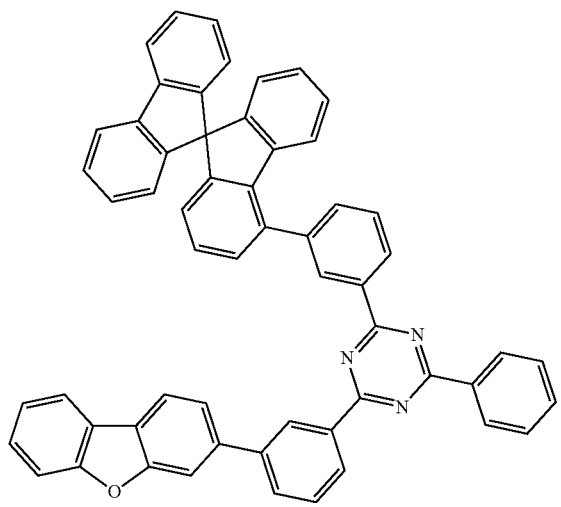
d-92
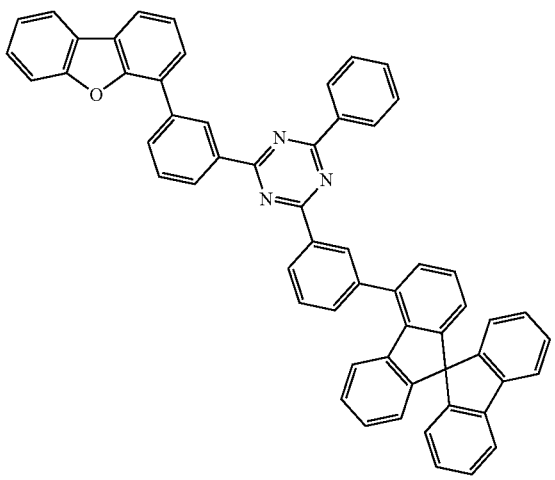

-continued
d-93
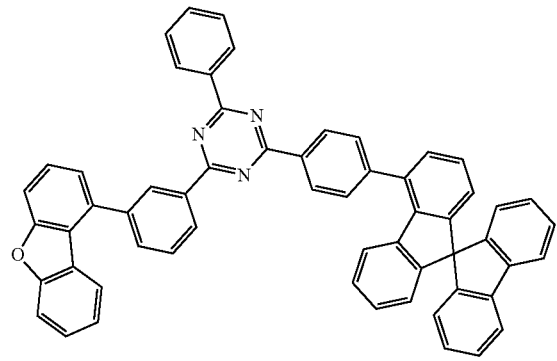
d-94
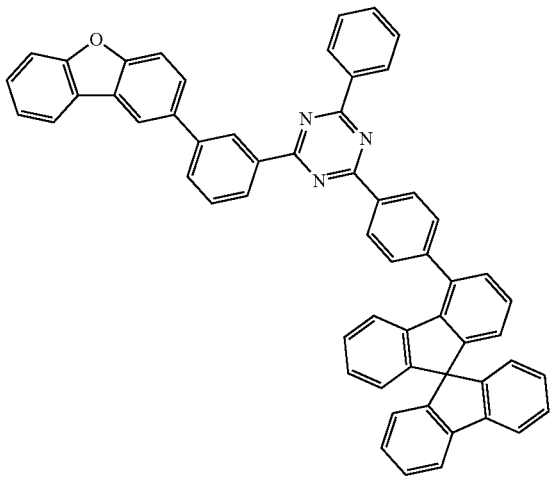
d-95
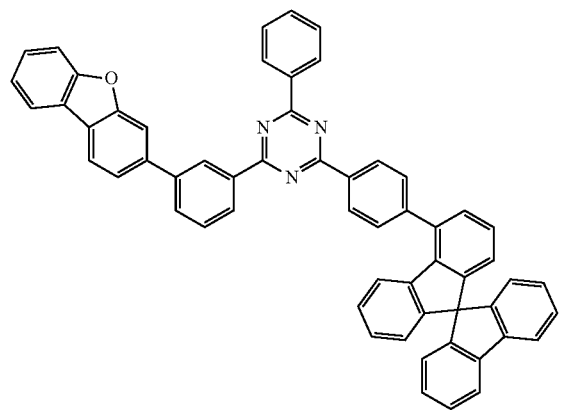
d-96
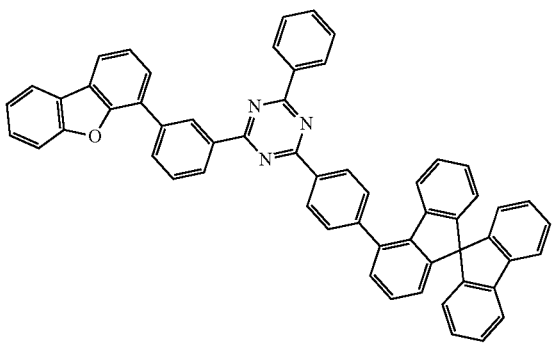
d-97
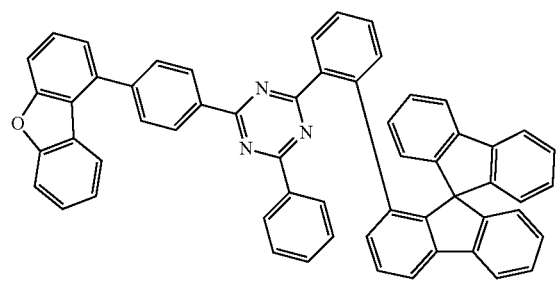
d-98
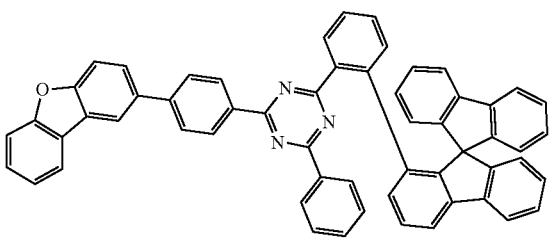
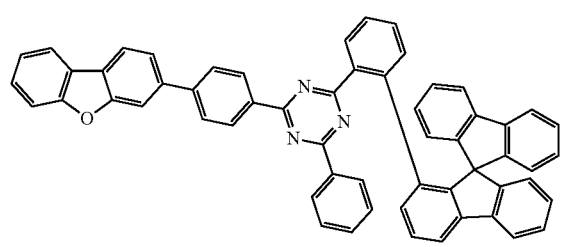
d-100
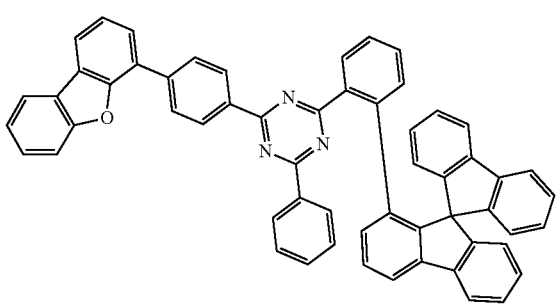

d-101
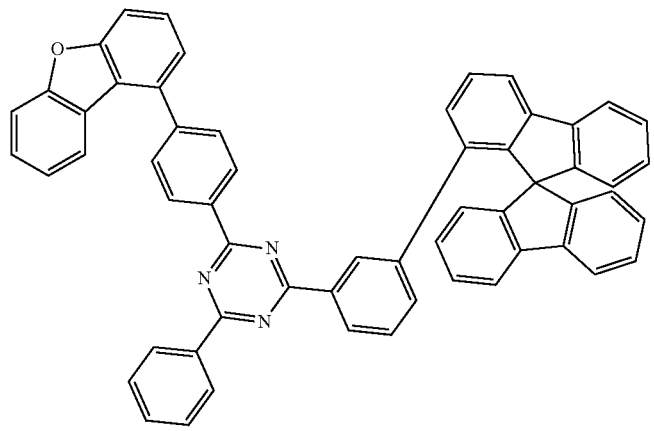
d-102
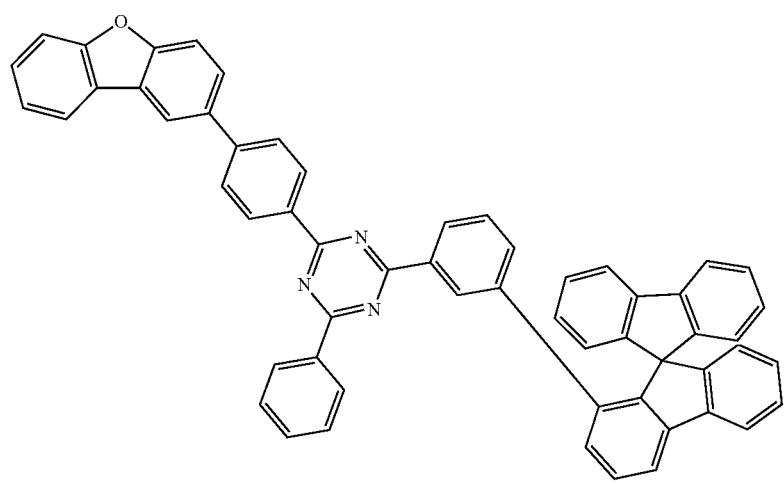
d-103
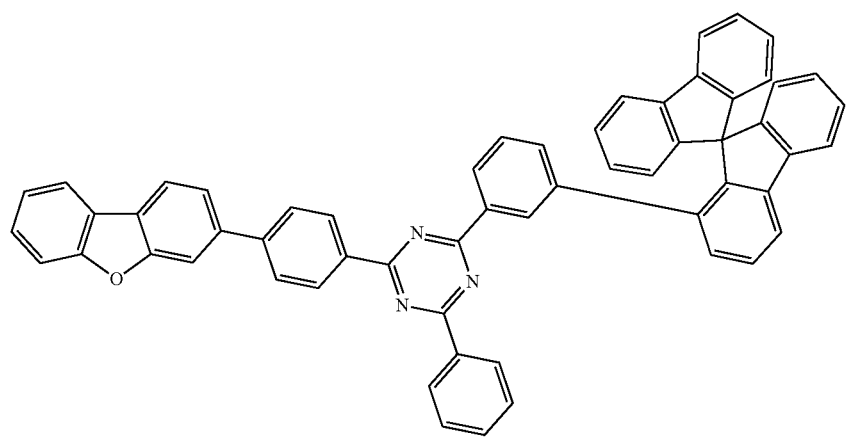

-continued
d-104
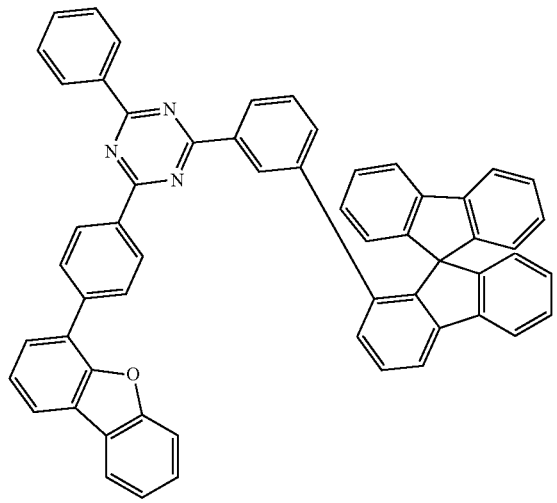
d-105
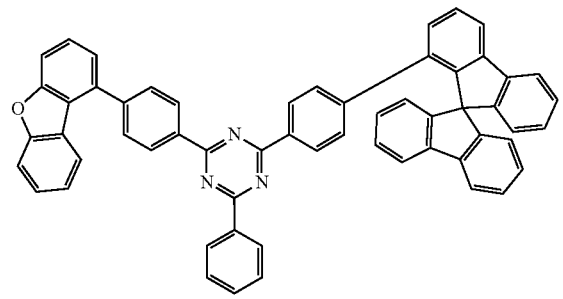
d-106
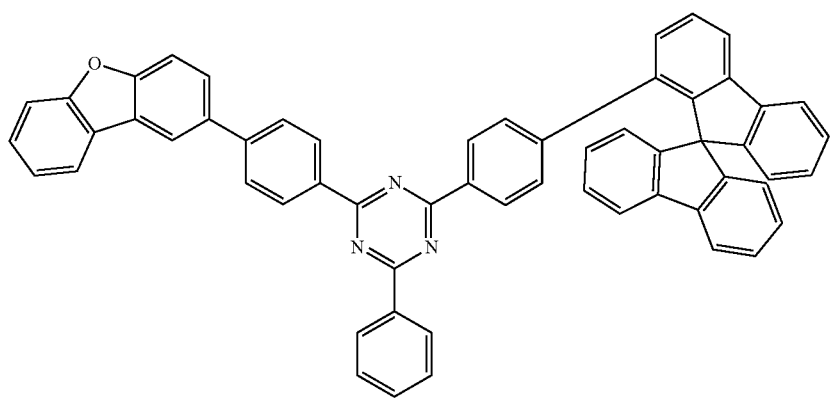
d-107
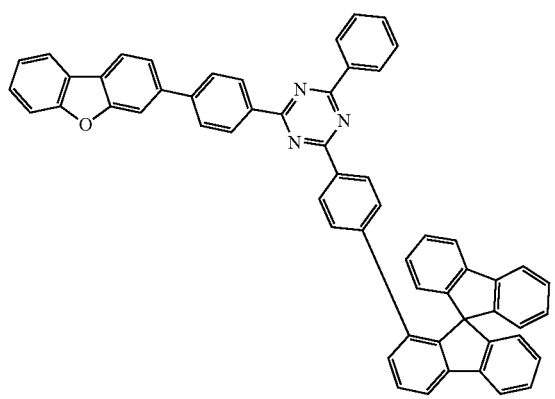
d-108
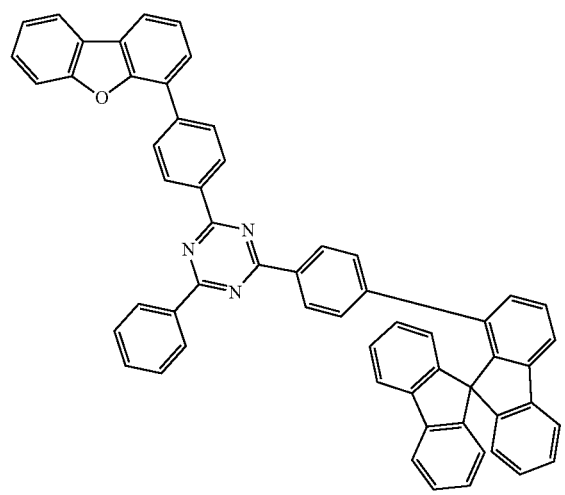

-continued
d-109
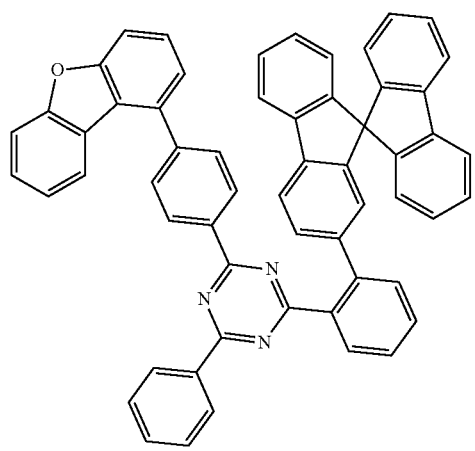
d-110
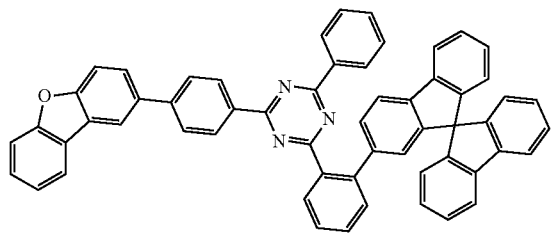
d-111
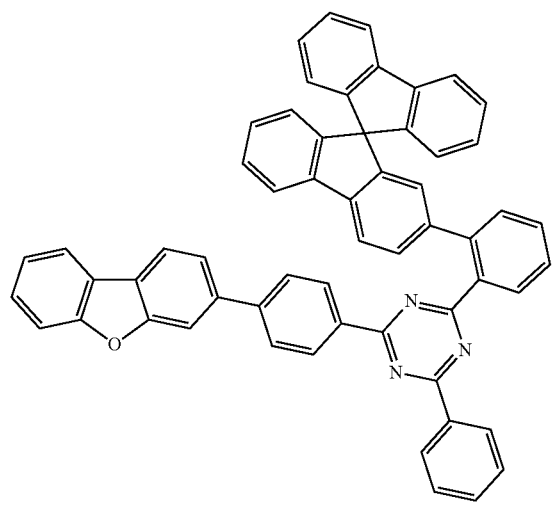
d-112
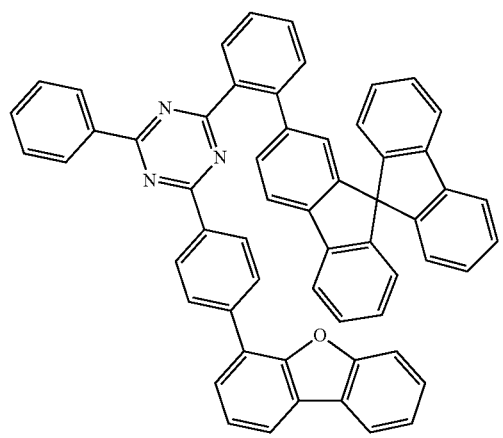
d-113
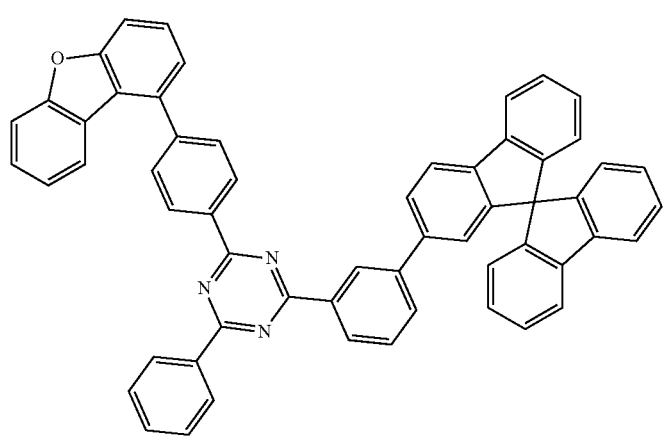

-continued
d-114
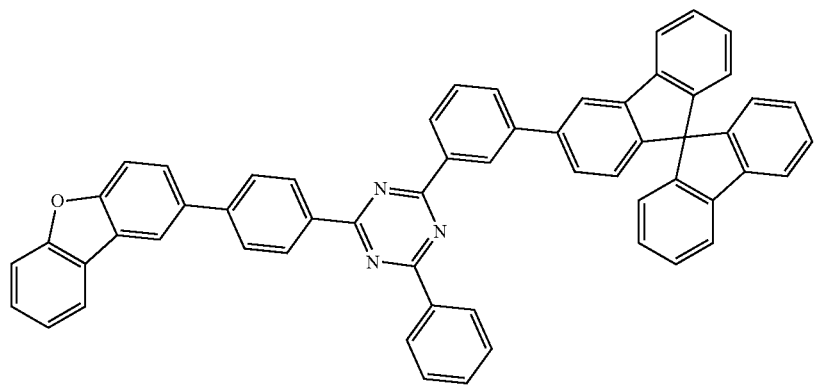
d-115
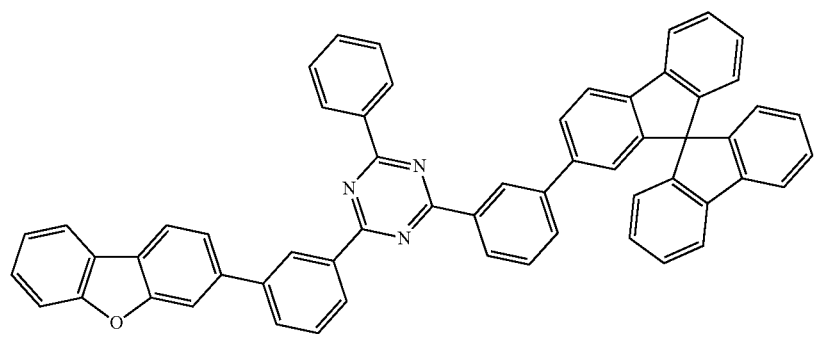
d-116 d-117
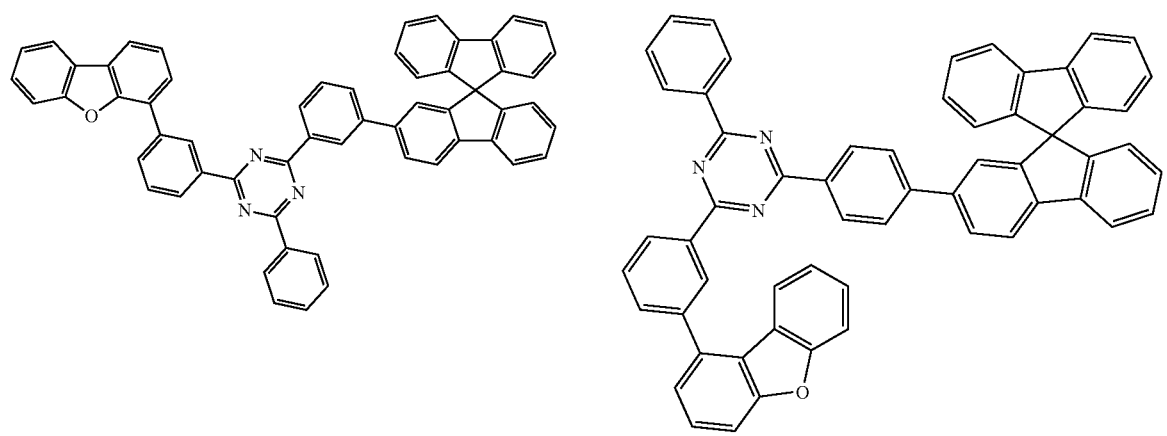
d-118
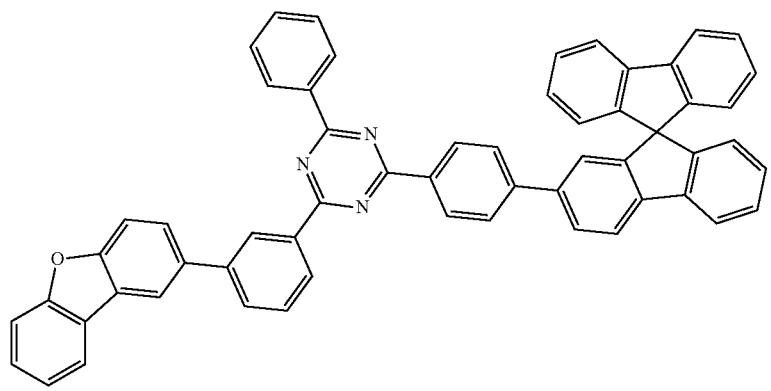

-continued
d-119
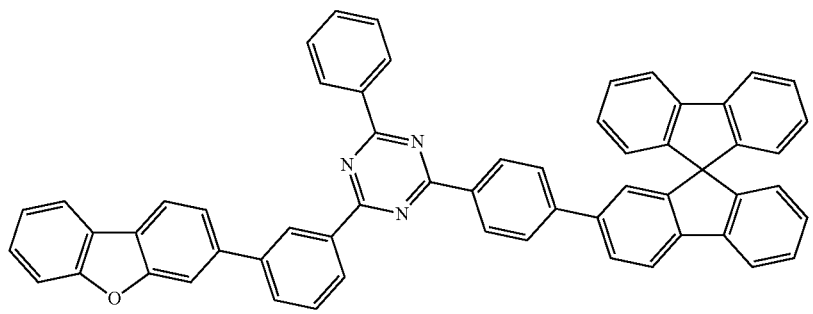
d-120
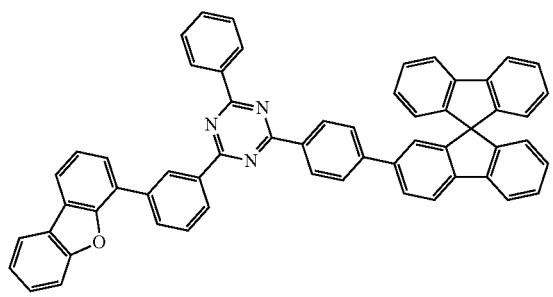
d-121
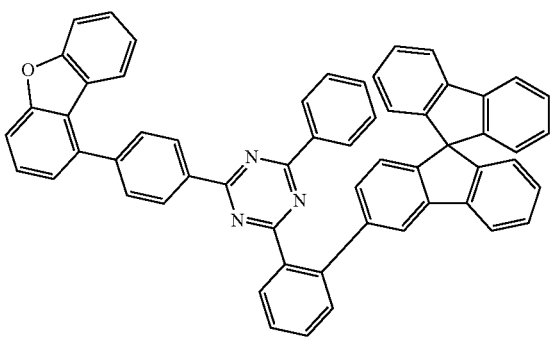
d-122
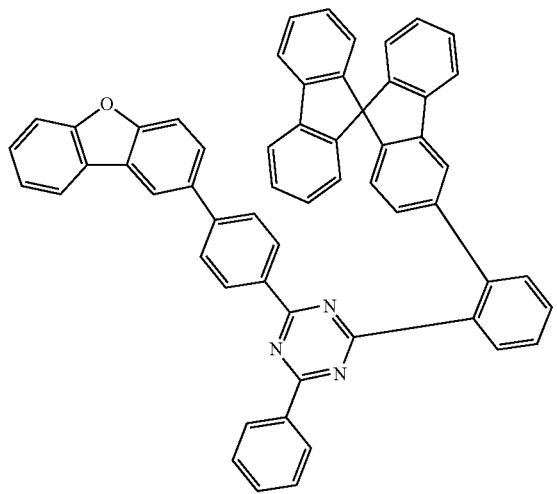
d-123
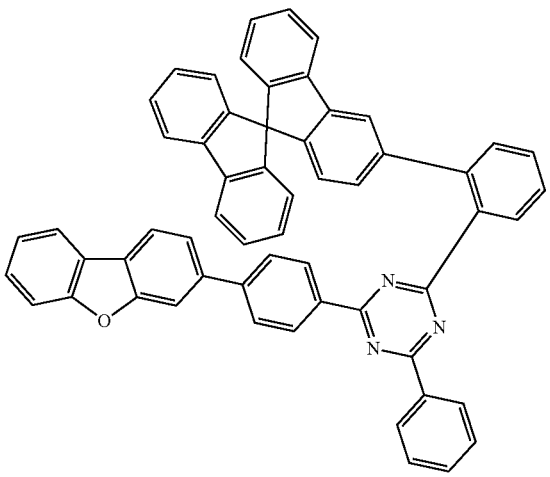
d-124
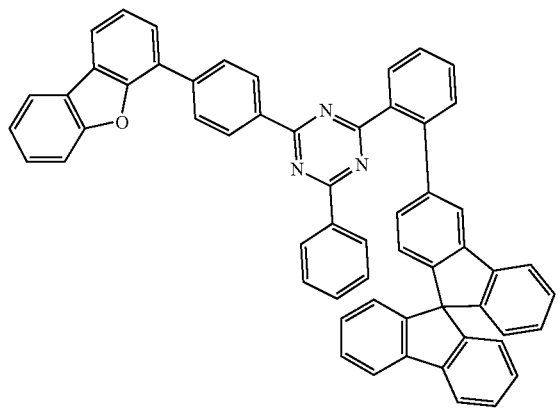
d-125
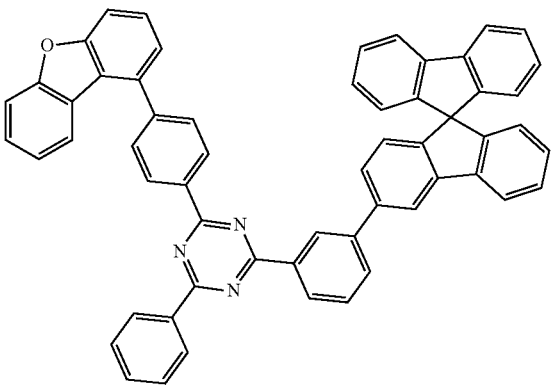

-continued
d-126
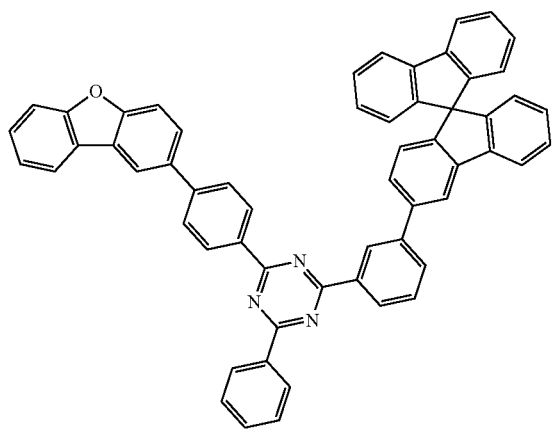
d-127
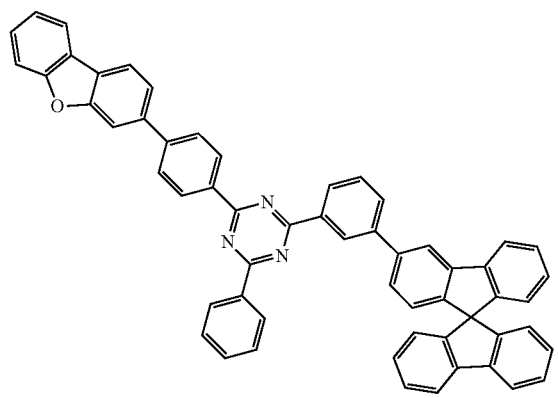
d-128
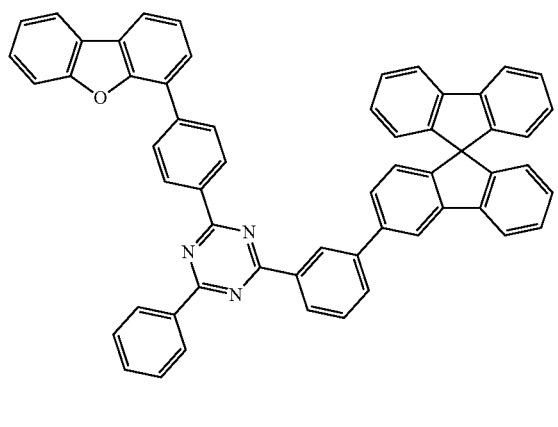
d-129
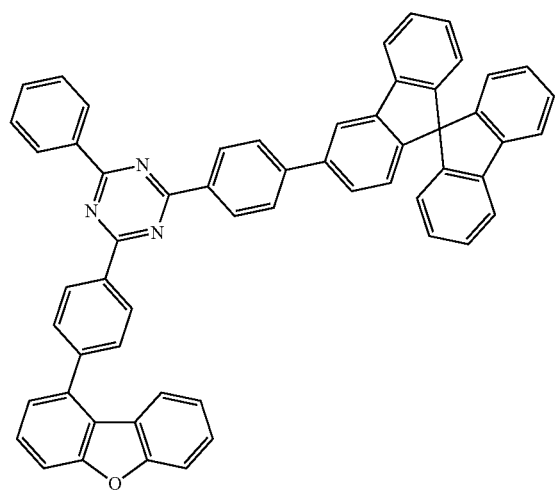
d-130
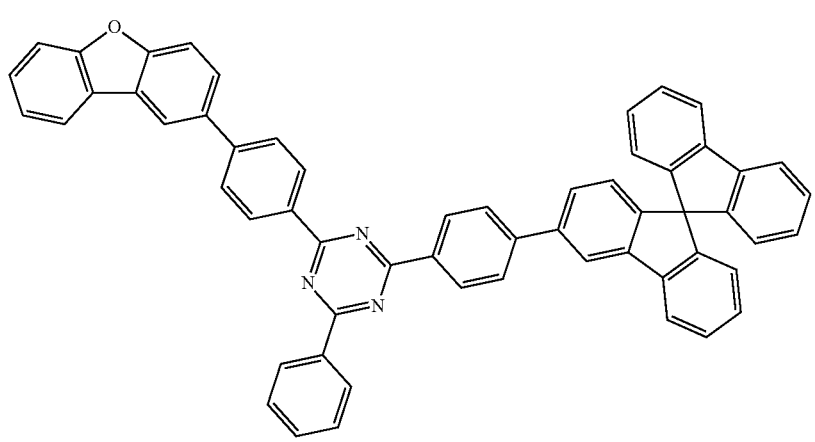

-continued
d-131
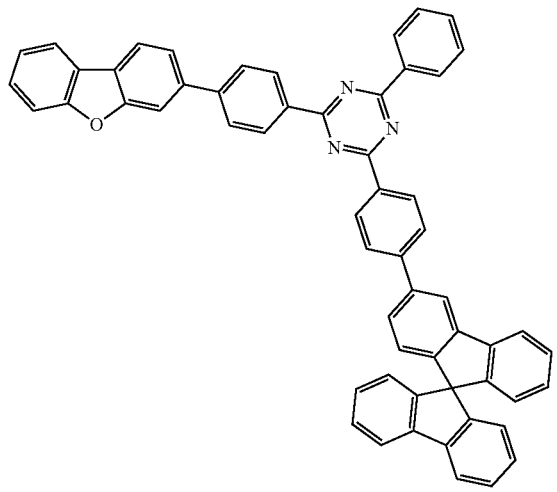
d-132
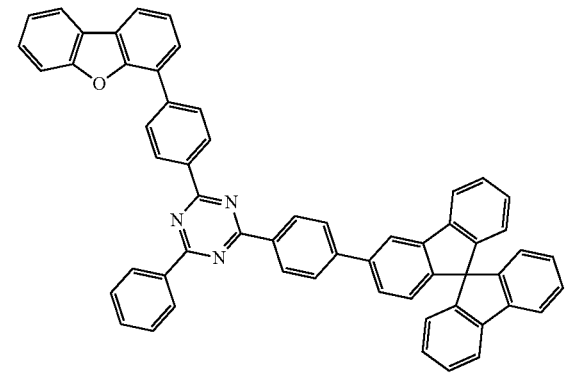
d-133
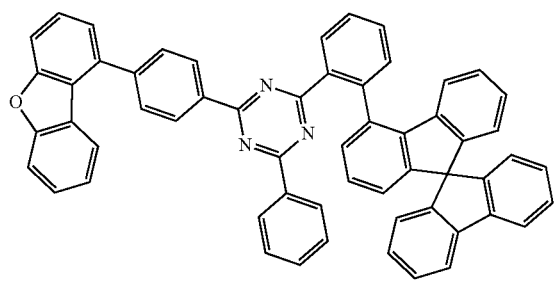
d-134
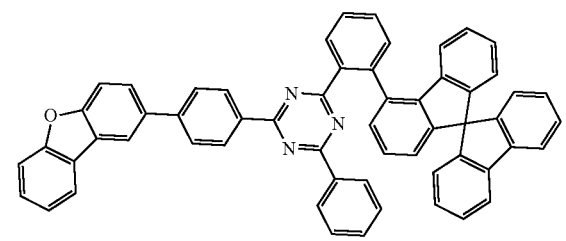
d-135
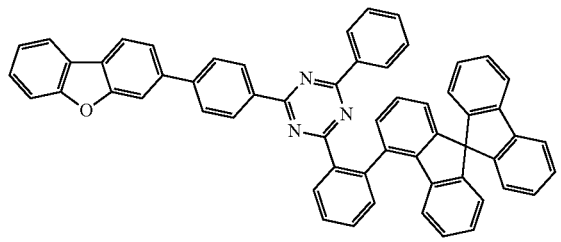
d-136
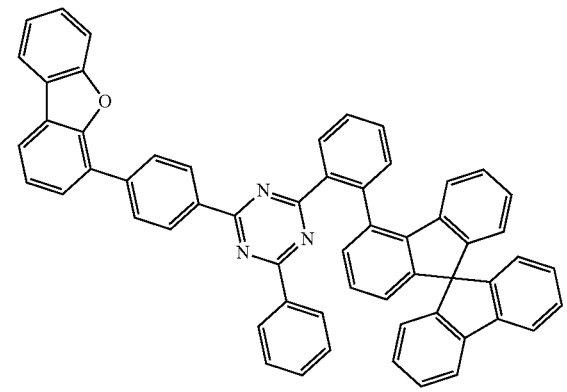

-continued
d-137
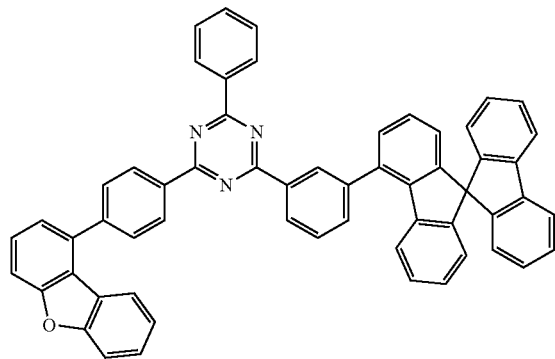
d-138
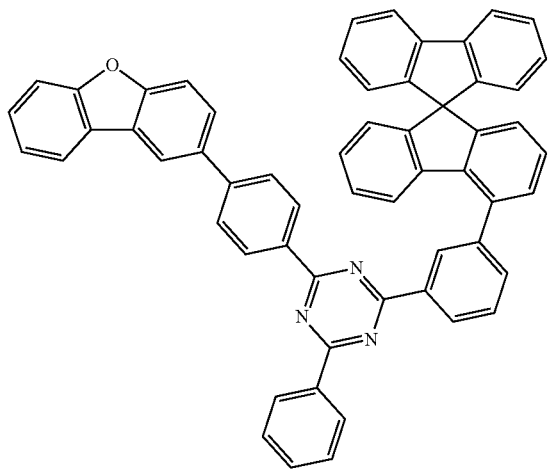
d-139
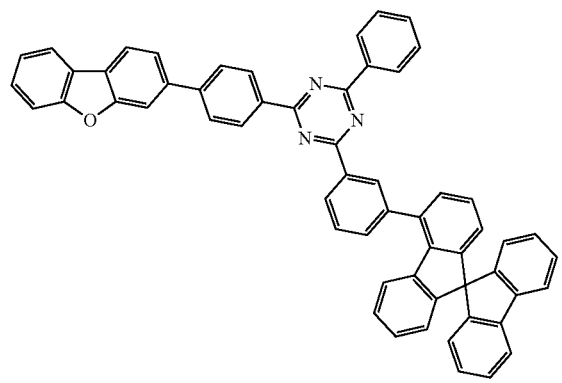
d-140
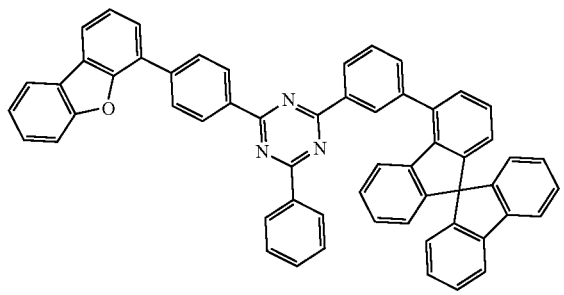
d-141
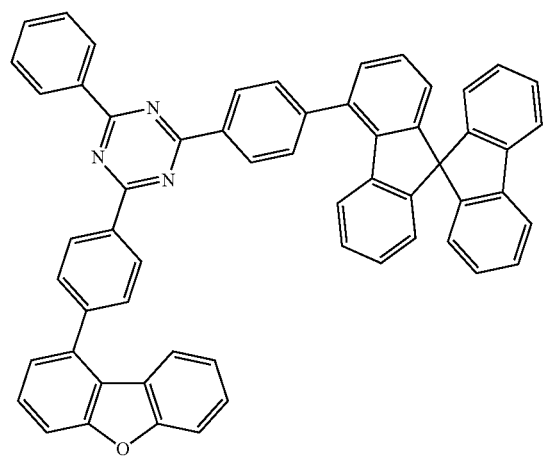
d-142
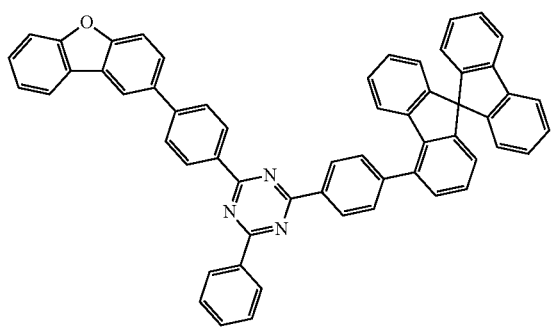

-continued
d-143
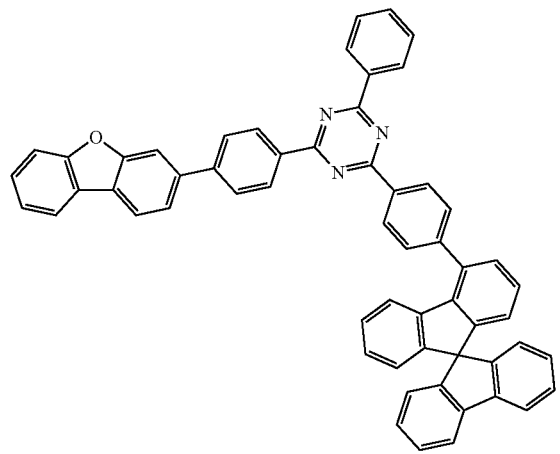
d-144
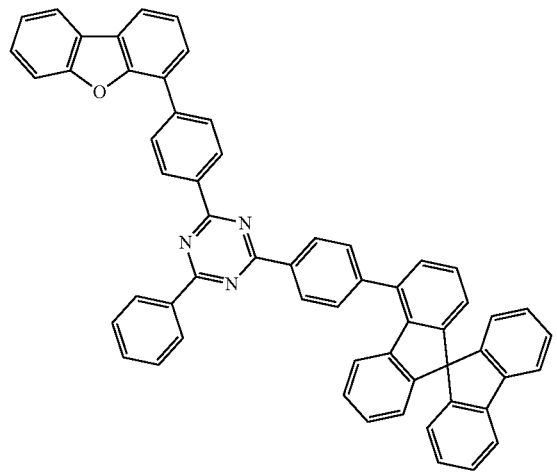
d-145
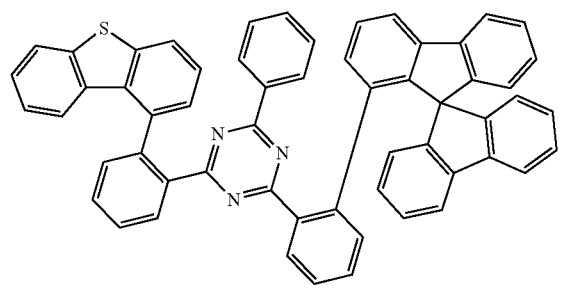
d-146
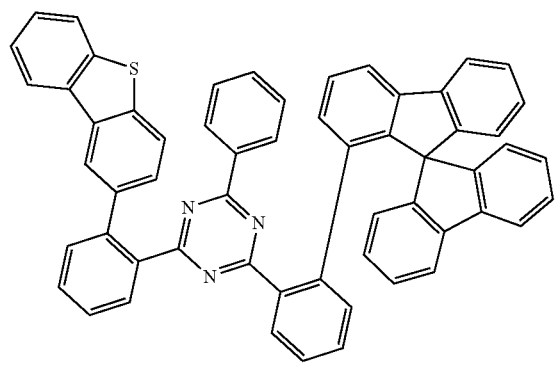
d-147
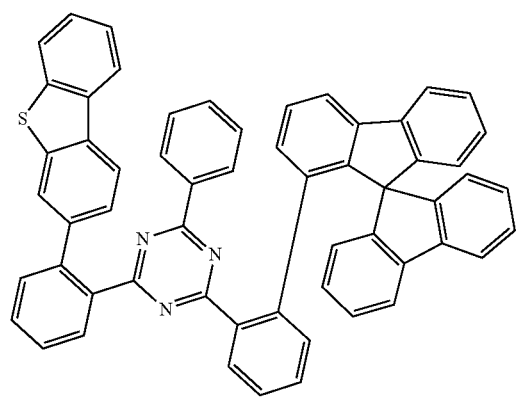
d-148
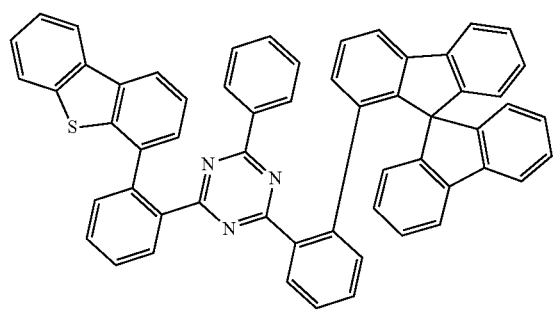

429 430
d-149
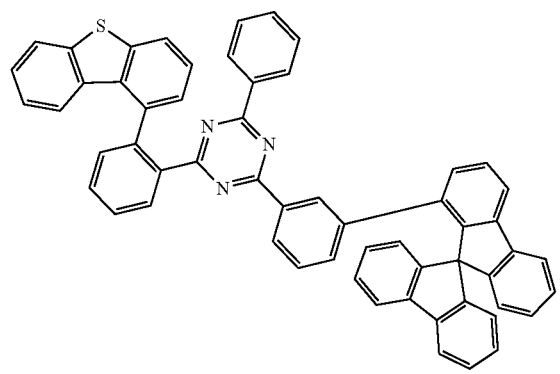
d-150
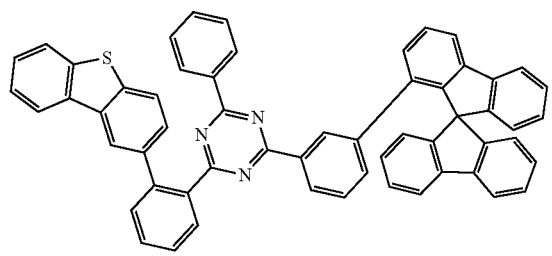
d-151
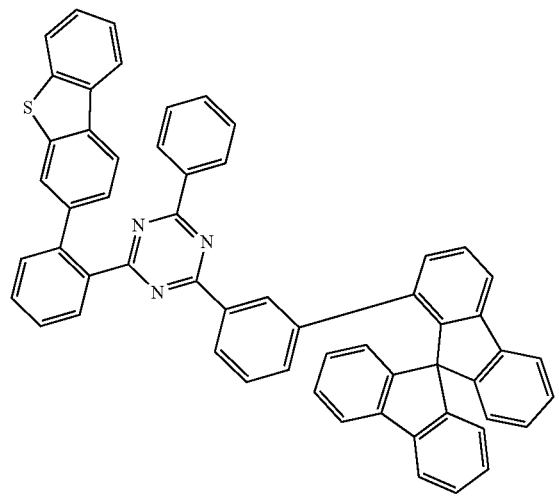
d-152
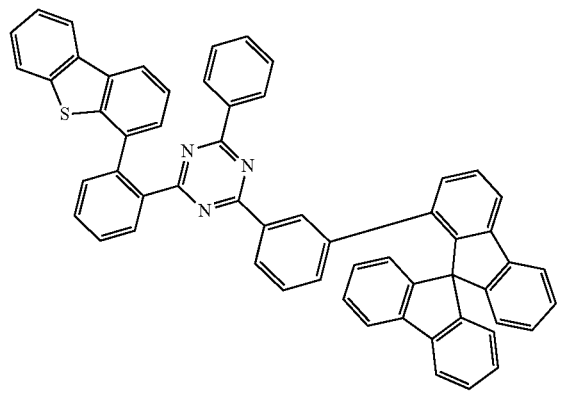
d-153
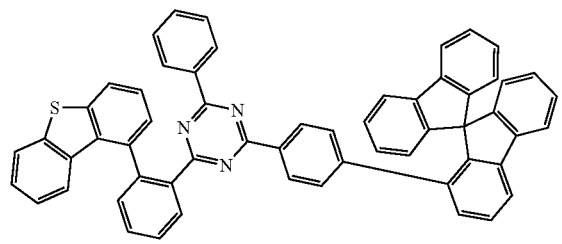
d-154
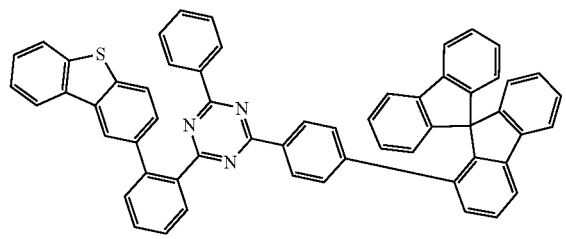

-continued
d-155
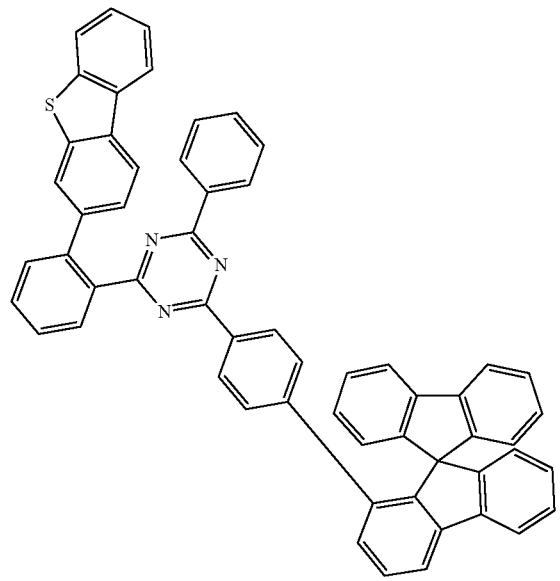
d-156
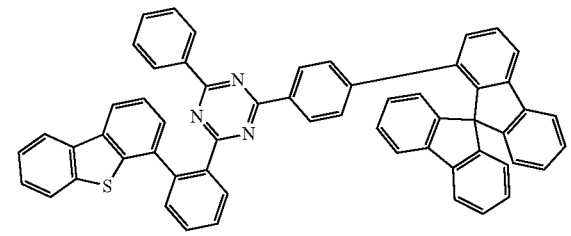
d-157
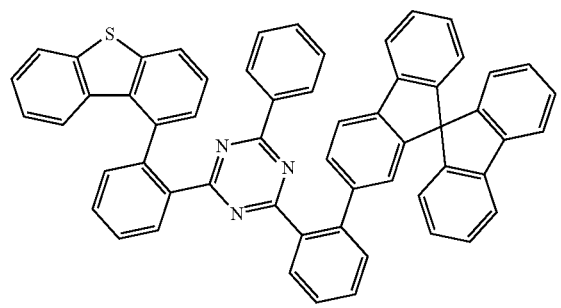
d-158
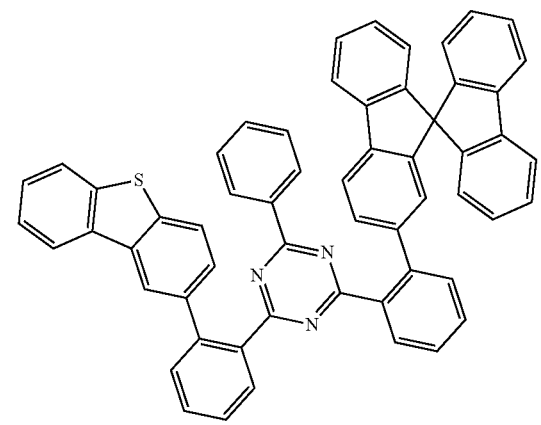
d-159
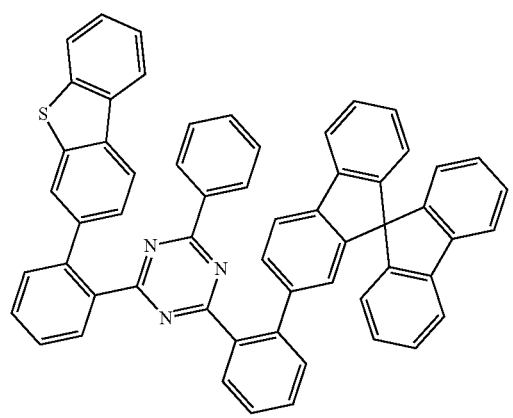
d-160
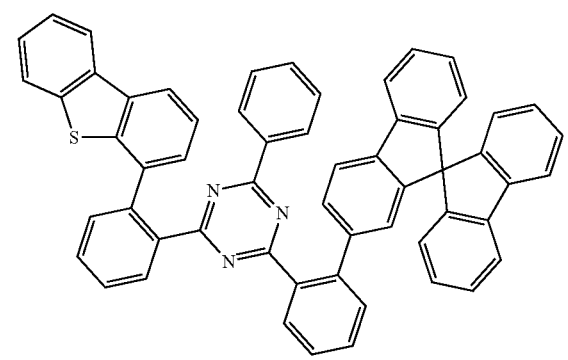

-continued
d-161
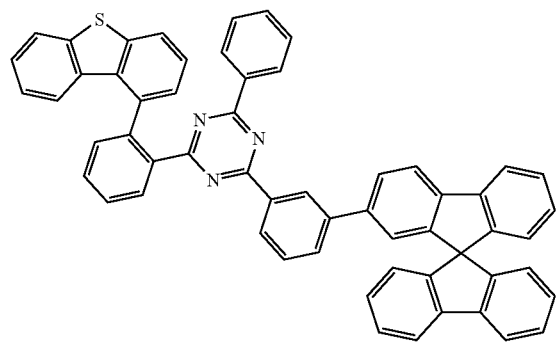
d-162
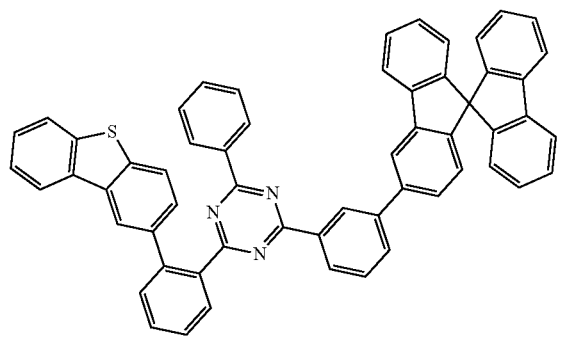
d-163
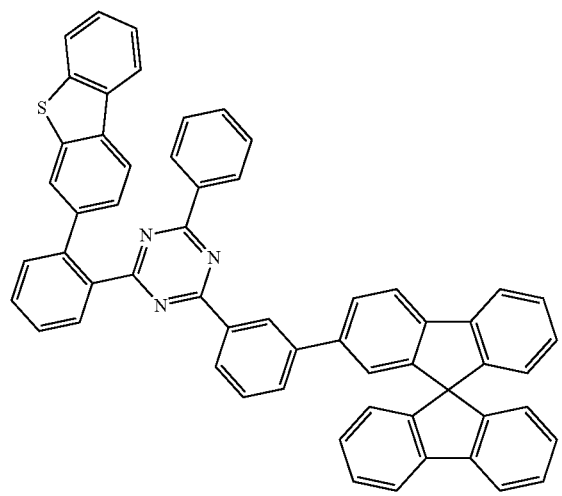
d-164
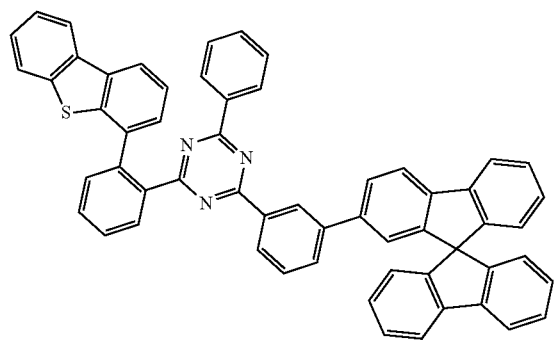
d-165
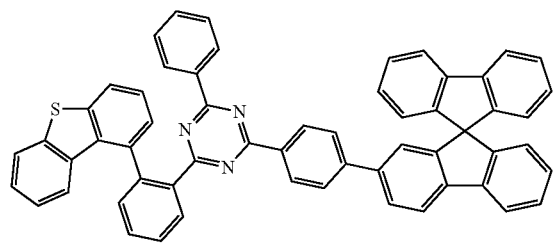
d-166
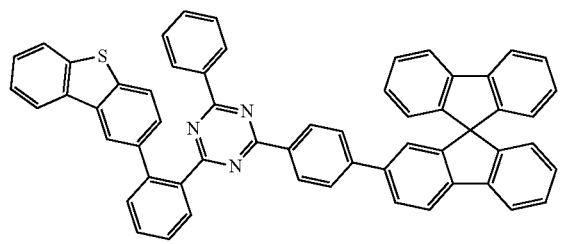

-continued
d-167
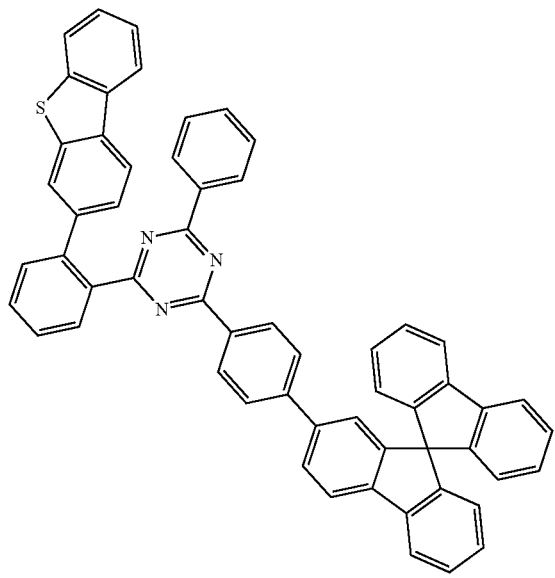
d-168
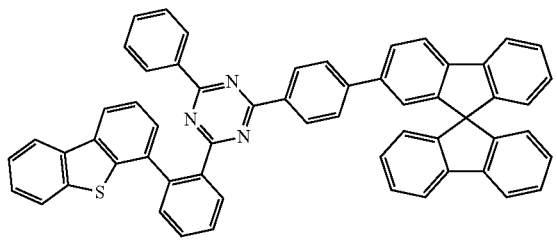
d-169
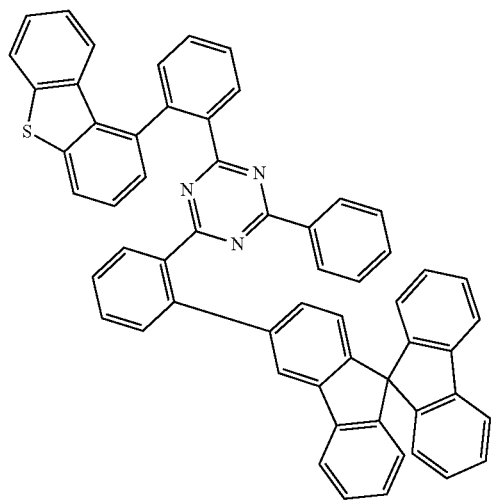
d-170
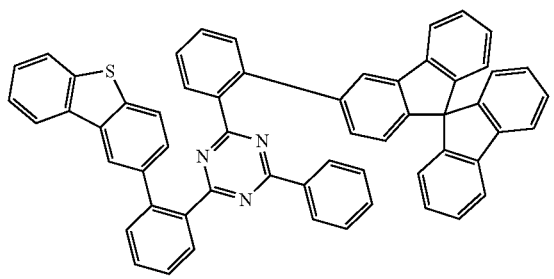

-continued
d-171
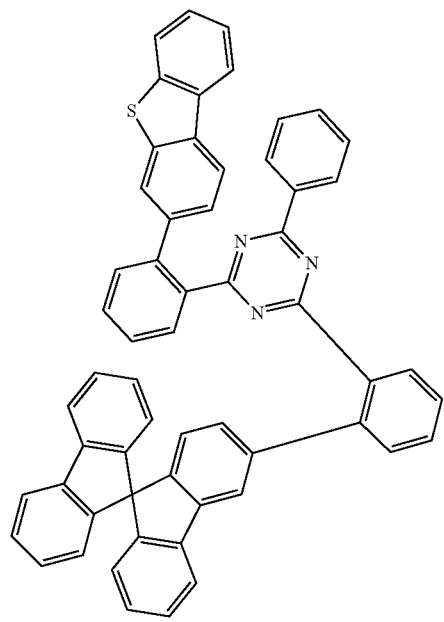
d-172
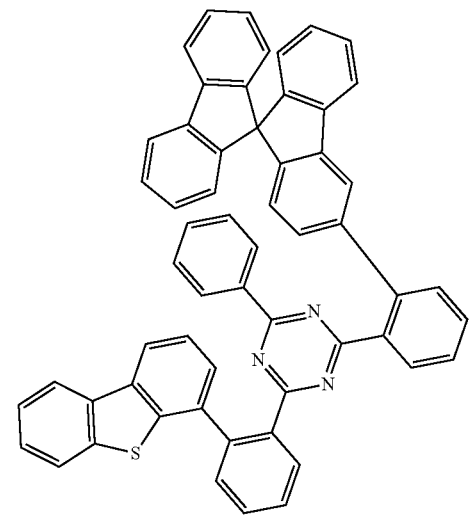
d-173
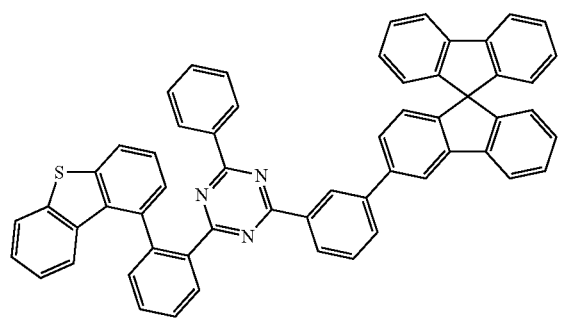
d-174
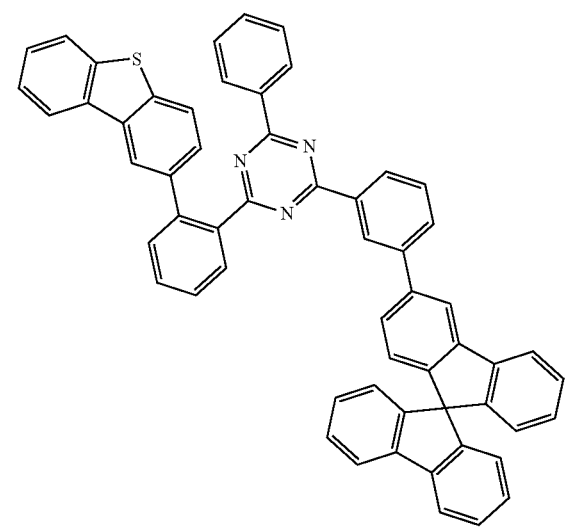
d-175
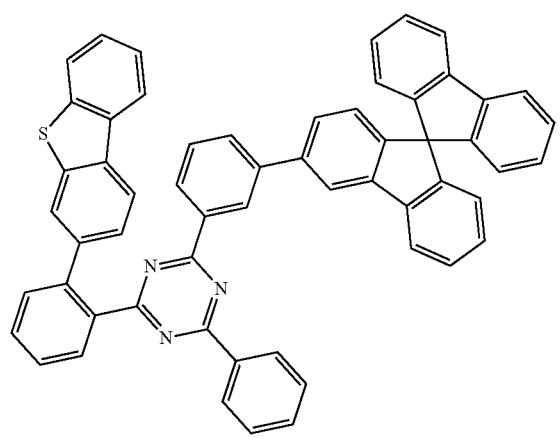
d-176
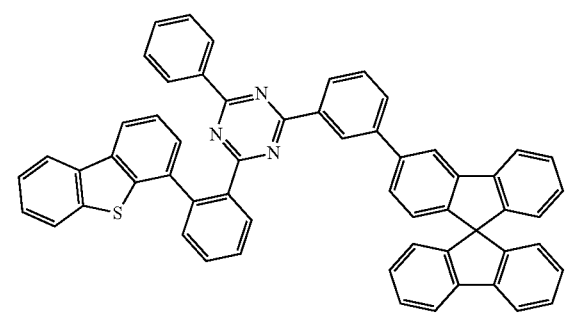

-continued
d-177
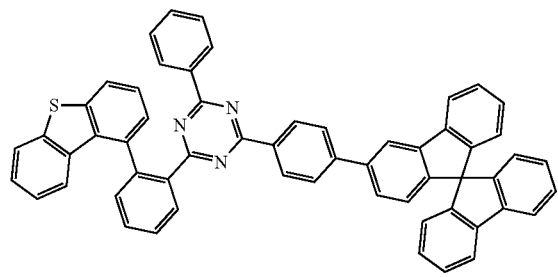
d-178
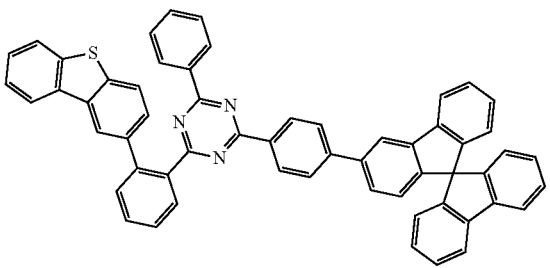
d-179
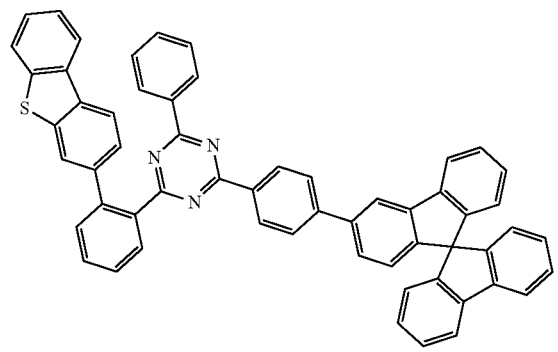
d-180
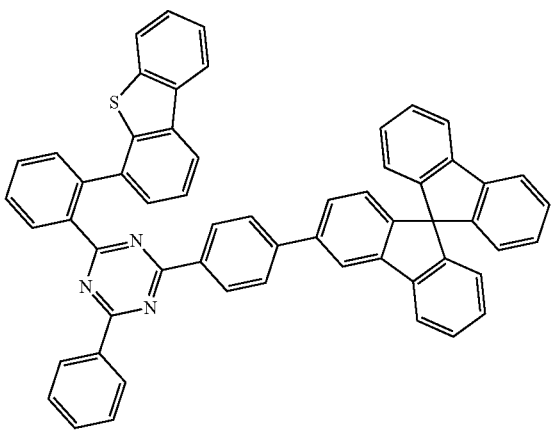
d-181
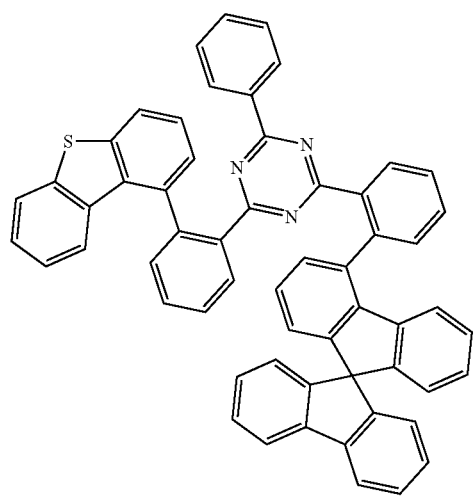
d-182
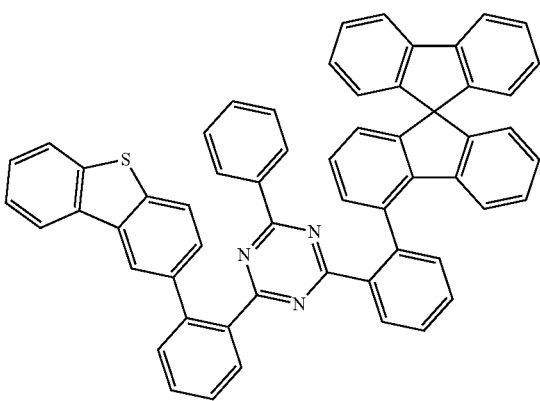

-continued
d-183
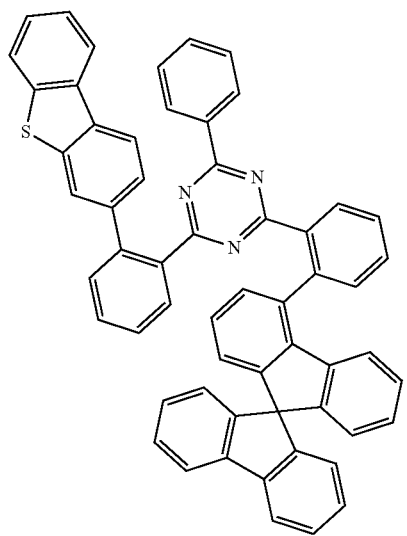
d-184
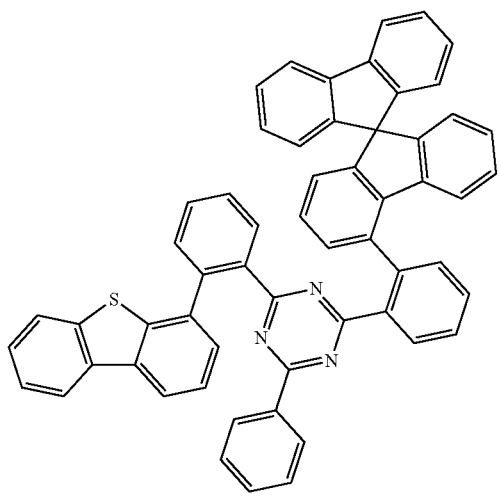
d-185
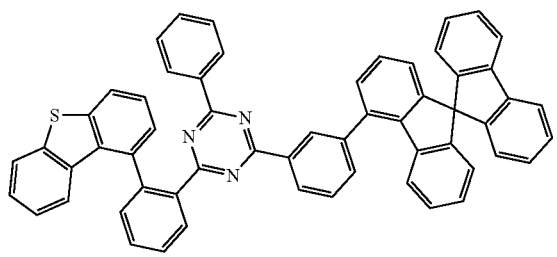
d-186
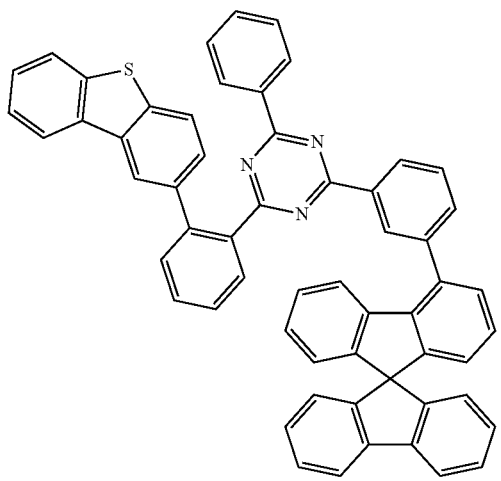
d-187
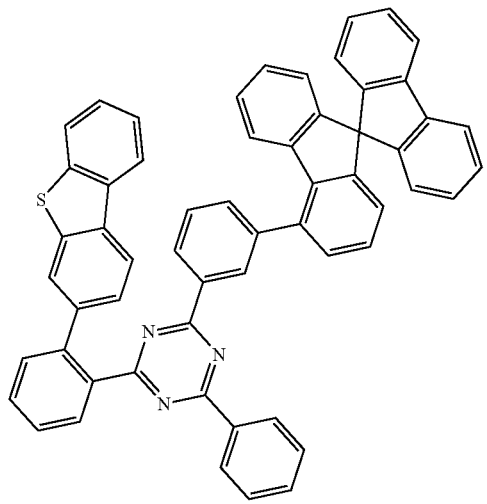
d-188
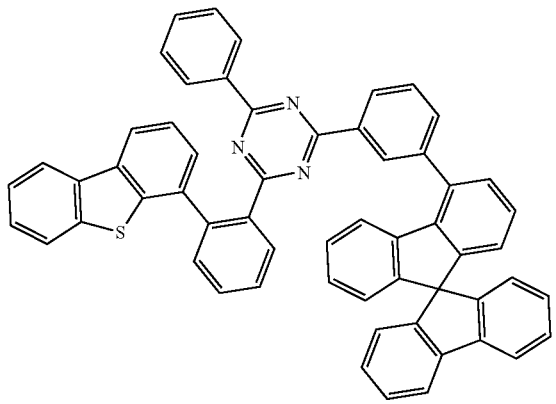

-continued
d-189
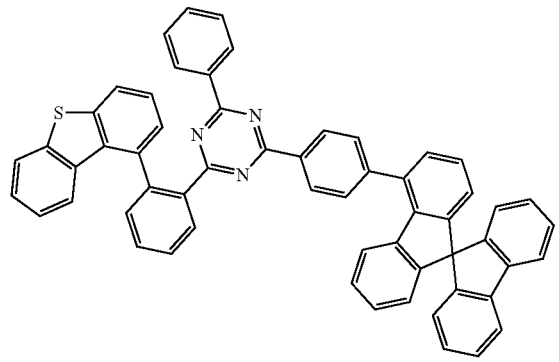
d-190
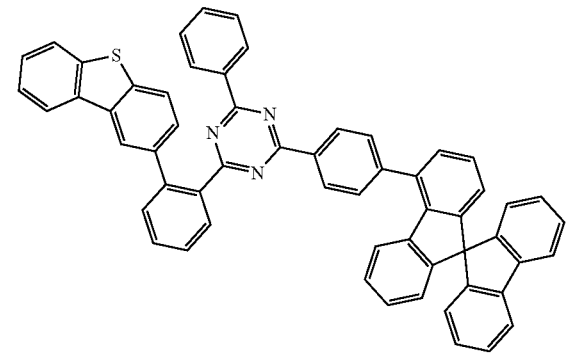
d-191
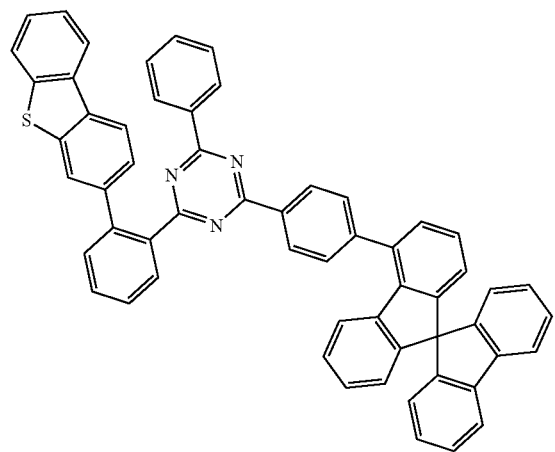
d-192
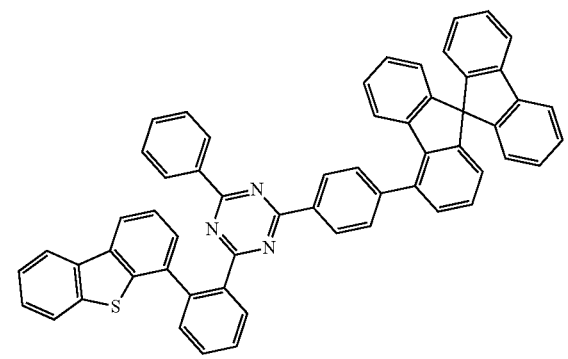
d-193
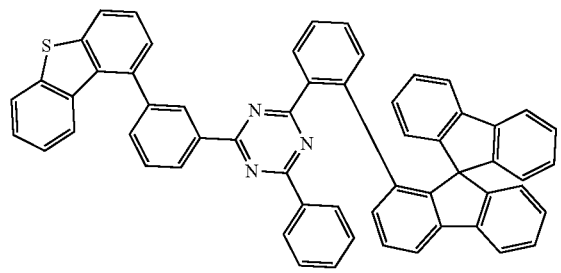
d-194
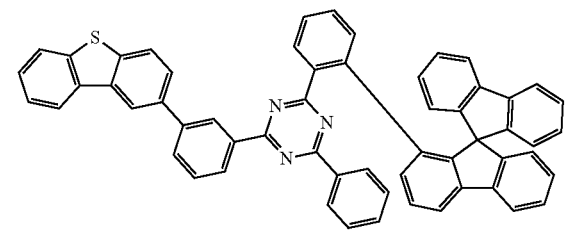
d-195
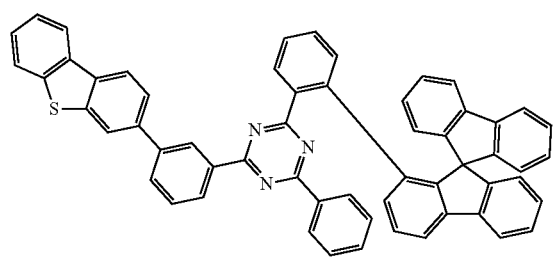
d-196
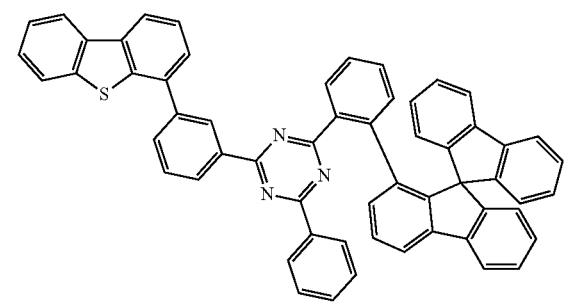

-continued
d-197
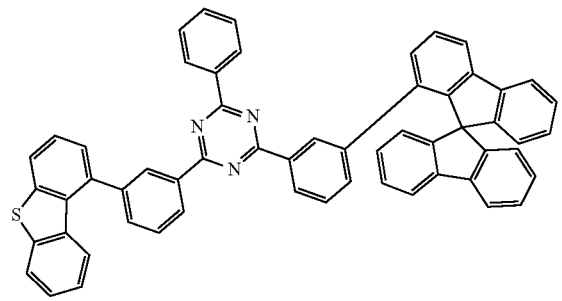
d-198
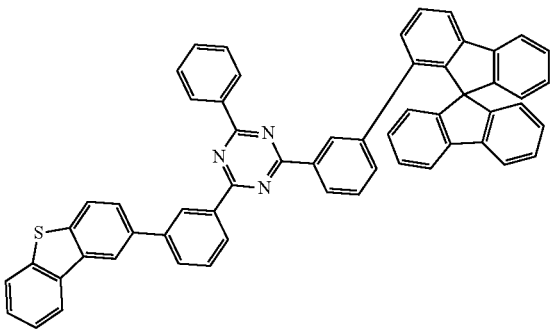
d-199
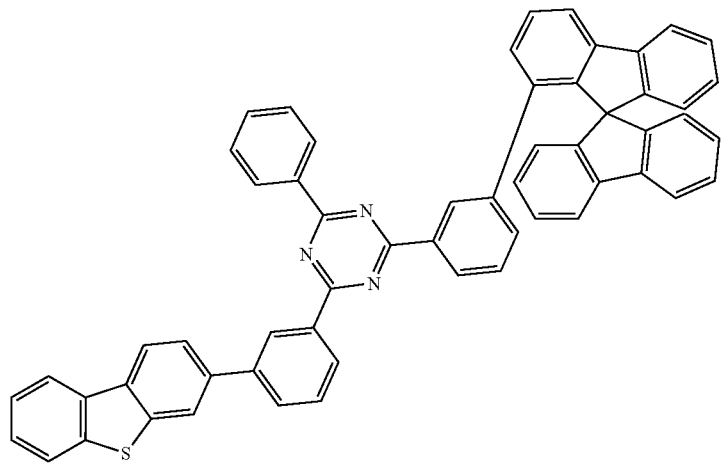
d-200
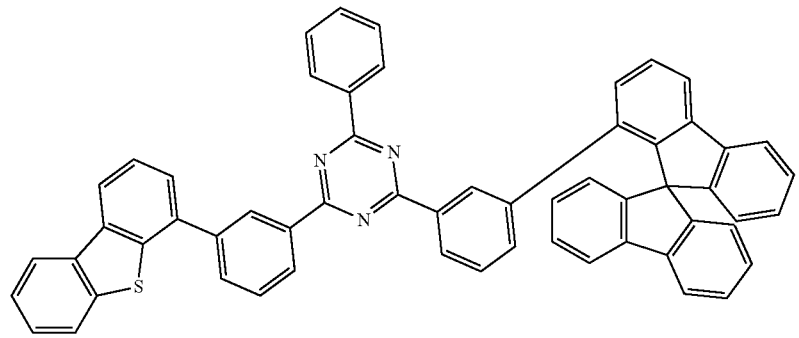
d-201
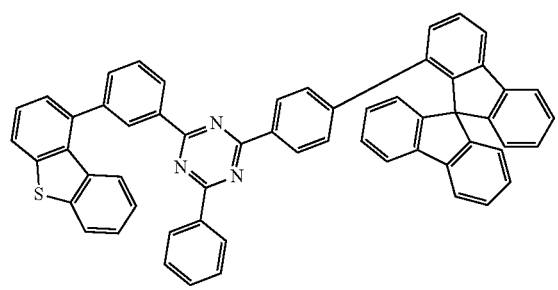
d-202
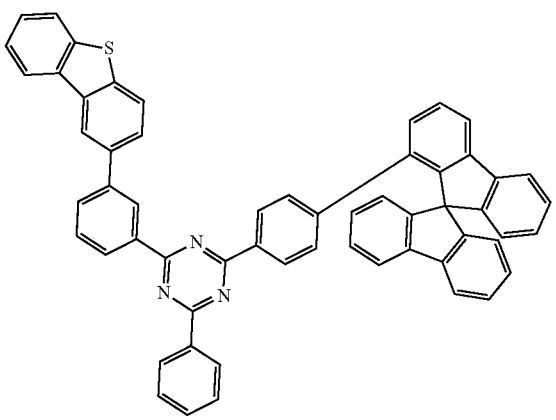

d-203
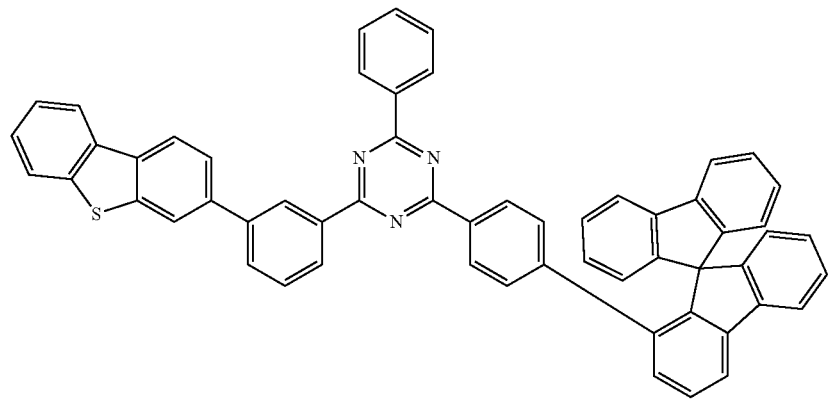
d-204
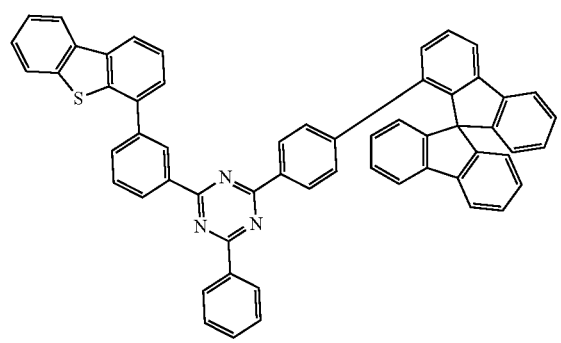
d-205
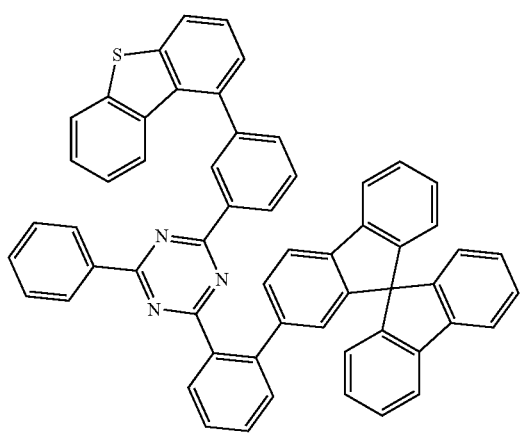
d-206
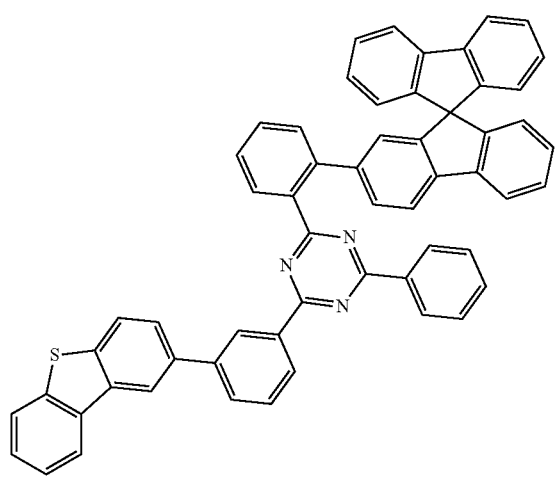
d-207
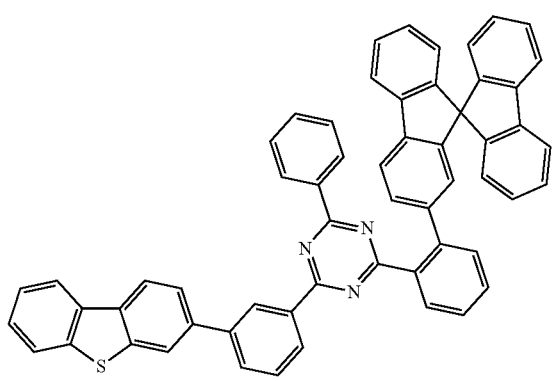

-continued
d-208
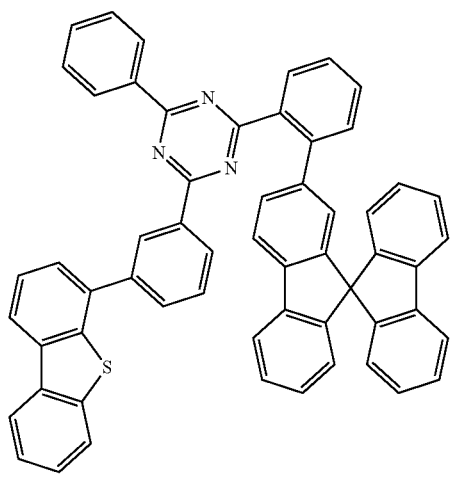
d-209
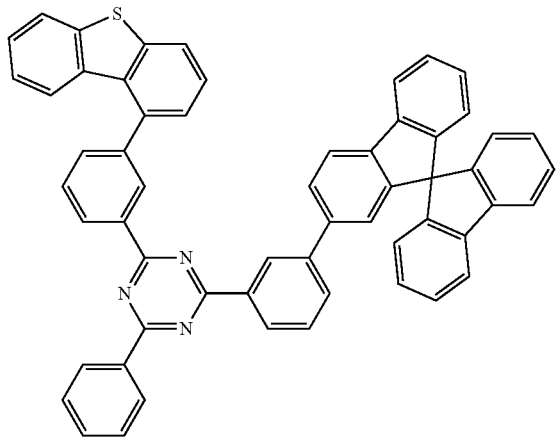
d-210
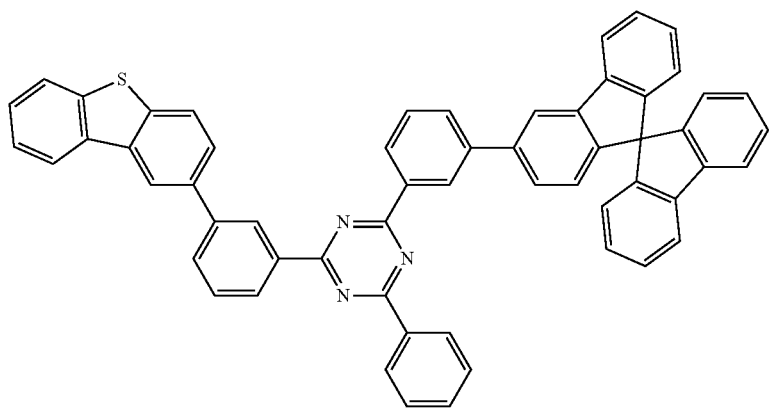
d-211
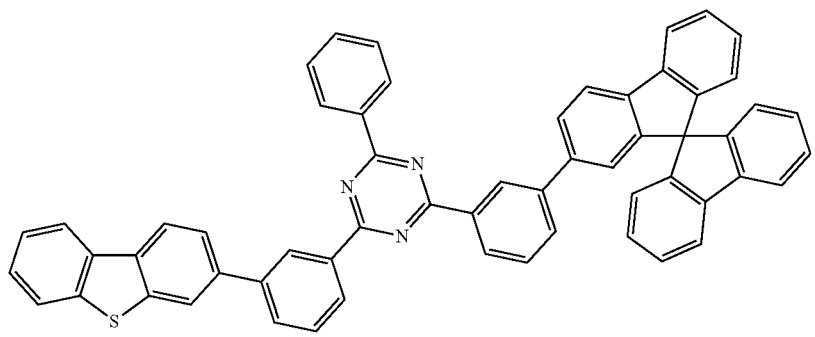

-continued
d-212
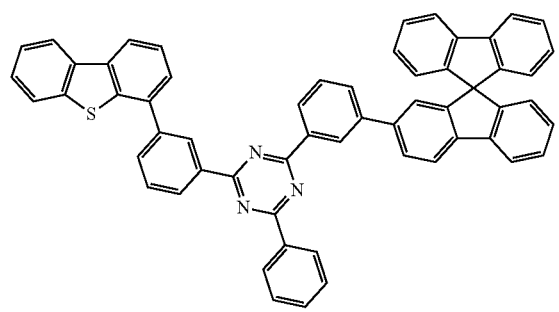
d-213
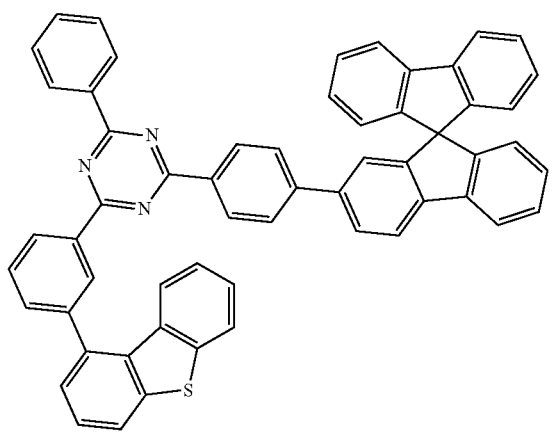
d-214
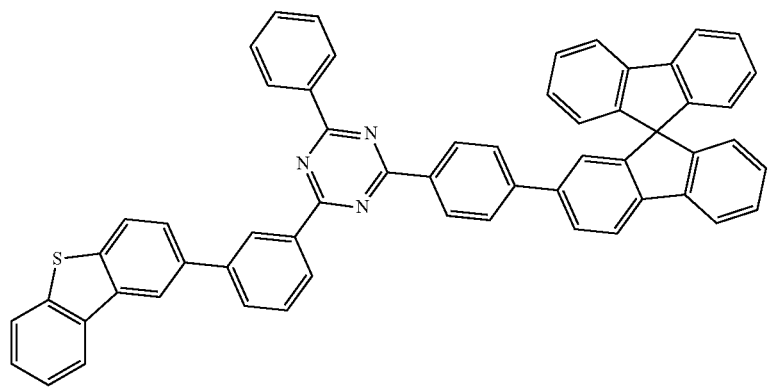
d-215
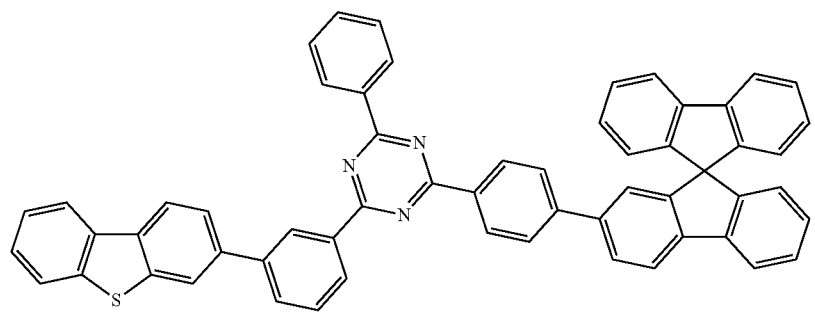
d-216
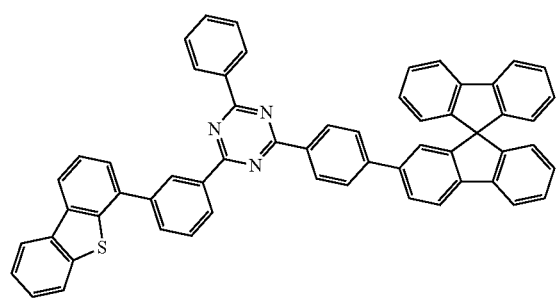
d-217
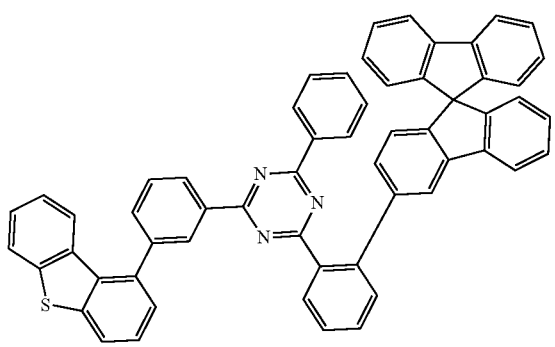

-continued
d-218
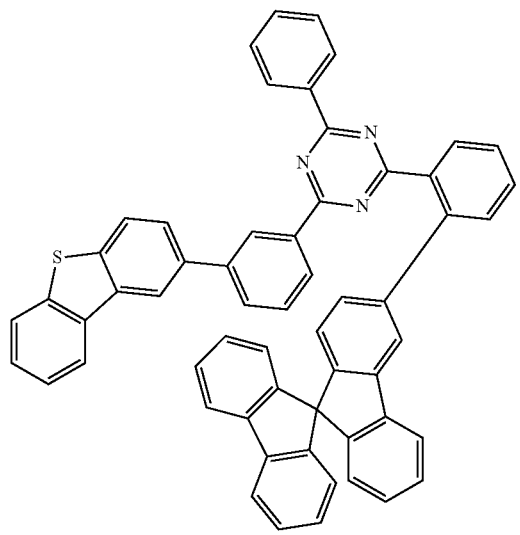
d-219
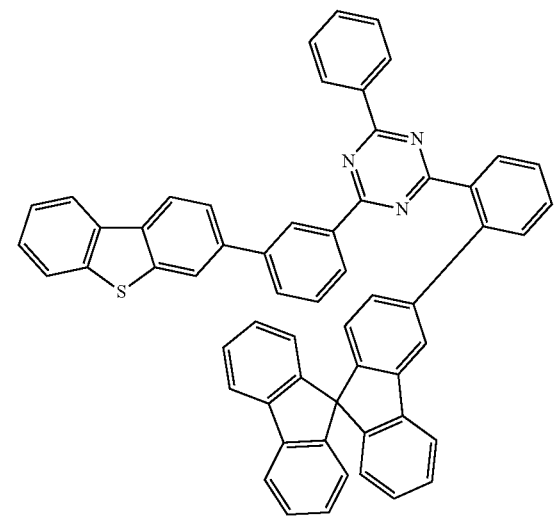
d-220
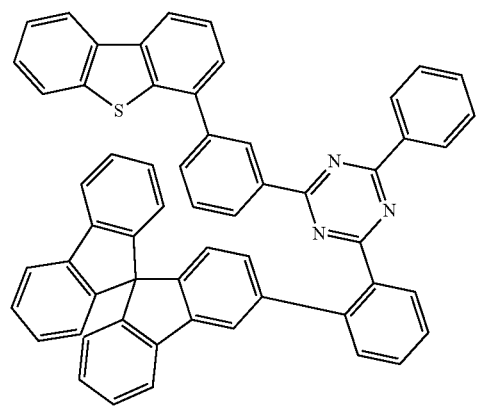
d-221
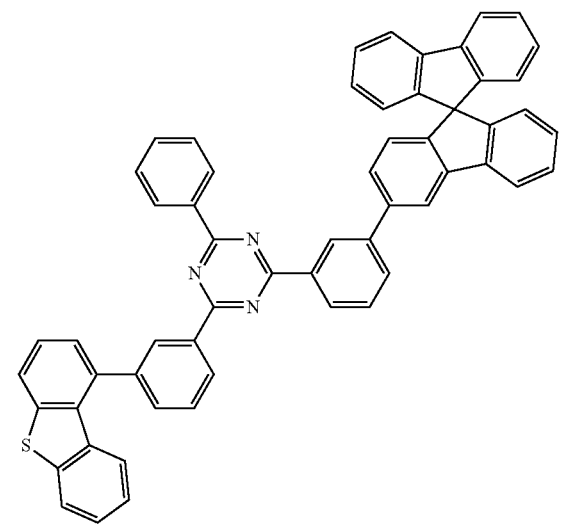
d-222
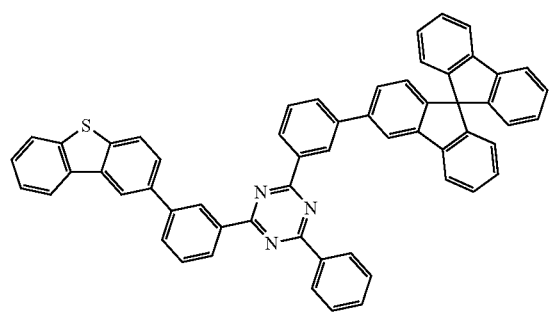
d-223
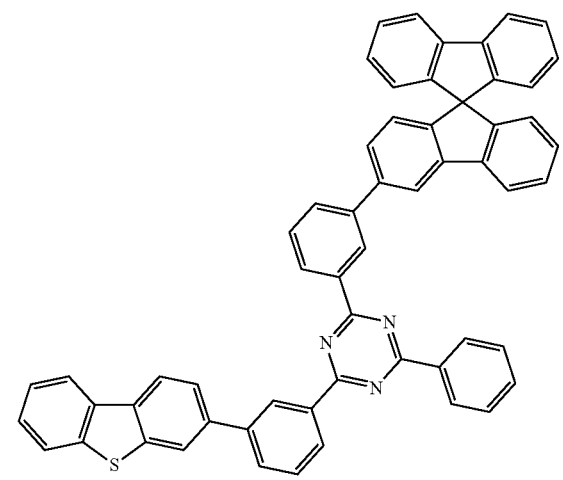

-continued
d-224
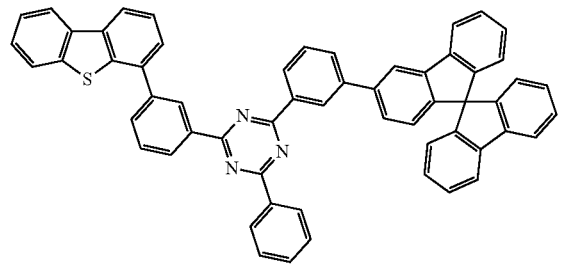
d-225
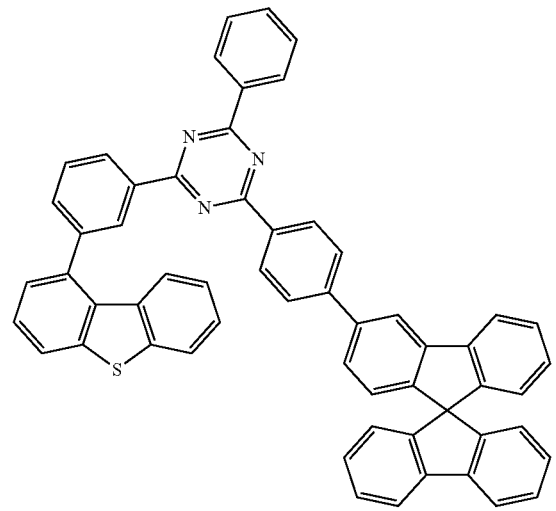
d-226
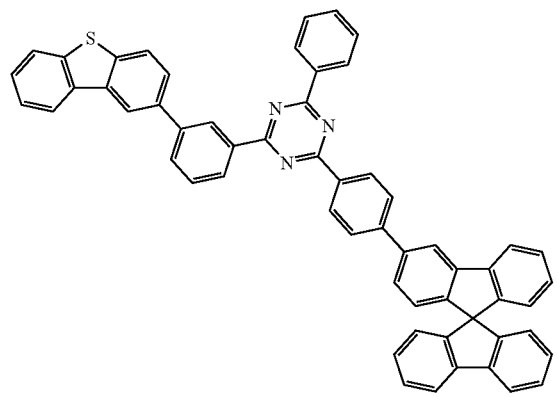
d-227
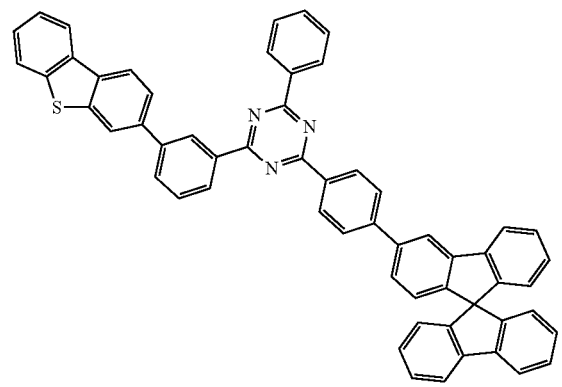
d-228
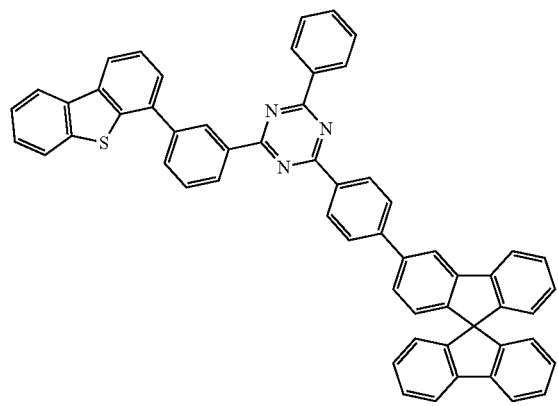
d-229
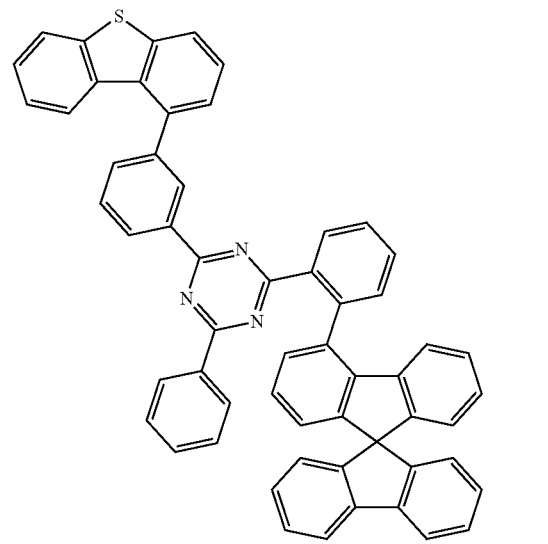

-continued
d-230
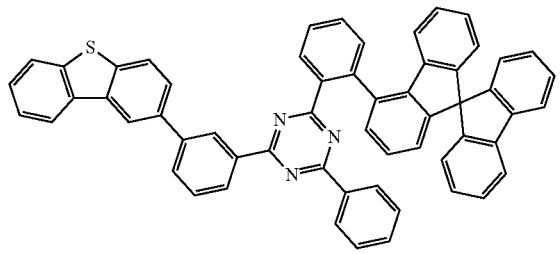
d-231
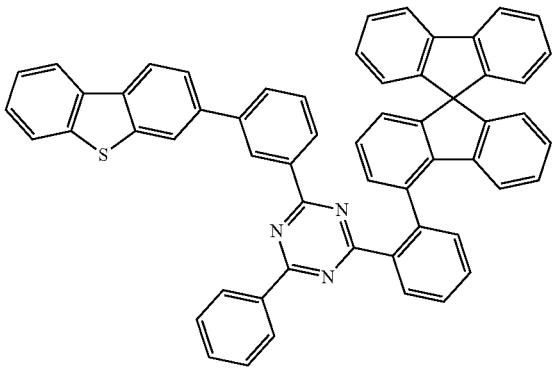
d-232
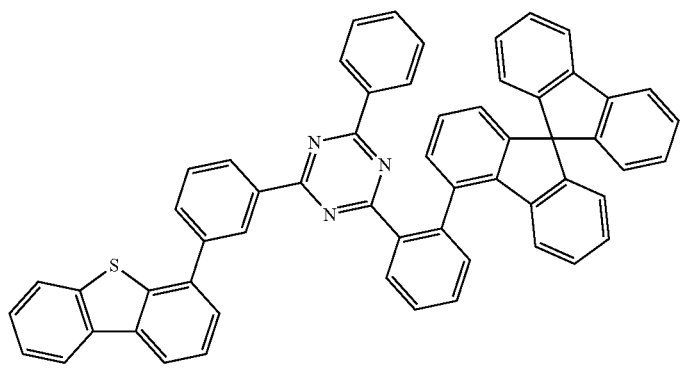
d-233
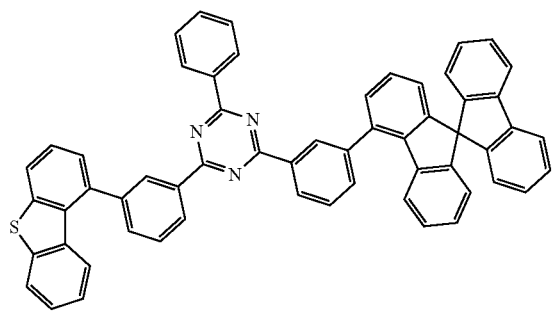
d-234
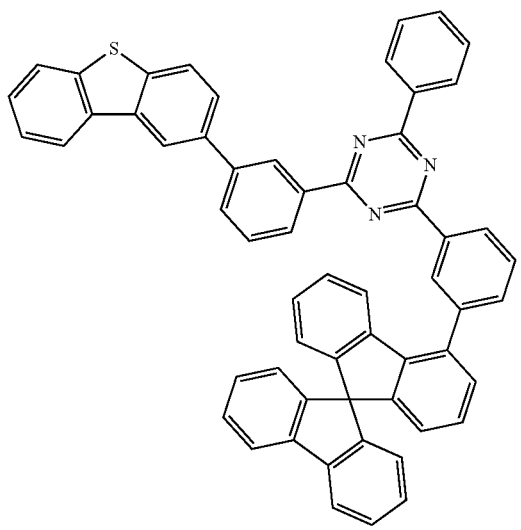

-continued
d-235
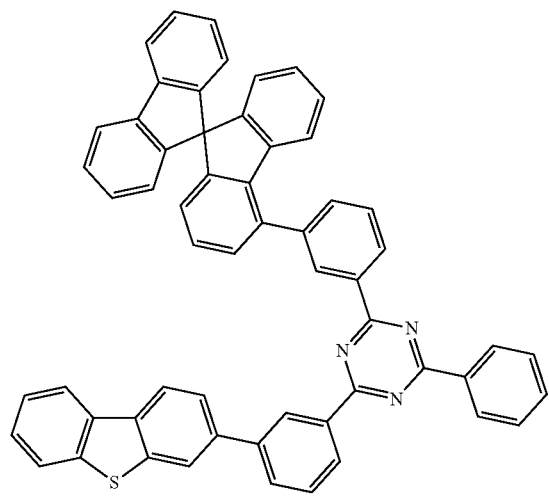
d-236
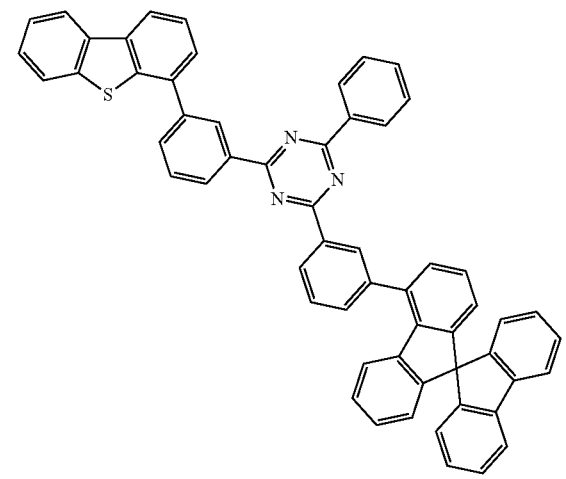
d-237
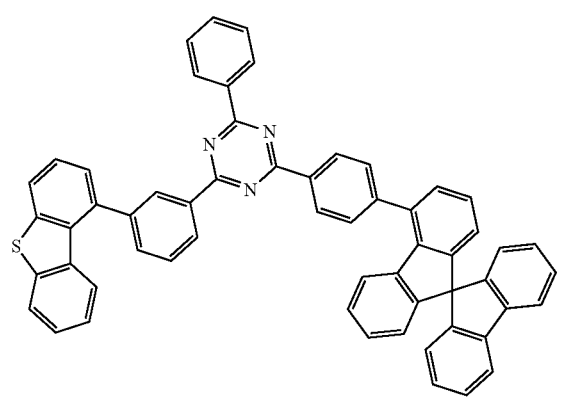
d-238
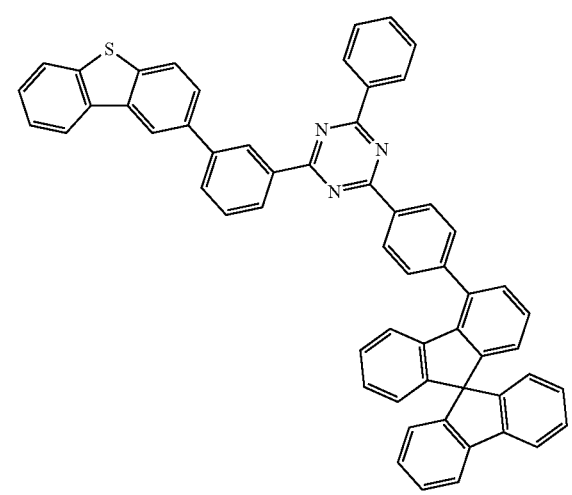
d-239
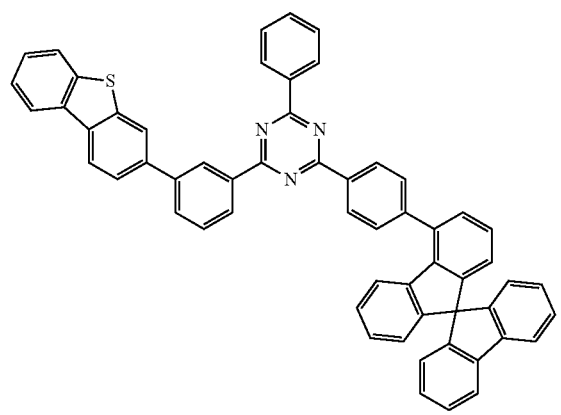
d-240
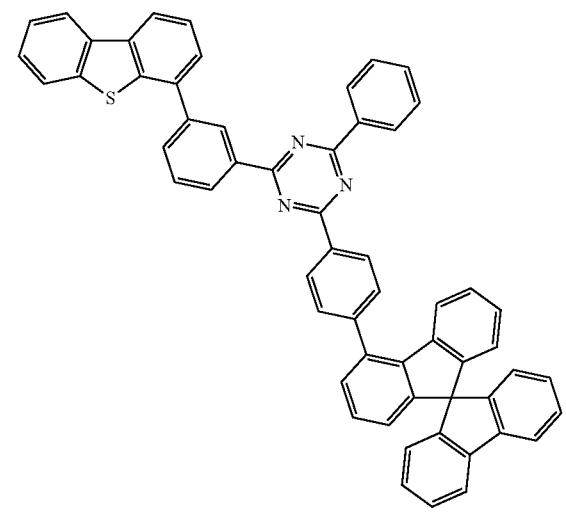

-continued
d-241
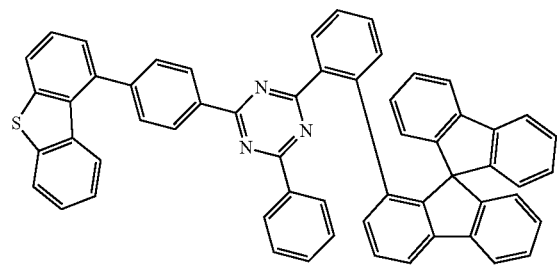
d-242
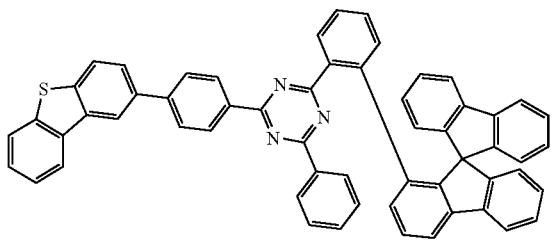
d-243
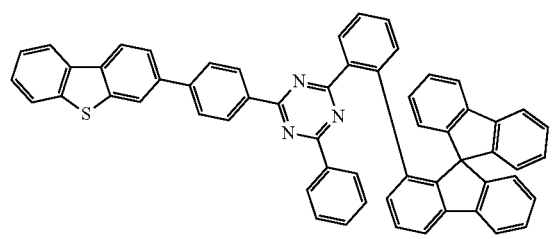
d-244
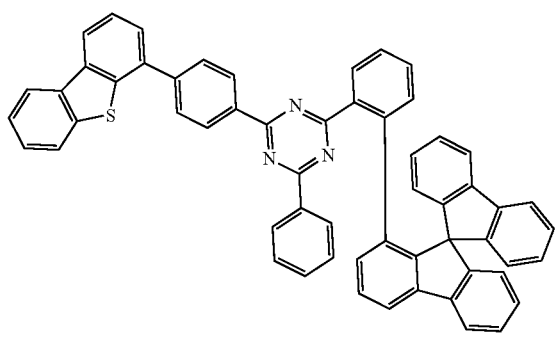
d-245
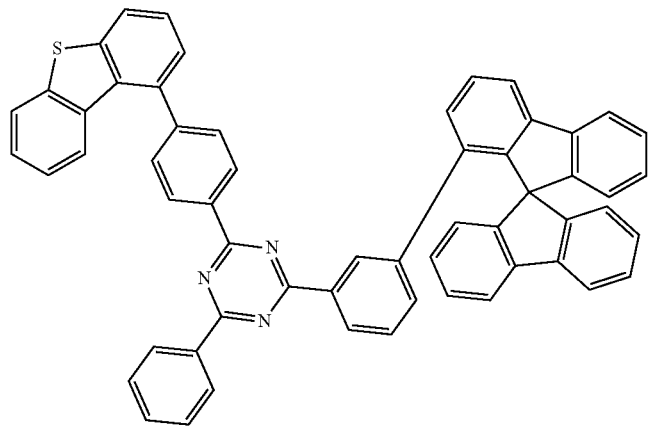
d-246
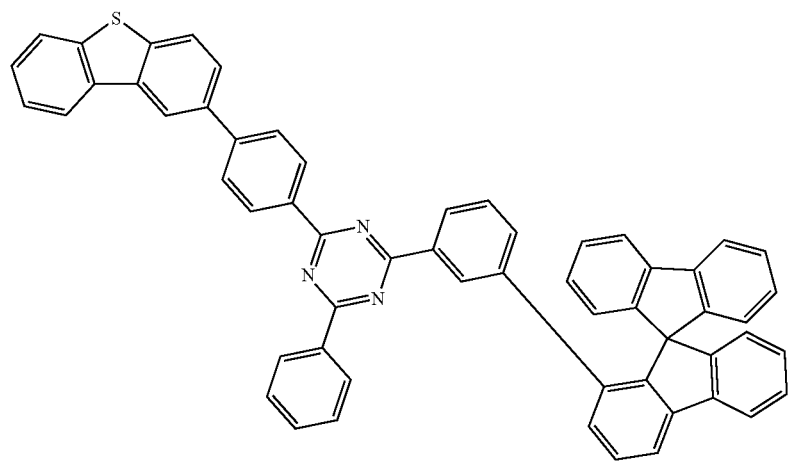

-continued
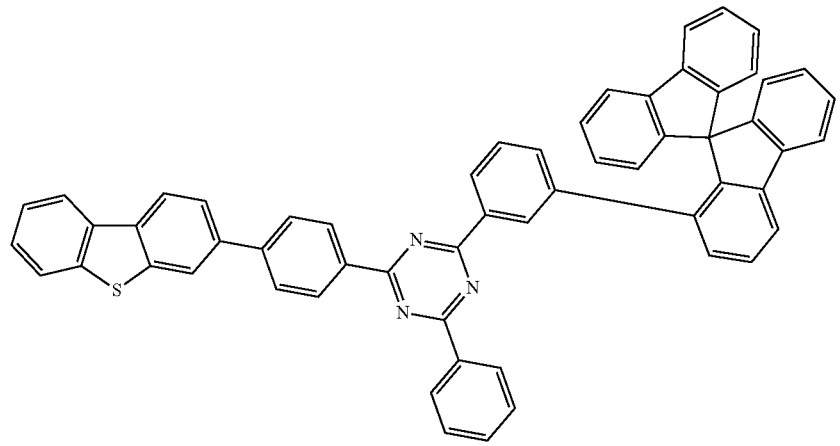
d-247
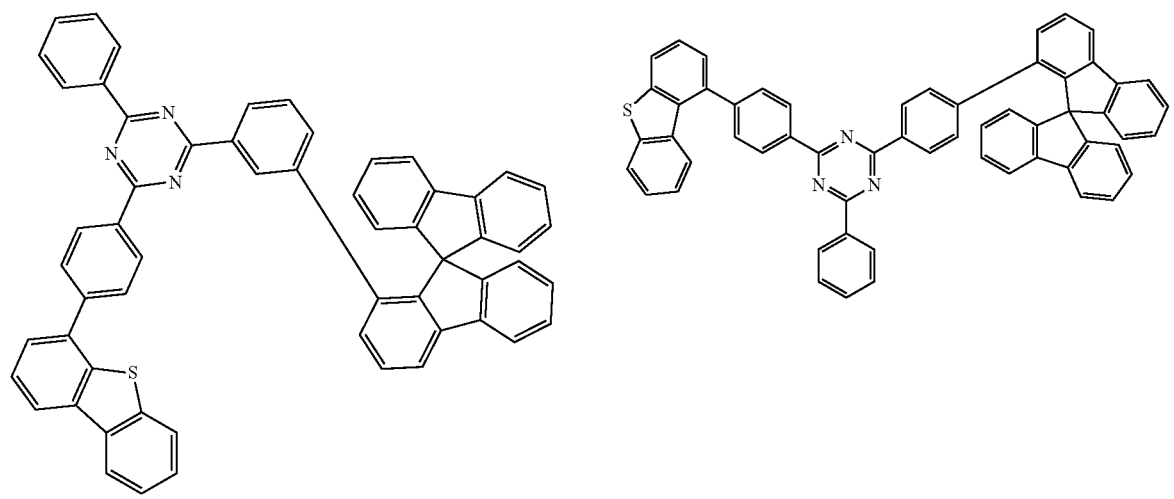
d-248
d-249
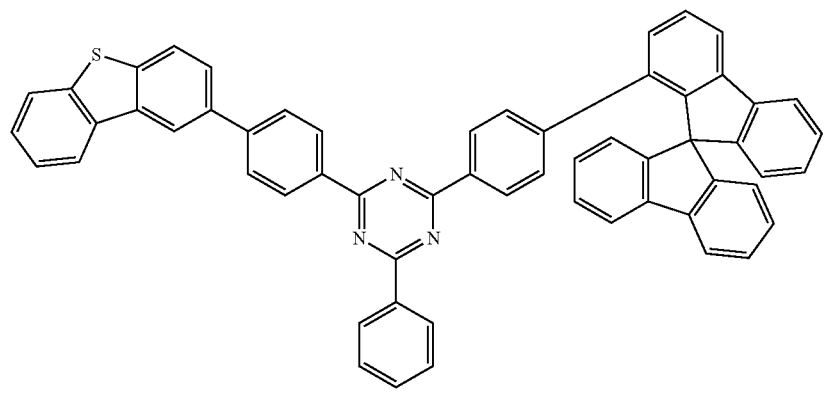
d-250

-continued
d-251
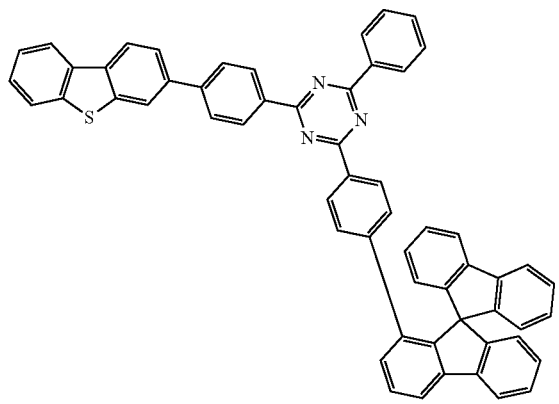
d-252
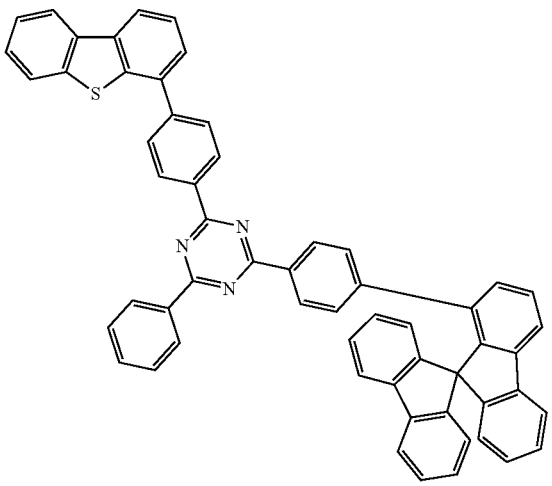
d-253
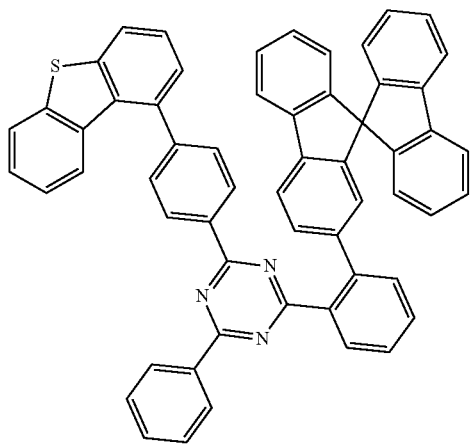
d-254
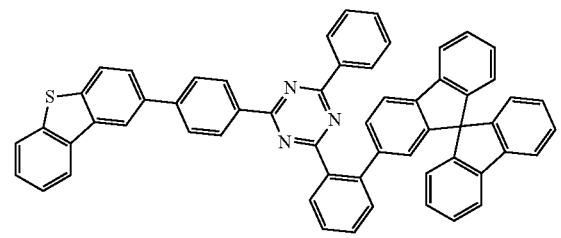
d-255
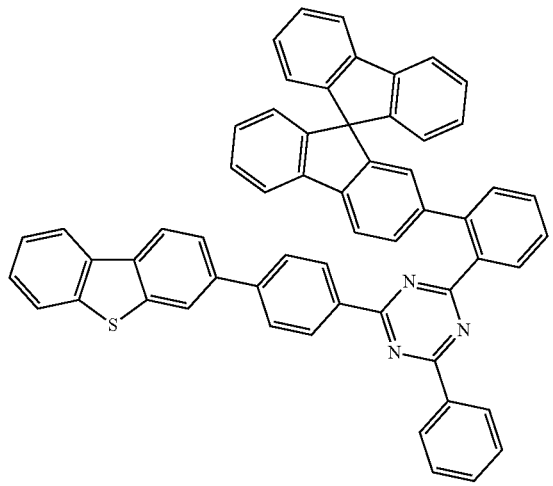
d-256
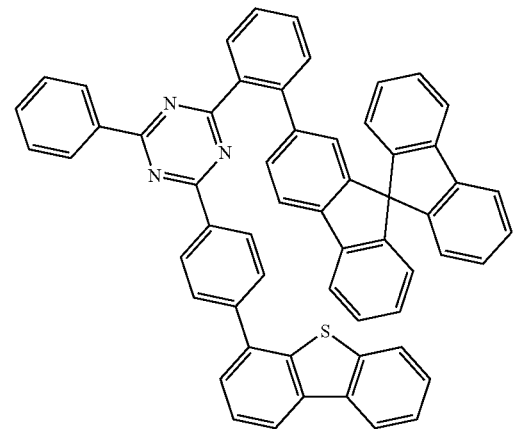

-continued
d-257
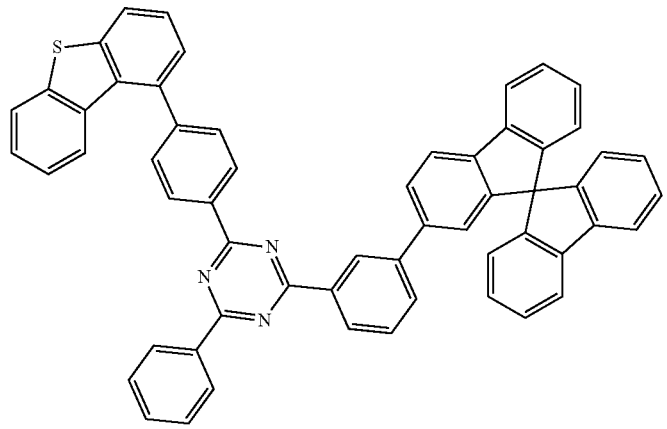
d-258
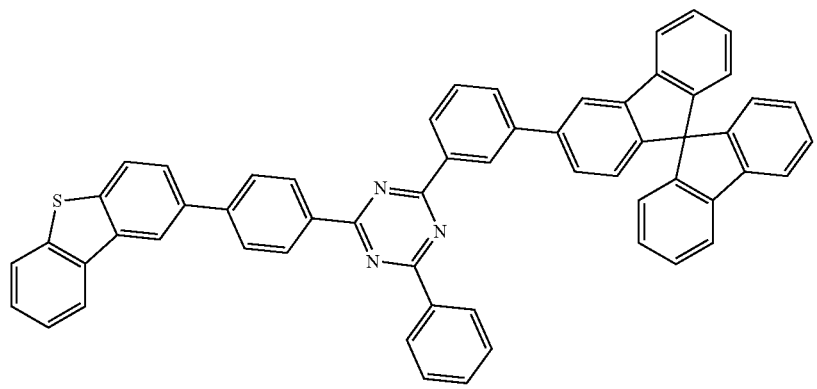
d-259
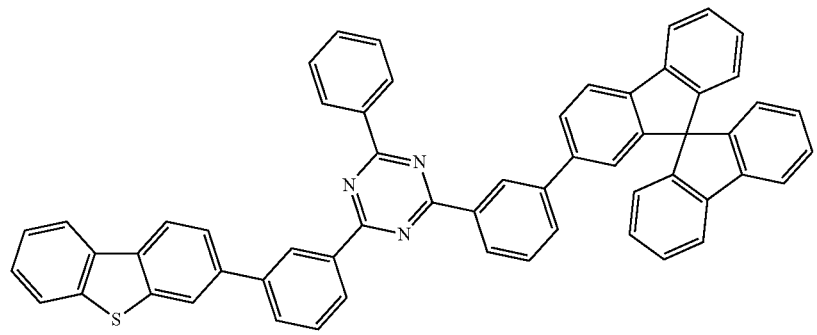
d-260
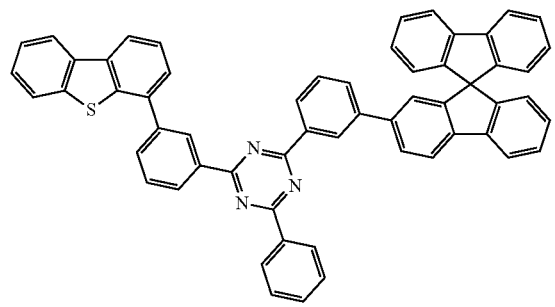
d-261
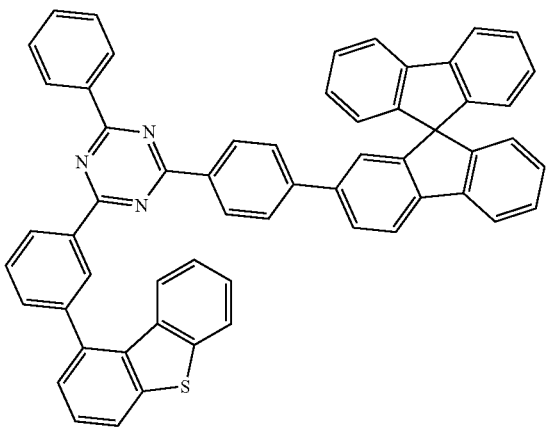

-continued
d-262
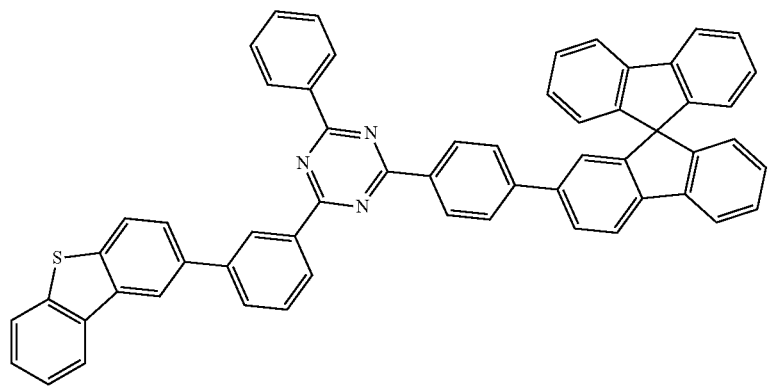
d-263
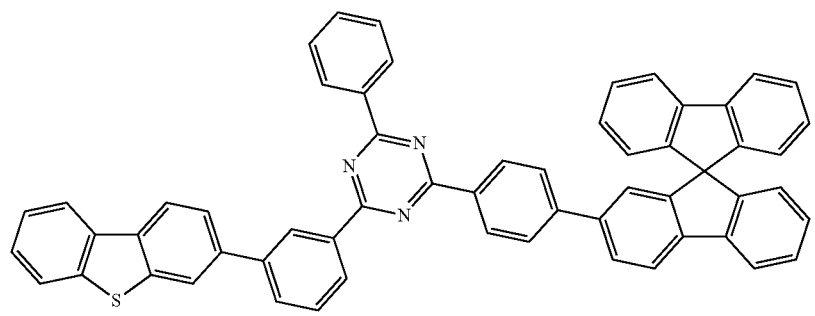
d-264
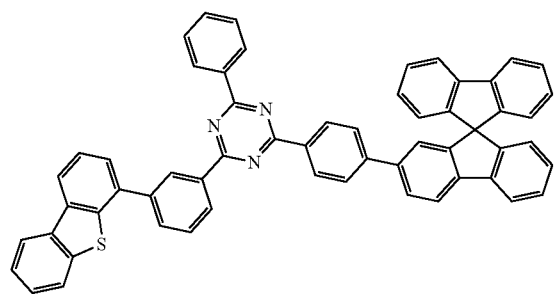
d-265
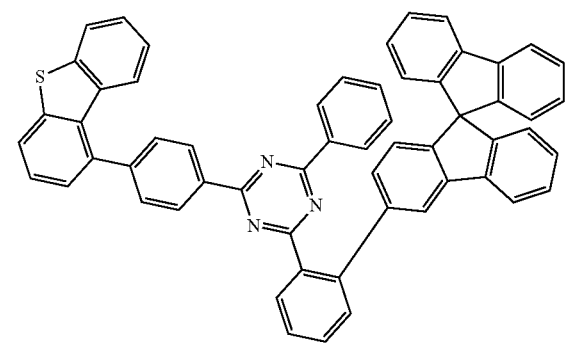
d-266
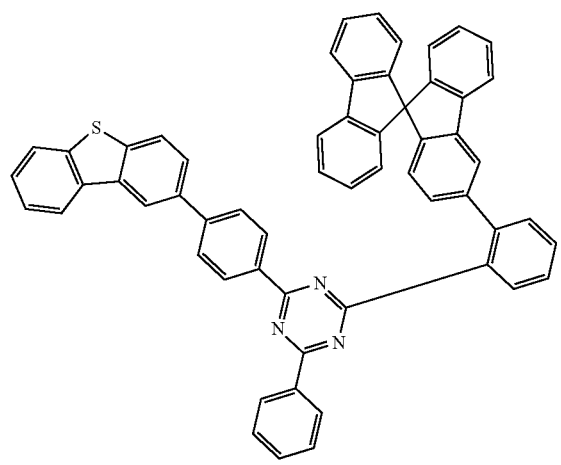
d-267
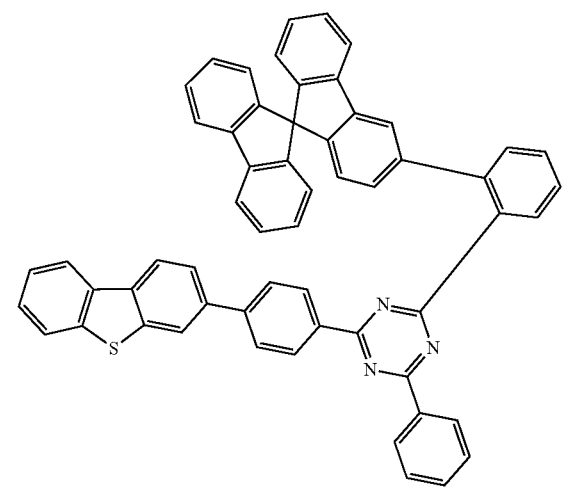

-continued
d-268
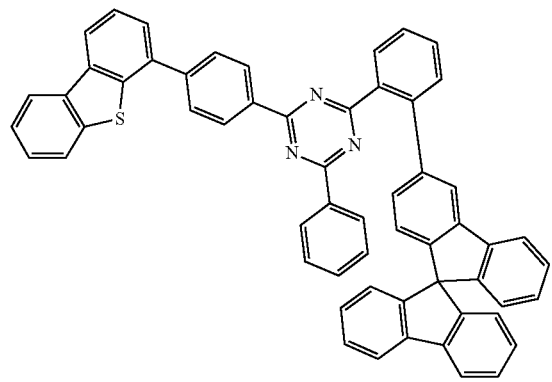
d-269
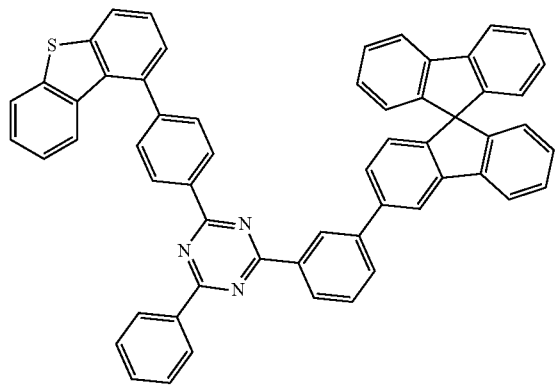
d-270
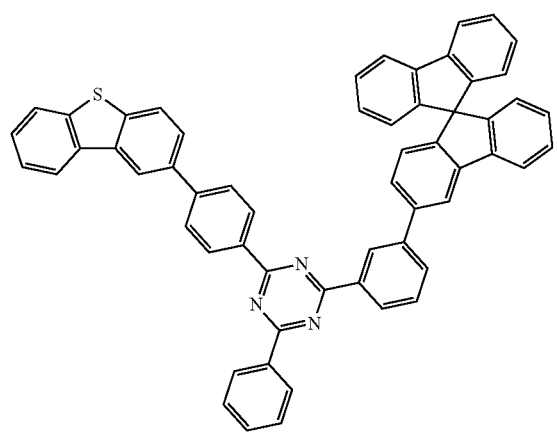
d-271
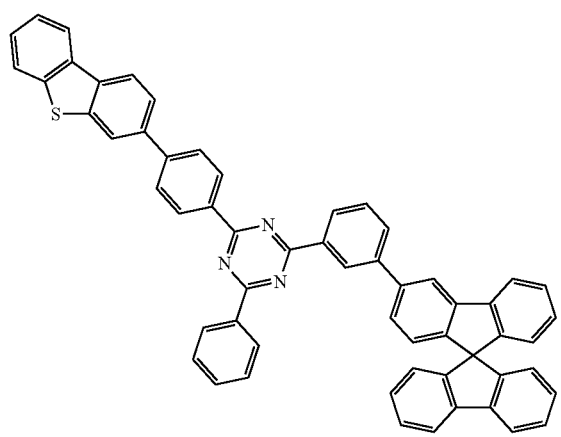
d-272
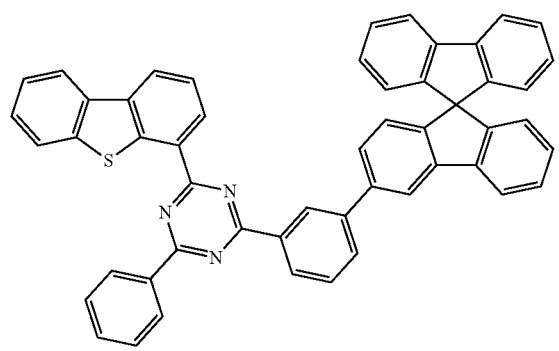
d-273
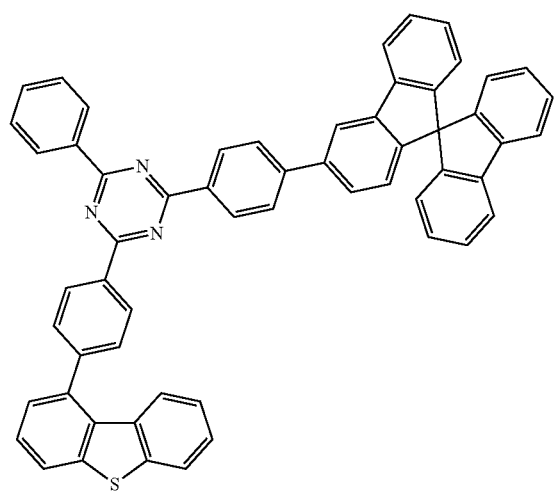

-continued
d-274
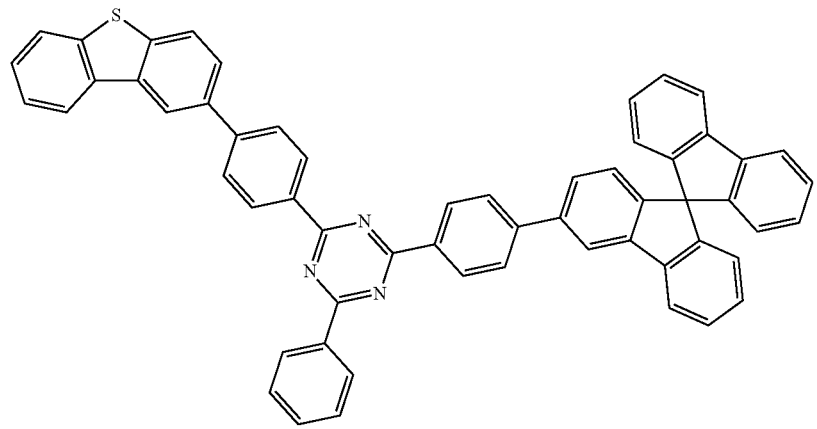
d-275
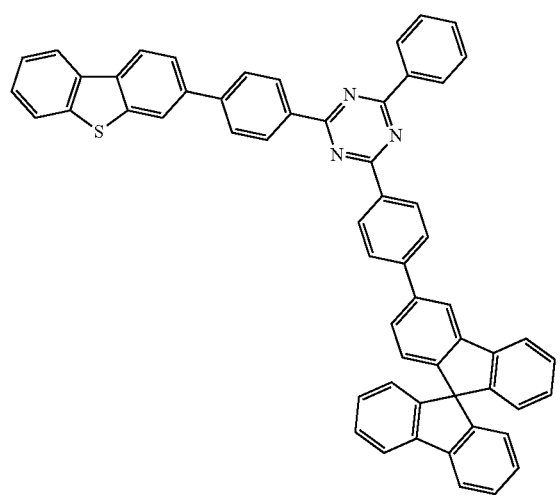
d-276
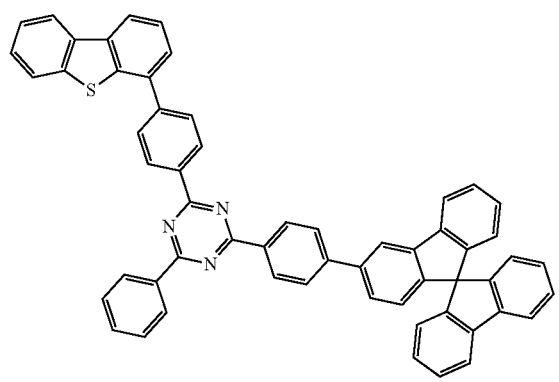
d-277
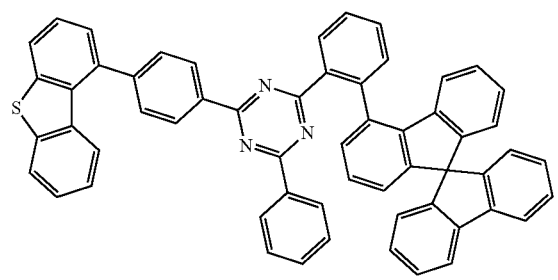
d-278
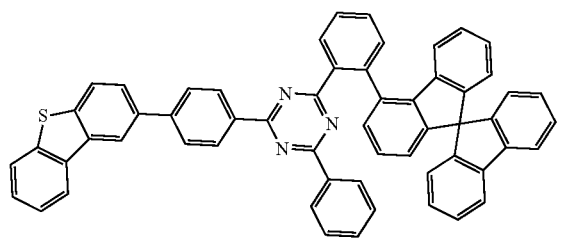
d-279
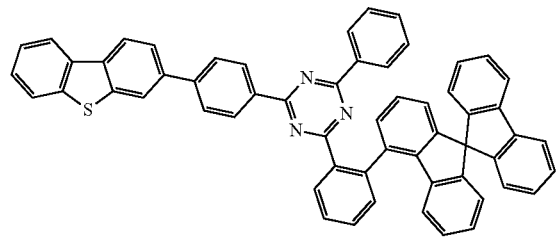
d-280
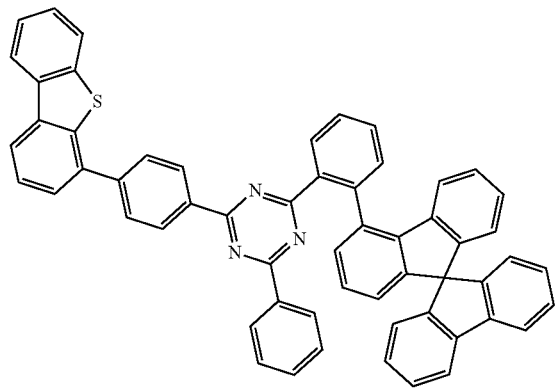

-continued
d-281
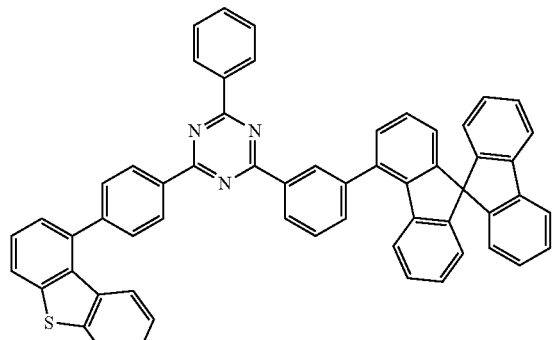
d-282
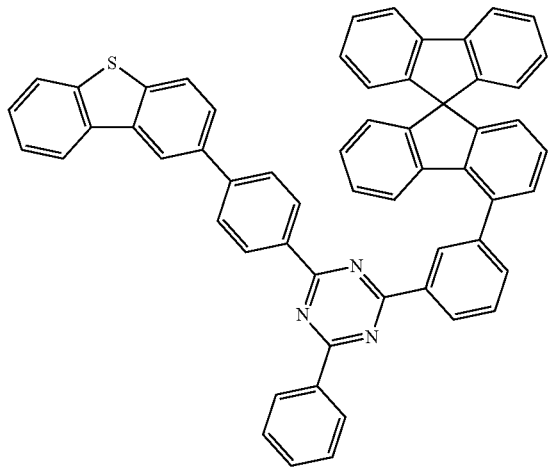
d-283
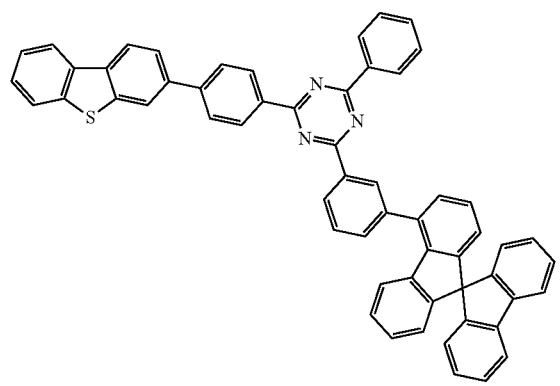
d-284
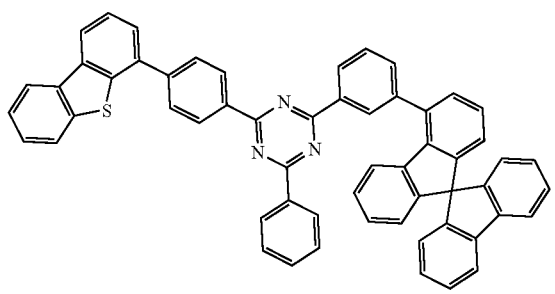
d-285
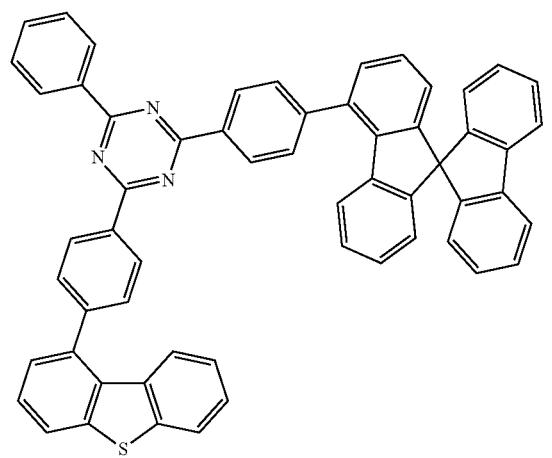
d-286
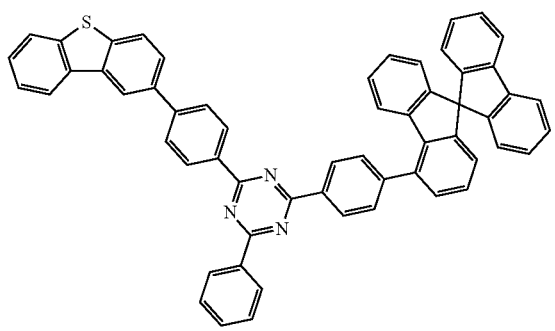

-continued
d-287
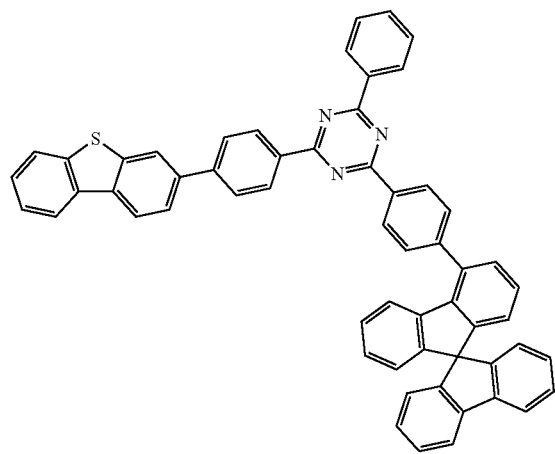
d-288
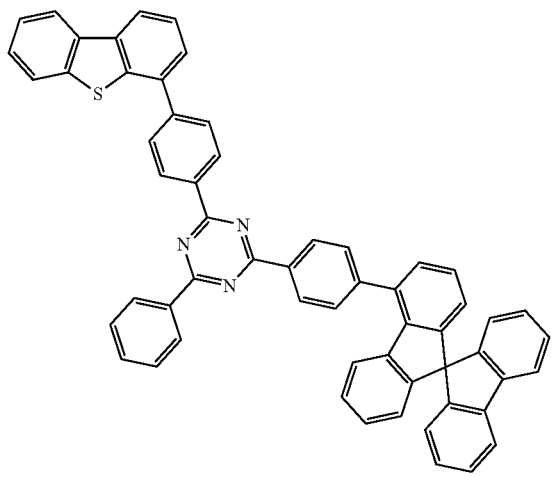
e-1
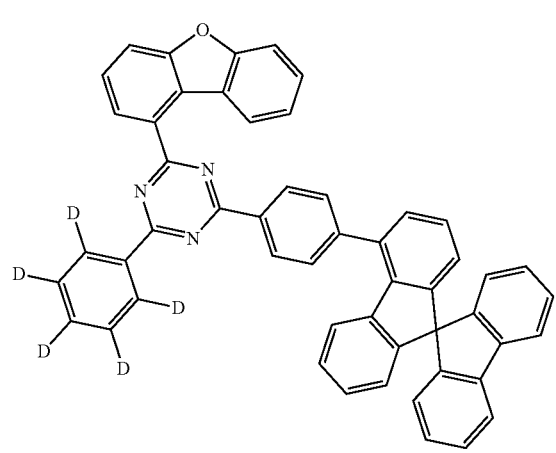
e-2
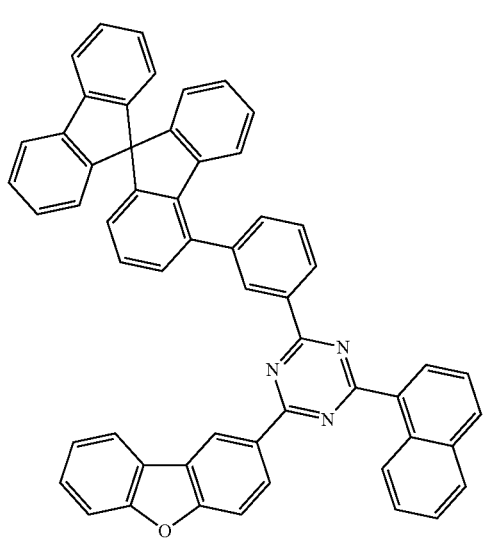
e-3
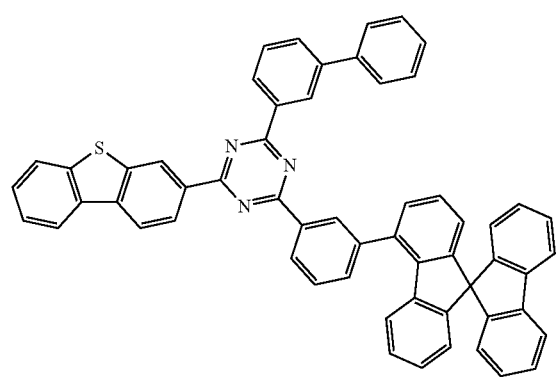
e-4
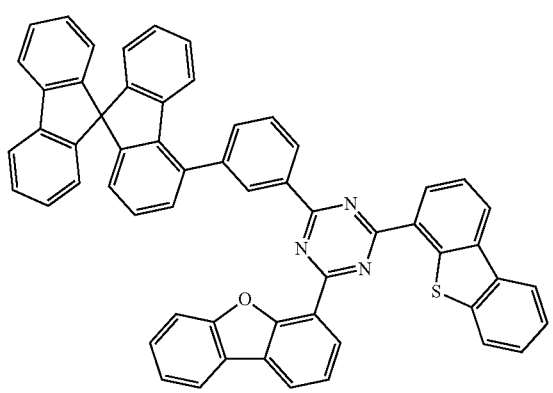

-continued
e-5
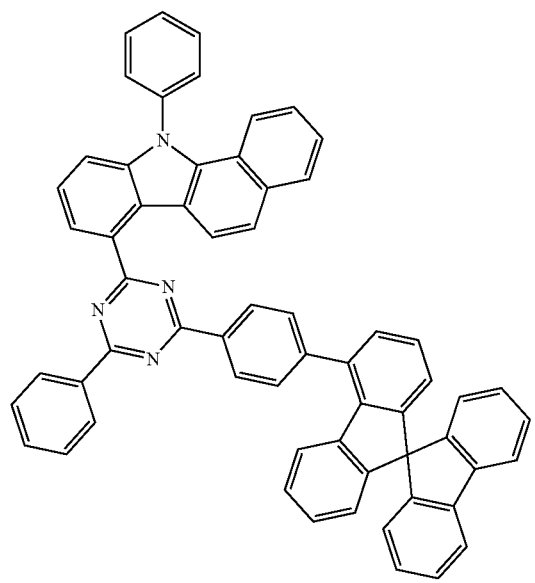
e-6
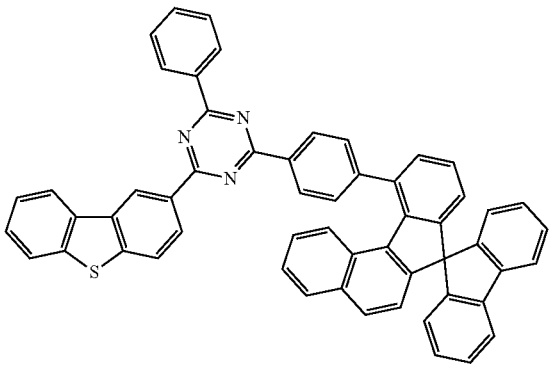
e-7
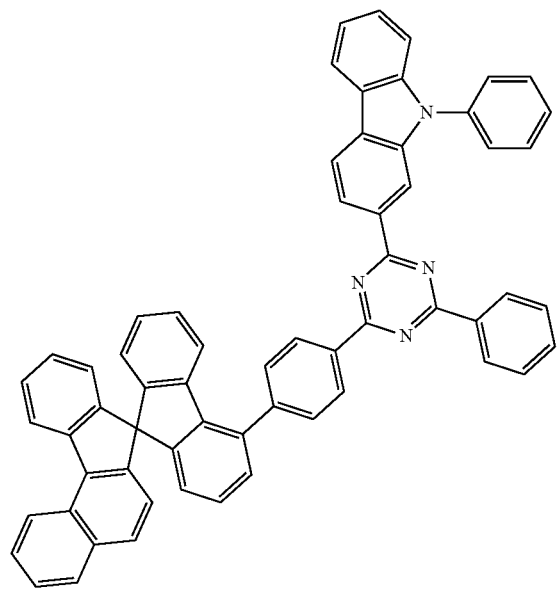
e-8
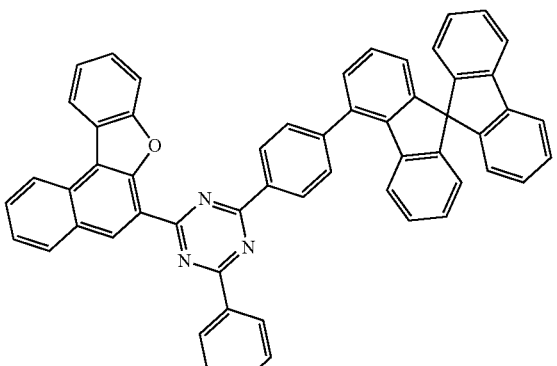
e-9
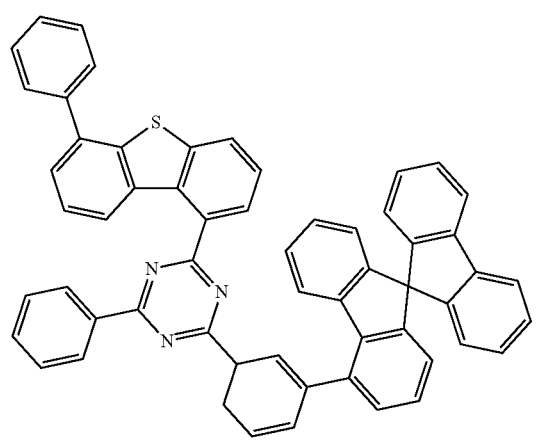
e-10
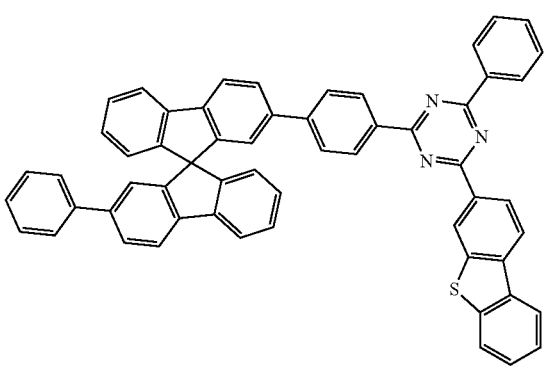

e-11

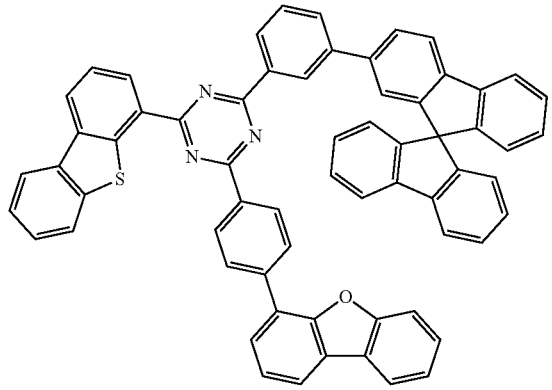

e-12

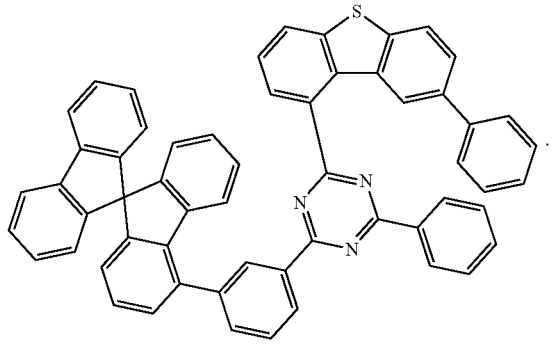

5. An organic electric element comprising a first electrode, a second electrode, and an organic material layer formed between the first electrode and the second electrode, wherein the organic material layer comprises the compound represented by Formula 1 of claim 1.

6. The organic electric element of claim 5, wherein the organic material layer comprises a light emitting layer, and the compound is comprised in the light emitting layer of the organic material layer.

7. The organic electric element of claim 5, wherein the organic material layer is formed by a process of spin coating, nozzle printing, inkjet printing, slot coating, dip coating or roll-to-roll.

8. The organic electric element of claim 5, wherein the organic electric element further comprises a layer for improving luminous efficiency formed on one side of sides of the first electrode or the second electrode, and the one side is not facing the organic material layer.

9. An electronic device comprising a display device and a control unit for driving the display device, wherein the display device comprises the organic electric element of claim 5.

10. The electronic device of claim 9, wherein the organic electric element is selected from the group consisting of an organic electroluminescent element, an organic solar cell, an organic photo conductor, an organic transistor, an element for monochromatic illumination and element for quantum dot display.

11. A compound of Formula 1:

[Formula 1]

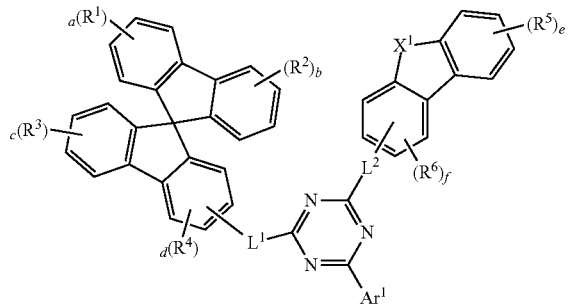

wherein:

$X^1$ is S, O or $N(Ar^1)$, $R^1$ to $R^4$ are each independently selected from the group consisting of hydrogen, deuterium, halogen, a cyano group, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ -alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L^1$-$N(R_a)(R_b)$, and adjacent groups together may be bonded to each other to form a ring, wherein the ring is selected from the group consisting of a $C_2$-$C_{60}$ heterocyclic ring, a $C_3$-$C_{60}$ aliphatic ring and a combination thereof, $R^5$ and $R^6$ are each independently selected from the group consisting of hydrogen, deuterium, halogen, a $C_6$-$C^{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L'$-$N(R_a)(R_b)$, and adjacent groups together may be bonded to each other to form a ring, wherein the ring is selected from the group consisting of a $C_6$-$C_{60}$ aromatic hydrocarbon, a $C_2$-$C_{60}$ heterocyclic ring, a $C_3$-$C_{60}$ aliphatic ring and a combination thereof, a, b, c and e are each represent an integer of 0-4, d and f are each represent an integer of 0-3, and when each of these is an integer of 2 or more, each of $R^1$s, each of $R^2$s, each of $R^3$s, each of $R^4$s, each of $R^5$s or each of $R^6$s may be the same or different from each other, $L^1$ is selected from the group consisting of a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof, $L^2$ is selected from the group consisting of a single bond, a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P, and a combination thereof, $Ar^1$ is selected from the group consisting of a $C_6$-$C_{60}$ aryl group, a fluorenyl group, a $C_2$-$C_{60}$ heterocyclic group containing at least one heteroatom of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), $Ar^1$ is selected from the group consisting of a $C_6$-$C_{60}$ aryl group, a fluorenyl group, a $C_2$-$C_{60}$ heterocyclic group containing at least one heteroatom of O, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), L' is selected from the group consisting of a single bond, a $C_6$-$C_{60}$ arylene group, a fluorenylene group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, $R_a$ and $R_b$ are each independently selected from the group consisting of a $C_6$-$C_{60}$ aryl group, a fluorenyl group, a fused ring group formed by a $C_3$-$C_{60}$ aliphatic ring with a $C_6$-$C_{60}$ aromatic ring, and a $C_2$-$C_{60}$ heterocyclic group containing at least one heteroatom of O, N, S, Si, and P, and the $R^1$ to $R^6$, $Ar^1$, $Ar^{40}$, $L^1$, $L^2$, L', $R_a$, $R_b$, a ring formed by adjacent $R^1$ groups, adjacent $R^2$ groups, adjacent $R^3$ groups, adjacent $R^4$ groups, adjacent $R^5$ groups and adjacent $R^6$ groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, S, Si, and P, a $C_3$-$C_{20}$ cycloalkyl group, a $C_7$-$C_{20}$ arylalkyl group and a $C_8$-$C_{20}$ arylalkenyl group.

* * * * *